United States Patent
Do et al.

(10) Patent No.: US 9,309,265 B2
(45) Date of Patent: *Apr. 12, 2016

(54) BENZOPYRAN AND BENZOXEPIN PI3K INHIBITOR COMPOUNDS AND METHODS OF USE

(71) Applicants: Genentech, Inc., South San Francisco, CA (US); F. HOFFMANN—LA ROCHE AG, Basel (CH)

(72) Inventors: Steven Do, South San Francisco, CA (US); Richard Goldsmith, South San Francisco, CA (US); Tim Heffron, South San Francisco, CA (US); Aleksandr Kolesnikov, South San Francisco, CA (US); Steven Staben, South San Francisco, CA (US); Alan G. Olivero, South San Francisco, CA (US); Michael Siu, South San Francisco, CA (US); Daniel P. Sutherlin, South San Francisco, CA (US); Bing-Yan Zhu, South San Francisco, CA (US); Paul Goldsmith, Basel (CH); Tracy Bayliss, Basel (CH); Adrian Folkes, Basel (CH); Neil Pegg, Basel (CH)

(73) Assignees: Genentech, Inc., South San Francisco, CA (US); Hoffmann-La Roche Inc., Nutley, NJ (US)

( * ) Notice: Subject to any disclaimer, the term of this patent is extended or adjusted under 35 U.S.C. 154(b) by 123 days.

This patent is subject to a terminal disclaimer.

(21) Appl. No.: 14/446,154

(22) Filed: Jul. 29, 2014

(65) Prior Publication Data

US 2014/0336154 A1 Nov. 13, 2014

Related U.S. Application Data

(60) Continuation of application No. 13/738,846, filed on Jan. 10, 2013, now Pat. No. 8,846,762, and a division of application No. 13/018,068, filed on Jan. 31, 2011, now Pat. No. 8,399,690, and a division of application (Continued)

(51) Int. Cl.
*A01N 37/00* (2006.01)
*C07D 333/00* (2006.01)
(Continued)

(52) U.S. Cl.
CPC .................. *C07F 5/02* (2013.01); *A61K 31/381* (2013.01); *A61K 31/4155* (2013.01); *A61K 31/4196* (2013.01); *A61K 31/427* (2013.01); *A61K 31/429* (2013.01); *A61K 31/4245* (2013.01); *A61K 31/4365* (2013.01); *A61K 31/4436* (2013.01); *A61K 31/496* (2013.01);

(Continued)

(58) Field of Classification Search
CPC ...................................................... C07D 495/04
USPC ............................................. 514/577; 549/43
See application file for complete search history.

(56) References Cited

U.S. PATENT DOCUMENTS

4,797,414 A 1/1989 Rimbault
5,314,889 A 5/1994 Boigegrain et al.
(Continued)

FOREIGN PATENT DOCUMENTS

WO 2001064675 A1 9/2001
WO WO 01/64675 9/2001
(Continued)

OTHER PUBLICATIONS

Freshney (Culture of Animal Cells, A Manual of Basic Technique, Alan R. Liss, Inc., 1983, New York, p. 4).*

(Continued)

*Primary Examiner* — Nizal Chandrakumar
(74) *Attorney, Agent, or Firm* — Viksnins Harris & Padys PLLP

(57) ABSTRACT

Benzopyran and benzoxepin compounds of Formulas I and II, and including stereoisomers, geometric isomers, tautomers, solvates, metabolites and pharmaceutically acceptable salts thereof, are useful for inhibiting lipid kinases including p110 alpha and other isoforms of PI3K, and for treating disorders such as cancer mediated by lipid kinases. Methods of using compounds of Formulas I and II for in vitro, in situ, and in vivo diagnosis, prevention or treatment of such disorders in mammalian cells, or associated pathological conditions, are disclosed.

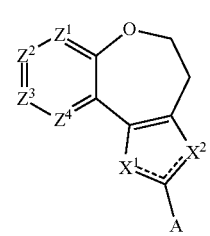

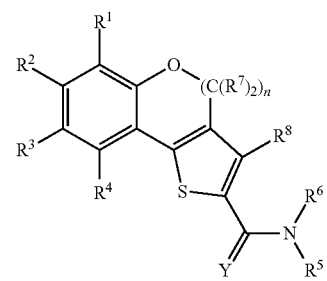

12 Claims, 5 Drawing Sheets

Related U.S. Application Data

No. 12/414,403, filed on Mar. 30, 2009, now Pat. No. 7,928,248.

(60) Provisional application No. 61/040,827, filed on Mar. 31, 2008, provisional application No. 61/102,220, filed on Oct. 2, 2008.

(51) Int. Cl.

| | | |
|---|---|---|
| *C07F 5/02* | (2006.01) | |
| *C07D 495/04* | (2006.01) | |
| *C07D 495/14* | (2006.01) | |
| *C07D 513/14* | (2006.01) | |
| *A61K 31/381* | (2006.01) | |
| *A61K 31/4155* | (2006.01) | |
| *A61K 31/4196* | (2006.01) | |
| *A61K 31/4245* | (2006.01) | |
| *A61K 31/427* | (2006.01) | |
| *A61K 31/429* | (2006.01) | |
| *A61K 31/4365* | (2006.01) | |
| *A61K 31/4436* | (2006.01) | |
| *A61K 31/496* | (2006.01) | |
| *A61K 31/53* | (2006.01) | |

(52) U.S. Cl.
CPC ............. *A61K 31/53* (2013.01); *C07D 495/04* (2013.01); *C07D 495/14* (2013.01); *C07D 513/14* (2013.01)

(56) References Cited

U.S. PATENT DOCUMENTS

| | | | |
|---|---|---|---|
| 5,612,356 | A | 3/1997 | Yoshimura et al. |
| 5,985,799 | A | 11/1999 | Tseng |
| 6,187,801 | B1 | 2/2001 | Jaehne et al. |
| 6,251,922 | B1 | 6/2001 | Jaehne et al. |
| 6,329,407 | B1 | 12/2001 | Jaehne et al. |
| 6,476,059 | B1 | 11/2002 | Jaehne et al. |
| 7,273,880 | B2 | 9/2007 | Marzabadi et al. |
| 7,928,248 | B2 | 4/2011 | Do et al. |
| 8,399,690 | B2 | 3/2013 | Do et al. |
| 2004/0082602 | A1 | 4/2004 | Hagen et al. |
| 2005/0277630 | A1 | 12/2005 | Chupak et al. |
| 2006/0100254 | A1 | 5/2006 | Betzemeier et al. |
| 2006/0106013 | A1 | 5/2006 | Breitfelder et al. |
| 2008/0132513 | A1 | 6/2008 | Che et al. |

FOREIGN PATENT DOCUMENTS

| | | |
|---|---|---|
| WO | 2006040279 | 4/2006 |
| WO | WO 2006/040279 | 4/2006 |
| WO | 2008019139 A2 | 2/2008 |
| WO | WO 2008/019139 | 2/2008 |
| WO | 2008039520 | 4/2008 |
| WO | WO 2008/039520 | 4/2008 |

OTHER PUBLICATIONS

Krymskaya, Blodrugs 2007, 21 (2); 85-95.*
Maira et al. Biochemical Society Transactions (2009), 37(1), 265-272.*
Wu et al. Current Medicinal Chemistry (2009), 16(8), 916-930.*
Banaszak et al., "New and efficient RCM in pyridinic series: synthesis of 2H-dihydropyrano- or 2, 3H-dihydrooxepino [3,2-b]pyridines," *Tetrahedron Letters*, 47 (35), pp. 6235-6238, (2006).
Freshney, "Culture of Animal Cells, A Manual of Basic Technique", Alan R. Liss, Inc., New York, p. 4 (1983).
Heindel et al., "Salicylidene-thiolactone Rearrangement. A Direct Synthesis of 4H-2-Arylthieno [3,2-c] [1] benzopyran-4-ones," *J. Org. Chem*. 42(8), pp. 1465-1466, (1977).
Katsura et al., "Anti-Helicobacter pylori Agents. 4. 2-(Substituted guanidino)-4-phenylthiazoles and Some Structurally Rigid derivatives," *J. Med. Chem.* 43 (17), pp. 3315-3321, (2000).
Krymskaya, "Targeting the Phosphatidylinositol 3-Kinase Pathway in Airway Smooth Muscle", *Biodrugs* 21(2), 85-95 (2007).
Maira et al., "PI3K inhibitors for cancer treatment: where do we stand?", *Biochemical Society Transactions*, 37(1), 265-272 (2009).
Majumdar et al., "Regioselective Synthesis of Thieno[3,2-*c*] [1] benzopyran-4-ones by Thio-Claisen Rearrangement," *Monatshefte fur Chemie* 135(8), pp. 1001-1007, (2004).
Navarro et al., "Synthesis of 1H-[1] Benzopyrano [4,3-*b*] Pyrrole and 4*H*-thieno [3,2-*c*] Benzopyran Derivatives, functionalisation by Aromatic Electrophilic substitution," *Heterocycles*, 55 (12), pp. 2369-2386, (2001).
Potts et al., "Carbon-Carbon Bond Formation via Intramolecular Cycloadditions: Use of the Thiocarbonyl Ylide Dipole in anhydro-4-Hydroxythiazolium Hydroxides," *J. Org. Chem*. 54, pp. 1077-1088, (1989).
Potts et al., "Intramolecular 1, 3-Dipolar Cycloadditions with Thiocarbonyl Ylides," *J. Chem. Soc., Chem. Commun.*, 7, pp. 561-563, (1986).
Reiter et al., "Pyrimidine benzamide-based thrombopoietin receptor agonists," *Bioorganic & Medicinal Chemistry Letters*, 17 (19) pp. 5447-5454, (2007).
Rueeger et al., "Discovery and SAR of potent, orally available and brain-penetrable 5,6-dihydro-4H-3-thia-1-aza-benzo[e]azulen-derivatives as neuropeptide Y Y5 receptor antagonists," *Bioorganic & Medicinal Chem. Letters*, 14 (10), pp. 2451-2457, (2004).
Sekhar et al., "A Simple and Convenient Method for the Synthesis of Condensed Thiophene Derivatives Starting from Heterocyclic Chloro Aldehydes. Part II," *Sulfur Heterocyclic Letters*, 9 (6), pp. 271-277, (1989).
Staben et al., "Structure-based design of thienobenzoxepin inhibitors of PI3-kinase", *Bioorganic & Medicinal Chemistry Letters 21*, 4054-4058 (2011).
Trieu et al., "The Condensation of (beta-chlorovinyl) Carbonyl Compounds with alpha-mercaptocarboxylic acids (translated from German)," *Zeitschrift fuer Chemie*, (translated from German), 13 (2), pp. 57-58, (1973).
Patent Cooperation Treaty, International Searching Authority, Search Report and Written Opinion for PCT/US2009/038795, 15 pages, dated Jul. 7, 2009.
Wu et al., "PI3K Inhibitors for Cancer Therapy: What has been Achieved So Far?", *Current Medicinal Chemistry*, 16(8), 916-930 (2009).

* cited by examiner

BENZOPYRAN AND BENZOXEPIN PI3K INHIBITOR COMPOUNDS AND METHODS OF USE

CROSS REFERENCE TO RELATED APPLICATIONS

This application is a continuation application of U.S. application Ser. No. 13/738,846, filed Jan. 10, 2013, which is a divisional application of U.S. application Ser. No. 13/018,068, filed Jan. 31, 2011, which issued as U.S. Pat. No. 8,399,690, which is a divisional application of U.S. application Ser. No. 12/414,403, filed Mar. 30, 2009, which issued as U.S. Pat. No. 7,928,248, and claims the benefit under 35 USC §119(e) of U.S. Provisional Application Ser. No. 61/040,827 filed on Mar. 31, 2008 and U.S. Provisional Application Ser. No. 61/102,220 filed on Oct. 2, 2008, all of which are incorporated by reference in entirety.

FIELD OF THE INVENTION

The invention relates generally to compounds with anti-cancer activity and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110α (alpha) (U.S. Pat. No. 5,824,492; U.S. Pat. No. 5,846,824; U.S. Pat. No. 6,274,327). Other isoforms are implicated in cardiovascular and immune-inflammatory disease (WorkmanP(2004) Biochem Soc Trans 32:393-396; Patel et al (2004) Proceedings of the American Association of Cancer Research (Abstract LB-247) 95th Annual Meeting, March 27-31, Orlando, Fla., USA; AhmadiKand Waterfield M D (2004) Encyclopedia of Biological Chemistry (Lennarz W J, Lane M D eds) Elsevier/Academic Press).

The PI3 kinase/Akt/PTEN pathway is an attractive target for cancer drug development since such agents would be expected to inhibit proliferation, reverse the repression of apoptosis and surmount resistance to cytotoxic agents in cancer cells. PI3 kinase inhibitors have been reported (Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; U.S. Pat. No. 6,703,414; WO 97/15658; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070). including p110 alpha binding activity (US 2008/0207611; US 2008/0039459; US 2008/0076768; WO 2008/073785; WO 2008/070740).

SUMMARY OF THE INVENTION

The invention relates generally to benzoxepin compounds of Formula I with anti-cancer activity, and more specifically with PI3 kinase inhibitory activity. Certain hyperproliferative disorders are characterized by the modulation of PI3 kinase function, for example by mutations or overexpression of the proteins. Accordingly, the compounds of the invention may be useful in the treatment of hyperproliferative disorders such as cancer. The compounds may inhibit tumor growth in mammals and may be useful for treating human cancer patients.

The invention also relates to methods of using the benzoxepin compounds of Formula I for in vitro, in situ, and in vivo diagnosis or treatment of mammalian cells, organisms, or associated pathological conditions.

Formula I compounds include:

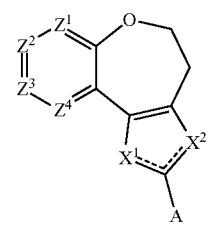

and stereoisomers, geometric isomers, tautomers, or pharmaceutically acceptable salts thereof. The various substituents are as defined herein.

Another aspect of the invention provides a pharmaceutical composition comprising a benzoxepin compound of Formula I and a pharmaceutically acceptable carrier. The pharmaceutical composition may further comprise one or more additional therapeutic agent.

Another aspect of the invention provides methods of inhibiting PI3 kinase activity, comprising contacting a PI3 kinase with an effective inhibitory amount of a compound of Formula I.

Another aspect of the invention provides methods of preventing or treating a hyperproliferative disease or disorder modulated by PI3 kinases, comprising administering to a mammal in need of such treatment an effective amount of a compound of Formula I. Examples of such hyperproliferative disease or disorder include, but are not limited to, cancer.

Another aspect of the invention provides methods of preventing or treating a hyperproliferative disorder, comprising administering to a mammal in need of such treatment an effective amount of a compound of Formula I, alone or in combination with one or more additional compounds having anti-hyperproliferative properties.

In a further aspect the present invention provides a method of using a compound of this invention to treat a hyperproliferative disease or condition modulated by PI3 kinase in a mammal.

An additional aspect of the invention is the use of a compound of this invention for treating cancer modulated by PI3 kinase in a mammal.

Another aspect of the invention includes kits comprising a compound of Formula I, a container, and optionally a package insert or label indicating a treatment.

Another aspect of the invention includes methods of preparing, methods of separating, and methods of purifying compounds of Formula I.

Another aspect of the invention includes novel intermediates useful for preparing Formula I compounds.

The invention also relates to methods of using the benzopyran and benzoxepin compounds of Formula II for in vitro, in situ, and in vivo diagnosis or treatment of mammalian cells, organisms, or associated pathological conditions.

Formula II compounds include:

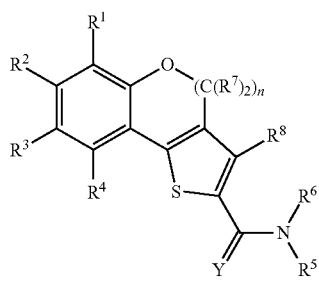

and stereoisomers, geometric isomers, tautomers, or pharmaceutically acceptable salts thereof. The various substituents are as defined herein.

Another aspect of the invention provides a pharmaceutical composition comprising a benzoxepin compound of Formula II and a pharmaceutically acceptable carrier. The pharmaceutical composition may further comprise one or more additional therapeutic agent.

Another aspect of the invention provides methods of inhibiting PI3 kinase activity, comprising contacting a PI3 kinase with an effective inhibitory amount of a compound of Formula II.

Another aspect of the invention provides methods of preventing or treating a hyperproliferative disease or disorder modulated by PI3 kinases, comprising administering to a mammal in need of such treatment an effective amount of a compound of Formula II. Examples of such hyperproliferative disease or disorder include, but are not limited to, cancer.

Another aspect of the invention provides methods of preventing or treating a hyperproliferative disorder, comprising administering to a mammal in need of such treatment an effective amount of a compound of Formula II, alone or in combination with one or more additional compounds having anti-hyperproliferative properties.

Another aspect of the invention includes methods of preparing, methods of separating, and methods of purifying compounds of Formula II.

Another aspect of the invention includes novel intermediates useful for preparing Formula II compounds.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Figure 1:
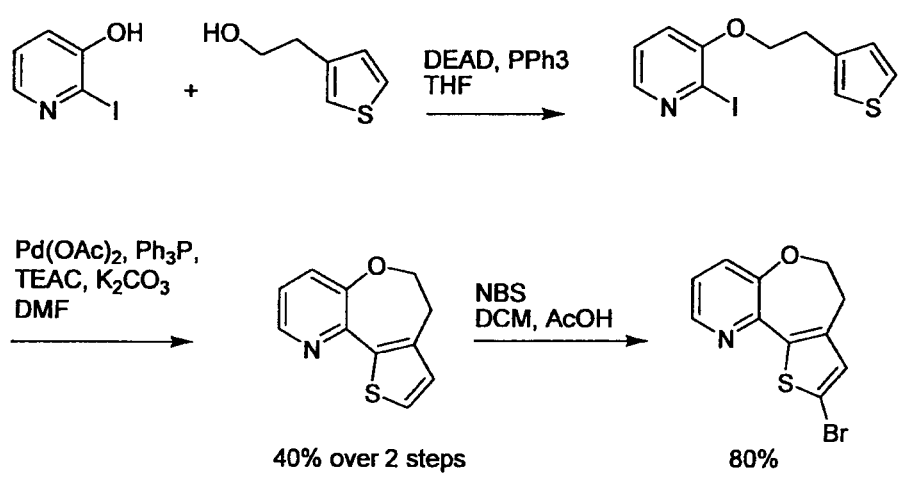
FIG. 1 shows a general exemplary route to 10-pyridooxepin compounds
Figure 2:
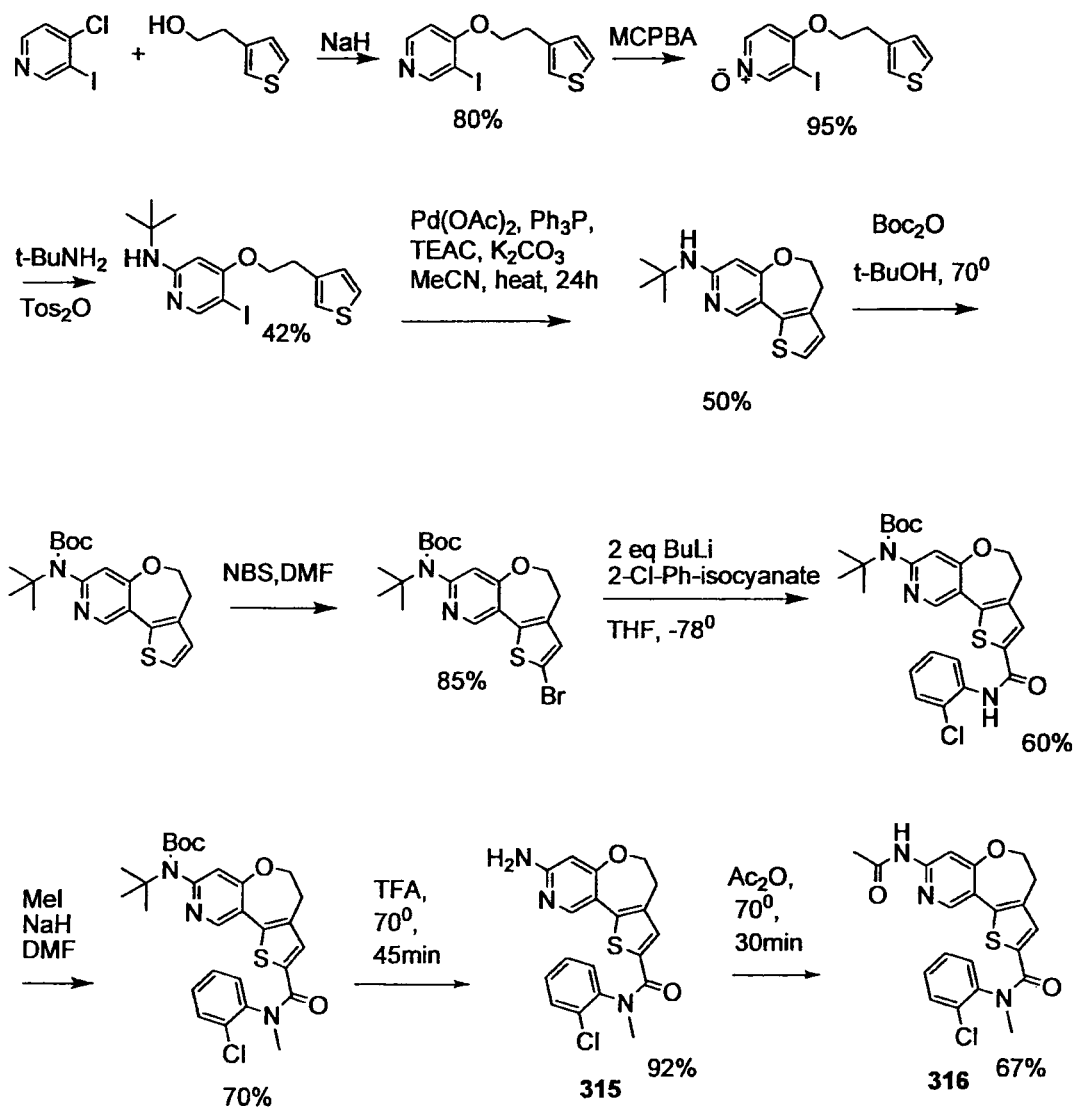
FIG. 2 shows an exemplary synthetic route to 9-pyridooxepin compounds 315 and 316.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynyl radical may be optionally. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum (II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifamib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaII (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof Benzoxepin Compounds The present invention provides benzoxepin compounds, and pharmaceutical formulations thereof, which are potentially useful in the treatment of diseases, conditions and/or disorders modulated by PI3 kinases. More specifically, the present invention provides compounds of Formula I

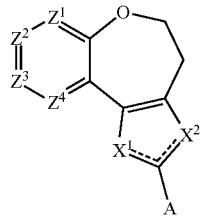

I and stereoisomers, geometric isomers, tautomers, or pharmaceutically acceptable salts thereof, wherein:

$Z^1$ is $CR^1$ or N;
$Z^2$ is $CR^2$ or N;
$Z^3$ is $CR^3$ or N;
$Z^4$ is $CR^4$ or N;
where (i) $X^1$ is N and $X^2$ is S, (ii) $X^1$ is S and $X^2$ is N, (iii) $X^1$ is $CR^7$ and $X^2$ is S, or (iv) $X^1$ is S and $X^2$ is $CR^7$;

$R^1$, $R^2$, $R^3$, $R^4$, and $R^7$ are independently selected from H, F, Cl, Br, I, —CN, —CF$_3$, —CH$_2$OR$^{10}$, —CH$_2$R$^{10}$, —(C$_1$-C$_{12}$ alkylene)NR$^{10}$R$^{11}$, —(C$_1$-C$_{12}$ alkylene)NR$^{12}$C(=O)R$^{10}$, —(C$_1$-C$_{12}$ alkylene)C(=O)OR$^{10}$, —(C$_1$-C$_{12}$ alkylene)OR$^{10}$, —CO$_2$R$^{10}$, —C(=O)N(R$^{10}$)OR$^{11}$, —NO$_2$, —NR$^{10}$R$^{11}$, —OR$^{10}$, —S(O)$_2$R$^{10}$, —C(=O)NR$^{10}$R$^{11}$, —C(=O)NR$^{10}$ (C$_1$-C$_{12}$ alkylene)NR$^{10}$R$^{11}$, —C(=O)NR$^{10}$ (C$_1$-C$_{12}$ alkylene)NR$^{10}$C(=O)OR$^{11}$, —C(=O)NR$^{10}$ (C$_1$-C$_{12}$ alkylene)NR$^{10}$C(=O)R$^{11}$, —C(=O)NR$^{10}$(C$_1$-C$_{12}$ alkylene)R$^{10}$, —C(=NR$^{10}$)NR$^{10}$R$^{11}$, —NR$^{12}$C(=O)R$^{10}$, —NR$^{12}$C(=O)OR$^{11}$, —NR$^{12}$C(=O)NR$^{10}$R$^{11}$, —NR$^{12}$C(=O) (C$_1$-C$_{12}$ alkylene)NR$^{10}$R$^{11}$, —NR$^{12}$(C$_1$-C$_{12}$ alkylene)NR$^{10}$R$^{11}$, —NR$^{12}$(C$_1$-C$_{12}$ alkylene)OR$^{10}$, —NR$^{12}$(C$_1$-C$_{12}$ alkylene)C(=O)NR$^{10}$R$^{11}$, —C≡CR$^{10}$, —CH═CHR$^{10}$, —NR$^{12}$(C$_1$-C$_{12}$ alkylene)C(=O)NR$^{10}$R$^{11}$, —C≡CR$^{10}$, —CH═CHR$^{10}$, C$_2$-C$_{20}$ heterocyclyl, C$_1$-C$_{20}$ heteroaryl, and phenyl, where heterocyclyl, heteroaryl, phenyl and alkylene are optionally substituted with one or more groups selected from F, Cl, Br, I, —CH$_2$OH, —(CH$_2$)$_2$OH, —CH$_2$CO$_2$H, —CN, —CH$_2$NH$_2$, —(CH$_2$)$_2$N(CH$_3$)$_2$, —CH$_3$, —C(=O)CH$_3$, —C(=O)NHCH$_3$, —CO$_2$H, —CH$_2$CO$_2$CH$_3$, —NH$_2$, —OCH$_3$, —S(O)$_2$CH$_3$, 4-methylpiperazin-1-yl, and 4-morpholinyl;

A is selected from —C(=O)NR$^5$R$^6$, C$_2$-C$_{20}$ heterocyclyl and C$_1$-C$_{20}$ heteroaryl wherein C$_2$-C$_{20}$ heterocyclyl and C$_1$-C$_{20}$ heteroaryl are optionally substituted with one or more groups independently selected from F, Cl, Br, I, —CH$_2$OH, —CH$_2$CO$_2$H, —CH(CH$_3$)CH$_2$OCH$_3$, —CN, C$_1$-C$_{12}$ alkyl, —(C$_1$-C$_{12}$ alkylene)NR$^{10}$R$^{11}$, —(C$_1$-C$_{12}$ alkylene)OR$^{10}$, —CH$_3$, —C(=O)CH$_3$, —C(=O)NHCH$_3$, —C(=O)N(CH$_3$)$_2$, —CO$_2$H, —CO$_2$CH$_3$, —CH$_2$CO$_2$CH$_3$, —NH$_2$, —NHC(=O)CH$_3$, —OCH$_3$, —S(O)$_2$CH$_3$, 1-methylpiperid-4-yl, 4-methylpiperazin-1-yl, 4-morpholinyl, isopropyl, isobutyl, cyclopropyl, cyclopropylmethyl, cyclobutyl, triazolylmethyl, benzyl, and phenyl, where alkyl, alkylene, benzyl and phenyl are optionally substituted with one or more groups independently selected from F, Cl, Br, I, —CF$_3$, —CH$_2$OH, —CH$_2$CO$_2$H, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, —OH, —OCH$_3$, —S(O)$_2$CH$_3$, 1-methylpiperid-4-yl, (4-methylpiperazin-1-yl)carboxamide, —CH$_2$(1H-1,2,4-triazol-5-yl), 4-methylpiperazin-1-yl, and 4-morpholinyl;

$R^5$ is selected from H, C$_1$-C$_{12}$ alkyl, optionally substituted with one or more groups independently selected from F, Cl, Br, I, —CN, —CO$_2$H, —CONH$_2$, —CONHCH$_3$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

$R^6$ is selected from C$_1$-C$_{12}$ alkyl, C$_3$-C$_{12}$ carbocyclyl, C$_2$-C$_{20}$ heterocyclyl, C$_1$-C$_{20}$ heteroaryl, and C$_6$-C$_{20}$ aryl, each optionally substituted with one or more groups independently selected from F, Cl, Br, I, —CH$_2$OH, —CH$_2$C$_6$H$_5$, —CN, —CF$_3$, —CO$_2$H, —C(=O)NR$^{10}$R$^{11}$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, —S(O)$_2$CH$_3$, —C(=O)NR$^{10}$(C$_1$-C$_{12}$ alkylene)NR$^{10}$R$^{11}$, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR$^{13}$, —CH═CHR$^{13}$, and —C(=O)NR$^{10}$R$^{11}$;

or $R^5$ and $R^6$ together with the nitrogen atom to which they are attached form morpholin-4-yl, piperidin-1-yl, piperazinyl, piperazin-4-yl-2-one, piperazin-4-yl-3-one, pyrrolidin-1-yl, thiomorpholin-4-yl or S-dioxothiomorpholin-4-yl, each optionally substituted with one or more groups selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

$R^7$ is selected from H and F;

$R^{10}$, $R^{11}$ and $R^{12}$ are independently selected from H, C$_1$-C$_{12}$ alkyl, C$_1$-C$_{12}$ alkylene-C$_2$-C$_{20}$ heterocyclyl, C$_1$-C$_{12}$ alkylene-C$_6$-C$_{20}$ aryl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl, where C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl are optionally substituted with one or more groups independently selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, 2-oxopyrrolidin-1-yl, —S(O)$_2$NH$_2$, and —S(O)$_2$CH$_3$;

or $R^{10}$ and $R^{11}$ together with the nitrogen atom to which they are attached form a C$_2$-C$_{20}$ heterocyclyl ring or C$_1$-C$_{20}$ heteroaryl each optionally substituted with one or more groups independently selected from F, Cl, Br, I, —CH$_3$, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, oxo, —OCH$_3$, —OCH$_2$CH$_3$, —S(O)$_2$NH$_2$, and —S(O)$_2$CH$_3$; and R$^{13}$ is selected from H, F, Cl, Br, I, —CH$_3$, —CH$_2$CH$_3$, —CN, —CF$_3$, —CH$_2$N(CH$_3$)$_2$, —CH$_2$OH, —CO$_2$H, —CONH$_2$, —CON(CH$_3$)$_2$, —NO$_2$, and —S(O)$_2$CH$_3$.

In addition, the present invention provides compounds of Formula I wherein:

R$^1$, R$^2$, R$^3$, and R$^4$ are independently selected from H, F, Cl, Br, I, —CN, —CF$_3$, —CH$_2$OR$^{10}$, —CH$_2$R$^{10}$, —CH$_2$NR$^{10}$R$^{11}$, (C$_1$-C$_{12}$ alkylene)C(=O)OR$^{10}$, —(C$_1$-C$_{12}$ alkylene)OR$^{10}$, —CO$_2$R$^{10}$, —C(=O)N(R$^{10}$)OR$^{11}$, —NO$_2$, —NR$^{10}$R$^{11}$, —OR$^{10}$, —S(O)$_2$R$^{10}$, —C(=O)NR$^{10}$R$^{11}$, —C(=O)NR$^{10}$(C$_1$-C$_{12}$ alkylene)NR$^{10}$R$^{11}$, —C(=O)NR$^{10}$(C$_1$-C$_{12}$ alkylene)NR$^{10}$C(=O)OR$^{11}$, —C(=O)NR$^{10}$(C$_1$-C$_{12}$ alkylene)NR$^{10}$C(=O)R$^{11}$, —C(=O)NR$^{10}$(C$_1$-C$_{12}$ alkylene)R$^{10}$, —NR$^{12}$C(=O)R$^{10}$, —NR$^{12}$C(=O)OR$^{11}$, —NR$^{12}$C(=O)NR$^{10}$R$^{11}$, —NR$^{12}$(C$_1$-C$_{12}$ alkylene)NR$^{10}$R$^{11}$, —NR$^{12}$(C$_1$-C$_{12}$ alkylene)OR$^{10}$, —NR$^{12}$(C$_1$-C$_{12}$ alkylene)C(=O)NR$^{10}$R$^{11}$, —C≡CR$^{10}$, —CH=CHR$^{10}$, C$_2$-C$_{20}$ heterocyclyl, C$_1$-C$_{20}$ heteroaryl, and phenyl, where heterocyclyl, heteroaryl, and phenyl are optionally substituted with one or more groups selected from F, Cl, Br, I, —CH$_2$OH, —CH$_2$CO$_2$H, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, —OCH$_3$, —S(O)$_2$CH$_3$, 4-methylpiperazin-1-yl, and 4-morpholinyl, and where alkylene is optionally substituted with one or more F;

A is selected from —C(=O)NR$^5$R$^6$ and C$_1$-C$_{20}$ heteroaryl optionally substituted with one or more groups independently selected from F, Cl, Br, I, —CH$_2$OH, —CH$_2$CO$_2$H, —CH(CH$_3$)CH$_2$OCH$_3$, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, —OCH$_3$, —S(O)$_2$CH$_3$, 1-methylpiperid-4-yl, 4-methylpiperazin-1-yl, 4-morpholinyl, isopropyl, isobutyl, benzyl, and phenyl, where benzyl and phenyl are optionally substituted with F, Cl, Br, I, —CH$_2$OH, —CH$_2$CO$_2$H, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, —OCH$_3$, —S(O)$_2$CH$_3$, 1-methylpiperid-4-yl, 4-methylpiperazin-1-yl, and 4-morpholinyl;

R$^5$ is selected from C$_1$-C$_{12}$ alkyl, optionally substituted with one or more groups independently selected from F, Cl, Br, I, —CN, —CO$_2$H, —CONH$_2$, —CONHCH$_3$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

R$^6$ is selected from C$_3$-C$_{12}$ carbocyclyl, C$_2$-C$_{20}$ heterocyclyl, C$_1$-C$_{20}$ heteroaryl, and C$_6$-C$_{20}$ aryl, each optionally substituted with one or more groups independently selected from F, Cl, Br, I, —CH$_2$OH, —CH$_2$C$_6$H$_5$, —CN, —CF$_3$, —CO$_2$H, —CONH$_2$, —CONHCH$_3$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, —S(O)$_2$CH$_3$, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR$^{13}$, —CH=CHR$^{13}$, and —C(=O)NR$^{10}$R$^{11}$;

or R$^5$ and R$^6$ together with the nitrogen atom to which they are attached form morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, each optionally substituted with one or more groups selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

R$^7$ is selected from H and F;

R$^{10}$, R$^{11}$ and R$^{12}$ are independently selected from H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl, where C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl are optionally substituted with one or more groups independently selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

or R$^{10}$ and R$^{11}$ together with the nitrogen atom to which they are attached form a C$_2$-C$_{20}$ heterocyclyl ring, optionally substituted with one or more groups independently selected from F, Cl, Br, I, —CH$_3$, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$; and R$^{13}$ is selected from H, F, Cl, Br, I, —CH$_3$, —CH$_2$CH$_3$, —CN, —CF$_3$, —CH$_2$N(CH$_3$)$_2$, —CH$_2$OH, —CO$_2$H, —CONH$_2$, —CON(CH$_3$)$_2$, —NO$_2$, and —S(O)$_2$CH$_3$.

Exemplary embodiments of Formula I compounds include the structures:

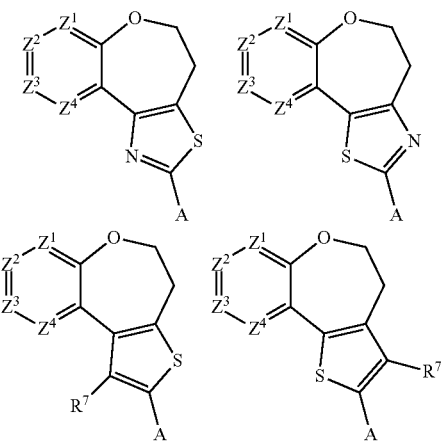

In one embodiment, each of Z$^1$, Z$^2$, Z$^3$, Z$^4$ is a substituted carbon (CR$^1$, CR$^2$, CR$^3$, CR$^4$). In another embodiment three of Z$^1$, Z$^2$, Z$^3$, Z$^4$ are substituted carbon and one of Z$^1$, Z$^2$, Z$^3$, Z$^4$ is N. Typically at least one of Z$^1$, Z$^2$, Z$^3$, Z$^4$ are substituted carbon, i.e. not all of Z$^1$, Z$^2$, Z$^3$, Z$^4$ are N.

Exemplary embodiments of Formula I compounds include the structures:

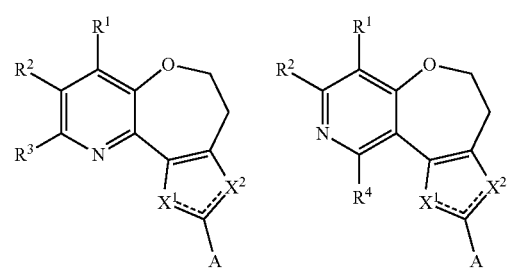

-continued

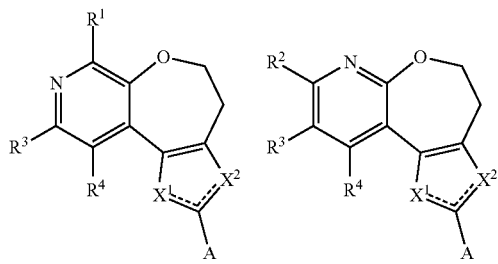

Exemplary embodiments of Formula I compounds include the structures:

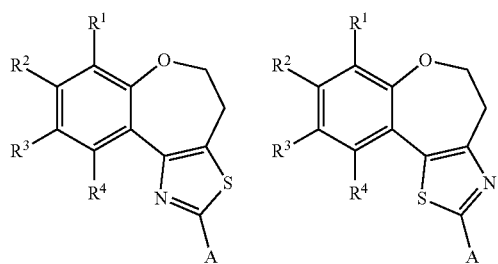

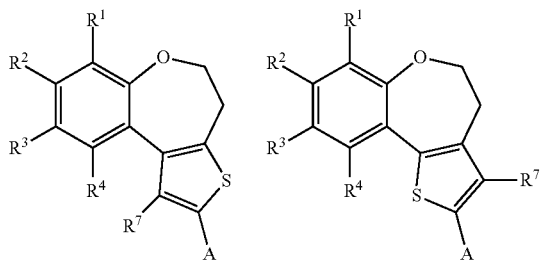

Exemplary embodiments of Formula I compounds include the structures:

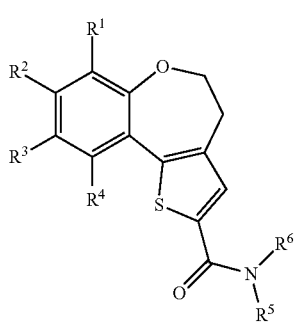

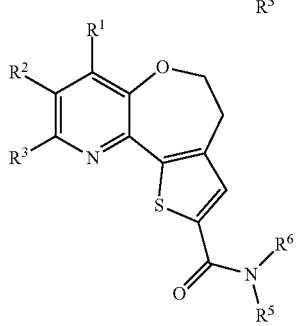

-continued

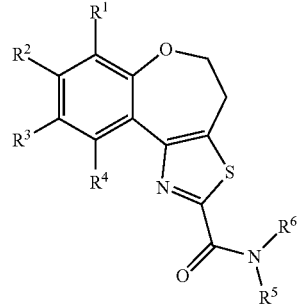

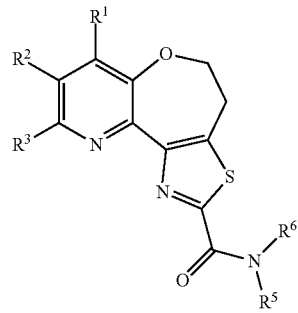

wherein $R^1$, $R^3$, and $R^4$ are each H; and $R^2$ is selected from F, Cl, Br, I, —CN, —CF$_3$, —CH$_2$OR$^{10}$, —CH$_2$R$^{10}$, —CH$_2$NR$^{10}$R$^{11}$, —(C$_1$-C$_{12}$ alkylene)C(=O)OR$^{10}$, —(C$_1$-C$_{12}$ alkylene)OR$^{10}$, —CO$_2$R$^{10}$, —C(=O)N(R$^{10}$)OR$^{11}$, —NO$_2$, —NR$^{10}$R$^{11}$, —OR$^{10}$, —S(O)$_2$R$^{10}$, —C(=O)NR$^{10}$R$^{11}$, —C(=O)NR$^{10}$(C$_1$-C$_{12}$ alkylene)NR$^{10}$R$^{11}$, —C(=O)NR$^{10}$(C$_1$-C$_{12}$ alkylene)NR$^{10}$C(=O)OR$^{11}$, —C(=O)NR$^{10}$ (C$_1$-C$_{12}$ alkylene)NR$^{10}$C(=O)R$^{11}$, —C(=O)NR$^{10}$ (C$_1$-C$_{12}$ alkylene)R$^{10}$, —NR$^{12}$C(=O)R$^{10}$, —NR$^{12}$C(=O)OR$^{11}$, —NR$^{12}$C(=O)NR$^{10}$R$^{11}$, —NR$^{12}$(C$_1$-C$_{12}$ alkylene)NR$^{10}$R$^{11}$, —NR$^{12}$(C$_1$-C$_{12}$ alkylene)OR$^{10}$, —NR$^{12}$(C$_1$-C$_{12}$ alkylene)C(=O)NR$^{10}$R$^{11}$, —C≡CR$^{10}$, —CH=CHR$^{10}$, C$_2$-C$_{20}$ heterocyclyl, C$_1$-C$_{20}$ heteroaryl, and phenyl, where heterocyclyl, heteroaryl, phenyl and alkylene are optionally substituted with one or more groups selected from F, Cl, Br, I, —CH$_2$OH, —CH$_2$CO$_2$H, —CN, —CH$_2$NH$_2$, —CH$_3$, —C(=O)CH$_3$, —C(=O)NHCH$_3$, —CO$_2$H, —CH$_2$CO$_2$CH$_3$; —OCH$_3$, —S(O)$_2$CH$_3$, 4-methylpiperazin-1-yl, and 4-morpholinyl.

Exemplary embodiments include wherein $R^5$ is CH$_3$.

Exemplary embodiments include wherein $R^6$ is phenyl substituted with one or more groups independently selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, —S(O)$_2$CH$_3$, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR$^{13}$, and —CH=CHR$^{13}$.

Exemplary embodiments include wherein A is a C$_1$-C$_{20}$ heteroaryl selected from pyridyl, isoxazolyl, imidazolyl, pyrazolyl, pyrrolyl, thiazolyl, pyridazinyl, pyrimidinyl, pyrazinyl, oxazolyl, oxadiazolyl, 1,3,4-oxadiazol-2(3H)-one, furanyl, thienyl, 1,2,3-triazolyl, 1,2,4-triazolyl, 1,2,4-triazol-5(4H)-one, 4,5-dihydro-1,2,4-triazin-6(1H)-one, tetrazolyl; pyrrolo[2,3-b]pyridinyl, indazolyl, 3,4-dihydroquinolinyl, and benzo[d]thiazole.

Exemplary embodiments include wherein A is selected from the heteroaryl structures:

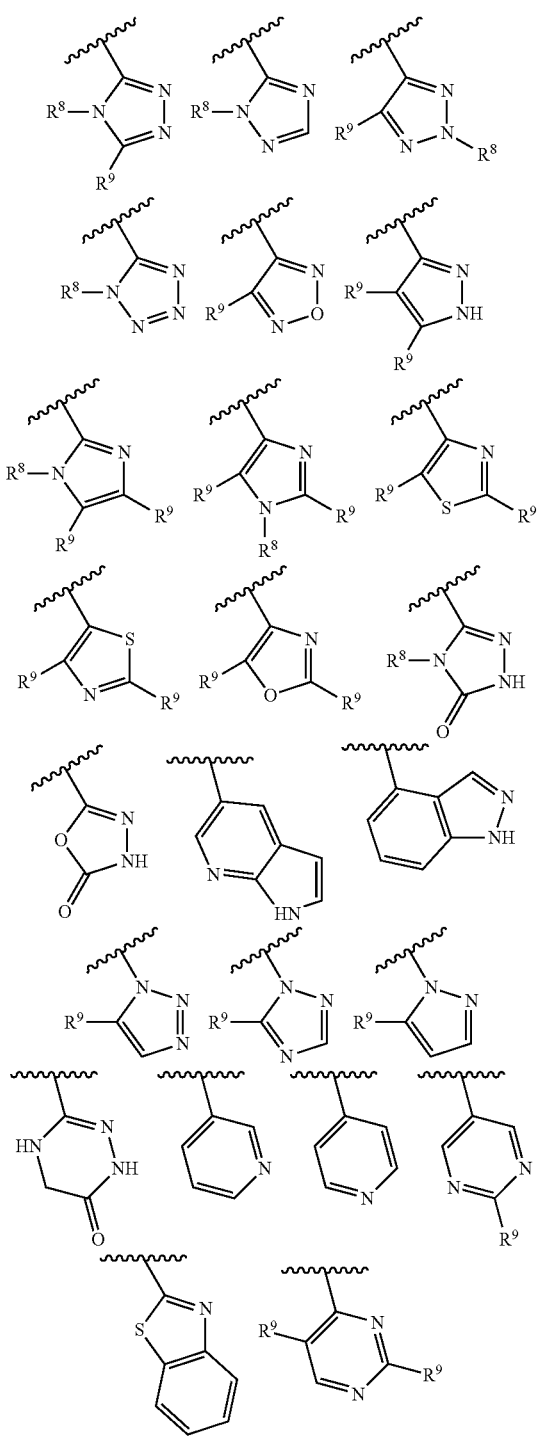

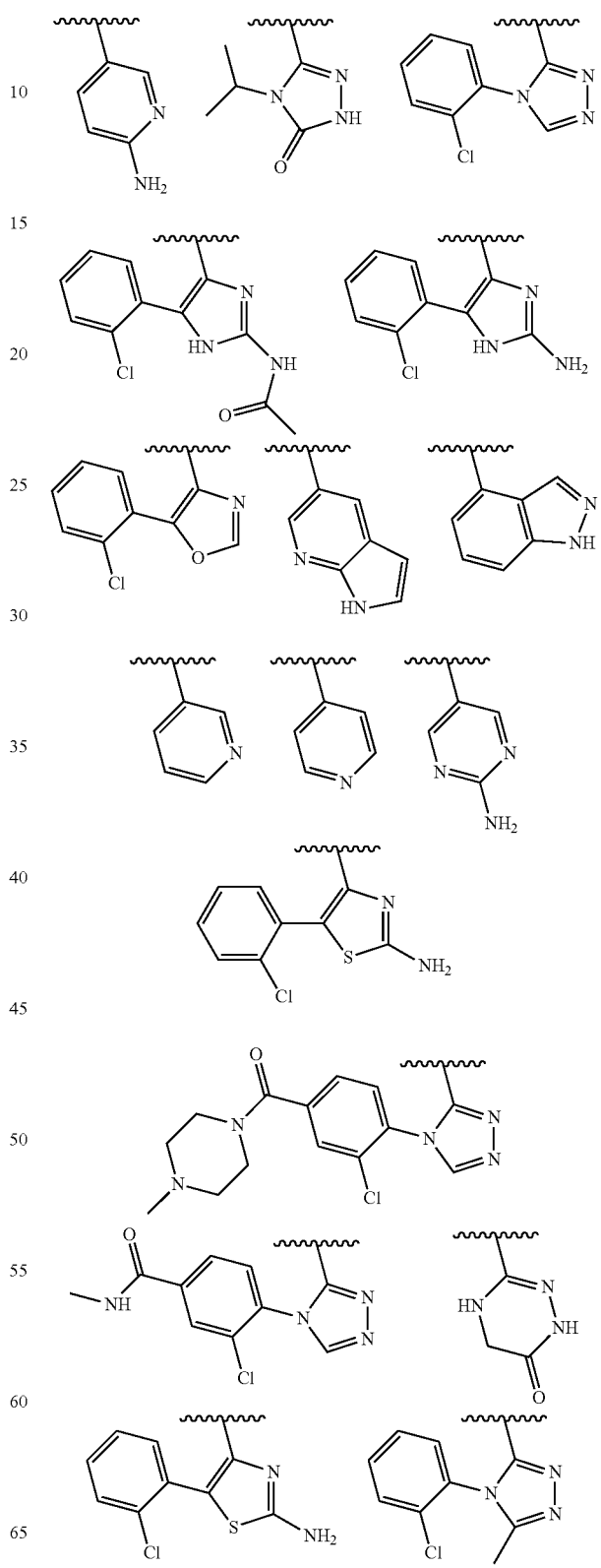

—OCH$_3$, —S(O)$_2$CH$_3$, 1-methylpiperid-4-yl, 4-methylpiperazin-1-yl, and 4-morpholinyl.

Exemplary embodiments include wherein A is selected from the heteroaryl structures:

where R$^8$ and R$^9$ are independently selected from H, F, Cl, Br, I, —CH$_2$OH, —CH$_2$CO$_2$H, —CH(CH$_3$)CH$_2$OCH$_3$, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, —OCH$_3$, —S(O)$_2$CH$_3$, 1-methylpiperid-4-yl, 4-methylpiperazin-1-yl, 4-morpholinyl, isopropyl, isobutyl, benzyl, and phenyl, where benzyl and phenyl are optionally substituted with one or more groups selected from F, Cl, Br, I, —CH$_2$OH, —CH$_2$CO$_2$H, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, -continued

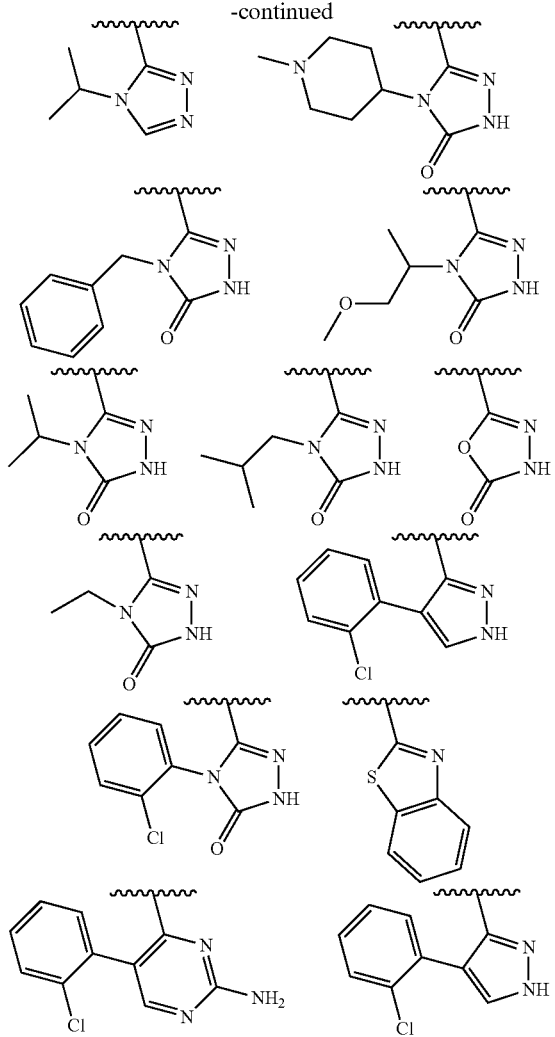

where the wavy line indicates the site of attachment.

Benzopyran and Benzoxepin Compounds

The present invention provides benzopyran and benzoxepin compounds, and pharmaceutical formulations thereof, which are potentially useful in the treatment of diseases, conditions and/or disorders modulated by PI3 kinases. More specifically, the present invention provides compounds of Formula II

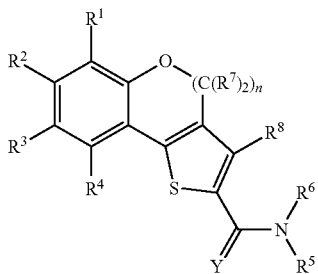

II and stereoisomers, geometric isomers, tautomers, or pharmaceutically acceptable salts thereof, wherein:

$R^1$, $R^2$, $R^3$, and $R^4$ are independently selected from H, F, Cl, Br, I, —CN, —CF$_3$, —CH$_2$OR$^{10}$, —CH$_2$R$^{10}$, —CH$_2$NR$^{10}$R$^{11}$, —(C$_1$-C$_{12}$ alkylene)C(=O)OR$^{10}$, —CO$_2$R$^{10}$, —C(=O)N(R$^{10}$)OR$^{11}$, —NO$_2$, —NR$^{10}$R$^{11}$, —OR$^{10}$, —S(O)$_2$R$^{10}$, —C(=O)NR$^{10}$R$^{11}$, —C(=O)NR$^{10}$(C$_1$-C$_{12}$ alkylene)NR$^{10}$R$^{11}$, —C(=O)NR$^{10}$(C$_1$-C$_{12}$ alkylene)NR$^{10}$C(=O)OR$^{11}$, —C(=O)NR$^{10}$(C$_1$-C$_{12}$ alkylene)NR$^{10}$C(=O)R$^{11}$, —C(=O)NR$^{10}$(C$_1$-C$_{12}$ alkylene)R$^{10}$, —NR$^{12}$C(=O)R$^{10}$, —NR$^{12}$C(=O)OR$^{11}$, —NR$^{12}$C(=O)NR$^{10}$R$^{11}$, —NR(C$_1$-C$_{12}$ alkylene)NR$^{10}$R$^{11}$, —NR(C$_1$-C$_{12}$ alkylene)OR$^{10}$, —NR$^{12}$(C$_1$-C$_{12}$ alkylene)C(=O)NR$^{10}$R$^{11}$, —C≡CR$^{10}$, —CH=CHR$^{10}$, C$_2$-C$_{20}$ heterocyclyl, C$_1$-C$_{20}$ heteroaryl, and phenyl, where heterocyclyl, heteroaryl, and phenyl are optionally substituted with one or more groups selected from —CH$_2$OH, —CH$_2$CO$_2$H, —CN, —CH$_2$NH$_2$, —C(=O)CH$_3$, —CO$_2$H, —CH$_2$CO$_2$CH$_3$, —NH$_2$, —S(O)$_2$CH$_3$, 4-methylpiperazin-1-yl, and 4-morpholinyl;

$R^5$ is selected from C$_1$-C$_{12}$ alkyl, optionally substituted with one or more groups independently selected from F, Cl, Br, I, —CN, —CO$_2$H, —CONH$_2$, —CONHCH$_3$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

$R^6$ is selected from C$_3$-C$_{12}$ carbocyclyl, C$_2$-C$_{20}$ heterocyclyl, C$_1$-C$_{20}$ heteroaryl, and C$_6$-C$_{20}$ aryl, each optionally substituted with one or more groups independently selected from F, Cl, Br, I, —CH$_2$OH, —CH$_2$C$_6$H$_5$, —CN, —CF$_3$, —CO$_2$H, —CONH$_2$, —CONHCH$_3$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, —S(O)$_2$CH$_3$, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR$^{13}$, —CH=CHR$^{13}$, and —C(=O)NR$^{10}$R$^{11}$;

or $R^5$ and $R^6$ together with the nitrogen atom to which they are attached form morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, each optionally substituted with one or more groups selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

each $R^7$ is independently selected from H, F, Cl, Br, I, —CH$_2$OH, —CH$_3$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$; or both R$^7$ together are =O;

$R^8$ is selected from H and F;

$R^{10}$, $R^{11}$ and $R^{12}$ are independently selected from H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl, where C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl are optionally substituted with one or more groups independently selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

or $R^{10}$ and $R^{11}$ together with the nitrogen atom to which they are attached form a C$_2$-C$_{20}$ heterocyclyl ring, optionally substituted with one or more groups independently selected from F, Cl, Br, I, —CH$_3$, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

$R^{13}$ is selected from H, F, Cl, Br, I, —CH$_3$, —CH$_2$CH$_3$, —CN, —CF$_3$, —CH$_2$N(CH$_3$)$_2$, —CH$_2$OH, —CO$_2$H, —CONH$_2$, —CON(CH$_3$)$_2$, —NO$_2$, and —S(O)$_2$CH$_3$;

n is 1 or 2; and
Y is O, S, N—NR$^{10}$R$^{11}$;
with the provisos:
when n is 1, Y is O, and R$^1$, R$^2$, R$^3$, R$^7$, R$^8$ are each H, then R$^4$ is not H or CH$_3$; and
when n is 1, then both R$^7$ together are not =O.

Exemplary embodiments include where the Formula II compound has the structures:

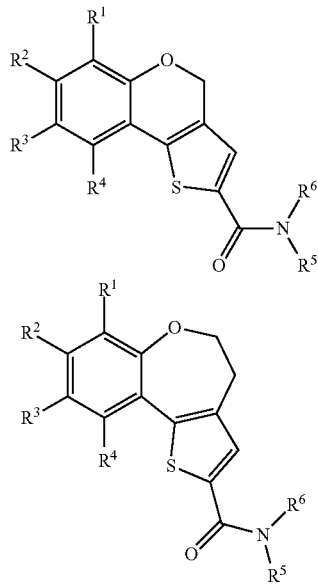

Exemplary embodiments include wherein R$^5$ is CH$_3$.

Exemplary embodiments include wherein R$^6$ is phenyl substituted with one or more groups independently selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, —S(O)$_2$CH$_3$, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR$^{13}$, and —CH=CHR$^{13}$.

Preparation of Formula I Compounds

Benzoxepin compounds of Formula I may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

In certain embodiments, compounds of Formula I may be readily prepared using well-known procedures to prepare benzoxepin compounds (Sekhar et al (1989) Sulfur Letters 9(6):271-277; Katsura et al (2000 J. Med. Chem. 43:3315-3321; Rueeger et al (2004) Biorganic & Med. Chem. Letters 14:2451-2457; Reiter et al (2007) Biorganic & Med. Chem. Letters 17:5447-5454; Banaszak et al (2006) Tetrahedron Letters 47:6235-6238;) and other heterocycles, which are described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes 1-8 show general methods which may be applied for preparation of Formula I compounds, as well as key intermediates. The General Procedures and Examples sections contain more detailed description of individual reaction steps. Those skilled in the art will appreciate that other synthetic routes may be used to synthesize the inventive compounds. Although certain starting materials and routes are depicted in the Schemes, General Procedures and Examples, other similar starting materials and routes can be substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, Third Ed., 1999.

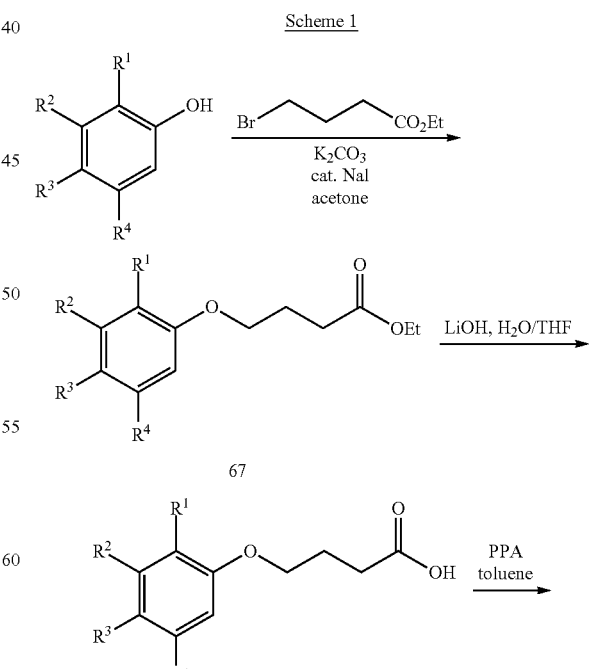

Scheme 1

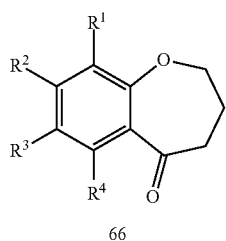

Scheme 1 shows a general method for preparation of 3,4-dihydrobenzo[b]oxepin-5(2H)-one intermediates 66 by O-alkylation of a phenolic compound with ethyl 4-bromobutanoate to give a ethyl 4-phenoxybutanoate intermediate 67, followed by saponification to the carboxylic acid 68 and intramolecular cyclization under acidic conditions.

Scheme 2

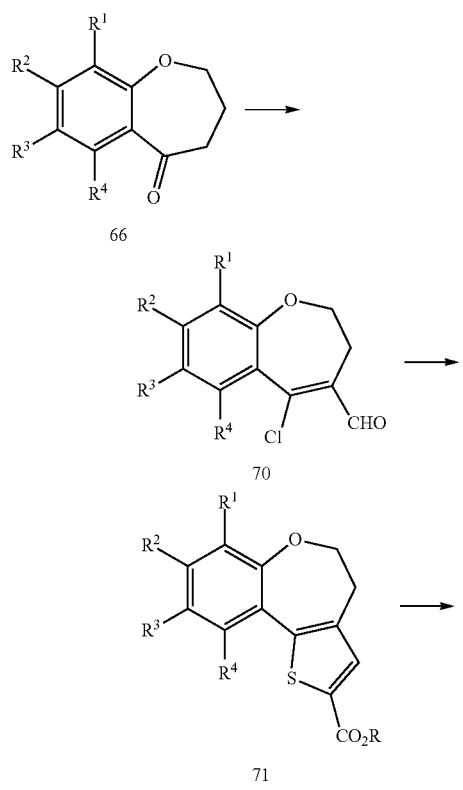

Scheme 2 shows a general method of preparation of N,N-disubstituted 4,5-dihydrobenzo[b]thieno[2,3-d]oxepine-2-carboxamide intermediates 69. 3,4-Dihydrobenzo[b]oxepin-5(2H)-one intermediates 66 are formylated with phosphorus oxytrichloride and dimethylformamide (DMF) to give 5-chloro-2,3-dihydrobenzo[b]oxepine-4-carbaldehyde intermediate 70. Cyclization of 70 with a mercapto acetate ester ($HSCH_2CO_2R$ where R is alkyl or aryl) in potassium carbonate and DMF gives the 4,5-dihydrobenzo[b]thieno[2,3-d]oxepine-2-carboxylate ester intermediate 71. Saponification of 71 with lithium hydroxide in THF and water gives the acid (R=H) which is treated with thionyl chloride at reflux followed by a secondary amine ($HNR^5R^6$), such as N-methyl-2-chloroaniline, with a catalytic amount of DMAP (4,4-dimethylaminopyridine), triethylamine, and dichloromethane to give 4,5-dihydrobenzo[b]thieno[2,3-d]oxepine-2-carboxamide intermediates 69. Alternatively, the acid is treated with oxalyl chloride and a catalytic amount of DMF to generate the acid chloride, followed by reaction with the amine and potassium carbonate in acetonitrile to give amides such as 69. Where one of $R^1$, $R^2$, $R^3$, or $R^4$ is bromo, the bromine of 69, or of another intermediate such as 66, 70, 71, may be displaced by: (i) carbonylative amination to give amide ($-NR^{12}C(=O)R^{10}$, (ii) formylation ($-CHO$) followed by reductive amination to $-CH_2NR^{10}R^{11}$, (iii) Suzuki coupling with aryl or heteroaryl, (iv) Sonagoshira coupling to give alkynyl ($-C\equiv CR^{10}$), or (v) amination ($-NR^{10}R^{11}$).

A variety of palladium catalysts can be used during the Suzuki coupling step to form compounds where $R^1$, $R^2$, $R^3$, or $R^4$ is aryl or heteroaryl. Suzuki coupling is a palladium mediated cross coupling reaction of an arylhalide, with a boronic acid or boronate esters such as pinacolato. Low valent, Pd(II) and Pd(0) catalysts may be used, including $PdCl_2(PPh_3)_2$, $Pd(t-Bu)_3$, $PdCl_2$ dppf $CH_2Cl_2$, $Pd(PPh_3)_4$, $Pd(OAc)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PMePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2Pd[P(4-COOH-Ph)(Ph)_2]_2$, and encapsulated catalysts Pd EnCat™ 30, Pd EnCat™ TPP30, and Pd(II) EnCat™ BINAP30 (US 2004/0254066).

A variety of solid adsorbent palladium scavengers can be used to remove palladium after the Suzuki coupling step. Exemplary embodiments of palladium scavengers include FLORISIL® and SILIABOND® Thiourea. Other palladium scavengers include silica gel, controlled-pore glass (Toso-Haas), and derivatized low crosslinked polystyrene QuadraPure™ AEA, QuadraPure™ IMDAZ, QuadraPure™ MPA, QuadraPure™ TU (Reaxa Ltd., Sigma-Aldrich Chemical Co.).

Scheme 3

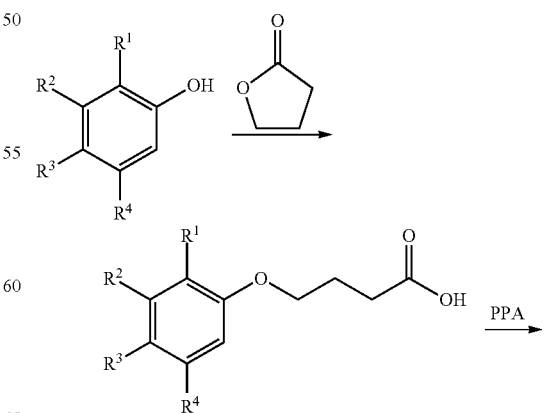

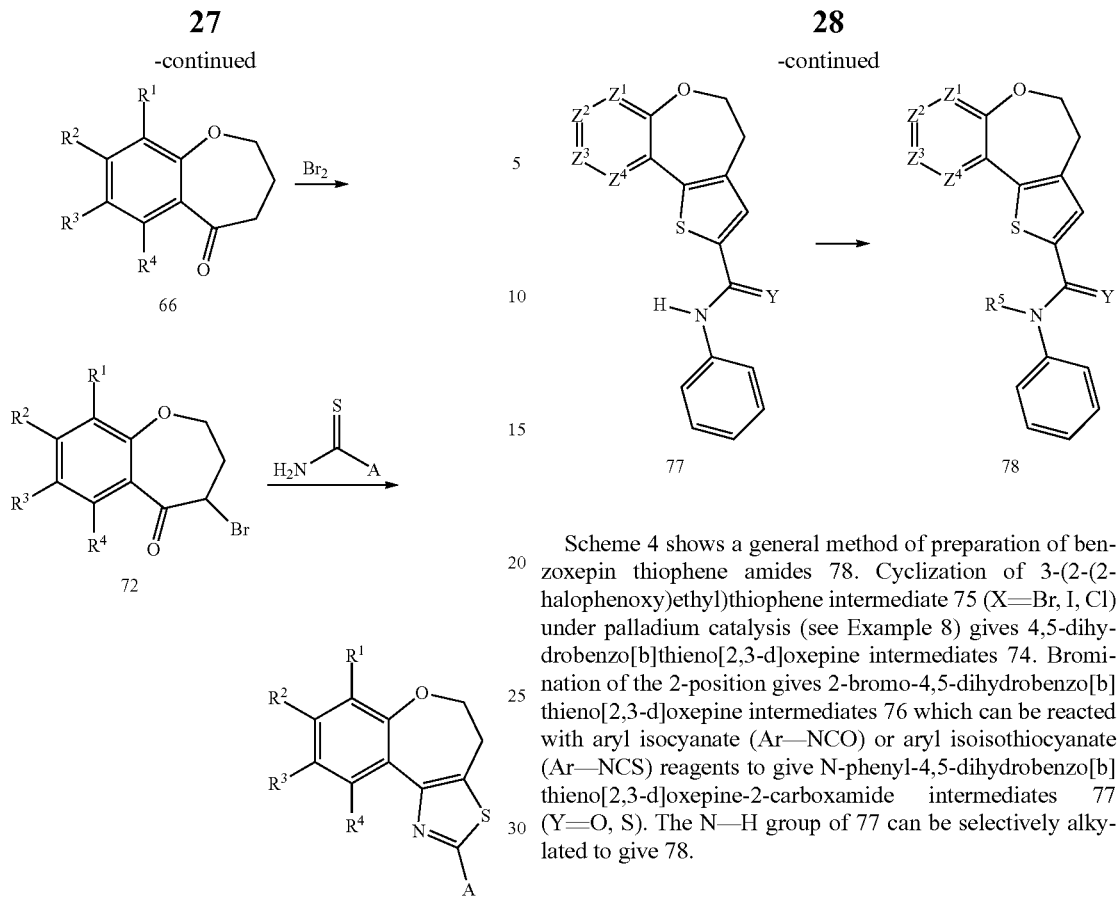

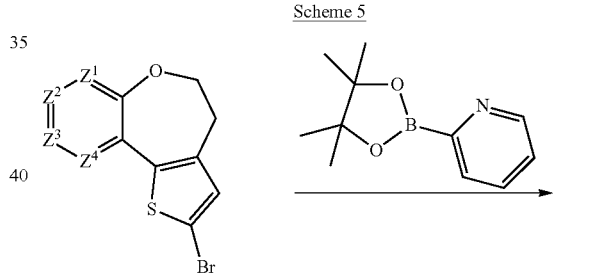

Scheme 4 shows a general method of preparation of benzoxepin thiophene amides 78. Cyclization of 3-(2-(2-halophenoxy)ethyl)thiophene intermediate 75 (X=Br, I, Cl) under palladium catalysis (see Example 8) gives 4,5-dihydrobenzo[b]thieno[2,3-d]oxepine intermediates 74. Bromination of the 2-position gives 2-bromo-4,5-dihydrobenzo[b]thieno[2,3-d]oxepine intermediates 76 which can be reacted with aryl isocyanate (Ar—NCO) or aryl isoisothiocyanate (Ar—NCS) reagents to give N-phenyl-4,5-dihydrobenzo[b]thieno[2,3-d]oxepine-2-carboxamide intermediates 77 (Y=O, S). The N—H group of 77 can be selectively alkylated to give 78.

Scheme 3 shows a general method of preparation of benzoxepin thiazoles 73. Bromination of keto benzoxepin (3,4-dihydrobenzo[b]oxepin-5(2H)-one) 66 forms the 2-bromo keto benzoxepin intermediates 72. Cyclization with thioamides form 73 (Rueeger et al (2004) Bioorganic & Med. Chem. Letters 14:2451-2457; US 2005/0277630; WO 2001/064675; U.S. Pat. No. 6,222,040; U.S. Pat. No. 6,225,330; U.S. Pat. No. 5,314,889).

Scheme 5

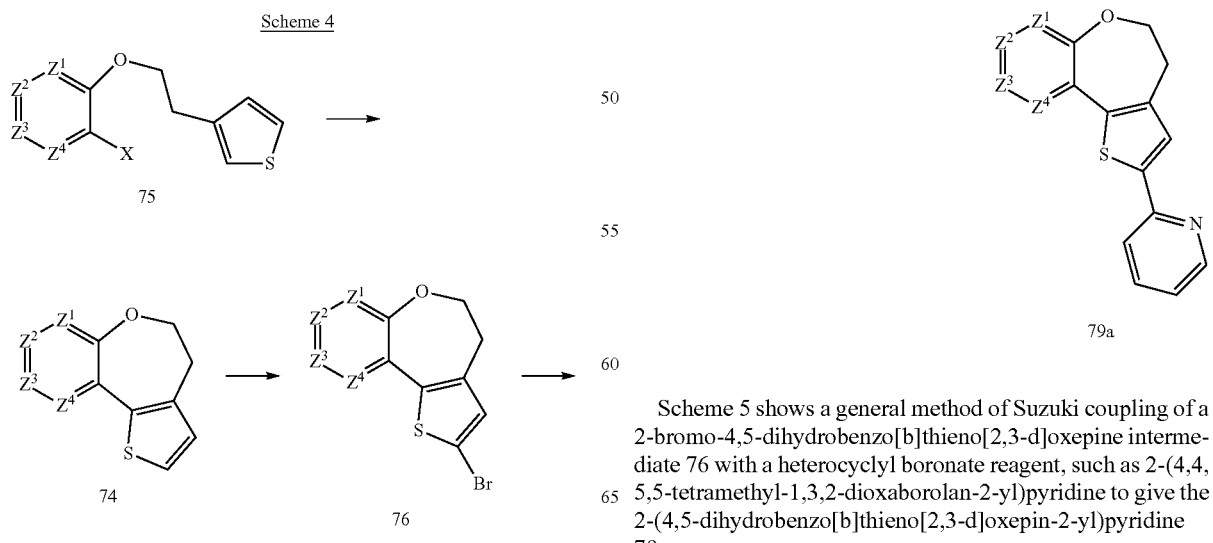

Scheme 5 shows a general method of Suzuki coupling of a 2-bromo-4,5-dihydrobenzo[b]thieno[2,3-d]oxepine intermediate 76 with a heterocyclyl boronate reagent, such as 2-(4,4,5,5-tetramethyl-1,3,2-dioxaborolan-2-yl)pyridine to give the 2-(4,5-dihydrobenzo[b]thieno[2,3-d]oxepin-2-yl)pyridine 79a.

Scheme 6

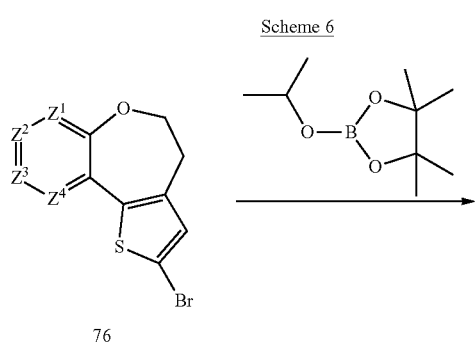

76

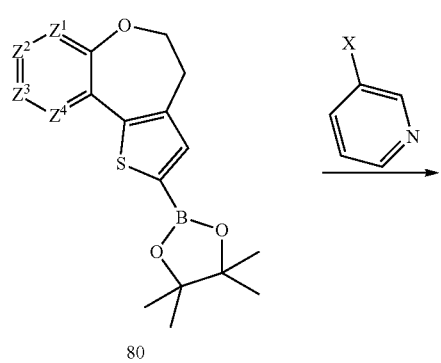

80

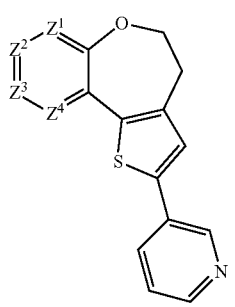

79b

Scheme 6 shows a general method forming a thiophenyl benzoxepin boronate compound 80 by reaction of 2-bromo-4,5-dihydrobenzo[b]thieno[2,3-d]oxepine intermediate 76 with a heterocyclyl boronate reagent, such as 2-isopropoxy-4,4,5,5-tetramethyl-1,3,2-dioxaborolane. Boronate 80 undergoes Suzuki coupling with a heterocyclyl halide reagent, such as 3-iodopyridine to give 3-(4,5-dihydrobenzo[b]thieno[2,3-d]oxepin-2-yl)pyridine 79b.

Scheme 7

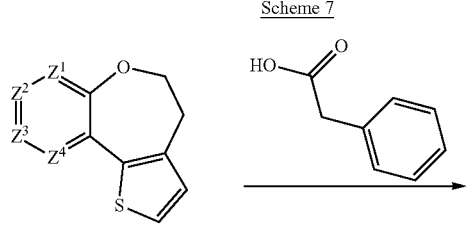

74

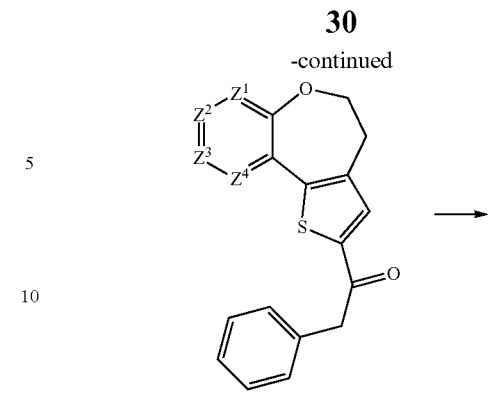

81

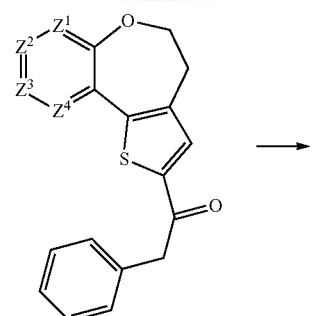

82     83

Scheme 7 shows a general method for substitution at the 2-position of 4,5-dihydrobenzo[b]thieno[2,3-d]oxepine intermediates 74 by acylation with a carboxylic acid such as 2-phenylacetic acid to give 1-(4,5-dihydrobenzo[b]thieno[2,3-d]oxepin-2-yl)-2-phenylethanone intermediate 81. Bromination gives 2-bromo-1-(4,5-dihydrobenzo[b]thieno[2,3-d]oxepin-2-yl)-2-phenylethanone intermediate 82. Cyclization with a thioamide compound gives 4-(4,5-dihydrobenzo[b]thieno[2,3-d]oxepin-2-yl)-5-phenylthiazole 83.

Scheme 8

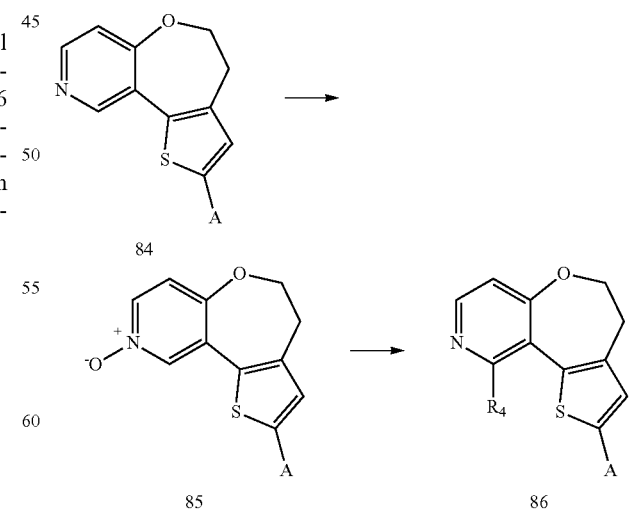

84

85    86

Scheme 8 shows a general method for regiospecific alkylation of 4,5-dihydropyrido[4,3-b]thieno[2,3-d]oxepin-2-yl intermediates 84 oxidation to form the N-oxide 85, and alkylation to give 10-substituted 4,5-dihydropyrido[4,3-b]thieno[2,3-d]oxepin-2-yl 86.

Preparation of Formula II Compounds

In certain embodiments, compounds of Formula II may be readily prepared using well-known procedures to prepare benzopyran and benzoxepin compounds (Sekhar et al (1989) Sulfur Letters 9(6):271-277; Navarro et al (2001) Heterocycles 55(12):2369-2386; Majumdar et al (2004) Monatshefte fur Chemie 135(8):1001-1007; Potts et al (1986) Journal of the Chemical Society, Chemical Communications 7:561-3) and other heterocycles, which are described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990).

For illustrative purposes, Schemes 1bp-5bp show general methods which may be applied for preparation of benzopyran Formula I compounds, as well as key intermediates. The General Procedures and Examples sections contain more detailed description of individual reaction steps. Those skilled in the art will appreciate that other synthetic routes may be used to synthesize the inventive compounds. Although certain starting materials and routes are depicted in the Schemes, General Procedures and Examples, other similar starting materials and routes can be substituted to provide a variety of derivatives and/or reaction conditions. In addition, many of the compounds prepared by the methods described below can be further modified in light of this disclosure using conventional chemistry well known to those skilled in the art.

In preparing compounds of Formulas II, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, Third Ed., 1999.

Scheme 1bp

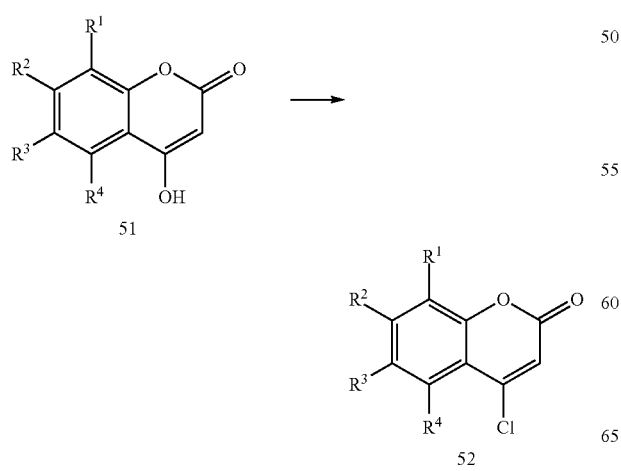

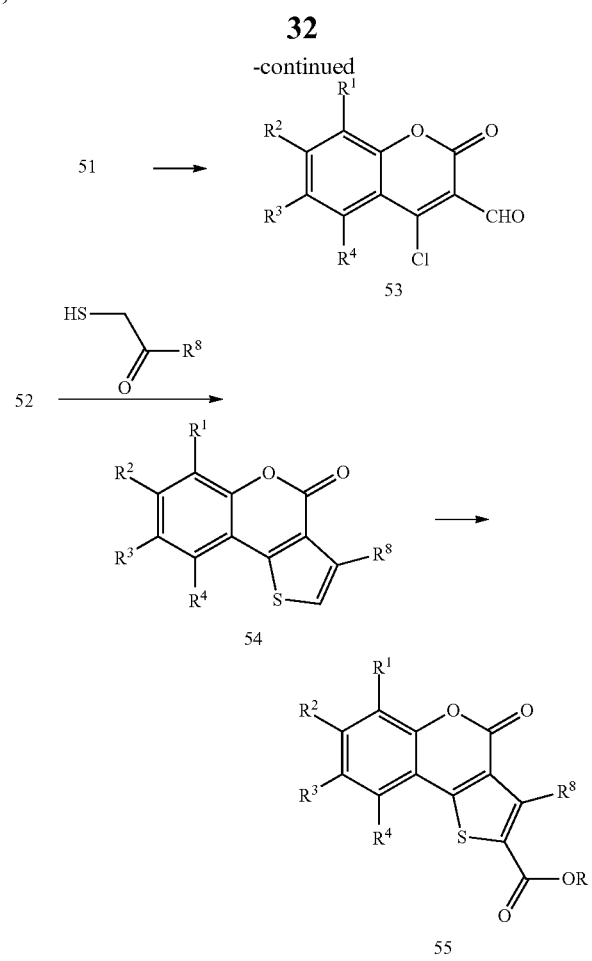

Scheme 1bp shows a general method for preparation of 4-chloro-2H-chromen-2-one 52bp and 4-chloro-2-oxo-2H-chromene-3-carbaldehyde 53bp intermediates from 4-hydroxy-2H-chromen-2-one compounds 51bp (Navarro et al (2001) Heterocycles 55(12):2369-2386). Intermediate 52bp can be cyclized with mercapto acetyl compounds to give 3-substituted 4H-thieno[3,2-c]chromen-4-one intermediates 54bp. Deprotonation and acylation of the 2-position of the thiophene ring of 54bp gives 2-esterified 4H-thieno[3,2-c]chromen-4-one intermediates 55bp.

Scheme 2bp

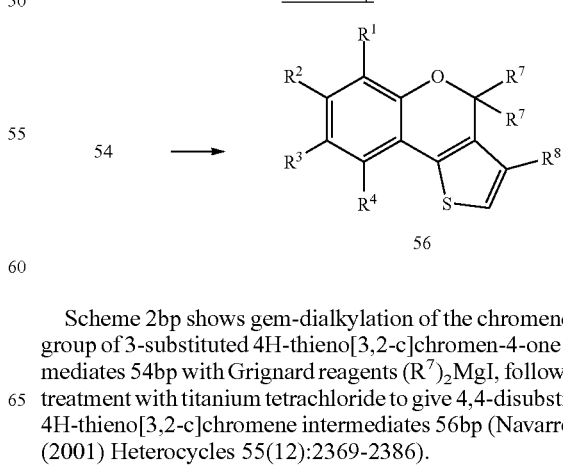

Scheme 2bp shows gem-dialkylation of the chromene acyl group of 3-substituted 4H-thieno[3,2-c]chromen-4-one intermediates 54bp with Grignard reagents $(R^7)_2MgI$, followed by treatment with titanium tetrachloride to give 4,4-disubstituted 4H-thieno[3,2-c]chromene intermediates 56bp (Navarro et al (2001) Heterocycles 55(12):2369-2386).

Scheme 3bp

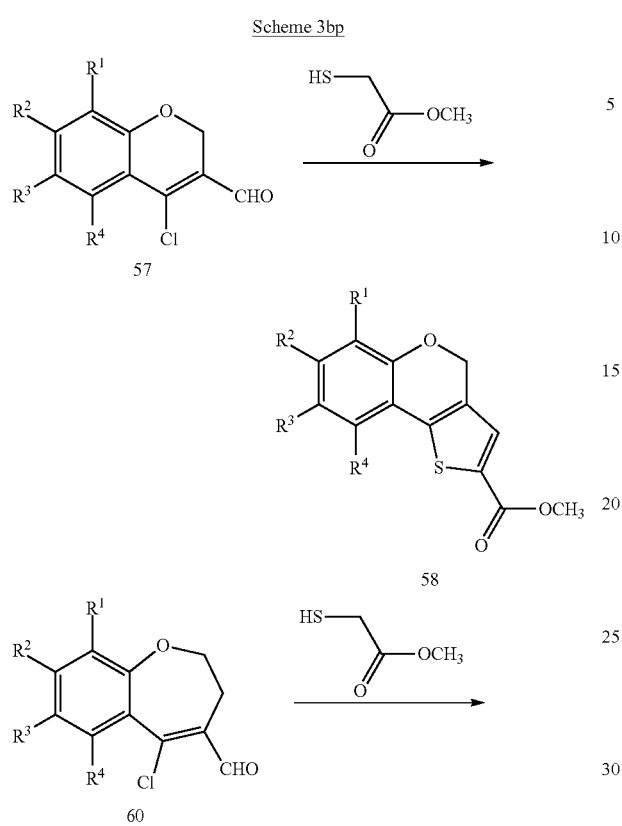

Scheme 3 shows a general method for preparation of methyl 4H-thieno[3,2-c]chromene-2-carboxylate 58bp and methyl 4,5-dihydrobenzo[b]thieno[2,3-d]oxepine-2-carboxylate 59bp intermediates from 4-chloro-2H-chromene-3-carbaldehyde 57bp and (Z)-5-chloro-2,3-dihydrobenzo[b]oxepine-4-carbaldehyde 60bp, respectively, by cyclization with methyl mercaptoacetate in acetonitrile and potassium carbonate (Sekhar et al (1989) Sulfur Letters 9(6):271-277).

Scheme 4bp

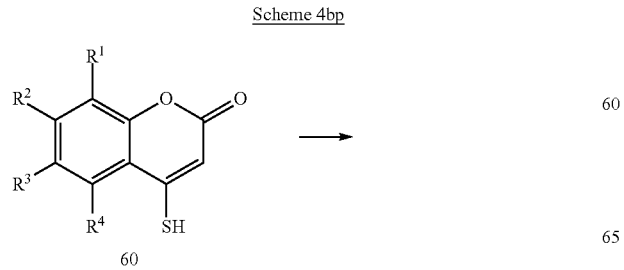

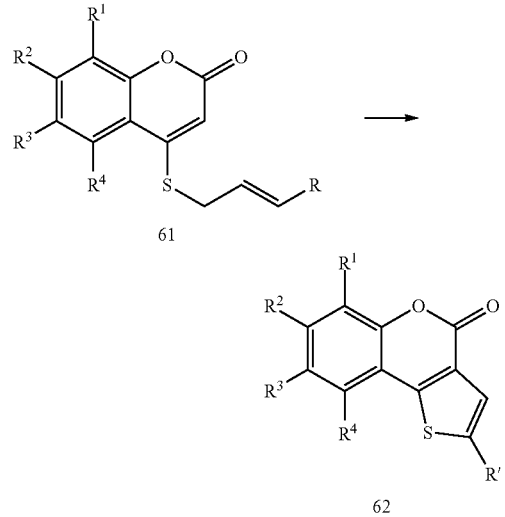

Scheme 4 shows a general method for preparation of 2-substituted 4H-thieno[3,2-c]chromen-4-one intermediates 62bp from allylation of 4-mercapto-2H-chromen-2-one intermediates 60bp with allylic halides to give 4-(but-2-enylthio)-2H-chromen-2-one intermediates 61bp and thermal thio-Claisen rearrangement (Majumdar et al (2004) Monatshefte fur Chemie 135(8):1001-1007).

Scheme 5bp

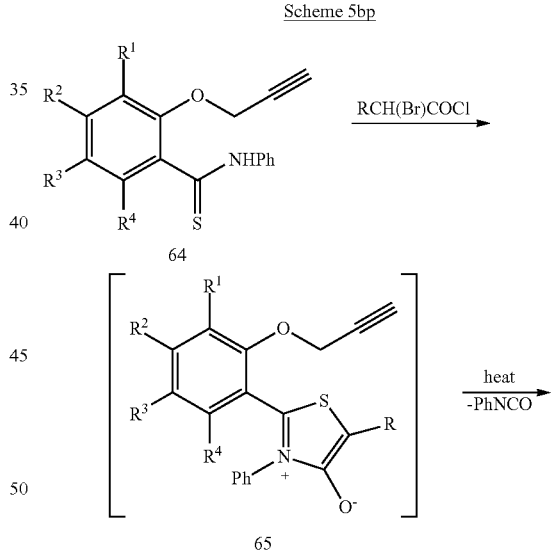

Scheme 5bp shows a general method for preparation of 2-substituted, 4H-thieno[3,2-c]chromene intermediates 63bp by reaction of N-phenyl-2-(prop-2-ynyloxy)benzothioamide compounds 64bp with an alpha-bromo acid chloride (R=alkyl or aryl) to presumably generate the thiazolium intermediate 65bp which undergoes loss of phenylisocyanate and 1,3-dipolar cycloaddition with (Potts et al (1986) Journal of the Chemical Society, Chemical Communications 7:561-3; Potts et al (1989) J. Org. Chem. 54:1077-1088).

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Biological Evaluation

Determination of the PI3 kinase activity of a Formula I or Formula II compound is possible by a number of direct and indirect detection methods. Certain exemplary compounds described herein were assayed for their p110α (alpha), and other isoform, PI3K binding activity (Example 275) and in vitro activity against tumor cells (Example 276). The range of PI3K binding activities was less than 1 nM (nanomolar) to about 10 μM (micromolar). Certain exemplary compounds of the invention had PI3K binding activity $IC_{50}$ values less than 10 nM. Certain compounds of the invention had tumor cell-based activity $IC_{50}$ values less than 100 nM.

The cytotoxic or cytostatic activity of Formula I and II exemplary compounds was measured by: establishing a proliferating mammalian tumor cell line in a cell culture medium, adding a Formula I compound, culturing the cells for a period from about 6 hours to about 5 days; and measuring cell viability (Example 276). Cell-based in vitro assays were used to measure viability, i.e. proliferation ($IC_{50}$), cytotoxicity ($EC_{50}$), and induction of apoptosis (caspase activation).

The in vitro potency of Formula I and II exemplary compounds was measured by the cell proliferation assay, CellTiter-Glo® Luminescent Cell Viability Assay, commercially available from Promega Corp., Madison, Wis. (Example 276). This homogeneous assay method is based on the recombinant expression of Coleoptera luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay an be used with various multiwell formats, e.g. 96 or 384 well format. Data can be recorded by luminometer or CCD camera imaging device. The luminescence output is presented as relative light units (RLU), measured over time.

The anti-proliferative effects of Formula I and II exemplary compounds were measured by the CellTiter-Glo® Assay (Example 276) against several tumor cell lines, including PC3, Detroit 562, and MDAMB361.1. $EC_{50}$ values were established for the tested compounds. The range of in vitro cell potency activities was about 100 nM to about 10

Certain ADME properties were measured for certain exemplary compounds by assays including: Caco-2 Permeability (Example 277), Hepatocyte Clearance (Example 278), Cytochrome P450 Inhibition (Example 279), Cytochrome P450 Induction (Example 280), Plasma Protein Binding (Example 281), and hERG channel blockage (Example 282).

Figure 3:
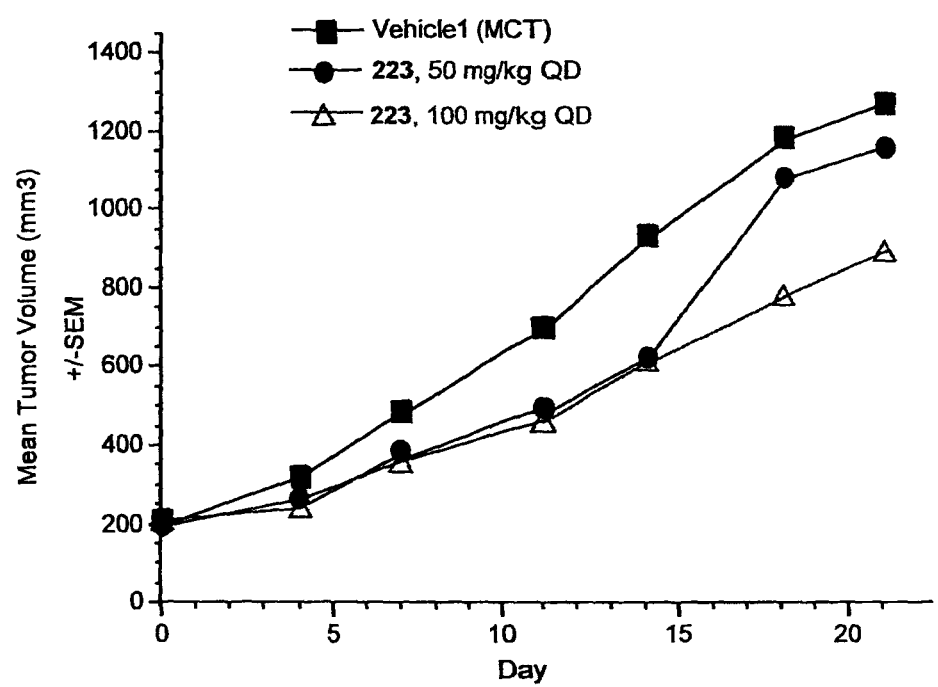
FIG. 3 shows the mean tumor volume change over time with Taconic nude mice with MDA-MB-361.1 breast tumor cell xenografts dosed daily for 21 days with: MCT Vehicle (0.5% methycellulose/0.2% Tween 80); 50 mg/kg Compound 223; and 100 mg/kg Compound 223.
Figure 4:
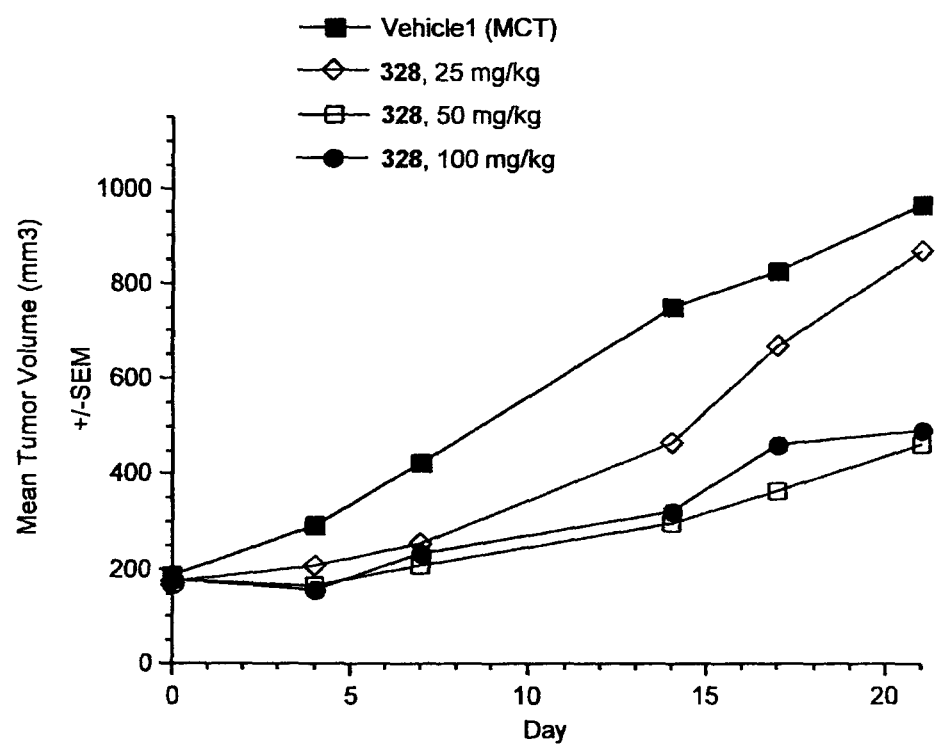
FIG. 4 shows the mean tumor volume change over time with Taconic nude mice with MDA-MB-361.1 breast tumor cell xenografts dosed daily for 21 days with: MCT Vehicle (0.5% methycellulose/0.2% Tween 80); 25 mg/kg Compound 328; 50 mg/kg Compound 328; and 100 mg/kg Compound 328.
Figure 5:
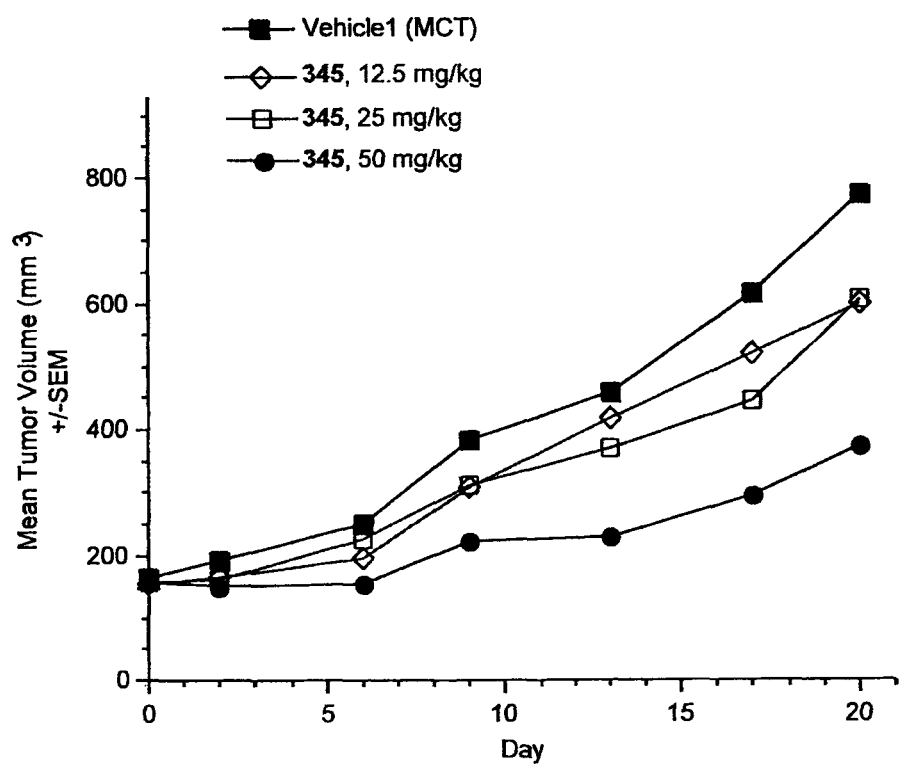
FIG. 5 shows the mean tumor volume change over time with Taconic nude mice with MDA-MB-361.1 breast tumor cell xenografts dosed daily for 21 days with: MCT Vehicle (0.5% methycellulose/0.2% Tween 80); 12.5 mg/kg Compound 345; 25 mg/kg Compound 345; and 50 mg/kg Compound 345.

Certain exemplary compounds were tested for efficacy by a dose escalation studies by administration in tumor xenograft Taconic nude mouse models (Example 283). The breast cancer cell line MDA-MB-361.1 mouse model was administered Compound 223 along with Vehicle (MCT, negative control). The tumor growth delay was measured when dosed orally daily for 21 days at 50 and 100 mg/kg (FIG. 3). Body weight change over the course of treatment was measured as an indicator of safety. The body weights of the group administered Compound 223 at 50 and 100 mg/kg did not significantly differ from the group administered Vehicle. Treatment of the MDA-MB-361.1 mouse model with Compound 328 caused tumor growth inhibition when dosed orally daily for 21 days at 25, 50 and 100 mg/kg (FIG. 4). At least one of the 10 mice treated at 25 mg/kg showed a partial response. The body weights of the group administered Compound 328 at 50 and 100 mg/kg did not significantly differ from the group administered Vehicle. Treatment of the MDA-MB-361.1 mouse model with Compound 345 caused tumor growth inhibition when dosed orally daily for 21 days at 12.5, 25 and 50 mg/kg (FIG. 5). The body weights of the group administered Compound 345 at 12.5, 25, and 50 mg/kg did not significantly differ from the group administered Vehicle. In each study, Compounds 223, 328, and 345 suppressed pAkt (phospho-Akt), a potential biomarker of PI3K signal transduction disruption (Example 284).

Exemplary Formula I compounds No. 101-533 in Table 1, were made, characterized, and tested for PI3K activity according to the methods of this invention, and have the following structures and corresponding names (ChemDraw Ultra, Version 9.0.1, CambridgeSoft Corp., Cambridge Mass.).

TABLE 1

| No. | Structure | Name |
|---|---|---|
| 101 | 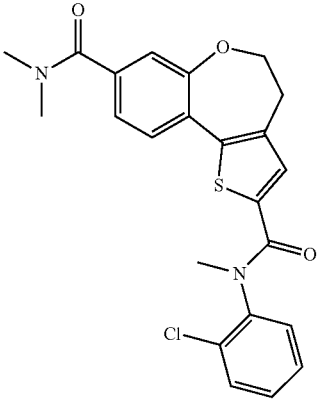 [SMILES: CN(C)C(=O)c1ccc2c(c1)OCCc1cc(C(=O)N(C)c3ccccc3Cl)sc1-2] | N2-(2-chlorophenyl)-N2,N8,N8-trimethyl-4,5-dihydrobenzo[b]thieno[2,3-d]oxepine-2,8-dicarboxamide |

TABLE 1-continued
| No. | Structure | Name |
|---|---|---|
| 102 | 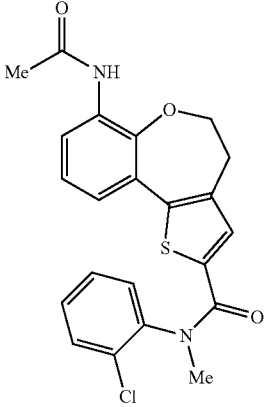 [SMILES: CC(=O)Nc1cccc2c1OCCc1cc(C(=O)N(C)c3ccccc3Cl)sc1-2] | 7-acetamido-N-(2-chlorophenyl)-N-methyl-4,5-dihydrobenzo[b]thieno[2,3-d]oxepine-2-carboxamide |
| 103 | 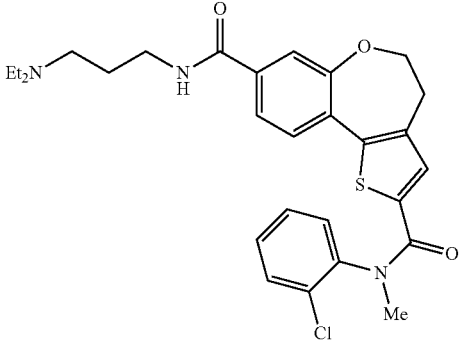 | N2-(2-chlorophenyl)-N8-(3-(diethylamino)propyl)-N2-methyl-4,5-dihydrobenzo[b]thieno[2,3-d]oxepine-2,8-dicarboxamide |
| 104 | 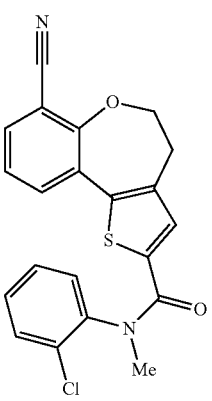 [SMILES: CN(C(=O)c1cc2c(s1)-c1cccc(C#N)c1OCC2)c1ccccc1Cl] | N-(2-chlorophenyl)-7-cyano-N-methyl-4,5-dihydrobenzo[b]thieno[2,3-d]oxepine-2-carboxamide |
| 105 | 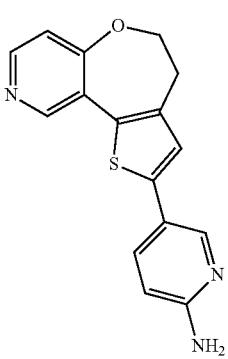 [SMILES: Nc1ccc(-c2cc3c(s2)-c2cnccc2OCC3)cn1] | 5-(4,5-dihydropyrido[4,3-b]thieno[2,3-d]oxepin-2-yl)pyridin-2-amine |

TABLE 1-continued

| No. | Structure | Name |
|---|---|---|
| 106 | 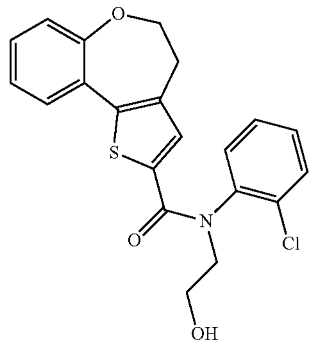 [SMILES: O=C(c1cc2c(s1)-c1ccccc1OCC2)N(CCO)c1ccccc1Cl] | N-(2-chlorophenyl)-N-(2-hydroxyethyl)-4,5-dihydrobenzo[b]thieno[2,3-d]oxepine-2-carboxamide |
| 107 | 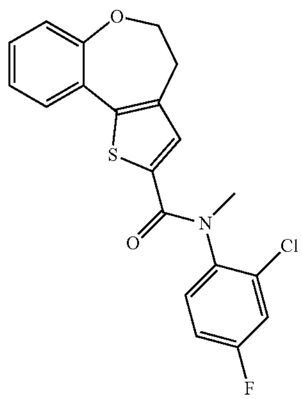 [SMILES: CN(C(=O)c1cc2c(s1)-c1ccccc1OCC2)c1ccc(F)cc1Cl] | N-(2-chloro-4-fluorophenyl)-N-methyl-4,5-dihydrobenzo[b]thieno[2,3-d]oxepine-2-carboxamide |
| 108 | 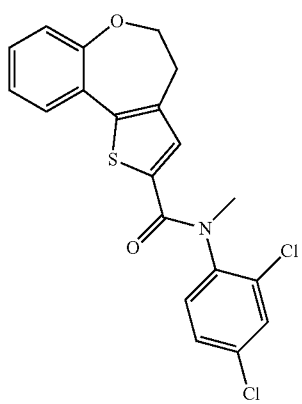 [SMILES: CN(C(=O)c1cc2c(s1)-c1ccccc1OCC2)c1ccc(Cl)cc1Cl] | N-(2,4-dichloropheny])-N-methyl-4,5-dihydrobenzo[b]thieno[2,3-d]oxepine-2-carboxamide |
| 109 | 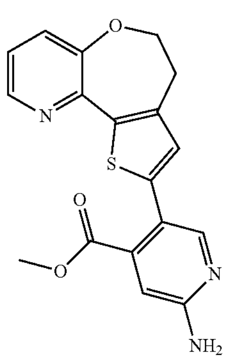 [SMILES: COC(=O)c1cc(N)ncc1-c1cc2c(s1)-c1ncccc1OCC2] | methyl 5-(6,7-dihydropyrido[3,2-b]thieno[2,3-d]oxepin-9-yl)2-aminoisonicotinate |

TABLE 1-continued

| No. | Structure | Name |
|-----|-----------|------|
| 110 | 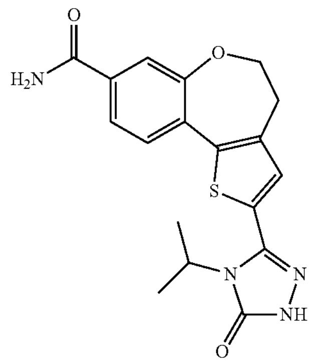 | 2-(4-isopropyl-5-oxo-4,5-dihydro-1H-1,2,4-triazol-3-yl)-4,5-dihydrobenzo[b]thieno[2,3-d]oxepine-8-carboxamide |
| 111 | 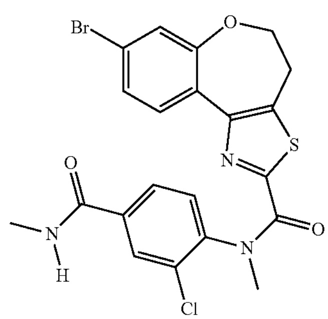 [SMILES: CNC(=O)c1ccc(N(C)C(=O)c2nc3c(s2)CCOc2cc(Br)ccc2-3)c(Cl)c1] | 8-bromo-4,5-dihydro-6-oxa-3-thia-1-aza-benzo[e]azulene-2-carboxylic acid(2-chloro-4-methylcarbamoyl-phenyl)-methyl-amide |
| 112 | 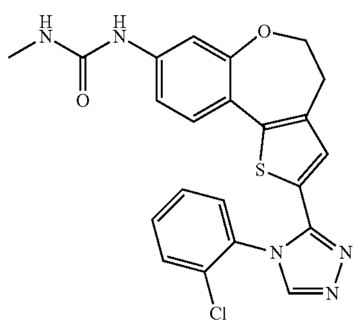 [SMILES: CNC(=O)Nc1ccc2c(c1)OCCc1cc(-c3nncn3-c3ccccc3Cl)sc1-2] | 1-(2-(4-(2-chlorophenyl)-4H-1,2,4-triazol-3-yl)-4,5-dihydrobenzo[b]thieno[2,3-d]oxepin-8-yl)-3-methylurea |
| 113 | 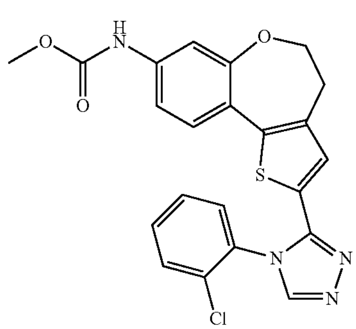 [SMILES: COC(=O)Nc1ccc2c(c1)OCCc1cc(-c3nncn3-c3ccccc3Cl)sc1-2] | methyl 2-(4-(2-chlorophenyl)-4H-1,2,4-triazol-3-yl)-4,5-dihydrobenzo[b]thieno[2,3-d]oxepin-8-ylcarbamate |

TABLE 1-continued

| No. | Structure | Name |
|-----|-----------|------|
| 114 | 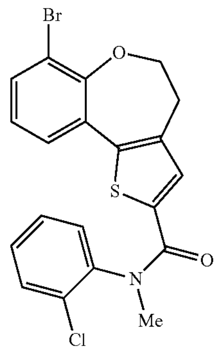 [SMILES: CN(C(=O)c1cc2c(s1)-c1cccc(Br)c1OCC2)c1ccccc1Cl] | 7-bromo-N-(2-chlorophenyl)-N-methyl-4,5-dihydrobenzo[b]thieno[2,3-d]oxepine-2-carboxamide |
| 115 | 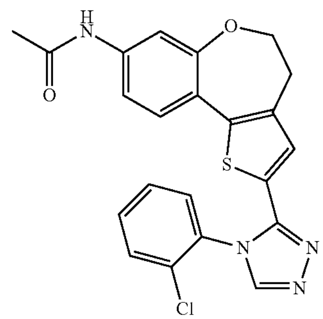 [SMILES: CC(=O)Nc1ccc2c(c1)OCCc1cc(-c3nncn3-c3ccccc3Cl)sc1-2] | N-(2-(4-(2-chlorophenyl)-4H-1,2,4-triazol-3-yl)-4,5-dihydrobenzo[b]thieno[2,3-d]oxepin-8-yl)acetamide |
| 116 | 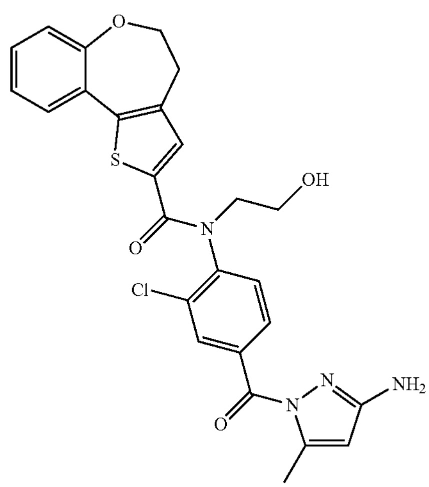 [SMILES: Cc1cc(N)nn1C(=O)c1ccc(N(CCO)C(=O)c2cc3c(s2)-c2ccccc2OCC3)c(Cl)c1] | N-(4-(3-amino-5-methyl-1H-pyrazole-1-carbonyl)-2-chlorophenyl)-N-(2-hydroxyethyl)-4,5-dihydrobenzo[b]thieno[2,3-d]oxepine-2-carboxamide |
| 117 | 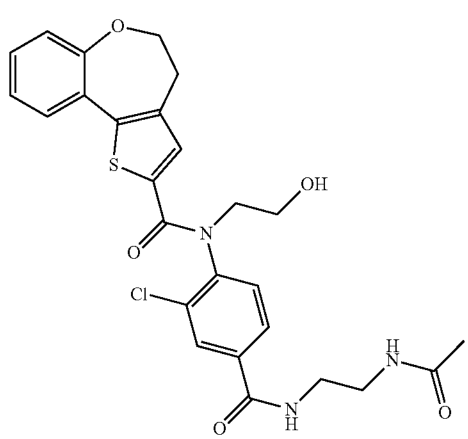 [SMILES: CC(=O)NCCNC(=O)c1ccc(N(CCO)C(=O)c2cc3c(s2)-c2ccccc2OCC3)c(Cl)c1] | N-(4-(2-acetamidoethylcarbamoyl)-2-chlorophenyl)-N-(2-hydroxyethyl)-4,5-dihydrobenzo[b]thieno[2,3-d]oxepine-2-carboxamide |

TABLE 1-continued

| No. | Structure | Name |
|---|---|---|
| 118 | 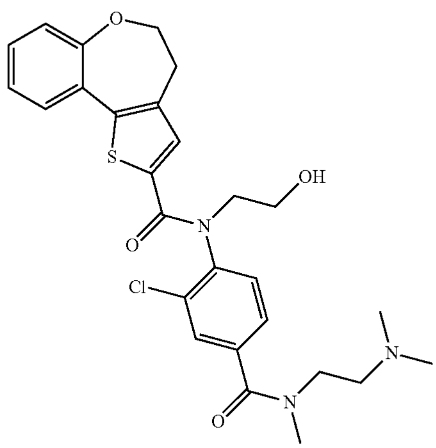 [SMILES: CN(C)CCN(C)C(=O)c1ccc(N(CCO)C(=O)c2cc3c(s2)-c2ccccc2OCC3)c(Cl)c1] | N-(2-chloro-4-((2-(dimethylamino)ethyl)(methyl)carbamoyl)phenyl)-N-(2-hydroxyethyl)-4,5-dihydrobenzo[b]thieno[2,3-d]oxepine-2-carboxamide |
| 119 | 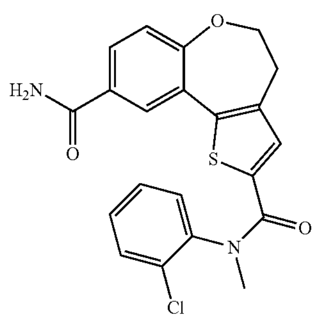 [SMILES: CN(C(=O)c1cc2c(s1)-c1cc(C(N)=O)ccc1OCC2)c1ccccc1Cl] | N2-(2-chlorophenyl)-N2-methyl-4,5-dihydrobenzo[b]thieno[2,3-d]oxepine-2,9-dicarboxamide |
| 120 | 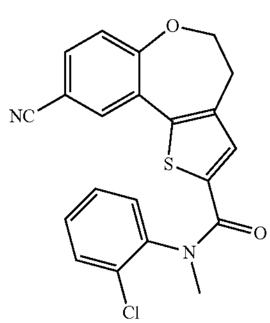 [SMILES: CN(C(=O)c1cc2c(s1)-c1cc(C#N)ccc1OCC2)c1ccccc1Cl] | N-(2-chlorophenyl)-9-cyano-N-methyl-4,5-dihydrobenzo[b]thieno[2,3-d]oxepine-2-carboxamide |
| 121 | 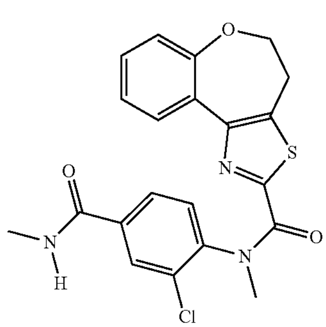 [SMILES: CNC(=O)c1ccc(N(C)C(=O)c2nc3c(s2)CCOc2ccccc2-3)c(Cl)c1] | 4,5-dihydro-6-oxa-3-thia-1-aza-benzo[e]azulene-2-carboxylic acid(2-chloro-4-methylcarbamoyl-phenyl)-methyl-amide |

TABLE 1-continued

| No. | Structure | Name |
|---|---|---|
| 122 | 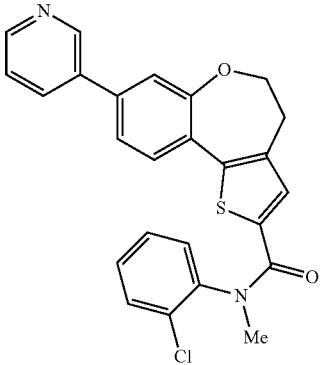 [SMILES: CN(C(=O)c1cc2c(s1)-c1ccc(-c3cccnc3)cc1OCC2)c1ccccc1Cl] | N-(2-chlorophenyl)-N-methyl-8-(pyridin-3-yl)-4,5-dihydrobenzo[b]thieno[2,3-d]oxepine-2-carboxamide |
| 123 | 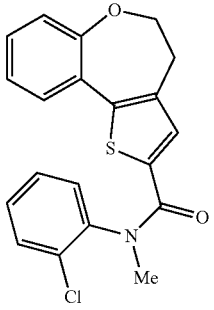 [SMILES: CN(C(=O)c1cc2c(s1)-c1ccccc1OCC2)c1ccccc1Cl] | N-(2-chlorophenyl)-N-methyl-4,5-dihydrobenzo[b]thieno[2,3-d]oxepine-2-carbothioamide |
| 124 | 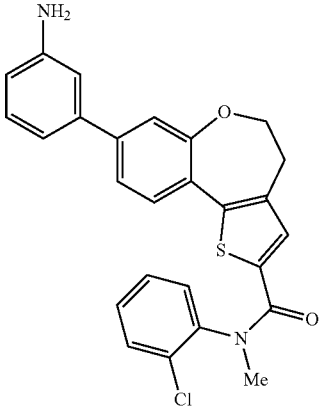 [SMILES: CN(C(=O)c1cc2c(s1)-c1ccc(-c3cccc(N)c3)cc1OCC2)c1ccccc1Cl] | 8-(3-aminophenyl)-N-(2-chlorophenyl)-N-methyl-4,5-dihydrobenzo[b]thieno[2,3-d]oxepine-2-carboxamide |
| 125 | 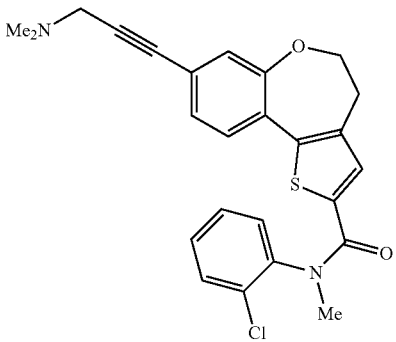 [SMILES: CN(C)CC#Cc1ccc2c(c1)OCCc1cc(C(=O)N(C)c3ccccc3Cl)sc1-2] | N-(2-chlorophenyl)-8-(3-(dimethylamino)prop-1-ynyl)-N-methyl-4,5-dihydrobenzo[b]thieno[2,3-d]oxepine-2-carboxamide |

TABLE 1-continued

| No. | Structure | Name |
|---|---|---|
| 126 | 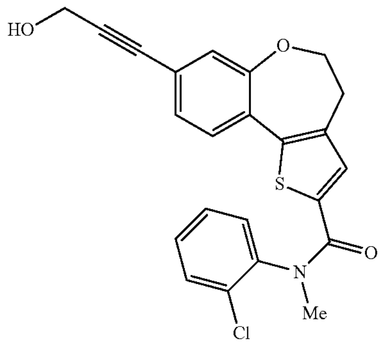 [SMILES: CN(C(=O)c1cc2c(s1)-c1ccc(C#CCO)cc1OCC2)c1ccccc1Cl] | N-(2-chlorophenyl)-8-(3-hydroxyprop-1-ynyl)-N-methyl-4,5-dihydrobenzo[b]thieno[2,3-d]oxepine-2-carboxamide |
| 127 | 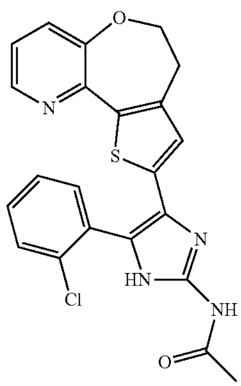 [SMILES: CC(=O)Nc1nc(-c2cc3c(s2)-c2ncccc2OCC3)c(-c2ccccc2Cl)[nH]1] | 4-(6,7-dihydropyrido[3,2-b]thieno[2,3-d]oxepin-9-yl)-(2-chlorophenyl)-2-acetamino-1H-imidazole |
| 128 | 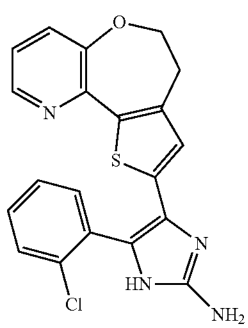 [SMILES: Nc1nc(-c2cc3c(s2)-c2ncccc2OCC3)c(-c2ccccc2Cl)[nH]1] | 4-(6,7-dihydropyrido[3,2-b]thieno[2,3-d]oxepin-9-yl)-(2-chlorophenyl)-2-amino-1H-imidazole |
| 129 | 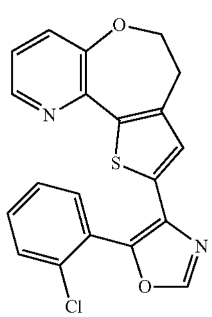 [SMILES: Clc1ccccc1-c1ocnc1-c1cc2c(s1)-c1ncccc1OCC2] | 4-(6,7-dihydropyrido[3,2-b]thieno[2,3-d]oxepin-9-yl)-(5-(2-chlorophenyl))-oxazole |

TABLE 1-continued

| No. | Structure | Name |
|---|---|---|
| 130 | 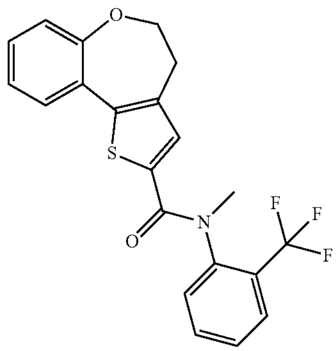 [SMILES: CN(C(=O)c1cc2c(s1)-c1ccccc1OCC2)c1ccccc1C(F)(F)F] | N-methyl-N-(2-(trifluoromethyl)phenyl)-4,5-dihydrobenzo[b]thieno[2,3-d]oxepine-2-carboxamide |
| 131 | 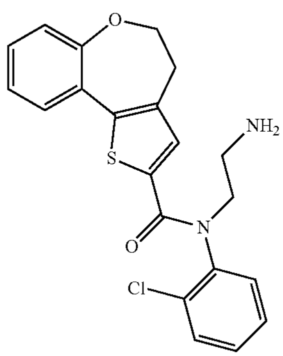 [SMILES: NCCN(C(=O)c1cc2c(s1)-c1ccccc1OCC2)c1ccccc1Cl] | N-(2-aminoethyl)-N-(2-chlorophenyl)-4,5-dihydrobenzo[b]thieno[2,3-d]oxepine-2-carboxamide |
| 132 | 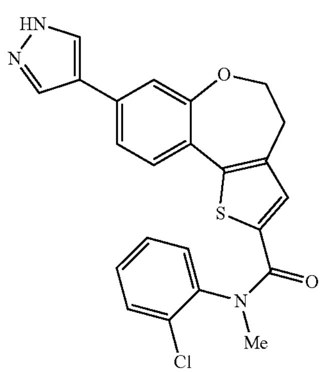 [SMILES: CN(C(=O)c1cc2c(s1)-c1ccc(-c3cn[nH]c3)cc1OCC2)c1ccccc1Cl] | N-(2-chlorophenyl)-N-methyl-8-(1H-pyrazol-4-yl)-4,5-dihydrobenzo[b]thieno[2,3-d]oxepine-2 carboxamide |
| 133 | 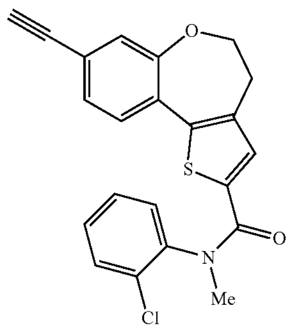 [SMILES: C#Cc1ccc2c(c1)OCCc1cc(C(=O)N(C)c3ccccc3Cl)sc1-2] | N-(2-chlorophenyl)-8-ethynyl-N-methyl-4,5-dihydrobenzo[b]thieno[2,3-d]oxepine-2-carboxamide |

TABLE 1-continued

| No. | Structure | Name |
|---|---|---|
| 134 | 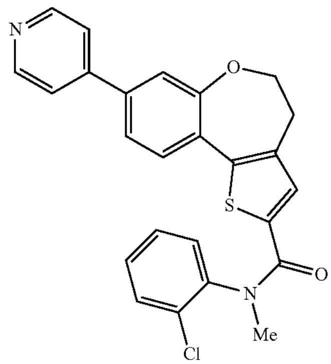 [SMILES: CN(C(=O)c1cc2c(s1)-c1ccc(-c3ccncc3)cc1OCC2)c1ccccc1Cl] | N-(2-chlorophenyl)-N-methyl-8-(pyridin-4-yl)-4,5-dihydrobenzo[b]thieno[2,3-d]oxepine-2-carboxamide |
| 135 | 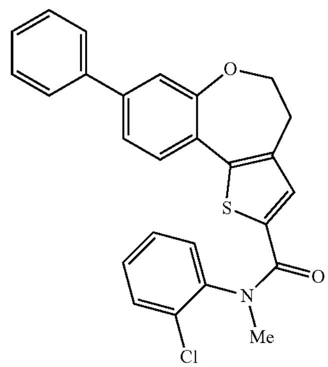 [SMILES: CN(C(=O)c1cc2c(s1)-c1ccc(-c3ccccc3)cc1OCC2)c1ccccc1Cl] | N-(2-chlorophenyl)-N-methyl-8-phenyl-4,5-dihydrobenzo[b]thieno[2,3-d]oxepine-2-carboxamide |
| 136 | 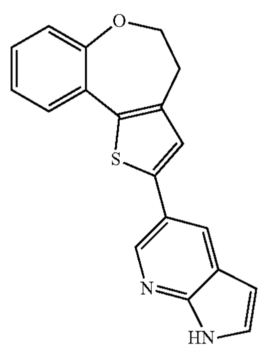 [SMILES: c1ccc2c(c1)OCCc1cc(-c3cnc4[nH]ccc4c3)sc1-2] | 5-(4,5-dihydrobenzo[b]thieno[2,3-d]oxepin-2-yl)-1H-pyrrolo[2,3-b]pyridine |
| 137 | 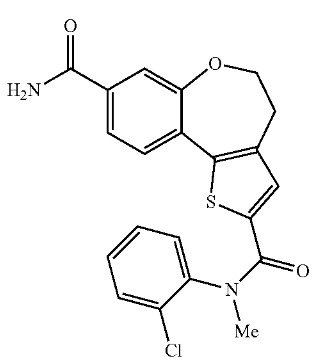 [SMILES: CN(C(=O)c1cc2c(s1)-c1ccc(C(N)=O)cc1OCC2)c1ccccc1Cl] | N2-(2-chlorophenyl)-N2-methyl-4,5-dihydrobenzo[b]thieno[2,3-d]oxepine-2,8-dicarboxamide |

TABLE 1-continued

| No. | Structure | Name |
| --- | --- | --- |
| 138 | 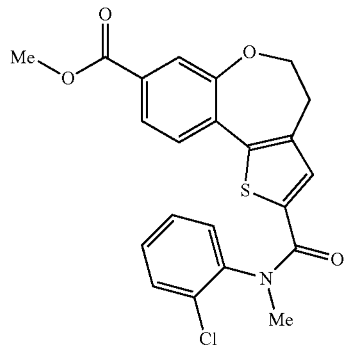 [SMILES: COC(=O)c1ccc2c(c1)OCCc1cc(C(=O)N(C)c3ccccc3Cl)sc1-2] | methyl 2-((2-chlorophenyl)(methyl)carbamoyl)-4,5-dihydrobenzo[b]thieno[2,3-d]oxepine-8-carboxylate |
| 139 | 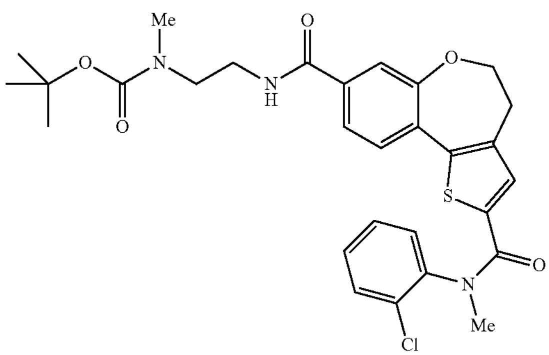 [SMILES: CN(CCNC(=O)c1ccc2c(c1)OCCc1cc(C(=O)N(C)c3ccccc3Cl)sc1-2)C(=O)OC(C)(C)C] | tert-butyl 2-(2-((2-chlorophenyl)(methyl)carbamoyl)-4,5-dihydrobenzo[b]thieno[2,3-d]oxepine-8-carboxamido)ethyl(methyl)carbamate |
| 140 | 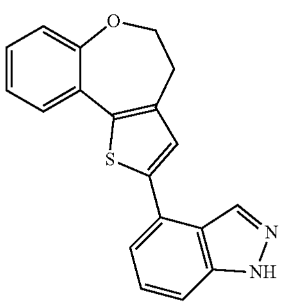 [SMILES: c1ccc2c(c1)OCCc1cc(-c3cccc4[nH]ncc34)sc1-2] | 4-(4,5-dihydrobenzo[b]thieno[2,3-d]oxepin-2-yl)-1H-indazole |
| 141 | 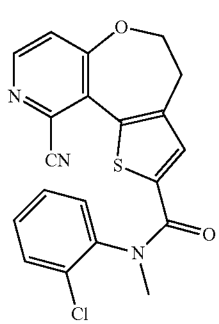 [SMILES: CN(C(=O)c1cc2c(s1)-c1c(ccnc1C#N)OCC2)c1ccccc1Cl] | N-(2-chlorophenyl)-N-methyl-(10-cyano-4,5-dihydropyrido-[4,3-b]thieno[2,3-d]oxepin-2)-carboxamide |

TABLE 1-continued

| No. | Structure | Name |
|---|---|---|
| 142 | 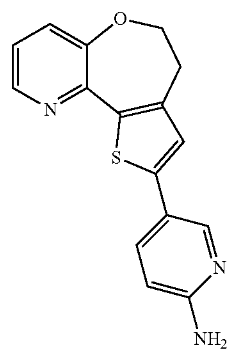 [SMILES: Nc1ccc(-c2cc3c(s2)-c2ncccc2OCC3)cn1] | 5-(6,7-dihydropyrido[3,2-b]thieno[2,3-d]oxepin-9-yl)pyridin-2-amine |
| 143 | 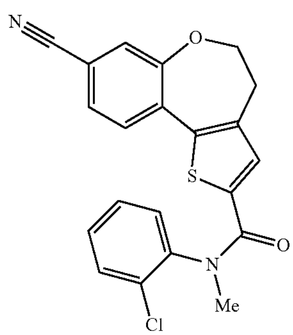 [SMILES: CN(C(=O)c1cc2c(s1)-c1ccc(C#N)cc1OCC2)c1ccccc1Cl] | N-(2-chlorophenyl)-8-cyano-N-methyl-4,5-dihydrobenzo[b]thieno[2,3-d]oxepine-2-carboxamide |
| 144 | 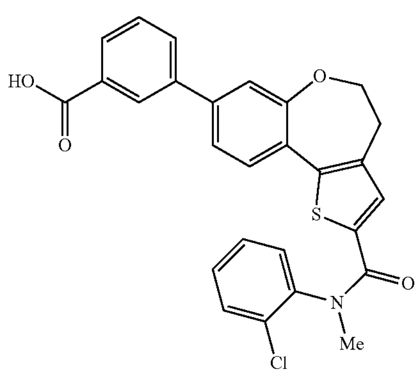 [SMILES: CN(C(=O)c1cc2c(s1)-c1ccc(-c3cccc(C(=O)O)c3)cc1OCC2)c1ccccc1Cl] | 3-(2-((2-chlorophenyl)(methyl)carbamoyl)-4,5-dihydrobenzo[b]thieno[2,3-d]oxepin-8-yl)benzoic acid |
| 145 | 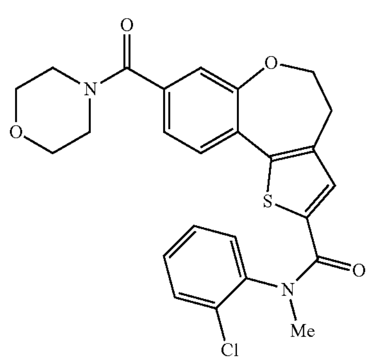 [SMILES: CN(C(=O)c1cc2c(s1)-c1ccc(C(=O)N3CCOCC3)cc1OCC2)c1ccccc1Cl] | N-(2-chlorophenyl)-N-methyl-8-(morpholine-4-carbonyl)-4,5-dihydrobenzo[b]thieno[2,3-d]oxepine-2-carboxamide |

TABLE 1-continued

| No. | Structure | Name |
|---|---|---|
| 146 | 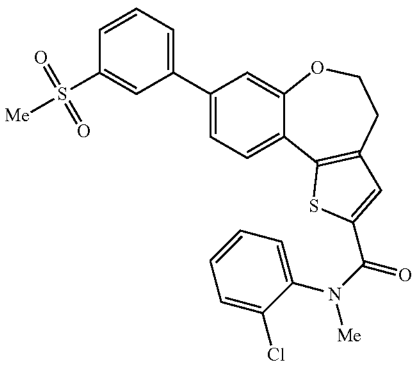 [SMILES: CN(C(=O)c1cc2c(s1)-c1ccc(-c3cccc(S(C)(=O)=O)c3)cc1OCC2)c1ccccc1Cl] | N-(2-chlorophenyl)-N-methyl-8-(3-(methylsulfonyl)phenyl)-4,5-dihydrobenzo[b]thieno[2,3-d]oxepine-2-carboxamide |
| 147 | 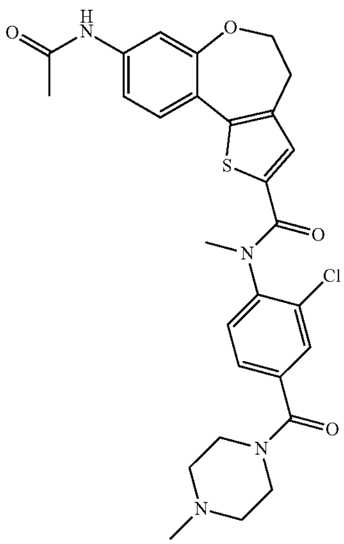 [SMILES: CC(=O)Nc1ccc2c(c1)OCCc1cc(C(=O)N(C)c3ccc(C(=O)N4CCN(C)CC4)cc3Cl)sc1-2] | 8-acetamido-N-(2-chloro-4-(4-methylpiperazine-1-carbonyl)phenyl)-N-methyl-4,5-dihydrobenzo[b]thieno[2,3-d]oxepine-2-carboxamide |
| 148 | 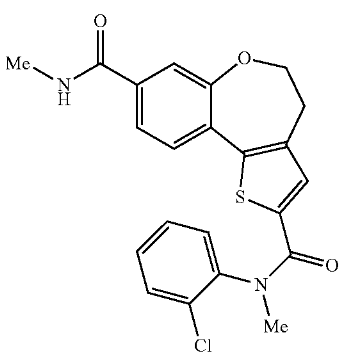 [SMILES: CNC(=O)c1ccc2c(c1)OCCc1cc(C(=O)N(C)c3ccccc3Cl)sc1-2] | N2-(2-chlorophenyl)-N2,N8-dimethyl-4,5-dihydrobenzo[b]thieno[2,3-d]oxepine-2,8-dicarboxamide |
| 149 | 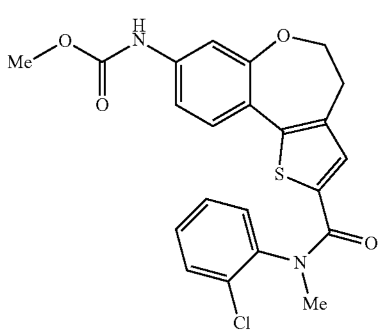 [SMILES: COC(=O)Nc1ccc2c(c1)OCCc1cc(C(=O)N(C)c3ccccc3Cl)sc1-2] | methyl 2-((2-chlorophenyl)(methyl)carbamoyl)-4,5-dihydrobenzo[b]thieno[2,3-d]oxepin-8-ylcarbamate |

TABLE 1-continued

| No. | Structure | Name |
|---|---|---|
| 150 | 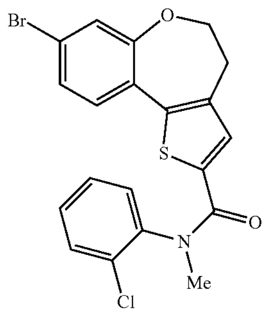 [SMILES: CN(C(=O)c1cc2c(s1)-c1ccc(Br)cc1OCC2)c1ccccc1Cl] | 8-bromo-N-(2-chlorophenyl)-N-methyl-4,5-dihydrobenzo[b]thieno[2,3-d]oxepine-2-carboxamide |
| 151 | 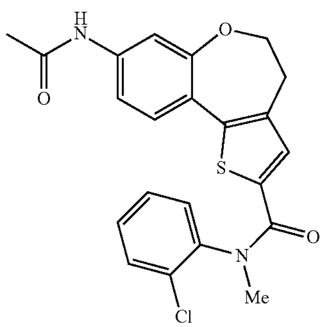 [SMILES: CC(=O)Nc1ccc2c(c1)OCCc1cc(C(=O)N(C)c3ccccc3Cl)sc1-2] | 8-acetamido-N-(2-chlorophenyl)-N-methyl-4,5-dihydrobenzo[b]thieno[2,3-d]oxepine-2-carboxamide |
| 152 | 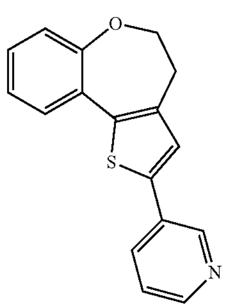 [SMILES: c1cncc(-c2cc3c(s2)-c2ccccc2OCC3)c1] | 3-(4,5-dihydrobenzo[b]thieno[2,3-d]oxepin-2-yl)pyridine |
| 153 | 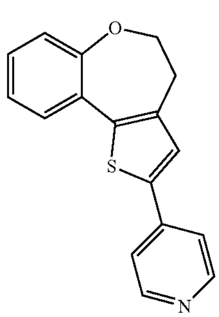 [SMILES: c1ccc2c(c1)OCCc1cc(-c3ccncc3)sc1-2] | 4-(4,5-dihydrobenzo[b]thieno[2,3-d]oxepin-2-yl)pyridine |

TABLE 1-continued

| No. | Structure | Name |
|---|---|---|
| 154 | 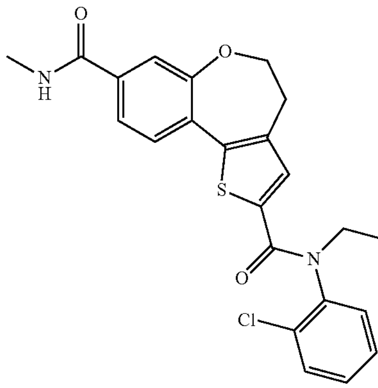 | N2-(2-chlorophenyl)-N2-(2-hydroxyethyl)-N8-methyl-4,5-dihydrobenzo[b]thieno[2,3-d]oxepine-2,8-dicarboxamide |
| 155 | 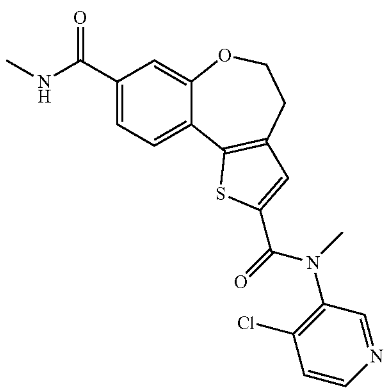 [SMILES: CNC(=O)c1ccc2c(c1)OCCc1cc(C(=O)N(C)c3cnccc3Cl)sc1-2] | N2-(4-chloropyridin-3-yl)-N2,N8-dimethyl-4,5-dihydrobenzo[b]thieno[2,3-d]oxepine-2,8-dicarboxamide |
| 156 | 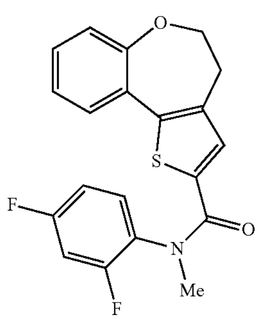 [SMILES: CN(C(=O)c1cc2c(s1)-c1ccccc1OCC2)c1ccc(F)cc1F] | N-(2,4-difluorophenyl)-N-methyl-4,5-dihydrobenzo[b]thieno[2,3-d]oxepine-2-carboxamide |
| 157 | 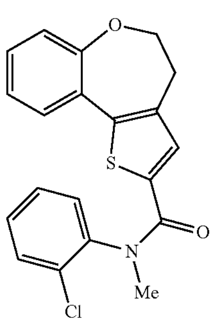 [SMILES: CN(C(=O)c1cc2c(s1)-c1ccccc1OCC2)c1ccccc1Cl] | N-(2-chlorophenyl)-N-methyl-4,5-dihydrobenzo[b]thieno[2,3-d]oxepine-2-carboxamide |

TABLE 1-continued

| No. | Structure | Name |
|---|---|---|
| 158 | 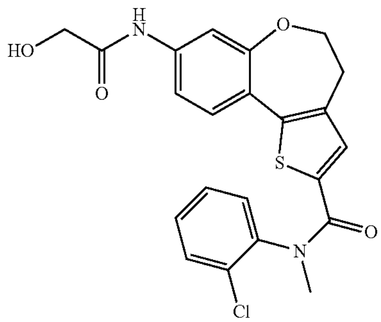 [SMILES: CN(C(=O)c1cc2c(s1)-c1ccc(NC(=O)CO)cc1OCC2)c1ccccc1Cl] | N-(2-chlorophenyl)-8-(2-hydroxyacetamido)-N-methyl-4,5-dihydrobenzo[b]thieno[2,3-d]oxepine-2-carboxamide |
| 159 | 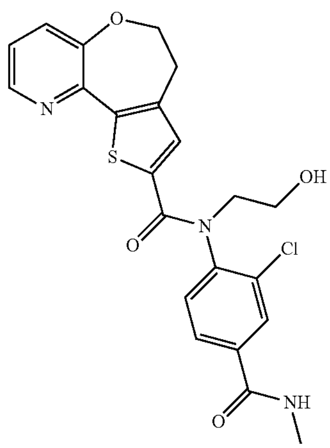 [SMILES: CNC(=O)c1ccc(N(CCO)C(=O)c2cc3c(s2)-c2ncccc2OCC3)c(Cl)c1] | N-(2-chloro-4-(methylcarbamoyl)phenyl)-N-(2-hydroxyethyl)-10-aza-4,5-dihydrobenzo[b]thieno[2,3-d]oxepine-2-carboxamide |
| 160 | 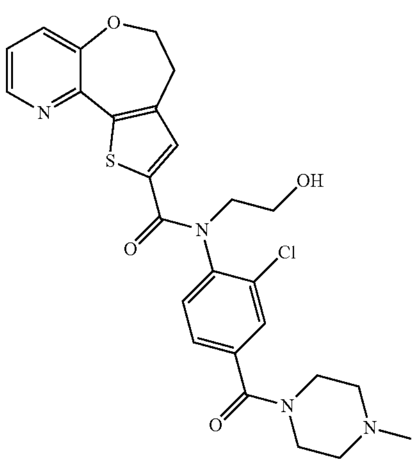 [SMILES: CN1CCN(C(=O)c2ccc(N(CCO)C(=O)c3cc4c(s3)-c3ncccc3OCC4)c(Cl)c2)CC1] | N-(2-chloro-4-(4-methylpiperazine-1-carbonyl)phenyl)-N-(2-hydroxyethyl)-10-aza-4,5-dihydrobenzo[b]thieno[2,3-d]oxepine-2-carboxamide |
| 161 | 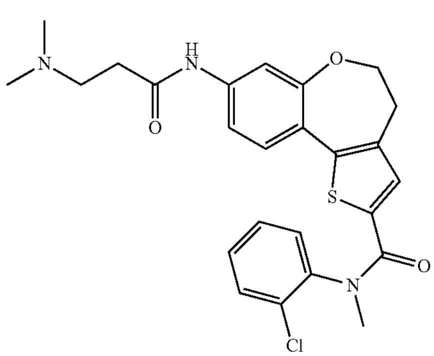 [SMILES: CN(C)CCC(=O)Nc1ccc2c(c1)OCCc1cc(C(=O)N(C)c3ccccc3Cl)sc1-2] | N-(2-chlorophenyl)-8-(3-(dimethylamino)propanamido)-N-methyl-4,5-dihydrobenzo[b]thieno[2,3-d]oxepine-2-carboxamide |

| No. | Structure | Name |
|---|---|---|
| 162 | 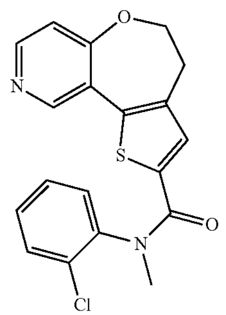 [SMILES: CN(C(=O)c1cc2c(s1)-c1cnccc1OCC2)c1ccccc1Cl] | N-(2-chlorophenyl)-N-methyl-4,5-dihydropyrido[4,3-b]thieno[2,3-d]oxepin-2-carboxamide |
| 163 | 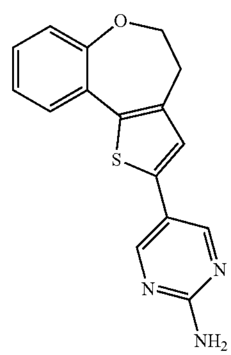 [SMILES: Nc1ncc(-c2cc3c(s2)-c2ccccc2OCC3)cn1] | 5-(4,5-dihydrobenzo[b]thieno[2,3-d]oxepin-2-yl)pyrimidin-2-amine |
| 164 | 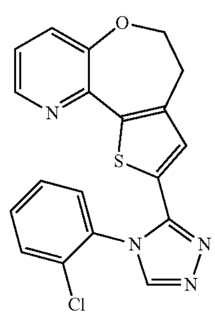 | 3-(6,7-dihydropyrido[3,2-b]thieno[2,3-d]oxepin-9-yl)-4-(2-chlorophenyl)-4H-1,2,4-triazole |
| 165 | 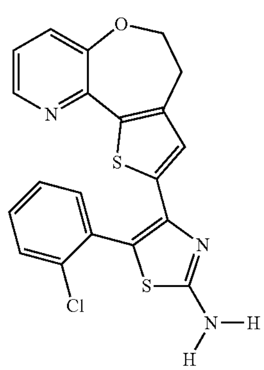 [SMILES: Nc1nc(-c2cc3c(s2)-c2ncccc2OCC3)c(-c2ccccc2Cl)s1] | 4-(6,7-dihydropyrido[3,2-b]thieno[2,3-d]oxepin-9-yl)-(5-(2-chlorophenyl))-thiazol-2-amine |

TABLE 1-continued

| No. | Structure | Name |
|---|---|---|
| 166 | 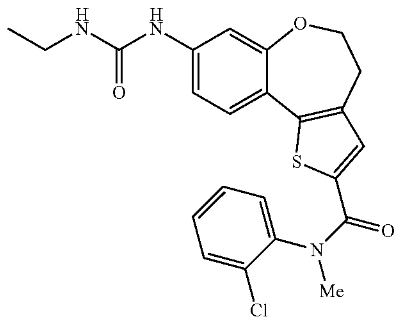 [SMILES: CCNC(=O)Nc1ccc2c(c1)OCCc1cc(C(=O)N(C)c3ccccc3Cl)sc1-2] | N-(2-chlorophenyl)-8-(3-ethylureido)-N-methyl-4,5-dihydrobenzo[b]thieno[2,3-d]oxepine-2-carboxamide |
| 167 | 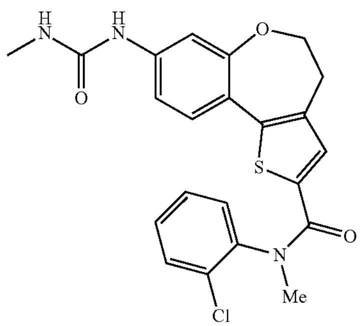 [SMILES: CNC(=O)Nc1ccc2c(c1)OCCc1cc(C(=O)N(C)c3ccccc3Cl)sc1-2] | N-(2-chlorophenyl)-N-methyl-8-(3-methylureido)-4,5-dihydrobenzo[b]thieno[2,3-d]oxepine-2-carboxamide |
| 168 | 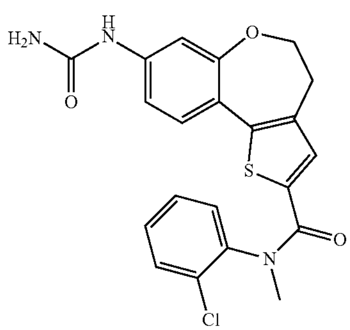 [SMILES: CN(C(=O)c1cc2c(s1)-c1ccc(NC(N)=O)cc1OCC2)c1ccccc1Cl] | N-(2-chlorophenyl)-N-methyl-8-ureido-4,5-dihydrobenzo[b]thieno[2,3-d]oxepine-2-carboxamide |
| 169 | 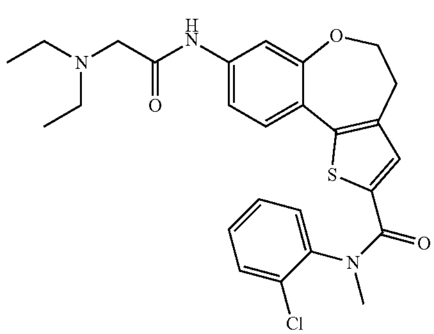 [SMILES: CCN(CC)CC(=O)Nc1ccc2c(c1)OCCc1cc(C(=O)N(C)c3ccccc3Cl)sc1-2] | N-(2-chlorophenyl)-8-(2-(diethylamino)acetamido)-N-methyl-4,5-dihydrobenzo[b]thieno[2,3-d]oxepine-2-carboxamide |

TABLE 1-continued

| No. | Structure | Name |
|---|---|---|
| 170 | 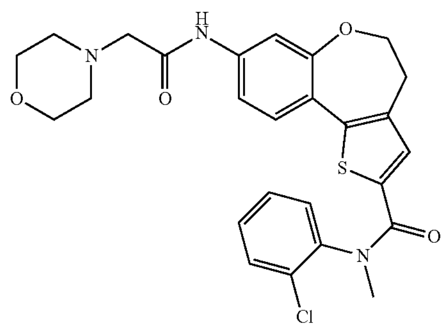 [SMILES: CN(C(=O)c1cc2c(s1)-c1ccc(NC(=O)CN3CCOCC3)cc1OCC2)c1ccccc1Cl] | N-(2-chlorophenyl)-N-methyl-8-(2-morpholinoacetamido)-4,5-dihydrobenzo[b]thieno[2,3-d]oxepine-2-carboxamide |
| 171 | 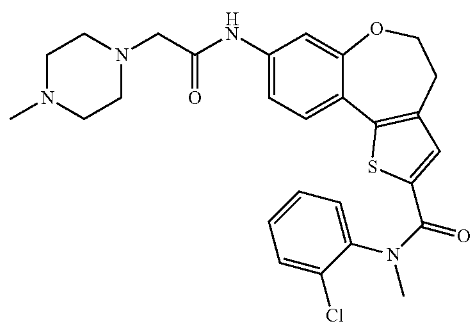 [SMILES: CN1CCN(CC(=O)Nc2ccc3c(c2)OCCc2cc(C(=O)N(C)c4ccccc4Cl)sc2-3)CC1] | N-(2-chlorophenyl)-N-methyl-8-(2-(4-methylpiperazin-1-yl)acetamido)-4,5-dihydrobenzo[b]thieno[2,3-d]oxepine-2-carboxamide |
| 172 | 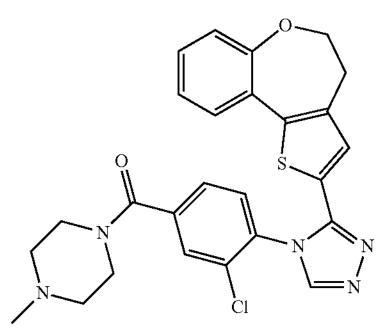 [SMILES: CN1CCN(C(=O)c2ccc(-n3cnnc3-c3cc4c(s3)-c3ccccc3OCC4)c(Cl)c2)CC1] | (3-chloro-4-(3-(4,5-dihydrobenzo[b]thieno[2,3-d]oxepin-2-yl)-4H-1,2,4-triazol-4-yl)phenyl)(4-methylpiperazin-1-yl)methanone |
| 173 | 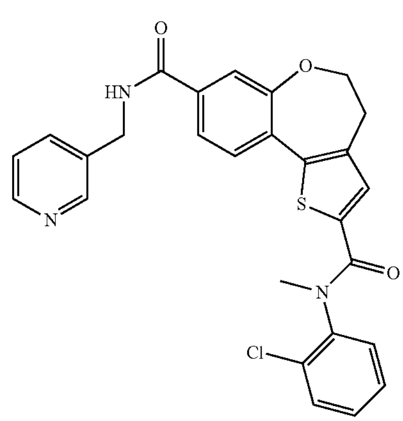 [SMILES: CN(C(=O)c1cc2c(s1)-c1ccc(C(=O)NCc3cccnc3)cc1OCC2)c1ccccc1Cl] | N2-(2-chlorophenyl)-N2-methyl-N8-(pyridin-3-ylmethyl)-4,5-dihydrobenzo[b]thieno[2,3-d]oxepine-2,8-dicarboxamide |

TABLE 1-continued

| No. | Structure | Name |
|---|---|---|
| 174 | 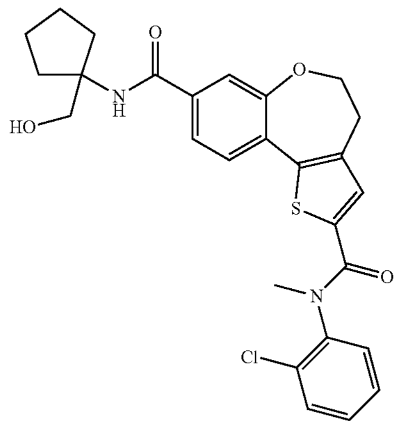 [SMILES: CN(C(=O)c1cc2c(s1)-c1ccc(C(=O)NC3(CO)CCCC3)cc1OCC2)c1ccccc1Cl] | N2-(2-chlorophenyl)-N8-(1-(hydroxymethyl)cyclopentyl)-N2-methyl-4,5-dihydrobenzo[b]thieno[2,3-d]oxepine-2,8-dicarboxamide |
| 175 | 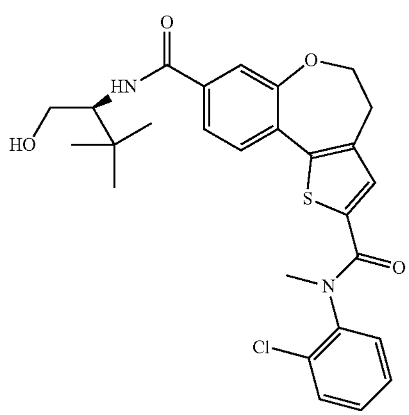 [SMILES: CN(C(=O)c1cc2c(s1)-c1ccc(C(=O)N[C@H](CO)C(C)(C)C)cc1OCC2)c1ccccc1Cl] | N2-(2-chlorophenyl)-N8-((S)-1-hydroxy-3,3-dimethylbutan-2-yl)-N2-methyl-4,5-dihydrobenzo[b]thieno[2,3-d]oxepine-2,8-dicarboxamide |
| 176 | 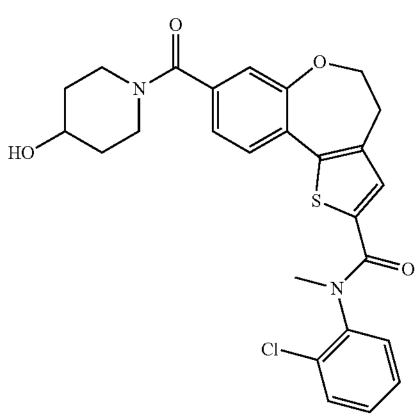 [SMILES: CN(C(=O)c1cc2c(s1)-c1ccc(C(=O)N3CCC(O)CC3)cc1OCC2)c1ccccc1Cl] | N-(2-chlorophenyl)-8-(4-hydroxypiperidine-1-carbonyl)-N-methyl-4,5-dihydrobenzo[b]thieno[2,3-d]oxepine-2-carboxamide |

TABLE 1-continued

| No. | Structure | Name |
|-----|-----------|------|
| 177 | 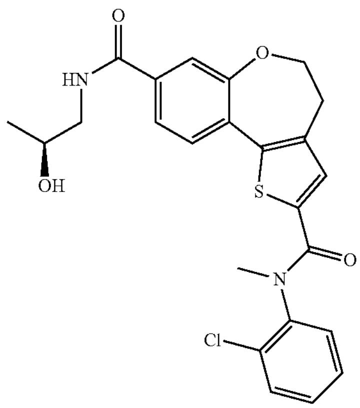 [SMILES: C[C@H](O)CNC(=O)c1ccc2c(c1)OCCc1cc(C(=O)N(C)c3ccccc3Cl)sc1-2] | N2-(2-chlorophenyl)-N8-((S)-2-hydroxypropyl)-N2-methyl-4,5-dihydrobenzo[b]thieno[2,3-d]oxepine-2,8-dicarboxamide |
| 178 | 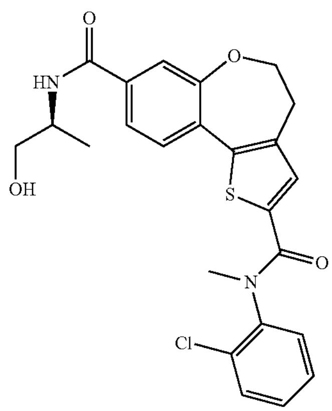 [SMILES: C[C@@H](CO)NC(=O)c1ccc2c(c1)OCCc1cc(C(=O)N(C)c3ccccc3Cl)sc1-2] | N2-(2-chlorophenyl)-N8-((S)-1-hydroxypropan-2-yl)-N2-methyl-4,5-dihydrobenzo[b]thieno[2,3-d]oxepine-2,8-dicarboxamide |
| 179 | 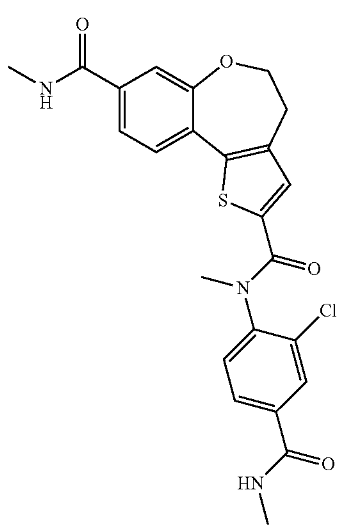 [SMILES: CNC(=O)c1ccc(N(C)C(=O)c2cc3c(s2)-c2ccc(C(=O)NC)cc2OCC3)c(Cl)c1] | N2-(2-chloro-4-(methylcarbamoyl)phenyl)-N2,N8-dimethyl-4,5-dihydrobenzo[b]thieno[2,3-d]oxepine-2,8-dicarboxamide |

TABLE 1-continued

| No. | Structure | Name |
|---|---|---|
| 180 | 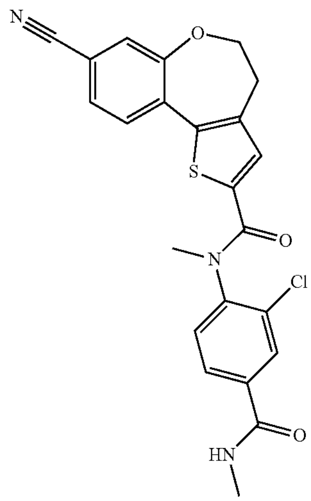 [SMILES: CNC(=O)c1ccc(N(C)C(=O)c2cc3c(s2)-c2ccc(C#N)cc2OCC3)c(Cl)c1] | N-(2-chloro-4-(methylcarbamoyl)phenyl)-8-cyano-N-methyl-4,5-dihydrobenzo[b]thieno[2,3-d]oxepine-2-carboxamide |
| 181 | 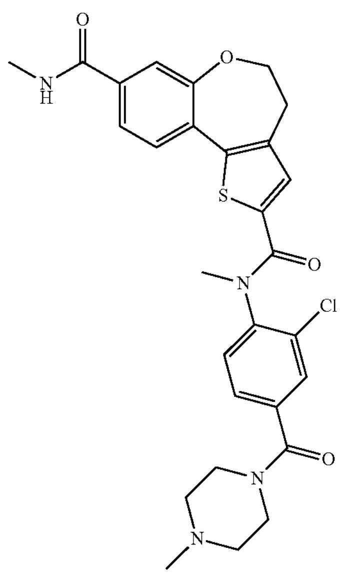 [SMILES: CNC(=O)c1ccc2c(c1)OCCc1cc(C(=O)N(C)c3ccc(C(=O)N4CCN(C)CC4)cc3Cl)sc1-2] | N2-(2-chloro-4-(4-methylpiperazine-1-carbonyl)phenyl)-N2,N8-dimethyl-4,5-dihydrobenzo[b]thieno[2,3-d]oxepine-2,8-dicarboxamide |
| 182 | 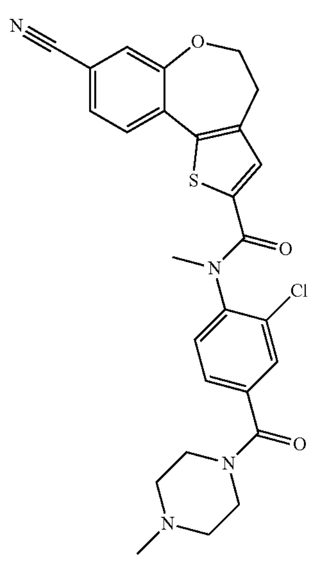 [SMILES: CN1CCN(C(=O)c2ccc(N(C)C(=O)c3cc4c(s3)-c3ccc(C#N)cc3OCC4)c(Cl)c2)CC1] | N-(2-chloro-4-(4-methylpiperazine-1-carbonyl)phenyl)-8-cyano-N-methyl-4,5-dihydrobenzo[b]thieno[2,3-d]oxepine-2-carboxamide |

| No. | Structure | Name |
| --- | --- | --- |
| 183 | 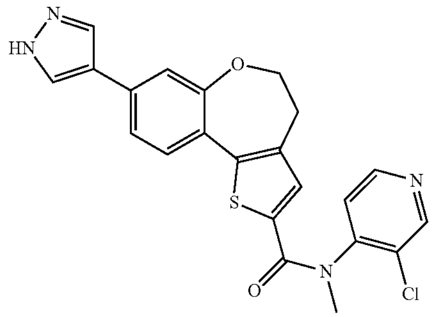 [SMILES: CN(C(=O)c1cc2c(s1)-c1ccc(-c3cn[nH]c3)cc1OCC2)c1ccncc1Cl] | N-(3-chloropyridin-4-yl)-N-methyl-8-(1H-pyrazol-4-yl)-4,5-dihydrobenzo[b]thieno[2,3-d]oxepine-2-carboxamide |
| 184 | 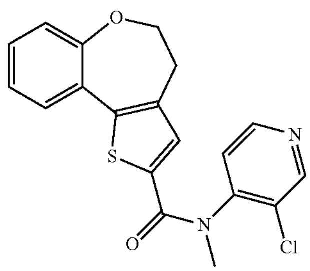 [SMILES: CN(C(=O)c1cc2c(s1)-c1ccccc1OCC2)c1ccncc1Cl] | N-(3-chloropyridin-4-yl)-N-methyl-4,5-dihydrobenzo[b]thieno[2,3-d]oxepine-2-carboxamide |
| 185 | 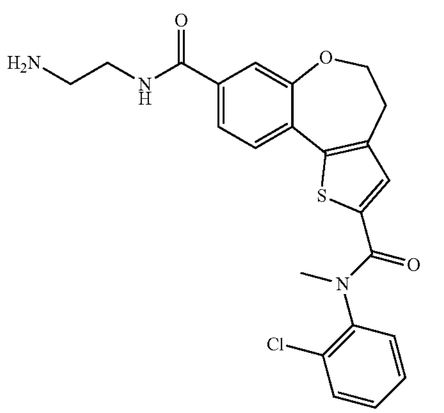 [SMILES: CN(C(=O)c1cc2c(s1)-c1ccc(C(=O)NCCN)cc1OCC2)c1ccccc1Cl] | N8-(2-aminoethyl)-N2-(2-chlorophenyl)-N2-methyl-4,5-dihydrobenzo[b]thieno[2,3-d]oxepine-2,8-dicarboxamide |
| 186 | 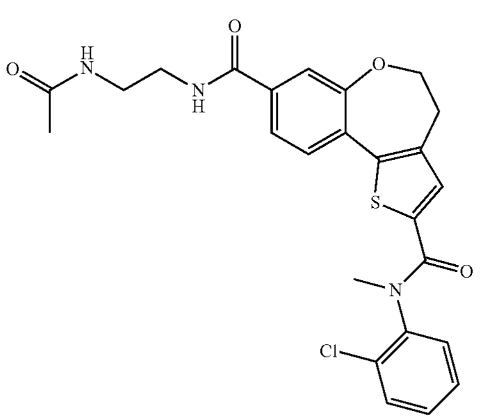 [SMILES: CC(=O)NCCNC(=O)c1ccc2c(c1)OCCc1cc(C(=O)N(C)c3ccccc3Cl)sc1-2] | N8-(2-acetamidoethyl)-N2-(2-chlorophenyl)-N2-methyl-4,5-dihydrobenzo[b]thieno[2,3-d]oxepine-2,8-dicarboxamide |

TABLE 1-continued

| No. | Structure | Name |
|---|---|---|
| 187 | 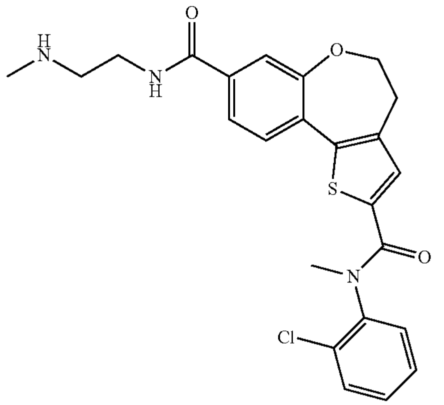 [SMILES: CNCCNC(=O)c1ccc2c(c1)OCCc1cc(C(=O)N(C)c3ccccc3Cl)sc1-2] | N2-(2-chlorophenyl)-N2-methyl-N8-(2-(methylamino)ethyl)-4,5-dihydrobenzo[b]thieno[2,3-d]oxepine-2,8-dicarboxamide |
| 188 | 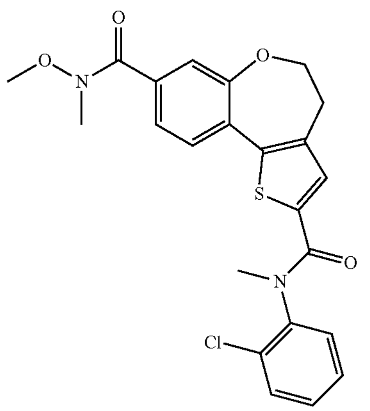 [SMILES: CON(C)C(=O)c1ccc2c(c1)OCCc1cc(C(=O)N(C)c3ccccc3Cl)sc1-2] | N2-(2-chlorophenyl)-N8-methoxy-N2,N8-dimethyl-4,5-dihydrobenzo[b]thieno[2,3-d]oxepine-2,8-dicarboxamide |
| 189 | 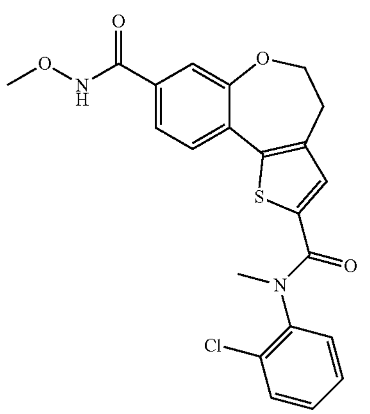 [SMILES: CONC(=O)c1ccc2c(c1)OCCc1cc(C(=O)N(C)c3ccccc3Cl)sc1-2] | N2-(2-chlorophenyl)-N8-methoxy-N2-methyl-4,5-dihydrobenzo[b]thieno[2,3-d]oxepine-2,8-dicarboxamide |
| 190 | 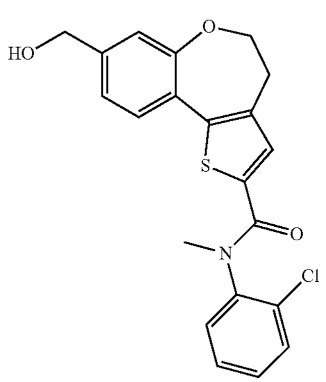 [SMILES: CN(C(=O)c1cc2c(s1)-c1ccc(CO)cc1OCC2)c1ccccc1Cl] | N-(2-chlorophenyl)-8-(hydroxymethyl)-N-methyl-4,5-dihydrobenzo[b]thieno[2,3-d]oxepine-2-carboxamide |

| No. | Structure | Name |
|---|---|---|
| 191 | 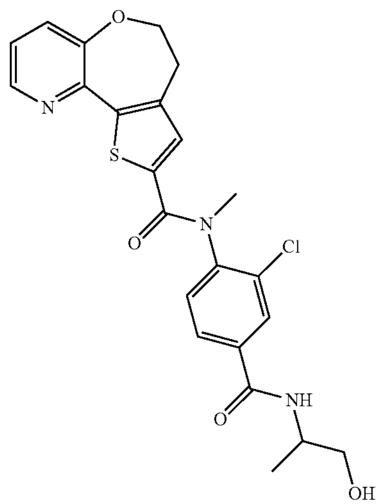 [SMILES: CC(CO)NC(=O)c1ccc(N(C)C(=O)c2cc3c(s2)-c2ncccc2OCC3)c(Cl)c1] | N-(2-chloro-4-(1-hydroxypropan-2-ylcarbamoyl)phenyl)-N,10-dimethyl-4,5-dihydrobenzo[b]thieno[2,3-d]oxepine-2-carboxamide |
| 192 | 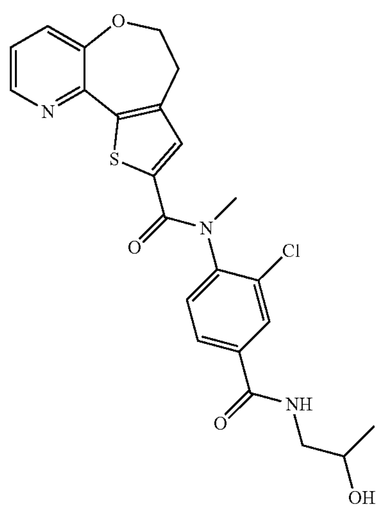 [SMILES: CC(O)CNC(=O)c1ccc(N(C)C(=O)c2cc3c(s2)-c2ncccc2OCC3)c(Cl)c1] | N-(2-chloro-4-(2-hydroxypropylcarbamoyl)phenyl)-N-methyl(10-aza-4,5-dihydrobenzo[b]thieno[2,3-d]oxepine)-2-carboxamide |
| 193 | 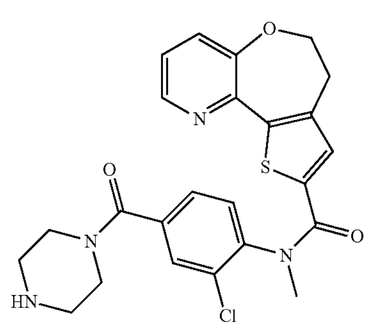 [SMILES: CN(C(=O)c1cc2c(s1)-c1ncccc1OCC2)c1ccc(C(=O)N2CCNCC2)cc1Cl] | N-(2-chloro-4-(piperazine-1-carbonyl)phenyl)-N-methyl(10-aza-4,5-dihydrobenzo[b]thieno[2,3-d]oxepine)-2-carboxamide |

TABLE 1-continued

| No. | Structure | Name |
|---|---|---|
| 194 | 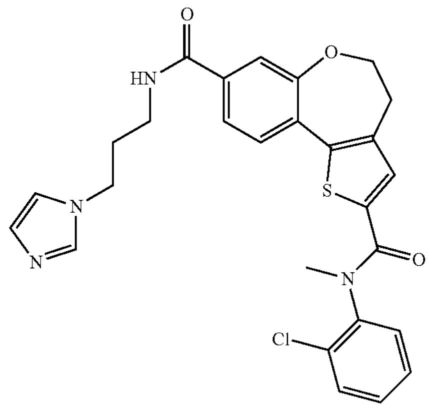 [SMILES: CN(C(=O)c1cc2c(s1)-c1ccc(C(=O)NCCCn3ccnc3)cc1OCC2)c1ccccc1Cl] | N8-(3-(1H-imidazol-1-yl)propyl)-N2-(2-chlorophenyl)-N2-methyl-4,5-dihydrobenzo[b]thieno[2,3-d]oxepine-2,8-dicarboxamide |
| 195 | 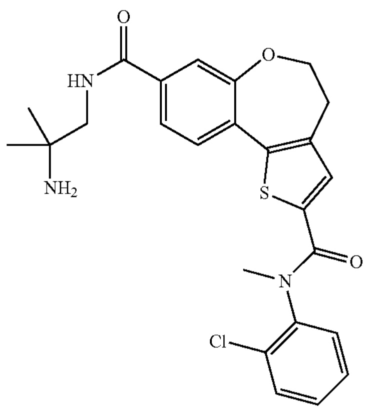 [SMILES: CN(C(=O)c1cc2c(s1)-c1ccc(C(=O)NCC(C)(C)N)cc1OCC2)c1ccccc1Cl] | N8-(2-amino-2-methylpropyl)-N2-(2-chlorophenyl)-N2-methyl-4,5-dihydrobenzo[b]thieno[2,3-d]oxepine-2,8-dicarboxamide |
| 196 | 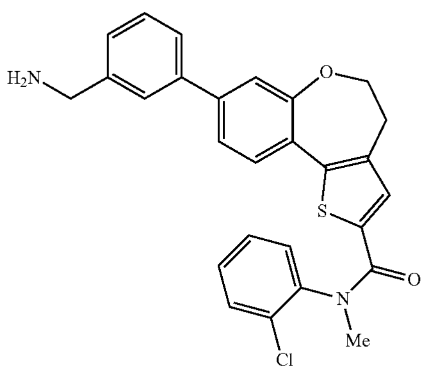 [SMILES: CN(C(=O)c1cc2c(s1)-c1ccc(-c3cccc(CN)c3)cc1OCC2)c1ccccc1Cl] | 8-(3-(aminomethyl)phenyl)-N-(2-chlorophenyl)-N-methyl-4,5-dihydrobenzo[b]thieno[2,3-d]oxepine-2-carboxamide |
| 197 | 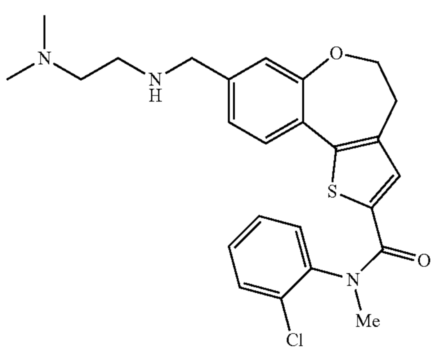 [SMILES: CN(C)CCNCc1ccc2c(c1)OCCc1cc(C(=O)N(C)c3ccccc3Cl)sc1-2] | N-(2-chlorophenyl)-8-((2-(dimethylamino)ethylamino)methyl)-N-methyl-4,5-dihydrobenzo[b]thieno[2,3-d]oxepine-2-carboxamide |

TABLE 1-continued

| No. | Structure | Name |
|---|---|---|
| 198 | 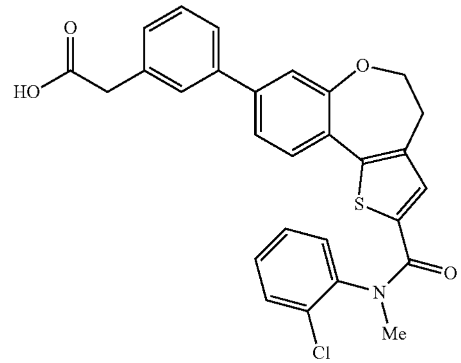 [SMILES: CN(C(=O)c1cc2c(s1)-c1ccc(-c3cccc(CC(=O)O)c3)cc1OCC2)c1ccccc1Cl] | 2-(3-(2-((2-chlorophenyl)(methyl)carbamoyl)-4,5-dihydrobenzo[b]thieno[2,3-d]oxepin-8-yl)phenyl)acetic acid |
| 199 | 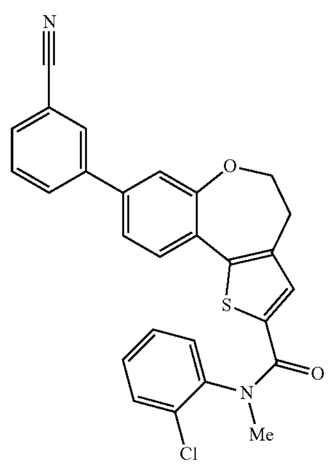 [SMILES: CN(C(=O)c1cc2c(s1)-c1ccc(-c3cccc(C#N)c3)cc1OCC2)c1ccccc1Cl] | N-(2-chlorophenyl)-8-(3-cyanophenyl)-N-methyl-4,5-dihydrobenzo[b]thieno[2,3-d]oxepine-2-carboxamide |
| 200 | 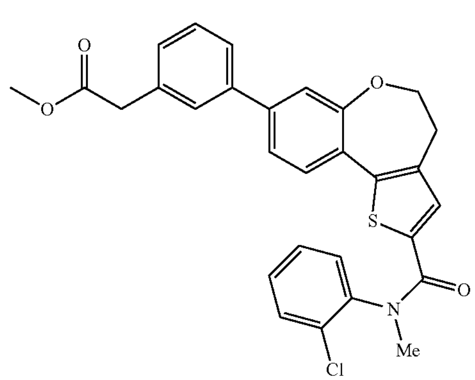 [SMILES: COC(=O)Cc1cccc(-c2ccc3c(c2)OCCc2cc(C(=O)N(C)c4ccccc4Cl)sc2-3)c1] | methyl 2-(3-(2-((2-chlorophenyl)(methyl)carbamoyl)-4,5-dihydrobenzo[b]thieno[2,3-d]oxepin-8-yl)phenyl)acetate |

| No. | Structure | Name |
| --- | --- | --- |
| 201 | 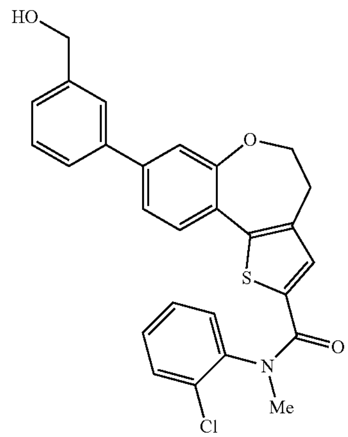 [SMILES: CN(C(=O)c1cc2c(s1)-c1ccc(-c3cccc(CO)c3)cc1OCC2)c1ccccc1Cl] | N-(2-chlorophenyl)-8-(3-(hydroxymethyl)phenyl)-N-methyl-4,5-dihydrobenzo[b]thieno[2,3-d]oxepine-2-carboxamide |
| 202 | 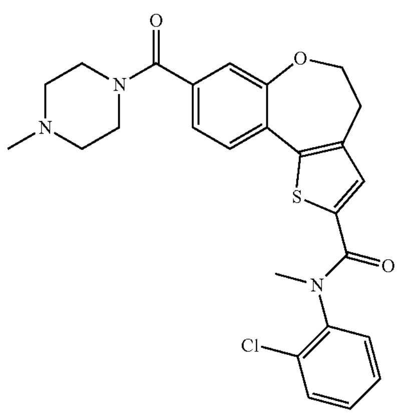 [SMILES: CN1CCN(C(=O)c2ccc3c(c2)OCCc2cc(C(=O)N(C)c4ccccc4Cl)sc2-3)CC1] | N-(2-chlorophenyl)-N-methyl-8-(4-methylpiperazine-1-carbonyl)-4,5-dihydrobenzo[b]thieno[2,3-d]oxepine-2-carboxamide |
| 203 | 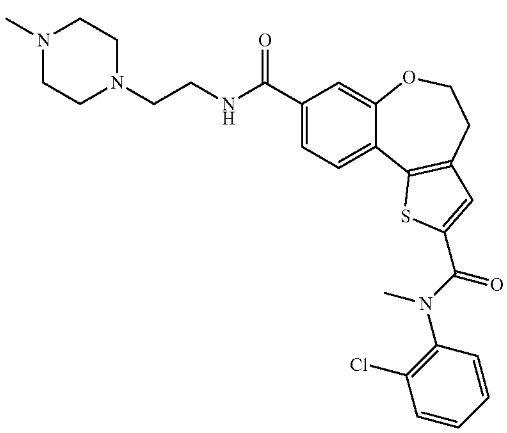 [SMILES: CN1CCN(CCNC(=O)c2ccc3c(c2)OCCc2cc(C(=O)N(C)c4ccccc4Cl)sc2-3)CC1] | N2-(2-chlorophenyl)-N2-methyl-N8-(2-(4-methylpiperazin-1-yl)ethyl)-4,5-dihydrobenzo[b]thieno[2,3-d]oxepine-2,8-dicarboxamide |

TABLE 1-continued

| No. | Structure | Name |
|---|---|---|
| 204 | 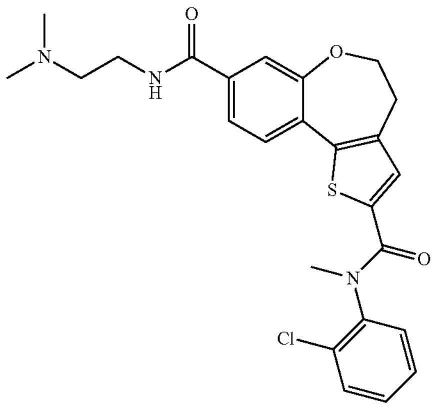 [SMILES: CN(C)CCNC(=O)c1ccc2c(c1)OCCc1cc(C(=O)N(C)c3ccccc3Cl)sc1-2] | N2-(2-chlorophenyl)-N8-(2-(dimethylamino)ethyl)-N2-methyl-4,5-dihydrobenzo[b]thieno[2,3-d]oxepine-2,8-dicarboxamide |
| 205 | 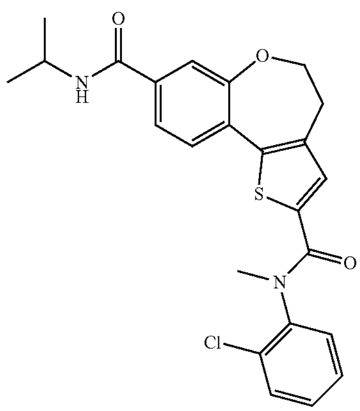 [SMILES: CC(C)NC(=O)c1ccc2c(c1)OCCc1cc(C(=O)N(C)c3ccccc3Cl)sc1-2] | N2-(2-chlorophenyl)-N8-isopropyl-N2-methyl-4,5-dihydrobenzo[b]thieno[2,3-d]oxepine-2,8-dicarboxamide |
| 206 | 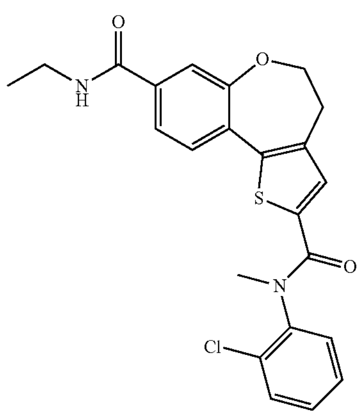 [SMILES: CCNC(=O)c1ccc2c(c1)OCCc1cc(C(=O)N(C)c3ccccc3Cl)sc1-2] | N2-(2-chlorophenyl)-N8-ethyl-N2-methyl-4,5-dihydrobenzo[b]thieno[2,3-d]oxepine-2,8-dicarboxamide |
| 207 | 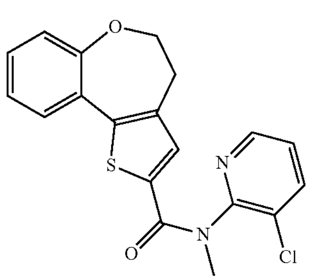 [SMILES: CN(C(=O)c1cc2c(s1)-c1ccccc1OCC2)c1ncccc1Cl] | N-(3-chloropyridin-2-yl)-N-methyl-4,5-dihydrobenzo[b]thieno[2,3-d]oxepine-2-carboxamide |

TABLE 1-continued

| No. | Structure | Name |
|---|---|---|
| 208 | 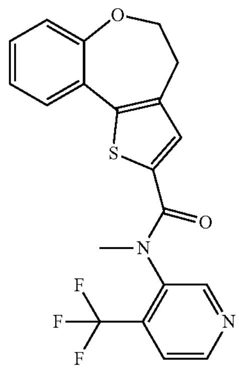 [SMILES: CN(C(=O)c1cc2c(s1)-c1ccccc1OCC2)c1cnccc1C(F)(F)F] | N-methyl-N-(4-(trifluoromethyl)pyridin-3-yl)-4,5-dihydrobenzo[b]thieno[2,3-d]oxepine-2-carboxamide |
| 209 | 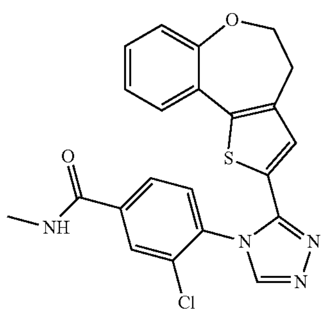 [SMILES: CNC(=O)c1ccc(-n2cnnc2-c2cc3c(s2)-c2ccccc2OCC3)c(Cl)c1] | 3-chloro-4-(3-(4,5-dihydrobenzo[b]thieno[2,3-d]oxepin-2-yl)-4H-1,2,4-triazol-4-yl)-N-methylbenzamide |
| 210 | 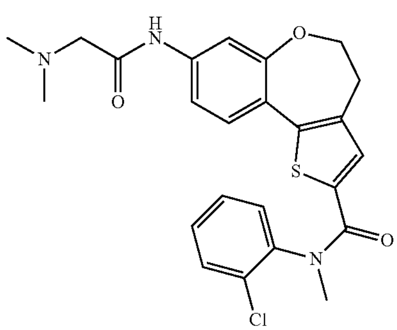 [SMILES: CN(C)CC(=O)Nc1ccc2c(c1)OCCc1cc(C(=O)N(C)c3ccccc3Cl)sc1-2] | N-(2-chlorophenyl)-8-(2-(dimelhylamino)acetamido)-N-methyl-4,5-dihydrobenzo[b]thieno[2,3-d]oxepine-2-carboxamide |
| 211 | 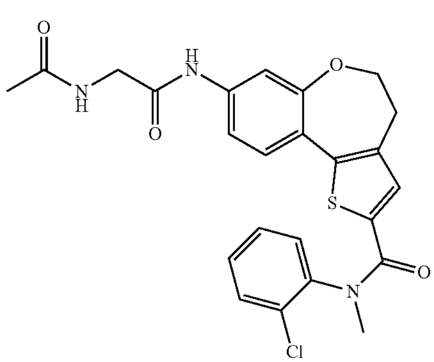 [SMILES: CC(=O)NCC(=O)Nc1ccc2c(c1)OCCc1cc(C(=O)N(C)c3ccccc3Cl)sc1-2] | 8-(2-acetamidoacetamido)-N-(2-chlorophenyl)-N-methyl-4,5-dihydrobenzo[b]thieno[2,3-d]oxepine-2-carboxamide |

TABLE 1-continued

| No. | Structure | Name |
|---|---|---|
| 212 | 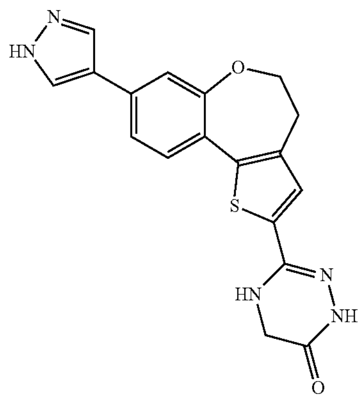 [SMILES: O=C1CNC(c2cc3c(s2)-c2ccc(-c4cn[nH]c4)cc2OCC3)=NN1] | 3-(8-(1H-pyrazol-4-yl)-4,5-dihydrobenzo[b]thieno[2,3-d]oxepin-2-yl)-4,5-dihydro-1,2,4-triazin-6(1H)-one |
| 213 | 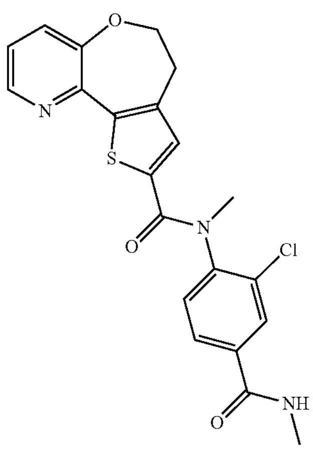 [SMILES: CNC(=O)c1ccc(N(C)C(=O)c2cc3c(s2)-c2ncccc2OCC3)c(Cl)c1] | N-(2-chloro-4-(methylcarbamoyl)phenyl)-N-methyl(10-aza,4,5-dihydrobenzo[b]thieno[2,3-d]oxepine-2-carboxamide |
| 214 | 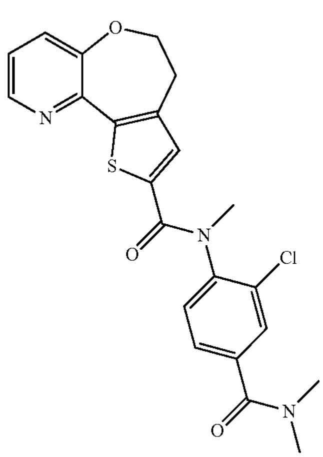 [SMILES: CN(C)C(=O)c1ccc(N(C)C(=O)c2cc3c(s2)-c2ncccc2OCC3)c(Cl)c1] | N-(2-chloro-4-(dimethylcarbamoyl)phenyl)-N-methyl(10-aza,4,5-dihydrobenzo[b]thieno[2,3-d]oxepine)-2-carboxamide |

TABLE 1-continued

| No. | Structure | Name |
|---|---|---|
| 215 | 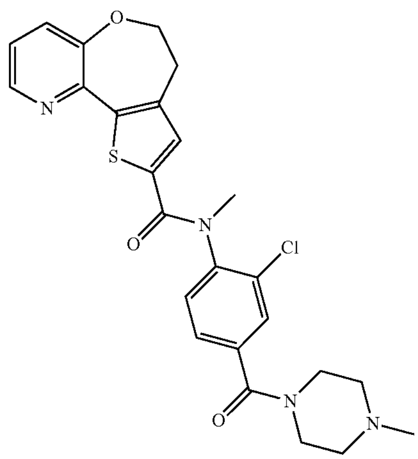 [SMILES: CN1CCN(C(=O)c2ccc(N(C)C(=O)c3cc4c(s3)-c3ncccc3OCC4)c(Cl)c2)CC1] | N-(2-chloro-4-(4-methylpiperazine-1-carbonyl)phenyl)-N-methyl(10-aza-4,5-dihydrobenzo[b]thieno[2,3-d]oxepine)-2-carboxamide |
| 216 | 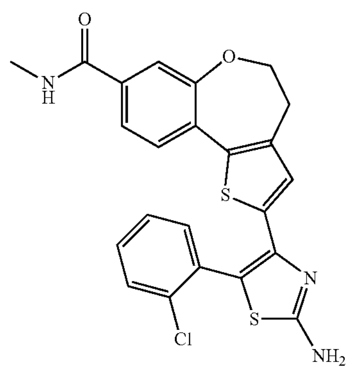 [SMILES: CNC(=O)c1ccc2c(c1)OCCc1cc(-c3nc(N)sc3-c3ccccc3Cl)sc1-2] | 2-(2-amino-5-(2-chlorophenyl)thiazol-4-yl)-N-methyl-4,5-dihydrobenzo[b]thieno[2,3-d]oxepine-8-carboxamide |
| 217 | 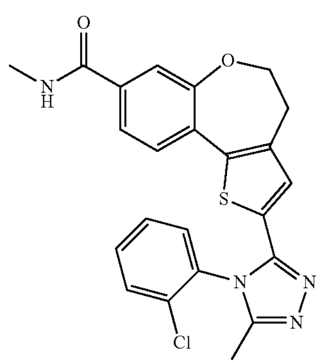 [SMILES: CNC(=O)c1ccc2c(c1)OCCc1cc(-c3nnc(C)n3-c3ccccc3Cl)sc1-2] | 2-(4-(2-chlorophenyl)-5-methyl-4H-1,2,4-triazol-3-yl)-N-methyl-4,5-dihydrobenzo[b]thieno[2,3-d]oxepine-8 carboxamide |
| 218 | 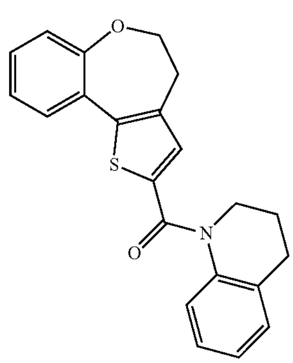 [SMILES: O=C(c1cc2c(s1)-c1ccccc1OCC2)N1CCCc2ccccc21] | (4,5-dihydrobenzo[b]thieno[2,3-d]oxepin-2-yl)(3,4-dihydroquinolin-1(2H)-yl)methanone |

TABLE 1-continued

| No. | Structure | Name |
| --- | --- | --- |
| 219 | 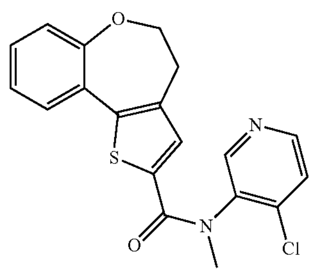 [SMILES: CN(C(=O)c1cc2c(s1)-c1ccccc1OCC2)c1cnccc1Cl] | N-(4-chloropyridin-3-yl)-N-methyl-4,5-dihydrobenzo[b]thieno[2,3-d]oxepine-2-carboxamide |
| 220 | 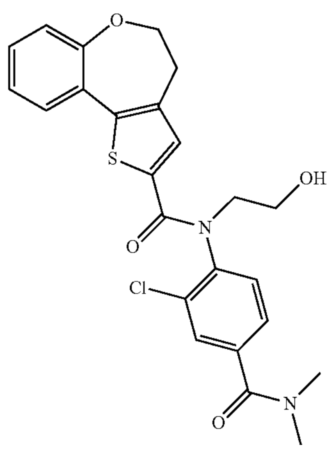 [SMILES: CN(C)C(=O)c1ccc(N(CCO)C(=O)c2cc3c(s2)-c2ccccc2OCC3)c(Cl)c1] | N-(2-chloro-4-(dimethylcarbamoyl)phenyl)-N-(2-hydroxyethyl)-4,5-dihydrobenzo[b]thieno[2,3-d]oxepine-2-carboxamide |
| 221 | 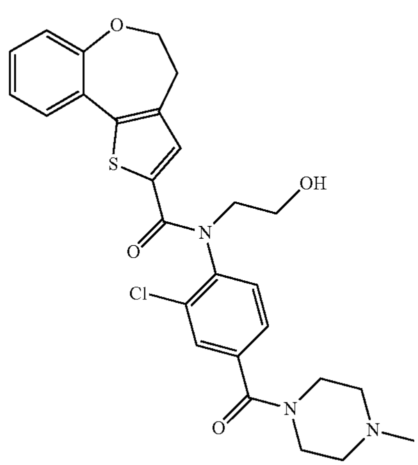 [SMILES: CN1CCN(C(=O)c2ccc(N(CCO)C(=O)c3cc4c(s3)-c3ccccc3OCC4)c(Cl)c2)CC1] | N-(2-chloro-4-(4-methylpiperazine-1-carbonyl)phenyl)-N-(2-hydroxyethyl)-4,5-dihydrobenzo[b]thieno[2,3-d]oxepine-2-carboxamide |
| 222 | 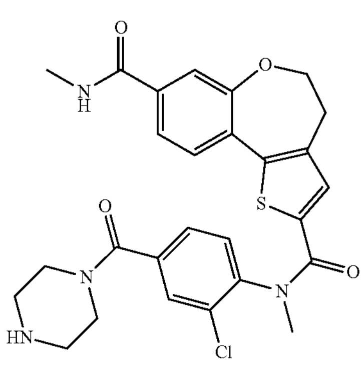 [SMILES: CNC(=O)c1ccc2c(c1)OCCc1cc(C(=O)N(C)c3ccc(C(=O)N4CCNCC4)cc3Cl)sc1-2] | N2-(2-chloro-4-(piperazine-1-carbonyl)phenyl)-N2,N8-dimethyl-4,5-dihydrobenzo[b]thieno[2,3-d]oxepine-2,8-dicarboxamide |

TABLE 1-continued

| No. | Structure | Name |
| --- | --- | --- |
| 223 | 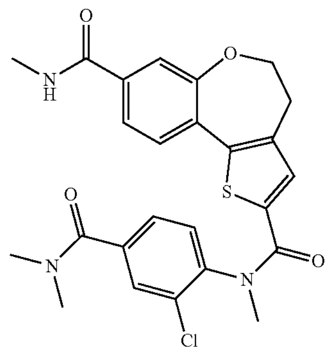 [SMILES: CNC(=O)c1ccc2c(c1)OCCc1cc(C(=O)N(C)c3ccc(C(=O)N(C)C)cc3Cl)sc1-2] | N2-(2-chloro-4-(dimethylcarbamoyl)phenyl)-N2,N8-dimethyl-4,5-dihydrobenzo[b]thieno[2,3-d]oxepine-2,8-dicarboxamide |
| 224 | 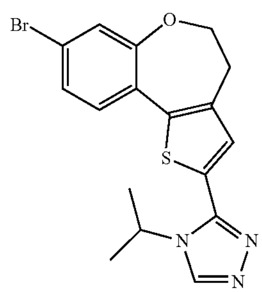 [SMILES: CC(C)n1cnnc1-c1cc2c(s1)-c1ccc(Br)cc1OCC2] | 3-(8-bromo-4,5-dihydrobenzo[b]thieno[2,3-d]oxepin-2-yl)-4-isopropyl-4H-1,2,4-triazole |
| 225 | 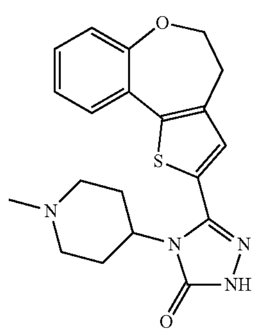 [SMILES: CN1CCC(n2c(-c3cc4c(s3)-c3ccccc3OCC4)n[nH]c2=O)CC1] | 3-(4,5-dihydrobenzo[b]thieno[2,3-d]oxepin-2-yl)-4-(1-methylpiperidin-4-yl)-1H-1,2,4-triazol-5(4H)-one |
| 226 | 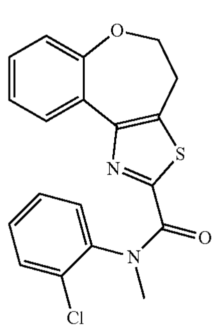 [SMILES: CN(C(=O)c1nc2c(s1)CCOc1ccccc1-2)c1ccccc1Cl] | 4,5-dihydro-6-oxa-3-thia-1-aza-benzo[e]azulene-2-carboxylic acid(2-chloro-phenyl)-methyl-amide |

TABLE 1-continued
| No. | Structure | Name |
|---|---|---|
| 227 | 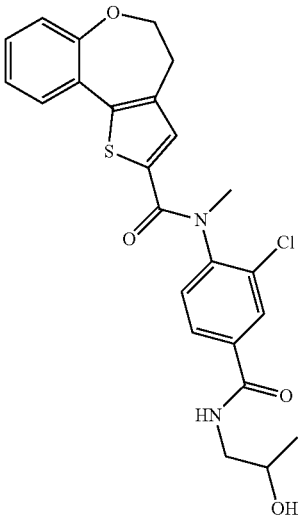 [SMILES: CC(O)CNC(=O)c1ccc(N(C)C(=O)c2cc3c(s2)-c2ccccc2OCC3)c(Cl)c1] | N-(2-chloro-4-(2-hydroxypropylcarbamoyl)phenyl)-N-methyl-4,5-dihydrobenzo[b]thieno[2,3-d]oxepine-2-carboxamide |
| 228 | 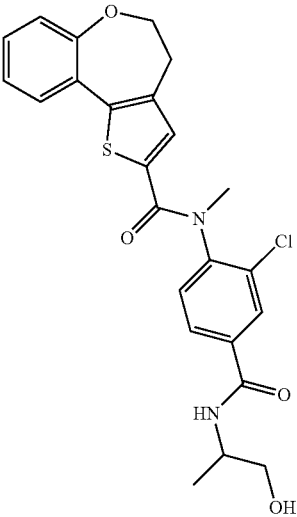 [SMILES: CC(CO)NC(=O)c1ccc(N(C)C(=O)c2cc3c(s2)-c2ccccc2OCC3)c(Cl)c1] | N-(2-chloro-4-(1-hydroxypropan-2-ylcarbamoyl)phenyl)-N-methyl-4,5-dihydrobenzo[b]thieno[2,3-d]oxepine-2-carboxamide |
| 229 | 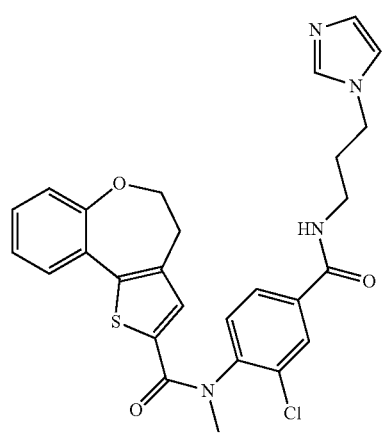 [SMILES: CN(C(=O)c1cc2c(s1)-c1ccccc1OCC2)c1ccc(C(=O)NCCCn2ccnc2)cc1Cl] | N-(4-(3-(1H-imidazol-1-yl)propylcarbamoyl)-2-chlorophenyl)-N-methyl-4,5-dihydrobenzo[b]thieno[2,3-d]oxepine-2-carboxamide |

TABLE 1-continued

| No. | Structure | Name |
|---|---|---|
| 230 | 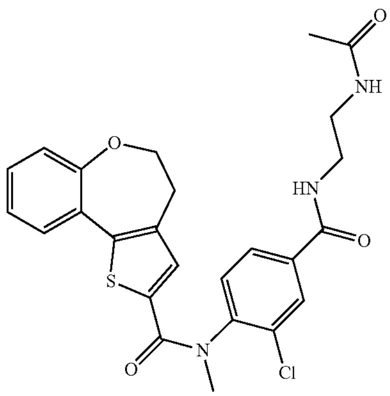 [SMILES: CC(=O)NCCNC(=O)c1ccc(N(C)C(=O)c2cc3c(s2)-c2ccccc2OCC3)c(Cl)c1] | N-(4-(2-acetamidoethylcarbamoyl)-2-chlorophenyl)-N-methyl-4,5-dihydrobenzo[b]thieno[2,3-d]oxepine-2-carboxamide |
| 231 | 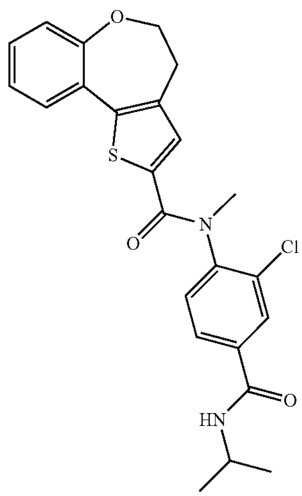 [SMILES: CC(C)NC(=O)c1ccc(N(C)C(=O)c2cc3c(s2)-c2ccccc2OCC3)c(Cl)c1] | N-(2-chloro-4-(isopropylcarbamoyl)phenyl)-N-methyl-4,5-dihydrobenzo[b]thieno[2,3-d]oxepine-2-carboxamide |
| 232 | 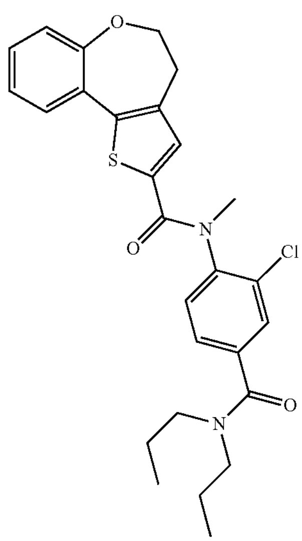 [SMILES: CCCN(CCC)C(=O)c1ccc(N(C)C(=O)c2cc3c(s2)-c2ccccc2OCC3)c(Cl)c1] | N-(2-chloro-4-(dipropylcarbamoyl)phenyl)-N-methyl-4,5-dihydrobenzo[b]thieno[2,3-d]oxepine-2-carboxamide |

TABLE 1-continued

| No. | Structure | Name |
|---|---|---|
| 233 | 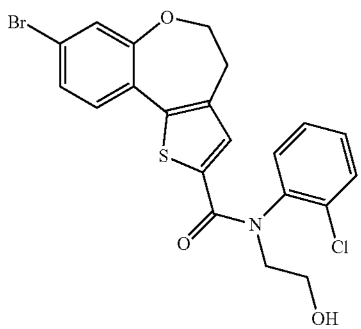 [SMILES: O=C(c1cc2c(s1)-c1ccc(Br)cc1OCC2)N(CCO)c1ccccc1Cl] | 8-bromo-N-(2-chlorophenyl)-N-(2-hydroxyethyl)-4,5-dihydrobenzo[b]thieno(2,3-d)oxepine-2-carboxamide |
| 234 | 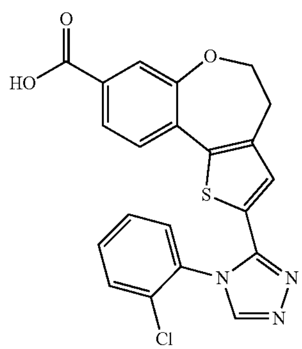 [SMILES: O=C(O)c1ccc2c(c1)OCCc1cc(-c3nncn3-c3ccccc3Cl)sc1-2] | 2-(4-(2-chlorophenyl)-4H-1,2,4-triazol-3-yl)-4,5-dihydrobenzo[b]thieno[2,3-d]oxepine-8-carboxylic acid |
| 235 | 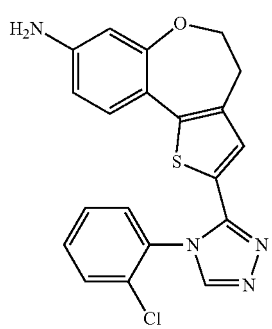 [SMILES: Nc1ccc2c(c1)OCCc1cc(-c3nncn3-c3ccccc3Cl)sc1-2] | 2-(4-(2-chlorophenyl)-4H-1,2,4-triazol-3-yl)-4,5-dihydrobenzo[b]thieno[2,3-d]oxepin-8-amine |
| 236 | 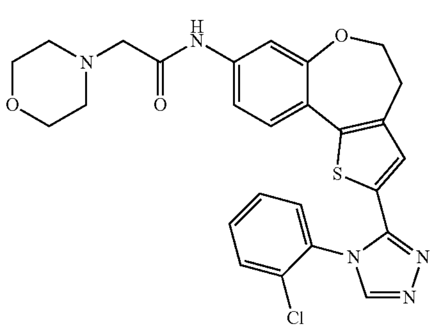 [SMILES: O=C(CN1CCOCC1)Nc1ccc2c(c1)OCCc1cc(-c3nncn3-c3ccccc3Cl)sc1-2] | N-(2-(4-(2-chlorophenyl)-4H-1,2,4-triazol-3-yl)-4,5-dihydrobenzo[b]thieno[2,3-d]oxepin-8-yl)-2-morpholinoacetamide |

| No. | Structure | Name |
|---|---|---|
| 237 | 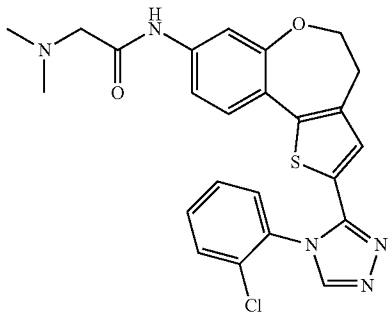 [SMILES: CN(C)CC(=O)Nc1ccc2c(c1)OCCc1cc(-c3nncn3-c3ccccc3Cl)sc1-2] | N-(2-(4-(2-chlorophenyl)-4H-1,2,4-triazol-3-yl)-4,5-dihydrobenzo[b]thieno[2,3-d]oxepin-8-yl)-2-(dimethylamino)acetamide |
| 238 | 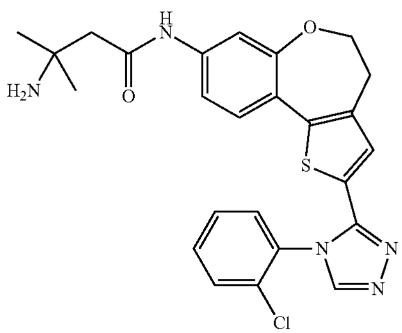 [SMILES: CC(C)(N)CC(=O)Nc1ccc2c(c1)OCCc1cc(-c3nncn3-c3ccccc3Cl)sc1-2] | N-(2-amino-2-methylpropyl)-2-(4-(2-chlorophenyl)-4H-1,2,4-triazol-3-yl)-4,5-dihydrobenzo[b]thieno[2,3-d]oxepine-8-carboxamide |
| 239 | 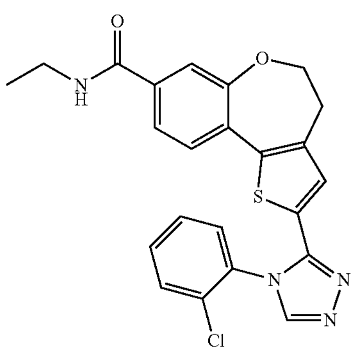 [SMILES: CCNC(=O)c1ccc2c(c1)OCCc1cc(-c3nncn3-c3ccccc3Cl)sc1-2] | 2-(4-(2-chlorophenyl)-4H-1,2,4-triazol-3-yl)-N-ethyl-4,5-dihydrobenzo[b]thieno[2,3-d]oxepine-8-carboxamide |
| 240 | 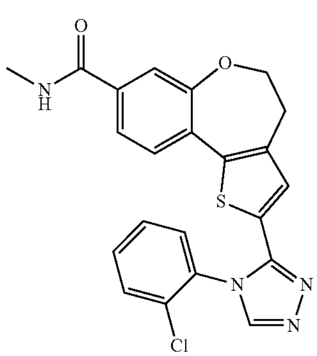 [SMILES: CNC(=O)c1ccc2c(c1)OCCc1cc(-c3nncn3-c3ccccc3Cl)sc1-2] | 2-(4-(2-chlorophenyl)-4H-1,2,4-triazol-3-yl)-N-methyl-4,5-dihydrobenzo[b]thieno[2,3-d]oxepine-8-carboxamide |

TABLE 1-continued

| No. | Structure | Name |
|---|---|---|
| 241 | 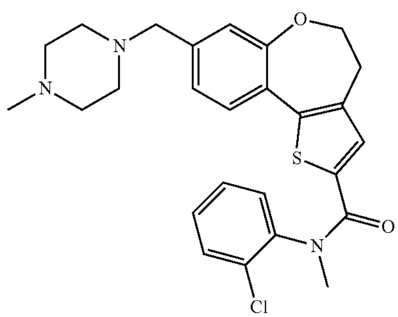 [SMILES: CN1CCN(Cc2ccc3c(c2)OCCc2cc(C(=O)N(C)c4ccccc4Cl)sc2-3)CC1] | N-(2-chlorophenyl)-N-methyl-8-((4-methylpiperazin-1-yl)methyl)-4,5-dihydrobenzo[b]thieno[2,3-d]oxepine-2-carboxamide |
| 242 | 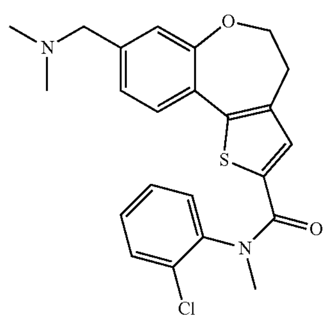 [SMILES: CN(C)Cc1ccc2c(c1)OCCc1cc(C(=O)N(C)c3ccccc3Cl)sc1-2] | N-(2-chlorophenyl)-8-((dimethylamino)methyl)-N-methyl-4,5-dihydrobenzo[b]thieno[2,3-d]oxepine-2 carboxamide |
| 243 | 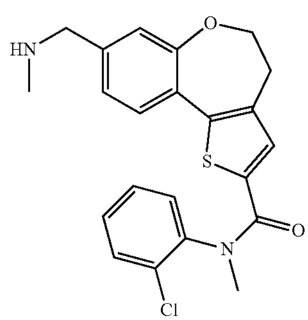 [SMILES: CNCc1ccc2c(c1)OCCc1cc(C(=O)N(C)c3ccccc3Cl)sc1-2] | N-(2-chlorophenyl)-N-methyl-8-((methylamino)methyl)-4,5-dihydrobenzo[b]thieno[2,3-d]oxepine-2-carboxamide |
| 244 | 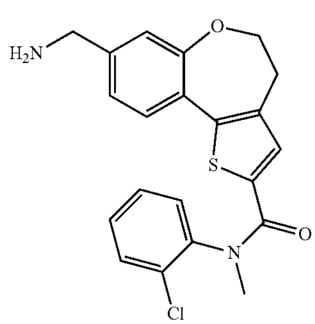 [SMILES: CN(C(=O)c1cc2c(s1)-c1ccc(CN)cc1OCC2)c1ccccc1Cl] | 8-(aminomethyl)-N-(2-chlorophenyl)-N-methyl-4,5-dihydrobenzo[b]thieno[2,3-d]oxepine-2-carboxamide |
| 245 | 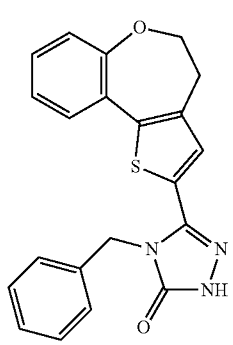 [SMILES: O=c1[nH]nc(-c2cc3c(s2)-c2ccccc2OCC3)n1Cc1ccccc1] | 4-benzyl-3-(4,5-dihydrobenzo[b]thieno[2,3-d]oxepin-2-yl)-1H-1,2,4-triazol-5(4H)-one |

TABLE 1-continued

| No. | Structure | Name |
|---|---|---|
| 246 | 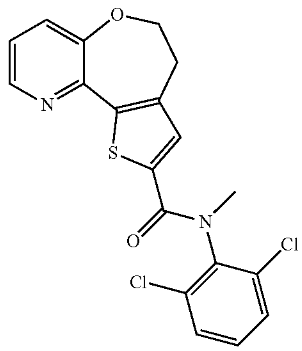 [SMILES: CN(C(=O)c1cc2c(s1)-c1ncccc1OCC2)c1c(Cl)cccc1Cl] | N-(2,6-dichlorophenyl)-N-methyl-(10-aza-4,5-dihydrobenzo[b]thieno[2,3-d]oxepine-2-carboxamide |
| 247 | 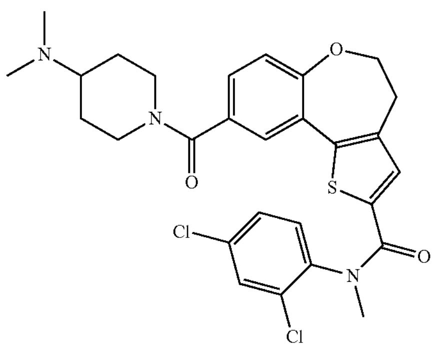 [SMILES: CN(C(=O)c1cc2c(s1)-c1cc(C(=O)N3CCC(N(C)C)CC3)ccc1OCC2)c1ccc(Cl)cc1Cl] | N-(2,4-dichlorophenyl)-9-(4-(dimethylamino)piperidine-1-carbonyl)-N-methyl-4,5-dihydrobenzo[b]thieno[2,3-d]oxepine-2-carboxamide |
| 248 | 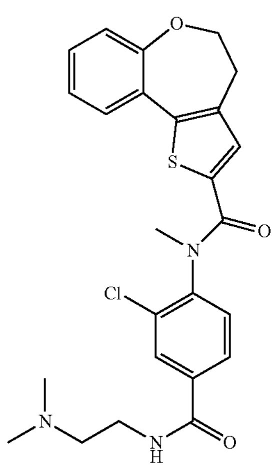 [SMILES: CN(C)CCNC(=O)c1ccc(N(C)C(=O)c2cc3c(s2)-c2ccccc2OCC3)c(Cl)c1] | N-(2-chloro-4-(2-(dimethylamino)ethylcarbamoyl)phenyl)-N-methyl-4,5-dihydrobenzo[b]thieno[2,3-d]oxepine-2-carboxamide |

TABLE 1-continued

| No. | Structure | Name |
|---|---|---|
| 249 | 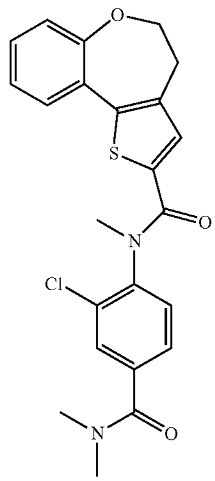 [SMILES: CN(C)C(=O)c1ccc(N(C)C(=O)c2cc3c(s2)-c2ccccc2OCC3)c(Cl)c1] | N-(2-chloro-4-(dimethylcarbamoyl)phenyl)-N-methyl-4,5-dihydrobenzo[b]thieno[2,3-d]oxepine-2-carboxamide |
| 250 | 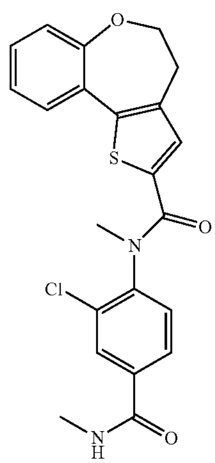 [SMILES: CNC(=O)c1ccc(N(C)C(=O)c2cc3c(s2)-c2ccccc2OCC3)c(Cl)c1] | N-(2-chloro-4-(methylcarbamoyl)phenyl)-N-methyl-4,5-dihydrobenzo[b]thieno[2,3-d]oxepine-2-carboxamide |
| 251 | 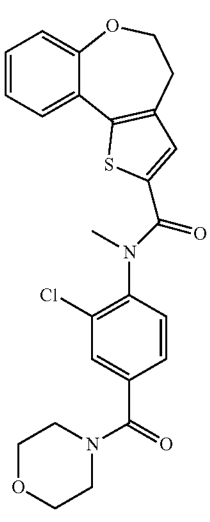 [SMILES: CN(C(=O)c1cc2c(s1)-c1ccccc1OCC2)c1ccc(C(=O)N2CCOCC2)cc1Cl] | N-(2-chloro-4-(morpholine-4-carbonyl)phenyl)-N-methyl-4,5-dihydrobenzo[b]thieno[2,3-d]oxepine-2-carboxamide |

TABLE 1-continued

| No. | Structure | Name |
|---|---|---|
| 252 | 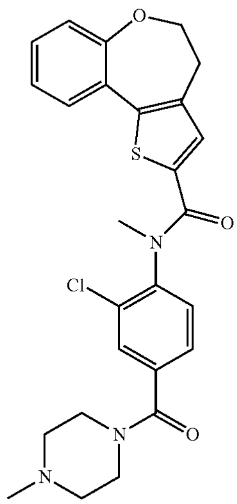 [SMILES: CN1CCN(C(=O)c2ccc(N(C)C(=O)c3cc4c(s3)-c3ccccc3OCC4)c(Cl)c2)CC1] | N-(2-chloro-4-(4-methylpiperazine-1-carbonyl)phenyl)-N-methyl-4,5-dihydrobenzo[b]thieno[2,3-d]oxepine-2-carboxamide |
| 253 | 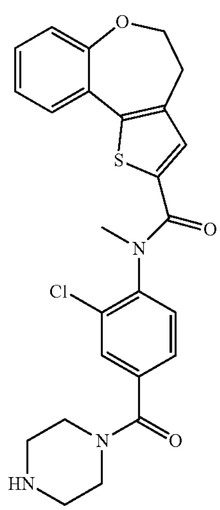 [SMILES: CN(C(=O)c1cc2c(s1)-c1ccccc1OCC2)c1ccc(C(=O)N2CCNCC2)cc1Cl] | N-(2-chloro-4-(piperazine-1-carbonyl)phenyl)-N-methyl-4,5-dihydrobenzo[b]thieno[2,3-d]oxepine-2-carboxamide |
| 254 | 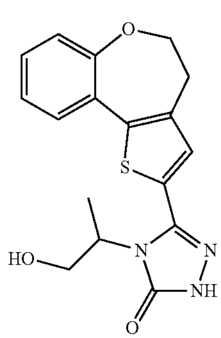 [SMILES: CC(CO)n1c(-c2cc3c(s2)-c2ccccc2OCC3)n[nH]c1=O] | 3-(4,5-dihydrobenzo[b]thieno[2,3-d]oxepin-2-yl)-4-(1-hydroxypropan-2-yl)-1H-1,2,4-triazol-5(4H)-one |

| No. | Structure | Name |
|---|---|---|
| 255 | 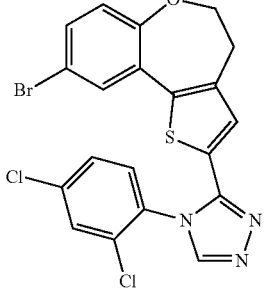 | 3-(9-bromo-4,5-dihydrobenzo[b]thieno[2,3-d]oxepin-2-yl)-4-(2,4-dichlorophenyl)-4H-1,2,4-triazole |
| 256 | 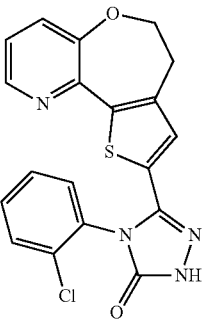 [SMILES: O=c1[nH]nc(-c2cc3c(s2)-c2ncccc2OCC3)n1-c1ccccc1Cl] | 4-(2-chlorophenyl)-3-(10-aza-4,5-dihydrobenzo[b]thieno[2,3-d]oxepin-2-yl)-1H-1,2,4-triazol-5(4H)-one |
| 257 | 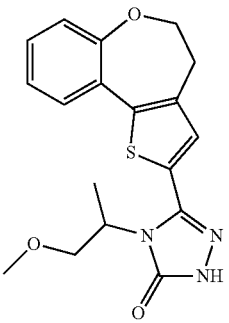 [SMILES: COCC(C)n1c(-c2cc3c(s2)-c2ccccc2OCC3)n[nH]c1=O] | 3-(4,5-dihydrobenzo[b]thieno[2,3-d]oxepin-2-yl)-4-(1-methoxypropan-2-yl)-1H-1,2,4-triazol-5(4H)-one |
| 258 | 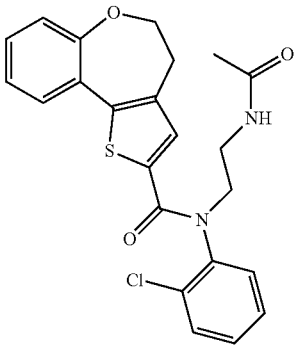 [SMILES: CC(=O)NCCN(C(=O)c1cc2c(s1)-c1ccccc1OCC2)c1ccccc1Cl] | N-(2-acetamidoethyl)-N-(2-chlorophenyl)-4,5-dihydrobenzo[b]thieno[2,3-d]oxepine-2-carboxamide |

TABLE 1-continued

| No. | Structure | Name |
|---|---|---|
| 259 | 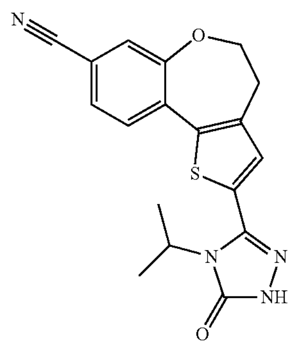 [SMILES: CC(C)n1c(-c2cc3c(s2)-c2ccc(C#N)cc2OCC3)n[nH]c1=O] | 2-(4-isopropyl-5-oxo-4,5-dihydro-1H-1,2,4-triazol-3-yl)-4,5-dihydrobenzo[b]thieno[2,3-d]oxepine-8-carbonitrile |
| 260 | 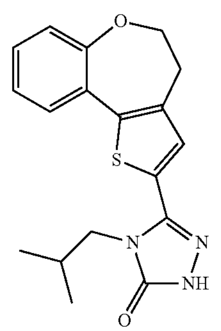 [SMILES: CC(C)Cn1c(-c2cc3c(s2)-c2ccccc2OCC3)n[nH]c1=O] | 3-(4,5-dihydrobenzo[b]thieno[2,3-d]oxepin-2-yl)-4-isobutyl-1H-1,2,4-triazol-5(4H)-one |
| 261 | 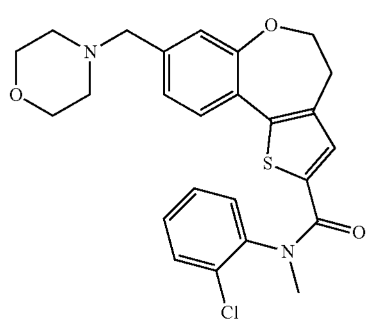 [SMILES: CN(C(=O)c1cc2c(s1)-c1ccc(CN3CCOCC3)cc1OCC2)c1ccccc1Cl] | N-(2-chlorophenyl)-N-methyl-8-(morpholinomethyl)-4,5-dihydrobenzo[b]thieno[2,3-d]oxepine-2-carboxamide |
| 262 | 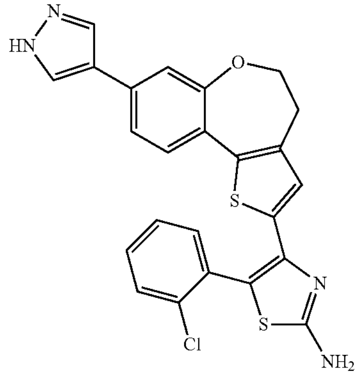 [SMILES: Nc1nc(-c2cc3c(s2)-c2ccc(-c4cn[nH]c4)cc2OCC3)c(-c2ccccc2Cl)s1] | 4-(8-(1H-pyrazol-4-yl)-4,5-dihydrobenzo[b]thieno[2,3-d]oxepin-2-yl)-5-(2-chlorophenyl)thiazol-2-amine |

TABLE 1-continued

| No. | Structure | Name |
|---|---|---|
| 263 | 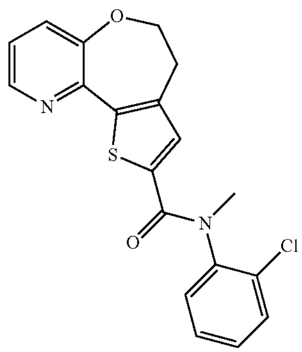 [SMILES: CN(C(=O)c1cc2c(s1)-c1ncccc1OCC2)c1ccccc1Cl] | N-(2-chlorophenyl)-N-methyl-(10-aza-4,5-dihydrobenzo[b]thieno[2,3-d]oxepine-2-carboxamide |
| 264 | 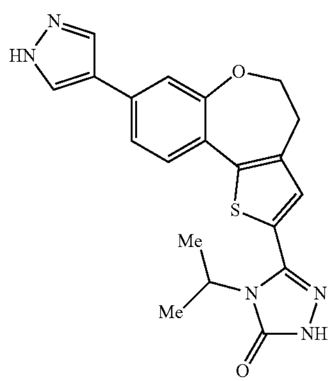 [SMILES: CC(C)n1c(-c2cc3c(s2)-c2ccc(-c4cn[nH]c4)cc2OCC3)n[nH]c1=O] | 3-(8-(1H-pyrazol-4-yl)-4,5-dihydrobenzo[b]thieno[2,3-d]oxepin-2-yl)-4-isopropyl-1H-1,2,4-triazol-5(4H), one |
| 265 | 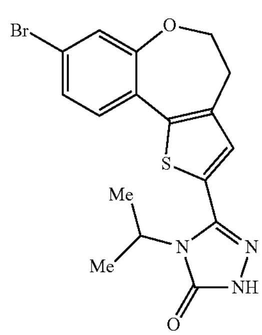 [SMILES: CC(C)n1c(-c2cc3c(s2)-c2ccc(Br)cc2OCC3)n[nH]c1=O] | 3-(8-bromo-4,5-dihydrobenzo[b]thieno[2,3-d]oxepin-2-yl)-4-isopropyl-1H-1,2,4-triazol-5(4H)-one |
| 266 | 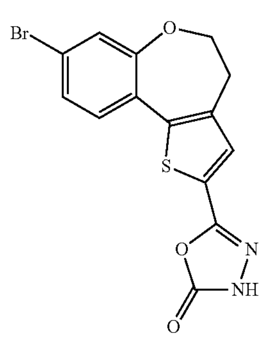 [SMILES: O=c1[nH]nc(-c2cc3c(s2)-c2ccc(Br)cc2OCC3)o1] | 5-(8-bromo-4,5-dihydrobenzo[b]thieno[2,3-d]oxepin-2-yl)-1,3,4-oxadiazol-2(3H)-one |

TABLE 1-continued

| No. | Structure | Name |
|-----|-----------|------|
| 267 | 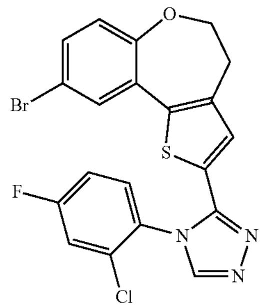 | 3-(9-bromo-4,5-dihydrobenzo[b]thieno[2,3-d]oxepin-2-yl)-4-(2-chloro-4-fluorophenyl)-4H-1,2,4-triazole |
| 268 | 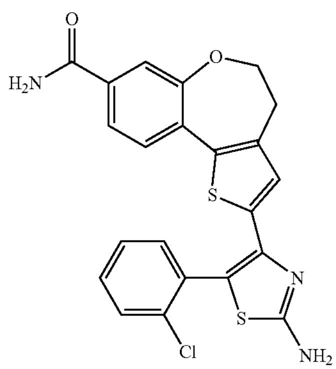 [SMILES: NC(=O)c1ccc2c(c1)OCCc1cc(-c3nc(N)sc3-c3ccccc3Cl)sc1-2] | 2-(2-amino-5-(2-chlorophenyl)thiazol-4-yl)-4,5-dihydrobenzo[b]thieno[2,3-d]oxepine-8-carboxamide |
| 269 | 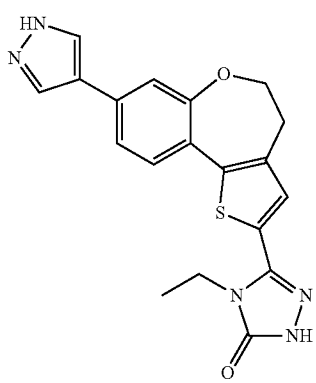 [SMILES: CCn1c(-c2cc3c(s2)-c2ccc(-c4cn[nH]c4)cc2OCC3)n[nH]c1=O] | 3-(8-(1H-pyrazol-4-yl)-4,5-dihydrobenzo[b]thieno[2,3-d]oxepin-2-yl)-4-ethyl-1H-1,2,4-triazol-5(4H)-one |
| 270 | 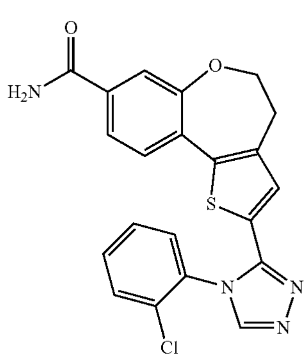 [SMILES: NC(=O)c1ccc2c(c1)OCCc1cc(-c3nncn3-c3ccccc3Cl)sc1-2] | 2-(4-(2-chlorophenyl)-4H-1,2,4-triazol-3-yl)-4,5-dihydrobenzo[b]thieno[2,3-d]oxepine-8-carboxamide |

TABLE 1-continued

| No. | Structure | Name |
|---|---|---|
| 271 | 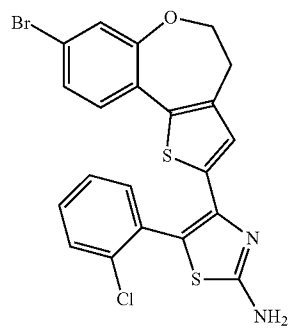 [SMILES: Nc1nc(-c2cc3c(s2)-c2ccc(Br)cc2OCC3)c(-c2ccccc2Cl)s1] | 4-(8-bromo-4,5-dihydrobenzo[b]thieno[2,3-d]oxepin-2-yl)-5-(2-chlorophenyl)thiazol-2-amine |
| 272 | 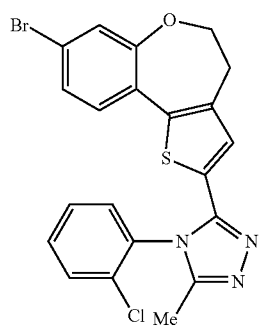 [SMILES: Cc1nnc(-c2cc3c(s2)-c2ccc(Br)cc2OCC3)n1-c1ccccc1Cl] | 3-(8-bromo-4,5-dihydrobenzo[b]thieno[2,3-d]oxepin-2-yl)-4-(2-chlorophenyl)-5-methyl-4H-1,2,4-triazole |
| 273 | 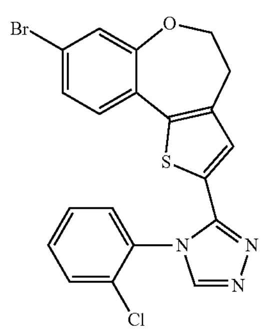 [SMILES: Clc1ccccc1-n1cnnc1-c1cc2c(s1)-c1ccc(Br)cc1OCC2] | 3-(8-bromo-4,5-dihydrobenzo[b]thieno[2,3-d]oxepin-2-yl)-4-(2-chlorophenyl)-4H-1,2,4-triazole |
| 274 | 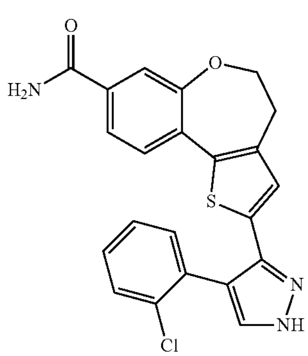 [SMILES: NC(=O)c1ccc2c(c1)OCCc1cc(-c3n[nH]cc3-c3ccccc3Cl)sc1-2] | 2-(4-(2-chlorophenyl)-1H-pyrazol-3-yl)-4,5-dihydrobenzo[b]thieno[2,3-d]oxepine-8-carboxamide |

TABLE 1-continued

| No. | Structure | Name |
|---|---|---|
| 275 | 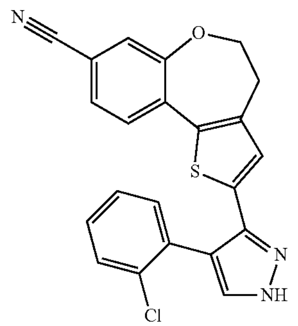 [SMILES: N#Cc1ccc2c(c1)OCCc1cc(-c3n[nH]cc3-c3ccccc3Cl)sc1-2] | 2-(4-(2-chlorophenyl)-1H-pyrazol-3-yl)-4,5-dihydrobenzo[b]thieno[2,3-d]oxepine-8-carbonitrile |
| 276 | 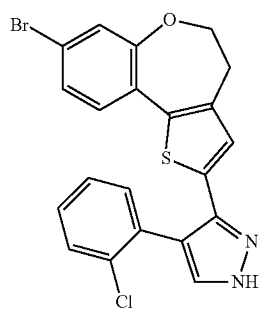 [SMILES: Clc1ccccc1-c1c[nH]nc1-c1cc2c(s1)-c1ccc(Br)cc1OCC2] | 3-(8-bromo-4,5-dihydrobenzo[b]thieno[2,3-d]oxepin-2-yl)-4-(2-chlorophenyl)-1H-pyrazole |
| 277 | 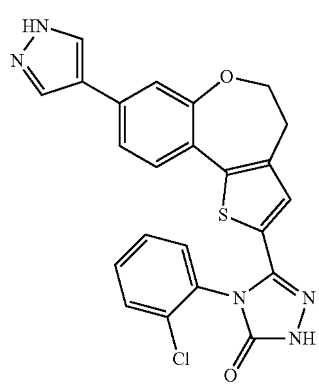 [SMILES: O=c1[nH]nc(-c2cc3c(s2)-c2ccc(-c4cn[nH]c4)cc2OCC3)n1-c1ccccc1Cl] | 3-(8-(1H-pyrazol-4-yl)-4,5-dihydrobenzo[b]thieno[2,3-d]oxepin-2-yl)-4-(2-chlorophenyl)-1H-1,2,4-triazol-5(4H)-one |
| 278 | 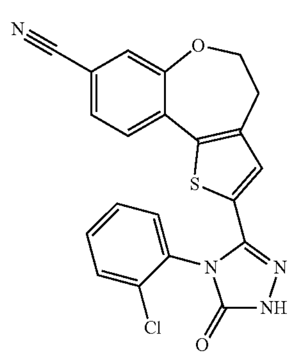 [SMILES: N#Cc1ccc2c(c1)OCCc1cc(-c3n[nH]c(=O)n3-c3ccccc3Cl)sc1-2] | 2-(4-(2-chlorophenyl)-5-oxo-4,5-dihydro-1H-1,2,4-triazol-3-yl)-4,5-dihydrobenzo[b]thieno[2,3-d]oxepine-8-carbonitrile |

TABLE 1-continued

| No. | Structure | Name |
|---|---|---|
| 279 | 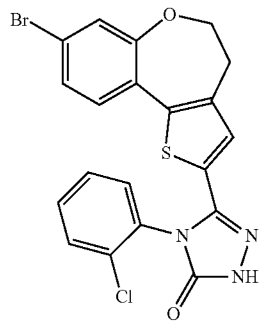 [SMILES: O=c1[nH]nc(-c2cc3c(s2)-c2ccc(Br)cc2OCC3)n1-c1ccccc1Cl] | 3-(8-bromo-4,5-dihydrobenzo[b]thieno[2,3-d]oxepin-2-yl)-4-(2-chlorophenyl)-1H-1,2,4-triazol-5(4H)-one |
| 280 | 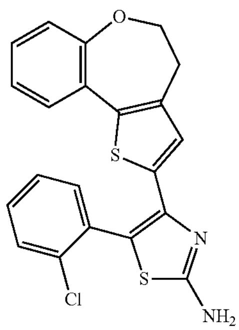 [SMILES: Nc1nc(-c2cc3c(s2)-c2ccccc2OCC3)c(-c2ccccc2Cl)s1] | 5-(2-chlorophenyl)-4-(4,5-dihydrobenzo[b]thieno[2,3-d]oxepin-2-yl)thiazol-2-amine |
| 281 | 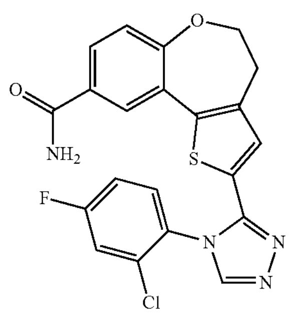 [SMILES: NC(=O)c1ccc2c(c1)-c1sc(-c3nncn3-c3ccc(F)cc3Cl)cc1CCO2] | 2-(4-(2-chloro-4-fluorophenyl)-4H-1,2,4-triazol-3-yl)-4,5-dihydrobenzo[b]thieno[2,3-d]oxepine-9-carboxamide |
| 282 | 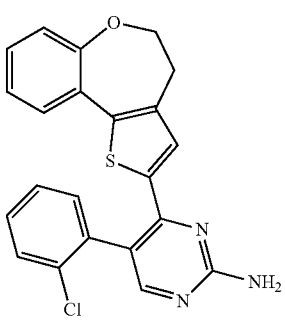 [SMILES: Nc1ncc(-c2ccccc2Cl)c(-c2cc3c(s2)-c2ccccc2OCC3)n1] | 5-(2-chlorophenyl)-4-(4,5-dihydrobenzo[b]thieno[2,3-d]oxepin-2-yl)pyrimidin-2-amine |
| 283 | 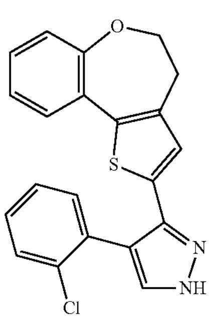 [SMILES: Clc1ccccc1-c1c[nH]nc1-c1cc2c(s1)-c1ccccc1OCC2] | 4-(2-chlorophenyl)-3-(4,5-dihydrobenzo[b]thieno[2,3-d]oxepin-2-yl)-1H-pyrazole |

TABLE 1-continued

| No. | Structure | Name |
|---|---|---|
| 284 | 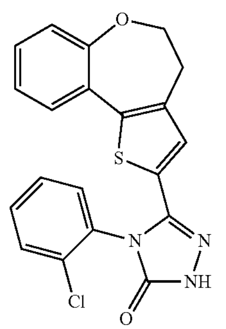 [SMILES: O=c1[nH]nc(-c2cc3c(s2)-c2ccccc2OCC3)n1-c1ccccc1Cl] | 4-(2-chlorophenyl)-3-(4,5-dihydrobenzo[b]thieno[2,3-d]oxepin-2yl)-1H-1,2,4-triazol-5(4H)-one |
| 285 | 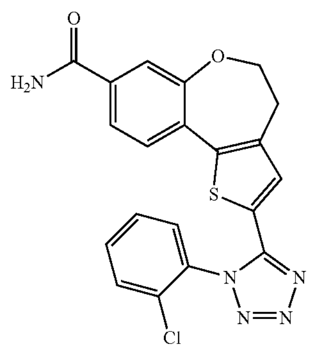 | 2-(1-(2-chlorophenyl)-1H-tetrazol-5-yl)-4,5-dihydrobenzo[b]thieno[2,3-d]oxepine-8-carboxamide |
| 286 | 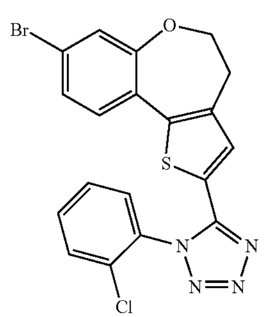 [SMILES: Clc1ccccc1-n1nnnc1-c1cc2c(s1)-c1ccc(Br)cc1OCC2] | 5-(8-bromo-4,5-dihydrobenzo[b]thieno[2,3-d]oxepin-2-yl)-1-(2-chlorophenyl)-1H-tetrazole |
| 287 | 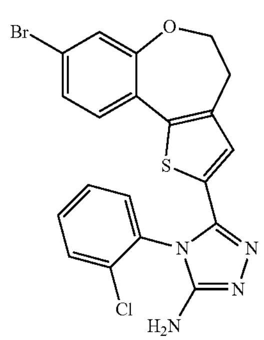 [SMILES: Nc1nnc(-c2cc3c(s2)-c2ccc(Br)cc2OCC3)n1-c1ccccc1Cl] | 5-(8-bromo-4,5-dihydrobenzo[b]thieno[2,3-d]oxepin-2-yl)-4-(2-chlorophenyl)-4H-1,2,4-triazol-3-amine |

TABLE 1-continued

| No. | Structure | Name |
|---|---|---|
| 288 | 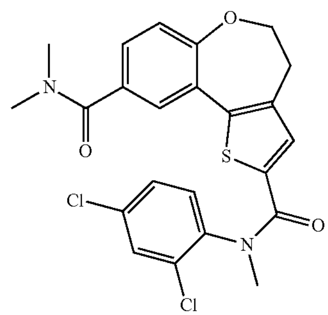 [SMILES: CN(C)C(=O)c1ccc2c(c1)-c1sc(C(=O)N(C)c3ccc(Cl)cc3Cl)cc1CCO2] | N2-(2,4-dichlorophenyl)-N2,N9,N9-trimethyl-4,5-dihydrobenzo[b]thieno[2,3-d]oxepine-2,9-dicarboxamide |
| 289 | 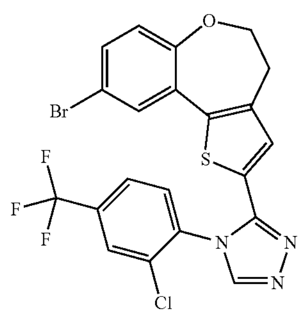 [SMILES: FC(F)(F)c1ccc(-n2cnnc2-c2cc3c(s2)-c2cc(Br)ccc2OCC3)c(Cl)c1] | 3-(9-bromo-4,5-dihydrobenzo[b]thieno[2,3-d]oxepin-2-yl)-4-(2-chloro-4-(trifluoromethyl)phenyl)-4H-1,2,4-triazole |
| 290 | 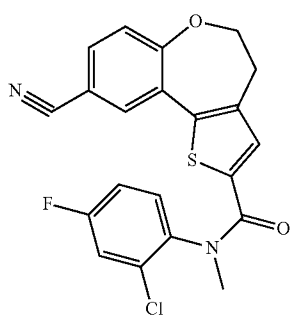 [SMILES: CN(C(=O)c1cc2c(s1)-c1cc(C#N)ccc1OCC2)c1ccc(F)cc1Cl] | N-(2-chloro-4-fluorophenyl)-9-cyano-N-methyl-4,5-dihydrobenzo[b]thieno[2,3-d]oxepine-2-carboxamide |
| 291 | 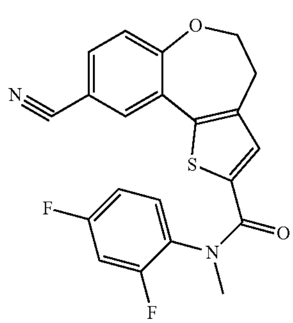 [SMILES: CN(C(=O)c1cc2c(s1)-c1cc(C#N)ccc1OCC2)c1ccc(F)cc1F] | 9-cyano-N-(2,4-difluorophenyl)-N-methyl-4,5-dihydrobenzo[b]thieno[2,3-d]oxepine-2-carboxamide |
| 292 | 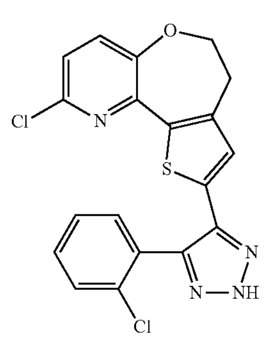 [SMILES: Clc1ccc2c(n1)-c1sc(-c3n[nH]nc3-c3ccccc3Cl)cc1CCO2] | 4-(2-chloro-6,7-dihydropyrido[3,2-b]thieno[2,3-d]oxepin-9-yl)-5-(2-chlorophenyl)-2H-1,2,3-triazole |

TABLE 1-continued

| No. | Structure | Name |
|---|---|---|
| 293 | 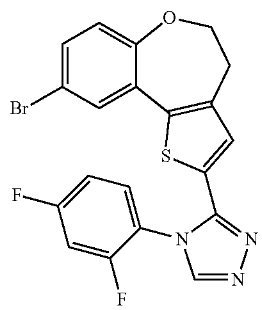 | 3-(9-bromo-4,5-dihydrobenzo[b]thieno[2,3-d]oxepin-2-yl)-4-(2,4-difluorophenyl)-4H-1,2,4-triazole |
| 294 | 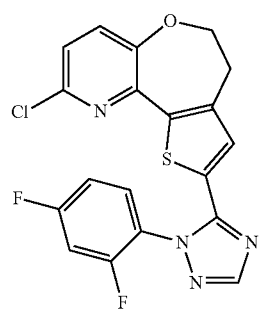 [SMILES: Fc1ccc(-n2ncnc2-c2cc3c(s2)-c2nc(Cl)ccc2OCC3)c(F)c1] | 5-(2-chloro-6,7-dihydropyrido[3,2-b]thieno[2,3-d]oxepin-9-yl)-1-(2,4-difluorophenyl)-1,2,4-triazole |
| 295 | 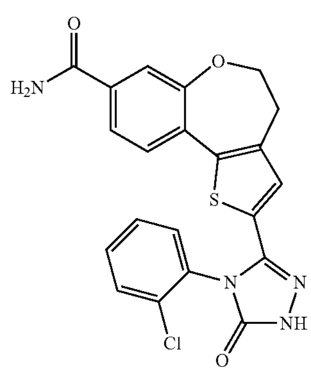 | 2-(4-(2-chlorophenyl)-5-oxo-4,5-dihydro-1H-1,2,4-triazol-3-yl)-4,5-dihydrobenzo[b]thieno[2,3-d]oxepine-8-carboxamide |
| 296 | 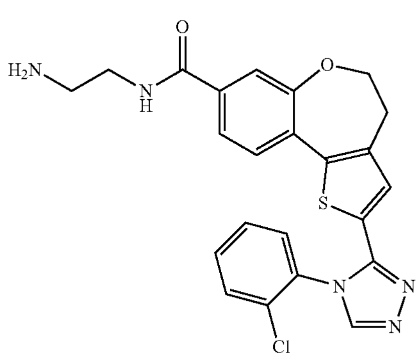 [SMILES: NCCNC(=O)c1ccc2c(c1)OCCc1cc(-c3nncn3-c3ccccc3Cl)sc1-2] | N-(2-aminoethyl)-2-(4-(2-chlorophenyl)-4H-1,2,4-triazol-3-yl)-4,5-dihydrobenzo[b]thieno[2,3-d]oxepine-8-carboxamide |

| No. | Structure | Name |
| --- | --- | --- |
| 297 | 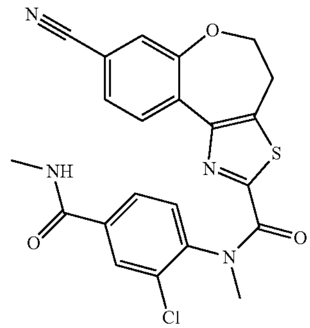 [SMILES: CNC(=O)c1ccc(N(C)C(=O)c2nc3c(s2)CCOc2cc(C#N)ccc2-3)c(Cl)c1] | 8-cyano-4,5-dihydro-6-oxa-1-aza-3-thia-benzo[e]azulene-2-carboxylic acid(2-chloro-(4-methylcarbamoyl)phenyl)-methyl-amide |
| 298 | 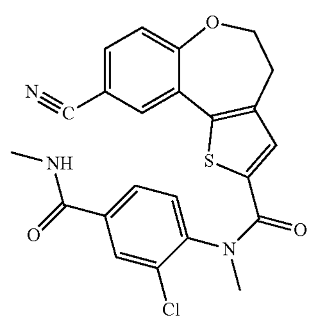 [SMILES: CNC(=O)c1ccc(N(C)C(=O)c2cc3c(s2)-c2cc(C#N)ccc2OCC3)c(Cl)c1] | N-(2-chloro-4-(methylcarbamoyl)phenyl)-9-cyano-N-methyl-4,5-dihydrobenzo[b]thieno[2,3-d]oxepine-2-carboxamide |
| 299 | 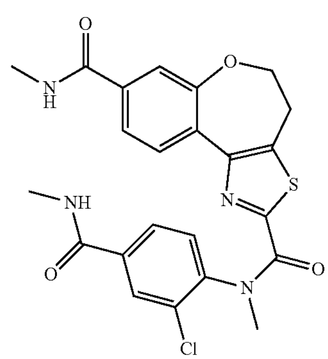 [SMILES: CNC(=O)c1ccc(N(C)C(=O)c2nc3c(s2)CCOc2cc(C(=O)NC)ccc2-3)c(Cl)c1] | 8-methylcarbamoyl-4,5-dihydro-6-oxa-1-aza-3-thia-benzo[e]azulene-2-carboxylic acid(2-chloro-(4-methylcarbamoyl)phenyl)-methyl-amide |
| 300 | 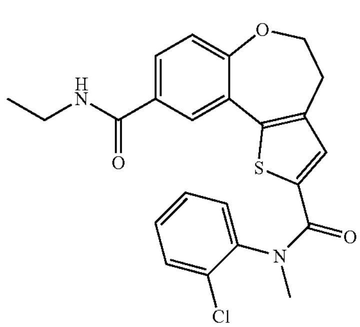 [SMILES: CCNC(=O)c1ccc2c(c1)-c1sc(C(=O)N(C)c3ccccc3Cl)cc1CCO2] | N2-(2-chlorophenyl)-N9-ethyl-N2-methyl-4,5-dihydrobenzo[b]thieno[2,3-d]oxepine-2,9-dicarboxamide |

TABLE 1-continued

| No. | Structure | Name |
|---|---|---|
| 301 | 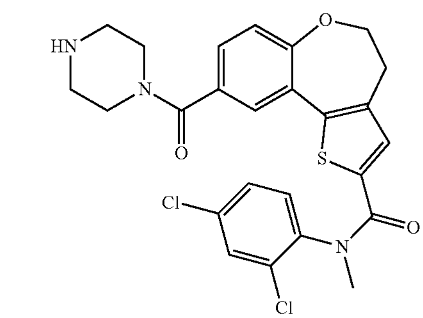 [SMILES: CN(C(=O)c1cc2c(s1)-c1cc(C(=O)N3CCNCC3)ccc1OCC2)c1ccc(Cl)cc1Cl] | N-(2,4-dichlorophenyl)-N-methyl-9-(piperazine-1-carbonyl)-4,5-dihydrobenzo[b]thieno[2,3-d]oxepine-2-carboxamide |
| 302 | 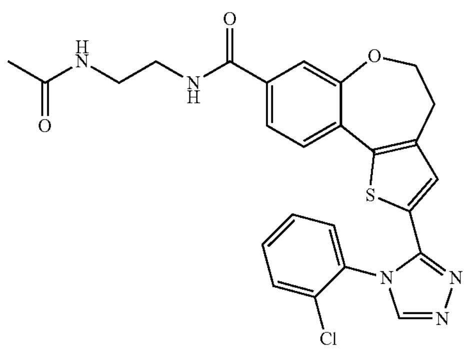 [SMILES: CC(=O)NCCNC(=O)c1ccc2c(c1)OCCc1cc(-c3nncn3-c3ccccc3Cl)sc1-2] | N-(2-acetamidoethyl)-2-(4-(2-chlorophenyl)-4H-1,2,4-triazol-3-yl)-4,5-dihydrobenzo[b]thieno[2,3-d]oxepine-8-carboxamide |
| 303 | 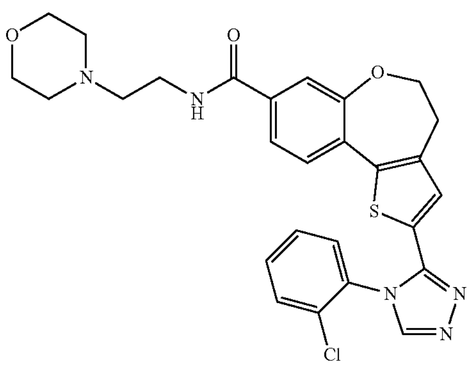 [SMILES: O=C(NCCN1CCOCC1)c1ccc2c(c1)OCCc1cc(-c3nncn3-c3ccccc3Cl)sc1-2] | 2-(4-(2-chlorophenyl)-4H-1,2,4-triazol-3-yl)-N-(2-morpholinoethyl)-4,5-dihydrobenzo[b]thieno[2,3-d]oxepine-8-carboxamide |
| 304 | 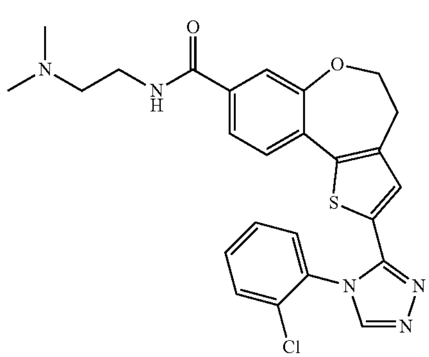 [SMILES: CN(C)CCNC(=O)c1ccc2c(c1)OCCc1cc(-c3nncn3-c3ccccc3Cl)sc1-2] | 2-(4-(2-chlorophenyl)-4H-1,2,4-triazol-3-yl)-N-(2-(dimethylamino)ethyl)-4,5-dihydrobenzo[b]thieno[2,3-d]oxepine-8-carboxamide |

TABLE 1-continued

| No. | Structure | Name |
|---|---|---|
| 305 | 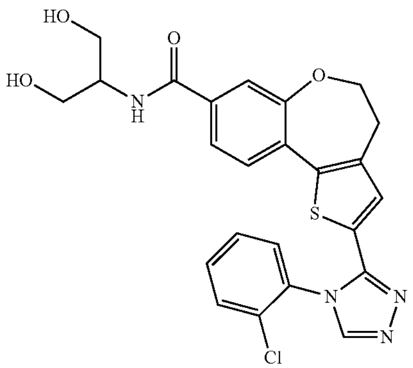 [SMILES: O=C(NC(CO)CO)c1ccc2c(c1)OCCc1cc(-c3nncn3-c3ccccc3Cl)sc1-2] | 2-(4-(2-chlorophenyl)-4H-1,2,4-triazol-3-yl)-N-(1,3-dihydroxypropan-2-yl)-4,5-dihydrobenzo[b]thieno[2,3-d]oxepine-8-carboxamide |
| 306 | 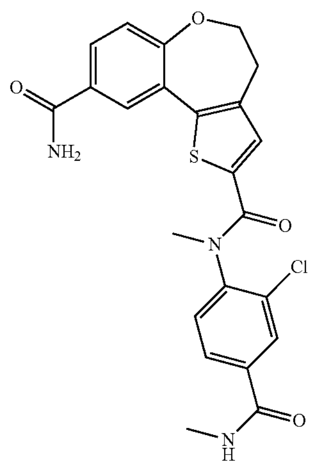 [SMILES: CNC(=O)c1ccc(N(C)C(=O)c2cc3c(s2)-c2cc(C(N)=O)ccc2OCC3)c(Cl)c1] | N2-(2-chloro-4-(methylcarbamoyl)phenyl)-N2-methyl-4,5-dihydrobenzo[b]thieno[2,3-d]oxepine-2,9-dicarboxamide |
| 307 | 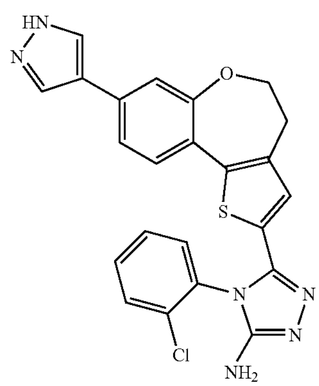 [SMILES: Nc1nnc(-c2cc3c(s2)-c2ccc(-c4cn[nH]c4)cc2OCC3)n1-c1ccccc1Cl] | 5-(8-(1H-pyrazol-4-yl)-4,5-dihydrobenzo[b]thieno[2,3-d]oxepin-2-yl)-4-(2-chlorophenyl)-4H-1,2,4-triazol-3-amine |
| 308 | 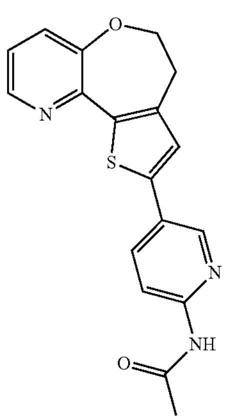 [SMILES: CC(=O)Nc1ccc(-c2cc3c(s2)-c2ncccc2OCC3)cn1] | 5-(6,7-dihydropyrido[3,2-b]thieno[2,3-d]oxepin-9-yl)-2-acetaminopyridine |

TABLE 1-continued

| No. | Structure | Name |
|---|---|---|
| 309 | 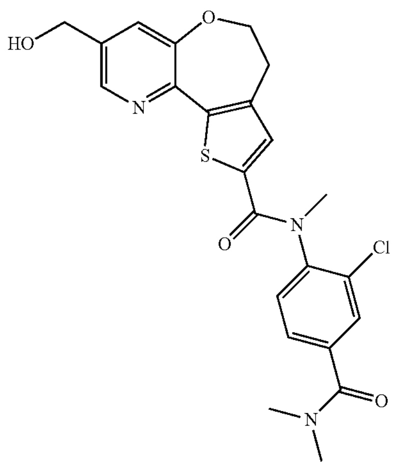 [SMILES: CN(C)C(=O)c1ccc(N(C)C(=O)c2cc3c(s2)-c2ncc(CO)cc2OCC3)c(Cl)c1] | N-(2-chloro-4-(dimethylcarbamoyl)phenyl)-N-methyl-(3-hydroxymethyl-6,7-dihydropyrido[3,2-b]thieno[2,3-d]oxepine)-9-carboxamide |
| 310 | 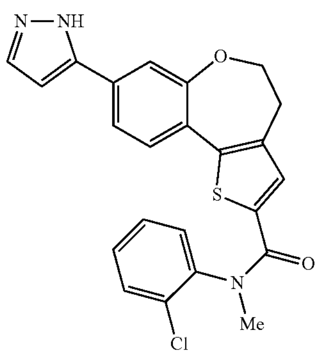 [SMILES: CN(C(=O)c1cc2c(s1)-c1ccc(-c3ccn[nH]3)cc1OCC2)c1ccccc1Cl] | N-(2-chlorophenyl)-N-methyl-8-(1H-pyrazol-5-yl)-4,5-dihydrobenzo[b]thieno[2,3-d]oxepine-2-carboxamide |
| 311 | 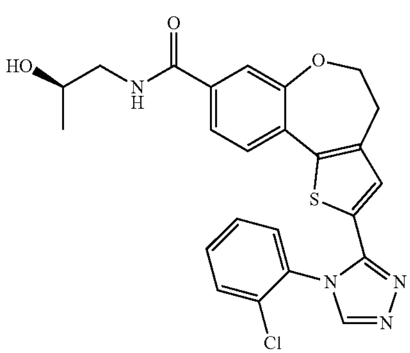 [SMILES: C[C@@H](O)CNC(=O)c1ccc2c(c1)OCCc1cc(-c3nncn3-c3ccccc3Cl)sc1-2] | 2-(4-(2-chlorophenyl)-4H-1,2,4-triazol-3-yl)-N-((R)-2-hydroxypropyl)-4,5-dihydrobenzo[b]thieno[2,3-d]oxepine-8-carboxamide |
| 312 | 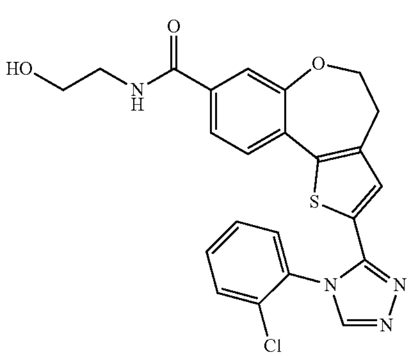 [SMILES: O=C(NCCO)c1ccc2c(c1)OCCc1cc(-c3nncn3-c3ccccc3Cl)sc1-2] | 2-(4-(2-chlorophenyl)-4H-1,2,4-triazol-3-yl)-N-(2-hydroxyethyl)-4,5-dihydrobenzo[b]thieno[2,3-d]oxepine-8-carboxamide |

TABLE 1-continued

| No. | Structure | Name |
|---|---|---|
| 313 | 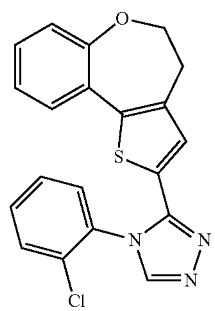 [SMILES: Clc1ccccc1-n1cnnc1-c1cc2c(s1)-c1ccccc1OCC2] | 4-(2-chlorophenyl)-3-(4,5-dihydrobenzo[b]thieno[2,3-d]oxepin-2-yl)-4H-1,2,4-triazole |
| 314 | 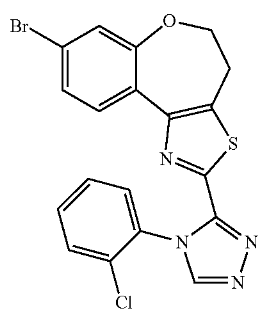 [SMILES: Clc1ccccc1-n1cnnc1-c1nc2c(s1)CCOc1cc(Br)ccc1-2] | 8-bromo-2-[4-(2-chloro-phenyl)-4H-[1,2,4]triazol-3-yl]-4,5-dihydro-6-oxa-3 thia-1-aza-benzo[e]azulene |
| 315 | 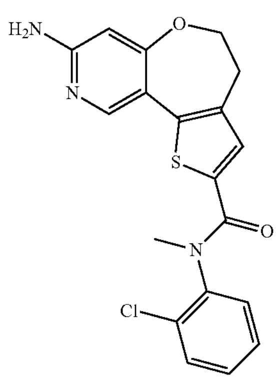 [SMILES: CN(C(=O)c1cc2c(s1)-c1cnc(N)cc1OCC2)c1ccccc1Cl] | N-(2-chlorophenyl)-N-methyl-(8-amino-4,5-dihydropyrido-[4,3-b]thieno[2,3-d]oxepin-2)-carboxamide |
| 316 | 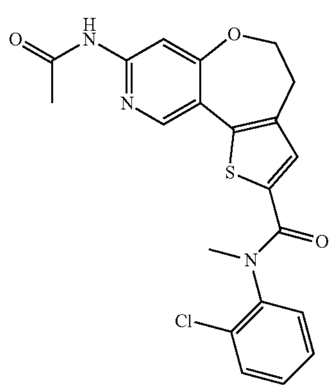 [SMILES: CC(=O)Nc1cc2c(cn1)-c1sc(C(=O)N(C)c3ccccc3Cl)cc1CCO2] | N-(2-chlorophenyl)-N-methyl-(8-acetamino-4,5-dihydropyrido-[4,3-b]thieno[2,3-d]oxepin-2)-carboxamide |

TABLE 1-continued

| No. | Structure | Name |
|---|---|---|
| 317 | 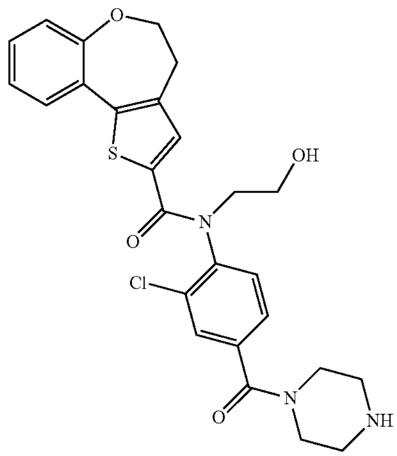 [SMILES: O=C(c1ccc(N(CCO)C(=O)c2cc3c(s2)-c2ccccc2OCC3)c(Cl)c1)N1CCNCC1] | N-(2-chloro-4-(piperazine-1-carbonyl)phenyl)-N-(2-hydroxyethyl)-4,5-dihydrobenzo[b]thieno[2,3-d]oxepine-2-carboxamide |
| 318 | 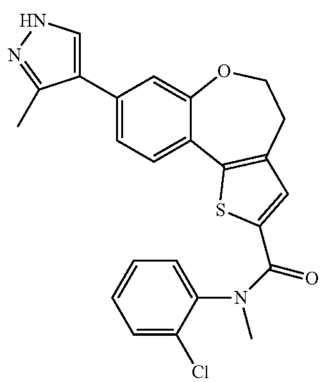 [SMILES: Cc1n[nH]cc1-c1ccc2c(c1)OCCc1cc(C(=O)N(C)c3ccccc3Cl)sc1-2] | N-(2-chlorophenyl)-N-methyl-8-(3-methyl-1H-pyrazol-4-yl)-4,5-dihydrobenzo[b]thieno[2,3-d]oxepine-2-carboxamide |
| 319 | 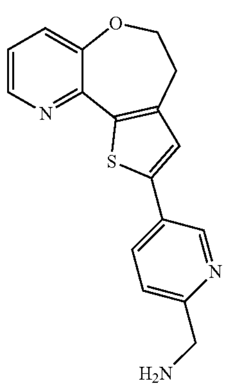 [SMILES: NCc1ccc(-c2cc3c(s2)-c2ncccc2OCC3)cn1] | 5-(6,7-dihydropyrido[3,2-b]thieno[2,3-d]oxepin-9-yl)pyridin-2-methylamine |
| 320 | 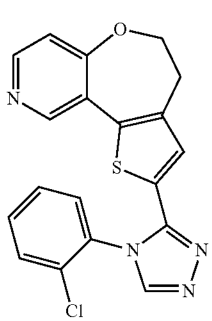 [SMILES: Clc1ccccc1-n1cnnc1-c1cc2c(s1)-c1cnccc1OCC2] | 3-(4,5-dihydropyrido[4,3-b]thieno[2,3-d]oxepin-2-yl)-4-(2-chlorophenyl)-4H-1,2,4-triazole |

TABLE 1-continued

| No. | Structure | Name |
| --- | --- | --- |
| 321 | 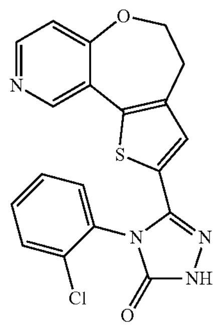 [SMILES: O=c1[nH]nc(-c2cc3c(s2)-c2cnccc2OCC3)n1-c1ccccc1Cl] | 3-(4,5-dihydropyrido[4,3-b]thieno[2,3-d]oxepin-2-yl)-4-(2-chlorophenyl)-1H-1,2,4-triazol-5(4H)-one |
| 322 | 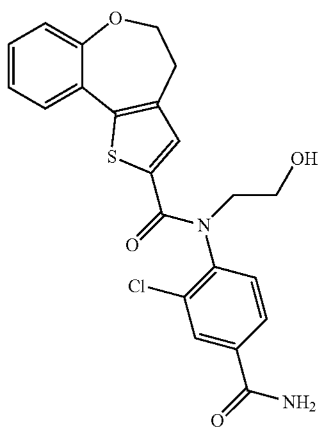 | N-(4-carbamoyl-2-chlorophenyl)-N-(2-hydroxyethyl)-4,5-dihydrobenzo[b]thieno[2,3-d]oxepine-2-carboxamide |
| 323 | 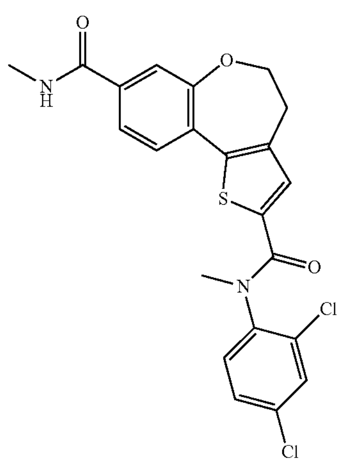 [SMILES: CNC(=O)c1ccc2c(c1)OCCc1cc(C(=O)N(C)c3ccc(Cl)cc3Cl)sc1-2] | N2-(2,4-dichlorophenyl)-N2,N8-dimethyl-4,5-dihydrobenzo[b]thieno[2,3-d]oxepine-2,8-dicarboxamide |
| 324 | 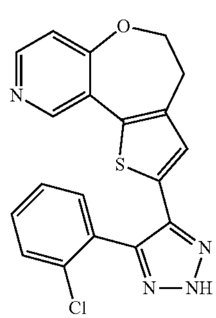 [SMILES: Clc1ccccc1-c1n[nH]nc1-c1cc2c(s1)-c1cnccc1OCC2] | 4-(4,5-dihydropyrido[4,3-b]thieno[2,3-d]oxepin-2-yl)-5-(2-chlorophenyl)-2H-1,2,3-triazole |

| No. | Structure | Name |
| --- | --- | --- |
| 325 | 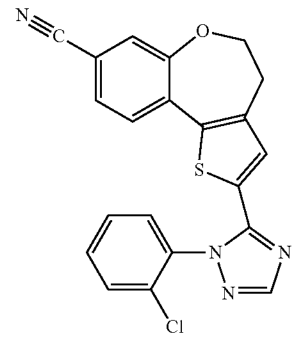 [SMILES: N#Cc1ccc2c(c1)OCCc1cc(-c3ncnn3-c3ccccc3Cl)sc1-2] | 2-(1-(2-chlorophenyl)-1H-1,2,4-triazol-5-yl)-4,5-dihydrobenzo[b]thieno[2,3-d]oxepine-8-carbonitrile |
| 326 | 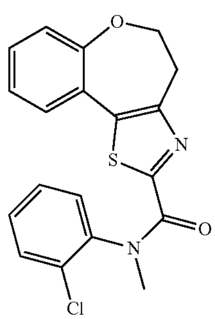 [SMILES: CN(C(=O)c1nc2c(s1)-c1ccccc1OCC2)c1ccccc1Cl] | 4,5-dihydro-6-oxa-1-thia-3-aza-benzo[e]azulene-2-carboxylic acid(2-chloro-phenyl)-methyl-amide |
| 327 | 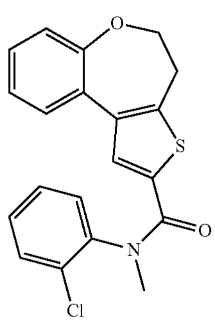 [SMILES: CN(C(=O)c1cc2c(s1)CCOc1ccccc1-2)c1ccccc1Cl] | N-(2-chlorophenyl)-N-methyl-4,5-dihydrobenzo[b]thieno[3,2-d]oxepine-2-carboxamide |
| 328 | 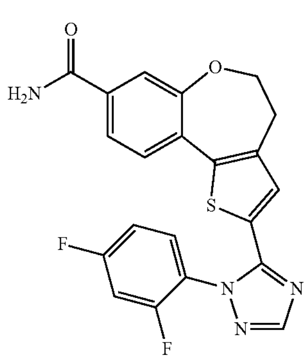 [SMILES: NC(=O)c1ccc2c(c1)OCCc1cc(-c3ncnn3-c3ccc(F)cc3F)sc1-2] | 2-(1-(2,4-difluorophenyl)-1H-1,2,4-triazol-5-yl)-4,5-dihydrobenzo[b]thieno[2,3-d]oxepine-8 carboxamide |

TABLE 1-continued

| No. | Structure | Name |
|---|---|---|
| 329 | 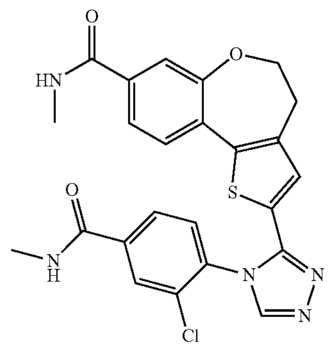 [SMILES: CNC(=O)c1ccc(-n2cnnc2-c2cc3c(s2)-c2ccc(C(=O)NC)cc2OCC3)c(Cl)c1] | 2-(4-(2-chloro-4-(methylcarbamoyl)phenyl)-4H-1,2,4-triazol-3-yl)-N-methyl-4,5-dihydrobenzo[b]thieno[2,3-d]oxepine-8-carboxamide |
| 330 | 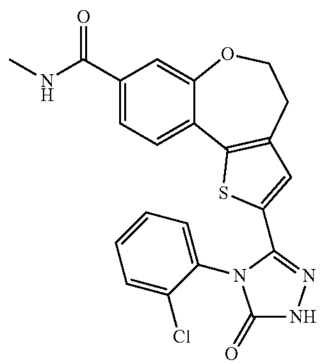 [SMILES: CNC(=O)c1ccc2c(c1)OCCc1cc(-c3n[nH]c(=O)n3-c3ccccc3Cl)sc1-2] | 2-(4-(2-chlorophenyl)-5-oxo-4,5-dihydro-1H-1,2,4-triazol-3-yl)-N-methyl-4,5-dihydrobenzo[b]thieno[2,3-d]oxepine-8-carboxamide |
| 331 | 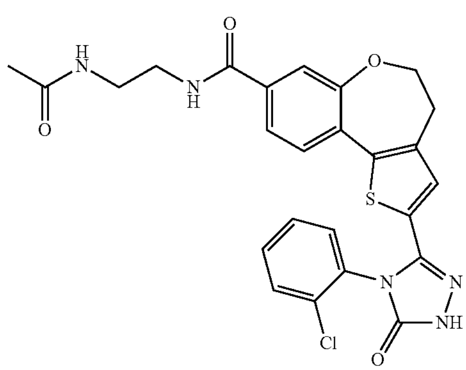 [SMILES: CC(=O)NCCNC(=O)c1ccc2c(c1)OCCc1cc(-c3n[nH]c(=O)n3-c3ccccc3Cl)sc1-2] | N-(2-acetamidoethyl)-2-(4-(2-chlorophenyl)-5-oxo-4,5-dihydro-1H-1,2,4-triazol-3-yl)-4,5-dihydrobenzo[b]thieno[2,3-d]oxepine-8-carboxamide |
| 332 | 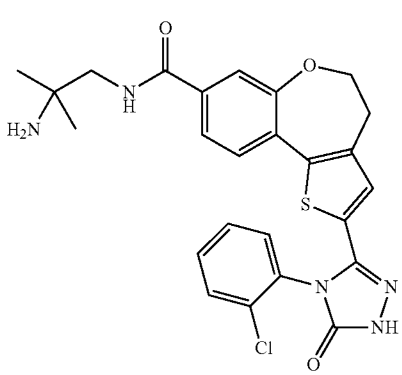 [SMILES: CC(C)(N)CNC(=O)c1ccc2c(c1)OCCc1cc(-c3n[nH]c(=O)n3-c3ccccc3Cl)sc1-2] | N-(2-amino-2-methylpropyl)-2-(4-(2-chlorophenyl)-5-oxo-4,5-dihydro-1H-1,2,4-triazol-3-yl)-4,5-dihydrobenzo[b]thieno[2,3-d]oxepine-8-carboxamide |

TABLE 1-continued

| No. | Structure | Name |
|---|---|---|
| 333 | 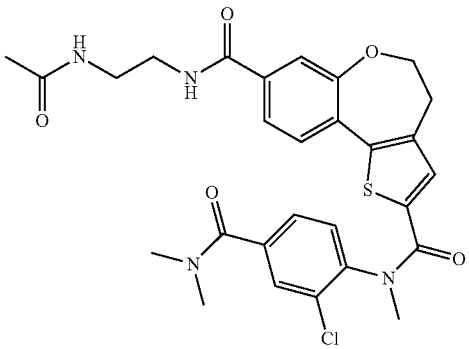 [SMILES: CC(=O)NCCNC(=O)c1ccc2c(c1)OCCc1cc(C(=O)N(C)c3ccc(C(=O)N(C)C)cc3Cl)sc1-2] | N8-(2-acetamidoethyl)-N2-(2-chloro-4-(dimethylcarbamoyl)phenyl)-N2-methyl-4,5-dihydrobenzo[b]thieno[2,3-d]oxepine-2,8-dicarboxamide |
| 334 | 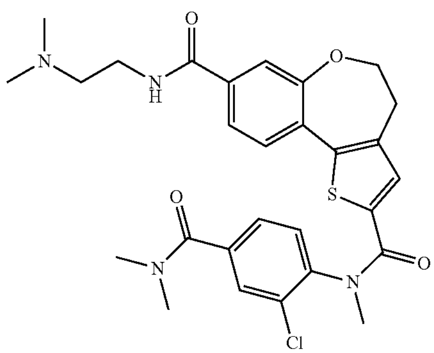 [SMILES: CN(C)CCNC(=O)c1ccc2c(c1)OCCc1cc(C(=O)N(C)c3ccc(C(=O)N(C)C)cc3Cl)sc1-2] | N2-(2-chloro-4-(dimethylcarbamoyl)phenyl)-N8-(2-(dimethylamino)ethyl)-N2-methyl-4,5-dihydrobenzo[b]thieno[2,3-d]oxepine-2,8-dicarboxamide |
| 335 | 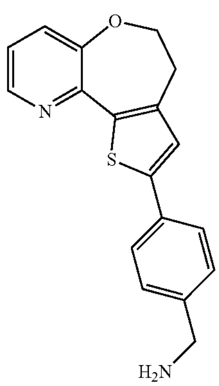 [SMILES: NCc1ccc(-c2cc3c(s2)-c2ncccc2OCC3)cc1] | 5-(6,7-dihydropyrido[3,2-b]thieno[2,3-d]oxepin-9-yl)benzen-2-methylamine |
| 336 | 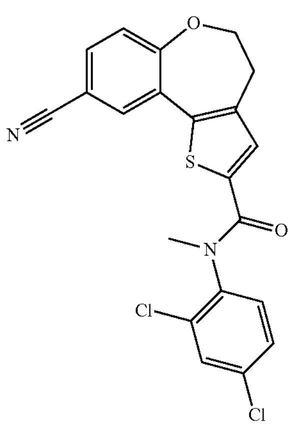 [SMILES: CN(C(=O)c1cc2c(s1)-c1cc(C#N)ccc1OCC2)c1ccc(Cl)cc1Cl] | 9-cyano-N-(2,4-dichlorophenyl)-N-methyl-4,5-dihydrobenzo[b]thieno[2,3-d]oxepine-2-carboxamide |

TABLE 1-continued

| No. | Structure | Name |
|---|---|---|
| 337 | 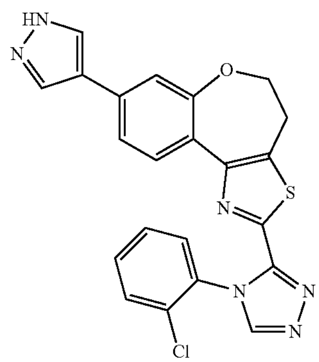 [SMILES: Clc1ccccc1-n1cnnc1-c1nc2c(s1)CCOc1cc(-c3cn[nH]c3)ccc1-2] | 3-(8-(pyrazol-4-yl)-4,5-dihydro-6-oxa-1-aza-3-thia-benzo[e]azulen-2-yl)-4-(2-chlorophenyl)-4H-1,2,4-triazole |
| 338 | 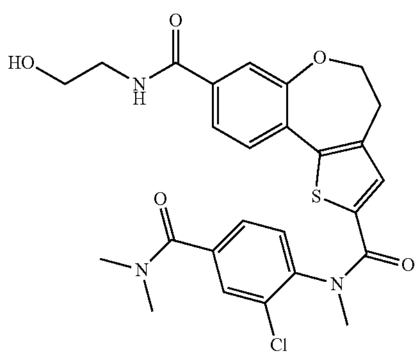 [SMILES: CN(C)C(=O)c1ccc(N(C)C(=O)c2cc3c(s2)-c2ccc(C(=O)NCCO)cc2OCC3)c(Cl)c1] | N2-(2-chloro-4-(dimethylcarbamoyl)phenyl)-N8-(2-hydroxyethyl)-N2-methyl-4,5-dihydrobenzo[b]thieno[2,3-d]oxepine-2,8-dicarboxamide |
| 339 | 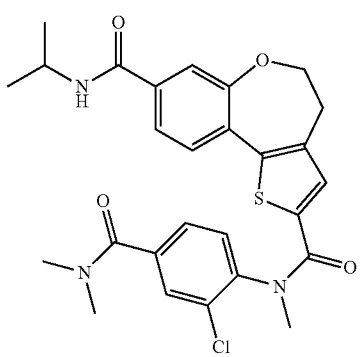 [SMILES: CC(C)NC(=O)c1ccc2c(c1)OCCc1cc(C(=O)N(C)c3ccc(C(=O)N(C)C)cc3Cl)sc1-2] | N2-(2-chloro-4-(dimethylcarbamoyl)phenyl)-N8-isopropyl-N2-methyl-4,5-dihydrobenzo[b]thieno[2,3-d]oxepine-2,8-dicarboxamide |
| 340 | 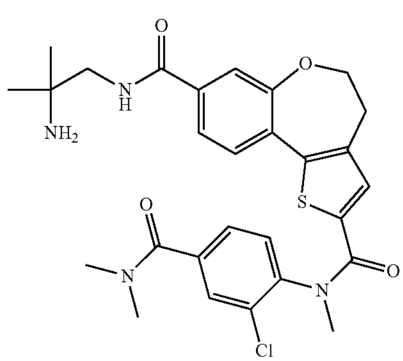 [SMILES: CN(C)C(=O)c1ccc(N(C)C(=O)c2cc3c(s2)-c2ccc(C(=O)NCC(C)(C)N)cc2OCC3)c(Cl)c1] | N8-(2-amino-2-methylpropyl)-N2-(2-chloro-4-(dimethylcarbamoyl)phenyl)-N2-methyl-4,5-dihydrobenzo[b]thieno[2,3-d]oxepine-2,8-dicarboxamide |

TABLE 1-continued

| No. | Structure | Name |
|---|---|---|
| 341 | 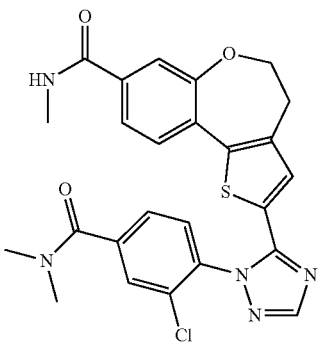 [SMILES: CNC(=O)c1ccc2c(c1)OCCc1cc(-c3ncnn3-c3ccc(C(=O)N(C)C)cc3Cl)sc1-2] | 2-(1-(2-chloro-4-(dimethylcarbamoyl)phenyl)-1H-1,2,4-triazol-5-yl)-N-methyl-4,5-dihydrobenzo[b]thieno[2,3-d]oxepine-8-carboxamide |
| 342 | 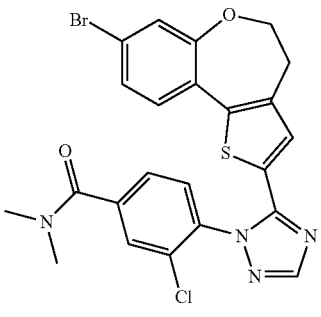 [SMILES: CN(C)C(=O)c1ccc(-n2ncnc2-c2cc3c(s2)-c2ccc(Br)cc2OCC3)c(Cl)c1] | 4-(5-(8-bromo-4,5-dihydrobenzo[b]thieno[2,3-d]oxepin-2-yl)-1H-1,2,4-triazol-1-yl)-3-chloro-N,N-dimethylbenzamide |
| 343 | 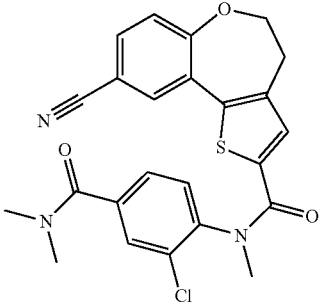 [SMILES: CN(C)C(=O)c1ccc(N(C)C(=O)c2cc3c(s2)-c2cc(C#N)ccc2OCC3)c(Cl)c1] | N-(2-chloro-4-(dimethylcarbamoyl)phenyl)-9-cyano-N-methyl-4,5-dihydrobenzo[b]thieno[2,3-d]oxepine-2-carboxamide |
| 344 | 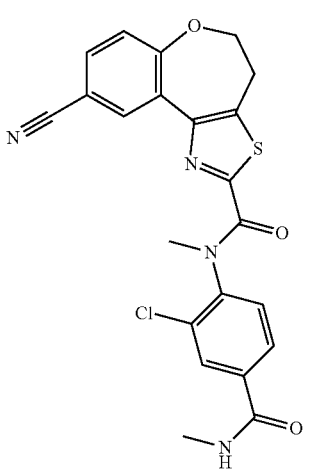 [SMILES: CNC(=O)c1ccc(N(C)C(=O)c2nc3c(s2)CCOc2ccc(C#N)cc2-3)c(Cl)c1] | 2-(9-cyano-4,5-dihydro-6-oxa-1-aza-3-thia-benzo[e]azulene)-N-(2-chloro-4-(methylcarbamoyl)phenyl)-N-methyl-carboxamide |

| No. | Structure | Name |
|---|---|---|
| 345 | 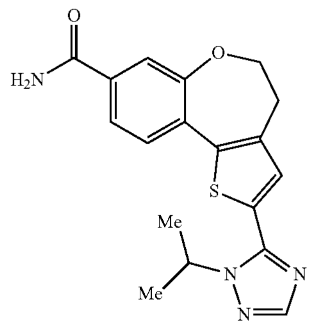 [SMILES: CC(C)n1ncnc1-c1cc2c(s1)-c1ccc(C(N)=O)cc1OCC2] | 2-(1-isopropyl-1H-1,2,4-triazol-5-yl)-4,5-dihydrobenzo[b]thieno[2,3-d]oxepine-8-carboxamide |
| 346 | 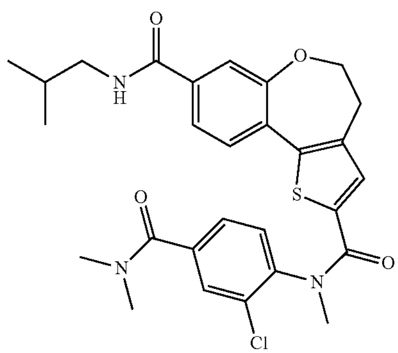 [SMILES: CC(C)CNC(=O)c1ccc2c(c1)OCCc1cc(C(=O)N(C)c3ccc(C(=O)N(C)C)cc3Cl)sc1-2] | N2-(2-chloro-4-(dimethylcarbamoyl)phenyl)-N8-isobutyl-N2-methyl-4,5-dihydrobenzo[b]thieno[2,3-d]oxepine-2,8-dicarboxamide |
| 347 | 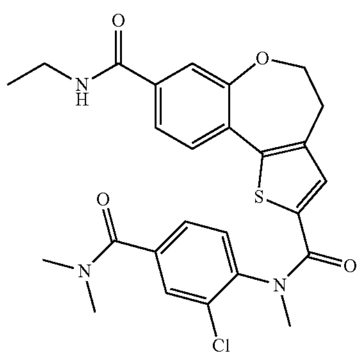 [SMILES: CCNC(=O)c1ccc2c(c1)OCCc1cc(C(=O)N(C)c3ccc(C(=O)N(C)C)cc3Cl)sc1-2] | N2-(2-chloro-4-(dimethylcarbamoyl)phenyl)-N8-ethyl-N2-methyl-4,5-dihydrobenzo[b]thieno[2,3-d]oxepine-2,8-dicarboxamide |
| 348 | 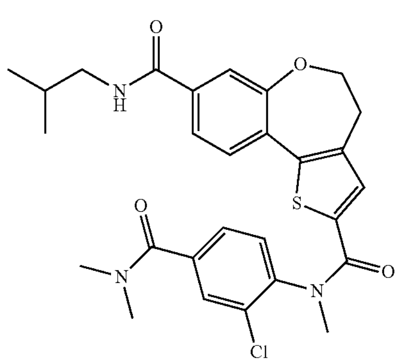 [SMILES: CC(C)CNC(=O)c1ccc2c(c1)OCCc1cc(C(=O)N(C)c3ccc(C(=O)N(C)C)cc3Cl)sc1-2] | N2-(2-chloro-4-(dimethylcarbamoyl)phenyl)-N8-isobutyl-N2-methyl-4,5-dihydrobenzo[b]thieno[2,3-d]oxepine-2,8-dicarboxamide |

TABLE 1-continued

| No. | Structure | Name |
|---|---|---|
| 349 | 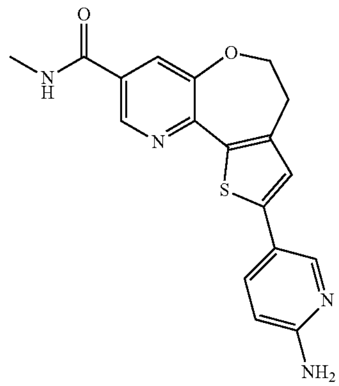 [SMILES: CNC(=O)c1cnc2c(c1)OCCc1cc(-c3ccc(N)nc3)sc1-2] | 5-(3-methylcarbamoyl-6,7-dihydropyrido[3,2-b]thieno[2,3-d]oxepin-9-yl)pyridin-2-amine |
| 350 | 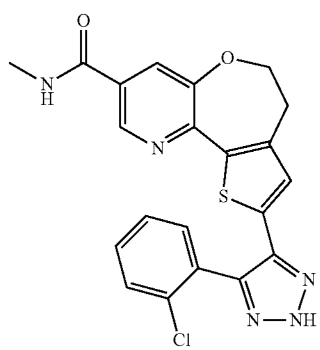 [SMILES: CNC(=O)c1cnc2c(c1)OCCc1cc(-c3n[nH]nc3-c3ccccc3Cl)sc1-2] | 4-(3-methylcarbamoyl-6,7-dihydropyrido[3,2-b]thieno[2,3-d]oxepin-9-yl)-5-(2-chlorophenyl)-2H-1,2,3-triazole |
| 351 | 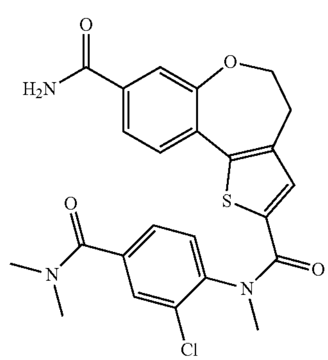 [SMILES: CN(C)C(=O)c1ccc(N(C)C(=O)c2cc3c(s2)-c2ccc(C(N)=O)cc2OCC3)c(Cl)c1] | N2-(2-chloro-4-(dimethylcarbamoyl)phenyl)-N2-methyl-4,5-dihydrobenzo[b]thieno[2,3-d]oxepine-2,8-dicarboxamide |
| 352 | 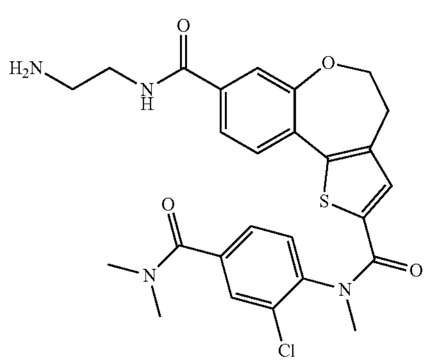 [SMILES: CN(C)C(=O)c1ccc(N(C)C(=O)c2cc3c(s2)-c2ccc(C(=O)NCCN)cc2OCC3)c(Cl)c1] | N8-(2-aminoethyl)-N2-(2-chloro-4-(dimethylcarbamoyl)phenyl)-N2-methyl-4,5-dihydrobenzo[b]thieno[2,3-d]oxepine-2,8-dicarboxamide |

TABLE 1-continued

| No. | Structure | Name |
|---|---|---|
| 353 | 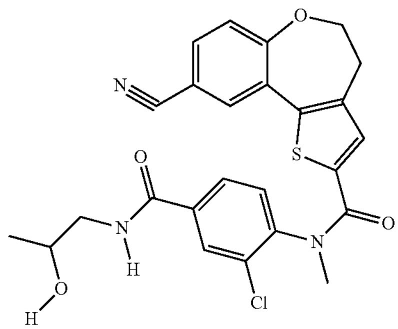 [SMILES: CC(O)CNC(=O)c1ccc(N(C)C(=O)c2cc3c(s2)-c2cc(C#N)ccc2OCC3)c(Cl)c1] | N-(2-chloro-4-(2-hydroxypropylcarbamoyl)phenyl)-9-cyano-N-methyl-4,5-dihydrobenzo[b]thieno[2,3-d]oxepine-2-carboxamide |
| 354 | 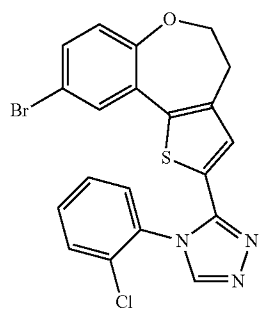 [SMILES: Clc1ccccc1-n1cnnc1-c1cc2c(s1)-c1cc(Br)ccc1OCC2] | 3-(9-bromo-4,5-dihydrobenzo[b]thieno[2,3-d]oxepin-2-yl)-4-(2-chlorophenyl)-4H-1,2,4-triazole |
| 355 | 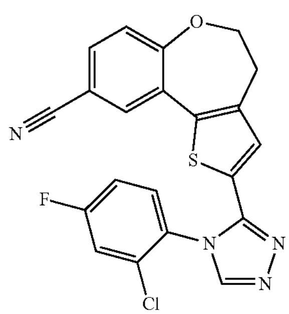 [SMILES: N#Cc1ccc2c(c1)-c1sc(-c3nncn3-c3ccc(F)cc3Cl)cc1CCO2] | 2-(4-(2-chloro-4-fluorophenyl)-4H-1,2,4-triazol-3-yl)-4,5-dihydrobenzo[b]thieno[2,3-d]oxepine-9-carbonitrile |
| 356 | 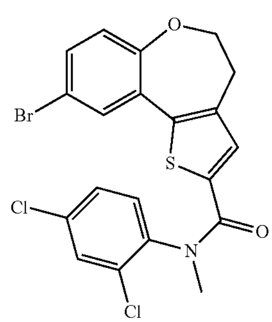 [SMILES: CN(C(=O)c1cc2c(s1)-c1cc(Br)ccc1OCC2)c1ccc(Cl)cc1Cl] | 9-bromo-N-(2,4-dichlorophenyl)-N-methyl-4,5-dihydrobenzo[b]thieno[2,3-d]oxepine-2-carboxamide |
| 357 | 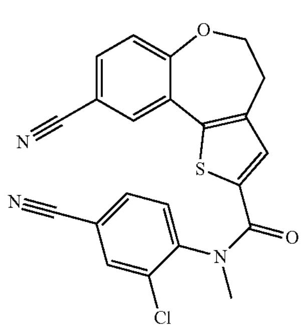 [SMILES: CN(C(=O)c1cc2c(s1)-c1cc(C#N)ccc1OCC2)c1ccc(C#N)cc1Cl] | N-(2-chloro-4-cyanophenyl)-9-cyano-N-methyl-4,5-dihydrobenzo[b]thieno[2,3-d]oxepine-2-carboxamide |

TABLE 1-continued

| No. | Structure | Name |
| --- | --- | --- |
| 358 | 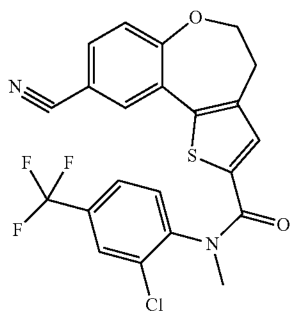 [SMILES: CN(C(=O)c1cc2c(s1)-c1cc(C#N)ccc1OCC2)c1ccc(C(F)(F)F)cc1Cl] | N-(2-chloro-4-(trifluoromethyl)phenyl)-9-cyano-N-methyl-4,5-dihydrobenzo[b]thieno[2,3-d]oxepine-2-carboxamide |
| 359 | 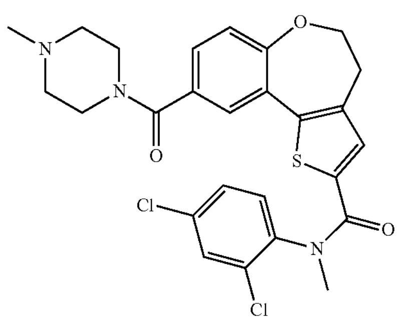 [SMILES: CN1CCN(C(=O)c2ccc3c(c2)-c2sc(C(=O)N(C)c4ccc(Cl)cc4Cl)cc2CCO3)CC1] | N-(2,4-dichlorophenyl)-N-methyl-9-(4-methylpiperazine-1-carbonyl)-4,5-dihydrobenzo[b]thieno[2,3-d]oxepine-2-carboxamide |
| 360 | 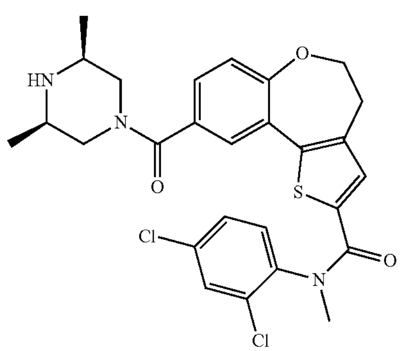 [SMILES: C[C@@H]1CN(C(=O)c2ccc3c(c2)-c2sc(C(=O)N(C)c4ccc(Cl)cc4Cl)cc2CCO3)C[C@H](C)N1] | N-(2,4-dichlorophenyl)-9-((3S,5R)-3,5-dimethylpiperazine-1-carbonyl)-N-methyl-4,5-dihydrobenzo[b]thieno[2,3-d]oxepine-2-carboxamide |
| 361 | 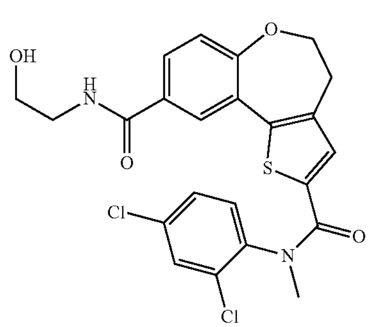 [SMILES: CN(C(=O)c1cc2c(s1)-c1cc(C(=O)NCCO)ccc1OCC2)c1ccc(Cl)cc1Cl] | N2-(2,4-dichlorophenyl)-N9-(2-hydroxyethyl)-N2-methyl-4,5-dihydrobenzo[b]thieno[2,3-d]oxepine-2,9-dicarboxamide |

TABLE 1-continued

| No. | Structure | Name |
| --- | --- | --- |
| 362 | 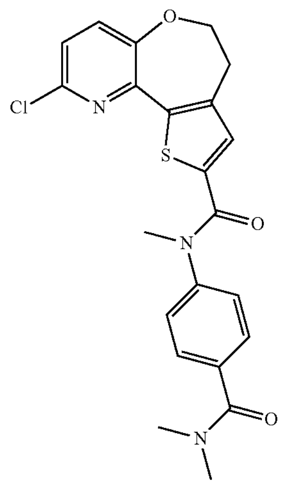 [SMILES: CN(C)C(=O)c1ccc(N(C)C(=O)c2cc3c(s2)-c2nc(Cl)ccc2OCC3)cc1] | N-(4-(dimethylcarbamoyl)phenyl)-N-methyl-(2-chloro-6,7-dihydropyrido[3,2-b]thieno[2,3-d]oxepine)-9-carboxamide |
| 363 | 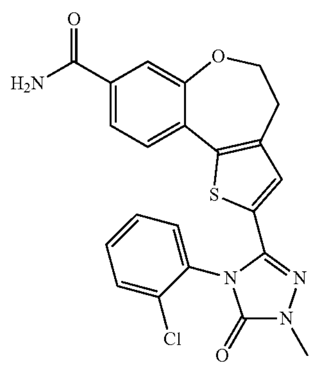 [SMILES: Cn1nc(-c2cc3c(s2)-c2ccc(C(N)=O)cc2OCC3)n(-c2ccccc2Cl)c1=O] | 2-(4-(2-chlorophenyl)-1-methyl-5-oxo-4,5-dihydro-1H-1,2,4-triazol-3-yl)-4,5-dihydrobenzo[b]thieno[2,3-d]oxepine-8-carboxamide |
| 364 | 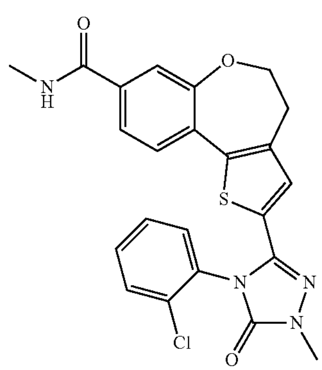 | 2-(4-(2-chlorophenyl)-1-methyl-5-oxo-4,5-dihydro-1H-1,2,4-triazol-3-yl)-N-methyl-4,5-dihydrobenzo[b]thieno[2,3-d]oxepine-8-carboxamide |
| 365 | 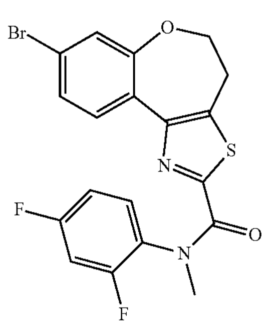 [SMILES: CN(C(=O)c1nc2c(s1)CCOc1cc(Br)ccc1-2)c1ccc(F)cc1F] | 2-(8-bromo-4,5-dihydro-6-oxa-1-aza-3-thia-benzo[e]azulene)-N-(2,4-difluoro)phenyl)-N-methyl-carboxamide |

TABLE 1-continued

| No. | Structure | Name |
|---|---|---|
| 366 | 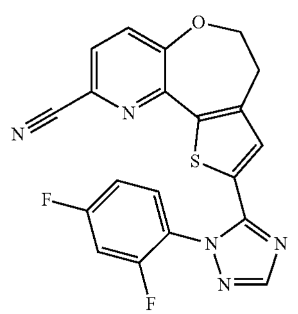 [SMILES: N#Cc1ccc2c(n1)-c1sc(-c3ncnn3-c3ccc(F)cc3F)cc1CCO2] | 3-(2-cyano-6,7-dihydropyrido[3,2-b]thieno[2,3-d]oxepin-9-yl)-2-(2,4-difluorophenyl)-2H-1,2,4-triazole |
| 367 | 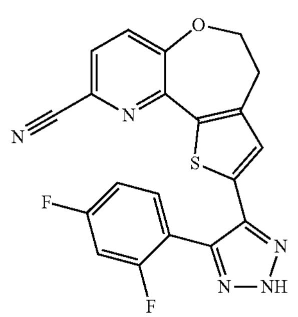 [SMILES: N#Cc1ccc2c(n1)-c1sc(-c3n[nH]nc3-c3ccc(F)cc3F)cc1CCO2] | 4-(2-cyano-6,7-dihydropyrido[3,2-b]thieno[2,3-d]oxepin-9-yl)-5-(2,4-difluorophenyl)-2H-1,2,3-triazole |
| 368 | 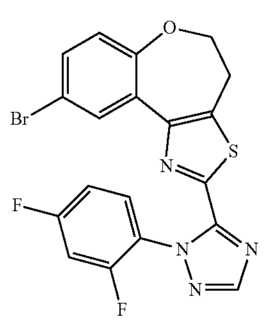 [SMILES: Fc1ccc(-n2ncnc2-c2nc3c(s2)CCOc2ccc(Br)cc2-3)c(F)c1] | 3-(9-bromo-4,5-dihydro-6-oxa-1-aza-3-thia-benzo[e]azulen-2-yl)-4-(2,4-difluorophenyl)-4H-1,2,4-triazole |
| 369 | 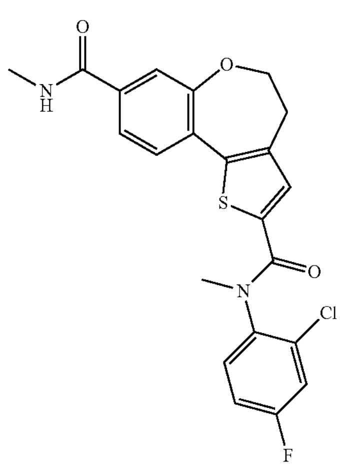 [SMILES: CNC(=O)c1ccc2c(c1)OCCc1cc(C(=O)N(C)c3ccc(F)cc3Cl)sc1-2] | N2-(2-chloro-4-fluorophenyl)-N2,N8-dimethyl-4,5-dihydrobenzo[b]thieno[2,3-d]oxepine-2,8-dicarboxamide |

TABLE 1-continued

| No. | Structure | Name |
|---|---|---|
| 370 | 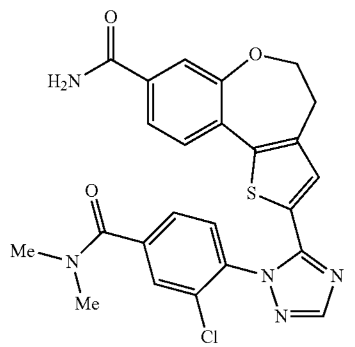 [SMILES: CN(C)C(=O)c1ccc(-n2ncnc2-c2cc3c(s2)-c2ccc(C(N)=O)cc2OCC3)c(Cl)c1] | 2-(1-(2-chloro-4-(dimethylcarbamoyl)phenyl)-1H-1,2,4-triazol-5-yl)-4,5-dihydrobenzo[b]thieno[2,3-d]oxepine-8-carboxamide |
| 371 | 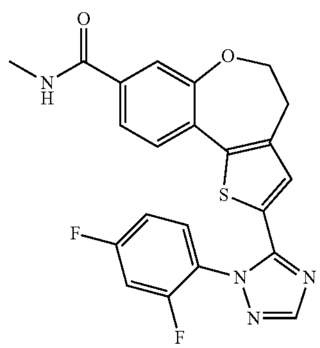 [SMILES: CNC(=O)c1ccc2c(c1)OCCc1cc(-c3ncnn3-c3ccc(F)cc3F)sc1-2] | 2-(1-(2,4-difluorophenyl)-1H-1,2,4-triazol-5-yl)-N-methyl-4,5-dihydrobenzo[b]thieno[2,3-d]oxepine-8-carboxamide |
| 372 | 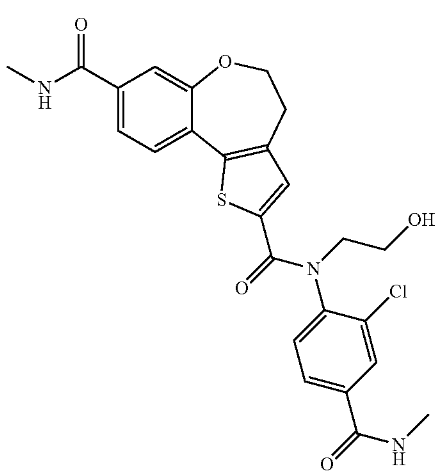 | N2-(2-chloro-4-(methylcarbamoyl)phenyl)-N2-(2-hydroxyethyl)-N8-methyl-4,5-dihydrobenzo[b]thieno[2,3-d]oxepine-2,8-dicarboxamide |
| 373 | 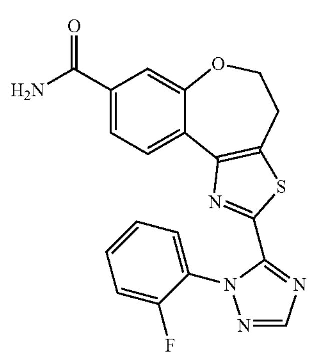 [SMILES: NC(=O)c1ccc2c(c1)OCCc1sc(-c3ncnn3-c3ccccc3F)nc1-2] | 3-(8-carbamoyl-4,5-dihydro-6-oxa-1-aza-3-thia-benzo[e]azulen-2-yl)-4-(2-fluorophenyl)-4H-1,2,4-triazole |

TABLE 1-continued

| No. | Structure | Name |
|---|---|---|
| 374 | 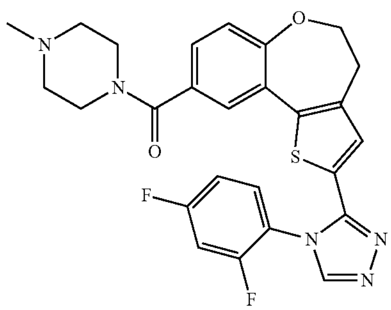 | (2-(4-(2,4-difluorophenyl)-4H-1,2,4-triazol-3-yl)-4,5-dihydrobenzo[b]thieno[2,3-d]oxepin-9-yl)(4-methylpiperazin-1-yl)methanone |
| 375 | 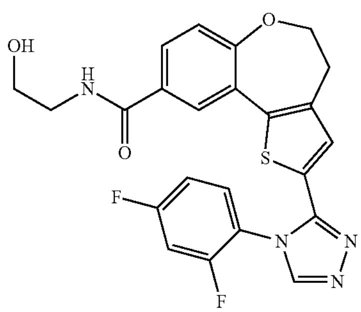 [SMILES: O=C(NCCO)c1ccc2c(c1)-c1sc(-c3nncn3-c3ccc(F)cc3F)cc1CCO2] | 2-(4-(2,4-difluorophenyl)-4H-1,2,4-triazol-3-yl)-N-(2-hydroxyethyl)-4,5-dihydrobenzo[b]thieno[2,3-d]oxepine-9-carboxamide |
| 376 | 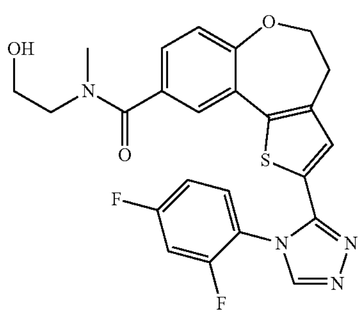 [SMILES: CN(CCO)C(=O)c1ccc2c(c1)-c1sc(-c3nncn3-c3ccc(F)cc3F)cc1CCO2] | 2-(4-(2,4-difluorophenyl)-4H-1,2,4-triazol-3-yl)-N-(2-hydroxyethyl)-N-methyl-4,5-dihydrobenzo[b]thieno[2,3-d]oxepine-9-carboxamide |
| 377 | 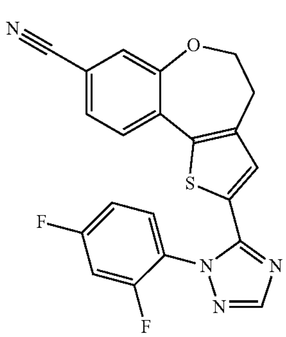 [SMILES: N#Cc1ccc2c(c1)OCCc1cc(-c3ncnn3-c3ccc(F)cc3F)sc1-2] | 2-(1-(2,4-difluorophenyl)-1H-1,2,4-triazol-5-yl)-4,5-dihydrobenzo[b]thieno[2,3-d]oxepine-8-carbonitrile |

TABLE 1-continued
| No. | Structure | Name |
|---|---|---|
| 378 | 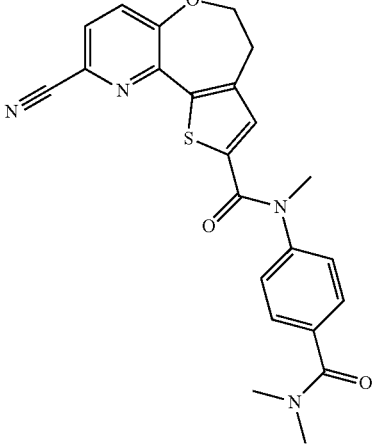 | N-(4-(dimethylcarbamoyl)phenyl)-N-methyl-(2-cyano-6,7-dihydropyrido[3,2-b]thieno[2,3-d]oxepine)-9-carboxamide |
| 379 | 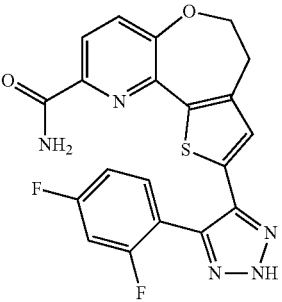 [SMILES: NC(=O)c1ccc2c(n1)-c1sc(-c3n[nH]nc3-c3ccc(F)cc3F)cc1CCO2] | 4-(2-carbamoyl-6,7-dihydropyrido[3,2-b]thieno[2,3-d]oxepin-9-yl)-5-(2,4-difluorophenyl)-2H-1,2,3-triazole |
| 380 | 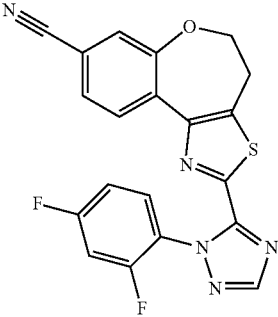 [SMILES: N#Cc1ccc2c(c1)OCCc1sc(-c3ncnn3-c3ccc(F)cc3F)nc1-2] | 3-(8-cyano-4,5-dihydro-6-oxa-1-aza-3-thia-benzo[e]azulen-2-yl)-4-(2,4-difluorophenyl)-4H-1,2,4-triazole |
| 381 | 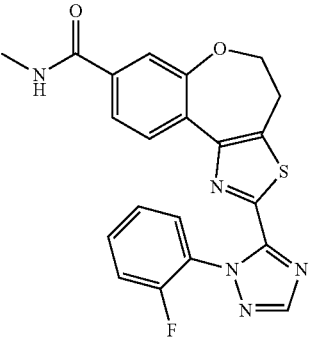 [SMILES: CNC(=O)c1ccc2c(c1)OCCc1sc(-c3ncnn3-c3ccccc3F)nc1-2] | 3-(8-methylcarbamoyl-4,5-dihydro-6-oxa-1-aza-3-thia-benzo[e]azulen-2-yl)-4-(2-fluorophenyl)-4H-1,2,4-triazole |

TABLE 1-continued

| No. | Structure | Name |
|---|---|---|
| 382 | 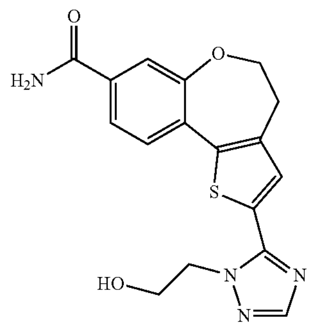 [SMILES: NC(=O)c1ccc2c(c1)OCCc1cc(-c3ncnn3CCO)sc1-2] | 2-(1-(2-hydroxyethyl)-1H-1,2,4-triazol-5-yl)-4,5-dihydrobenzo[b]thieno[2,3-d]oxepine-8-carboxamide |
| 383 | 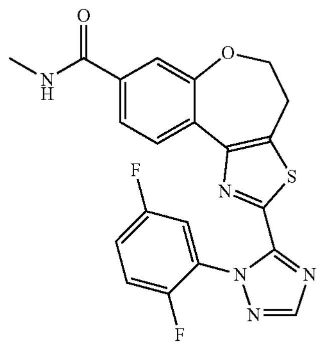 | 3-(8-methylcarbamoyl-4,5-dihydro-6-oxa-1-aza-3-thia-benzo[e]azulen-2-yl)-2-(2,5-difluorophenyl)-2H-1,2,4-triazole |
| 384 | 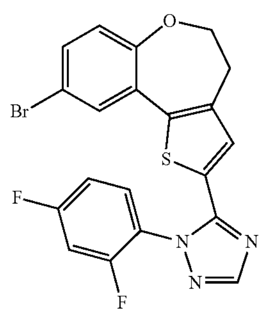 | 5-(9-bromo-4,5-dihydrobenzo[b]thieno[2,3-d]oxepin-2-yl)-1-(2,4-difluorophenyl)-1H-1,2,4-triazole |
| 385 | 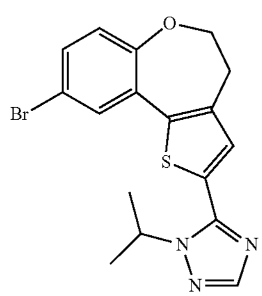 [SMILES: CC(C)n1ncnc1-c1cc2c(s1)-c1cc(Br)ccc1OCC2] | 5-(9-bromo-4,5-dihydrobenzo[b]thieno[2,3-d]oxepin-2-yl)-1-isopropyl-1H-1,2,4-triazole |
| 386 | 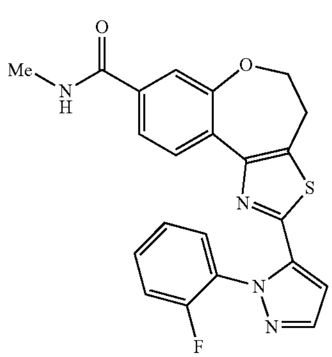 [SMILES: CNC(=O)c1ccc2c(c1)OCCc1sc(-c3ccnn3-c3ccccc3F)nc1-2] | 3-(8-methylcarbamoyl-4,5-dihydro-6-oxa-1-aza-3-thia-benzo[e]azulen-2-yl)-2-(2-fluorophenyl)-2H-pyrazole |

TABLE 1-continued

| No. | Structure | Name |
|---|---|---|
| 387 | 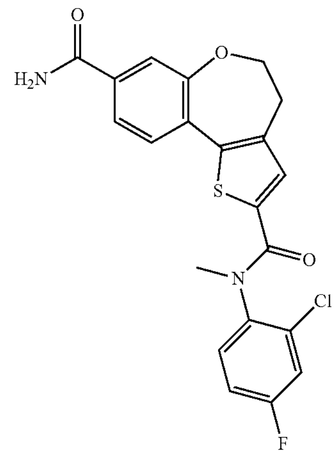 [SMILES: CN(C(=O)c1cc2c(s1)-c1ccc(C(N)=O)cc1OCC2)c1ccc(F)cc1Cl] | N2-(2-chloro-4-fluorophenyl)-N2-methyl-4,5-dihydrobenzo[b]thieno[2,3-d]oxepine-2,8-dicarboxamide |
| 388 | 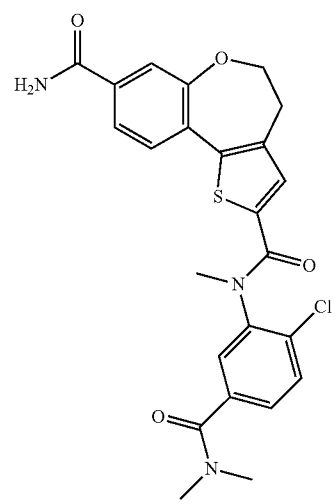 [SMILES: CN(C)C(=O)c1ccc(Cl)c(N(C)C(=O)c2cc3c(s2)-c2ccc(C(N)=O)cc2OCC3)c1] | N2-(2-chloro-5-(dimethylcarbamoyl)phenyl)-N2-methyl-4,5-dihydrobenzo[b]thieno[2,3-d]oxepine-2,8-dicarboxamide |
| 389 | 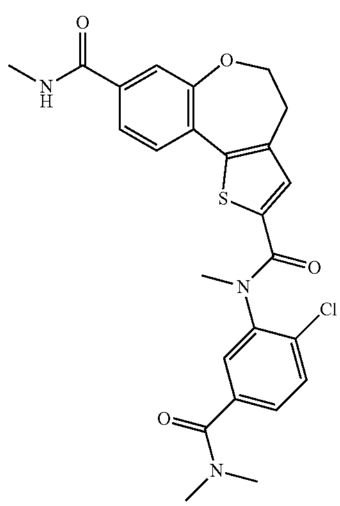 [SMILES: CNC(=O)c1ccc2c(c1)OCCc1cc(C(=O)N(C)c3cc(C(=O)N(C)C)ccc3Cl)sc1-2] | N2-(2-chloro-5-(dimethylcarbamoyl)phenyl)-N2,N8-dimelhyl-4,5-dihydrobenzo[b]thieno[2,3-d]oxepine-2,8-dicarboxamide |

TABLE 1-continued

| No. | Structure | Name |
|---|---|---|
| 390 | 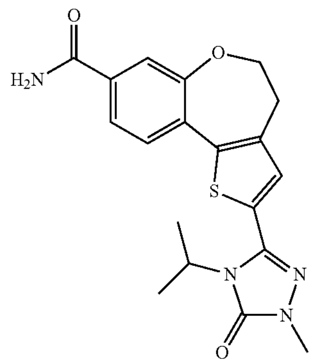 [SMILES: CC(C)n1c(-c2cc3c(s2)-c2ccc(C(N)=O)cc2OCC3)nn(C)c1=O] | 2-(4-isopropyl-1-methyl-5-oxo-4,5-dihydro-1H-1,2,4-triazol-3-yl)-4,5-dihydrobenzo[b]thieno[2,3-d]oxepine-8-carboxamide |
| 391 | 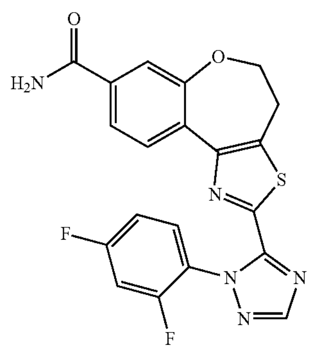 [SMILES: NC(=O)c1ccc2c(c1)OCCc1sc(-c3ncnn3-c3ccc(F)cc3F)nc1-2] | 3-(8-carbamoyl-4,5-dihydro-6-oxa-1-aza-3-thia-benzo[e]azulen-2-yl)-2-(2,4-difluorophenyl)-2H-1,2,4-triazole |
| 392 | 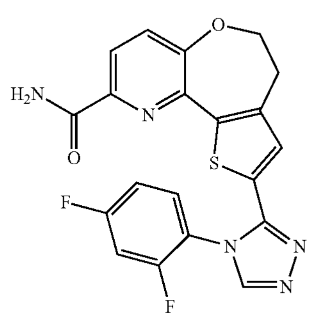 [SMILES: NC(=O)c1ccc2c(n1)-c1sc(-c3nncn3-c3ccc(F)cc3F)cc1CCO2] | 3-(2-carbamoyl-6,7-dihydropyrido[3,2-b]thieno[2,3-d]oxepin-9-yl)-4-(2,4-difluorophenyl)-4H-1,2,4-triazole |
| 393 | 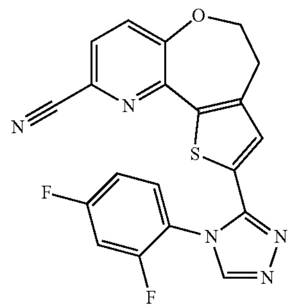 [SMILES: N#Cc1ccc2c(n1)-c1sc(-c3nncn3-c3ccc(F)cc3F)cc1CCO2] | 3-(2-cyano-6,7-dihydropyrido[3,2-b]thieno[2,3-d]oxepin-9-yl)-4-(2,4-difluorophenyl)-4H-1,2,4-triazole |

TABLE 1-continued

| No. | Structure | Name |
|---|---|---|
| 394 | 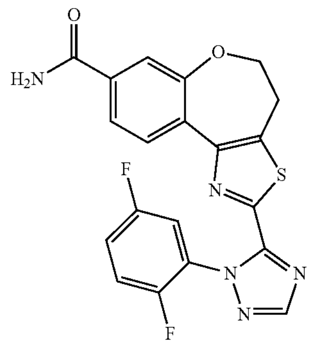 [SMILES: NC(=O)c1ccc2c(c1)OCCc1sc(-c3ncnn3-c3cc(F)ccc3F)nc1-2] | 3-(8-carbamoyl-4,5-dihydro-6-oxa-1-aza-3-thia-benzo[e]azulen-2-yl)-2-(2,5-difluorophenyl)-2H-1,2,4-triazole |
| 395 | 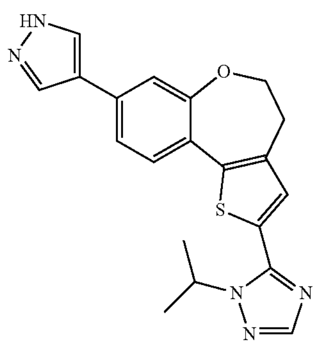 [SMILES: CC(C)n1ncnc1-c1cc2c(s1)-c1ccc(-c3cn[nH]c3)cc1OCC2] | 5-(8-(1H-pyrazol-4-yl)-4,5-dihydrobenzo[b]thieno[2,3-d]oxepin-2-yl)-1-isopropyl-1H-1,2,4-triazole |
| 396 | 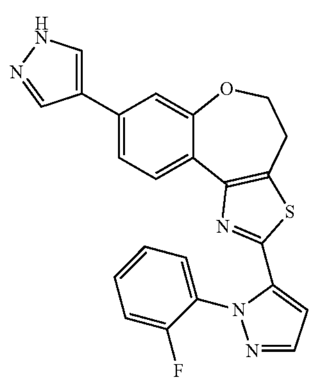 [SMILES: Fc1ccccc1-n1nccc1-c1nc2c(s1)CCOc1cc(-c3cn[nH]c3)ccc1-2] | 3-(8-(1H-pyrazol-4-yl)-4,5-dihydro-6-oxa-1-aza-3-thia-benzo[e]azulen-2-yl)-2-(2-fluorophenyl)-2H-pyrazole |
| 397 | 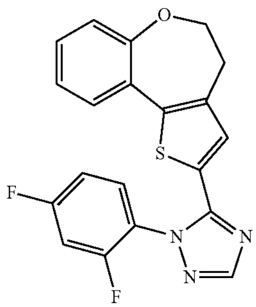 [SMILES: Fc1ccc(-n2ncnc2-c2cc3c(s2)-c2ccccc2OCC3)c(F)c1] | 1-(2,4-difluorophenyl)-5-(4,5-dihydrobenzo[b]thieno[2,3-d]oxepin-2-yl)-1H-1,2,4-triazole |

TABLE 1-continued

| No. | Structure | Name |
|---|---|---|
| 398 | 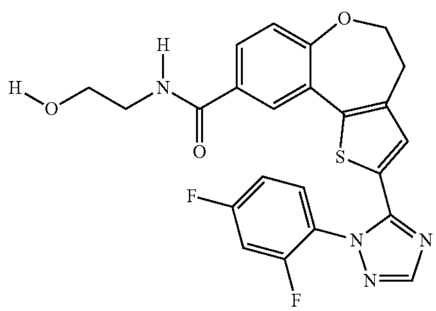 [SMILES: O=C(NCCO)c1ccc2c(c1)-c1sc(-c3ncnn3-c3ccc(F)cc3F)cc1CCO2] | 2-(1-(2,4-difluorophenyl)-1H-1,2,4-triazol-5-yl)-N-(2-hydroxyethyl)-4,5-dihydrobenzo[b]thieno[2,3-d]oxepine-9-carboxamide |
| 399 | 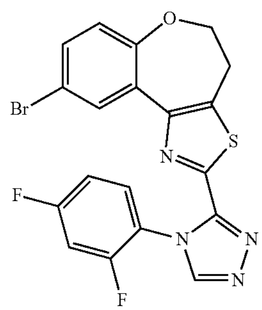 [SMILES: Fc1ccc(-n2cnnc2-c2nc3c(s2)CCOc2ccc(Br)cc2-3)c(F)c1] | 9-bromo-2-[2-(2,4-difluoro-phenyl)-2H-[1,2,4]triazol-3-yl]-4,5-dihydro-6-oxa-3-thia-1-aza-benzo[e]azulene |
| 400 | 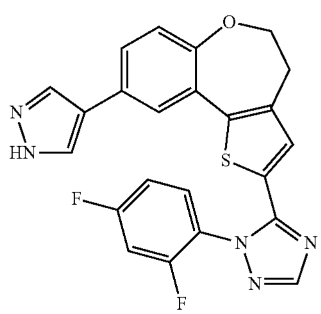 [SMILES: Fc1ccc(-n2ncnc2-c2cc3c(s2)-c2cc(-c4cn[nH]c4)ccc2OCC3)c(F)c1] | 5-(9-(1H-pyrazol-4-yl)-4,5-dihydrobenzo[b]thieno[2,3-d]oxepin-2-yl)-1-(2,4-difluorophenyl)-1H-1,2,4-triazole |
| 401 | 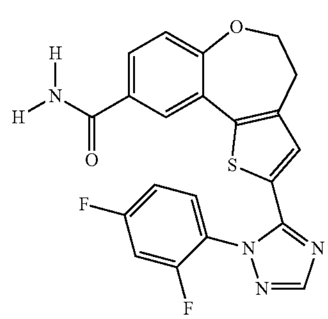 [SMILES: NC(=O)c1ccc2c(c1)-c1sc(-c3ncnn3-c3ccc(F)cc3F)cc1CCO2] | 2-(1-(2,4-difluorophenyl)-1H-1,2,4-triazol-5-yl)-4,5-dihydrobenzo[b]thieno[2,3-d]oxepine-9-carboxamide |
| 402 | 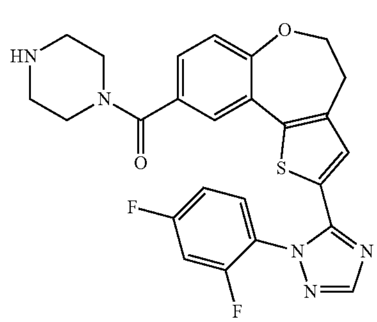 [SMILES: O=C(c1ccc2c(c1)-c1sc(-c3ncnn3-c3ccc(F)cc3F)cc1CCO2)N1CCNCC1] | (2-(1-(2,4-difluorophenyl)-1H-1,2,4-triazol-5-yl)-4,5-dihydrobenzo[b]thieno[2,3-d]oxepin-9-yl)(piperazin-1-yl)methanone |

TABLE 1-continued

| No. | Structure | Name |
|---|---|---|
| 403 | 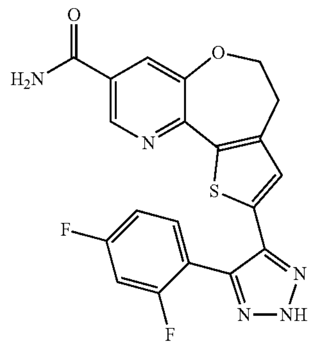 [SMILES: NC(=O)c1cnc2c(c1)OCCc1cc(-c3n[nH]nc3-c3ccc(F)cc3F)sc1-2] | 4-(3-carbamoyl-6,7-dihydropyrido[3,2-b]thieno[2,3-d]oxepin-9-yl)-5-(2,4-difluorophenyl)-2H-1,2,3-triazole |
| 404 | 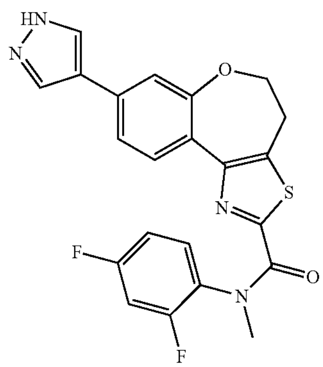 [SMILES: CN(C(=O)c1nc2c(s1)CCOc1cc(-c3cn[nH]c3)ccc1-2)c1ccc(F)cc1F] | 8-(1H-pyrazol-4-yl)-4,5-dihydro-6-oxa-1-aza-3-thia-benzo[e]azulene-2-carboxylic acid-N-(2,4-difluorophenyl)-N-methyl-amide |
| 405 | 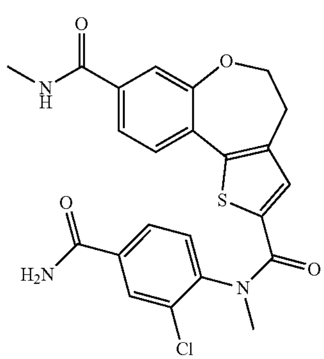 [SMILES: CNC(=O)c1ccc2c(c1)OCCc1cc(C(=O)N(C)c3ccc(C(N)=O)cc3Cl)sc1-2] | N2-(4-carbamoyl-2-chlorophenyl)-N2,N8-dimethyl-4,5-dihydrobenzo[b]thieno[2,3-d]oxepine-2,8-dicarboxamide |
| 406 | 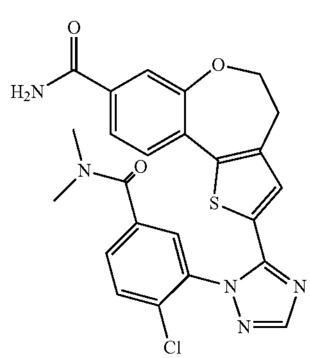 [SMILES: CN(C)C(=O)c1ccc(Cl)c(-n2ncnc2-c2cc3c(s2)-c2ccc(C(N)=O)cc2OCC3)c1] | 2-(1-(2-chloro-5-(dimethylcarbamoyl)phenyl)-1H-1,2,4-triazol-5-yl)-4,5-dihydrobenzo[b]thieno[2,3-d]oxepine-8-carboxamide |

TABLE 1-continued

| No. | Structure | Name |
|---|---|---|
| 407 | 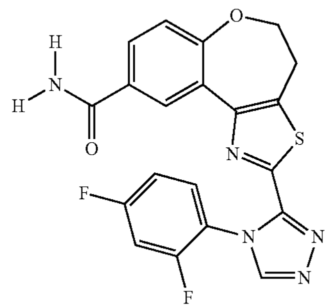 [SMILES: NC(=O)c1ccc2c(c1)-c1nc(-c3nncn3-c3ccc(F)cc3F)sc1CCO2] | 2-[4-(2,4-Difluoro-phenyl)-4H-[1,2,4]triazol-3-yl]-4,5-dihydro-6-oxa-3-thia-1-aza-benzo[e]azulene-9-carboxylic acid amide |
| 408 | 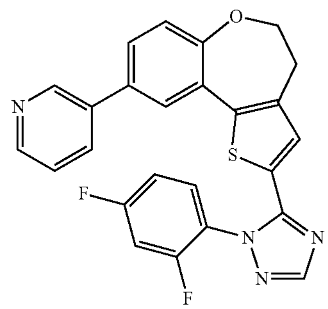 [SMILES: Fc1ccc(-n2ncnc2-c2cc3c(s2)-c2cc(-c4cccnc4)ccc2OCC3)c(F)c1] | 3-(2-(1-(2,4-difluorophenyl)-1H-1,2,4-triazol-5-yl)-4,5-dihydrobenzo[b]thieno[2,3-d]oxepin-9-yl)pyridine |
| 409 | 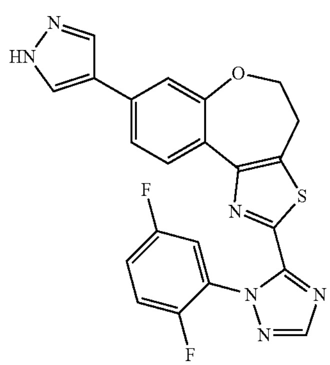 [SMILES: Fc1ccc(F)c(-n2ncnc2-c2nc3c(s2)CCOc2cc(-c4cn[nH]c4)ccc2-3)c1] | 8-(1H-pyrazol-4-yl)-2-[2-(2,5-difluoro-phenyl)-2H-[1,2,4]triazol-3-yl]-4,5-dihydro-6-oxa-3-thia-1-aza-benzo[e]azulene |
| 410 | 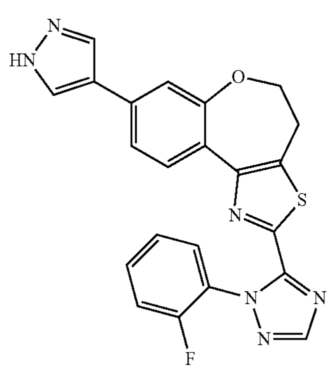 [SMILES: Fc1ccccc1-n1ncnc1-c1nc2c(s1)CCOc1cc(-c3cn[nH]c3)ccc1-2] | 8-(1H-pyrazol-4-yl)-2-[2-(2-fluoro-phenyl)-2H-[1,2,4]triazol-3-yl]-4,5-dihydro-6-oxa-3-thia-1-aza-benzo[e]azulene |

| No. | Structure | Name |
| --- | --- | --- |
| 411 | 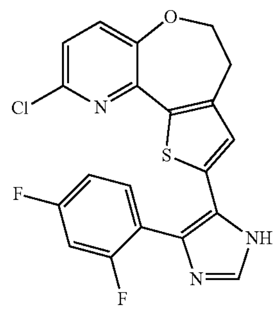 [SMILES: Fc1ccc(-c2nc[nH]c2-c2cc3c(s2)-c2nc(Cl)ccc2OCC3)c(F)c1] | 5-(2-chloro-6,7-dihydropyrido[3,2-b]thieno[2,3-d]oxepin-9-yl)-4-(2,4-difluorophenyl)-1H-imidazole |
| 412 | 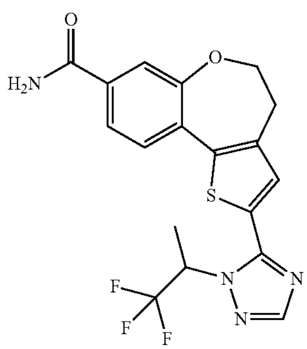 [SMILES: CC(n1ncnc1-c1cc2c(s1)-c1ccc(C(N)=O)cc1OCC2)C(F)(F)F] | 2-(1-(1,1,1-trifluoropropan-2-yl)-1H-1,2,4-triazol-5-yl)-4,5-dihydrobenzo[b]thieno[2,3-d]oxepine-8-carboxamide |
| 413 | 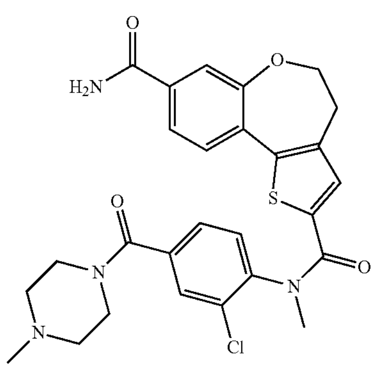 [SMILES: CN1CCN(C(=O)c2ccc(N(C)C(=O)c3cc4c(s3)-c3ccc(C(N)=O)cc3OCC4)c(Cl)c2)CC1] | N2-(2-chloro-4-(4-methylpiperazine-1-carbonyl)phenyl)-N2-methyl-4,5-dihydrobenzo[b]thieno[2,3-d]oxepine-2,8-dicarboxamide |
| 414 | 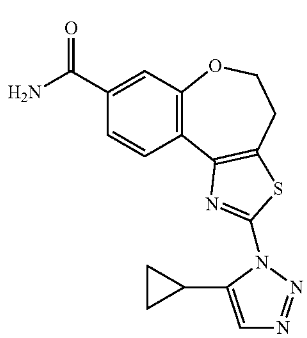 [SMILES: NC(=O)c1ccc2c(c1)OCCc1sc(-n3nncc3C3CC3)nc1-2] | 2-(5-cyclopropyl-[1,2,3]triazol-1-yl)-4,5-dihydro-6-oxa-3-thia-1-aza-benzo[e]azulene-8-carboxylic acid amide |

TABLE 1-continued

| No. | Structure | Name |
|---|---|---|
| 415 | 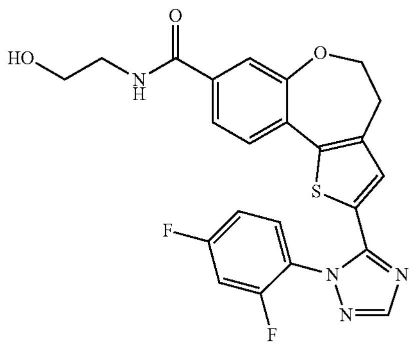 [SMILES: O=C(NCCO)c1ccc2c(c1)OCCc1cc(-c3ncnn3-c3ccc(F)cc3F)sc1-2] | 2-(1-(2,4-difluorophenyl)-1H-1,2,4-triazol-5-yl)-N-(2-hydroxyethyl)-4,5-dihydrobenzo[b]thieno[2,3-d]oxepine-8-carboxamide |
| 416 | 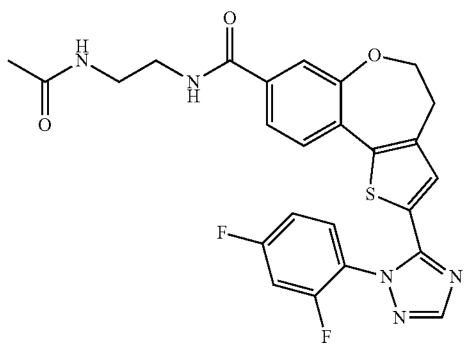 [SMILES: CC(=O)NCCNC(=O)c1ccc2c(c1)OCCc1cc(-c3ncnn3-c3ccc(F)cc3F)sc1-2] | N-(2-acetamidoethyl)-2-(1-(2,4-difluorophenyl)-1H-1,2,4-triazol-5-yl)-4,5-dihydrobenzo[b]thieno[2,3-d]oxepine-8-carboxamide |
| 417 | 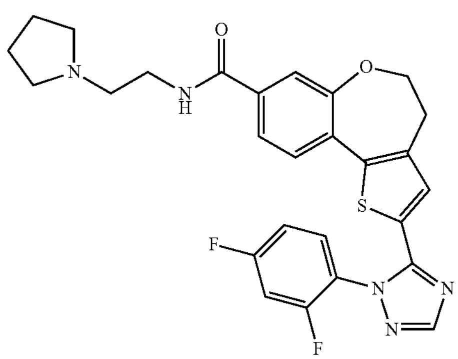 [SMILES: O=C(NCCN1CCCC1)c1ccc2c(c1)OCCc1cc(-c3ncnn3-c3ccc(F)cc3F)sc1-2] | 2-(1-(2,4-difluorophenyl)-1H-1,2,4-triazol-5-yl)-N-(2-(pyrrolidin-1-yl)ethyl)-4,5-dihydrobenzo[b]thieno[2,3-d]oxepine-8-carboxamide |
| 418 | 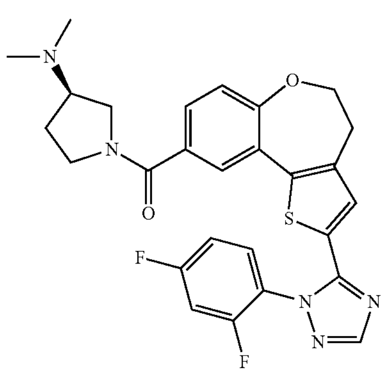 [SMILES: CN(C)[C@@H]1CCN(C(=O)c2ccc3c(c2)-c2sc(-c4ncnn4-c4ccc(F)cc4F)cc2CCO3)C1] | (2-(1-(2,4-difluorophenyl)-1H-1,2,4-triazol-5-yl)-4,5-dihydrobenzo[b]thieno[2,3-d]oxepin-9-yl)((R)-3-(dimethylamino)pyrrolidin-1-yl)methanone |

201
202
TABLE 1-continued
| No. | Structure | Name |
|---|---|---|
| 419 | 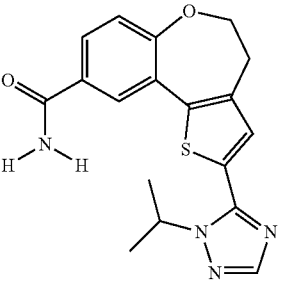 [SMILES: CC(C)n1ncnc1-c1cc2c(s1)-c1cc(C(N)=O)ccc1OCC2] | 2-(1-isopropyl-1H-1,2,4-triazol-5-yl)-4,5-dihydrobenzo[b]thieno[2,3-d]oxepine-9-carboxamide |
| 420 | 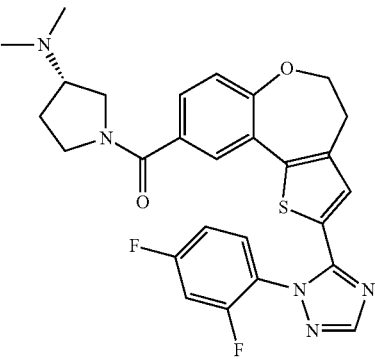 [SMILES: CN(C)[C@H]1CCN(C(=O)c2ccc3c(c2)-c2sc(-c4ncnn4-c4ccc(F)cc4F)cc2CCO3)C1] | (2-(1-(2,4-difluorophenyl)-1H-1,2,4-triazol-5-yl)-4,5-dihydrobenzo[b]thieno[2,3-d]oxepin-9-yl)((S)-3-(dimethylamino)pyrrolidin-1-yl)methanone |
| 421 | 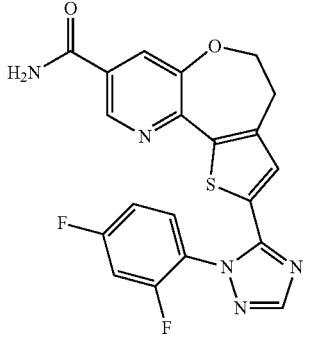 [SMILES: NC(=O)c1cnc2c(c1)OCCc1cc(-c3ncnn3-c3ccc(F)cc3F)sc1-2] | 5-(3-carbamoyl-6,7-dihydropyrido[3,2-b]thieno[2,3-d]oxepin-9-yl)-1-(2,4-difluorophenyl)-1H-1,2,4-triazole |
| 422 | 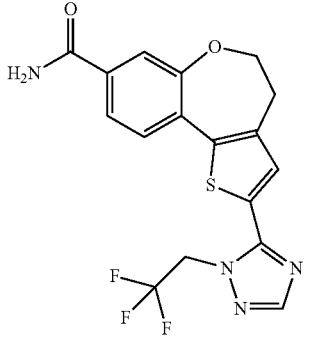 [SMILES: NC(=O)c1ccc2c(c1)OCCc1cc(-c3ncnn3CC(F)(F)F)sc1-2] | 2-(1-(2,2,2-trifluoroethyl)-1H-1,2,4-triazol-5-yl)-4,5-dihydrobenzo[b]thieno[2,3-d]oxepine-8-carboxamide |

TABLE 1-continued

| No. | Structure | Name |
|---|---|---|
| 423 | 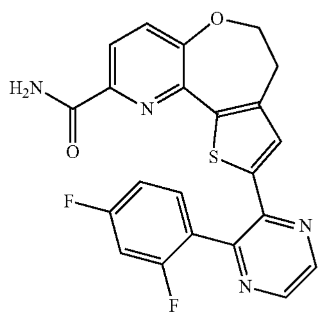 [SMILES: NC(=O)c1ccc2c(n1)-c1sc(-c3nccnc3-c3ccc(F)cc3F)cc1CCO2] | 2-(2-carbamoyl-6,7-dihydropyrido[3,2-b]thieno[2,3-d]oxepin-9-yl)-3-(2,4-difluorophenyl)-pyrazine |
| 424 | 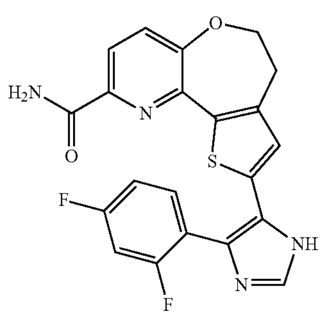 [SMILES: NC(=O)c1ccc2c(n1)-c1sc(-c3[nH]cnc3-c3ccc(F)cc3F)cc1CCO2] | 5-(2-carbamoyl-6,7-dihydropyrido[3,2-b]thieno[2,3-d]oxepin-9-yl)-4-(2,4-difluorophenyl)-1H-imidazole |
| 425 | 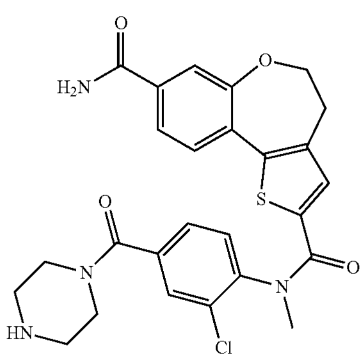 [SMILES: CN(C(=O)c1cc2c(s1)-c1ccc(C(N)=O)cc1OCC2)c1ccc(C(=O)N2CCNCC2)cc1Cl] | N2-(2-chloro-4-(piperazine-1-carbonyl)phenyl)-N2-methyl-4,5-dihydrobenzo[b]thieno[2,3-d]oxepine-2,8-dicarboxamide |
| 426 | 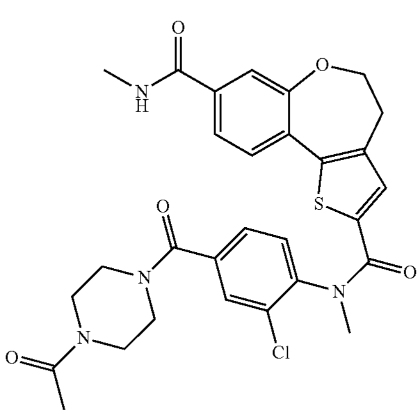 [SMILES: CNC(=O)c1ccc2c(c1)OCCc1cc(C(=O)N(C)c3ccc(C(=O)N4CCN(C(C)=O)CC4)cc3Cl)sc1-2] | N2-(4-(4-acetylpiperazine-1-carbonyl)-2-chlorophenyl)-N2,N8-dimethyl-4,5-dihydrobenzo[b]thieno[2,3-d]oxepine-2,8-dicarboxamide |

TABLE 1-continued

| No. | Structure | Name |
|---|---|---|
| 427 | 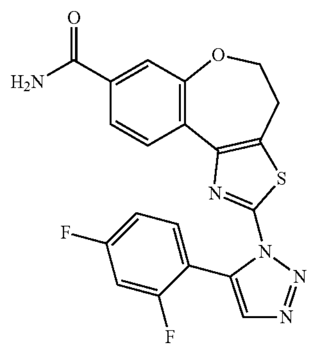 [SMILES: NC(=O)c1ccc2c(c1)OCCc1sc(-n3nncc3-c3ccc(F)cc3F)nc1-2] | 2-[5-(2,4-Difluoro-phenyl)-[1,2,3]triazol-1-yl]-4,5-dihydro-6-oxa-3-thia-1-aza-benzo[e]azulene-8-carboxylic acid amide |
| 428 | 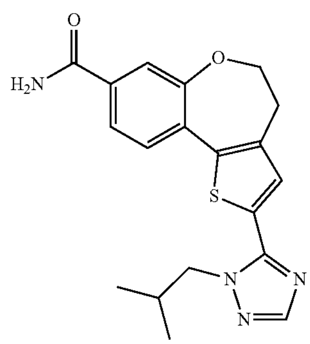 [SMILES: CC(C)Cn1ncnc1-c1cc2c(s1)-c1ccc(C(N)=O)cc1OCC2] | 2-(1-isobutyl-1H-1,2,4-triazol-5-yl)-4,5-dihydrobenzo[b]thieno[2,3-d]oxepine-8-carboxamide |
| 429 | 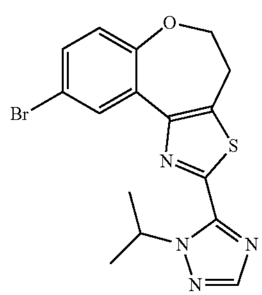 [SMILES: CC(C)n1ncnc1-c1nc2c(s1)CCOc1ccc(Br)cc1-2] | 9-bromo-2-isopropyl-2H-1,2,4-triazol-3-yl-4,5-dihydro-6-oxa-3-thia-1-aza-benzo[e]azulene |
| 430 | 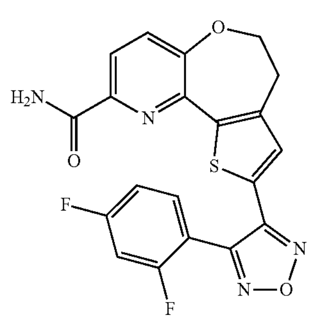 [SMILES: NC(=O)c1ccc2c(n1)-c1sc(-c3nonc3-c3ccc(F)cc3F)cc1CCO2] | 4-(2-carbamoyl-6,7-dihydropyrido[3,2-b]thieno[2,3-d]oxepin-9-yl)-3-(2,4-difluorophenyl)-1,2,5-oxadiazole |
| 431 | 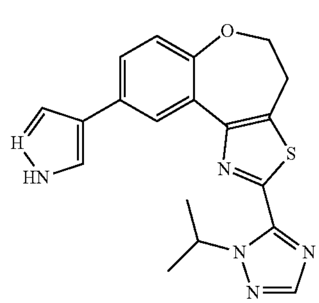 | 9-(1H-pyrazol-4-yl)-2-isopropyl-2H-1,2,4-triazol-3-yl-4,5-dihydro-6-oxa-3-thia-1-aza-benzo[e]azulene |

TABLE 1-continued

| No. | Structure | Name |
|-----|-----------|------|
| 432 | 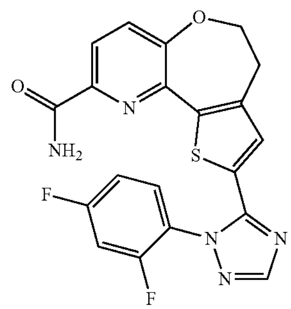 [SMILES: NC(=O)c1ccc2c(n1)-c1sc(-c3ncnn3-c3ccc(F)cc3F)cc1CCO2] | 5-(2-carbamoyl-6,7-dihydropyrido[3,2-b]thieno[2,3-d]oxepin-9-yl)-1-(2,4-difluorophenyl)-1H-1,2,4-triazole |
| 433 | 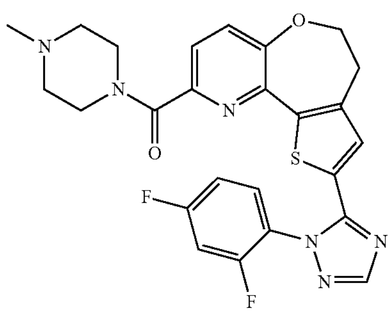 [SMILES: CN1CCN(C(=O)c2ccc3c(n2)-c2sc(-c4ncnn4-c4ccc(F)cc4F)cc2CCO3)CC1] | (9-(1-(2,4-difluorophenyl)-1H-1,2,4-triazol-5-yl)-6,7-dihydropyrido[3,2-b]thieno[2,3-d]oxepin-2-yl)(4-methylpiperazin-1-yl)methanone |
| 434 | 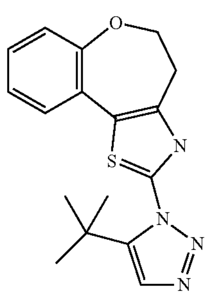 | 2-(5-tert-Butyl-[1,2,3]triazol-1-yl)-4,5-dihydro-6-oxa-3-thia-1-aza-benzo[e]azulene |
| 435 | 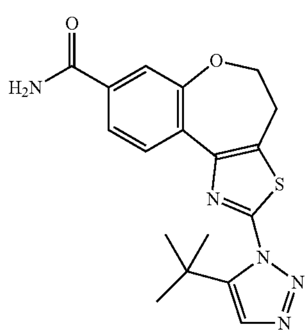 [SMILES: CC(C)(C)c1cnnn1-c1nc2c(s1)CCOc1cc(C(N)=O)ccc1-2] | 2-(5-tert-Butyl-[1,2,3]triazol-1-yl)-4,5-dihydro-6-oxa-3-thia-1-aza-benzo[e]azulene-8-carboxylic acid amide |
| 436 | 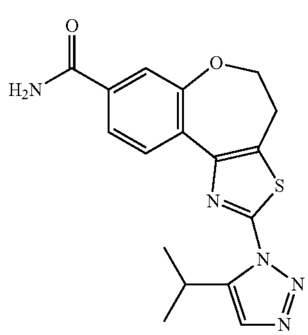 [SMILES: CC(C)c1cnnn1-c1nc2c(s1)CCOc1cc(C(N)=O)ccc1-2] | 2-(5-Isopropyl-[1,2,3]triazol-1-yl)-4,5-dihydro-6-oxa-3-thia-1-aza-benzo[e]azulene-8-carboxylic acid amide |

TABLE 1-continued

| No. | Structure | Name |
|---|---|---|
| 437 | 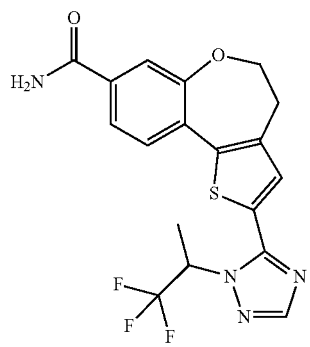 [SMILES: CC(n1ncnc1-c1cc2c(s1)-c1ccc(C(N)=O)cc1OCC2)C(F)(F)F] | 2-(1-(1,1,1-trifluoropropan-2-yl)-1H-1,2,4-triazol-5-yl)-4,5-dihydrobenzo[b]thieno[2,3-d]oxepine-8-carboxamide |
| 438 | 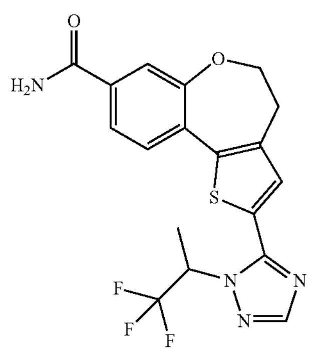 [SMILES: CC(n1ncnc1-c1cc2c(s1)-c1ccc(C(N)=O)cc1OCC2)C(F)(F)F] | 2-(1-(1,1,1-trifluoropropan-2-yl)-1H-1,2,4-triazol-5-yl)-4,5-dihydrobenzo[b]thieno[2,3-d]oxepine-8-carboxamide |
| 439 | 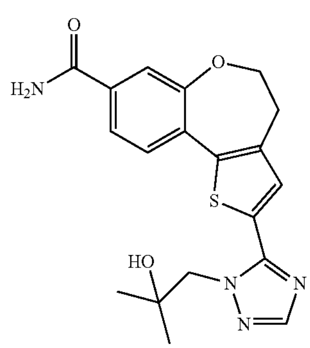 [SMILES: CC(C)(O)Cn1ncnc1-c1cc2c(s1)-c1ccc(C(N)=O)cc1OCC2] | 2-(1-(2-hydroxy-2-methylpropyl)-1H-1,2,4-triazol-5-yl)-4,5-dihydrobenzo[b]thieno[2,3-d]oxepine-8-carboxamide |
| 440 | 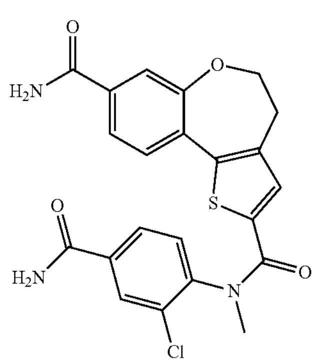 [SMILES: CN(C(=O)c1cc2c(s1)-c1ccc(C(N)=O)cc1OCC2)c1ccc(C(N)=O)cc1Cl] | N2-(4-carbamoyl-2-chlorophenyl)-N2-methyl-4,5-dihydrobenzo[b]thieno[2,3-d]oxepine-2,8-dicarboxamide |

TABLE 1-continued

| No. | Structure | Name |
|---|---|---|
| 441 | 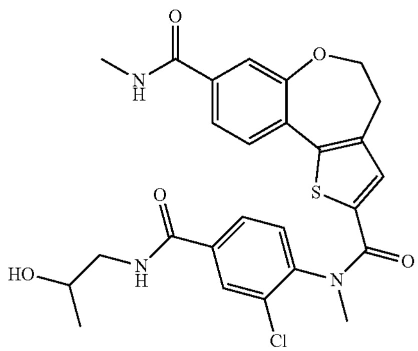 [SMILES: CNC(=O)c1ccc2c(c1)OCCc1cc(C(=O)N(C)c3ccc(C(=O)NCC(C)O)cc3Cl)sc1-2] | N2-(2-chloro-4-(2-hydroxypropylcarbamoyl)phenyl)-N2,N8-dimethyl-4,5-dihydrobenzo[b]thieno[2,3-d]oxepine-2,8-dicarboxamide |
| 442 | 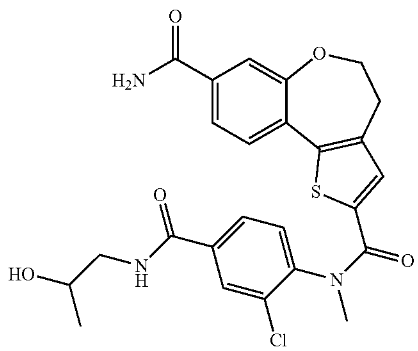 [SMILES: CC(O)CNC(=O)c1ccc(N(C)C(=O)c2cc3c(s2)-c2ccc(C(N)=O)cc2OCC3)c(Cl)c1] | N2-(2-chloro-4-(2-hydroxypropylcarbamoyl)phenyl)-N2-methyl-4,5-dihydrobenzo[b]thieno[2,3-d]oxepine-2,8-dicarboxamide |
| 443 | 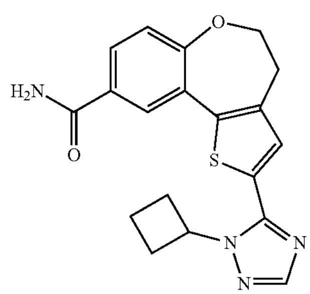 [SMILES: NC(=O)c1ccc2c(c1)-c1sc(-c3ncnn3C3CCC3)cc1CCO2] | 2-(1-cyclobutyl-1H-1,2,4-triazol-5-yl)-4,5-dihydrobenzo[b]thieno[2,3-d]oxepine-9-carboxamide |
| 444 | 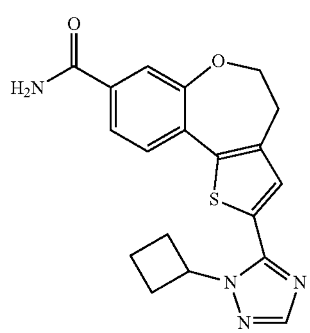 [SMILES: NC(=O)c1ccc2c(c1)OCCc1cc(-c3ncnn3C3CCC3)sc1-2] | 2-(1-cyclobuty-1H-1,2,4-triazol-5-yl)-4,5-dihydrobenzo[b]thieno[2,3-d]oxepine-8-carboxamide |
| 445 | 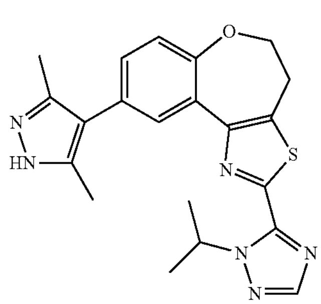 [SMILES: Cc1n[nH]c(C)c1-c1ccc2c(c1)-c1nc(-c3ncnn3C(C)C)sc1CCO2] | 9-(1H-3,5-dimethylpyrazol-4-yl)-2-isopropyl-2H-1,2,4-triazol-3-yl-4,5-dihydro-6-oxa-3-thia-1-aza-benzo[e]azulene |

| No. | Structure | Name |
| --- | --- | --- |
| 446 | 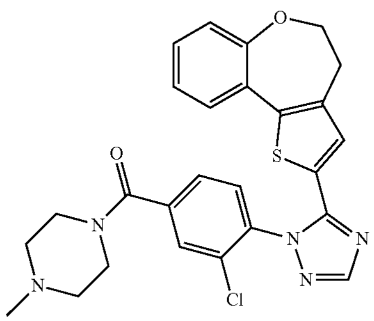 | (3-chloro-4-(5-(4,5-dihydrobenzo[b]thieno[2,3-d]oxepin-2-yl)-1H-1,2,4-triazol-1-yl)phenyl)(4-methylpiperazin-1-yl)methanone |
| 447 | 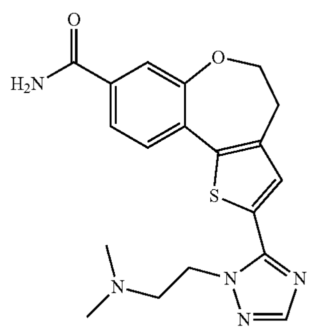 [SMILES: CN(C)CCn1ncnc1-c1cc2c(s1)-c1ccc(C(N)=O)cc1OCC2] | 2-(1-(2-(dimethylamino)ethyl)-1H-1,2,4-triazol-5-yl)-4,5-dihydrobenzo[b]thieno[2,3-d]oxepine-8-carboxamide |
| 448 | 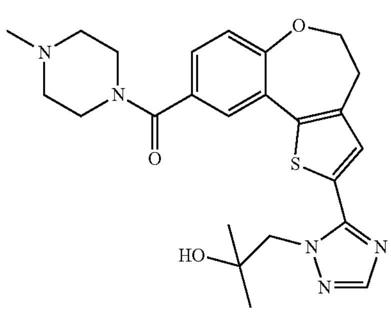 [SMILES: CN1CCN(C(=O)c2ccc3c(c2)-c2sc(-c4ncnn4CC(C)(C)O)cc2CCO3)CC1] | (2-(1-(2-hydroxy-2-methylpropyl)-1H-1,2,4-triazol-5-yl)-4,5-dihydrobenzo[b]thieno[2,3-d]oxepin-9-yl)(4-methylpiperazin-1-yl)methanone |
| 449 | 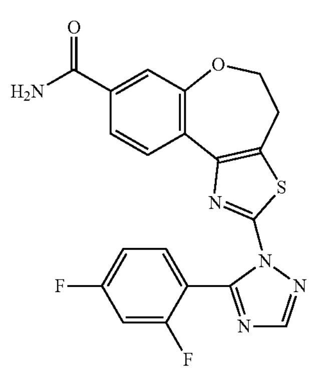 [SMILES: NC(=O)c1ccc2c(c1)OCCc1sc(-n3ncnc3-c3ccc(F)cc3F)nc1-2] | 2-[5-(2,4-Difluoro-phenyl)-[1,2,4]triazol-1-yl]-4,5-dihydro-6-oxa-3-thia-1-aza-benzo[e]azulene-8-carboxylic acid amide |

TABLE 1-continued

| No. | Structure | Name |
|---|---|---|
| 450 | 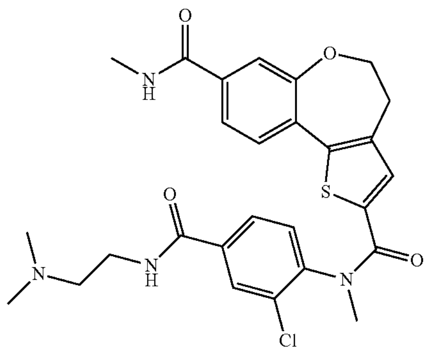 [SMILES: CNC(=O)c1ccc2c(c1)OCCc1cc(C(=O)N(C)c3ccc(C(=O)NCCN(C)C)cc3Cl)sc1-2] | N2-(2-chloro-4-(2-(dimethylamino)ethylcarbamoyl)phenyl)-N2,N8-dimethyl-4,5-dihydrobenzo[b]thieno[2,3-d]oxepine-2,8-dicarboxamide |
| 451 | 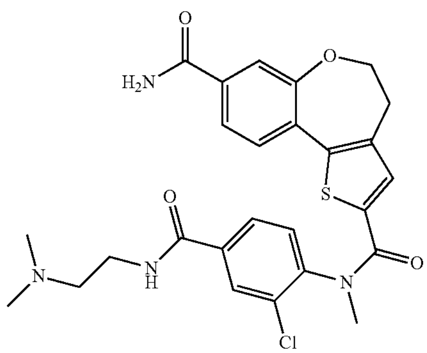 [SMILES: CN(C)CCNC(=O)c1ccc(N(C)C(=O)c2cc3c(s2)-c2ccc(C(N)=O)cc2OCC3)c(Cl)c1] | N2-(2-chloro-4-(2-(dimethylamino)ethylcarbamoyl)phenyl)-N2-methyl-4,5-dihydrobenzo[b]thieno[2,3-d]oxepine-2,8-dicarboxamide |
| 452 | 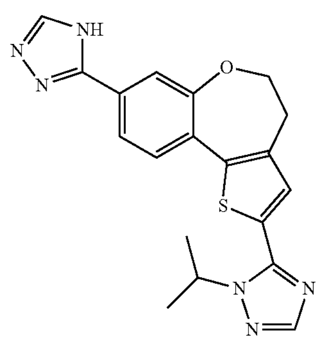 [SMILES: CC(C)n1ncnc1-c1cc2c(s1)-c1ccc(-c3nnc[nH]3)cc1OCC2] | 5-(8-(4H-1,2,4-triazol-3-yl)-4,5-dihydrobenzo[b]thieno[2,3-d]oxepin-2-yl)-1-isopropyl-1H-1,2,4-triazole |
| 453 | 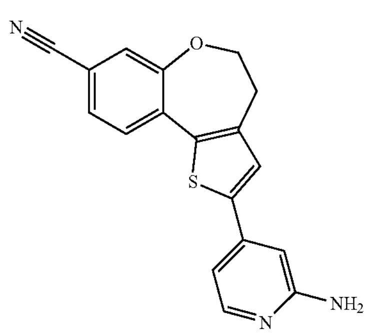 [SMILES: N#Cc1ccc2c(c1)OCCc1cc(-c3ccnc(N)c3)sc1-2] | 2-(2-aminopyridin-4-yl)-4,5-dihydrobenzo[b]thieno[2,3-d]oxepine-8-carbonitrile |

TABLE 1-continued

| No. | Structure | Name |
|---|---|---|
| 454 | 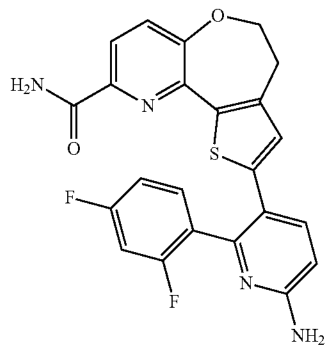 [SMILES: NC(=O)c1ccc2c(n1)-c1sc(-c3ccc(N)nc3-c3ccc(F)cc3F)cc1CCO2] | 5-(2-carbamoyl-6,7-dihydropyrido[3,2-b]thieno[2,3-d]oxepin-9-yl)-6-(2,4-difluorophenyl)pyridin-2-amine |
| 455 | 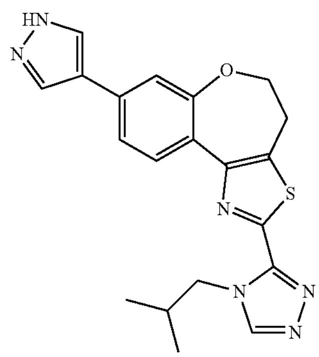 [SMILES: CC(C)Cn1cnnc1-c1nc2c(s1)CCOc1cc(-c3cn[nH]c3)ccc1-2] | 8-(1H-pyrazol-4-yl)-(4H-4-isobutyl-1,2,4-triazol-5-yl)-4,5-dihydro-6-oxa-3-thia-1-aza-benzo[e]azulene |
| 456 | 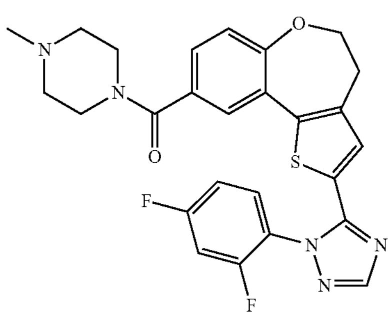 [SMILES: CN1CCN(C(=O)c2ccc3c(c2)-c2sc(-c4ncnn4-c4ccc(F)cc4F)cc2CCO3)CC1] | (2-(1-(2,4-difluorophenyl)-1H-1,2,4-triazol-5-yl)-4,5-dihydrobenzo[b]thieno[2,3-d]oxepin-9-yl)(4-methylpiperazin-1-yl)methanone |
| 457 | 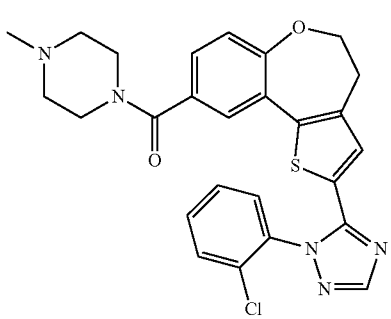 [SMILES: CN1CCN(C(=O)c2ccc3c(c2)-c2sc(-c4ncnn4-c4ccccc4Cl)cc2CCO3)CC1] | (2-(1-(2-chlorophenyl)-1H-1,2,4-triazol-5-yl)-4,5-dihydrobenzo[b]thieno[2,3-d]oxepin-9-yl)(4-methylpiperazin-1-yl)methanone |

| No. | Structure | Name |
| --- | --- | --- |
| 458 | 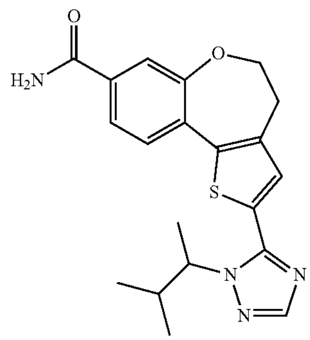 [SMILES: CC(C)C(C)n1ncnc1-c1cc2c(s1)-c1ccc(C(N)=O)cc1OCC2] | 2-(1-(3-methylbutan-2-yl)-1H-1,2,4-triazol-5-yl)-4,5-dihydrobenzo[b]thieno[2,3-d]oxepine-8-carboxamide |
| 459 | 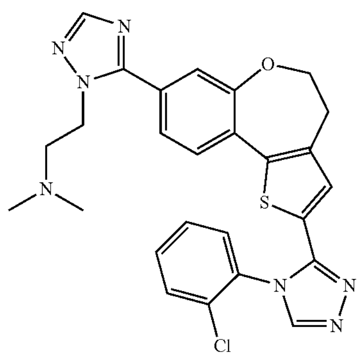 [SMILES: CN(C)CCn1ncnc1-c1ccc2c(c1)OCCc1cc(-c3nncn3-c3ccccc3Cl)sc1-2] | 2-(5-(2-(4-(2-chlorophenyl)-4H-1,2,4-triazol-3-yl)-4,5-dihydrobenzo[b]thieno[2,3-d]oxepin-8-yl)-1H-1,2,4-triazol-1-yl)-N,N-dimethylethanamine |
| 460 | 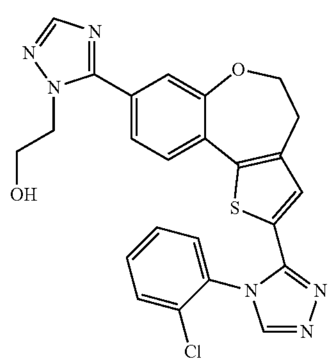 [SMILES: OCCn1ncnc1-c1ccc2c(c1)OCCc1cc(-c3nncn3-c3ccccc3Cl)sc1-2] | 2-(5-(2-(4-(2-chlorophenyl)-4H-1,2,4-triazol-3-yl)-4,5-dihydrobenzo[b]thieno[2,3-d]oxepin-8-yl)-1H-1,2,4-triazol-1-yl)ethanol |
| 461 | 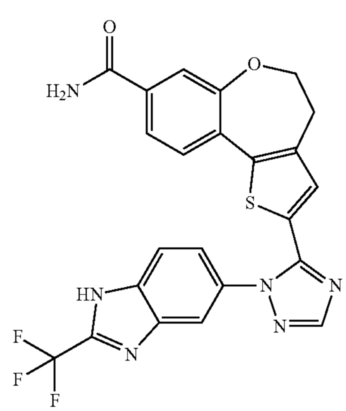 [SMILES: NC(=O)c1ccc2c(c1)OCCc1cc(-c3ncnn3-c3ccc4[nH]c(C(F)(F)F)nc4c3)sc1-2] | 2-(1-(2-(trifluoromethyl)-1H-benzo[d]imidazol-5-yl)-1H-1,2,4-triazol-5-yl)-4,5-dihydrobenzo[b]thieno[2,3-d]oxepine-8-carboxamide |

TABLE 1-continued

| No. | Structure | Name |
|---|---|---|
| 462 | 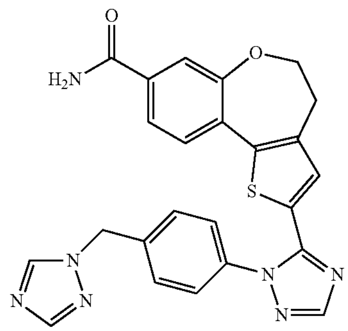 [SMILES: NC(=O)c1ccc2c(c1)OCCc1cc(-c3ncnn3-c3ccc(Cn4cncn4)cc3)sc1-2] | 2-(1-(4-((1H-1,2,4-triazol-1-yl)methyl)phenyl)-1H-1,2,4-triazol-5-yl)-4,5-dihydrobenzo[b]thieno[2,3-d]oxepine-8-carboxamide |
| 463 | 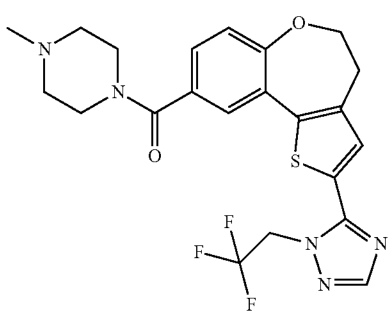 [SMILES: CN1CCN(C(=O)c2ccc3c(c2)-c2sc(-c4ncnn4CC(F)(F)F)cc2CCO3)CC1] | (4-methylpiperazin-1-yl)(2-(1-(2,2,2-trifluoroethyl)-1H-1,2,4-triazol-5-yl)-4,5-dihydrobenzo[b]thieno[2,3-d]oxepin-9-yl)methanone |
| 464 | 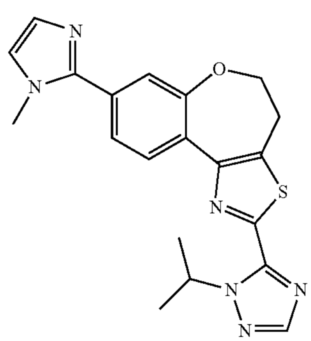 [SMILES: CC(C)n1ncnc1-c1nc2c(s1)CCOc1cc(-c3nccn3C)ccc1-2] | 8-(1-methylimidazol-2-yl)-(4H-4-isopropyl-1,2,4-triazol-5-yl)-4,5-dihydro-6-oxa-3-thia-1-aza-benzo[e]azulene |
| 465 | 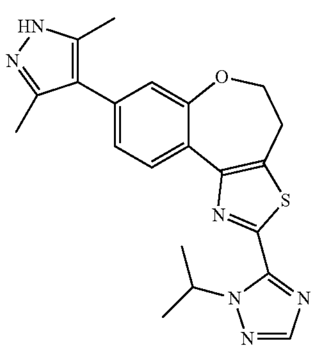 [SMILES: Cc1n[nH]c(C)c1-c1ccc2c(c1)OCCc1sc(-c3ncnn3C(C)C)nc1-2] | 8-(1H-3,5-dimethylpyrazol-4-yl)-2-isopropyl-2H-1,2,4-triazol-3-yl-4,5-dihydro-6-oxa-3-thia-1-aza-benzo[e]azulene |

TABLE 1-continued

| No. | Structure | Name |
|---|---|---|
| 466 | 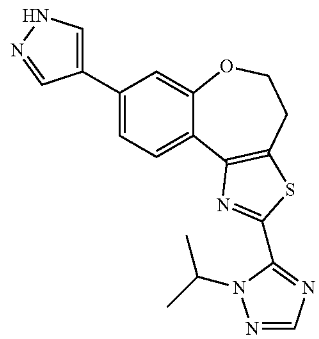 [SMILES: CC(C)n1ncnc1-c1nc2c(s1)CCOc1cc(-c3cn[nH]c3)ccc1-2] | 8-(1H-pyrazol-4-yl)-2-isopropyl-2H-1,2,4-triazol-3-yl-4,5-dihydro-6-oxa-3-thia-1-aza-benzo[e]azulene |
| 467 | 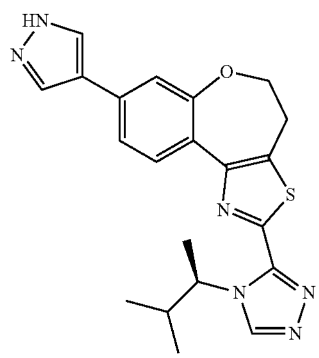 [SMILES: CC(C)[C@@H](C)n1cnnc1-c1nc2c(s1)CCOc1cc(-c3cn[nH]c3)ccc1-2] | 8-(1H-pyrazol-4-yl)-(4-(R-1-methylisobutyl-4H)-1,2,4-triazol-5-yl)-4,5-dihydro-6-oxa-3-thia-1-aza-benzo[e]azulene |
| 468 | 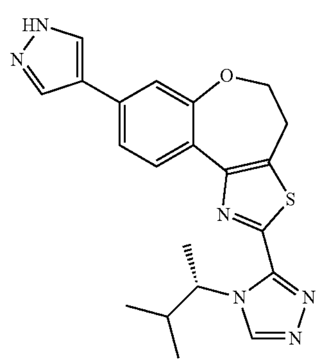 [SMILES: CC(C)[C@H](C)n1cnnc1-c1nc2c(s1)CCOc1cc(-c3cn[nH]c3)ccc1-2] | 8-(1H-pyrazol-4-yl)-(4-(S-1-methylisobutyl-4H)-1,2,4-triazol-5-yl)-4,5-dihydro-6-oxa-3-thia-1-aza-benzo[e]azulene |
| 469 | 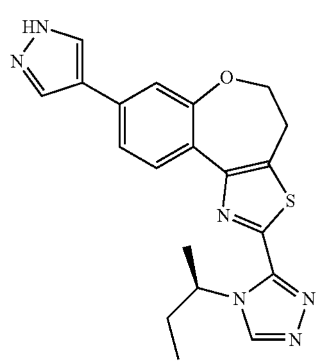 [SMILES: CC[C@@H](C)n1cnnc1-c1nc2c(s1)CCOc1cc(-c3cn[nH]c3)ccc1-2] | 8-(1H-pyrazol-4-yl)-(4-(R-1-methylpropyl-4H)-1,2,4-triazol-5-yl)-4,5-dihydro-6-oxa-3-thia-1-aza-benzo[e]azulene |

TABLE 1-continued

| No. | Structure | Name |
| --- | --- | --- |
| 470 | 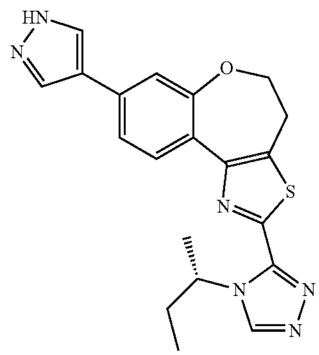 [SMILES: CC[C@H](C)n1cnnc1-c1nc2c(s1)CCOc1cc(-c3cn[nH]c3)ccc1-2] | 8-(1H-pyrazol-4-yl)-(4-(R-1-methylpropyl-4H)-1,2,4-triazol-5-yl)-4,5-dihydro-6-oxa-3-thia-1-aza-benzo[e]azulene |
| 471 | 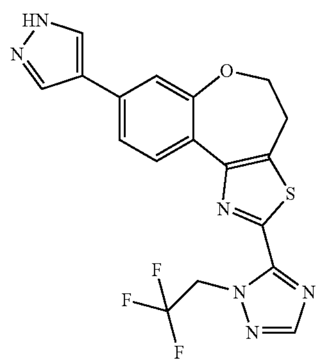 [SMILES: FC(F)(F)Cn1ncnc1-c1nc2c(s1)CCOc1cc(-c3cn[nH]c3)ccc1-2] | 8-(1H-pyrazol-4-yl)-(2-trifluoroethyl-2H-1,2,4-triazol-3-yl)-4,5-dihydro-6-oxa-3-thia-1-aza-benzo[e]azulene |
| 472 | 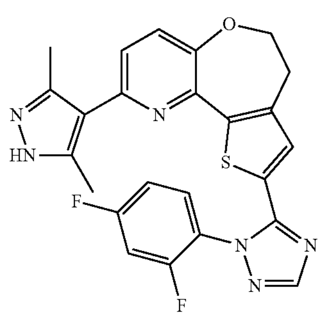 [SMILES: Cc1n[nH]c(C)c1-c1ccc2c(n1)-c1sc(-c3ncnn3-c3ccc(F)cc3F)cc1CCO2] | 5-(2-(1H-3,5-dimethylpyrazol-4-yl)-6,7-dihydropyrido[3,2-b]thieno[2,3-d]oxepin-9-yl)-1-(2,4-difluorophenyl)-1H-1,2,4-triazole |
| 473 | 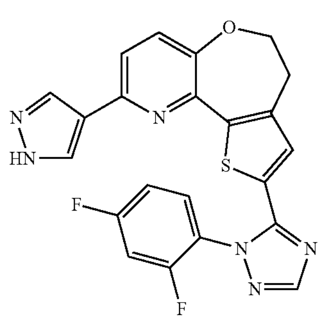 [SMILES: Fc1ccc(-n2ncnc2-c2cc3c(s2)-c2nc(-c4cn[nH]c4)ccc2OCC3)c(F)c1] | 5-(2-(1H-pyrazol-4-yl)-6,7-dihydropyrido[3,2-b]thieno[2,3-d]oxepin-9-yl)-1-(2,4-difluorophenyl)-1H-1,2,4-triazole |

TABLE 1-continued

| No. | Structure | Name |
|---|---|---|
| 474 | 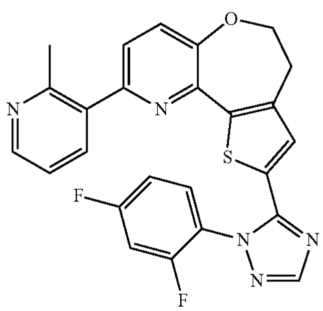 [SMILES: Cc1ncccc1-c1ccc2c(n1)-c1sc(-c3ncnn3-c3ccc(F)cc3F)cc1CCO2] | 5-(2-(2-methylpyrid-3-yl)-6,7-dihydropyrido[3,2-b]thieno[2,3-d]oxepin-9-yl)-1-(2,4-difluorophenyl)-1H-1,2,4-triazole |
| 475 | 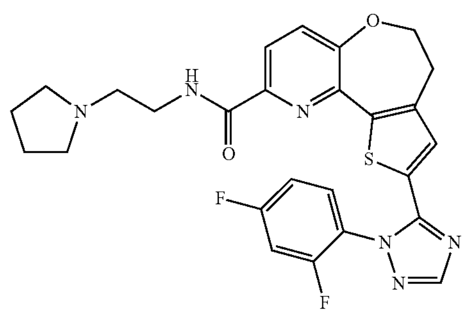 [SMILES: O=C(NCCN1CCCC1)c1ccc2c(n1)-c1sc(-c3ncnn3-c3ccc(F)cc3F)cc1CCO2] | 5-(2-(N-2-(pyrrolidin-1-yl)ethylcarbamoyl)-6,7-dihydropyrido[3,2-b]thieno[2,3-d]oxepin-9-yl)-1-(2,4-difluorophenyl)-1H-1,2,4-triazole |
| 476 | 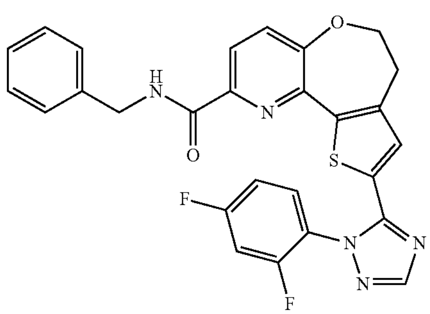 [SMILES: O=C(NCc1ccccc1)c1ccc2c(n1)-c1sc(-c3ncnn3-c3ccc(F)cc3F)cc1CCO2] | 5-((2-N-benzylcarbamoyl)-6,7-dihydropyrido[3,2-b]thieno[2,3-d]oxepin-9-yl)-1-(2,4-difluorophenyl)-1H-1,2,4-triazole |
| 477 | 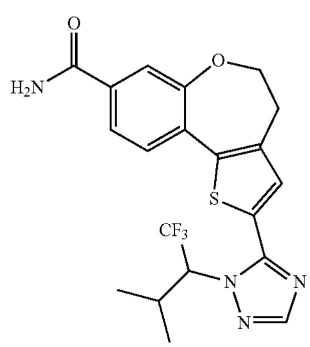 [SMILES: CC(C)C(n1ncnc1-c1cc2c(s1)-c1ccc(C(N)=O)cc1OCC2)C(F)(F)F] | 2-(1-(1,1,1-trifluoro-3-methylbutan-2-yl)-1H-1,2,4-triazol-5-yl)-4,5-dihydrobenzo[b]thieno[2,3-d]oxepine-8-carboxamide |
| 478 | 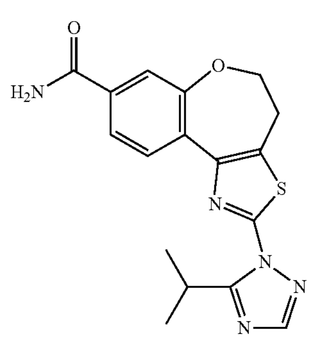 [SMILES: CC(C)c1ncnn1-c1nc2c(s1)CCOc1cc(C(N)=O)ccc1-2] | 2-(5-Isopropyl-[1,2,4]triazol-1-yl)-4,5-dihydro-6-oxa-3-thia-1-aza-benzo[e]azulene-8-carboxylic acid amide |

TABLE 1-continued

| No. | Structure | Name |
|---|---|---|
| 479 | 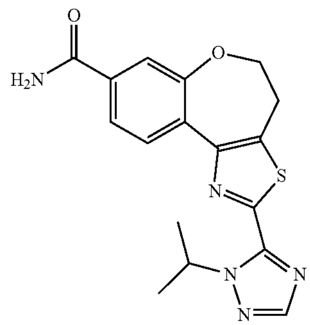 [SMILES: CC(C)n1ncnc1-c1nc2c(s1)CCOc1cc(C(N)=O)ccc1-2] | 8-carbamoyl-2-isopropyl-2H-1,2,4-triazol-3-yl-4,5-dihydro-6-oxa-3-thia-1-aza-benzo[e]azulene |
| 480 | 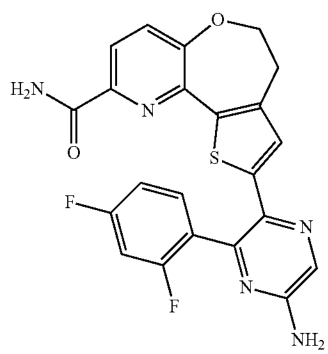 [SMILES: NC(=O)c1ccc2c(n1)-c1sc(-c3ncc(N)nc3-c3ccc(F)cc3F)cc1CCO2] | 2-(2-carbamoyl-6,7-dihydropyrido[3,2-b]thieno[2,3-d]oxepin-9-yl)-3-(2,4-difluorophenyl)-5-aminopyrazine |
| 481 | 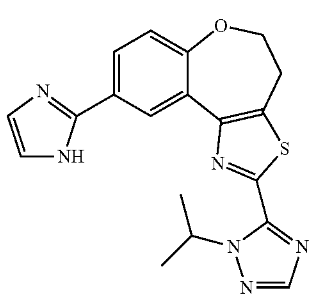 [SMILES: CC(C)n1ncnc1-c1nc2c(s1)CCOc1ccc(-c3ncc[nH]3)cc1-2] | 9-(imidazo-2-yl)-2-isopropyl-2H-1,2,4-triazol-3-yl-4,5-dihydro-6-oxa-3-thia-1-aza-benzo[e]azulene |
| 482 | 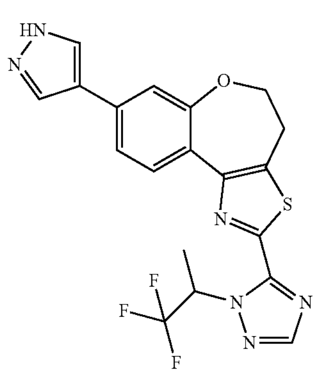 [SMILES: CC(n1ncnc1-c1nc2c(s1)CCOc1cc(-c3cn[nH]c3)ccc1-2)C(F)(F)F] | 8-(1H-pyrazol-4-yl)-((1,1,1-trifluoropropan-2-yl)-2H-1,2,4-triazol-3-yl)-4,5-dihydro-6-oxa-3-thia-1-aza-benzo[e]azulene |

TABLE 1-continued

| No. | Structure | Name |
|---|---|---|
| 483 | 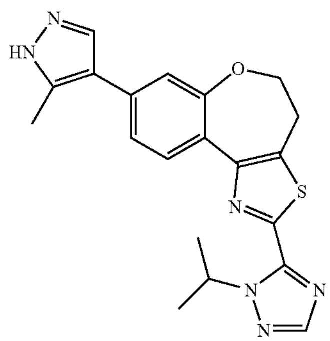 [SMILES: Cc1[nH]ncc1-c1ccc2c(c1)OCCc1sc(-c3ncnn3C(C)C)nc1-2] | 8-(1H-5-methyl-pyrazol-4-yl)-2-isopropyl-2H-1,2,4-triazol-3-yl-4,5-dihydro-6-oxa-3-thia-1-aza-benzo[e]azulene |
| 484 | 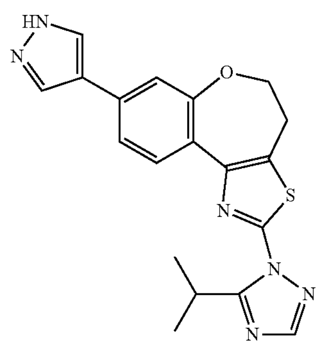 [SMILES: CC(C)c1ncnn1-c1nc2c(s1)CCOc1cc(-c3cn[nH]c3)ccc1-2] | 2-(5-Isopropyl-[1,2,4]triazol-1-yl)-8-(1H-pyrazol-4-yl)-4,5-dihydro-6-oxa-3-thia-1-aza-benzo[e]azulene |
| 485 | 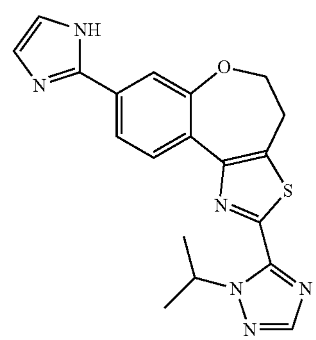 [SMILES: CC(C)n1ncnc1-c1nc2c(s1)CCOc1cc(-c3ncc[nH]3)ccc1-2] | 8-(imidazo-2-yl)-2-isopropyl-2H-1,2,4-triazol-3-yl-4,5-dihydro-6-oxa-3-thia-1-aza-benzo[e]azulene |
| 486 | 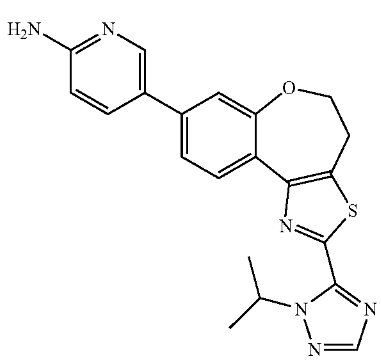 [SMILES: CC(C)n1ncnc1-c1nc2c(s1)CCOc1cc(-c3ccc(N)nc3)ccc1-2] | 8-(2-amino-pyrid-5-yl)-2-isopropyl-2H-1,2,4-triazol-3-yl-4,5-dihydro-6-oxa-3-thia-1-aza-benzo[e]azulene |

TABLE 1-continued

| No. | Structure | Name |
|---|---|---|
| 487 | 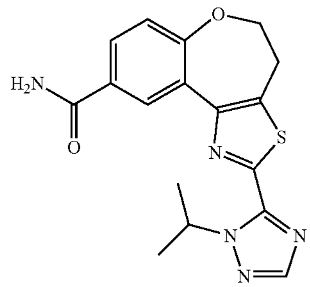 [SMILES: CC(C)n1ncnc1-c1nc2c(s1)CCOc1ccc(C(N)=O)cc1-2] | 9-(carbamoyl)-2-isopropyl-2H-1,2,4-triazol-3-yl-4,5-dihydro-6-oxa-3-thia-1-aza-benzo[e]azulene |
| 488 | 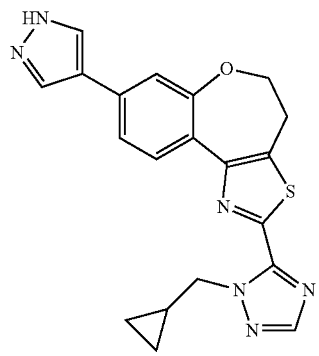 [SMILES: c1nc(-c2nc3c(s2)CCOc2cc(-c4cn[nH]c4)ccc2-3)n(CC2CC2)n1] | 8-(1H-pyrazol-4-yl)-(1-cyclopropylmethyl-1H-1,2,4-triazol-5-yl)-4,5-dihydro-6-oxa-3-thia-1-aza-benzo[e]azulene |
| 489 | 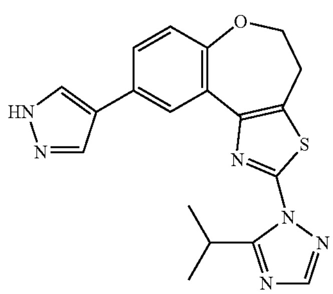 [SMILES: CC(C)c1ncnn1-c1nc2c(s1)CCOc1ccc(-c3cn[nH]c3)cc1-2] | 2-(5-Isopropyl-[1,2,4]triazol-1-yl)-9-(1H-pyrazol-4-yl)-4,5-dihydro-6-oxa-3-thia-1-aza-benzo[e]azulene |
| 490 | 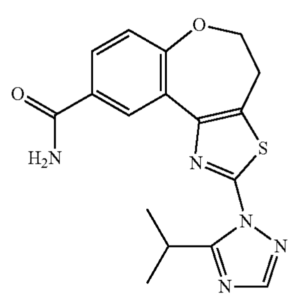 [SMILES: CC(C)c1ncnn1-c1nc2c(s1)CCOc1ccc(C(N)=O)cc1-2] | 2-(5-Isopropyl-[1,2,4]triazol-1-yl)-4,5-dihydro-6-oxa-3-thia-1-aza-benzo[e]azulene-9-carboxylic acid amide |
| 491 | 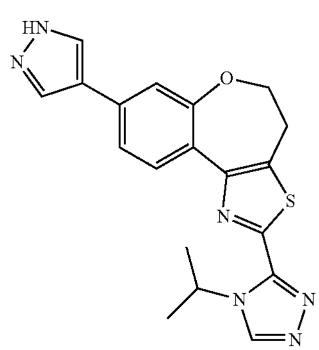 [SMILES: CC(C)n1cnnc1-c1nc2c(s1)CCOc1cc(-c3cn[nH]c3)ccc1-2] | 8-(1H-pyrazol-4-yl)-(4-isopropyl-4H-1,2,4-triazol-5-yl)-4,5-dihydro-6-oxa-3-thia-1-aza-benzo[e]azulene |

TABLE 1-continued

| No. | Structure | Name |
|---|---|---|
| 492 | 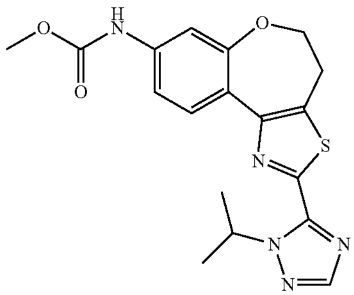 [SMILES: COC(=O)Nc1ccc2c(c1)OCCc1sc(-c3ncnn3C(C)C)nc1-2] | 8-(methylcarbamate)-(1-isopropyl-1H-1,2,4-triazol-5-yl)-4,5-dihydro-6-oxa-3-thia-1-aza-benzo[e]azulene |
| 493 | 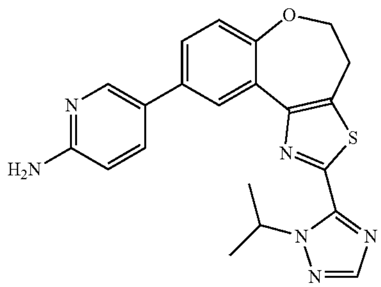 [SMILES: CC(C)n1ncnc1-c1nc2c(s1)CCOc1ccc(-c3ccc(N)nc3)cc1-2] | 9-(2-amino-pyrid-5-yl)-2-isopropyl-2H-1,2,4-triazol-3-yl-4,5-dihydro-6-oxa-3-thia-1-aza-benzo[e]azulene |
| 494 | 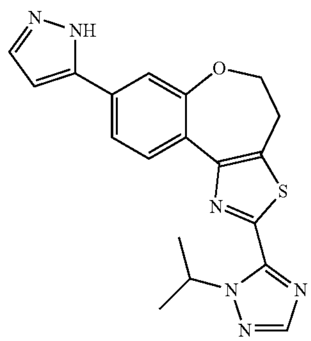 [SMILES: CC(C)n1ncnc1-c1nc2c(s1)CCOc1cc(-c3ccn[nH]3)ccc1-2] | 8-(1H-pyrazol-5-yl)-2-isopropyl-2H-1,2,4-triazol-3-yl-4,5-dihydro-6-oxa-3-thia-1-aza-benzo[e]azulene |
| 495 | 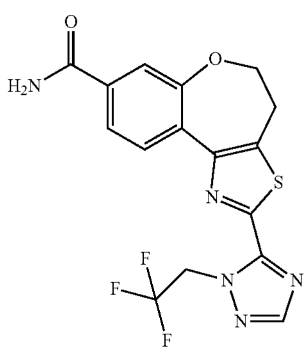 [SMILES: NC(=O)c1ccc2c(c1)OCCc1sc(-c3ncnn3CC(F)(F)F)nc1-2] | 8-(carbamoyl)-(2-trifluoroethyl-2H-1,2,4-triazol-3-yl)-4,5-dihydro-6-oxa-3-thia-1-aza-benzo[e]azulene |
| 496 | 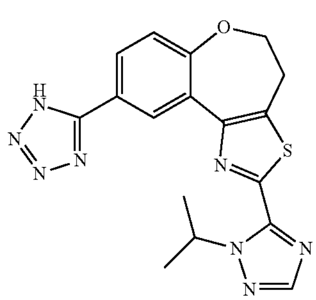 [SMILES: CC(C)n1ncnc1-c1nc2c(s1)CCOc1ccc(-c3nnn[nH]3)cc1-2] | 9-(tetrazol-5-yl)-2-isopropyl-2H-1,2,4-triazol-3-yl-4,5-dihydro-6-oxa-3-thia-1-aza-benzo[e]azulene |

| No. | Structure | Name |
| --- | --- | --- |
| 497 | 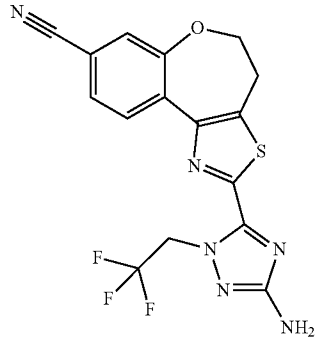 [SMILES: N#Cc1ccc2c(c1)OCCc1sc(-c3nc(N)nn3CC(F)(F)F)nc1-2] | 8-(cyano)-(2-trifluoroethyl-2H-5-amino-1,2,4-triazol-3-yl)-4,5-dihydro-6-oxa-3-thia-1-aza-benzo[e]azulene |
| 498 | 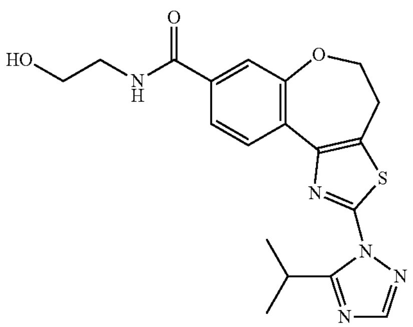 [SMILES: CC(C)c1ncnn1-c1nc2c(s1)CCOc1cc(C(=O)NCCO)ccc1-2] | 2-(5-isopropyl-[1,2,4]triazol-1-yl)-4,5-dihydro-6-oxa-3-thia-1-aza-benzo[e]azulene-8-carboxylic acid(2-hydroxy-ethyl)-amide |
| 499 | 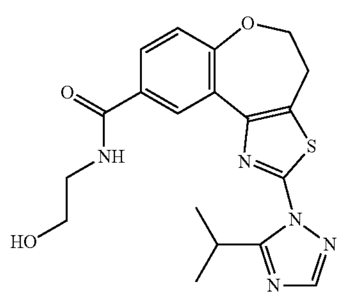 [SMILES: CC(C)c1ncnn1-c1nc2c(s1)CCOc1ccc(C(=O)NCCO)cc1-2] | 2-(5-Isopropyl-[1,2,4]triazol-1-yl)-4,5-dihydro-6-oxa-3-thia-1-aza-benzo[e]azulene-9-carboxylic acid(2-hydroxy-ethyl)-amide |
| 500 | 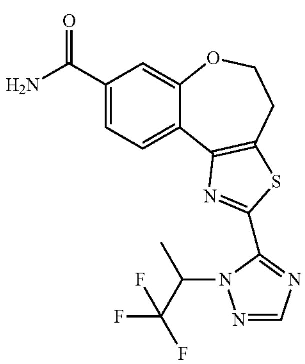 [SMILES: CC(n1ncnc1-c1nc2c(s1)CCOc1cc(C(N)=O)ccc1-2)C(F)(F)F] | 8-(carbamoyl)-((1,1,1-trifluoropropan-2-yl)-2H-1,2,4-triazol-3-yl)-4,5-dihydro-6-oxa-3-thia-1-aza-benzo[e]azulene |

TABLE 1-continued

| No. | Structure | Name |
|---|---|---|
| 501 | 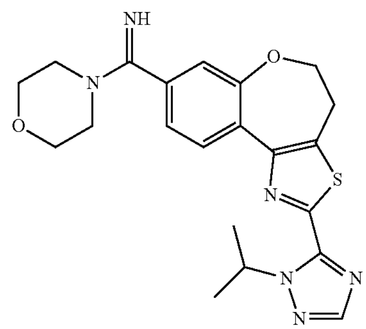 [SMILES: CC(C)n1ncnc1-c1nc2c(s1)CCOc1cc(C(=N)N3CCOCC3)ccc1-2] | 8-(morpholinomethanimine)-2-isopropyl-2H-1,2,4-triazol-3-yl-4,5-dihydro-6-oxa-3-thia-1-aza-benzo[e]azulene |
| 502 | 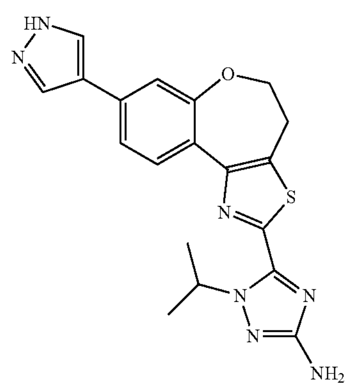 [SMILES: CC(C)n1nc(N)nc1-c1nc2c(s1)CCOc1cc(-c3cn[nH]c3)ccc1-2] | 8-(1H-pyrazol-4-yl)-(2-isopropyl-2H-5-amino-1,2,4-triazol-3-yl)-4,5-dihydro-6-oxa-3-thia-1-aza-benzo[e]azulene |
| 503 | 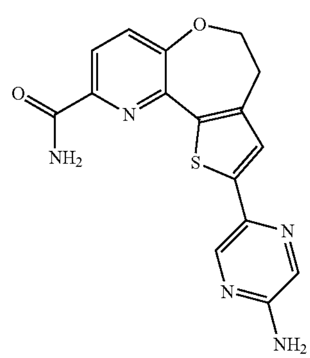 [SMILES: NC(=O)c1ccc2c(n1)-c1sc(-c3cnc(N)cn3)cc1CCO2] | 2-(2-carbamoyl-6,7-dihydropyrido[3,2-b]thieno[2,3-d]oxepin-9-yl)-5-aminopyrazine |
| 504 | 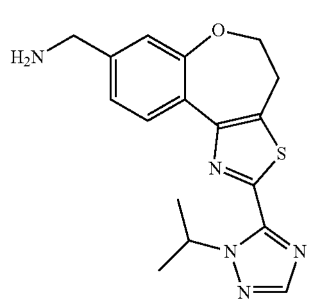 [SMILES: CC(C)n1ncnc1-c1nc2c(s1)CCOc1cc(CN)ccc1-2] | 8-(aminomethyl)-2-isopropyl-2H-1,2,4-triazol-3-yl-4,5-dihydro-6-oxa-3-thia-1-aza-benzo[e]azulene |

TABLE 1-continued

| No. | Structure | Name |
|---|---|---|
| 505 | 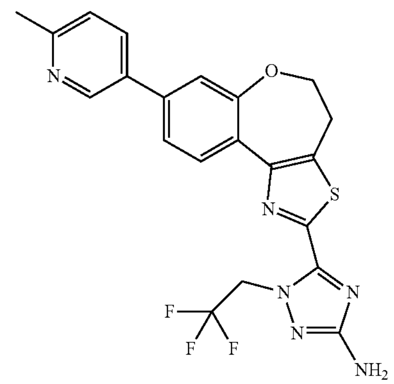 [SMILES: Cc1ccc(-c2ccc3c(c2)OCCc2sc(-c4nc(N)nn4CC(F)(F)F)nc2-3)cn1] | 8-(6-methylpyrid-3-yl)-(2-trifluoroethyl-2H-5-amino-1,2,4-triazol-3-yl)-4,5-dihydro-6-oxa-3-thia-1-aza-benzo[e]azulene |
| 506 | 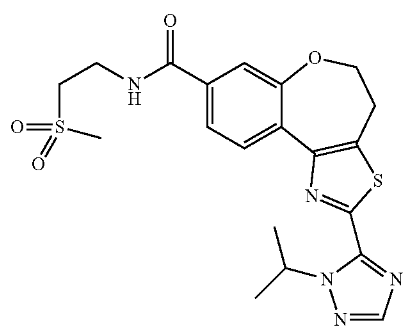 [SMILES: CC(C)n1ncnc1-c1nc2c(s1)CCOc1cc(C(=O)NCCS(C)(=O)=O)ccc1-2] | 8-((2-methylsulfonylethyl)-amide)-(4-isopropyl-4H-1,2,4-triazol-5-yl)-4,5-dihydro-6-oxa-3-thia-1-aza-benzo[e]azulene |
| 507 | 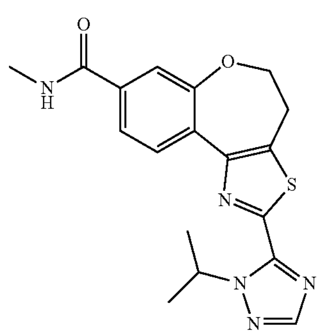 [SMILES: CNC(=O)c1ccc2c(c1)OCCc1sc(-c3ncnn3C(C)C)nc1-2] | 8-(methylcarbamoyl)-(1-isopropyl-1H-1,2,4-triazol-5-yl)-4,5-dihydro-6-oxa-3-thia-1-aza-benzo[e]azulene |
| 508 | 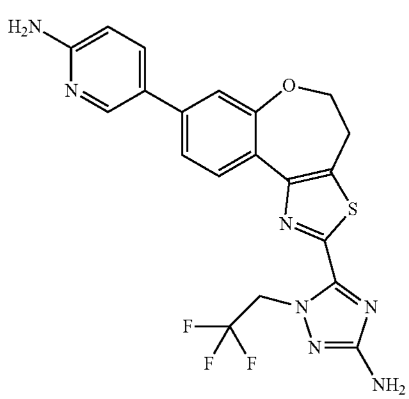 [SMILES: Nc1ccc(-c2ccc3c(c2)OCCc2sc(-c4nc(N)nn4CC(F)(F)F)nc2-3)cn1] | 8-(2-aminopyrid-5-yl)-(2-trifluoroethyl-2H-5-amino-1,2,4-triazol-3-yl)-4,5-dihydro-6-oxa-3-thia-1-aza-benzo[e]azulene |

TABLE 1-continued

| No. | Structure | Name |
| --- | --- | --- |
| 509 | 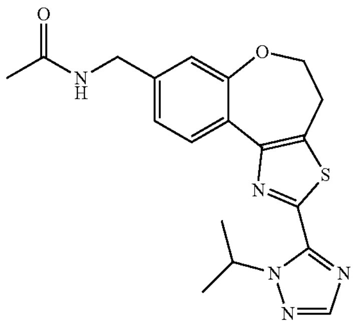 [SMILES: CC(=O)NCc1ccc2c(c1)OCCc1sc(-c3ncnn3C(C)C)nc1-2] | 8-(acetamidomethyl)-2-isopropyl-2H-1,2,4-triazol-3-yl-4,5-dihydro-6-oxa-3-thia-1-aza-benzo[e]azulene |
| 510 | 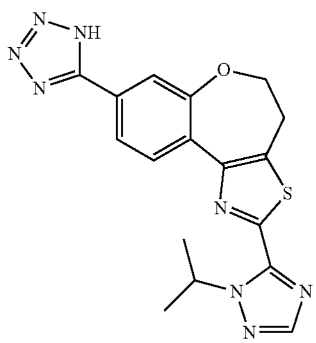 [SMILES: CC(C)n1ncnc1-c1nc2c(s1)CCOc1cc(-c3nnn[nH]3)ccc1-2] | 8-(tetrazol-5-yl)-2-isopropyl-2H-1,2,4-triazol-3-yl-4,5-dihydro-6-oxa-3-thia-1-aza-benzo[e]azulene |
| 511 | 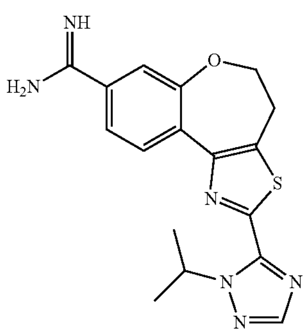 [SMILES: CC(C)n1ncnc1-c1nc2c(s1)CCOc1cc(C(=N)N)ccc1-2] | 8-(formamidinyl)-2-isopropyl-2H-1,2,4-triazol-3-yl-4,5-dihydro-6-oxa-3-thia-1-aza-benzo[e]azulene |
| 512 | 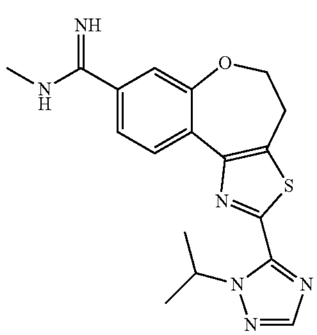 [SMILES: CNC(=N)c1ccc2c(c1)OCCc1sc(-c3ncnn3C(C)C)nc1-2] | 8-(methylformamidinyl)-2-isopropyl-2H-1,2,4-triazol-3-yl-4,5-dihydro-6-oxa-3-thia-1-aza-benzo[e]azulene |

TABLE 1-continued

| No. | Structure | Name |
|---|---|---|
| 513 | 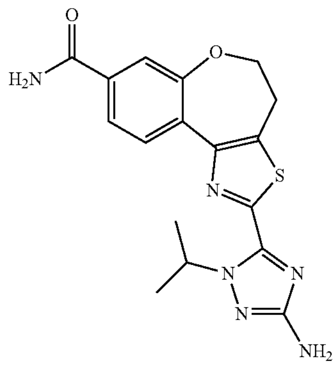 [SMILES: CC(C)n1nc(N)nc1-c1nc2c(s1)CCOc1cc(C(N)=O)ccc1-2] | 8-(carbamoyl)-(2-isopropyl-2H-5-amino-1,2,4-triazol-3-yl)-4,5-dihydro-6-oxa-3-thia-1-aza-benzo[e]azulene |
| 514 | 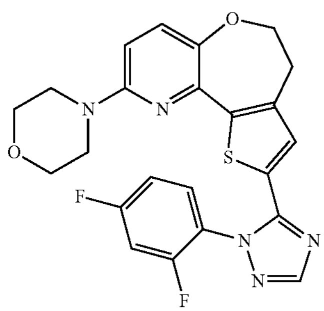 [SMILES: Fc1ccc(-n2ncnc2-c2cc3c(s2)-c2nc(N4CCOCC4)ccc2OCC3)c(F)c1] | 5-(2-(morpholin-4-yl)-6,7-dihydropyrido[3,2-b]thieno[2,3-d]oxepin-9-yl)-1-(2,4-difluorophenyl)-1H-1,2,4-triazole |
| 515 | 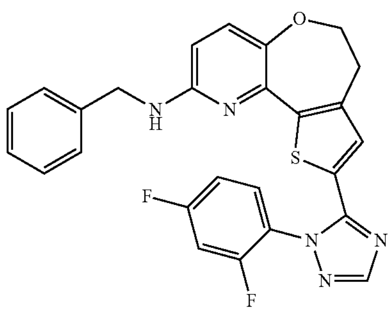 [SMILES: Fc1ccc(-n2ncnc2-c2cc3c(s2)-c2nc(NCc4ccccc4)ccc2OCC3)c(F)c1] | 5-(2-(N-benzylamino)-6,7-dihydropyrido[3,2-b]thieno[2,3-d]oxepin-9-yl)-1-(2,4-difluorophenyl)-1H-1,2,4-triazole |
| 516 | 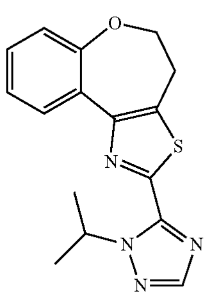 [SMILES: CC(C)n1ncnc1-c1nc2c(s1)CCOc1ccccc1-2] | (2-isopropyl-2H-1,2,4-triazol-3-yl)-4,5-dihydro-6-oxa-3-thia-1-aza-benzo[e]azulene |
| 517 | 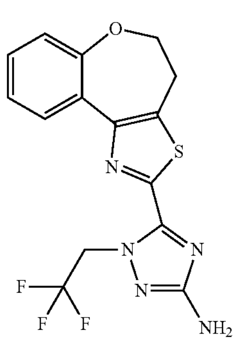 [SMILES: Nc1nc(-c2nc3c(s2)CCOc2ccccc2-3)n(CC(F)(F)F)n1] | (2-trifluoroethyl-2H-5-amino-1,2,4-triazol-3-yl)-4,5-dihydro-6-oxa-3-thia-1-aza-benzo[e]azulene |

TABLE 1-continued

| No. | Structure | Name |
|---|---|---|
| 518 | 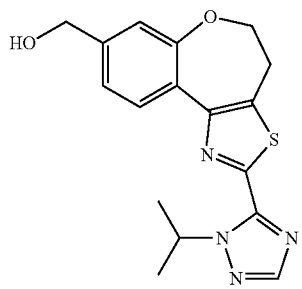 [SMILES: CC(C)n1ncnc1-c1nc2c(s1)CCOc1cc(CO)ccc1-2] | 8-(hydroxymethyl)-2-isopropyl-2H-1,2,4-triazol-3-yl-4,5-dihydro-6-oxa-3-thia-1-aza-benzo[e]azulene |
| 519 | 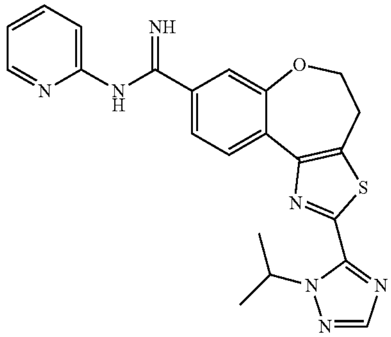 [SMILES: CC(C)n1ncnc1-c1nc2c(s1)CCOc1cc(C(=N)Nc3ccccn3)ccc1-2] | 8-(N-(pyrid-2-yl)formamidinyl)-2-isopropyl-2H-1,2,4-triazol-3-yl-4,5-dihydro-6-oxa-3-thia-1-aza-benzo[e]azulene |
| 520 | 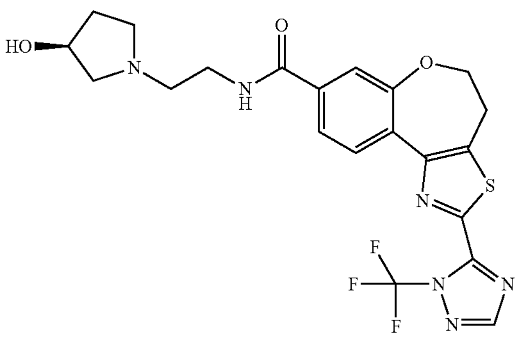 [SMILES: O=C(NCCN1CC[C@H](O)C1)c1ccc2c(c1)OCCc1sc(-c3ncnn3C(F)(F)F)nc1-2] | 8-(N-2-(S-3-hydroxypyrrolidin-1-yl)ethylcarbamoyl)-(2-trifluoroethyl-2H-1,2,4-triazol-3-yl)-4,5-dihydro-6-oxa-3-thia-1-aza-benzo[e]azulene |
| 521 | 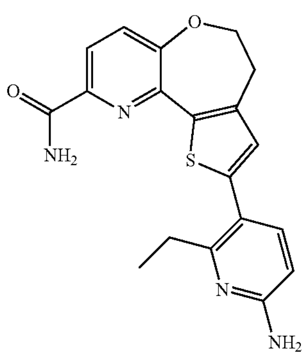 [SMILES: CCc1nc(N)ccc1-c1cc2c(s1)-c1nc(C(N)=O)ccc1OCC2] | 5-(2-carbamoyl-6,7-dihydropyrido[3,2-b]thieno[2,3-d]oxepin-9-yl)-2-amino-6-ethylpyridine |

TABLE 1-continued

| No. | Structure | Name |
|---|---|---|
| 522 | 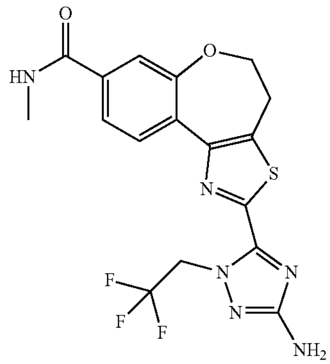 [SMILES: CNC(=O)c1ccc2c(c1)OCCc1sc(-c3nc(N)nn3CC(F)(F)F)nc1-2] | 8-(methylcarbamoyl)-(2-trifluoroethyl-2H-5-amino-1,2,4-triazol-3-yl)-4,5-dihydro-6-oxa-3-thia-1-aza-benzo[e]azulene |
| 523 | 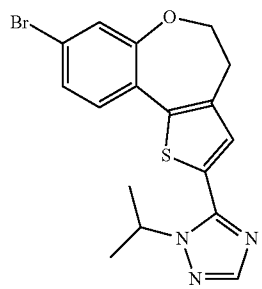 [SMILES: CC(C)n1ncnc1-c1cc2c(s1)-c1ccc(Br)cc1OCC2] | 5-(8-bromo-4,5-dihydrobenzo[b]thieno[2,3-d]oxepin-2-yl)-1-isopropyl-1H-1,2,4-triazole |
| 524 | 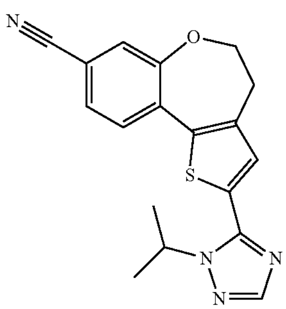 [SMILES: CC(C)n1ncnc1-c1cc2c(s1)-c1ccc(C#N)cc1OCC2] | 2-(1-isopropyl-1H-1,2,4-triazol-5-yl)-4,5-dihydrobenzo[b]thieno[2,3-d]oxepine-8-carbonitrile |
| 525 | 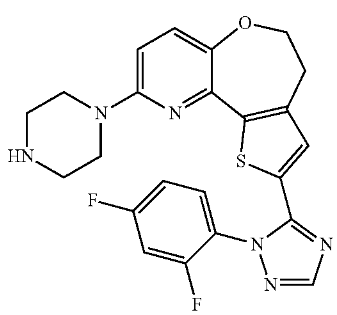 [SMILES: Fc1ccc(-n2ncnc2-c2cc3c(s2)-c2nc(N4CCNCC4)ccc2OCC3)c(F)c1] | 5-(2-(N-piperazinyl)-6,7-dihydropyrido[3,2-b]thieno[2,3-d]oxepin-9-yl)-1-(2,4-difluorophenyl)-1H-1,2,4-triazole |
| 526 | 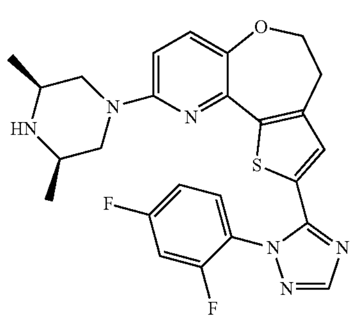 [SMILES: C[C@@H]1CN(c2ccc3c(n2)-c2sc(-c4ncnn4-c4ccc(F)cc4F)cc2CCO3)C[C@H](C)N1] | 5-(2-(3R,5S-dimethylpiperazin-1-yl)-6,7-dihydropyrido[3,2-b]thieno[2,3-d]oxepin-9-yl)-1-(2,4-difluorophenyl)-1H-1,2,4-triazole |

TABLE 1-continued

| No. | Structure | Name |
|---|---|---|
| 527 | 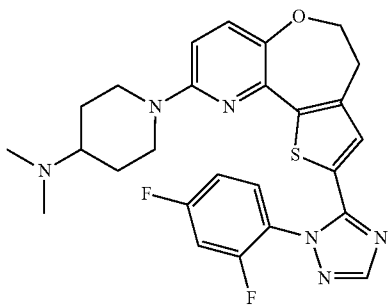 [SMILES: CN(C)C1CCN(c2ccc3c(n2)-c2sc(-c4ncnn4-c4ccc(F)cc4F)cc2CCO3)CC1] | 5-((2-(4-dimethylamino)piperidin-1-yl)-6,7-dihydropyrido[3,2-b]thieno[2,3-d]oxepin-9-yl)-1-(2,4-difluorophenyl)-1H-1,2,4-triazole |
| 528 | 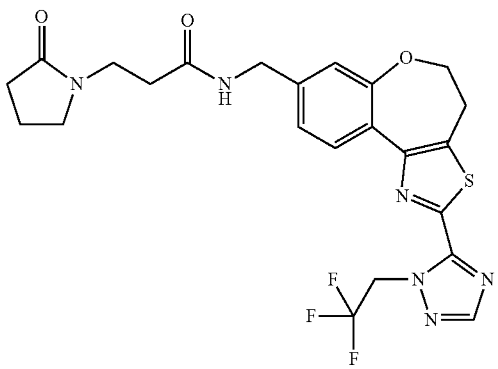 [SMILES: O=C(CCN1CCCC1=O)NCc1ccc2c(c1)OCCc1sc(-c3ncnn3CC(F)(F)F)nc1-2] | 8-(3-(2-oxopyrrolidin-1-yl)propanamidomethyl)-(2-trifluoroethyl-2H-1,2,4-triazol-3-yl)-4,5-dihydro-6-oxa-3-thia-1-aza-benzo[e]azulene |
| 529 | 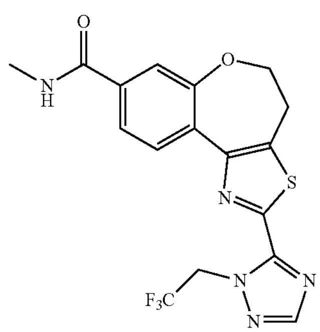 [SMILES: CNC(=O)c1ccc2c(c1)OCCc1sc(-c3ncnn3CC(F)(F)F)nc1-2] | 8-(methylcarbamoyl)-(2-trifluoroethyl-2H-1,2,4-triazol-3-yl)-4,5-dihydro-6-oxa-3-thia-1-aza-benzo[e]azulene |
| 530 | 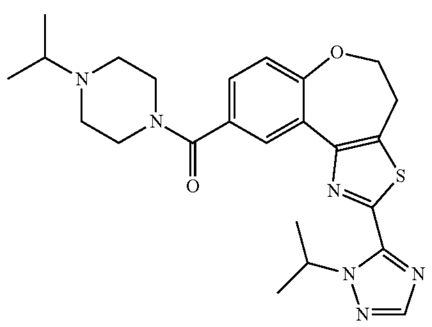 [SMILES: CC(C)N1CCN(C(=O)c2ccc3c(c2)-c2nc(-c4ncnn4C(C)C)sc2CCO3)CC1] | (2-(2-isopropyl-2H-1,2,4-triazol-3-yl)-4,5-dihydro-6-oxa-3-thia-1-aza-benzo[e]azulen-9-yl)(4-isopropylpiperazin-1-yl)methanone |
| 531 | 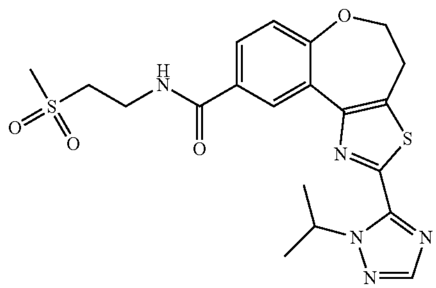 [SMILES: CC(C)n1ncnc1-c1nc2c(s1)CCOc1ccc(C(=O)NCCS(C)(=O)=O)cc1-2] | 9-((2-methylsulfonylethyl)-amide)-(4-isopropyl-4H-1,2,4-triazol-5-yl)-4,5-dihydro-6-oxa-3-thia-1-aza-benzo[e]azulene |

TABLE 1-continued

| No. | Structure | Name |
|---|---|---|
| 532 | 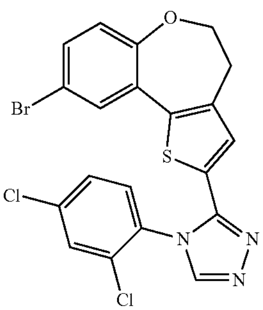 [SMILES: Clc1ccc(-n2cnnc2-c2cc3c(s2)-c2cc(Br)ccc2OCC3)c(Cl)c1] | 3-(9-bromo-4,5-dihydro-6-oxa-1-thia-benzo[e]azulen-2-yl)-4-(2,4-dichloro-phenyl)-4H-[1,2,4]triazole |
| 533 | 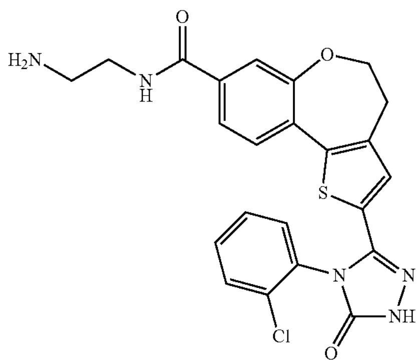 [SMILES: NCCNC(=O)c1ccc2c(c1)OCCc1cc(-c3n[nH]c(=O)n3-c3ccccc3Cl)sc1-2] | N-(2-aminoethyl)-2-(4-(2-chlorophenyl)-5-oxo-4,5-dihydro-1H-1,2,4-triazol-3-yl)-4,5-dihydrobenzo[b]thieno[2,3-d]oxepine-8-carboxamide |

Exemplary Formula II compounds in Table 2, were made, characterized, and tested for PI3K activity according to the methods of this invention, and have the following structures and corresponding names (ChemDraw Ultra, Version 9.0.1, CambridgeSoft Corp., Cambridge Mass.).

TABLE 2

| No. | Structure | Name |
|---|---|---|
| 105bp | 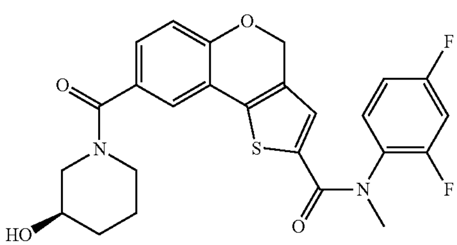 [SMILES: CN(C(=O)c1cc2c(s1)-c1cc(C(=O)N3CCC[C@@H](O)C3)ccc1OC2)c1ccc(F)cc1F] | (R)-N-(2,4-difluorophenyl)-8-(3-hydroxypiperidine-1-carbonyl)-N-methyl-4H-thieno[3,2-c]chromene-2-carboxamide |
| 109bp | 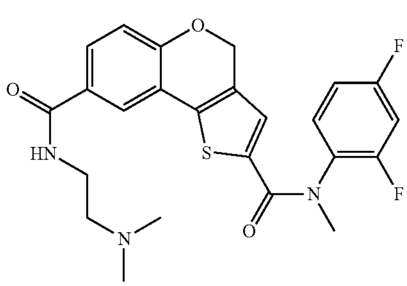 [SMILES: CN(C)CCNC(=O)c1ccc2c(c1)-c1sc(C(=O)N(C)c3ccc(F)cc3F)cc1CO2] | N2-(2,4-difluorophenyl)-N8-(2-(dimethylamino)ethyl)-N2-methyl-4H-thieno[3,2-c]chromene-2,8-dicarboxamide |

TABLE 2-continued

| No. | Structure | Name |
|---|---|---|
| 110bp | 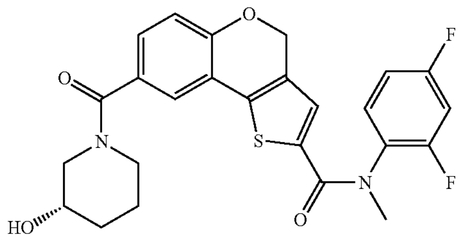 [SMILES: CN(C(=O)c1cc2c(s1)-c1cc(C(=O)N3CCC[C@H](O)C3)ccc1OC2)c1ccc(F)cc1F] | (S)-N-(2,4-difluorophenyl)-8-(3-hydroxypiperidine-1-carbonyl)-N-methyl-4H-thieno[3,2-c]chromene-2-carboxamide |
| 111bp | 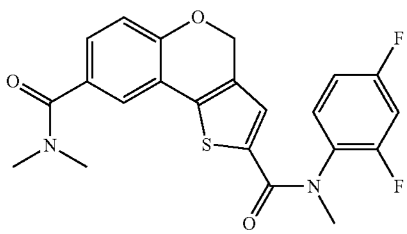 [SMILES: CN(C)C(=O)c1ccc2c(c1)-c1sc(C(=O)N(C)c3ccc(F)cc3F)cc1CO2] | N2-(2,4-difluorophenyl)-N2,N8,N8-trimethyl-4H-thieno[3,2-c]chromene-2,8-dicarboxamide |
| 112bp | 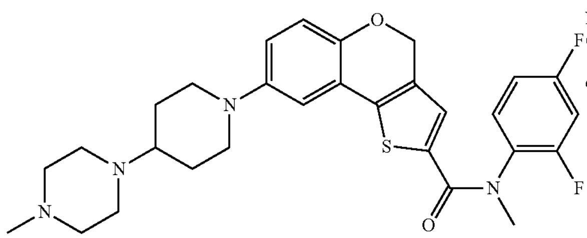 [SMILES: CN1CCN(C2CCN(c3ccc4c(c3)-c3sc(C(=O)N(C)c5ccc(F)cc5F)cc3CO4)CC2)CC1] | N-(2,4-difluorophenyl)-N-methyl-8-(4-(4-methylpiperazin-1-yl)piperidin-1-yl)-4H-thieno[3,2-c]chromene-2-carboxamide |
| 113bp | 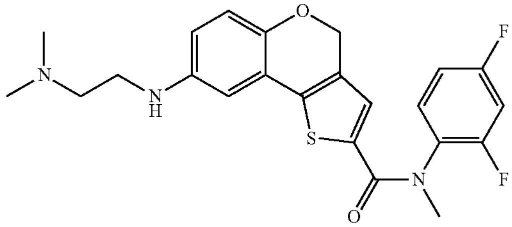 [SMILES: CN(C)CCNc1ccc2c(c1)-c1sc(C(=O)N(C)c3ccc(F)cc3F)cc1CO2] | N-(2,4-difluorophenyl)-8-(2-(dimethylamino)ethylamino)-N-methyl-4H-thieno[3,2-c]chromene-2-carboxamide |
| 115bp | 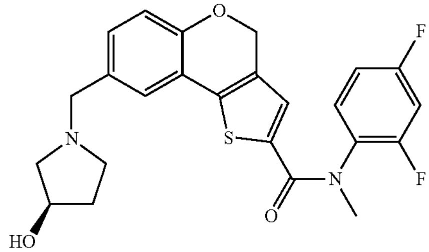 [SMILES: CN(C(=O)c1cc2c(s1)-c1cc(CN3CC[C@@H](O)C3)ccc1OC2)c1ccc(F)cc1F] | (R)-N-(2,4-difluorophenyl)-8-((3-hydroxypyrrolidin-1-yl)methyl)-N-methyl-4H-thieno[3,2-c]chromene-2-carboxamide |
| 116bp | 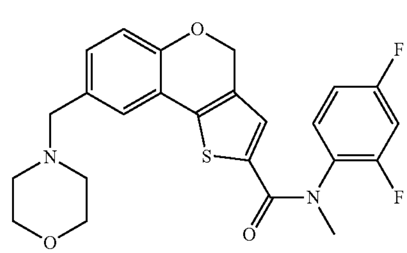 [SMILES: CN(C(=O)c1cc2c(s1)-c1cc(CN3CCOCC3)ccc1OC2)c1ccc(F)cc1F] | N-(2,4-difluorophenyl)-N-methyl-8-(morpholinomethyl)-4H-thieno[3,2-c]chromene-2-carboxamide |

TABLE 2-continued

| No. | Structure | Name |
|---|---|---|
| 117bp | 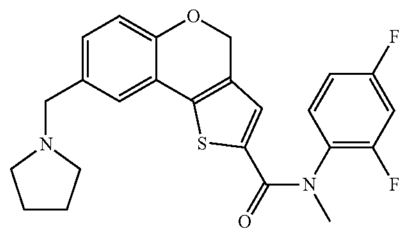 [SMILES: CN(C(=O)c1cc2c(s1)-c1cc(CN3CCCC3)ccc1OC2)c1ccc(F)cc1F] | N-(2,4-difluorophenyl)-N-methyl-8-(pyrrolidin-1-ylmethyl)-4H-thieno[3,2-c]chromene-2-carboxamide |
| 118bp | 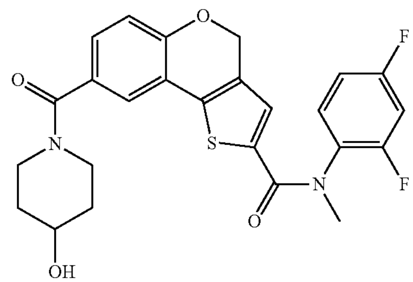 [SMILES: CN(C(=O)c1cc2c(s1)-c1cc(C(=O)N3CCC(O)CC3)ccc1OC2)c1ccc(F)cc1F] | N-(2,4-difluorophenyl)-8-(4-hydroxypiperidine-1-carbonyl)-N-methyl-4H-thieno[3,2-c]chromene-2-carboxamide |
| 119bp | 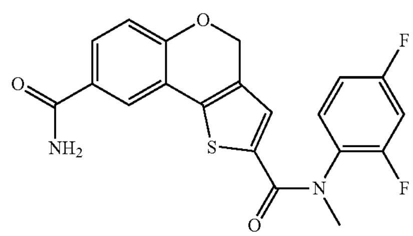 [SMILES: CN(C(=O)c1cc2c(s1)-c1cc(C(N)=O)ccc1OC2)c1ccc(F)cc1F] | N2-(2,4-difluorophenyl)-N2-methyl-4H-thieno[3,2-c]chromene-2,8-dicarboxamide |
| 120bp | 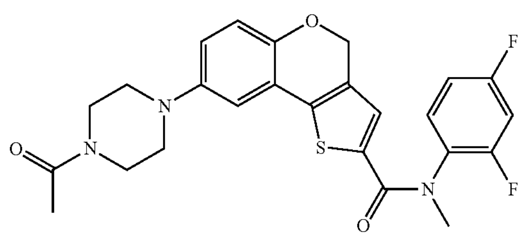 [SMILES: CC(=O)N1CCN(c2ccc3c(c2)-c2sc(C(=O)N(C)c4ccc(F)cc4F)cc2CO3)CC1] | 8-(4-acetylpiperazin-1-yl)-N-(2,4-difluorophenyl)-N-methyl-4H-thieno[3,2-c]chromene-2-carboxamide |
| 121bp | 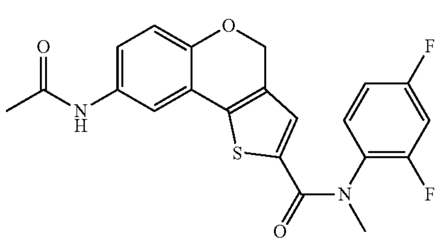 [SMILES: CC(=O)Nc1ccc2c(c1)-c1sc(C(=O)N(C)c3ccc(F)cc3F)cc1CO2] | 8-acetamido-N-(2,4-difluorophenyl)-N-methyl-4H-thieno[3,2-c]chromene-2-carboxamide |
| 127bp | 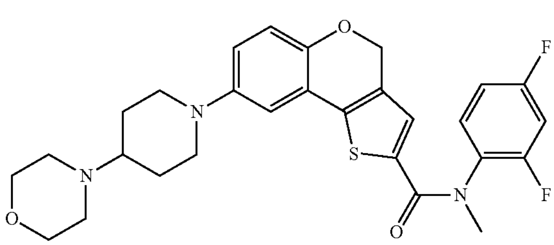 [SMILES: CN(C(=O)c1cc2c(s1)-c1cc(N3CCC(N4CCOCC4)CC3)ccc1OC2)c1ccc(F)cc1F] | N-(2,4-difluorophenyl)-N-methyl-8-(4-morpholinopiperidin-1-yl)-4H-thieno[3,2-c]chromene-2-carboxamide |

| No. | Structure | Name |
| --- | --- | --- |
| 128bp | 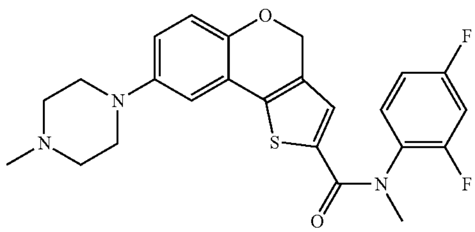 [SMILES: CN1CCN(c2ccc3c(c2)-c2sc(C(=O)N(C)c4ccc(F)cc4F)cc2CO3)CC1] | N-(2,4-difluorophenyl)-N-methyl-8-(4-methylpiperazin-1-yl)-4H-thieno[3,2-c]chromene-2-carboxamide |
| 129bp | 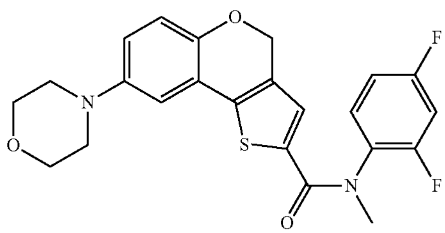 [SMILES: CN(C(=O)c1cc2c(s1)-c1cc(N3CCOCC3)ccc1OC2)c1ccc(F)cc1F] | N-(2,4-difluorophenyl)-N-methyl-8-morpholino-4H-thieno[3,2-c]chromene-2-carboxamide |
| 136bp | 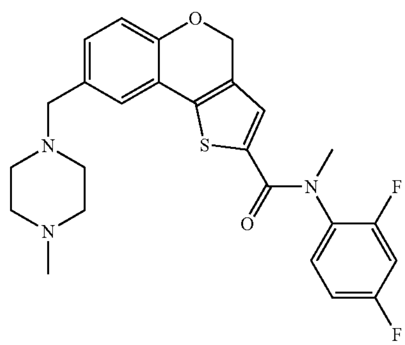 [SMILES: CN1CCN(Cc2ccc3c(c2)-c2sc(C(=O)N(C)c4ccc(F)cc4F)cc2CO3)CC1] | N-(2,4-difluorophenyl)-N-methyl-8-((4-methylpiperazin-1-yl)methyl)-4H-thieno[3,2-c]chromene-2-carboxamide |
| 140bp | 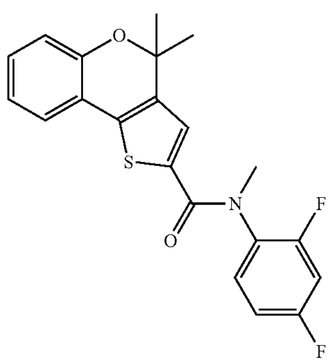 [SMILES: CN(C(=O)c1cc2c(s1)-c1ccccc1OC2(C)C)c1ccc(F)cc1F] | N-(2,4-difluorophenyl)-N,4,4-trimethyl-4H-thieno[3,2-c]chromene-2-carboxamide |
| 141bp | 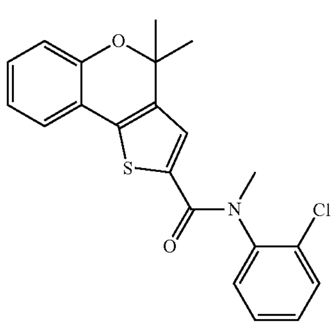 [SMILES: CN(C(=O)c1cc2c(s1)-c1ccccc1OC2(C)C)c1ccccc1Cl] | N-(2-chlorophenyl)-N,4,4-trimethyl-4H-thieno[3,2-c]chromene-2-carboxamide |

| No. | Structure | Name |
|---|---|---|
| 142bp | 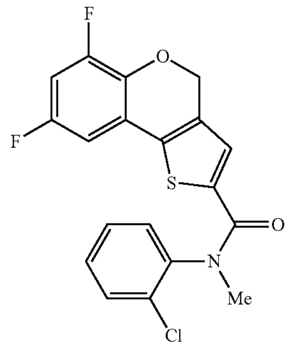 [SMILES: CN(C(=O)c1cc2c(s1)-c1cc(F)cc(F)c1OC2)c1ccccc1Cl] | N-(2-chlorophenyl)-6,8-difluoro-N-methyl-4H-thieno[3,2-c]chromene-2-carboxamide |
| 152bp | 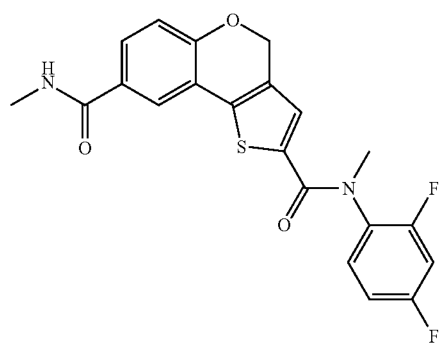 [SMILES: CNC(=O)c1ccc2c(c1)-c1sc(C(=O)N(C)c3ccc(F)cc3F)cc1CO2] | N2-(2,4-difluorophenyl)-N2,N8-dimethyl-4H-thieno[3,2-c]chromene-2,8-dicarboxamide |
| 153bp | 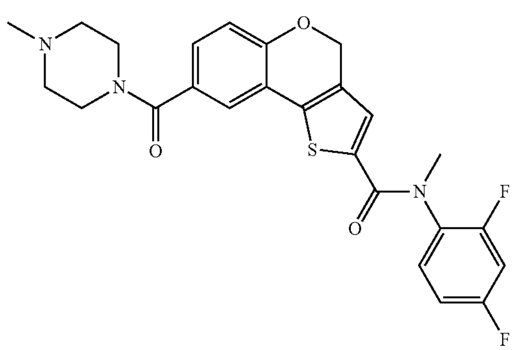 [SMILES: CN1CCN(C(=O)c2ccc3c(c2)-c2sc(C(=O)N(C)c4ccc(F)cc4F)cc2CO3)CC1] | N-(2,4-difluorophenyl)-N-methyl-8-(4-methylpiperazine-1-carbonyl)-4H-thieno[3,2-c]chromene-2-carboxamide |
| 154bp | 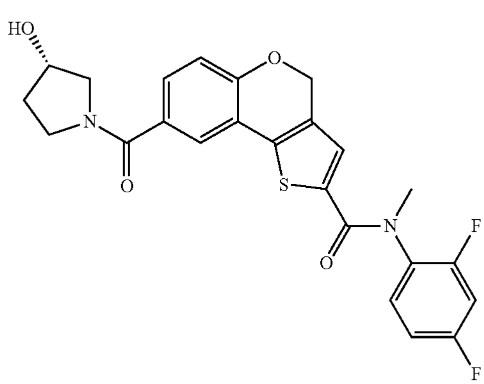 [SMILES: CN(C(=O)c1cc2c(s1)-c1cc(C(=O)N3CC[C@H](O)C3)ccc1OC2)c1ccc(F)cc1F] | (S)-N-(2,4-difluorophenyl)-8-(3-hydroxypyrrolidine-1-carbonyl)-N-methyl-4H-thieno[3,2-c]chromene-2-carboxamide |

TABLE 2-continued

| No. | Structure | Name |
|---|---|---|
| 155bp | 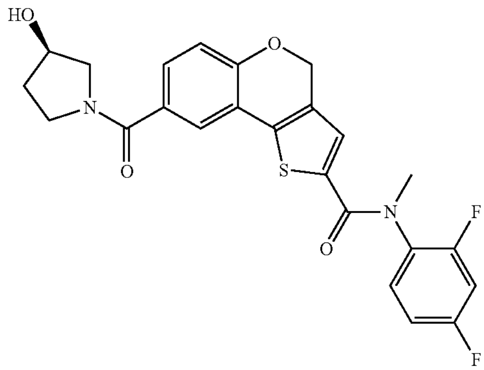 [SMILES: CN(C(=O)c1cc2c(s1)-c1cc(C(=O)N3CC[C@@H](O)C3)ccc1OC2)c1ccc(F)cc1F] | (R)-N-(2,4-difluorophenyl)-8-(3-hydroxypyrrolidine-1-carbonyl)-N-methyl-4H-thieno[3,2-c]chromene-2-carboxamide |
| 158bp | 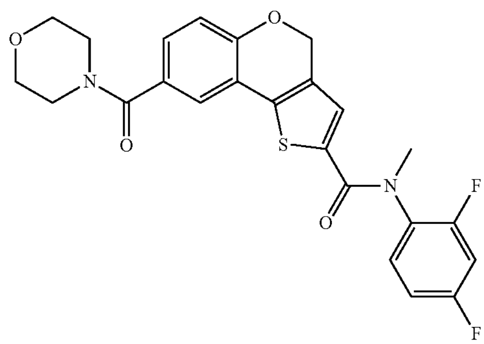 [SMILES: CN(C(=O)c1cc2c(s1)-c1cc(C(=O)N3CCOCC3)ccc1OC2)c1ccc(F)cc1F] | N-(2,4-difluorophenyl)-N-methyl-8-(morpholine-4-carbonyl)-4H-thieno[3,2-c]chromene-2-carboxamide |
| 159bp | 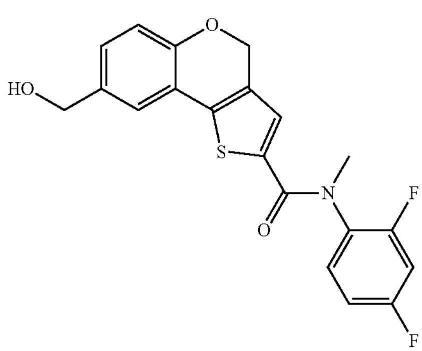 [SMILES: CN(C(=O)c1cc2c(s1)-c1cc(CO)ccc1OC2)c1ccc(F)cc1F] | N-(2,4-difluorophenyl)-8-(hydroxymethyl)-N-methyl-4H-thieno[3,2-c]chromene-2-carboxamide |
| 160bp | 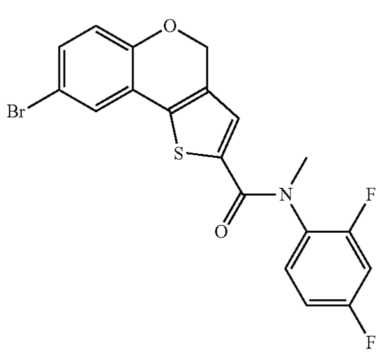 [SMILES: CN(C(=O)c1cc2c(s1)-c1cc(Br)ccc1OC2)c1ccc(F)cc1F] | 8-bromo-N-(2,4-difluorophenyl)-N-methyl-4H-thieno[3,2-c]chromene-2-carboxamide |

TABLE 2-continued

| No. | Structure | Name |
|---|---|---|
| 161bp | 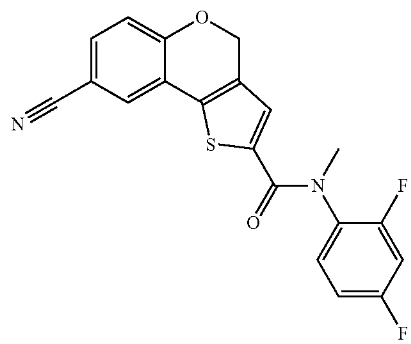 [SMILES: CN(C(=O)c1cc2c(s1)-c1cc(C#N)ccc1OC2)c1ccc(F)cc1F] | 8-cyano-N-(2,4-difluorophenyl)-N-methyl-4H-thieno[3,2-c]chromene-2-carboxamide |
| 162bp | 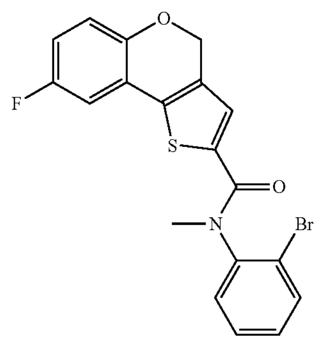 [SMILES: CN(C(=O)c1cc2c(s1)-c1cc(F)ccc1OC2)c1ccccc1Br] | N-(2-bromophenyl)-8-fluoro-N-methyl-4H-thieno[3,2-c]chromene-2-carboxamide |
| 163bp | 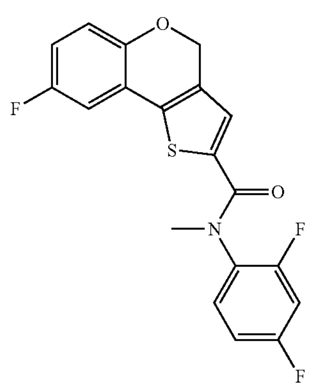 [SMILES: CN(C(=O)c1cc2c(s1)-c1cc(F)ccc1OC2)c1ccc(F)cc1F] | N-(2,4-difluorophenyl)-8-fluoro-N-methyl-4H-thieno[3,2-c]chromene-2-carboxamide |
| 164bp | 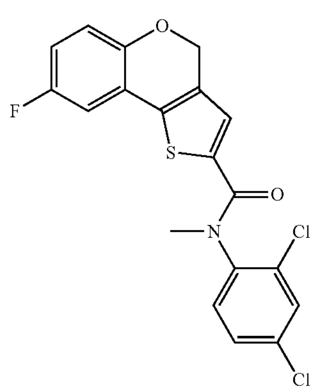 [SMILES: CN(C(=O)c1cc2c(s1)-c1cc(F)ccc1OC2)c1ccc(Cl)cc1Cl] | N-(2,4-dichlorophenyl)-8-fluoro-N-methyl-4H-thieno[3,2-c]chromene-2-carboxamide |

TABLE 2-continued

| No. | Structure | Name |
| --- | --- | --- |
| 165bp | 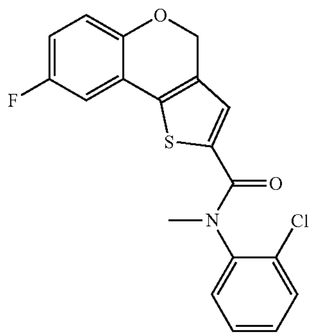 | N-(2-chlorophenyl)-8-fluoro-N-methyl-4H-thieno[3,2-c]chromene-2-carboxamide |
| 166bp | 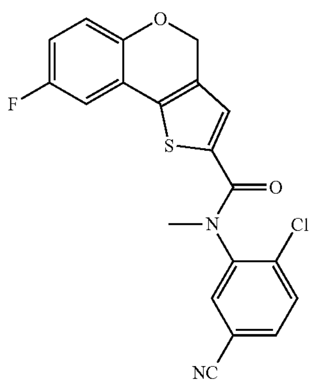 [SMILES: CN(C(=O)c1cc2c(s1)-c1cc(F)ccc1OC2)c1cc(C#N)ccc1Cl] | N-(2-chloro-5-cyanophenyl)-8-fluoro-N-methyl-4H-thieno[3,2-c]chromene-2-carboxamide |
| 167bp | 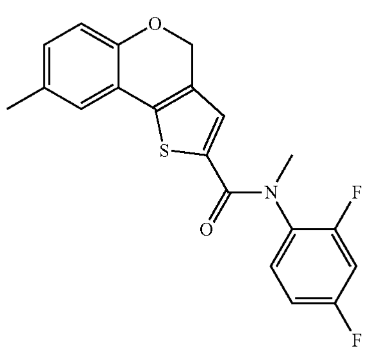 [SMILES: Cc1ccc2c(c1)-c1sc(C(=O)N(C)c3ccc(F)cc3F)cc1CO2] | N-(2,4-difluorophenyl)-N,8-dimethyl-4H-thieno[3,2-c]chromene-2-carboxamide |
| 168bp | 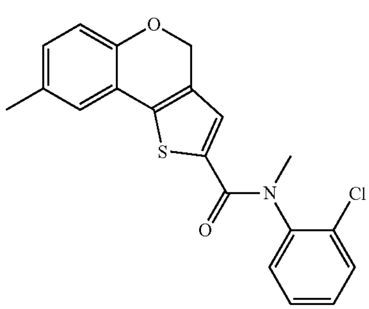 [SMILES: Cc1ccc2c(c1)-c1sc(C(=O)N(C)c3ccccc3Cl)cc1CO2] | N-(2-chlorophenyl)-N,8-dimethyl-4H-thieno[3,2-c]chromene-2-carboxamide |

TABLE 2-continued

| No. | Structure | Name |
|---|---|---|
| 169bp | 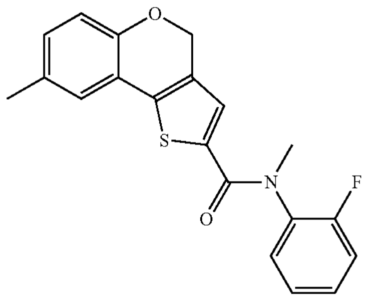 [SMILES: Cc1ccc2c(c1)-c1sc(C(=O)N(C)c3ccccc3F)cc1CO2] | N-(2-fluorophenyl)-N,8-dimethyl-4H-thieno[3,2-c]chromene-2-carboxamide |
| 170bp | 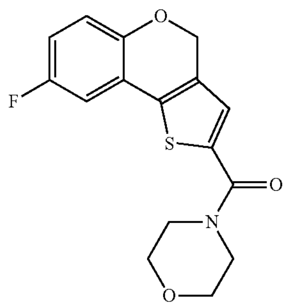 [SMILES: O=C(c1cc2c(s1)-c1cc(F)ccc1OC2)N1CCOCC1] | (8-fluoro-4H-thieno[3,2-c]chromen-2-yl)(morpholino)methanone |
| 171bp | 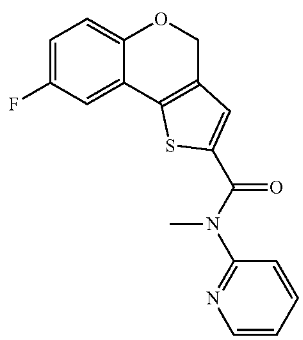 [SMILES: CN(C(=O)c1cc2c(s1)-c1cc(F)ccc1OC2)c1ccccn1] | 8-fluoro-N-methyl-N-(pyridin-2-yl)-4H-thieno[3,2-c]chromene-2-carboxamide |
| 172bp | 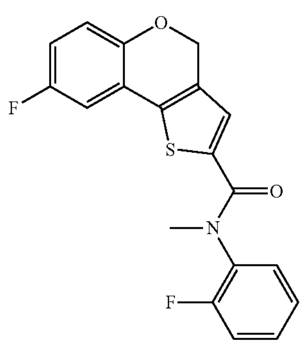 [SMILES: CN(C(=O)c1cc2c(s1)-c1cc(F)ccc1OC2)c1ccccc1F] | 8-fluoro-N-(2-fluorophenyl)-N-methyl-4H-thieno[3,2-c]chromene-2-carboxamide |
| 191bz | 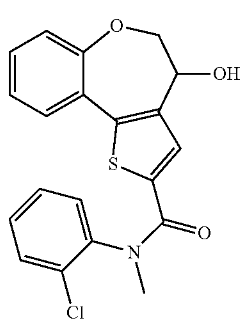 [SMILES: CN(C(=O)c1cc2c(s1)-c1ccccc1OCC2O)c1ccccc1Cl] | N-(2-chlorophenyl)-4-hydroxy-N-methyl-4,5-dihydrobenzo[b]thieno[2,3-d]oxepine-2-carboxamide |

TABLE 2-continued

| No. | Structure | Name |
|---|---|---|
| 192bp | 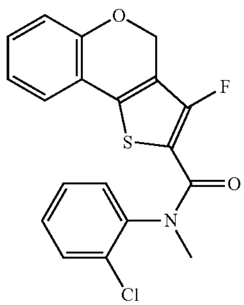 [SMILES: CN(C(=O)c1sc2c(c1F)COc1ccccc1-2)c1ccccc1Cl] | N-(2-chlorophenyl)-3-fluoro-N-methyl-4H-thieno[3,2-c]chromene-2-carboxamide |
| 193bz | 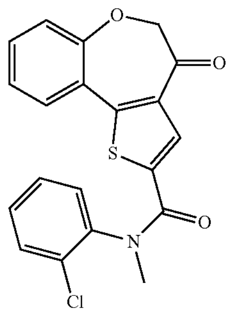 [SMILES: CN(C(=O)c1cc2c(s1)-c1ccccc1OCC2=O)c1ccccc1Cl] | N-(2-chlorophenyl)-N-methyl-4-oxo-4,5-dihydrobenzo[b]thieno[2,3-d]oxepine-2-carboxamide |

Administration of Compounds of Formula I and II

The Formula I and II compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I or II compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I and II Compounds

Compounds of the present invention are useful for treating hyperproliferative diseases, conditions and/or disorders including, but not limited to, those characterized by over expression of lipid kinases, e.g. PI3 kinase. Accordingly, another aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I and II may be prepared. Suitable examples of sustained-release preparations include semipermeable matrices of solid hydrophobic polymers containing a compound of Formula I or II, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I or II suitable for oral administration may be prepared as discrete units such as pills, capsules, cachets or tablets each containing a predetermined amount of a compound of Formula I or II.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I and II intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I or II compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I and II may be employed alone or in combination with other therapeutic agents for the treatment of a disease or disorder described herein, such as a hyperproliferative disorder (e.g., cancer). In certain embodiments, a compound of Formula I or II is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I or II, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Compounds of Formula I and II

Also falling within the scope of this invention are the in vivo metabolic products of Formula I and II described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I and II, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. The kit comprises a container comprising a compound of Formula I or II. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or II or a formulation thereof which is effective for treating the condition and may have a sterile access port (for example, the container may be an intravenous solution bag or a vial having a stopper pierceable by a hypodermic injection needle). At least one active agent in the composition is a compound of Formula I or II. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I or II can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I or II and, if present, the second pharmaceutical formulation. For example, if the kit comprises a first composition comprising a compound of Formula I or II, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I or II, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I or II contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

General Preparative Procedures

General Procedure A

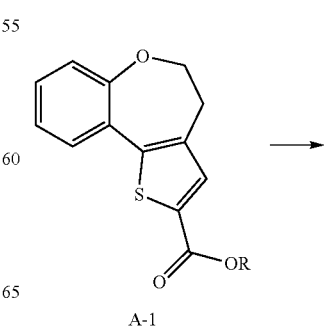

A-1

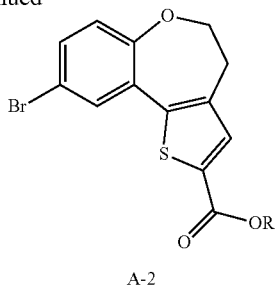

A-2

Benzoxepin intermediates, 4,5-dihydrobenzo[b]thieno[2,3-d]oxepine-2-carboxylate esters, A-1 can be selectively brominated with N-bromosuccinimide (NBS) in DMF to give 9-bromo-4,5-dihydrobenzo[b]thieno[2,3-d]oxepine-2-carboxylate esters A-2.

General Procedure B

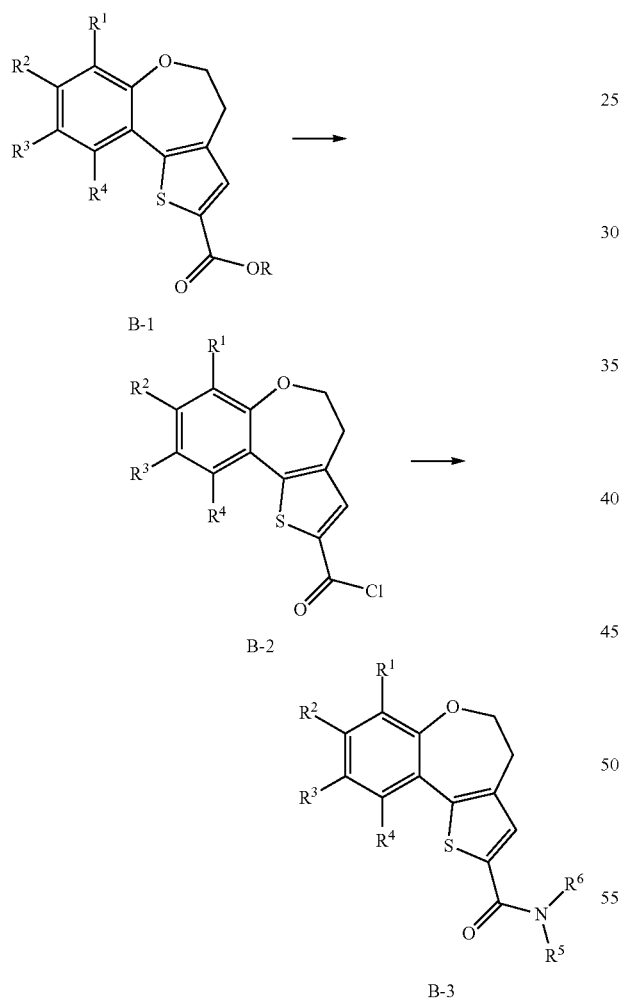

Benzoxepin carboxylic acid intermediates B-1 are converted to the acid chloride B-2 and reacted with primary or secondary amines with triethylamine, DMAP, and solvent such as dichloromethane. Reaction with a primary amine may be followed by N-alkylation, for example with methyl iodide and sodium hydride, to generate 4,5-dihydrobenzo[b]thieno[2,3-d]oxepine-2-carboxamide B-3.

For example, to a suspension of carboxylic acid (0.4 mmol) in anhydrous dichloromethane, is added oxalyl chloride (0.7 mmol) and one drop of dimethyl formamide. After 30 minutes, concentrate in-vacuo. Residue is dissolved in acetonitrile, and potassium carbonate (0.9 mmol) and an amine, e.g. aniline (0.48 mmol) are added. Reaction mixture is stirred overnight at room temperature before diluting with water and ethylacetate. Organic phase is dried (MgSO$_4$) and concentrated in-vacuo.

Alternatively, other active esters of benzoxepin carboxylic acid intermediates B-1 can be formed as anhydrides, acyl imidazolides, acyl azides, and NHS esters to react with amines. Also, benzoxepin carboxylic acid intermediates B-1 can be coupled with amines by in situ formation of active ester intermediates under the broad array of known peptide coupling reagents and methodology.

For example, to a solution of the carboxylic acid (1 eq) in DMF (6 mL) is added the amine (1.3 eq), HATU (1.3 eq) and diisopropylethyl amine (1.3 eq+1.3 eq for each HCl salt of the amine) and the reaction stirred at room temperature for 16 h. The mixture is partitioned between ethyl acetate and water. The organic layer was washed with brine (3×), dried (MgSO$_4$), reduced in vacuo and purified on silica to give the final amide.

General Procedure C

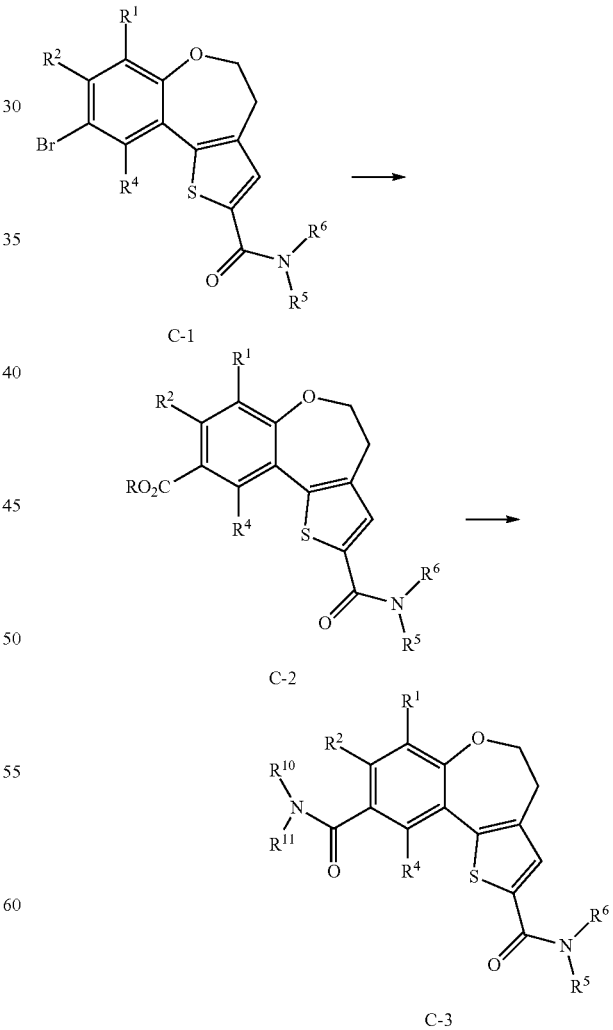

9-Bromo-4,5-dihydrobenzo[b]thieno[2,3-d]oxepine-2-carboxamide intermediates C-1 are carbonylated with carbon monoxide under high pressure with palladium catalysis, such as Pd(OAc)$_2$, and an alcohol, such as methanol to give the carboxamide intermediate C-2. Saponification with lithium hydroxide, sodium hydroxide or other aqueous base to the 8-carboxylic acid intermediate, followed by coupling of a primary or secondary amine with a coupling reagent, such as HATU or DCC gives the 9-carboxamide intermediate C-3.

Alternatively, intermediate C-3 may be prepared directly from bromo intermediate C-1 by aminocarbonylation, following the procedures of Wannberg et al (2003) J. Org. Chem. 68:5750-5753.

General Procedure D

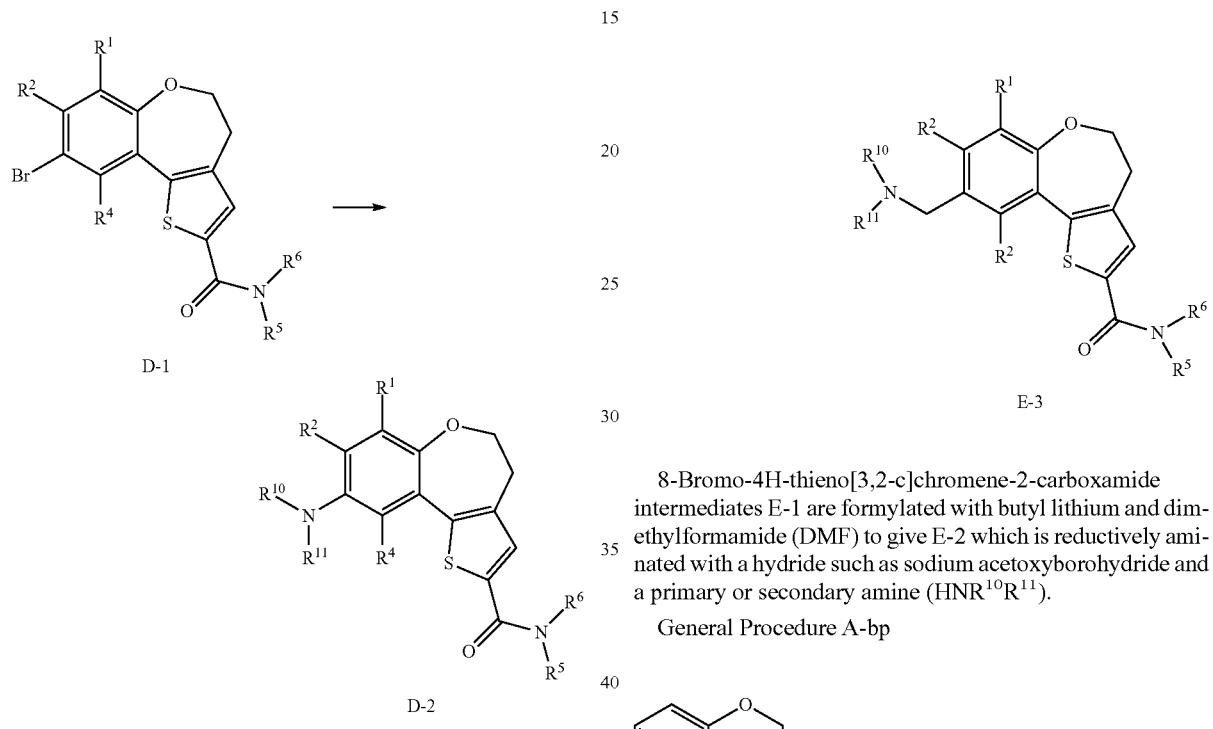

9-Bromo-4,5-dihydrobenzo[b]thieno[2,3-d]oxepine-2-carboxamide intermediates D-1 are aminated with primary or secondary amines (HNR$^{10}$R$^{11}$) or amides)(H$_2$NC(=O)R$^{10}$, palladium complexes such as Pd$_2$(dba)$_3$, catalysts such as xantphos and BINAP, alkoxides such as NaOt-Bu or carbonates such as cesium carbonate, in toluene or dioxane, and heating to give aminated products D-2.

General Procedure E

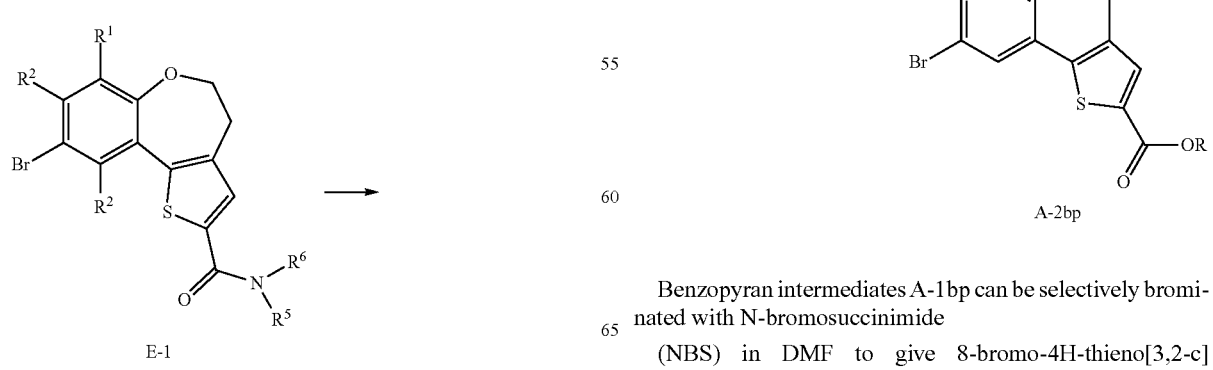

8-Bromo-4H-thieno[3,2-c]chromene-2-carboxamide intermediates E-1 are formylated with butyl lithium and dimethylformamide (DMF) to give E-2 which is reductively aminated with a hydride such as sodium acetoxyborohydride and a primary or secondary amine (HNR$^{10}$R$^{11}$).

General Procedure A-bp

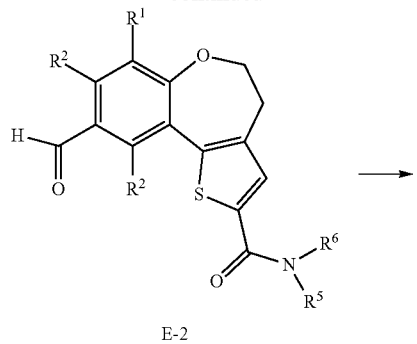

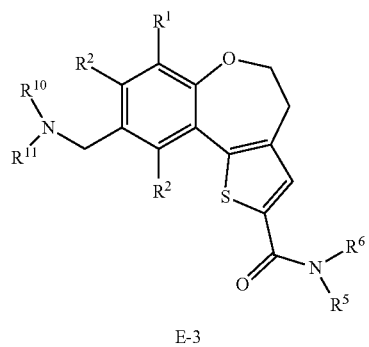

Benzopyran intermediates A-1bp can be selectively brominated with N-bromosuccinimide (NBS) in DMF to give 8-bromo-4H-thieno[3,2-c]chromene-2-carboxylate esters A-2bp.

General Procedure B-bp

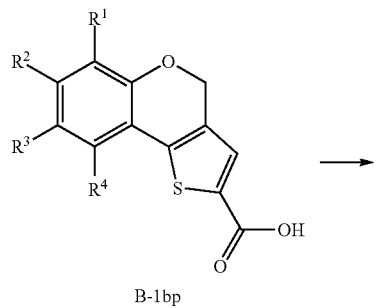

B-1bp

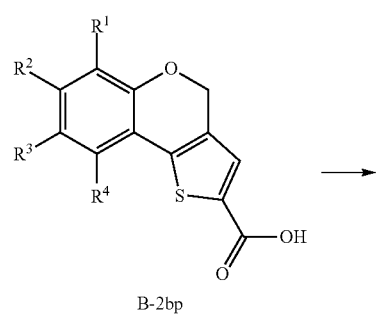

B-2bp

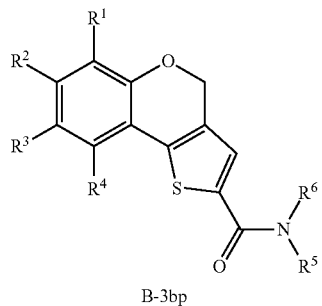

B-3bp

Benzopyran carboxylic acid intermediates B-1bp are converted to the acid chloride B-2bp and reacted with primary or secondary amines with triethylamine, DMAP, and solvent such as dichloromethane. Reaction with a primary amine may be followed by N-alkylation, for example with methyl iodide and sodium hydride, to generate carboxamide B-3bp.

General Procedure C-bp

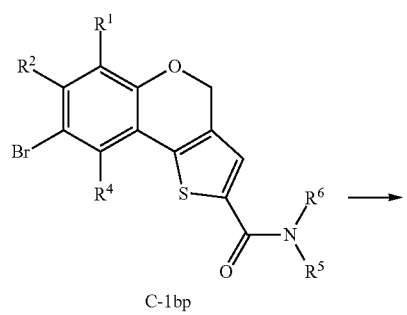

C-1bp

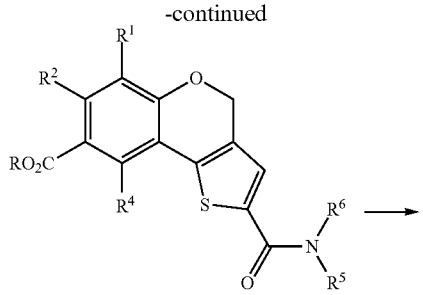

C-2bp

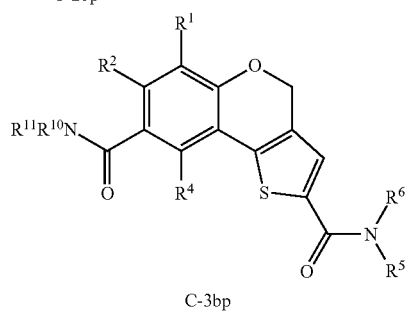

C-3bp

8-Bromo-4H-thieno[3,2-c]chromene-2-carboxamide intermediates C-1bp are carbonylated with carbon monoxide under high pressure with palladium catalysis, such as $Pd(OAc)_2$, and an alcohol, such as methanol to give the 8-carboxylate ester 4H-thieno[3,2-c]chromene-2-carboxamide intermediate C-2bp. Saponification with lithium hydroxide, sodium hydroxide or other aqueous base to the 8-carboxylic acid intermediate, followed by coupling of a primary or secondary amine with a coupling reagent, such as HATU or DCC gives the 8-carboxamide 4H-thieno[3,2-c]chromene-2-carboxamide intermediate C-3bp.

Alternatively, intermediate C-3bp may be prepared directly from bromo intermediate C-1bp by aminocarbonylation, following the procedures of Wannberg et al (2003) J. Org. Chem. 68:5750-5753.

General Procedure D-bp

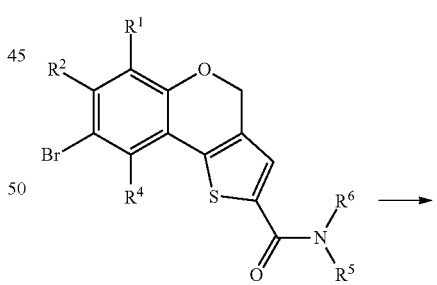

D-1bp

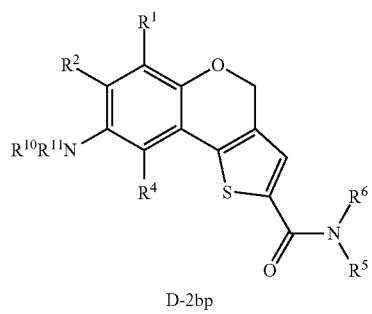

D-2bp

8-Bromo-4H-thieno[3,2-c]chromene-2-carboxamide intermediates D-1bp are aminated with primary or secondary amines (HNR$^{10}$R$^{11}$) or amides)(H$_2$NC(=O)R$^{10}$), palladium complexes such as Pd$_2$(dba)$_3$, catalysts such as xantphos and BINAP, alkoxides such as NaOt-Bu or carbonates such as cesium carbonate, in toluene or dioxane, and heating to give aminated products D-2bp.

General Procedure E-bp

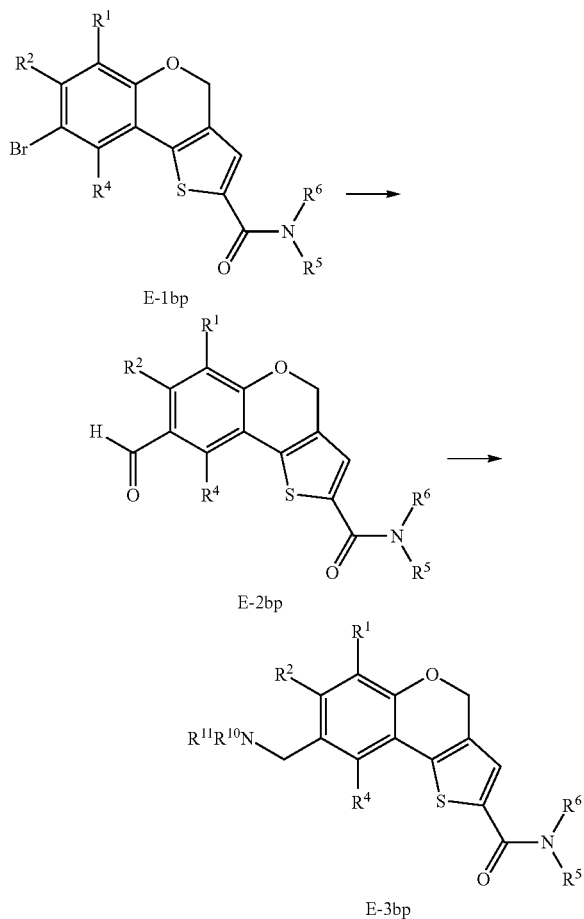

8-Bromo-4H-thieno[3,2-c]chromene-2-carboxamide intermediates E-1bp are formylated with butyl lithium and dimethylformamide (DMF) to give E-2bp which are reductively aminated with a hydride such as sodium acetoxyborohydride and a primary or secondary amine (HNR$^{10}$R$^{11}$) to give E-3bp.

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma Aldrich Chemical Company, and were used without further purification unless otherwise indicated. The reactions set forth below were conducted generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters). $^1$H NMR spectra were obtained at 400 MHz in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1 ethyl 4-(3-bromophenoxy)butanoate 6

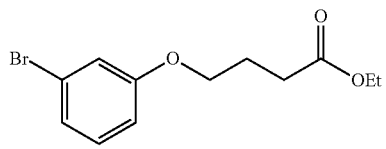

Solid 3-bromophenol (10.0 g, 58 mmol) was added portion wise to a stirred suspension of K$_2$CO$_3$ in acetone (100 mL) at room temperature. Sodium iodide (NaI, 1.0 g) was added, followed by ethyl-4-bromobutyrate (9.2 mL, 64 mmol). The reaction mixture was heated at 80° C. overnight, cooled to room temperature, diluted with water and extracted with ethylacetate to give ethyl 4-(3-bromophenoxy)butanoate 6.

Example 2

4-(3-bromophenoxy)butanoic acid 7

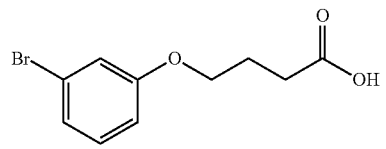

Ethyl 4-(3-bromophenoxy)butanoate 6 from Example 5 was taken up in 100 mL THF and 50 mL water and treated with lithium hydroxide LiOH (hydrate, 4.9 g). The whole was heated at 50° C. for 2 days. The mixture was cooled to room temperature and acidified to pH 1 with 2N HCl. The aqueous was extracted with ethylacetate. The combined organics were washed with brine and dried over sodium sulfate to give crude 4-(3-Bromophenoxy)butanoic acid 7 as a sticky solid. $^1$H NMR (DMSO-d$_6$, 500 MHz) 7.24 (m, 1H), 7.13 (m, 1H), 7.11 (m, 1H), 6.95 (m, 1H), 3.99 (m, 2H), 2.37 (m, 2H), 1.94 (m, 2H).

Example 3

8-bromo-3,4-dihydrobenzo[b]oxepin-5(2H)-one 8

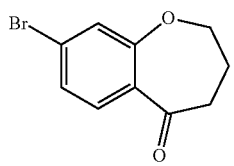

To a stirred suspension of polyphosphoric acid (PPA, ca. 60 g) and celite (ca. 40 g) in 100 mL toluene was added crude 4-(3-bromophenoxy)butanoic acid 7 (ca. 58 mmol) in one portion, 10 mL toluene rinse. The resultant suspension was heated at 110° C. for 5 hr. The toluene was decanted through a plug of celite and the remaining slurry was washed repeatedly with toluene and ethylacetate. The eluent was concentrated and purified by flash column chromatography (4:1 hex:EtOAc) to give 8-bromo-3,4-dihydrobenzo[b]oxepin-5 (2H)-one (7 g, ca. 50% y) 8. $^1$H NMR (DMSO-$d_6$, 500 MHz) 7.55 (d, J=8.5 Hz, 1H), 7.37 (d, J=1.5 Hz, 1H), 7.35 (dd, J=8.5, 1.5 Hz, 1H), 4.24 (t, J=6.5 Hz, 2H), 2.79 (t, J=7.0 Hz, 2H), 2.14 (m, 2H).

Example 4

(Z)-8-bromo-5-chloro-2,3-dihydrobenzo[b]oxepine-4-carbaldehyde 9

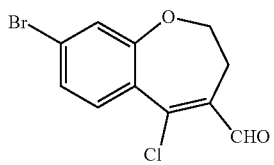

Phosphorus oxychloride, POCl$_3$ (1.88 mL, 20.8 mmol) was added dropwise to DMF (5 mL) at 0° C. After 30 min a solution of 8-bromo-3,4-dihydrobenzo[b]oxepin-5(2H)-one 8 (2.0 g, 8.3 mmol) in 8 mL DMF was added dropwise. The reaction mixture was allowed to reach room temperature to stir 2 hr, then poured slowly over rapidly stirred ice water. The aqueous phase was extracted with ethylacetate and the combined organics were washed with brine, dried over sodium sulfate and concentrated to give 9.

Example 5 methyl 8-bromo-4,5-dihydrobenzo[b]thieno[2,3-d] oxepine-2-carboxylate 10

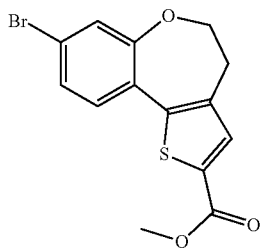

(Z)-8-Bromo-5-chloro-2,3-dihydrobenzo[b]oxepine-4-carbaldehyde 9 was dissolved in 10 mL DMF and treated sequentially with potassium carbonate (2.20 g, 16.6 mmol) and methyl thioglycolate (0.83 mL). The whole was heated at 50° C. overnight, cooled to room temperature, diluted with water and extracted with ethylacetate. The combined organics were washed with brine, dried over sodium sulfate and concentrated. The crude residue was purified by flash column chromatography (20-50% ethylacetate in hexanes) to give 2.20 g (78% yield) 10 as a colorless solid. $^1$H NMR (DMSO-$d_6$, 500 MHz) 7.70 (s, 1H), 7.67 (d, J=8.5 Hz, 1H), 7.31-7.28 (m, 2H), 4.32 (t, J=5.0 Hz, 2H), 3.84 (s, 3H), 3.21 (t, J=5.0 Hz, 2H).

Example 6

8-bromo-4,5-dihydrobenzo[b]thieno[2,3-d]oxepine-2-carboxylic acid 11

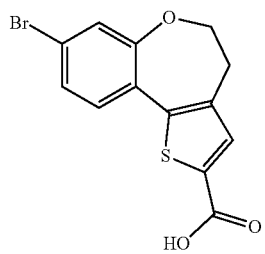

Methyl 8-bromo-4,5-dihydrobenzo[b]thieno[2,3-d]oxepine-2-carboxylate 10 was treated with lithium hydroxide in water and tetrahydrofuran (THF) to give 11.

Example 7

2-Iodo-3-(2-thiophen-3-yl-ethoxy)-pyridine 13

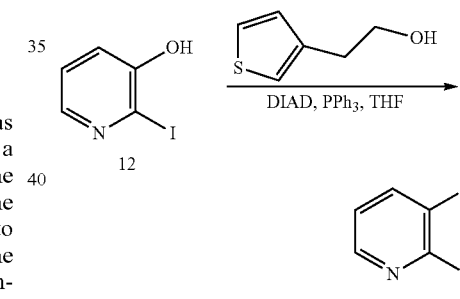

To a solution containing 2-iodo-3-hydroxypyridine 12 (1.85 g, 8.37 mmol), 2-(3-thienyl)ethanol (1.20 mL, 10.9 mmol), and triphenylphosphine (2.85 g, 10.9 mmol) in tetrahydrofuran (46.2 mL, 5.70 mmol) was added diisopropyl azodicarboxylate (2.14 mL, 10.9 mmol) dropwise. The reaction mixture was stirred at room temperature for 18 h. The reaction mixture was concentrated and purified by flash chromatography EtOAc/Hex (0-100%) eluted at 30% to give 13 (yield 90%). MS: (ESI+) 332.2

Example 8

10-aza-4,5-dihydrobenzo[b]thieno[2,3-d]oxepine 14

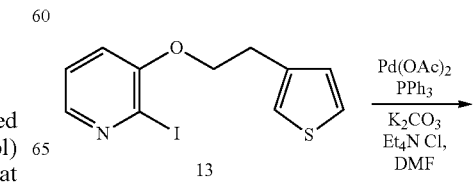

-continued

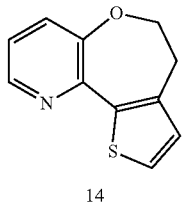

14

To a solution of 2-iodo-3-(2-thiophen-3-yl-ethoxy)-pyridine 13 (1.15 g, 4.05 mmol) in N,N-dimethylformamide (60.9 mL, 787 mmol) was added potassium carbonate (2.80 g, 20.2 mmol), triphenylphosphine (212 mg, 0.809 mmol), tetraethylammonium chloride (4.05 mmol) and palladium acetate (90.8 mg, 0.405 mmol). The reaction mixture was stirred at 90° C. 8 h. The reaction mixture was diluted with DCM then filtered through celite. The filtrate was concentrated and wash water. The crude product was purified by flash chromatography EtOAc/Hex (0-100%) product eluted at 30% to give 14 (yield 60%). MS: (ESI+) 204.3

Example 9

2-bromo-(10-aza-4,5-dihydrobenzo[b]thieno[2,3-d]oxepine) 15

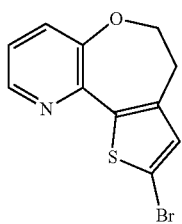

15

10-aza-4,5-dihydrobenzo[b]thieno[2,3-d]oxepine 14 (1.73 g, 8.51 mmol) was dissolved in methylene chloride (20 mL, 400 mmol) and acetic acid (20 mL, 400 mmol) and cooled to 0° C. N-Bromosuccinimide (1.67 g, 9.36 mmol) was added portionwise to the mixture. The reaction was stirred for 18 hours. Solvents were rotary evaporated, the residue partitioned between ethyl acetate and sat. sodium carbonate aqueous solution. The organic layer was washed with water, brine and dried over sodium sulfate. After rotary evaporation the crude product was chromatographed on Isco (hexane-EtOAc gradient, 0-100%) eluted 20% EtOAc to give 15. MS: (ESI+) 283.2

Example 10

10-aza-4,5-dihydrobenzo[b]thieno[2,3-d]oxepine-2-carboxylic acid 16

16

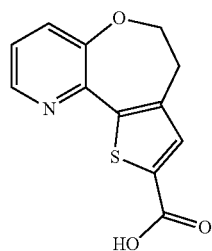

To a solution of 2-bromo-(10-aza-4,5-dihydrobenzo[b]thieno[2,3-d]oxepine) 15 (0.700 g, 2.48 mmol) in tetrahydrofuran (25.0 mL, 308 mmol) was added 2.50 M of n-butyllithium in hexane (1.19 mL) dropwise at −78° C. The reaction mixture was stirred at −78° C. for 1 h. The mixture was added to a slurry of dry ice in THF (15 ml) then stirred 2 h. The reaction mixture was quenched with water then slightly basified and extracted EtOAc (2×). The aqueous layer was acidified to pH 2 then extracted with DCM (2×). The organic layers were combined and concentrated to give 16 (yield 62%). MS: (ESI+) 248.3

Example 11

N2-(2-chlorophenyl)-N2,N8,N8-trimethyl-4,5-dihydrobenzo[b]thieno[2,3-d]oxepine-2,8-dicarboxamide 101

Following Example 47 and General Procedure C, methyl 2-((2-chlorophenyl)(methyl)carbamoyl)-4,5-dihydrobenzo[b]thieno[2,3-d]oxepine-8-carboxylate 138 and dimethylamine gave 101. MS: (ESI+) 441.1.

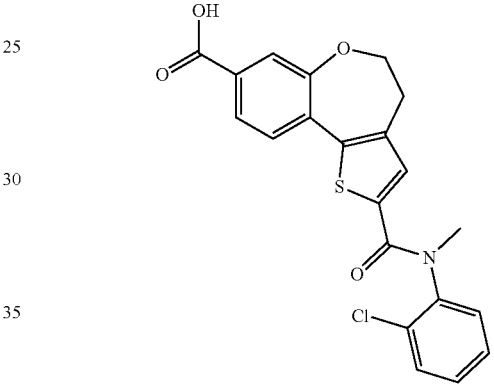

Alternatively, a solution of 2-((2-chlorophenyl)(methyl)carbamoyl)-4,5-dihydrobenzo[b]thieno[2,3-d]oxepine-8-carboxylic acid (100 mg, 0.24 mmol) in 2 mL of SOCl$_2$ was heated at 80° C. for 2 h. After removal of the solvent, the residue was co-evaporated with toluene to give the crude acid chloride 2-((2-chlorophenyl)(methyl)carbamoyl)-4,5-dihydrobenzo[b]thieno[2,3-d]oxepine-8-carbonyl chloride. To a solution of (CH$_3$)$_2$NH HCl salt (118 mg, 1.412 mmol) and pyridine (0.2 mL) in 5 mL of THF was slowly added 2-((2-chlorophenyl)(methyl)carbamoyl)-4,5-dihydrobenzo[b]thieno[2,3-d]oxepine-8-carbonyl chloride (417 mg, 0.966 mmol) in 20 mL of THF. The mixture was stirred at room temperature overnight, concentrated in vacuo, dissolved in ethyl acetate, washed with water and brine, dried over Na$_2$SO$_4$, and concentrated to give 101 (350 mg, yield: 82%). $^1$H NMR (CDCl$_3$, 400 MHz): δ 6.67-7.59 (m, 8H), 4.16 (t, J=4.8 Hz, 2H), 3.33 (s, 1H), 2.95-2.97 (m, 8H). MS (ESI): 441.

Example 12

7-acetamido-N-(2-chlorophenyl)-N-methyl-4,5-dihydrobenzo[b]thieno[2,3-d]oxepine-2-carboxamide 102

Following Example 61 and General Procedure C, 7-bromo-4,5-dihydrobenzo[b]thieno[2,3-d]oxepine-2-carboxylic acid and acetamide were reacted to give 102. MS: (ESI+) 427.1 1

Example 13

N2-(2-chlorophenyl)-N-8-(3-(diethylamino)propyl)-N2-methyl-4,5-dihydrobenzo[b]thieno[2,3-d]oxepine-2,8-dicarboxamide 103

A suspension of 8-bromo-N-(2-chlorophenyl)-N-methyl-4,5-dihydrobenzo[b]thieno[2,3-d]oxepine-2-carboxamide 150 (100 mg, 0.22 mmol), Mo(CO)$_6$ (58 mg), Hermann's palladacycle (trans-Di(mu-acetato)bis[o-(di-o-tolylphosphino)benzyl]dipalladium (II), 31 mg), and N,N-diethyl-1,3-propanediamine (58 mg) in THF (2.0 mL) in a 10 mL microwave vial was treated with DBU (0.02 mL, 0.5 equiv) and immediately sealed. The whole was heated in a microwave at 150° C. for 25 min, cooled to room temperature and diluted with ethylacetate. The crude suspension was filtered through celite and the eluent concentrated to give a residue that was purified by flash column chromatography (1-10% methanol in dichloromethane) to give 103 as a colorless solid. MS: (ESI+)=526.2. $^1$H NMR (DMSO-d$_6$) δ 8.53 (m, 1H), 7.66 (m, 2H), 7.55-7.44 (m, 4H), 6.55 (m, 1H), 4.20 (m, 2H), ca. 3.2 (m, 2H, obstructed by water), 3.24 (s, 3H, obstructed by water), 2.97 (m, 2H), 2.67-2.56 (m, 6H), 1.69 (m, 2H), 0.99 (m, 6H)

Example 14

7-acetamido-N-(2-chlorophenyl)-N-methyl-4,5-dihydrobenzo[b]thieno[2,3-d]oxepine-2-carboxamide 104

Following Example 53, 7-bromo-4,5-dihydrobenzo[b]thieno[2,3-d]oxepine-2-carboxylic acid and CuCN were reacted to give 104. MS: (ESI+) 395.1

Example 15

5-(4,5-dihydropyrido[4,3-b]thieno[2,3-d]oxepin-2-yl)pyridin-2-amine 105

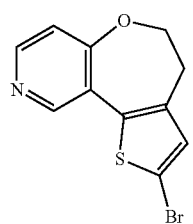 [SMILES: Brc1cc2c(s1)-c1cnccc1OCC2]

Following Example 52, 2-bromo-4,5-dihydropyrido[4,3-b]thieno[2,3-d]oxepine and 2-aminopyridine-5-boronic acid, pinacol ester were reacted to give 105. $^1$H NMR (400 MHz, DMSO) δ 8.79 (s, 1H), 8.27 (d, J=2.2, 1H), 8.22 (d, J=5.5, 1H), 7.67 (dd, J=2.6, 8.6, 1H), 7.22 (s, 1H), 6.99 (d, J=5.4, 1H), 6.51 (d, J=8.6, 1H), 6.25 (s, 2H), 4.37 (t, J=4.8, 2H), 3.20 (t, J=4.8, 2H). MS: (ESI+) 296.1

Example 16

N-(2-chlorophenyl)-N-(2-hydroxyethyl)-4,5-dihydrobenzo[b]thieno[2,3-d]oxepine-2-carboxamide 106

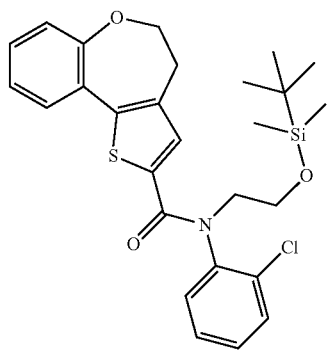 [SMILES: CC(C)(C)[Si](C)(C)OCCN(C(=O)c1cc2c(s1)-c1ccccc1OCC2)c1ccccc1Cl]

To a solution of N-(2-(tert-butyldimethylsilyloxy)ethyl)-2-chloroaniline (0.145 g, 0.508 mmol) and triethylamine (0.113 mL, 0.812 mmol) in tetrahydrofuran (1 mL, 10 mmol) was added a solution of 4,5-dihydrobenzo[b]thieno[2,3-d]oxepine-2-carbonyl chloride (0.107 g, 0.406 mmol) in tetrahydrofuran (4 mL). The reaction was stirred overnight and concentrated in vacuo. Aqueous work up gave a yellow solid which was purified on silica by MPLC to give 150 mg of N-(2-(tert-butyldimethylsilyloxy)ethyl)-N-(2-chlorophenyl)-4,5-dihydrobenzo[b]thieno[2,3-d]oxepine-2-carboxamide.

To a solution of N-(2-(tert-butyldimethylsilyloxy)ethyl)-N-(2-chlorophenyl)-4,5-dihydrobenzo[b]thieno[2,3-d]oxepine-2-carboxamide (0.030 g, 0.058 mmol) in acetic acid (0.0033 mL, 0.058 mmol) and tetrahydrofuran (0.3 mL, 4 mmol) was added 1 M of tetrabutylammonium fluoride hydrate in tetrahydrofuran (0.058 mL). The reaction was stirred at room temperature w/TLC and LC/MS monitor. Deprotection was complete after overnight stirring. The reaction mixture was concentrated in vacuo, taken into ethylacetate and washed with water/saline and concentrated to a glassy residue, which was purified by MPLC, eluting with ethylacetate/hexanes, gradient 0-50% B to give 22.4 mg of 106 (yield 40%). MS: (ESI+) 401

Example 17

N-(2-chloro-4-fluorophenyl)-N-methyl-4,5-dihydrobenzo[b]thieno[2,3-d]oxepine-2-carboxamide 107

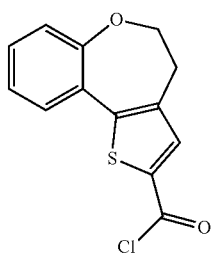 [SMILES: O=C(Cl)c1cc2c(s1)-c1ccccc1OCC2]

To a solution of 2-chloro-4-fluoroaniline (0.110 g, 0.755 mmol) and triethylamine (0.105 mL, 0.755 mmol) in tetrahydrofuran (1.5 mL, 18 mmol) was added portion wise as a solid 4,5-dihydrobenzo[b]thieno[2,3-d]oxepine-2-carbonyl chloride (0.100 g, 0.378 mmol). Reaction mix was stirred at room temperature with monitor for formation of desired product. The reaction was stirred overnight. The mixture containing the alkylated product was concentrated in vacuo to a solid residue, then taken into N,N-dimethylformamide (1.5 mL, 19 mmol) and treated with sodium hydride (0.0181 g, 0.755 mmol) followed by the addition of methyl iodide (0.0470 mL, 0.755 mmol). Reaction stirred at room temperature for about 1 hr with complete conversion to desired N-methyl derivative. After aqueous work up, the crude was taken into DMF at 100 mg/1 mL and purified by preparative RP-HPLC to give 107. Yield=22% of theoretical. MS: (ESI+) 375

Example 18

N-(2,4-dichlorophenyl)-N-methyl-4,5-dihydrobenzo[b]thieno[2,3-d]oxepine-2-carboxamide 108

To a solution of N-methyl-2,4-dichloroaniline (0.133 g, 0.755 mmol) and triethylamine (0.105 mL, 0.755 mmol) in tetrahydrofuran (1.5 mL, 18 mmol) was added 4,5-dihydrobenzo[b]thieno[2,3-d]oxepine-2-carbonyl chloride (0.100 g, 0.378 mmol) portion wise as a solid. Reaction was stirred at room temperature with monitor for formation of desired product. The reaction was stirred overnight. After aqueous workup, the crude was taken into DMF at a concentrated of 100 mg/ml and purified by preparative RP-HPLC to give 108. Yield=30% of theoretical. MS: (ESI+) 405.5

Example 19 methyl 5-(6,7-dihydropyrido[3,2-b]thieno[2,3-d]oxepin-9-yl)-2-aminoisonicotinate 109

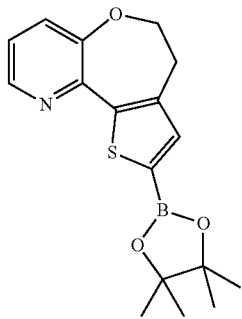 [SMILES: CC1(C)OB(c2cc3c(s2)-c2ncccc2OCC3)OC1(C)C]

n-Butyllithium in hexane (0.7833 mL, 1.6 M) was added dropwise to a solution of 9-bromo-6,7-dihydropyrido[3,2-b]thieno[2,3-d]oxepine (0.282 g, 1.00 mmol) in tetrahydrofuran (7.46 mL, 91.9 mmol) at −75° C. The dark brown mixture was stirred at −78° C. for 20 min. 2-isopropoxy-4,4,5,5-tetramethyl-1,3,2-dioxaborolane (0.31 mL, 1.5 mmol) in 2 ml of tetrahydrofuran was added dropwise and the mixture was kept at −78° C. for 20 min gradually warming up to −30° C. sat. aq. NH₄Cl (10 ml) was added and the mixture was poured into 25 ml of water, extracted with ethylacetate, the organic layer was washed with water, brine and dried over MgSO4. The solution was rotary evaporated and the residue purified on silicagel column eluting with 18% of ethyl acetate in hexane to give 9-(4,4,5,5-tetramethyl-1,3,2-dioxaborolane)-6,7-dihydropyrido[3,2-b]thieno[2,3-d]oxepine (yield 0.224 g, 68%). MS: (ESI+) 330.1

Following Example 52, 9-(4,4,5,5-tetramethyl-1,3,2-dioxaborolane)-6,7-dihydropyrido[3,2-b]thieno[2,3-d]oxepine and 2-amino-5-bromo-isonicotinic acid methyl ester were reacted to give 109. ¹H NMR (400 MHz, DMSO) δ 8.22 (dd, J=1.4, 4.5, 1H), 8.14 (s, 1H), 7.40 (dd, J=1.4, 8.1, 1H), 7.19 (dd, J=4.5, 8.1, 1H), 6.87 (s, 1H), 6.64 (s, 1H), 6.52 (s, 2H), 4.33 (t, J=4.8, 2H), 3.76 (s, 3H), 3.20 (t, J=4.8, 2H). MS: (ESI+) 354.1

Example 20

2-(4-isopropyl-5-oxo-4,5-dihydro-1H-1,2,4-triazol-3-yl)-4,5-dihydrobenzo[b]thieno[2,3-d]oxepine-8-carboxamide 110

2-(4-Isopropyl-5-oxo-4,5-dihydro-1H-1,2,4-triazol-3-yl)-4,5-dihydrobenzo[b]thieno[2,3-d]oxepine-8-carbonitrile was treated with potassium carbonate in DMSO, then hydrogen peroxide to give 110. MS: (ESI+) 371.1

Example 21

8-bromo-4,5-dihydro-6-oxa-3-thia-1-aza-benzo[e]azulene-2-carboxylic acid (2-chloro-4-methylcarbamoyl-phenyl)-methyl-amide 111

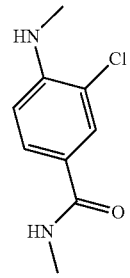

A solution of 3-chloro-4-fluorobenzonitrile (1.0 g), methylamine (16 mL of a 2 M solution in methanol) and diisopropylethylamine was reacted in the microwave at 120° C. for 15 min. The mixture was then partitioned between ethyl acetate (50 mL) and water (50 mL). The organic layer was washed with brine (30 mL), dried (MgSO₄) and reduced in vacuo to give 3-chloro-4-methylamino-benzonitrile. A suspension of 3-chloro-4-methylamino-benzonitrile (900 mg) in 2 M aqueous sodium hydroxide solution (30 mL) was heated at reflux for 3 h. After cooling to room temperature, the solution was acidified with 2 M aqueous hydrochloric acid and the resulting solid collected by filtration and air-dried to give 3-chloro-4-methylamino-benzoic acid. To a solution of 3-chloro-4-methylamino-benzoic acid (860 mg) in DMF (20 mL) was added carbonyl diimidazole (630 mg) and the reaction stirred at room temperature for 1 h. Then, methylamine hydrochloride (262 mg) and triethylamine (1.62 mL) were added and the reaction stirred at room temperature for 16 h. The reaction was partitioned between ethyl acetate (50 mL) and water (50 mL). The organic layer was washed with brine (3×40 mL), dried (MgSO4), reduced in vacuo and purified on silica to give 3-chloro-N-methyl-4-methylamino-benzamide.

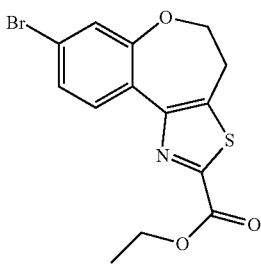 [SMILES: CCOC(=O)c1nc2c(s1)CCOc1cc(Br)ccc1-2]

8-Bromo-4,5-dihydro-6-oxa-3-thia-1-aza-benzo[e]azulene-2-carboxylic acid ethyl ester was prepared from 3-bromophenol according to Example 136 for 226, and hydrolyzed to the corresponding acid using General Procedure B. To a suspension of 8-bromo-4,5-dihydro-6-oxa-3-thia-1-aza-benzo[e]azulene-2-carboxylic acid (373 mg) in dry dichloromethane (20 mL) was added oxalyl chloride (170 µL) and DMF (1 drop). After 2 hours the solvent was removed in vacuo and to the residue was added acetonitrile (20 mL), 3-chloro-N-methyl-4-methylamino-benzamide (250 mg) and sodium bicarbonate (105 mg). After 3 hours, water was added to the reaction mixture and the resulting precipitate was collected by filtration. The solid was recrystallized form ethyl acetate/methanol/hexane to yield 111 (307 mg). NMR: (CDCl3): 3.04 (3H, d), 3.31 (2H, t), 3.48 (3H, s), 4.28-4.31 (2H, m), 6.05 (1H, sbr.), 6.91-6.93 (2H, m), 7.15 (1H, s), 7.45 (1H, d), 7.72 (1H, dd), 7.91 (1H, s). MS: (ESI+) MH+ 508

Example 22

1-(2-(4-(2-chlorophenyl)-4H-1,2,4-triazol-3-yl)-4,5-dihydrobenzo[b]thieno[2,3-d]oxepin-8-yl)-3-methylurea 112

Following the procedures of Example 76, 2-(4-(2-chlorophenyl)-4H-1,2,4-triazol-3-yl)-4,5-dihydrobenzo[b]thieno[2,3-d]oxepin-8-amine was reacted with methyl isocyanate to give 112. MS: (ESI+) 452.1

Example 23 methyl 2-(4-(2-chlorophenyl)-4H-1,2,4-triazol-3-yl)-4,5-dihydrobenzo[b]thieno[2,3-d]oxepin-8-ylcarbamate 113

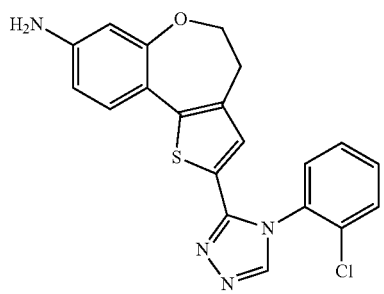 [SMILES: Nc1ccc2c(c1)OCCc1cc(-c3nncn3-c3ccccc3Cl)sc1-2]

To a solution of 2-(4-(2-chlorophenyl)-4H-1,2,4-triazol-3-yl)-4,5-dihydro-benzo[b]thieno[2,3-d]oxepin-8-amine HCl salt (0.2 g, 0.464 mmol) in 10 ml of dried DCM was added TEA (0.32 mL, 2.3 mmol). The mixture was stirred at 0° C. for 20 min and 0.2 ml of methyl chloroformate was added. The reaction mixture was stirred for 10 min and the solution was quenched with water and evaporated to the crude product, which was purified by preparative HPLC to give 113 (81 mg, 38%). $^1$HNMR (DMSO-d$_6$, 400 MHz): δ 9.78 (s, 1H), 8.81 (s, 1H), 7.79-7.12 (m, 7H), 6.53 (s, 1H), 4.15 (t, J=5.2 Hz, 2H), 3.63 (s, 3H), 2.93 (t, J=5.2 Hz, 2H). MS: (ESI+) 453.1

Example 24

7-bromo-N-(2-chlorophenyl)-N-methyl-4,5-dihydrobenzo[b]thieno[2,3-d]oxepine-2-carboxamide 114

Following Example 70 and General Procedure B, 114 was prepared from 7-bromo-4,5-dihydrobenzo[b]thieno[2,3-d]oxepine-2-carboxylic acid and 2-chloro-N-methylaniline. MS: (ESI+) 450.0

Example 25

N-(2-(4-(2-chlorophenyl)-4H-1,2,4-triazol-3-yl)-4,5-dihydrobenzo[b]thieno[2,3-d]oxepin-8-yl)acetamide 115

To a solution of 2-(4-(2-chlorophenyl)-4H-1,2,4-triazol-3-yl)-4,5-dihydro-benzo[b]thieno[2,3-d]oxepin-8-amine HCl salt (0.2 g, 0.464 mmol) in 10 ml of dried DCM was added TEA (0.32 mL, 2.3 mmol). The mixture was stirred at 0° C. for 20 min and 0.2 ml of acetic anhydride was added. After stirred for 10 min, the solution was quenched with water and evaporated to the crude product, which was purified by preparative TLC to give 115 (80 mg, 39%). $^1$H NMR (DMSO-d$_6$, 400 MHz): δ 10.02 (s, 1H), 8.81 (s, 1H), 7.79-7.15 (m, 7H), 6.54 (s, 1H), 4.16 (t, J=4.8 Hz, 2H), 2.95 (t, J=4.8 Hz, 2H), 1.99 (s, 3H). MS: (ESI+) 437.1

Example 26

N-(4-(3-amino-5-methyl-1H-pyrazole-1-carbonyl)-2-chlorophenyl)-N-(2-hydroxyethyl)-4,5-dihydrobenzo[b]thieno[2,3-d]oxepine-2-carboxamide 116

Following Example 91, 3-chloro-4-(N-(2-hydroxyethyl)-4,5-dihydrobenzo[b]thieno[2,3-d]oxepine-2-carboxamido) benzoic acid and 3-amino-5-methylpyrazole were reacted to give 116. Yield 25% of theoretical. MS: (ESI+) 523.1

Example 27

N-(4-(2-acetamidoethylcarbamoyl)-2-chlorophenyl)-N-(2-hydroxyethyl)-4,5-dihydrobenzo[b]thieno[2,3-d]oxepine-2-carboxamide 117

Following Example 91, 3-chloro-4-(N-(2-hydroxyethyl)-4,5-dihydrobenzo[b]thieno[2,3-d]oxepine-2-carboxamido) benzoic acid and N-(2-aminoethyl)acetamide were reacted to give 118. Yield 35% of theoretical. MS: (ESI+) 528.2

Example 28

N-(2-chloro-4-((2-(dimethylamino)ethyl)(methyl) carbamoyl)phenyl)-N-(2-hydroxyethyl)-4,5-dihydrobenzo[b]thieno[2,3-d]oxepine-2-carboxamide 118

Following Example 91, 3-chloro-4-(N-(2-hydroxyethyl)-4,5-dihydrobenzo[b]thieno[2,3-d]oxepine-2-carboxamido)

benzoic acid and N1,N1,N2-trimethylethane-1,2-diamine were reacted to give 118 (yield 35% of theoretical). MS: (ESI+) 528.2

Example 29

N2-(2-chlorophenyl)-N2-methyl-4,5-dihydrobenzo[b]thieno[2,3-d]oxepine-2,9-dicarboxamide 119

To a mixture of N-(2-chlorophenyl)-9-cyano-N-methyl-4,5-dihydrobenzo[b]thieno[2,3-d]oxepine-2-carboxamide 120 (120 mg) and K₂CO₃ (49 mg) in dry DMSO (2 mL) was added 33% hydrogen peroxide (40 µL). The resultant was stirred overnight at room temperature. Ice was added to the resulting solution and the solid formed was collected, washed with water and dried to give 119. NMR: (CDCl3): 3.04 (t, 2H, CH₂, J=5.02 Hz), 3.42 (s, 3H, CH₃), 4.28 (t, 2H, CH₂, J=5.06 Hz), 5.75 (sbr, 2H, NH₂), 6.71 (s, H, ArH), 7.03 (d, H, ArH, J=8.44 Hz), 7.39-7.45 (m, 3H, 3×ArH), 7.55-7.60 (m, 2H, 2×ArH), 7.99 (d, H, ArH, J=1.81 Hz). MS: (ESI+) MH+ 413.14

Example 30

N-(2-chlorophenyl)-9-cyano-N-methyl-4,5-dihydrobenzo[b]thieno[2,3-d]oxepine-2-carboxamide 120

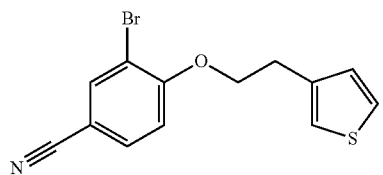 [SMILES: N#Cc1ccc(OCCc2ccsc2)c(Br)c1]

To a solution of 3-bromo-4-hydroxybenzonitrile (15.0 g) in THF (100 mL) was added 2-(3-thienyl)ethanol (7.94 mL) and triphenyl phosphine (19.84 g). The reaction was cooled to 0° C. and diethylazodicarboxylate (11.92 mL) was added dropwise. The reaction was stirred at room temperature for 16 h. The solvent was then reduced in vacuo and the residue redissolved in diethyl ether (100 mL) The mixture was stirred at 0° C. for 10 min and then filtered. The filtrate was washed with aqueous sodium carbonate solution (80 mL), 1 M aqueous hydrochloric acid (80 mL) and brine (80 mL), dried (MgSO₄), reduced in vacuo and purified on silica to give 3-bromo-4-(2-thiophen-3-yl-ethoxy)-benzonitrile.

To a solution of 3-bromo-4-(2-thiophen-3-yl-ethoxy)-benzonitrile (4.50 g) in DMF (20 mL) was added palladium acetate (327 mg), triphenylphosphine (766 mg) and potassium carbonate (4.03 g) and the reaction heated at 90° C. for 16 h. After cooling to room temperature the mixture was diluted with ethyl acetate (60 ml) and filtered. The filtrate was washed with brine (80 mL), dried (MgSO₄), reduced in vacuo and purified on silica to give 4,5-dihydro-6-oxa-1-thia-benzo[e]azulene-9-carbonitrile.

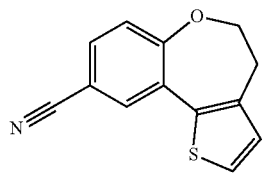 [SMILES: N#Cc1ccc2c(c1)-c1sccc1CCO2]

To a solution of 4,5-dihydro-6-oxa-1-thia-benzo[e]azulene-9-carbonitrile (4.58 g) in dichloromethane (30 mL) and acetic acid (30 mL) was added N-bromosuccinimide (3.95 g) and the reaction stirred at room temperature for 16 h. Water (100 mL) was then added and the solid collected by filtration and air-dried to give 2-bromo-4,5-dihydro-6-oxa-1-thia-benzo[e]azulene-9-carbonitrile.

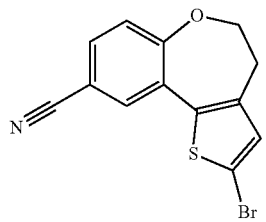 [SMILES: N#Cc1ccc2c(c1)-c1sc(Br)cc1CCO2]

To a solution of 2-bromo-4,5-dihydro-6-oxa-1-thia-benzo[e]azulene-9-carbonitrile (3.0 g) in THF (80 mL) at −78° C. was added n-butyllithium (4.31 mL) and the reaction allowed to warm to −10° C. over 1 h. The reaction was then recooled to −78° and carbon dioxide was bubbled through the solution for 15 min. The reaction was then allowed to warm to room temperature over 4 h. The reaction was quenched with water (10 mL) and the product extracted into aqueous sodium carbonate solution (100 mL). The aqueous layer was washed with ethyl acetate (100 mL) and then acidified to pH 2-3 with 2 M aqueous hydrochloric acid. The product was then extracted into ethyl acetate (2×100 mL) and the organic layers were dried (MgSO₄) and reduced in vacuo to give 9-cyano-4,5-dihydro-6-oxa-1-thia-benzo[e]azulene-2-carboxylic acid.

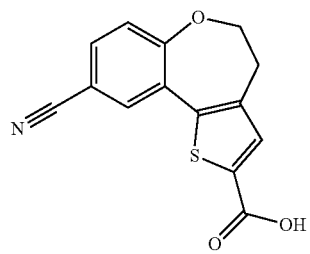 [SMILES: N#Cc1ccc2c(c1)-c1sc(C(=O)O)cc1CCO2]

To a solution of 9-cyano-4,5-dihydro-6-oxa-1-thia-benzo[e]azulene-2-carboxylic acid (300 mg) in dichloromethane (10 mL) was added DMF (1 drop) and oxalyl chloride (0.165 mL) and the reaction stirred at room temperature for 30 min. The solvent was then reduced in vacuo and the residue redissolved in acetonitrile (10 mL). To this solution was added 2-chloro-N-methylaniline (0.165 mL) and potassium carbonate (308 mg) and the reaction stirred at room temperature for 16 h. The mixture was partitioned between water (40 mL) and ethyl acetate (30 mL). The organic layer was dried (Na₂SO₄), reduced in vacuo and purified on silica to give 120. NMR:

(CDCl3): 3.08 (t, 2H, CH$_2$, J=5.00 Hz), 3.41 (s, 3H, CH$_3$), 4.29 (t, 2H, CH$_2$, J=5.02 Hz), 6.92 (s, H, ArH), 7.03 (d, H, ArH, J=8.43 Hz), 7.38-7.47 (m, 4H, 4×ArH), 7.57 (m, H, ArH), 7.72 (d, H, ArH, J=1.65 Hz). MS: (ESI+) MH+ 395

Example 31

4,5-dihydro-6-oxa-3-thia-1-aza-benzo[e]azulene-2-carboxylic acid (2-chloro-4-methylcarbamoyl-phenyl)-methyl-amide 121

4,5-Dihydro-6-oxa-3-thia-1-aza-benzo[e]azulene-2-carboxylic acid ethyl ester was prepared according to Example 136 for 226, and hydrolyzed to the corresponding acid using General Procedure B. To a suspension of 4,5-dihydro-6-oxa-3-thia-1-aza-benzo[e]azulene-2-carboxylic acid (130 mg) in dry dichloromethane (10 mL) was added oxalyl chloride (78 µL) and DMF (1 drop). After 1 hour the solvent was reduced in vacuo and the residue was dissolved in acetonitrile (10 mL) and to this was added 3-chloro-N-methyl-4-methylamino-benzamide from Example 21 (116 mg) and sodium bicarbonate (49 mg). The reaction mixture was warmed to 60° C. After 3 hours the reaction mixture was cooled, diluted with dichloromethane, washed with water, dried (MgSO$_4$) and the solvent removed in vacuo. The residue was recrystallized form ethyl acetate/methanol/hexane to yield 121 (132 mg). NMR: (CDCl3): 3.04 (3H, d), 3.31 (2H, t), 3.48 (3H, s), 4.28-4.31 (2H, m), 6.05 (1H, sbr.), 6.81-6.83 (1H, m), 6.96 (1H, d), 7.05-7.15 (2H, m), 7.48 (1H, d), 7.78 (1H, dd), 7.93 (1H, s). MS: (ESI+) MH+ 428

Example 32

N-(2-chlorophenyl)-N-methyl-8-(pyridin-3-yl)-4,5-dihydrobenzo[b]thieno[2,3-d]oxepine-2-carboxamide 122

Following Examples 44 and 60 and General Procedure C, 8-bromo-N-(2-chlorophenyl)-N-methyl-4,5-dihydrobenzo[b]thieno[2,3-d]oxepine-2-carboxamide 150 and 3-pyridyl-boronic acid were reacted to give 122. MS: (ESI+) 447.1

Example 33

N-(2-chlorophenyl)-N-methyl-4,5-dihydrobenzo[b]thieno[2,3-d]oxepine-2-carbothioamide 123

To a suspension of N-(2-chlorophenyl)-N-methyl-4,5-dihydrobenzo[b]thieno[2,3-d]oxepine-2-carboxamide 157 (60 mg, 0.16 mmol) in dry toluene (2 mL) in a 20 mL scintillation vial was added Lawesson's reagent (4-bis(4-methoxyphenyl)-1,3,2,4-dithiadiphosphetane-2,4-disulfide, 49 mg, 0.12 mmol, 0.75 equiv). The vial was sealed and heated at 90° C. for 36 hr. The mixture was cooled to room temperature, concentrated and purified by reverse phase HPLC to give 123 as a yellow solid. $^1$H NMR (CDCl$_3$) δ 7.57 (m, 1H), 7.48 (m, 1H), 7.35-7.27 (m, 4H), 7.14 (m, 1H), 6.96 (m, 1H), 6.52 (s, 1H), 4.19 (m, 2H), 3.80 (s, 3H), 2.92 (m, 2H). MS: (ESI+) 386.1

Example 34

8-(3-aminophenyl)-N-(2-chlorophenyl)-N-methyl-4,5-dihydrobenzo[b]thieno[2,3-d]oxepine-2-carboxamide 124

Following Examples 44 and 60 and General Procedure C, 8-bromo-N-(2-chlorophenyl)-N-methyl-4,5-dihydrobenzo[b]thieno[2,3-d]oxepine-2-carboxamide 150 and 3-aminophenyl boronic acid were reacted to give 124. MS: (ESI+) 461.1

Example 35

N-(2-chlorophenyl)-8-(3-(dimethylamino)prop-1-ynyl)-N-methyl-4,5-dihydrobenzo[b]thieno[2,3-d]oxepine-2-carboxamide 125

Following Examples 43 and 60, Sonagoshira coupling of 8-bromo-N-(2-chlorophenyl)-N-methyl-4,5-dihydrobenzo[b]thieno[2,3-d]oxepine-2-carboxamide 150 and N,N-dimethylpropargyl amine gave 125.

Example 36

N-(2-chlorophenyl)-8-(3-hydroxyprop-1-ynyl)-N-methyl-4,5-dihydrobenzo[b]thieno[2,3-d]oxepine-2-carboxamide 126

Following Examples 43 and 60, Sonagoshira coupling of 8-bromo-N-(2-chlorophenyl)-N-methyl-4,5-dihydrobenzo[b]thieno[2,3-d]oxepine-2-carboxamide 150 and 3-propargyl alcohol gave 126. MS: (ESI+) 424.1

Example 37

4-(6,7-dihydropyrido[3,2-b]thieno[2,3-d]oxepin-9-yl)-(2-chlorophenyl)-2-acetamino-1H-imidazole 127

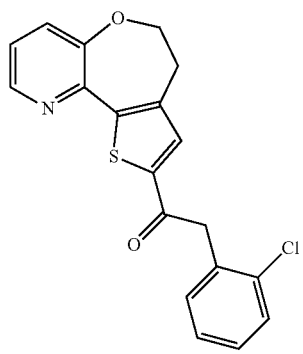 [SMILES: O=C(Cc1ccccc1Cl)c1cc2c(s1)-c1ncccc1OCC2]

A stirred mixture of 6,7-dihydropyrido[3,2-b]thieno[2,3-d]oxepine (1016 mg, 5.000 mmol) and (2-chlorophenyl)-acetic acid (1134 mg, 6.650 mmol) in polyphosphoric acid (30 g, 300 mmol) was heated for 4 hours at 110° C. Ice (200 g) was added and the mixture was shaken until a homogeneous suspension formed. The precipitate was filtered out, washed with water, ethyl acetate and dried in air. Recrystallized from 100 ml of hot dioxane gave 6,7-dihydropyrido[3,2-b]thieno[2,3-d]oxepin-9-yl-(2-chlorophenyl)ethanone (1.34 g, 70%). $^1$H NMR (400 MHz, DMSO) δ 8.30 (d, J=3.8, 1H), 8.03 (s, 1H), 7.50-7.44 (m, 2H), 7.41 (dt, J=3.7, 7.5, 1H), 7.37-7.30 (m, 3H), 4.48 (s, 2H), 4.39 (t, J=4.7, 2H), 3.28 (t, J=4.7, 2H). MS (ESI+) 356.0

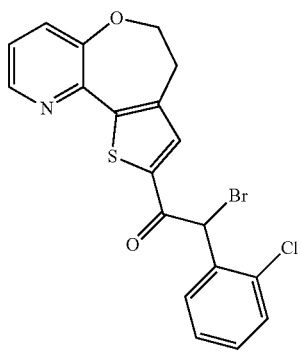 [SMILES: O=C(c1cc2c(s1)-c1ncccc1OCC2)C(Br)c1ccccc1Cl]

To a solution of 6,7-dihydropyrido[3,2-b]thieno[2,3-d]oxepin-9-yl-(2-chlorophenyl)ethanone (142 mg, 0.400 mmol) in hot 1,4-dioxane (4 mL, 60 mmol), copper(II) bromide (139 mg, 0.622 mmol) was added and the mixture was heated for 3 hours at 110° C. The mixture was then cooled to room temperature and partitioned between ethylacetate and water. The suspension was filtered through celite, the organic layer separated, washed with water and brine, dried over MgSO₄, and evaporated to dryness. The crude product was purified on silica gel column eluting with 20% ethylacetate in hexane to give 6,7-dihydropyrido[3,2-b]thieno[2,3-d]oxepin-9-yl-(2-chlorophenyl)-2-bromoethanone (yield 100 mg, 57%). ¹H NMR (400 MHz, CDCl3) δ 8.30 (d, J=4.4, 1H), 7.75 (dd, J=2.0, 7.4, 1H), 7.60 (s, 1H), 7.44-7.38 (m, 1H), 7.30 (ddd, J=1.7, 7.8, 9.6, 3H), 7.16 (dd, J=4.4, 8.2, 1H), 6.72 (s, 1H), 4.41-4.31 (m, 2H), 3.25 (d, J=3.0, 2H). MS (ESI+) 434.0

6,7-Dihydropyrido[3,2-b]thieno[2,3-d]oxepin-9-yl-(2-chlorophenyl)-2-bromoethanone (87.0 mg, 0.200 mmol) and N-acetyl-guanidine (101 mg, 1.00 mmol) were mixed in acetonitrile (2 mL, 50 mmol). The reaction was microwaved on 300 watts at 120° C. for 20 minutes. The mixture was kept at room temperature for 18 hours, the crystalline product was filtered out, washed with cold acetonitrile and purified on silicagel column eluting with 2% of methanol in methylene chloride to give 127 (yield 34 mg, 39%). MS (ESI+) 437.1.

Example 38

4-(6,7-dihydropyrido[3,2-b]thieno[2,3-d]oxepin-9-yl)-(2-chlorophenyl)-2-amino-1H-imidazole 128

From Example 37, 4-(6,7-dihydropyrido[3,2-b]thieno[2,3-d]oxepin-9-yl)-(2-chlorophenyl)-2-amino-1H-imidazole 127 (27 mg, 0.062 mmol) was added to ethanol (2 mL, 30 mmol) containing 1 ml of 10% aqueous sulfuric acid. The reaction was microwaved on 300 watts at 100° C. for 15 minutes. The reaction mixture was mixed with 10 ml of 1 M aq Na₂CO₃ and extracted with ethyl acetate twice. The organic layer was washed with brine and dried over K₂CO₃. The solvent was evaporated to afford 128. (18 mg, 74%). MS (ESI+) 395.1

Example 39

4-(6,7-dihydropyrido[3,2-b]thieno[2,3-d]oxepin-9-yl)-(5-(2-chlorophenyl))-oxazole 129

6,7-Dihydropyrido[3,2-b]thieno[2,3-d]oxepin-9-yl-(2-chlorophenyl)-2-bromoethanone from Example 37 (65.0 mg, 0.150 mmol) was suspended in formamide (2 mL, 50 mmol). The reaction was microwaved on 300 watts at 130° C. for 20 minutes. Water was added and the product was extracted with ethylacetate. The organic layer was washed with water twice and brine, dried over MgSO4, and evaporated to dryness. The crude product was purified on silica gel column, eluting with 25% of ethylacetate in hexane to give 129 (yield 10 mg, 18%). MS (ESI+) 381.1

Example 40

N-methyl-N-(2-(trifluoromethyl)phenyl)-4,5-dihydrobenzo[b]thieno[2,3-d]oxepine-2-carboxamide 130

To a solution of 2-(trifluoromethyl)aniline (0.122 g, 0.755 mmol) and triethylamine (0.105 mL, 0.756 mmol) in tetrahydrofuran (1.5 mL, 18 mmol) was added portion wise as a solid 4,5-dihydrobenzo[b]thieno[2,3-d]oxepine-2-carbonyl chloride (0.100 g, 0.378 mmol). The reaction mixture was stirred at room temperature with LC/MS monitor for formation of the alkylated product and noted complete after 2 hours. After aqueous work up, the reaction mixture was concentrated in vacuo, taken into DMF and treated with sodium hydride (0.03 g, 1 mmol) at room temperature for several minutes. Methyl iodide (0.06 g, 0.4 mmol) was added and the reaction was stirred at room temperature for several hours, then concentrated in vacuo. The residue was taken into EtOAc and washed with water and saline, concentrated to a solid residue, taken into DMF at a concentration of 100 mg/ml and purified by preparative RP-HPLC to give 130. Yield=25% of theoretical. MS: (ESI+) 404.1

Example 41

N-(2-aminoethyl)-N-(2-chlorophenyl)-4,5-dihydrobenzo[b]thieno[2,3-d]oxepine-2-carboxamide 131

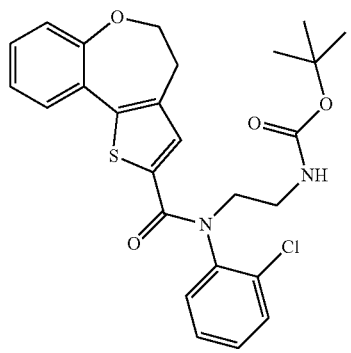 [SMILES: CC(C)(C)OC(=O)NCCN(C(=O)c1cc2c(s1)-c1ccccc1OCC2)c1ccccc1Cl]

To a solution of room temperature tert-butyl 2-(2-chlorophenylamino)ethylcarbamate (0.145 g, 0.508 mmol) and triethylamine (0.113 mL, 0.812 mmol) in tetrahydrofuran (1 mL, 10 mmol) was added a solution of 4,5-dihydrobenzo[b]thieno[2,3-d]oxepine-2-carbonylchloride in tetrahydrofuran (4 mL). The reaction mixture was stirred overnight and measured complete by LC/MS. Reaction concentrated in vacuo, and aqueous work up gave a yellow solid which was purified by MPLC to give 150 mg N-(2-(tert-butyldimethylsilyloxy)ethyl)-N-(2-chlorophenyl)-4,5-dihydrobenzo[b]thieno[2,3-d]oxepine-2-carboxamide.

To a solution of tert-butyl 2-(N-(2-chlorophenyl)-4,5-dihydrobenzo[b]thieno[2,3-d]oxepine-2-carboxamido)ethylcarbamate (0.022 g, 0.36 mmol)/in DCM (0.400 mL, 4.93 mmol) was added a solution of 95% TFA/5% water. The reaction was monitored by LC/MS for desired product. Reaction mix concentrated in vacuo, taken into EA and washed with H$_2$O, dried (Na$_2$SO$_4$), concentrated and crude purified by preparative RP-HLPC to give 131 (yield=98% of theoretical). MS: (ESI+) 400.1

Example 42

N-(2-chlorophenyl)-N-methyl-8-(1H-pyrazol-4-yl)-4,5-dihydrobenzo[b]thieno[2,3-d]oxepine-2-carboxamide 132

Following Examples 44 and 60, 8-bromo-N-(2-chlorophenyl)-N-methyl-4,5-dihydrobenzo[b]thieno[2,3-d]oxepine-2-carboxamide 150 and pyrazole-4-boronic acid pinacol ester were reacted to give 132. MS: (ESI+) 436.1

Example 43

N-(2-chlorophenyl)-8-ethynyl-N-methyl-4,5-dihydrobenzo[b]thieno[2,3-d]oxepine-2-carboxamide 133

A solution of 8-bromo-N-(2-chlorophenyl)-N-methyl-4,5-dihydrobenzo[b]thieno[2,3-d]oxepine-2-carboxamide 150 (50 mg, 0.11 mmol) in triethylamine (2 mL) containing CuI (2.1 mg, 0.011 mmol) was degassed with bubbling nitrogen for 10 min. Pd(PPh$_3$)$_4$ (13 mg, 0.011 mmol) was added followed by trimethylsilylacetylene (5 equiv). The reaction vessel was sealed and heated in the microwave at 130° C. for 30 min. The cooled mixture was diluted with water and extracted with ethylacetate. The combined organics were concentrated and the residue dissolved in 2 mL methanol. The solution was treated with potassium carbonate (100 mg) and the suspension stirred for 2 hr at room temperature. The reaction mixture was concentrated, diluted with water and extracted with ethylacetate. The combined organics were concentrated and the residue purified by reverse phase HPLC to give 133. MS: (ESI+) 394.1.

Example 44

N-(2-chlorophenyl)-N-methyl-8-(pyridin-4-yl)-4,5-dihydrobenzo[b]thieno[2,3-d]oxepine-2-carboxamide 134

A suspension of 8-bromo-N-(2-chlorophenyl)-N-methyl-4,5-dihydrobenzo[b]thieno[2,3-d]oxepine-2-carboxamide 150 (50 mg, 0.11 mmol) in 1.0 mL MeCN and 1.0 mL 1M KOAc in water in a 10 mL microwave vial was degassed with bubbling nitrogen for approximately 10 min. 4-pyridineboronic acid (16 mg) was added followed by Pd(PPh$_3$)$_4$ (13 mg). The vessel was sealed and heated in a microwave at 140° C. for 30 min. The reaction mixture was cooled to room temperature, diluted with water and extracted with ethylacetate. The combined organics were concentrated and the residue purified by reverse phase HPLC to give 134. $^1$H NMR (DMSO-d$_6$) δ 8.77 (m, 2H), 8.05 (m, 2H), 7.70-7.53 (m, 7H), 6.65 (br s, 1H), 4.25 (m, 2H), 3.31 (s, 3H), 3.02 (m, 2H). MS: (ESI+) 447.1

Example 45

N-(2-chlorophenyl)-N-methyl-8-phenyl-4,5-dihydrobenzo[b]thieno[2,3-d]oxepine-2-carboxamide 135

Following Examples 44 and 60, 8-bromo-N-(2-chlorophenyl)-N-methyl-4,5-dihydrobenzo[b]thieno[2,3-d]oxepine-2-carboxamide 150 and phenyl boronic acid were reacted to give 135. MS: (ESI+) 446.1

Example 46

5-(4,5-dihydrobenzo[b]thieno[2,3-d]oxepin-2-yl)-1H-pyrrolo[2,3-b]pyridine 136

2-Bromo-4,5-dihydrobenzo[b]thieno[2,3-d]oxepine from Example 73 was reacted with 7-azaindole-5-boronic acid pinacol ester using standard Suzuki coupling procedure. Purification on prep HPLC gave 136. $^1$H NMR (400 MHz, CDCl3): 3.30 (2H, t), 4.40 (2H, t), 6.56-6.58 (1H, m), 7.05-7.07 (2H, m), 7.15-7.18 (2H, m), 7.36 (1H, t), 7.75 (1H, d), 8.16 (1H, d), 8.63 (1H, d). MS: (ESI+) 318

Example 47

N2-(2-chlorophenyl)-N2-methyl-4,5-dihydrobenzo[b]thieno[2,3-d]oxepine-2,8-dicarboxamide 137

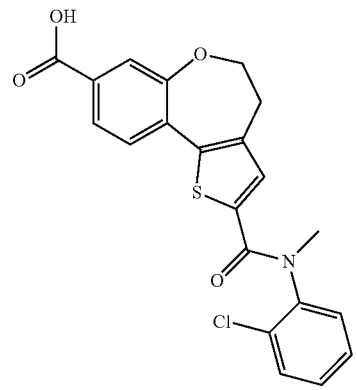 [SMILES: CN(C(=O)c1cc2c(s1)-c1ccc(C(=O)O)cc1OCC2)c1ccccc1Cl]

To a solution of methyl 2-((2-chlorophenyl)(methyl)carbamoyl)-4,5-dihydrobenzo[b]thieno[2,3-d]oxepine-8-carboxylate 138 (45 mg, 0.11 mmol) in 1.0 mL THF and 1.0 mL water in a 20 mL scintillation vial was added LiOH (monohydrate, 200 mg). The vessel was sealed and heated at 50° C. over night. The reaction mixture was cooled to room temperature, acidified to pH 2 with 2N HCl, and extracted with ethylacetate. The combined organic extracts were dried over Na$_2$SO$_4$ and concentrated to give the crude 2-((2-chlorophenyl)(methyl)carbamoyl)-4,5-dihydrobenzo[b]thieno[2,3-d]oxepine-8-carboxylic acid. To a solution of this acid in 2 mL DMF was added DIPEA (0.15 mL) and HATU, (N,N,N',N'-tetramethyl-O-(7-azabenzotriazol-1-yl)uronium hexafluorophosphate, 75 mg) followed by ammonium chloride (34 mg). The whole was stirred at room temperature for 2 hours, diluted with water and extracted with ethylacetate. The combined organics were concentrated and the residue purified by reverse phase HPLC to give 137 as a colorless solid. $^1$H NMR (500 MHz, DMSO-d$_6$) δ 7.94 (br s, 1H), 7.66 (m, 2H), 7.54-

7.46 (m, 4H), 7.35 (m, 1H), 6.59 (m, 1H), 4.21 (m, 2H), 3.26 (m, 3H, obstructed by water), 2.98 (m, 2H). MS: (ESI+) 413.1

Example 48 methyl 2-((2-chlorophenyl)(methyl)carbamoyl)-4,5-dihydrobenzo[b]thieno[2,3-d]oxepine-8-carboxylate 138

The mixture of 8-bromo-N-(2-chlorophenyl)-N-methyl-4,5-dihydrobenzo[b]thieno[2,3-d]-oxepine-2-carboxamide (10 g, 0.022 mol), Pd(OAc)$_2$ (2.47 g, 0.011 mmol), dppf (10 g, 0.018 mol), TEA (4.45 g, 0.044 mol) in DMF (50 mL) and MeOH (100 mL) was stirred under CO (50 psi) atmosphere at 70° C. for 2 days. After filtration over celite, the mixture was concentrated to give the crude product, which was purified by flash column chromatography (hexanes:EtOAc/5:1) to give 138. (6.59 g, yield: 69%). MS (ESI): 428.1

Alternatively, a suspension of 8-bromo-N-(2-chlorophenyl)-N-methyl-4,5-dihydrobenzo[b]thieno[2,3-d]oxepine-2-carboxamide 150 (113 mg, 0.25 mmol), Mo(CO)$_6$ (66 mg, 0.25 mmol), Hermann's palladacycle (trans-di(mu-acetato)bis[o-(di-o-tolylphosphino)benzyl]dipalladium (II), 23 mg) and tri-tert-butylphosphonium tetrafluoroborate (15 mg) in methanol (0.8 mL) and THF (0.8 mL) in a 10 mL microwave vial was treated with DBU (0.11 mL, 0.75 mmol) and immediately sealed. The whole was heated in a microwave at 110° C. for 20 min, cooled to room temperature and diluted with ethylacetate. The crude suspension was filtered through celite and the eluent concentrated to give a residue that was purified by flash column chromatography (10-100% ethylacetate in hexanes) to give 138 as a colorless solid. $^1$H NMR (500 MHz, DMSO-d$_6$) δ 7.69-7.49 (m, 7H), 6.57 (m, 1H), 4.22 (m, 2H), 3.85 (s, 3H), 3.23 (s, 3H, obstructed by water), 3.02 (m, 2H). MS: (ESI+) 428.1

Example 49 tert-butyl 2-(2-((2-chlorophenyl)(methyl)carbamoyl)-4,5-dihydrobenzo[b]thieno[2,3-d]oxepine-8-carboxamido)ethyl(methyl)carbamate 139

Following the procedure of Example 13 and General Procedure C, 8-bromo-N-(2-chlorophenyl)-N-methyl-4,5-dihydrobenzo[b]thieno[2,3-d]oxepine-2-carboxamide 150 and N-Boc-N-methyl-ethylenediamine (tert-butyl 2-aminoethyl (methyl)carbamate) were reacted to give 139. MS: (ESI+) 470.2.

Example 50

4-(4,5-dihydrobenzo[b]thieno[2,3-d]oxepin-2-yl)-1H-indazole 140

2-Bromo-4,5-dihydrobenzo[b]thieno[2,3-d]oxepine from Example 73 was reacted with indazole 4-boronic acid pinacol ester using standard Suzuki coupling procedure. Purification on prep HPLC and triturating with hexanes gave 140. 1H NMR (400 MHz, CDCl3): 3.34 (2H, t), 4.42 (2H, t), 7.07-7.11 (2H, m), 7.18-7.22 (1H, m), 7.35 (1H, s), 7.42-7.49 (3H, m), 7.79 (1H, dd), 8.50 (1H, s). MS: (ESI+) 319

Example 51

N-(2-chlorophenyl)-N-methyl-(10-cyano-4,5-dihydropyrido-[4,3-b]thieno[2,3-d]oxepin-2)-carboxamide 141

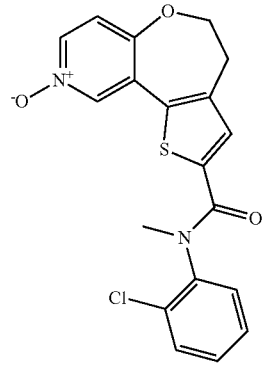

m-Chloroperbenzoic acid (88.0 mg, 0.36 mmol) was added to a solution of N-(2-chlorophenyl)-N-methyl-4,5-dihydropyrido[4,3-b]thieno[2,3-d]oxepine-2-carboxamide 162 (100 mg, 0.27 mmol) in 20 ml of methylene chloride. The reaction mixture was stirred for 18 hours. The solvent was removed under vacuum and the residue partitioned between 0.1 N aq. Na2CO3 and ethyl acetate. The organic layer was washed with water and brine, and dried over Na2SO4. Concentration under vacuum gave almost pure N-(2-chlorophenyl)-N-methyl-(9-oxo-4,5-dihydropyrido-[4,3-b]thieno[2,3-d]oxepin-2)-carboxamide (0.112 g, 90%). MS (ESI+) 387.0.

N,N-Dimethylcarbamoyl chloride (40 uL, 0.4 mmol) was added to a solution of N-(2-chlorophenyl)-N-methyl-(9-oxo-4,5-dihydropyrido-[4,3-b]thieno[2,3-d]oxepin-2)-carboxamide (56 mg, 0.14 mmol) and triethylamine (24 uL, 0.17 mmol) in 2 ml of acetonitrile. After stirring for 5 minutes, trimethylsilyl cyanide (96 uL, 0.72 mmol) was added and the mixture was kept for 4 hours. The mixture was concentrated under vacuum and the residue partitioned between ethyl acetate and 1 M aq Na2CO3. The organic layer was washed with water and brine, and dried over MgSO4. After concentration, the residue was purified on a silica gel column, eluting with 45% of ethyl acetate in hexane to give 141 (yield 27.2 mg, 47%). $^1$H NMR (400 MHz, DMSO) δ 8.51 (d, J=5.3, 1H), 7.72-7.61 (m, 2H), 7.58-7.47 (m, 2H), 7.41 (d, J=5.3, 1H), 6.82 (s, 1H), 4.48 (t, J=5.8, 2H), 3.30 (s, 3H), 2.93 (t, J=5.7, 2H). MS (ESI+) 396.1

Example 52

5-(6,7-dihydropyrido[3,2-b]thieno[2,3-d]oxepin-9-yl)pyridin-2-amine 142

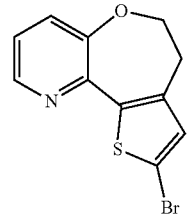 [SMILES: Brc1cc2c(s1)-c1ncccc1OCC2]

A mixture of 9-bromo-6,7-dihydropyrido[3,2-b]thieno[2,3-d]oxepine (113 mg, 0.400 mmol), 2-aminopyridine-5-boronic acid, pinacol ester (96.8 mg, 0.440 mmol) and bis(triphenylphosphine)palladium(II) chloride (14.0 mg, 0.0200 mmol) in 1.0 M of sodium carbonate in water (0.500 mL) and acetonitrile (3 mL, 60 mmol) was degassed and microwaved on 300 watts at 140° C. for 20 minutes. The reaction mixture was partitioned between ethyl acetate and water and filtered from inorganic salts. The organic layer was washed with water, brine, dried over MgSO4 and evaporated to dryness. The crude residue was purified on silicagel column, eluting with 50% of ethyl acetate in methylene chloride to give 142 (yield 43 mg, 36%).

$^1$H NMR (400 MHz, DMSO-d6) δ 8.27 (d, J=2.3, 1H), 8.21 (dd, J=1.4, 4.5, 1H), 7.68 (dd, J=2.5, 8.6, 1H), 7.38 (dd, J=1.4, 8.1, 1H), 7.21 (s, 1H), 7.17 (dd, J=4.5, 8.1, 1H), 6.50 (d, J=8.7, 1H), 6.21 (s, 2H), 4.32 (t, J=4.8, 2H), 3.19 (t, J=4.8, 2H). MS: (ESI+) 296.1

Example 53

N-(2-chlorophenyl)-8-cyano-N-methyl-4,5-dihydrobenzo[b]thieno[2,3-d]oxepine-2-carboxamide 143

To a solution of 8-bromo-N-(2-chlorophenyl)-N-methyl-4,5-dihydrobenzo[b]thieno[2,3-d]oxepine-2-carboxamide 150 (50 mg, 0.11 mmol) in 1 mL of DMF in a 10 mL microwave vial was added CuCN (30 mg). The reaction vessel was sealed and heated to 250° C. in a microwave for 20 min. The whole was cooled to room temperature, diluted with saturated aqueous ammonium chloride and extracted with ethylacetate. The combined organic extracts were concentrated and the crude residue purified by reverse phase HPLC to give 143. $^1$H NMR (500 MHz, DMSO-d$_6$) δ 7.65 (m, 2H), 7.58-7.46 (m, 5H), 6.64 (s, 1H), 4.22 (m, 2H), 3.28 (s, 3H), 3.00 (m, 2H). MS: (ESI+) 395.1

Example 54

3-(2-((2-chlorophenyl)(methyl)carbamoyl)-4,5-dihydrobenzo[b]thieno[2,3-d]oxepin-8-yl)benzoic acid 144

Following Examples 44 and 60 and General Procedure C, 8-bromo-N-(2-chlorophenyl)-N-methyl-4,5-dihydrobenzo[b]thieno[2,3-d]oxepine-2-carboxamide 150 and 3-carboxyphenyl boronic acid were reacted to give 144. MS: (ESI+) 490.1

Example 55

N-(2-chlorophenyl)-N-methyl-8-(morpholine-4-carbonyl)-4,5-dihydrobenzo[b]thieno[2,3-d]oxepine-2-carboxamide 145

Following the procedure of Example 13 and General Procedure C, 8-bromo-N-(2-chlorophenyl)-N-methyl-4,5-dihydrobenzo[b]thieno[2,3-d]oxepine-2-carboxamide 150 and morpholine were reacted to give 145. MS: (ESI+) 483.1

Example 56

N-(2-chlorophenyl)-N-methyl-8-(3-(methylsulfonyl)phenyl)-4,5-dihydrobenzo[b]thieno[2,3-d]oxepine-2-carboxamide 146

Following the procedure of Examples 44 and 60 and General Procedure C, 8-bromo-N-(2-chlorophenyl)-N-methyl-4,5-dihydrobenzo[b]thieno[2,3-d]oxepine-2-carboxamide 150 and 3-methylsulfonylphenyl boronic acid were reacted to give 146. MS: (ESI+) 524.1

Example 57

8-acetamido-N-(2-chloro-4-(4-methylpiperazine-1-carbonyl)phenyl)-N-methyl-4,5-dihydrobenzo[b]thieno[2,3-d]oxepine-2-carboxamide 147

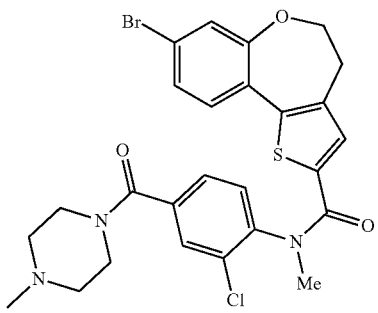 [SMILES: CN1CCN(C(=O)c2ccc(N(C)C(=O)c3cc4c(s3)-c3ccc(Br)cc3OCC4)c(Cl)c2)CC1]

Following the procedure of Example 91, to a solution containing 8-bromo-N-(2-chloro-4-(4-methylpiperazine-1-carbonyl)phenyl)-N-methyl-4,5-dihydrobenzo[b]thieno[2,3-d]oxepine-2-carboxamide (0.095 g, 0.16 mmol) in 1,4-dioxane (2.00 mL, 25.6 mmol;) was added 4,5-bis(diphenylphosphino)-9,9-dimethylxanthene (XantPhos, 9.6 mg, 0.016 mmol;), acetamide (15 mg, 0.25 mmol;), and cesium carbonate (120 mg, 0.36 mmol) then degassed with nitrogen gas for 15 min. To the reaction mixture was added tris(dibenzylideneacetone)dipalladium(0) (Pd$_2$(dba)$_3$, 7.6 mg, 0.0083 mmol;). The reaction mixture was heat at 100° C. for 18 h. The crude product was submitted for rHPLC to give 147 (5.5%). MS: (ESI+) 553.2

Example 58

N2-(2-chlorophenyl)-N2,N8-dimethyl-4,5-dihydrobenzo[b]thieno[2,3-d]oxepine-2,8-dicarboxamide 148

Following the procedure of Example 13 and General Procedure C, 8-bromo-N-(2-chlorophenyl)-N-methyl-4,5-dihydrobenzo[b]thieno[2,3-d]oxepine-2-carboxamide 150 and methylamine were reacted to give 148. MS: (ESI+) 427.1

Example 59 methyl 2-((2-chlorophenyl)(methyl)carbamoyl)-4,5-dihydrobenzo[b]thieno[2,3-d]oxepin-8-ylcarbamate 149

Following the procedure of Example 61, 8-bromo-N-(2-chlorophenyl)-N-methyl-4,5-dihydrobenzo[b]thieno[2,3-d]oxepine-2-carboxamide 150 and methyl carbamate were coupled to give 149. MS: (ESI+) 443.1

Example 60

8-bromo-N-(2-chlorophenyl)-N-methyl-4,5-dihydrobenzo[b]thieno[2,3-d]oxepine-2-carboxamide 150

Following Example 10 and General Procedure C, 150 is prepared from 8-bromo-4,5-dihydrobenzo[b]thieno[2,3-d]oxepine-2-carboxylic acid 11 and 2-chloro-N-methylaniline. MS: (ESI+) 449.9.

Example 61

8-acetamido-N-(2-chlorophenyl)-N-methyl-4,5-dihydrobenzo[b]thieno[2,3-d]oxepine-2-carboxamide 151

To a suspension of 8-bromo-N-(2-chlorophenyl)-N-methyl-4,5-dihydrobenzo[b]thieno[2,3-d]oxepine-2-carboxamide 150 (100 mg, 0.22 mmol), $Cs_2CO_3$ (158 mg), acetamide (20 mg), and xantphos (13 mg) in dry 1,4-dioxane (2 mL) was degassed with bubbling $N_2$. $Pd_2dba_3$ was added and the 10 mL tube was sealed and heated at 110° C. for 8 hr. After cooling to room temp., the mixture was diluted with water and extracted with ethylacetate. The combined organics were concentrated and the crude residue obtained purified by reverse phase HPLC to give 151. $^1H$ NMR (500 MHz, DMSO-$d_6$) δ 10.03 (s, 1H), 7.65 (m, 2H), 7.62 (m, 2H), 7.35 (m, 2H), 7.17 (m, 1H), 6.51 (br s, 1H), 4.15 (m, 2H), 3.29 (s, 3H), 2.91 (m, 2H), 2.03 (s, 3H) MS: (ESI+) 427.1

Example 62

3-(4,5-dihydrobenzo[b]thieno[2,3-d]oxepin-2-yl)pyridine 152

2-Bromo-4,5-dihydrobenzo[b]thieno[2,3-d]oxepine from Example 73 was reacted with 3-pyridine boronic acid pinacol ester using standard Suzuki coupling procedure. Purification on silica gave 152. $^1H$ NMR (400 MHz, CDCl3): 3.29 (2H, t), 4.39 (2H, t), 7.05-7.10 (2H, m), 7.18-7.22 (2H, m), 7.32-7.35 (1H, m), 7.74 (1H, dd), 7.89 (1H, dt), 8.55 (1H, dd), 8.91 (1H, s). MS: (ESI+) 280

Example 63

4-(4,5-dihydrobenzo[b]thieno[2,3-d]oxepin-2-yl)pyridine 153

2-Bromo-4,5-dihydrobenzo[b]thieno[2,3-d]oxepine from Example 73 was reacted with 4-pyridine boronic acid pinacol ester using standard Suzuki coupling procedure. Purification on silica gave 153. $^1H$ NMR (400 MHz, CDCl3): 3.29 (2H, t), 4.39 (2H, t), 7.06-7.11 (2H, m), 7.22 (1H, dt), 7.28 (1H, s), 7.49 (2H, dd), 7.75 (1H, dd), 8.62 (2H, dd). MS: (ESI+) 280

Example 64

N2-(2-chlorophenyl)-N2-(2-hydroxyethyl)-N-8-methyl-4,5-dihydrobenzo[b]thieno[2,3-d]oxepine-2,8-dicarboxamide 154

Under ambient conditions a sealable reaction vessel was charged with 8-bromo-N-(2-chlorophenyl)-N-(2-hydroxyethyl)-4,5-dihydrobenzo[b]thieno[2,3-d]oxepine-2-carboxamide (0.08 g, 0.17 mmol), molybdenum hexacarbonyl (0.044 g, 0.167 mmol) in methanol (0.5 ml, 10 mmol)/THF 1 ml, 10 mmol), followed by the addition of 2M methylamine in THF (0.251 ml),/trans-D(mu-acetato)bis[di-o-tolylphosphino)benzyl]dipalladium(II) (32.3 mg, 0.0334 mmol). Finally, DBU (0.025 ml, 0.167 mmol) was added and the reaction vial was quickly sealed. The charged reaction vial was flash heated on a Biotage Emrys Optimizer microwave at 150° C. for 20 minutes. The cooled reaction mixture was diluted with ethyl acetate and filtered through a bed of Celite. The filtrate was concentrated to a solid and purified by MPLC on silica to give 3.2 mg 154 (yield=4.3% of theoretical). MS: (ESI+) 458.2

Example 65

N2-(4-chloropyridin-3-yl)-N2,N8-dimethyl-4,5-dihydrobenzo[b]thieno[2,3-d]oxepine-2,8-dicarboxamide 155

Following the procedure of Example 64, 8-bromo-N-(4-chloropyridin-3-yl)-N-methyl-4,5-dihydrobenzo[b]thieno[2,3-d]oxepine-2-carboxamide and methylamine gave 155. Yield=2.5% of theoretical. MS: (ESI+) 429.1

Example 66

N-(2,4-difluorophenyl)-N-methyl-4,5-dihydrobenzo[b]thieno[2,3-d]oxepine-2-carboxamide 156

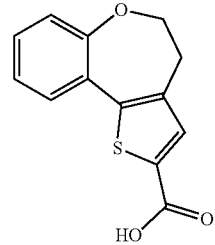 [SMILES: O=C(O)c1cc2c(s1)-c1ccccc1OCC2]

Following General Procedure C, 156 is prepared from 4,5-dihydrobenzo[b]thieno[2,3-d]oxepine-2-carboxylic acid and 2,4-difluoro-N-methylaniline. MS: (ESI+) 371.9

Example 67

N-(2-chlorophenyl)-N-methyl-4,5-dihydrobenzo[b]thieno[2,3-d]oxepine-2-carboxamide 157

Following General Procedure C, 157 is prepared from 4,5-dihydrobenzo[b]thieno[2,3-d]oxepine-2-carboxylic acid and 2-chloro-N-methylaniline. MS: (ESI+) 370.1

Example 68

N-(2-chlorophenyl)-8-(2-hydroxyacetamido)-N-methyl-4,5-dihydrobenzo[b]thieno[2,3-d]oxepine-2-carboxamide 158

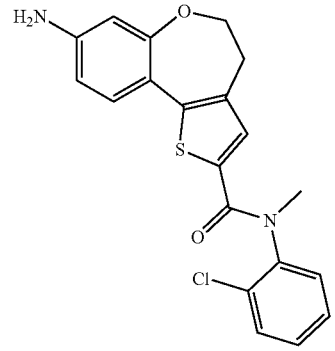 [SMILES: CN(C(=O)c1cc2c(s1)-c1ccc(N)cc1OCC2)c1ccccc1Cl]

To a mixture of 8-amino-N-(2-chlorophenyl)-N-methyl-4,5-dihydrobenzo[b]thieno[2,3-d]oxepine-2-carboxamide HCl salt (1.0 g, 2.37 mmol) in 30 mL of DCM (dichloromethane, methylene chloride) was added triethylamine (1 mL, 7.12 mmol). The mixture was stirred at 0° C. for 10 min and BnOCH₂COCl (0.53 g, 2.85 mmol) was added dropwise. After the addition was completed, the reaction mixture was raised to room temperature and stirred for another 2 hours. The mixture was quenched by water and extracted with EtOAc. The organic phases were combined, dried over Na₂SO₄ and evaporated to about 0.9 g of the crude product, which was used for the next step without further purification. A mixture of 8-(2-(benzyloxy)acetamido)-N-(2-chlorophenyl)-N-methyl-4,5-dihydrobenzo[b]thieno[2,3-d]oxepine-2-carboxamide (0.6 g, 1.13 mmol) in TFA (5 mL) and CF₃SO₃H (2 mL) was stirred at 60° C. overnight. After removal of the solvent, the crude product was purified by prep. TLC to give about 320 mg of 158 (isolated yield: 64%). ¹H NMR (DMSO-d₆, 400 MHz): δ 9.77 (s, 1H), 7.63-7.35 (m, 7H), 6.47 (s, 1H), 5.64 (s, 1H), 4.11 (s, 2H), 3.94 (d, J=5.2 Hz, 2H), 3.23 (s, 3H), 2.88 (d, J=5.2 Hz, 2H). MS: (ESI+) 443.0

Example 69

N-(2-chloro-4-(methylcarbamoyl)phenyl)-N-(2-hydroxyethyl)-10-aza-4,5-dihydrobenzo[b]thieno[2,3-d]oxepine-2-carboxamide 159

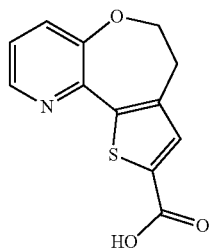 [SMILES: O=C(O)c1cc2c(s1)-c1ncccc1OCC2]

To a solution containing 10-aza-4,5-dihydrobenzo[b]thieno[2,3-d]oxepine-2-carboxylic acid (0.175 g, 0.708 mmol;) in methylene chloride (1.84 mL, 28.7 mmol;) was added thionyl chloride (0.155 mL, 2.12 mmol;). The mixture was stirred at 80° C. for 2 h, cooled and concentrated in vacuo. To the crude product acid chloride (0.400 g, 1.16 mmol) in tetrahydrofuran (5.22 mL, 64.4 mmol) was added 1.00 M of sodium bis(trimethylsilyl)amide in tetrahydrofuran (1.16 mL). The reaction mixture was stirred at room temperature 1 h then methyl 4-(2-(tert-butyldimethylsilyloxy)ethylamino)-3-chlorobenzoate was added at 0° C. The reaction mixture was stirred overnight, quenched with sat. NH₄Cl, and extracted with DCM (2×). The combined organics were dried (Na₂SO₄), filtered and concentrated. The crude product was purified by flash chromatography EtOAc/Hex (0-100%), eluted at 70% EtOAc, to give methyl 4-(N-(2-(tert-butyldimethylsilyloxy)ethyl)-10-methyl-4,5-dihydrobenzo[b]thieno[2,3-d]oxepine-2-carboxamido)-3-chlorobenzoate (yield 58%). MS: (ESI+) 573.2

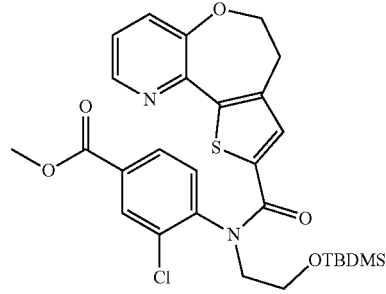 [SMILES: COC(=O)c1ccc(N(CCO[Si](C)(C)C(C)(C)C)C(=O)c2cc3c(s2)-c2ncccc2OCC3)c(Cl)c1]

To a solution of methyl 4-(N-(2-(tert-butyldimethylsilyloxy)ethyl)-10-methyl-4,5-dihydrobenzo[b]thieno[2,3-d]oxepine-2-carboxamido)-3-chlorobenzoate (0.250 g, 0.436 mmol) in tetrahydrofuran (10.2 mL, 126 mmol;) and water (10.2 mL, 566 mmol) was added lithium hydroxide, monohydrate (0.0732 g, 1.74 mmol). The reaction mixture was stirred at room temperature overnight. The reaction mixture was concentrated, acidified with 1M HCl, and extracted with DCM (3×). The combined organics were dried (Na₂SO₄), filtered and concentrated to give 4-(N-(2-(tert-butyldimethylsilyloxy)ethyl)-10-methyl-4,5-dihydrobenzo[b]thieno[2,3-d]oxepine-2-carboxamido)-3-chlorobenzoic acid (yield 60%). MS: (ESI+) 559.1

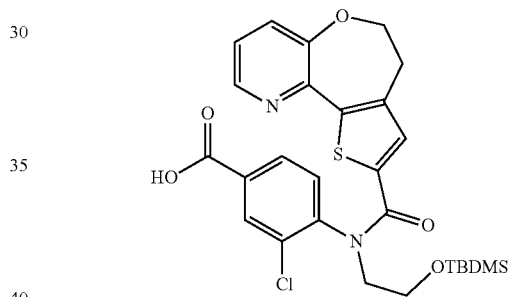

To a solution of 4-(N-(2-(tert-butyldimethylsilyloxy)ethyl)-10-methyl-4,5-dihydrobenzo[b]thieno[2,3-d]oxepine-2-carboxamido)-3-chlorobenzoic acid (0.0710 g, 0.127 mmol) in methylene chloride (1.8 mL, 28 mmol) was added methylamine (0.254 mmol) and N,N-diisopropylethylamine (0.221 mL, 1.27 mmol), and then N,N,N',N'-tetramethyl-O-(7-azabenzotriazol-1-yl)uronium hexafluorophosphate (HATU, 0.0966 g, 0.254 mmol). The mixture was stirred at room temperature for 2 h. LCMS indicated the reaction was complete. The reaction was quenched with sat. NH₄Cl and extracted with DCM (2×). The combined organics were dried (Na₂SO₄), filtered and concentrated. The crude TBDMS-amide product was purified by flash chromatography (MeOH/DCM, eluted at 5% MeOH) and dissolved in tetrahydrofuran (5.00 ml) and acetic acid (0.007 mL, 0.127 mmol). Tetra-n-butylammonium fluoride in tetrahydrofuran (0.127 mL, 1.00 M, 0.127 mmol) was added. The reaction mixture was stirred at room temperature for 14 h. The reaction mixture was diluted with ethyl acetate and washed with water. The crude product was purified by rHPLC to give 159 (yield 22%). MS: (ESI+) 558.1

Example 70 160

Following the procedure of Example 69 to prepare 159, 4-(N-(2-(tert-butyldimethylsilyloxy)ethyl)-10-methyl-4,5- dihydrobenzo[b]thieno[2,3-d]oxepine-2-carboxamido)-3-chlorobenzoic acid and 1-methylpiperazine were reacted to give 160, following fluoride treatment to remove the TBDMS group. MS: (ESI+) 527.2

Example 71

N-(2-chlorophenyl)-8-(3-(dimethylamino)propanamido)-N-methyl-4,5-dihydrobenzo[b]thieno[2,3-d]oxepine-2-carboxamide 161

Following the procedure of Example 68 for 158, 8-amino-N-(2-chlorophenyl)-N-methyl-4,5-dihydrobenzo[b]thieno[2,3-d]oxepine-2-carboxamide HCl salt and acryloyl chloride reacted to give 8-acrylamido-N-(2-chlorophenyl)-N-methyl-4,5-dihydrobenzo[b]thieno[2,3-d]oxepine-2-carboxamide which was treated with dimethylamine to give 161. MS: (ESI+) 484.1

Example 72

N-(2-chlorophenyl)-N-methyl-4,5-dihydropyrido[4,3-b]thieno[2,3-d]oxepin-2-carboxamide 162

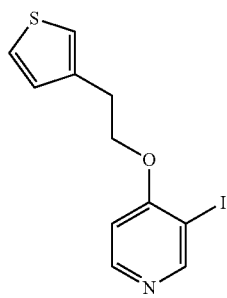 [SMILES: Ic1cnccc1OCCc1ccsc1]

To a solution of 4-chloro-3-iodo-pyridine (4.79 g, 20.0 mmol) and 2-(3-thienyl)ethanol (2.43 mL, 22.0 mmol) in a mixture of tetrahydrofuran (60 mL, 700 mmol) and N,N-dimethylformamide (20 mL, 200 mmol) was added sodium hydride, 60% dispersion in mineral oil (0.960 g, 24.0 mmol) portionwise over 30 min. The mixture was stirred for 2 hours, poured carefully into 200 ml of cold water and extracted with diethylether twice. The organic extract was washed with water and brine, and dried over MgSO₄. After concentration under vacuum, the crude residue was purified on silica gel column, eluting with 50% ethyl acetate in hexane to give 3-iodo-4-(2-(thiophen-3-yl)ethoxy)pyridine (yield 5.34 g, 81%). ¹H NMR (400 MHz, CDCl3) δ 8.75 (s, 1H), 8.35 (d, J=5.6, 1H), 7.29 (dd, J=3.0, 4.8, 1H), 7.19 (s, 1H), 7.12 (d, J=4.9, 1H), 6.70 (d, J=5.6, 1H), 4.26 (t, J=6.5, 2H), 3.21 (t, J=6.5, 2H). MS (ESI+) 332.0, 221.9.

3-Iodo-4-(2-(thiophen-3-yl)ethoxy)pyridine (1.66 g, 5.00 mmol), palladium acetate (112 mg, 0.500 mmol), triphenylphosphine (262 mg, 1.00 mmol) and potassium carbonate (1.38 g, 10.0 mmol) in N,N-dimethylformamide (80 mL, 1000 mmol) were heated at 115° C. for 2 hours. The reaction mixture was concentrated and partitioned between ethyl acetate and water. The organic layer was washed with water and brine, and dried over MgSO4. The crude product was purified on a silica gel column eluting with 50% ethyl acetate in hexane to give 4,5-dihydropyrido[4,3-b]thieno[2,3-d]oxepine (yield 0.86 g, 85%). ¹H NMR (400 MHz, CDCl3) δ 8.93 (s, 1H), 8.25 (d, J=5.5, 1H), 7.23 (d, J=5.2, 1H), 6.89 (dd, J=3.6, 5.3, 2H), 4.43-4.33 (m, 2H), 3.29-3.20 (m, 2H). MS (ESI+) 204.0

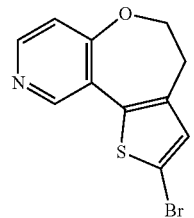 [SMILES: Brc1cc2c(s1)-c1cnccc1OCC2]

N-Bromosuccinimide (0.237 g, 1.33 mmol) in dimethylformamide (4 mL) was added dropwise to a solution of 4,5-dihydropyrido[4,3-b]thieno[2,3-d]oxepine (0.250 g, 1.23 mmol) in dimethylformamide (4 mL, 100 mmol) at 0° C. The reaction mixture was stirred for 18 hours at room temperature. The reaction mixture was mixed with 40 ml of water and extracted with 20 ml of ethylacetate twice. Combined organic extracts were washed with water and brine, and dried over MgSO₄. The solvent was evaporated affording 2-bromo-4,5-dihydropyrido[4,3-b]thieno[2,3-d]oxepine (0.227 g, 63%). ¹H NMR (500 MHz, CDCl3) δ 8.76 (s, 1H), 8.26 (d, J=5.4, 1H), 6.90 (d, J=5.5, 1H), 6.88 (s, 1H), 4.36 (t, J=4.7, 2H), 3.19 (t, J=4.8, 2H). MS (ESI+) 282.0

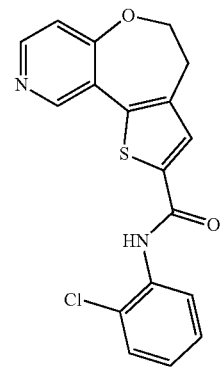 [SMILES: O=C(Nc1ccccc1Cl)c1cc2c(s1)-c1cnccc1OCC2]

1.6 M of n-Butyllithium in hexane (0.6302 mL) was added dropwise to a solution of 2-bromo-4,5-dihydropyrido[4,3-b]thieno[2,3-d]oxepine (0.227 g, 0.804 mmol) in tetrahydrofuran (6.00 mL, 74.0 mmol) at −75° C. The dark brown mixture was stirred at −78° C. for 20 min. 1-Chloro-2-isocyanatobenzene (0.1421 g, 0.9252 mmol) in 2 ml of tetrahydrofuran was added dropwise and the mixture was kept at −78° C. for 20 min. 4N aq. HCl (1 ml) was added and the mixture was poured into 50 ml of sat. aq NaHCO₃. The mixture was extracted twice with methylene chloride, combined, and washed with water and brine, and dried over MgSO4. After concentrating under vacuum, the residue was triturated with ethyl acetate. The collected precipitate was N-(2-chlorophenyl)-4,5-dihydropyrido[4,3-b]thieno[2,3-d]oxepin-2-carboxamide (0.19 g, 66% yield). MS (ESI+) 357.0.

Sodium hydride, 60% dispersion in mineral oil (80 mg, 2.0 mmol) was added to a solution of N-(2-chlorophenyl)-4,5-dihydropyrido[4,3-b]thieno[2,3-d]oxepin-2-carboxamide (71.4 mg, 0.2 mmol) in 10 ml of tetrahydrofuran. The mixture was stirred for 30 min and mixed with methyl iodide (0.12 mL, 2.0 mmol). The reaction mixture was stirred for 1 hour. The mixture was mixed with 50 ml of iced water and extracted with ethyl acetate twice. The combined ethyl acetate solution was washed with brine, dried over MgSO4, concentrated in vacuo, and purified on silica gel column eluting with 25% of ethylacetate in methylene chloride to give 162 (yield 50 mg, 67%). $^1$H NMR (400 MHz, DMSO) δ 8.57 (s, 1H), 8.25 (d, J=5.5, 1H), 7.68 (t, J=5.9, 2H), 7.60-7.50 (m, 2H), 6.98 (d, J=5.5, 1H), 6.64 (s, 1H), 4.27 (m, 2H), 3.28 (s, 3H), 2.99 (m, 2H). MS (ESI+) 371.1

Example 73

5-(4,5-dihydrobenzo[b]thieno[2,3-d]oxepin-2-yl)pyrimidin-2-amine 163

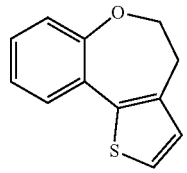 [SMILES: c1ccc2c(c1)OCCc1ccsc1-2]

To a stirred solution of 2-iodophenol (6.7 g, 30.6 mmol), 2-(3-thienyl)ethanol (3.57 g, 27.8 mol) and triphenylphosphene (8.00 g, 30.6 mmol) in THF, was slowly added a solution of DEAD (4.8 ml, 30.6 mmol). Reaction mixture was stirred at room temperature for 3 hours. Purification on silica gave 3-[2-(2-iodo-phenoxy)-ethyl]-thiophene. A mixture of 3-[2-(2-iodo-phenoxy)-ethyl]-thiophene (1.55 g, 4.69 mmol), palladium(II) acetate (105 mg, 0.47 mmol), potassium carbonate (3.2 g, 23.45 mmol), triphenylphosphene (246 mg, 0.94 mmol) and tetraethylammonium chloride (1.3 g, 4.69 mmol) in DMF was microwaved at 100° C. for 1 hour. The reaction was diluted with dichloromethane and filtered through celite. The filtrate was washed with water, dried (MgSO$_4$), and concentrated in-vacuo. Purification on silica gave 4,5-dihydrobenzo[b]thieno[2,3-d]oxepine.

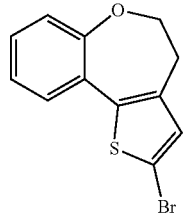 [SMILES: Brc1cc2c(s1)-c1ccccc1OCC2]

To a stirred solution of 4,5-dihydrobenzo[b]thieno[2,3-d]oxepine (440 mg, 2.2 mmol) and acetic acid (10 ml) in dichloromethane (10 ml) at 0° C., was added N-bromosuccinimide in portions. Reaction mixture was stirred for 18 hours, allowing solution to raise to room temperature before being concentrated in-vacuo. Residue was dissolved in ethyl acetate and sat. sodium carbonate solution. Organic phase was washed with water and brine, dried (Na$_2$SO$_4$) and concentrated in-vacuo to give 2-bromo-4,5-dihydrobenzo[b]thieno[2,3-d]oxepine.

2-Bromo-4,5-dihydrobenzo[b]thieno[2,3-d]oxepine was reacted with 2-aminopyrimidine-5-boronic acid pinacol ester using standard Suzuki coupling procedure. Purification on silica and triturating with diethyl ether gave 163. $^1$H NMR (400 MHz, CDCl3), 3.26 (2H, t, J=5.14), 4.37 (2H, t, J=5.18), 5.16 (2H, Broad s), 7.02-7.09 (3H, m), 7.16-7.22 (1H, m), 7.70 (1H, d, J=7.91), 8.56 (2H, s). MS: (ESI+) 396

Example 74

3-(6,7-dihydropyrido[3,2-b]thieno[2,3-d]oxepin-9-yl)-4-(2-chlorophenyl)-4H-1,2,4-triazole 164

Following the procedure of Example 166 to prepare 256, N-(2-chlorophenyl)-10-aza-4,5-dihydrobenzo[b]thieno[2,3-d]oxepine-2-carboxamide (0.167 g, 0.504 mmol) was dissolved in 1,4-dioxane (6.2 mL). 2,4-Bis(4-methoxyphenyl)-2,4-dithioxo-1,3,2,4-dithiadiphosphetane (Lawesson's reagent, 0.153 g, 0.378 mmol) was added. The reaction mixture was stirred at 85° C. for overnight. The reaction mixture was concentrated to give the crude thioamide intermediate. To a solution containing crude thioamide intermediate in methanol (7.3 mL) was added hydrazine (1.180 mL, 37 mmol). The reaction mixture was stirred at room temperature, concentrated, diluted with methylene chloride, washed with water and brine, and concentrated to give crude hydrazine intermediate. The crude hydrazine intermediate was sealed in a vial with ethyl chloroformate (2.33 mL, 0.014 mol) at 95° C. for 1 day, cooled to room temperature and concentrated. The crude product was purified by flash chromatograph (50-100% EtOAc/Hex) to give 164 (yield 14%). MS: (ESI+) 381.1

Example 75

4-(6,7-dihydropyrido[3,2-b]thieno[2,3-d]oxepin-9-yl)-(5-(2-chlorophenyl))-thiazol-2-amine 165

6,7-Dihydropyrido[3,2-b]thieno[2,3-d]oxepin-9-yl-(2-chlorophenyl)-2-bromoethanone from Example 37 (100.0 mg, 0.230 mmol) and thiourea (20.14 mg, 0.264 mmol) were heated in ethanol (5 mL, 80 mmol) for 1 hour. The solvent was evaporated to half of the volume, whereupon the product crystallized upon standing. The product 165 was collected by filtration and washed with cold ethanol (yield 43 mg, 45%). $^1$H NMR (400 MHz, DMSO) δ 8.15 (d, J=3.2, 1H), 7.66 (d, J=8.2, 1H), 7.54 (t, J=7.6, 2H), 7.47 (t, J=7.4, 1H), 7.36 (d, J=8.1, 1H), 7.16 (dd, J=4.5, 8.1, 1H), 6.73 (s, 1H), 5.80-4.90 (m, 2H), 4.24 (t, J=4.7, 2H), 3.04 (t, J=4.7, 2H). MS (ESI+) 412.1

Example 76

N-(2-chlorophenyl)-8-(3-ethylureido)-N-methyl-4,5-dihydrobenzo[b]thieno[2,3-d]oxepine-2-carboxamide 166

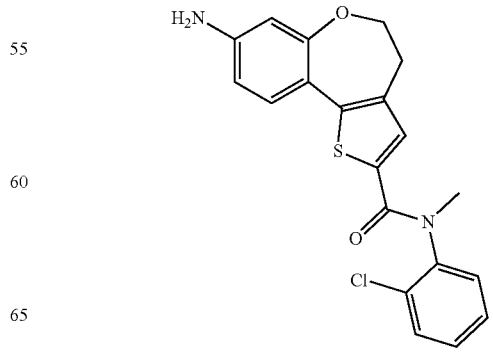

Solid Pd$_2$(dba)$_3$ (101 mg, 0.11 mmol) and BINAP (205 mg, 0.33 mmol) was added to a 10 mL flask and the whole purged with nitrogen. To the flask was added 8-bromo-N-(2-chlorophenyl)-N-methyl-4,5-dihydrobenzo[b]thieno[2,3-d]oxepine-2-carboxamide (500 mg, 1.11 mmol), benzophenone imine (303 mg, 1.67 mmol), NaO$^t$Bu (213 mg, 2.22 mmol) and toluene (30 mL). The mixture was heated to 80° C. with stirring until the starting material had been consumed (determined by TLC analysis). The mixture was cooled to room temperature, diluted with EtOAc, filtered and concentrated. The crude product was purified by column chromatography (5:1 hexanes:ethyl acetate) to give N-(2-chlorophenyl)-8-(diphenylmethyleneamino)-N-methyl-4,5-dihydrobenzo[b]thieno[2,3-d]oxepine-2-carboxamide as a yellow solid (400 mg, yield 65%). N-(2-chlorophenyl)-8-(diphenylmethyleneamino)-N-methyl-4,5-dihydrobenzo[b]thieno[2,3-d]oxepine-2-carboxamide (4.9 g, 8.92 mmol) was dissolved in 10 mL of MeOH. To the solution was added 6 mL of CH$_3$COCl in MeOH (1:10). The mixture was stirred at room temperature for 15 min before concentrated under vacuum. The residue was washed with EtOAc to give 8-amino-N-(2-chlorophenyl)-N-methyl-4,5-dihydrobenzo[b]thieno[2,3-d]oxepine-2-carboxamide as a white solid (3.6 g, yield 95%). $^1$H NMR (MeOD, 400 MHz): δ 7.59-6.60 (m, 8H), 4.21 (t, J=5.2 Hz, 2H), 3.31 (s, 3H), 2.96 (t, J=4.8 Hz, 2H).

To a solution of 8-amino-N-(2-chlorophenyl)-N-methyl-4,5-dihydrobenzo[b]thieno[2,3-d]oxepine-2-carboxamide HCl salt (0.25 g, 0.593 mmol) in anhydrous THF (15 mL) was added DIPEA (0.52 mL, 2.97 mmol) and ethyl isocyanate (0.1 g, 1.4 mmol). The solution was stirred at 40° C. overnight. The reaction mixture was poured into ammonium chloride aqueous solution and extracted with EtOAc. The organic phase was washed with brine and dried over anhydrous Na$_2$SO$_4$. After filtration, the filtrate was concentrated to the crude product, which was purified by preparative TLC to afford about 0.113 g of 166 (isolated yield: 42%). $^1$H NMR (DMSO-d$_6$, 400 MHz): δ 8.56 (s, 1H), 7.64-7.58 (m, 2H), 7.49 (t, J=3.6 Hz, 2H), 7.22 (d, J=4.4 Hz, 1H), 7.15 (d, J=2.4 Hz, 1H), 6.92 (dd, J=2.0, 8.4 Hz, 1H), 6.44 (s, 1H), 6.13 (t, J=5.6 Hz, 1H), 4.09 (d, J=4.4 Hz, 2H), 3.22 (s, 3H), 3.06 (dd, J=6.0, 7.2 Hz, 2H), 2.85 (s, 2H), 1.01 (t, J=7.2 Hz, 3H). MS: (ESI+) 456.1

Example 77

N-(2-chlorophenyl)-N-methyl-8-(3-methylureido)-4,5-dihydrobenzo[b]thieno[2,3-d]oxepine-2-carboxamide 167

Following the procedures of Example 76, 8-amino-N-(2-chlorophenyl)-N-methyl-4,5-dihydrobenzo[b]thieno[2,3-d]oxepine-2-carboxamide and methyl isocyanate gave 167. MS: (ESI+) 442.1

Example 78

N-(2-chlorophenyl)-N-methyl-8-ureido-4,5-dihydrobenzo[b]thieno[2,3-d]oxepine-2-carboxamide 168

Following the procedures of Example 76, 8-amino-N-(2-chlorophenyl)-N-methyl-4,5-dihydrobenzo[b]thieno[2,3-d] oxepine-2-carboxamide was reacted with carbonyl diimidazole and ammonium chloride to give 168. MS: (ESI+) 428.1

Example 79

N-(2-chlorophenyl)-8-(2-(diethylamino)acetamido)-N-methyl-4,5-dihydrobenzo[b]thieno[2,3-d]oxepine-2-carboxamide 169

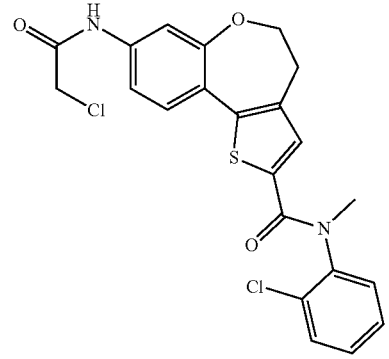 [SMILES: CN(C(=O)c1cc2c(s1)-c1ccc(NC(=O)CCl)cc1OCC2)c1ccccc1Cl]

Following the procedure in Example 147 for 237, 8-(2-chloroacetamido)-N-(2-chlorophenyl)-N-methyl-4,5-dihydro-benzo[b]thieno[2,3-d]oxepine-2-carboxamide and diethyl amine were reacted to give 169. MS: (ESI+) 498.2

Example 80

N-(2-chlorophenyl)-N-methyl-8-(2-morpholinoacetamido)-4,5-dihydrobenzo[b]thieno[2,3-d]oxepine-2-carboxamide 170

Following the procedure in Example 147 for 237, 8-(2-chloroacetamido)-N-(2-chlorophenyl)-N-methyl-4,5-dihydro-benzo[b]thieno[2,3-d]oxepine-2-carboxamide and morpholine were reacted to give 170. MS: (ESI+) 512.2

Example 81

N-(2-chlorophenyl)-N-methyl-8-(2-(4-methylpiperazin-1-yl)acetamido)-4,5-dihydrobenzo[b]thieno[2,3-d]oxepine-2-carboxamide 171

Following the procedure in Example 147 for 237, 8-(2-chloroacetamido)-N-(2-chlorophenyl)-N-methyl-4,5-dihydro-benzo[b]thieno[2,3-d]oxepine-2-carboxamide and N-methylpiperazine were reacted to give 171. MS: (ESI+) 525.3

Example 82

(3-chloro-4-(3-(4,5-dihydrobenzo[b]thieno[2,3-d]oxepin-2-yl)-4H-1,2,4-triazol-4-yl)phenyl)(4-methylpiperazin-1-yl)methanone 172

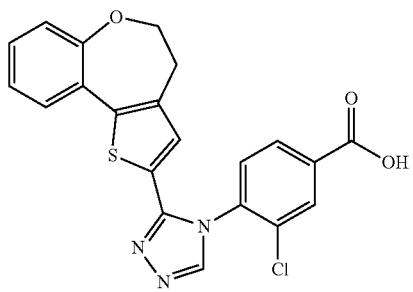 [SMILES: O=C(O)c1ccc(-n2cnnc2-c2cc3c(s2)-c2ccccc2OCC3)c(Cl)c1]

3-Chloro-4-(3-(4,5-dihydrobenzo[b]thieno[2,3-d]oxepin-2-yl)-4H-1,2,4-triazol-4-yl)benzoic acid N-methylpiperazine were reacted by a procedure similar to that to prepare 137 in Example 47 to give 172. MS: (ESI+) 506.2

Example 83

N2-(2-chlorophenyl)-N2-methyl-N-8-(pyridin-3-ylmethyl)-4,5-dihydrobenzo[b]thieno[2,3-d]oxepine-2,8-dicarboxamide 173

Following Example 47 and General Procedure C, methyl 2-((2-chlorophenyl)(methyl)carbamoyl)-4,5-dihydrobenzo[b]thieno[2,3-d]oxepine-8-carboxylate 138 and 3-aminomethylpyridine gave 173. MS: (ESI+) 504.0

Example 84

N2-(2-chlorophenyl)-N-8-(1-(hydroxymethyl)cyclopentyl)-N-2-methyl-4,5-dihydrobenzo[b]thieno[2,3-d]oxepine-2,8-dicarboxamide 174

Following Example 47 and General Procedure C, methyl 2-((2-chlorophenyl)(methyl)carbamoyl)-4,5-dihydrobenzo[b]thieno[2,3-d]oxepine-8-carboxylate 138 and 1-amino-1-cyclopentanemethanol gave 174. MS: (ESI+) 511.0

Example 85

N2-(2-chlorophenyl)-N-8-((S)-1-hydroxy-3,3-dimethylbutan-2-yl)-N-2-methyl-4,5-dihydrobenzo[b]thieno[2,3-d]oxepine-2,8-dicarboxamide 175

Following Example 47 and General Procedure C, methyl 2-((2-chlorophenyl)(methyl)carbamoyl)-4,5-dihydrobenzo[b]thieno[2,3-d]oxepine-8-carboxylate 138 and L-valinol gave 175. MS: (ESI+) 513.2

Example 86

N-(2-chlorophenyl)-8-(4-hydroxypiperidine-1-carbonyl)-N-methyl-4,5-dihydrobenzo[b]thieno[2,3-d]oxepine-2-carboxamide 176

Following Example 47 and General Procedure C, methyl 2-((2-chlorophenyl)(methyl)carbamoyl)-4,5-dihydrobenzo[b]thieno[2,3-d]oxepine-8-carboxylate 138 and 4-hydroxypiperidine gave 176. MS: (ESI+) 497.2

Example 87

N2-(2-chlorophenyl)-N8-((S)-2-hydroxypropyl)-N2-methyl-4,5-dihydrobenzo[b]thieno[2,3-d]oxepine-2,8-dicarboxamide 177

Following Example 47 and General Procedure C, methyl 2-((2-chlorophenyl)(methyl)carbamoyl)-4,5-dihydrobenzo[b]thieno[2,3-d]oxepine-8-carboxylate 138 and (S)-(+)-1-amino-2-propanol gave 177. MS: (ESI+) 471.0

Example 88

N2-(2-chlorophenyl)-N8-((S)-1-hydroxypropan-2-yl)-N2-methyl-4,5-dihydrobenzo[b]thieno[2,3-d]oxepine-2,8-dicarboxamide 178

Following Example 47 and General Procedure C, methyl 2-((2-chlorophenyl)(methyl)carbamoyl)-4,5-dihydrobenzo[b]thieno[2,3-d]oxepine-8-carboxylate 138 and L-alaninol gave 178. MS: (ESI+) 471.1

Example 89

N2-(2-chloro-4-(methylcarbamoyl)phenyl)-N2,N8-dimethyl-4,5-dihydrobenzo[b]thieno[2,3-d]oxepine-2,8-dicarboxamide 179

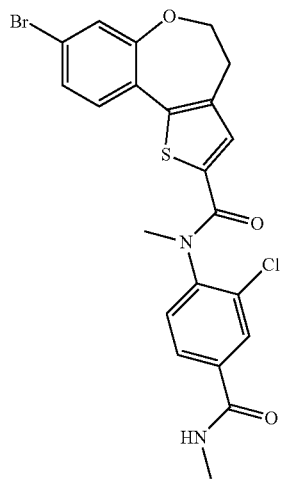 [SMILES: CNC(=O)c1ccc(N(C)C(=O)c2cc3c(s2)-c2ccc(Br)cc2OCC3)c(Cl)c1]

Following Example 91, to a solution of methyl 4-(8-bromo-N-methyl-4,5-dihydrobenzo[b]thieno[2,3-d]oxepine-2-carboxamido)-3-chlorobenzoate in tetrahydrofuran and water was added lithium hydroxide, monohydrate to give 4-(8-bromo-N-methyl-4,5-dihydrobenzo[b]thieno[2,3-d]oxepine-2-carboxamido)-3-chlorobenzoic acid, which was coupled with methylamine, HBTU, and DIEA in dichloromethane to give 8-bromo-N-(2-chloro-4-(methylcarbamoyl)phenyl)-N-methyl-4,5-dihydrobenzo[b]thieno[2,3-d]oxepine-2-carboxamide.

To a solution containing 8-bromo-N-(2-chloro-4-(methylcarbamoyl)phenyl)-N-methyl-4,5-dihydrobenzo[b]thieno[2,3-d]oxepine-2-carboxamide and methylamine in tetrahydrofuran was added molybdenumhexacarbonyl, trans-di(mu-acetato)bis[o-(di-o-tolylphosphino)benzyl]dipalladium (II). Then 1,8-diazabicyclo[5.4.0]undec-7-ene (DBU) was added and capped quickly to prevent CO gas from escaping. The reaction mixture was heated in a microwave, then diluted with EtOAc then filtered thru celite. The combined organics were dried (Na$_2$SO$_4$), filtered and concentrated. The crude was submitted for RP HPLC to give 179. MS: (ESI+) 484.1

Example 90

N-(2-chloro-4-(methylcarbamoyl)phenyl)-8-cyano-N-methyl-4,5-dihydrobenzo[b]thieno[2,3-d]oxepine-2-carboxamide 180

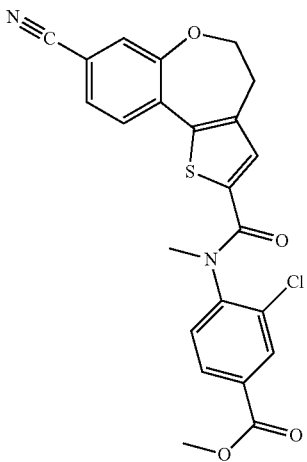 [SMILES: COC(=O)c1ccc(N(C)C(=O)c2cc3c(s2)-c2ccc(C#N)cc2OCC3)c(Cl)c1]

Following Example 53, methyl 4-(8-bromo-N-methyl-4,5-dihydrobenzo[b]thieno[2,3-d]oxepine-2-carboxamido)-3-chlorobenzoate and CuCN gave methyl chloro-4-(8-cyano-N-methyl-4,5-dihydrobenzo[b]thieno[2,3-d]oxepine-2-carboxamido)benzoate.

Following Example 91, methyl 3-chloro-4-(8-cyano-N-methyl-4,5-dihydrobenzo[b]thieno[2,3-d]oxepine-2-carboxamido)benzoate was saponified with lithium hydroxide in THF and water, then the carboxylic acid was coupled with methylamine, HBTU, DIEA in dichloromethane to give 180. MS: (ESI+) 452.1

Example 91

N2-(2-chloro-4-(4-methylpiperazine-1-carbonyl)phenyl)-N2,N8-dimethyl-4,5-dihydrobenzo[b]thieno[2,3-d]oxepine-2,8-dicarboxamide 181

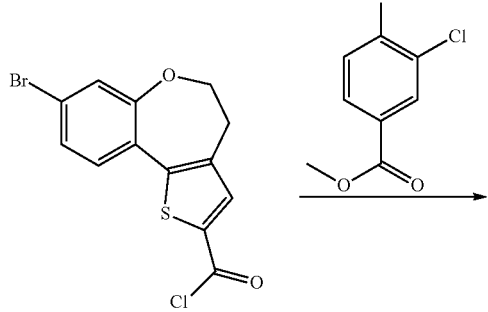

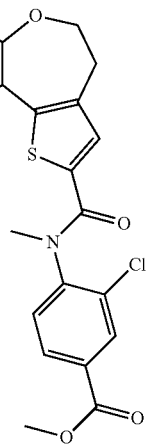

To a solution containing methyl 3-chloro-4-(methylamino)benzoate (0.184 g, 0.922 mmol) in N,N-dimethylformamide (11.0 mL, 142 mmol) was added sodium hydride (0.0369 g, 0.922 mmol). The mixture was stirred at room temperature 30 min then 8-bromo-4,5-dihydrobenzo[b]thieno[2,3-d]oxepine-2-carbonyl chloride (0.288 g, 0.838 mmol) was added. The reaction mixture was stirred for 16 hr. The reaction mixture was quenched with sat. NH4Cl, extracted with DCM (2×). The combined organics were dried (Na$_2$SO$_4$), filtered and concentrated. The crude product was purified by flash chromatography EtOAc/Hex (0-100%) to give methyl 4-(8-bromo-N-methyl-4,5-dihydrobenzo[b]thieno[2,3-d]oxepine-2-carboxamido)-3-chlorobenzoate (yield 65%). MS: (ESI+) 508.2

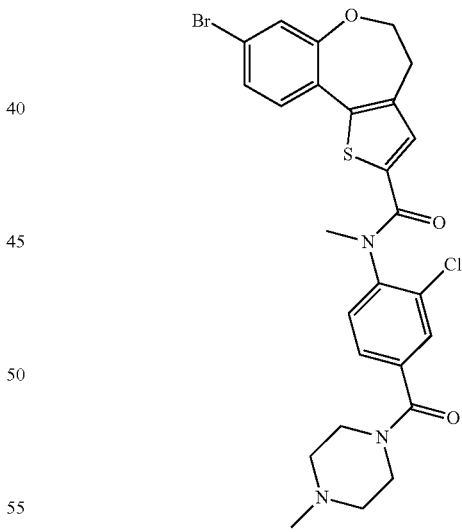

To a solution of methyl 4-(8-bromo-N-methyl-4,5-dihydrobenzo[b]thieno[2,3-d]oxepine-2-carboxamido)-3-chlorobenzoate (0.180 g, 0.355 mmol) in tetrahydrofuran (6.00 mL, 74.0 mmol) and water (6.00 mL, 333 mmol) was added lithium hydroxide, monohydrate (0.0596 g, 1.42 mmol). The reaction mixture was stirred at room temp. overnight. The reaction mixture was concentrated. The reaction mixture was acidified with 1M HCl then extracted with DCM (3×). The combined organics were dried (Na$_2$SO$_4$), filtered and concentrated to give 4-(8-bromo-N-methyl-4,5-dihydrobenzo[b]

thieno[2,3-d]oxepine-2-carboxamido)-3-chlorobenzoic acid. To a solution of 4-(8-bromo-N-methyl-4,5-dihydrobenzo[b]thieno[2,3-d]oxepine-2-carboxamido)-3-chlorobenzoic acid (175 mg, 0.355 mmol;) in methylene chloride (5.1 mL, 79 mmol) was added 1-methyl-piperazine, (0.047 mL, 0.43 mmol), N,N-diisopropylethylamine (0.618 mL, 3.55 mmol) then O-(benzotriazol-1-yl)-N,N,N',N'-tetramethyluronium hexafluorophosphate (0.269 g, 0.710 mmol). The mixture was stirred at room temp. for 2 hr. LCMS indicated the reaction was complete. The reaction was quenched with sat. NH₄Cl, extracted with DCM (2×). The combined organics were dried (Na₂SO₄), filtered and concentrated. The crude product was purified by flash chromatography (5% MeOH/DCM) to give 8-bromo-N-(2-chloro-4-(4-methylpiperazine-1-carbonyl)phenyl)-N-methyl-4,5-dihydrobenzo[b]thieno[2,3-d]oxepine-2-carboxamide (yield 82%). MS: (ESI+) 576.4

To a solution containing 8-bromo-N-(2-chloro-4-(4-methylpiperazine-1-carbonyl)phenyl)-N-methyl-4,5-dihydrobenzo[b]thieno[2,3-d]oxepine-2-carboxamide (0.075 g, 0.13 mmol) in tetrahydrofuran (1.50 mL, 18.5 mmol), 2.00 M of methylamine in tetrahydrofuran (0.196 mL) was added molybdenumhexacarbonyl (34.4 mg, 0.130 mmol), trans-di(mu-acetato)bis[o-(di-o-tolylphosphino)benzyl]dipalladium (II) (18.3 mg, 0.0196 mmol) then 1,8-diazabicyclo[5.4.0]undec-7-ene (9.75 uL, 0.0652 mmol) and capped quickly to prevent CO gas from escaping. The reaction mixture was heated in a microwave at 150° C. for 20 min. The reaction mixture was diluted with EtOAc then filtered thru celite. The combined organics were dried (Na₂SO₄), filtered and concentrated. The crude was submitted for RP HPLC to give 181 (yield 32%). MS: (ESI+) 553.2

Example 92

N-(2-chloro-4-(4-methylpiperazine-1-carbonyl)phenyl)-8-cyano-N-methyl-4,5-dihydrobenzo[b]thieno[2,3-d]oxepine-2-carboxamide 182

Following Examples 53 and 91, 8-bromo-N-(2-chloro-4-(4-methylpiperazine-1-carbonyl)phenyl)-N-methyl-4,5-dihydrobenzo[b]thieno[2,3-d]oxepine-2-carboxamide and CuCN gave 182. MS: (ESI+) 521.2

Example 93

N-(3-chloropyridin-4-yl)-N-methyl-8-(1H-pyrazol-4-yl)-4,5-dihydrobenzo[b]thieno[2,3-d]oxepine-2-carboxamide 183

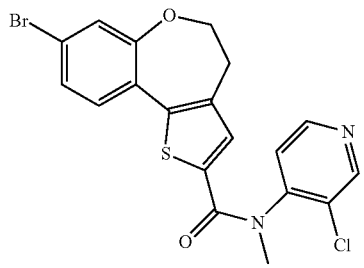 [SMILES: CN(C(=O)c1cc2c(s1)-c1ccc(Br)cc1OCC2)c1ccncc1Cl]

A solution of 8-bromo-N-methyl-(3-chloropyridin-4-yl)-4,5-dihydrobenzo[b]thieno[2,3-d]oxepine-2-carboxamide, (0.050 g, 0.100 mmol), 4,4,5,5,-tetramethyl-2-(1H-pyrazoyl-4-yl)-1,3,2-dioxaborane (0.033 g, 0.173 mmol), tetrakis(triphenylphosphine)palladium(0) 0.0133 g, 0.0115 mmol), and 1 M of sodium carbonate in water (0.2 mL, 0.2 mmol) in 1 mL of DMF was flash heated on Emry Optimizer microwave at 150° C. for 10 minutes. The reaction mix was then diluted with EtOAc and washed with water and saline, and concentrated to a solid residue, which was taken into DMF at a concentration of 100 mg/ml and purified by preparative RP-HPLC to give 183 (yield=25% of theoretical). MS: (ESI+) 437.1

Example 94

N-(3-chloropyridin-4-yl)-N-methyl-4,5-dihydrobenzo[b]thieno[2,3-d]oxepine-2-carboxamide 184

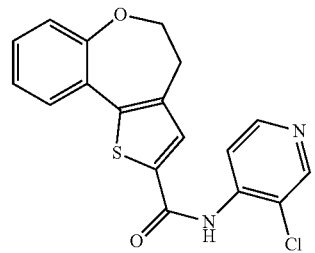 [SMILES: O=C(Nc1ccncc1Cl)c1cc2c(s1)-c1ccccc1OCC2]

Following Example 17, 4,5-dihydrobenzo[b]thieno[2,3-d]oxepine-2-carbonylchloride and 4-amino-3-chloropyridine were reacted to give N-(3-chloropyridin-4-yl)-4,5-dihydrobenzo[b]thieno[2,3-d]oxepine-2-carboxamide. To a solution of N-(3-chloropyridin-4-yl)-4,5-dihydrobenzo[b]thieno[2,3-d]oxepine-2-carboxamide (0.340 g, 0.953 mmol) in DMF (5 mL, 60 mmol) was added sodium hydride (0.0381 g, 0.953 mmol). The reaction mixture was stirred at room temperature for about 10 min. followed by the addition of methyl iodide (65.25 uL, 1.048 mmol) and stirred at room temperature for another 1 hr. An aliquot was analyzed by LC/MS showing clean conversion to desired product. The reaction mix was diluted with EtOAc and washed with water/saline, dried (Na₂SO₄) then concentrated to a residue which was analyzed by LC/MS and 1H NMR. The crude product was taken into DMF at about 100 mg/mL, but was not totally soluble. Soluble material was purified by preparative RP-HPLC to give 184 (yield 30% of theoretical). MS: (ESI+) 372.2

Example 95

N8-(2-aminoethyl)-N2-(2-chlorophenyl)-N2-methyl-4,5-dihydrobenzo[b]thieno[2,3-d]oxepine-2,8-dicarboxamide 185

Following Example 47 and General Procedure C, methyl 2-((2-chlorophenyl)(methyl)carbamoyl)-4,5-dihydrobenzo[b]thieno[2,3-d]oxepine-8-carboxylate 138 and ethanediamine gave 185. MS: (ESI+) 456.0

Alternatively, 2-((2-chlorophenyl)(methyl)carbamoyl)-4,5-dihydrobenzo[b]thieno[2,3-d]oxepine-8-carbonyl chloride and ethylene diamine gave 185. MS (ESI) 456.0

Example 96

N8-(2-acetamidoethyl)-N2-(2-chlorophenyl)-N2-methyl-4,5-dihydrobenzo[b]thieno[2,3-d]oxepine-2,8-dicarboxamide 186

Following Example 47 and General Procedure C, methyl 2-((2-chlorophenyl)(methyl)carbamoyl)-4,5-dihydrobenzo[b]thieno[2,3-d]oxepine-8-carboxylate 138 and N-acetylethanediamine gave 186. MS: (ESI+) 498.0

Alternatively, 2-((2-chlorophenyl)(methyl)carbamoyl)-4,5-dihydrobenzo[b]thieno[2,3-d]oxepine-8-carbonyl chloride and N-(2-aminoethyl)acetamide gave 186. MS (ESI) 498.0

Example 97

N2-(2-chlorophenyl)-N2-methyl-N-8-(2-(methylamino)ethyl)-4,5-dihydrobenzo[b]thieno[2,3-d]oxepine-2,8-dicarboxamide 187

Following Example 47 and General Procedure C, methyl 2-((2-chlorophenyl)(methyl)carbamoyl)-4,5-dihydrobenzo[b]thieno[2,3-d]oxepine-8-carboxylate 138 and N-methylethanediamine gave 187. MS: (ESI+) 470.1

Alternatively, 2-((2-chlorophenyl)(methyl)carbamoyl)-4,5-dihydrobenzo[b]thieno[2,3-d]oxepine-8-carbonyl chloride and N1-methylethane-1,2-diamine gave 187. MS (ESI): 470.1

Example 98

N2-(2-chlorophenyl)-N-8-methoxy-N2,N8-dimethyl-4,5-dihydrobenzo[b]thieno[2,3-d]oxepine-2,8-dicarboxamide 188

Following Example 47 and General Procedure C, methyl 2-((2-chlorophenyl)(methyl)carbamoyl)-4,5-dihydrobenzo[b]thieno[2,3-d]oxepine-8-carboxylate 138 and N,O-dimethylhydroxylamine gave 188. MS: (ESI+) 457.0

Alternatively, 2-((2-chlorophenyl)(methyl)carbamoyl)-4,5-dihydrobenzo[b]thieno[2,3-d]oxepine-8-carbonyl chloride and N,O-dimethylhydroxylamine hydrochloride gave 188. MS (ESI) 457.0

Example 99

N2-(2-chlorophenyl)-N-8-methoxy-N2-methyl-4,5-dihydrobenzo[b]thieno[2,3-d]oxepine-2,8-dicarboxamide 189

Following Example 47 and General Procedure C, methyl 2-((2-chlorophenyl)(methyl)carbamoyl)-4,5-dihydrobenzo[b]thieno[2,3-d]oxepine-8-carboxylate 138 and O-methylhydroxylamine gave 189. MS: (ESI+) 443.1

Alternatively, 2-((2-chlorophenyl)(methyl)carbamoyl)-4,5-dihydrobenzo[b]thieno[2,3-d]oxepine-8-carbonyl chloride and O-methylhydroxylamine hydrochloride gave 189. MS (ESI) 443.1

Example 100

N-(2-chlorophenyl)-8-(hydroxymethyl)-N-methyl-4,5-dihydrobenzo[b]thieno[2,3-d]oxepine-2-carboxamide 190

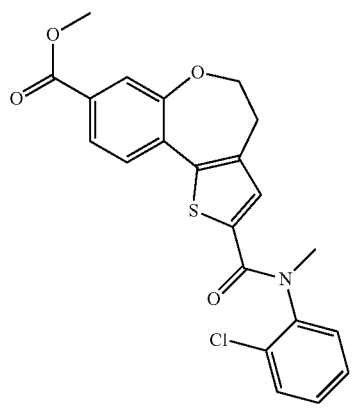 [SMILES: COC(=O)c1ccc2c(c1)OCCc1cc(C(=O)N(C)c3ccccc3Cl)sc1-2]

To a solution of 2-[(2-chloro-phenyl)-methyl-carbamoyl]-4,5-dihydro-6-oxa-1-thia-benzo[e]azulene-8-carboxylic acid methyl ester (1 g, 2.3 mmol) in dry THF (30 mL) was added lithium aluminum hydride (174 mg, 4.6 mmol) by portion at 0° C. The resulting mixture was stirred under nitrogen atmosphere for 30 minutes. The reaction was monitored by LC-MS. When the starting material was disappeared, the reaction mixture was quenched by the slow addition of water and 10% NaOH aqueous solution. After filtered, the filtrate was concentrated to the crude product, which was recrystallized from MeOH to give 190 as a yellow solid (450 mg, yield 48.9%). MS (ESI) 399.8

Example 101

N-(2-chloro-4-(1-hydroxypropan-2-ylcarbamoyl)phenyl)-N-methyl(10-aza-4,5-dihydrobenzo[b]thieno[2,3-d]oxepine)-2-carboxamide 191

Following the procedure in Example 124 for 214, methyl 3-chloro-4-(N-methyl, 10-aza, 4,5-dihydrobenzo[b]thieno[2,3-d]oxepine-2-carboxamido)benzoate and 2-aminopropan-1-ol were reacted to give 191. MS: (ESI+) 472.1

Example 102

N-(2-chloro-4-(2-hydroxypropylcarbamoyl)phenyl)-N-methyl(10-aza-4,5-dihydrobenzo[b]thieno[2,3-d]oxepine)-2-carboxamide 192

Following the procedure in Example 124 for 214, methyl 3-chloro-4-(N-methyl, 10-aza, 4,5-dihydrobenzo[b]thieno[2,3-d]oxepine-2-carboxamido)benzoate and 1-aminopropan-2-01 were reacted to give 192. MS: (ESI+) 472.1

Example 103

N-(2-chloro-4-(piperazine-1-carbonyl)phenyl)-N-methyl(10-aza-4,5-dihydrobenzo[b]thieno[2,3-d]oxepine)-2-carboxamide 193

Following the procedure in Example 124 for 214, methyl 3-chloro-4-(N-methyl, 10-aza, 4,5-dihydrobenzo[b]thieno[2,3-d]oxepine-2-carboxamido)benzoate and piperazine were reacted to give 193. MS: (ESI+) 483.2

Example 104

N8-(3-(1H-imidazol-1-yl)propyl)-N2-(2-chlorophenyl)-N-2-methyl-4,5-dihydrobenzo[b]thieno[2,3-d]oxepine-2,8-dicarboxamide 194

Following Example 47 and General Procedure C, methyl 2-((2-chlorophenyl)(methyl)carbamoyl)-4,5-dihydrobenzo[b]thieno[2,3-d]oxepine-8-carboxylate 138 and 2-(imidazol-1-yl)-ethylamine gave 194. MS: (ESI+) 520.8

Alternatively, 2-((2-chlorophenyl)(methyl)carbamoyl)-4,5-dihydrobenzo[b]thieno[2,3-d]oxepine-8-carbonyl chloride and 3-(1H-imidazol-1-yl)propan-1-amine gave 194. MS (ESI) 520.8

Example 105

N8-(2-amino-2-methylpropyl)-N2-(2-chlorophenyl)-N2-methyl-4,5-dihydrobenzo[b]thieno[2,3-d]oxepine-2,8-dicarboxamide 195

Following Example 47 and General Procedure C, methyl 2-((2-chlorophenyl)(methyl)carbamoyl)-4,5-dihydrobenzo

[b]thieno[2,3-d]oxepine-8-carboxylate 138 and 3-methyl-1,3-butanediamine gave 195. MS: (ESI+) 484.1

Alternatively, 2-((2-chlorophenyl)(methyl)carbamoyl)-4,5-dihydrobenzo[b]thieno[2,3-d]oxepine-8-carbonyl chloride and 2-methylpropane-1,2-diamine gave 195. MS (ESI): 484.1

Example 106

8-(3-(aminomethyl)phenyl)-N-(2-chlorophenyl)-N-methyl-4,5-dihydrobenzo[b]thieno[2,3-d]oxepine-2-carboxamide 196

Following the procedure of Example 93, Suzuki coupling of 8-bromo-N-(2-chlorophenyl)-N-methyl-4,5-dihydrobenzo[b]thieno[2,3-d]oxepine-2-carboxamide 150 and (3-aminophenyl)boronic acid gave 196.

Example 107

N-(2-chlorophenyl)-8-(2-(dimethylamino)ethylamino)methyl)-N-methyl-4,5-dihydrobenzo[b]thieno[2,3-d]oxepine-2-carboxamide 197

8-(Bromomethyl)-N-(2-chlorophenyl)-N-methyl-4,5-dihydrobenzo[b]thieno[2,3-d]oxepine-2-carboxamide was reacted with N1,N1-dimethylethane-1,2-diamine using the procedure of Example 153 to give 197.

Example 108

2-(3-(2-((2-chlorophenyl)(methyl)carbamoyl)-4,5-dihydrobenzo[b]thieno[2,3-d]oxepin-8-yl)phenyl)acetic acid 198

Methyl 2-(3-(2-((2-chlorophenyl)(methyl)carbamoyl)-4,5-dihydrobenzo[b]thieno[2,3-d]oxepin-8-yl)phenyl)acetate 200 was treated with lithium hydroxide in THF and water to give 198. MS: (ESI+) 503.7

Example 109

N-(2-chlorophenyl)-8-(3-cyanophenyl)-N-methyl-4,5-dihydrobenzo[b]thieno[2,3-d]oxepine-2-carboxamide 199

Following the procedure of Example 93, Suzuki coupling of 8-bromo-N-(2-chlorophenyl)-N-methyl-4,5-dihydrobenzo[b]thieno[2,3-d]oxepine-2-carboxamide 150 and 3-cyanophenylboronic acid gave 199. MS: (ESI+) 471.1

Example 110 methyl 2-(3-(2-((2-chlorophenyl)(methyl)carbamoyl)-4,5-dihydrobenzo[b]thieno[2,3-d]oxepin-8-yl)phenyl)acetate 200

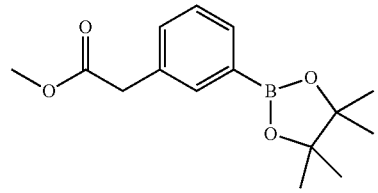

Following the procedure of Example 93, 8-bromo-N-(2-chlorophenyl)-N-methyl-4,5-dihydrobenzo[b]thieno[2,3-d]oxepine-2-carboxamide 150, methyl 2-(3-(4,4,5,5-tetramethyl-1,3,2-dioxaborolan-2-yl)phenyl)acetate, potassium acetate, and Pd(dppf)Cl$_2$ in acetonitrile and DMSO were heated at 80° C. overnight to give 200. MS: (ESI+) 518.2

Example 111

N-(2-chlorophenyl)-8-(3-(hydroxymethyl)phenyl)-N-methyl-4,5-dihydrobenzo[b]thieno[2,3-d]oxepine-2-carboxamide 201

Following the procedure of Example 93, 8-bromo-N-(2-chlorophenyl)-N-methyl-4,5-dihydrobenzo[b]thieno[2,3-d]oxepine-2-carboxamide 150 and 3-hydroxymethylphenylboronic acid were reacted to give 201. MS: (ESI+) 476.16

Example 112

N-(2-chlorophenyl)-N-methyl-8-(4-methylpiperazine-1-carbonyl)-4,5-dihydrobenzo[b]thieno[2,3-d]oxepine-2-carboxamide 202

Following Example 47 and General Procedure C, methyl 2-((2-chlorophenyl)(methyl)carbamoyl)-4,5-dihydrobenzo[b]thieno[2,3-d]oxepine-8-carboxylate 138 and N-methylpiperazine gave 202. MS: (ESI+) 496.2

Alternatively, 2-((2-chlorophenyl)(methyl)carbamoyl)-4,5-dihydrobenzo[b]thieno[2,3-d]oxepine-8-carbonyl chloride and 1-methylpiperazine gave 202. MS (ESI) 496.2

Example 113

N2-(2-chlorophenyl)-N2-methyl-N-8-(2-(4-methylpiperazin-1-yl)ethyl)-4,5-dihydrobenzo[b]thieno[2,3-d]oxepine-2,8-dicarboxamide 203

Following Example 47 and General Procedure C, methyl 2-((2-chlorophenyl)(methyl)carbamoyl)-4,5-dihydrobenzo[b]thieno[2,3-d]oxepine-8-carboxylate 138 and 1-(N-aminoethyl)-4-methyl piperazine gave 203. MS: (ESI+) 539.2

Alternatively, 2-((2-chlorophenyl)(methyl)carbamoyl)-4,5-dihydrobenzo[b]thieno[2,3-d]oxepine-8-carbonyl chloride and 2-(4-methylpiperazin-1-yl)ethanamine gave 203. MS (ESI) 539.2

Example 114

N2-(2-chlorophenyl)-N-8-(2-(dimethylamino)ethyl)-N2-methyl-4,5-dihydrobenzo[b]thieno[2,3-d]oxepine-2,8-dicarboxamide 204

Following Example 47 and General Procedure C, methyl 2-((2-chlorophenyl)(methyl)carbamoyl)-4,5-dihydrobenzo[b]thieno[2,3-d]oxepine-8-carboxylate 138 and N,N'-dimethylethanediamine gave 204. MS: (ESI+) 484.0

Alternatively, 2-((2-chlorophenyl)(methyl)carbamoyl)-4,5-dihydrobenzo[b]thieno[2,3-d]oxepine-8-carbonyl chloride and N1,N1-dimethylethane-1,2-diamine gave 204. MS (ESI) 484.0

Example 115

N2-(2-chlorophenyl)-N-8-isopropyl-N2-methyl-4,5-dihydrobenzo[b]thieno[2,3-d]oxepine-2,8-dicarboxamide 205

Following Example 47 and General Procedure C, methyl 2-((2-chlorophenyl)(methyl)carbamoyl)-4,5-dihydrobenzo[b]thieno[2,3-d]oxepine-8-carboxylate 138 and isopropylamine gave 205. MS: (ESI+) 455.0

Alternatively, 2-((2-chlorophenyl)(methyl)carbamoyl)-4,5-dihydrobenzo[b]thieno[2,3-d]oxepine-8-carbonyl chloride and isopropylamine gave 205. MS (ESI) 455.0

Example 116

N2-(2-chlorophenyl)-N-8-ethyl-N2-methyl-4,5-dihydrobenzo[b]thieno[2,3-d]oxepine-2,8-dicarboxamide 206

Following Example 47 and General Procedure C, methyl 2-((2-chlorophenyl)(methyl)carbamoyl)-4,5-dihydrobenzo[b]thieno[2,3-d]oxepine-8-carboxylate 138 and ethylamine gave 206. MS: (ESI+) 441.0

Example 117

N-(3-chloropyridin-2-yl)-N-methyl-4,5-dihydrobenzo[b]thieno[2,3-d]oxepine-2-carboxamide 207

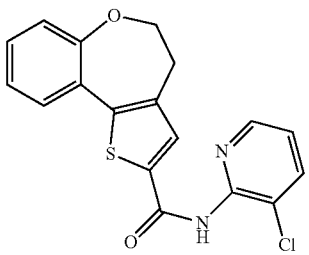 [SMILES: O=C(Nc1ncccc1Cl)c1cc2c(s1)-c1ccccc1OCC2]

An ice water cooled solution of 2-amino-3-chloropyridine (0.200 g, 0.755 mmol) in tetrahydrofuran (1.5 mL, 18 mmol) was reacted with a THF solution of 1 M sodium hexamethyldisilazane to give a clear solution. This reaction mix was stirred at cooled temperature for 30 minutes. Next, 4,5-dihydrobenzo[b]thieno[2,3-d]oxepine-2-carbonylchloride (0.100 g, 0.378 mmol) was added portionwise as a solid. Reaction mix was stirred at room temperature with monitor for formation of desired product and concentrated in vacuo to a solid residue. This residue was taken into ethyl acetate and the organic was washed with water, then saline and dried (Na$_2$SO$_4$). The crude material was purified by MPLC on silica, eluting with 10% to 80% ethyl acetate/hexanes to give 128 mg N-(3-chloropyridin-2-yl)-4,5-dihydrobenzo[b]thieno[2,3-d]oxepine-2-carboxamide, 34% of theoretical yield.

To a solution of N-(3-chloropyridin-2-yl)-4,5-dihydrobenzo[b]thieno[2,3-d]oxepine-2-carboxamide in acetonitrile (0.702 ml) was added hexamethyldisilazane (0.029 ml, 0.140 mmol) and heated at reflux for 3 hours. Chloro(chloromethyl)dimethylsilane (0.029 ml, 0.224 mmol) was added to the refluxing solution drop-wise and the reaction mixture was refluxed overnight. Next, the reaction mixture was equilibrated to room temperature and concentrated to a solid residue. This solid was taken into diglyme (2 ml, 10 mmol) and treated with cesium fluoride (0.21 g, 1.4 mmol) at reflux for 3 hours. The reaction mixture was cooled to room temperature and diluted with water and ethyl acetate. The organic was separated from the aqueous in a separatory funnel. The organic was washed with saline, dried (Na$_2$SO$_4$) and concentrated to a solid. This crude material was taken into methanol at 100 mg/ml and purified by RP-HPLC to give 24 mg of 207, 29% of theoretical yield. MS: (ESI+) 371.1

Example 118

N-methyl-N-(4-(trifluoromethyl)pyridin-3-yl)-4,5-dihydrobenzo[b]thieno[2,3-d]oxepine-2-carboxamide 208

Following Example X to prepare 207, 4,5-dihydrobenzo[b]thieno[2,3-d]oxepine-2-carbonylchloride and 3-amino-4-trifluoromethylpyridine were reacted, followed by methylation to give 208 (yield 8% of theoretical). MS: (ESI+) 344.1

Example 119

3-chloro-4-(3-(4,5-dihydrobenzo[b]thieno[2,3-d]oxepin-2-yl)-4H-1,2,4-triazol-4-yl)-N-methylbenzamide 209

3-Chloro-4-(3-(4,5-dihydrobenzo[b]thieno[2,3-d]oxepin-2-yl)-4H-1,2,4-triazol-4-yl)benzoic acid and methylamine were reacted by a procedure similar to that to prepare 137 in Example 47 to give 209. MS: (ESI+) 437.1

Example 120

N-(2-chlorophenyl)-8-(2-(dimethylamino)acetamido)-N-methyl-4,5-dihydrobenzo[b]thieno[2,3-d]oxepine-2-carboxamide 210

Following the procedure in Example 147 for the synthesis of 237, 8-(2-chloroacetamido)-N-(2-chlorophenyl)-N-methyl-4,5-dihydrobenzo[b]thieno[2,3-d]oxepine-2-carboxamide was reacted with dimethylamine to give 210. MS: (ESI+) 470.2

Example 121

8-(2-acetamidoacetamido)-N-(2-chlorophenyl)-N-methyl-4,5-dihydrobenzo[b]thieno[2,3-d]oxepine-2-carboxamide 211

Following the procedure in Example 147 for 237, 8-(2-chloroacetamido)-N-(2-chlorophenyl)-N-methyl-4,5-dihydro-benzo[b]thieno[2,3-d]oxepine-2-carboxamide and acetamide were reacted to give 211. MS: (ESI+) 484.1

Example 122

3-(8-(1H-pyrazol-4-yl)-4,5-dihydrobenzo[b]thieno[2,3-d]oxepin-2-yl)-4,5-dihydro-1,2,4-triazin-6(1H)-one 212

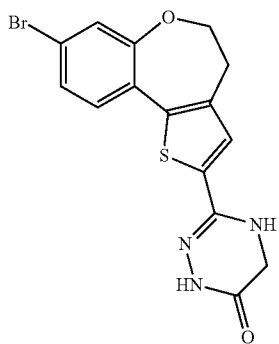 [SMILES: O=C1CNC(c2cc3c(s2)-c2ccc(Br)cc2OCC3)=NN1]

Following the procedure in Example 44 for 134, 3-(8-bromo-4,5-dihydrobenzo[b]thieno[2,3-d]oxepin-2-yl)-4,5-dihydro-1,2,4-triazin-6(1H)-one and 4-(4,4,5,5-tetramethyl-1,3,2-dioxaborolan-2-yl)-1H-pyrazole were reacted to give 212. MS: (ESI+) 366.2

Example 123

N-(2-chloro-4-(methylcarbamoyl)phenyl)-N-methyl (10-aza, 4,5-dihydrobenzo[b]thieno[2,3-d]oxepine-2-carboxamide 213

Following the procedure in Example 124 for 214, methyl 3-chloro-4-(N-methyl, 10-aza, 4,5-dihydrobenzo[b]thieno[2,3-d]oxepine-2-carboxamido)benzoate and methylamine were reacted to give 213. MS: (ESI+) 428.1

Example 124

N-(2-chloro-4-(dimethylcarbamoyl)phenyl)-N-methyl(10-aza, 4,5-dihydrobenzo[b]thieno[2,3-d]oxepine)-2-carboxamide 214

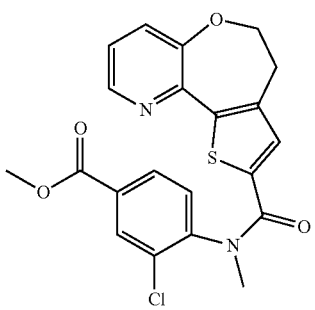 [SMILES: COC(=O)c1ccc(N(C)C(=O)c2cc3c(s2)-c2ncccc2OCC3)c(Cl)c1]

To a solution of 10-aza-4,5-dihydrobenzo[b]thieno[2,3-d]oxepine-2-carboxylic acid 16 from Example 10 (0.350 g, 1.42 mmol;) in methylene chloride (3.68 mL, 57.4 mmol) was added thionyl chloride (0.310 mL, 4.25 mmol;). The mixture was stirred at 80° C. for 2 h. The reaction mixture was concentrated in vacuo. The crude acid chloride (0.424 g, 2.12 mmol) was dissolved in tetrahydrofuran (10.4 mL, 129 mmol;) and 1.00 M of sodium bis(trimethylsilyl)amide in tetrahydrofuran (2.12 mL) was added. The reaction mixture was stirred at room temperature 1 h then methyl 3-chloro-4-(methylamino)benzoate was added at 0° C. The reaction mixture was stirred overnight, quenched with sat. NH$_4$Cl, and extracted with DCM (2×). The combined organics were dried (Na$_2$SO$_4$), filtered and concentrated. The crude product was purified by flash chromatography EtOAc/Hex (0-100%) (eluted 70% EtOAc) to give methyl 3-chloro-4-(N-methyl, 10-aza, 4,5-dihydrobenzo[b]thieno[2,3-d]oxepine-2-carboxamido)benzoate (yield 77%). MS: (ESI+) 430.0

The methyl ester of methyl 3-chloro-4-(N-methyl, 10-aza, 4,5-dihydrobenzo[b]thieno[2,3-d]oxepine-2-carboxamido)benzoate was hydrolyzed and the resulting acid (53.0 mg, 0.128 mmol;) was dissolved in methylene chloride (1.8 mL, 28 mmol). Dimethylamine hydrochloride (0.0208 g, 0.256 mmol), N,N-diisopropylethylamine (0.222 mL, 1.28 mmol) and N,N,N',N'-tetramethyl-O-(7-azabenzotriazol-1-yl)uronium hexafluorophosphate (0.0972 g, 0.256 mmol) were added. The mixture was stirred at room temperature for 2 h whereupon LCMS indicated the reaction was complete. The reaction was quenched with sat. NH$_4$Cl and extracted with DCM (2×). The combined organics were dried (Na$_2$SO$_4$), filtered and concentrated. The crude product was purified by flash chromatography (MeOH/DCM) (eluted at 5% MeOH) to give 214 (yield 88%). MS: (ESI+) 442.1

Example 125

N-(2-chloro-4-(4-methylpiperazine-1-carbonyl)phenyl)-N-methyl(10-aza-4,5-dihydrobenzo[b]thieno[2,3-d]oxepine)-2-carboxamide 215

Following the procedure in Example 124 for 214, methyl 3-chloro-4-(N-methyl, 10-aza, 4,5-dihydrobenzo[b]thieno[2,3-d]oxepine-2-carboxamido)benzoate and 1-methypiperazine were reacted to give 215. MS: (ESI+) 497.2

Example 126

2-(2-amino-5-(2-chlorophenyl)thiazol-4-yl)-N-methyl-4,5-dihydrobenzo[b]thieno[2,3-d]oxepine-8-carboxamide 216

Following the procedure of Example 13 and General Procedure C, 4-(8-bromo-4,5-dihydrobenzo[b]thieno[2,3-d]oxepin-2-yl)-5-(2-chlorophenyl)thiazol-2-amine 271 and methylamine (1.0 M in tetrahydrofuran) gave 216. MS: (ESI+) 468.1

Example 127

2-(4-(2-chlorophenyl)-5-methyl-4H-1,2,4-triazol-3-yl)-N-methyl-4,5-dihydrobenzo[b]thieno[2,3-d]oxepine-8-carboxamide 217

Following the procedure of Example 13 and General Procedure C, 3-(8-bromo-4,5-dihydrobenzo[b]thieno[2,3-d]oxepin-2-yl)-4-(2-chlorophenyl)-5-methyl-4H-1,2,4-triazole and methylamine (1.0 M in tetrahydrofuran) gave 217. MS: (ESI+) 451.1

Example 128

(4,5-dihydrobenzo[b]thieno[2,3-d]oxepin-2-yl)(3,4-dihydroquinolin-1(2H)-yl)methanone 218

To a solution of 1,2,3,4-tetrahydroquinoline (0.755 mmol) and triethylamine (0.105 mL, 0.755 mmol) in tetrahydrofuran (1.5 mL, 18 mmol) was added 4,5-dihydrobenzo[b]thieno[2,3-d]oxepine-2-carbonylchloride (0.100 g, 0.378 mmol) portionwise as a solid. Reaction was stirred at room temperature with monitor for formation of desired product. The reaction was stirred overnight. After aqueous workup, the crude was taken into DMF at a concentrated of 100 mg/ml and purified by preparative RP-HPLC to give 218 (yield 80% of theoretical). MS: (ESI+) 362.2

Example 129

N-methyl-N-(4-(trifluoromethyl)pyridin-3-yl)-4,5-dihydrobenzo[b]thieno[2,3-d]oxepine-2-carboxamide 219

Following Example 117 to prepare 207, 4,5-dihydrobenzo[b]thieno[2,3-d]oxepine-2-carbonylchloride and 3-amino-4-chloropyridine were reacted, followed by methylation to give 219 (yield 29% of theoretical). MS: (ESI+) 371.2

Example 130

N-(2-chloro-4-(dimethylcarbamoyl)phenyl)-N-(2-hydroxyethyl)-4,5-dihydrobenzo[b]thieno[2,3-d]oxepine-2-carboxamide 220

Following the procedure of Example 91, 3-chloro-4-(N-(2-hydroxyethyl)-4,5-dihydrobenzo[b]thieno[2,3-d]oxepine-2-carboxamido)benzoic acid and dimethylamine were reacted to give 220 (yield 50%). MS: (ESI+) 471.1

Example 131

N-methyl-N-(4-(trifluoromethyl)pyridin-3-yl)-4,5-dihydrobenzo[b]thieno[2,3-d]oxepine-2-carboxamide 221

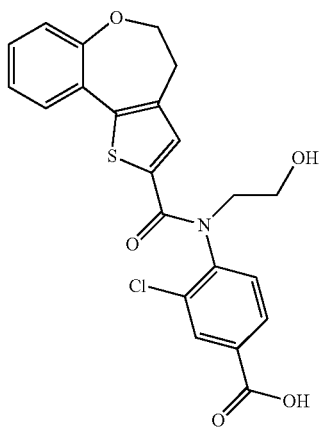 [SMILES: O=C(O)c1ccc(N(CCO)C(=O)c2cc3c(s2)-c2ccccc2OCC3)c(Cl)c1]

Following Example 91, 3-chloro-4-(N-(2-hydroxyethyl)-4,5-dihydrobenzo[b]thieno[2,3-d]oxepine-2-carboxamido) benzoic acid and 1-methylpiperazine were reacted to give 221 (yield 30%). MS: (ESI+) 526.2

Example 132

N2-(2-chloro-4-(piperazine-1-carbonyl)phenyl)-N2,N8-dimethyl-4,5-dihydrobenzo[b]thieno[2,3-d]oxepine-2,8-dicarboxamide 222

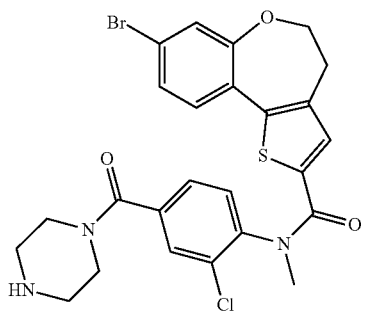 [SMILES: CN(C(=O)c1cc2c(s1)-c1ccc(Br)cc1OCC2)c1ccc(C(=O)N2CCNCC2)cc1Cl]

Following the procedure of Example 91 to prepare 181, 8-bromo-N-(2-chloro-4-(piperazine-1-carbonyl)phenyl)-N-methyl-4,5-dihydrobenzo[b]thieno[2,3-d]oxepine-2-carboxamide and methylamine were reacted to give 222. MS: (ESI+) 539.2

Example 133

N2-(2-chloro-4-(dimethylcarbamoyl)phenyl)-N2,N8-dimethyl-4,5-dihydrobenzo[b]thieno[2,3-d]oxepine-2,8-dicarboxamide 223

Following the procedure of Example 91 to prepare 181, 8-bromo-N-(2-chloro-4-(dimethylcarbamoyl)phenyl)-N-methyl-4,5-dihydrobenzo[b]thieno[2,3-d]oxepine-2-carboxamide, methylamine, and molybdenumhexacarbonyl under palladium catalysis were reacted to give 223. MS: (ESI+) 498.1.

Step 1: Preparation of 4-amino-3-chloro-N,N-dimethylbenzamide

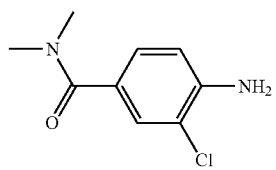

DIPEA (116 mL, 699.5 mmol) was added into a suspension of dimethylamine hydrochloride (28.51 g, 349.6 mmol) in THF (600 mL). The mixture was stirred at room temperature for 0.5 h. Then 4-amino-3-chlorobenzoic acid (30.00 g, 174.8 mmol) and HATU (86.41 g, 227.2 mmol) were added into the above suspension separately. The reaction mixture was continued to be stirred for 1.5 h. Then it was concentrated and the residue was partitioned between EtOAc (300 mL) and water (150 mL). The separated organic phase was washed with water, dried over $Na_2SO_4$ and evaporated in vacuum. The crude product was purified by silica gel chromatography, eluted with Hexanes: EtOAc=1:1 to afford 4-amino-3-chloro-N,N-dimethylbenzamide (34.72 g, yield: 89%). ESI-MS: 199.06. ¹H NMR (CDCl₃, 400 MHz): 0.39 (s, 1H, ArH), 7.19 (d, J=8.4 Hz, 1H, ArH), 6.74 (d, J=8.4 Hz, 1H, ArH), 4.24 (br, 2H, NH₂), 3.05 (s, 6H, 2CH₃).

Step 2: Preparation of 8-bromo-N-(2-chloro-4-(dimethylcarbamoyl)phenyl)-4,5-dihydro-benzo[b]thieno[2,3-d]oxepine-2-carboxamide

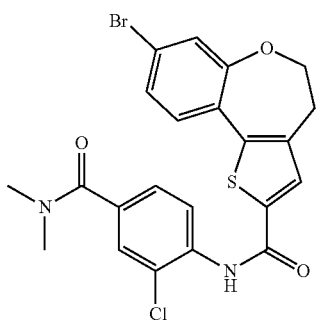 [SMILES: CN(C)C(=O)c1ccc(NC(=O)c2cc3c(s2)-c2ccc(Br)cc2OCC3)c(Cl)c1]

A solution of 8-bromo-4,5-dihydrobenzo[b]thieno[2,3-d]oxepine-2-carboxylic acid (25.00 g, 76.9 mmol) in SOCl₂ (200 mL) was heated at 90-100° C. for 3 h. Concentration of the reaction mixture gave the crude acid chloride. A suspension of the acid chloride in THF (600 mL) was treated with a solution of 4-amino-3-chloro-N,N-dimethylbenzamide (18.23 g, 92.3 mmol) and pyridine (14 mL) in THF (200 mL) at 0° C. The mixture was allowed to reach room temperature and stirred overnight. After concentration, water (200 mL) was added into the mixture. The resulting precipitate was collected by filtration, washed with water and dried to give 8-bromo-N-(2-chloro-4-(dimethylcarbamoyl)phenyl)-4,5-dihydro-benzo[b]thieno[2,3-d]oxepine-2-carboxamide (29.88 g, yield: 77%). ESI-MS: 504.99. ¹H NMR (DMSO-d₆, 400 MHz): 610.14 (s, 1H, NH), 7.86 (s, 1H, ArH), 7.67-7.57 (m, 3H, ArH), 7.40-7.25 (m, 3H, ArH), 4.32 (t, J=5.2 Hz, 2H, CH₂), 3.21 (t, J=5.2 Hz, 2H, CH₂), 2.95 (s, 3H, CH₃), 2.92 (s, 3H, CH₃).

Step 3: Preparation of 8-bromo-N-(2-chloro-4-(dimethylcarbamoyl)phenyl)-N-methyl-4,5-dihydrobenzo[b]thieno[2,3-d]oxepine-2-carboxamide (5)

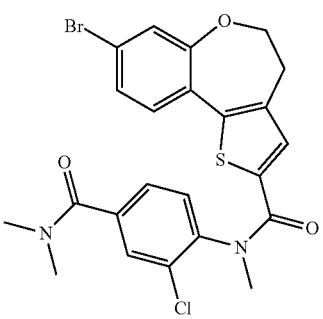 [SMILES: CN(C)C(=O)c1ccc(N(C)C(=O)c2cc3c(s2)-c2ccc(Br)cc2OCC3)c(Cl)c1]

To solution of 8-bromo-N-(2-chloro-4-(dimethylcarbamoyl)phenyl)-4,5-dihydro-benzo[b]thieno[2,3-d]oxepine-2-carboxamide (29.0 g, 57.3 mmol), Cs₂CO₃ (37.40 g, 114.7 mmol) in DMF (600 mL), CH₃I (30 mL, 479.8 mmol) was slowly added. The reaction mixture was stirred at room temperature overnight. Concentration removed about 200 mL of DMF, and then water (100 mL) was added to the mixture. The resulting precipitate was filtered, washed with water, dried to give 8-bromo-N-(2-chloro-4-(dimethylcarbamoyl)phenyl)-N-methyl-4,5-dihydrobenzo[b]thieno[2,3-d]oxepine-2-carboxamide (29.50 g, yield: 99%). ESI-MS: 519.4. ¹H NMR (DMSO-d₆, 400 MHz): δ7.72-7.68 (m, 2H, ArH), 7.52-7.49 (m, 1H, ArH), 7.30-7.20 (m, 3H, ArH), 6.76 (s, 1H, =CH), 4.19 (s, 2H, CH₂), 3.29 (s, 3H, CH₃), 3.00 (s, 3H, CH₃), 2.96 (s, 2H, CH₂), 2.93 (s, 3H, CH₃).

Step 4: Preparation of methyl 2-((2-chloro-4-(dimethylcarbamoyl)phenyl)(methyl)-carbamoyl)-4,5-dihydrobenzo[b]thieno[2,3-d]oxepine-8-carboxylate

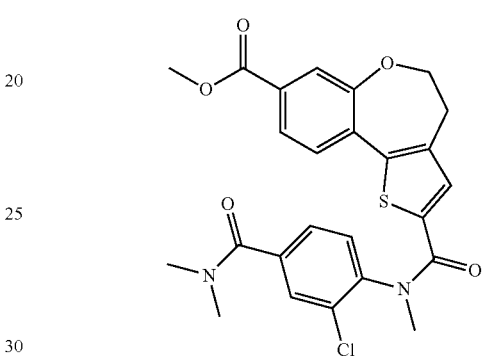

The mixture of 8-bromo-N-(2-chloro-4-(dimethylcarbamoyl)phenyl)-N-methyl-4,5-dihydrobenzo[b]thieno[2,3-d]oxepine-2-carboxamide (27.0 g, 51.9 mmol), dppf (23.20 g, 41.9 mmol), Pd(OAc)₂ (5.8 g, 25.8 mmol), TEA (27 mL), in DMF (270 mL) and MeOH (400 mL) was stirred under CO (50 psi) atmosphere at 70° C. for 2 days. The reaction mixture was filtrated and the filtrate was concentrated. The crude product was purified by silica gel chromatography eluted with Hexanes: EtOAc=1:1 to give methyl 2-((2-chloro-4-(dimethylcarbamoyl)phenyl)(methyl)-carbamoyl)-4,5-dihydrobenzo[b]thieno[2,3-d]oxepine-8-carboxylate (23.00 g, 89%). ESI-MS: 499.1. ¹H NMR (DMSO-d₆, 400 MHz): δ7.74-7.69 (m, 2H, ArH), 7.58-7.47 (m, 4H, ArH), 6.79 (s, 1H, =CH), 4.23 (t, J=4.8 Hz, 2H, CH₂), 3.83 (s, 3H, CH₃), 3.31 (s, 3H, CH₃), 3.01 (br, 5H, CH₂, CH₃), 2.94 (s, 3H, CH₃).

Step 5: Preparation of 2-((2-chloro-4-(dimethylcarbamoyl)phenyl)(methyl)carbamoyl)-4,5-dihydrobenzo[b]thieno[2,3-d]oxepine-8-carboxylic acid

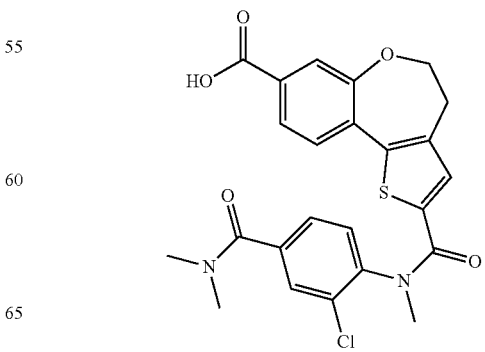

Methyl 2-((2-chloro-4-(dimethylcarbamoyl)phenyl)(methyl)-carbamoyl)-4,5-dihydrobenzo[b]thieno[2,3-d]oxepine-8-carboxylate (25.00 g, 50.1 mmol) was dissolved in THF (50 mL) and water (50 mL). The solution was treated with LiOH.H$_2$O (5.26 g, 125.3 mmol). The reaction mixture was stirred at room temperature for 2 h. Concentrated to remove the solvent THF and the mixture was acidified by 2N HCl. The resulting precipitate was filtrated, washed by water, dried to give 2-((2-chloro-4-(dimethylcarbamoyl)phenyl)(methyl)carbamoyl)-4,5-dihydrobenzo[b]thieno[2,3-d]oxepine-8-carboxylic acid (20.00 g, 82%). ESI-MS: 485.1. $^1$H NMR (CDCl$_3$, 400 MHz): δ7.66-7.60 (m, 3H, ArH), 7.46-7.42 (m, 3H, ArH), 6.99 (s, 1H, =CH), 4.23 (t, J=5.0 Hz, 2H, CH$_2$), 3.39 (s, 3H, CH$_3$), 3.14 (s, 3H, CH$_3$), 3.07 (t, J=5.0 Hz, 2H, CH$_2$), 3.02 (s, 3H, CH$_3$).

Step 6: Preparation of N$^2$-(2-chloro-4-(dimethylcarbamoyl)phenyl)-N$^2$,N$^8$-dimethyl-4,5-dihydrobenzo[b]thieno[2,3-d]oxepine-2,8-dicarboxamide 223

DIPEA (16.83 g, 130.2 mmol) was added to a suspension of H$_2$NMe.HCl (5.02 g, 74.4 mmol) in THF (180 mL) and stirred at room temperature for 0.5 h. 2-((2-Chloro-4-(dimethylcarbamoyl)phenyl)(methyl) carbamoyl)-4,5-dihydrobenzo[b]thieno[2,3-d]oxepine-8-carboxylic aci (9.00 g, 18.6 mmol) and HATU (21.22 g, 55.8 mmol) were added into the suspension separately. The reaction mixture was stirred at room temperature for 2 h. Concentrated to remove solvent, the resulting mixture was dissolved in CH$_2$Cl$_2$ (200 mL), washed by 2N HCl (200 mL), water (100 mL), and dried over Na$_2$SO$_4$. The crude product was purified by silica gel chromatography eluted with CH$_2$Cl$_2$:MeOH=10:1 (3.70 g, 40%) to furnish 223. ESI-MS: 498. $^1$H NMR (CDCl$_3$, 400 MHz): δ7.58 (s, 1H, ArH), 7.42-7.29 (m, 4H, ArH), 6.92 (s, 1H, ArH), 6.34 (d, J=4.0 Hz, 1H, NH), 4.20 (t, J=5.0 Hz, 2H, CH$_2$), 3.37 (s, 3H, CH$_3$), 3.12 (s, 3H, CH$_3$), 3.04-2.98 (m, 8H, CH$_2$, 2CH$_3$).

Example 134

3-(8-bromo-4,5-dihydrobenzo[b]thieno[2,3-d]oxepin-2-yl)-4-isopropyl-4H-1,2,4-triazole 224

To a solution of in 8-bromo-N-isopropyl-4,5-dihydrobenzo[b]thieno[2,3-d]oxepine-2-carboxamide (180 mg, 0.49 mmol) in 5 mL toluene was added phosphorus pentachloride (0.184 g, 0.88 mmol) under nitrogen and the reaction mixture was heated at 80° C. for 2 h. The mixture was cooled and carefully concentrated. The crude residue was dissolved in 10 mL THF and treated sequentially with formyl hydrazine (118 mg, 2.0 mmol) and potassium carbonate (0.340 g, 2.46 mmol). The mixture was stirred overnight at room temperature, diluted with water and extracted with ethyl acetate. The combined organics were washed with brine, dried over sodium sulfate and concentrated. The crude residue was dissolved in toluene (10 mL) and treated with p-toluenesulfonic acid (15 mg, 0.087 mmol). The whole was sealed and heated at 90° C. for 15 min. The reaction mixture was cooled to room temperature, concentrated, diluted with ethyl acetate and washed with water, sodium bicarbonate and brine. The organics were dried over sodium sulfate and concentrated to give 224 as the crude product which could be used without purification in subsequent operations. A small amount was purified by reverse-phase HPLC for analytical purposes. $^1$H NMR (dmso-d$_6$, 400 MHz) δ 11.9 8.84 (s, 1H), 7.65 (d, 1H), 7.45 (s, 1H), 7.32-7.27 (m, 2H), 4.75 (m, 1H), 4.34 (t, 2H), 3.25 (t, 2H), 1.48 (d, 6H). MS (ESI) 392.1

Example 135

3-(4,5-dihydrobenzo[b]thieno[2,3-d]oxepin-2-yl)-4-(1-methylpiperidin-4-yl)-1H-1,2,4-triazol-5(4H)-one 225

Prepared from N-(1-methylpiperidin-4-yl)-4,5-dihydrobenzo[b]thieno[2,3-d]oxepine-2-carboxamide to give 225 using a procedure similar to that described in Example 175. MS (ESI) 383.2

Example 136

4,5-dihydro-6-oxa-3-thia-1-aza-benzo[e]azulene-2-carboxylic acid (2-chloro-phenyl)-methyl-amide 226

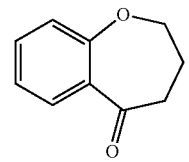 [SMILES: O=C1CCCOc2ccccc21]

To a solution of phenol (3.16 g, 33.6 mmol) in acetonitrile, was added ethyl 4-bromobutyrate (4.8 ml, 33.6 mmol), potassium carbonate (4.64 g, 33.6 mmol) and tetrabutylammonium iodide (370 mg, 1 mmol). The reaction mixture was stirred vigorously and heated to reflux for 2 days before being cooled, filtered, dried (MgSO$_4$) and concentrated in-vacuo to yield 4-phenoxy-butyric acid ethyl ester. 4-Phenoxy-butyric acid ethyl ester was hydrolyzed to its corresponding carboxylic acid using sodium hydroxide mediated hydrolysis to yield 4-phenoxy-butyric acid. To a solution of 4-phenoxy-butyric acid (7.67 g, 29.6 mmol) in anhydrous dichloromethane was added oxalyl chloride (4.4 ml, 50.3 mmol) and one drop of dimethyl formamide and the reaction mixture stirred at room temperature for 30 minutes. Reaction mixture was concentrated in-vacuo and the residue dissolved in 1,2-dichloroethane (90 ml). This solution was added drop wise to a suspension of aluminum trichloride (4.73 g, 35.5 mmol) in 1,2-dichloroethane (50 ml) at 0° C. Reaction mixture was left stirring in ice bath which rose to room temperature overnight. The reaction mixture was poured over conc. hydrochloric acid (30 ml) stirred into 100 g ice, and then stirred for a further 90 minutes until the ice fully melted. The aqueous phase was washed with dichloromethane 3 times, before the organics were combined, dried (Na$_2$SO$_4$) and concentrated in-vacuo. Purification by triturating with diethyl ether gave 3,4-dihydro-2H-benzo[b]oxepin-5-one.

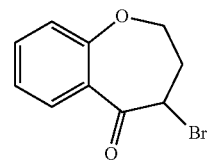 [SMILES: O=C1c2ccccc2OCCC1Br]

To a solution of 3,4-dihydro-2H-benzo[b]oxepin-5-one (3.10 g, 12.8 mmol) in diethyl ether at 0° C., bromine (625 µl, 12.2 mmol) was added and stirred for 2.5 hours, gradually raising the temperature to room temperature. Purification on silica and triturating using diethyl ether and hexanes gave 4-bromo-3,4-dihydro-2H-benzo[b]oxepin-5-one.

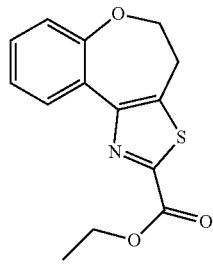 [SMILES: CCOC(=O)c1nc2c(s1)CCOc1ccccc1-2]

To a solution of 4-bromo-3,4-dihydro-2H-benzo[b]oxepin-5-one (4.0 g, 12.4 mmol) in ethanol, was added ethyl thiooxamate (5.0 g, 37.4 mmol) and the reaction mixture was heated to reflux for 3 days. Purification on silica gave 4,5-dihydro-6-oxa-3-thia-1-aza-benzo[e]azulene-2-carboxylic acid ethyl ester, which was hydrolyzed to the carboxylic acid, 4,5-dihydro-6-oxa-3-thia-1-aza-benzo[e]azulene-2-carboxylic acid, in THF, sodium hydroxide, and water. 4,5-Dihydro-6-oxa-3-thia-1-aza-benzo[e]azulene-2-carboxylic acid was coupled with 2-chloro-N-methylaniline using General Procedure B. Purification on silica gave 226. $^1$H NMR (400 MHz, CDCl3): 3.24 (2H, t), 3.37 (3H, s), 4.17-4.25 (2H, m), 6.74-6.79 (1H, m), 6.85 (1H, dd), 7.02-7.07 (1H, m), 7.11 (1H, dd), 7.27-7.33 (3H, m), 7.42-7.45 (1H, m). MS: (ESI+) MH 371

Example 137

N-(2-chloro-4-(2-hydroxypropylcarbamoyl)phenyl)-N-methyl-4,5-dihydrobenzo[b]thieno[2,3-d]oxepine-2-carboxamide 227

3-Chloro-4-(N-methyl-4,5-dihydrobenzo[b]thieno[2,3-d]oxepine-2-carboxamido)benzoic acid and 1-aminopropan-2-ol were reacted by a procedure similar to that to prepare 137 in Example 47 to give 227. MS: (ESI+) 471.1

Example 138

N-(2-chloro-4-(1-hydroxypropan-2-ylcarbamoyl)phenyl)-N-methyl-4,5-dihydrobenzo[b]thieno[2,3-d]oxepine-2-carboxamide 228

3-Chloro-4-(N-methyl-4,5-dihydrobenzo[b]thieno[2,3-d]oxepine-2-carboxamido)benzoic acid and 2-aminopropan-1-ol were reacted by a procedure similar to that to prepare 137 in Example 47 to give 228. MS: (ESI+) 471.0

Example 139

N-(4-(3-(1H-imidazol-1-yl)propylcarbamoyl)-2-chlorophenyl)-N-methyl-4,5-dihydrobenzo[b]thieno[2,3-d]oxepine-2-carboxamide 229

3-Chloro-4-(N-methyl-4,5-dihydrobenzo[b]thieno[2,3-d]oxepine-2-carboxamido)benzoic acid and 3-(1H-imidazol-1-yl)propan-1-amine were reacted by a procedure similar to that to prepare 137 in Example 47 to give 229. MS: (ESI+) 521.1

Example 140

N-(4-(2-acetamidoethylcarbamoyl)-2-chlorophenyl)-N-methyl-4,5-dihydrobenzo[b]thieno[2,3-d]oxepine-2-carboxamide 230

3-Chloro-4-(N-methyl-4,5-dihydrobenzo[b]thieno[2,3-d]oxepine-2-carboxamido)benzoic acid and N-(2-aminoethyl)acetamide were reacted by a procedure similar to that to prepare 137 in Example 47 to give 230. MS: (ESI+) 498.1

Example 141

N-(2-chloro-4-(isopropylcarbamoyl)phenyl)-N-methyl-4,5-dihydrobenzo[b]thieno[2,3-d]oxepine-2-carboxamide 231

3-Chloro-4-(N-methyl-4,5-dihydrobenzo[b]thieno[2,3-d]oxepine-2-carboxamido)benzoic acid and isopropylamine were reacted by a procedure similar to that to prepare 137 in Example 47 to give 231. MS: (ESI+) 455.1

Example 142

N-(2-chloro-4-(dipropylcarbamoyl)phenyl)-N-methyl-4,5-dihydrobenzo[b]thieno[2,3-d]oxepine-2-carboxamide 232

3-Chloro-4-(N-methyl-4,5-dihydrobenzo[b]thieno[2,3-d]oxepine-2-carboxamido)benzoic acid and diethylamine were reacted by a procedure similar to that to prepare 137 in Example 47 to give 232. MS: (ESI+) 497.0

Example 143

8-bromo-N-(2-chlorophenyl)-N-(2-hydroxyethyl)-4,5-dihydrobenzo[b]thieno[2,3-d]oxepine-2-carboxamide 233

Following Example 16, 8-bromo-4,5-dihydrobenzo[b]thieno[2,3-d]oxepine-2-carboxylic acid was converted to the acid chloride and reacted with N-(2-(tert-butyldimethylsilyloxy)ethyl)-2-chloroaniline. Desilylation gave 233 (yield 25%). MS: (ESI+) 480

Example 144

2-(4-(2-chlorophenyl)-4H-1,2,4-triazol-3-yl)-4,5-dihydrobenzo[b]thieno[2,3-d]oxepine-8-carboxylic acid 234

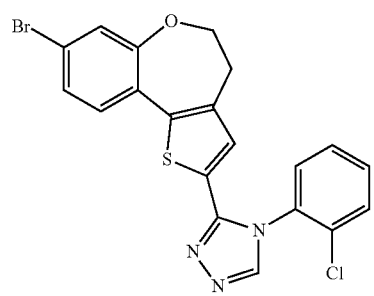 [SMILES: Clc1ccccc1-n1cnnc1-c1cc2c(s1)-c1ccc(Br)cc1OCC2]

Following the procedures to prepare 138, 3-(8-bromo-4,5-dihydrobenzo[b]thieno[2,3-d]oxepin-2-yl)-4-(2-chlorophenyl)-4H-1,2,4-triazole was methoxycarbonylated to give methyl 2-(4-(2-chlorophenyl)-4H-1,2,4-triazol-3-yl)-4,5-dihydrobenzo[b]thieno[2,3-d]oxepine-8-carboxylate which was treated with LiOH in THF and water at 50° C. for 2 h, cooled and acidified with 2N HCl. The precipitate was collected and dried to give 234. MS (ESI): 424.0

Example 145

2-(4-(2-chlorophenyl)-4H-1,2,4-triazol-3-yl)-4,5-dihydrobenzo[b]thieno[2,3-d]oxepin-8-amine 235

Following the procedure of Example 76, 3-(8-Bromo-4,5-dihydrobenzo[b]thieno[2,3-d]oxepin-2-yl)-4-(2-chlorophenyl)-4H-1,2,4-triazole was converted to 235. MS: (ESI+) 395.2

Example 146

N-(2-(4-(2-chlorophenyl)-4H-1,2,4-triazol-3-yl)-4,5-dihydrobenzo[b]thieno[2,3-d]oxepin-8-yl)-2-morpholinoacetamide 236

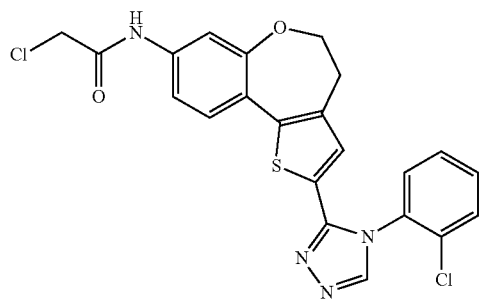 [SMILES: O=C(CCl)Nc1ccc2c(c1)OCCc1cc(-c3nncn3-c3ccccc3Cl)sc1-2]

Following the procedure in Example 147 for 237, 2-chloro-N-(2-(4-(2-chlorophenyl)-4H-1,2,4-triazol-3-yl)-4,5-dihydrobenzo[b]thieno[2,3-d]oxepin-8-yl)acetamide was reacted with morpholine to give 236. MS: (ESI+) 522.3

Example 147

N-(2-(4-(2-chlorophenyl)-4H-1,2,4-triazol-3-yl)-4,5-dihydrobenzo[b]thieno[2,3-d]oxepin-8-yl)-2-(dimethylamino)acetamide 237

To a solution of 2-(4-(2-chlorophenyl)-4H-1,2,4-triazol-3-yl)-4,5-dihydrobenzo[b]thieno[2,3-d]oxepin-8-amine HCl salt (0.5 g, 1.16 mmol) in dried DCM (30 mL) was added DIPEA (0.61 mL, 3.48 mmol). The solution was stirred at 0° C. for 20 min and 2-chloro-acetyl chloride (0.2 g, 1.74 mmol) was added dropwise. The mixture was allowed to reach room temperature and stirred for a further 2 hours. The reaction solution was poured into ice water and extracted with EtOAc. The organics were combined, dried over $Na_2SO_4$ and evaporated in vacuum to afford the crude product (0.45 g, yield: 82%). 2-chloro-N-(2-(4-(2-chlorophenyl)-4H-1,2,4-triazol-3-yl)-4,5-dihydrobenzo[b]thieno[2,3-d]oxepin-8-yl)acetamide (0.2 g, 0.424 mmol) was mixed with HCl salt of $NH(CH_3)_2$ (0.172 g, 2.12 mmol) and $NEt_3$ (0.3 mL, 2.12 mmol) in 15 mL of DCM. The solution was stirred at room temperature for 4 hours and quenched with ice water. Extraction with EtOAc and evaporation of the organics gave the crude product. It was purified by preparative TLC to afford 237 (40 mg, isolated yield: 20%). $^1$H NMR (DMSO-$d_6$, 400 MHz): δ 9.81 (s, 1H), 8.81 (s, 1H), 7.79-7.38 (m, 7H), 6.55 (s, 1H), 4.16 (t, J=5.2 Hz, 2H), 3.02 (s, 3H), 2.96 (t, J=5.2 Hz, 2H), 2.21 (s, 6H). MS: (ESI+) 480.1

Example 148

N-(2-amino-2-methylpropyl)-2-(4-(2-chlorophenyl)-4H-1,2,4-triazol-3-yl)-4,5-dihydrobenzo[b]thieno[2,3-d]oxepine-8-carboxamide 238

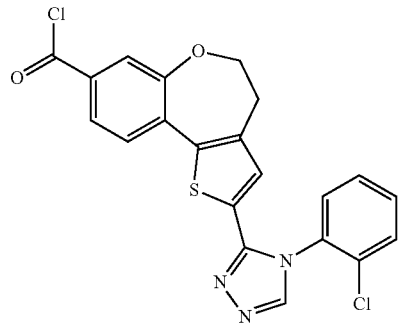 [SMILES: O=C(Cl)c1ccc2c(c1)OCCc1cc(-c3nncn3-c3ccccc3Cl)sc1-2]

2-(4-(2-Chlorophenyl)-4H-1,2,4-triazol-3-yl)-4,5-dihydrobenzo[b]thieno[2,3-d]oxepine-8-carbonyl chloride and 2-methylpropane-1,2-diamine gave 238. MS (ESI) 494.1

Example 149

2-(4-(2-chlorophenyl)-4H-1,2,4-triazol-3-yl)-N-ethyl-4,5-dihydrobenzo[b]thieno[2,3-d]oxepine-8-carboxamide 239

2-(4-(2-Chlorophenyl)-4H-1,2,4-triazol-3-yl)-4,5-dihydrobenzo[b]thieno[2,3-d]oxepine-8-carbonyl chloride and ethylamine gave 239. MS (ESI) 450.9

Example 150

2-(4-(2-chlorophenyl)-4H-1,2,4-triazol-3-yl)-N-methyl-4,5-dihydrobenzo[b]thieno[2,3-d]oxepine-8-carboxamide 240

2-(4-(2-Chlorophenyl)-4H-1,2,4-triazol-3-yl)-4,5-dihydrobenzo[b]thieno[2,3-d]oxepine-8-carbonyl chloride and methylamine gave 240. MS (ESI) 436.9

Example 151

N-(2-chlorophenyl)-N-methyl-8-((4-methylpiperazin-1-yl)methyl)-4,5-dihydrobenzo[b]thieno[2,3-d]oxepine-2-carboxamide 241

8-(Bromomethyl)-N-(2-chlorophenyl)-N-methyl-4,5-dihydrobenzo[b]thieno[2,3-d]oxepine-2-carboxamide was reacted with N-methylpiperazine using the procedure of Example 153 for 243 to give 241. MS: (ESI+) 482.0

Example 152

N-(2-chlorophenyl)-8-((dimethylamino)methyl)-N-methyl-4,5-dihydrobenzo[b]thieno[2,3-d]oxepine-2-carboxamide 242

8-(Bromomethyl)-N-(2-chlorophenyl)-N-methyl-4,5-dihydrobenzo[b]thieno[2,3-d]oxepine-2-carboxamide was reacted with dimethylamine using the procedure of Example 153 for 243 to give 242. MS: (ESI+) 427.0

Example 153

N-(2-chlorophenyl)-N-methyl-8-((methylamino)methyl)-4,5-dihydrobenzo[b]thieno[2,3-d]oxepine-2-carboxamide 243

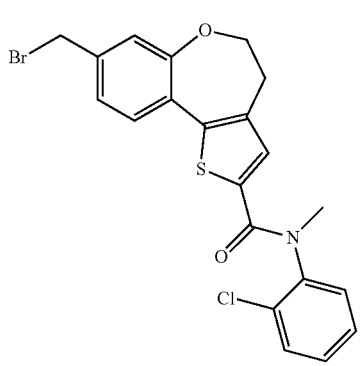 [SMILES: CN(C(=O)c1cc2c(s1)-c1ccc(CBr)cc1OCC2)c1ccccc1Cl]

To a solution of CH$_3$NH$_2$ in EtOH (0.25 mL) was added TEA (0.5 mL) and 8-(bromomethyl)-N-(2-chlorophenyl)-N-methyl-4,5-dihydrobenzo[b]thieno[2,3-d]oxepine-2-carboxamide (250 mg). The reaction mixture was stirred for 2 h at 60° C. before added water. The mixture was extracted with EtOAc (20 mL×3), dried over Na$_2$SO$_4$ and filtered. The filtrate was concentrated to give the crude product, which was purified by preparative TLC(CH$_2$Cl$_2$: MeOH=10:1) to afford 243 as a light yellow solid (95.6 mg, 42.8%). MS: (ESI+) 412.9

Example 154

8-(aminomethyl)-N-(2-chlorophenyl)-N-methyl-4,5-dihydrobenzo[b]thieno[2,3-d]oxepine-2-carboxamide 244

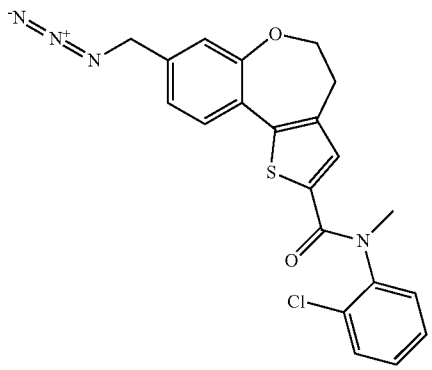

8-(Azidomethyl)-N-(2-chlorophenyl)-N-methyl-4,5-dihydrobenzo[b]thieno[2,3-d]oxepine-2-carboxamide (100 mg, 0.23 mmol) was dissolved in 10 mL of MeOH. To the solution was added Pd/C (10 mg) and charged with H$_2$. The mixture was stirred at 40° C. for 3 h. Filtered and concentrated in vacuo to obtain 244 (54.1 mg, yield 59%). $^1$H NMR (CDCl$_3$, 400 MHz) δ 8.48-8.52 (m, 2H$_2$), 6.55-7.47 (m, 8H), 4.15 (t, J=4.8 Hz, 2H), 3.91-3.95 (m, 2H), 3.28 (s, 3H), 2.94 (t, J=4.8 Hz, 2H). MS: (ESI+) 382.1

Example 155

4-benzyl-3-(4,5-dihydrobenzo[b]thieno[2,3-d]oxepin-2-yl)-1H-1,2,4-triazol-5(4H)-one 245

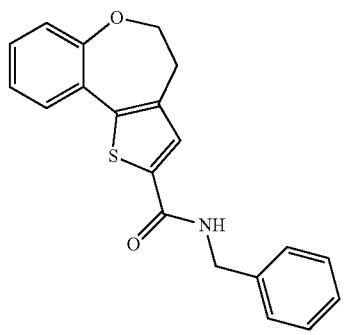 [SMILES: O=C(NCc1ccccc1)c1cc2c(s1)-c1ccccc1OCC2]

Prepared from N-benzyl-4,5-dihydrobenzo[b]thieno[2,3-d]oxepine-2-carboxamide to give 245 using a procedure similar to that described for 265 in Example 175. Removal of the acetoxy group is spontaneous under conditions for cyclization (potassium carbonate, ethanol and water). MS (ESI) 376.2

Example 156

N-(2,6-dichlorophenyl)-N-methyl-(10-aza-4,5-dihydrobenzo[b]thieno[2,3-d]oxepine-2-carboxamide 246

Following the procedures of Example 166, 2-bromo-10-aza-4,5-dihydrobenzo[b]thieno[2,3-d]oxepine (0.112 g, 0.397 mmol) was dissolved in tetrahydrofuran (6.03 mL). n-Butyllithium in hexane (2.50 M, 0.190 mL) was added dropwise at −78° C. The reaction mixture was stirred at −78° C. for 1 h. 2,6-Dichlorophenyl isocyanate (0.149 g, 0.794 mmol;) was added to the mixture at −78° C. then let stirred overnight. The reaction mixture was quenched with sat. NaHCO3 then extracted EtOAc (2×). The combined organic layers was dried Na$_2$SO$_4$ and concentrated. The crude product was purified by flash chromatography (0-100% EtOAc/Hex) (eluted 40%) to give the amide intermediate which was dissolved in DMF (5.00 mL) at 0° C. Sodium hydride (19.0 mg, 0.794 mmol) was added. The reaction mixture was stirred 30 min then methyl iodide (0.113 g, 0.794 mmol) was added and stirred 2 h. The reaction mixture was quenched 5 mL water then extracted DCM (3×5 mL). The organic layers were combined, concentrated, and purified by rHPLC to give 246 (yield 30%). MS: (ESI+) 405.1

Example 157

N-(2,4-dichlorophenyl)-9-(4-(dimethylamino)piperidine-1-carbonyl)-N-methyl-4,5-dihydrobenzo[b]thieno[2,3-d]oxepine-2-carboxamide 247

2-[(2,4-Dichloro-phenyl)-methyl-carbamoyl]-4,5-dihydro-6-oxa-1-thia-benzo[e]azulene-9-carboxylic acid and 4-(dimethylamino)piperidine were reacted by General Procedure B to give 247. NMR: (CDCl$_3$): 1.45-1.62 (2H, br m), 1.88-2.01 (2H, br, m), 2.39 (6H, s, Me), 2.50-2.61 (1H, br m), 2.82-3.10 (2H, br m), 3.07-3.09 (2H, m), 3.38 (3H, s, Me), 3.80-4.01 (1H, m), 4.26-4.29 (2H, m), 4.58-4.79 (1H, br m), 6.85 (1H, s, Ar), 7.02 (1H, d, J 8.3, Ar), 7.25 (1H, dd, J 8.2 and 2.0, Ar), 7.28-7.32 (1H, m, Ar), 7.37-7.39 (1H, m, Ar), 7.55 (1H, s, Ar) and 7.60 (1H, s, Ar). MS: (ESI+) MH+=558.14

Example 158

N-(2-chloro-4-(2-(dimethylamino)ethylcarbamoyl)phenyl)-N-methyl-4,5-dihydrobenzo[b]thieno[2,3-d]oxepine-2-carboxamide 248

3-Chloro-4-(N-methyl-4,5-dihydrobenzo[b]thieno[2,3-d]oxepine-2-carboxamido)benzoic acid and N1,N1-dimethylethane-1,2-diamine were reacted by a procedure similar to that to prepare 137 in Example 47 to give 248. MS: (ESI+) 484.3

Example 159

N-(2-chloro-4-(dimethylcarbamoyl)phenyl)-N-methyl-4,5-dihydrobenzo[b]thieno[2,3-d]oxepine-2-carboxamide 249

3-Chloro-4-(N-methyl-4,5-dihydrobenzo[b]thieno[2,3-d]oxepine-2-carboxamido)benzoic acid and dimethylamine hydrochloride were reacted by a procedure similar to Example 47 to give 249. MS: (ESI+) 441.0

Example 160

N-(2-chloro-4-(methylcarbamoyl)phenyl)-N-methyl-4,5-dihydrobenzo[b]thieno[2,3-d]oxepine-2-carboxamide 250

3-Chloro-4-(N-methyl-4,5-dihydrobenzo[b]thieno[2,3-d]oxepine-2-carboxamido)benzoic acid and methylamine were reacted by a procedure similar to Example 47 to give 250. MS: (ESI+) 427.2

Example 161

N-(2-chloro-4-(morpholine-4-carbonyl)phenyl)-N-methyl-4,5-dihydrobenzo[b]thieno[2,3-d]oxepine-2-carboxamide 251

3-Chloro-4-(N-methyl-4,5-dihydrobenzo[b]thieno[2,3-d]oxepine-2-carboxamido)benzoic acid and morpholine were reacted by a procedure similar to Example 47 to give 251. MS: (ESI+) 483.1

Example 162

N-(2-chloro-4-(4-methylpiperazine-1-carbonyl)phenyl)-N-methyl-4,5-dihydrobenzo[b]thieno[2,3-d]oxepine-2-carboxamide 252

3-Chloro-4-(N-methyl-4,5-dihydrobenzo[b]thieno[2,3-d]oxepine-2-carboxamido)benzoic acid and N-methylpiperazine were reacted by a procedure similar to Example 47 to give 252. MS: (ESI+) 496.2

Example 163

N-(2-chloro-4-(piperazine-1-carbonyl)phenyl)-N-methyl-4,5-dihydrobenzo[b]thieno[2,3-d]oxepine-2-carboxamide 253

3-Chloro-4-(N-methyl-4,5-dihydrobenzo[b]thieno[2,3-d]oxepine-2-carboxamido)benzoic acid and piperazine were reacted by a procedure similar to Example 47 to give 253. MS: (ESI+) 482.1

Example 164

3-(4,5-dihydrobenzo[b]thieno[2,3-d]oxepin-2-yl)-4-(1-hydroxypropan-2-yl)-1H-1,2,4-triazol-5(4H)-one 254

Prepared from 2-(4,5-dihydrobenzo[b]thieno[2,3-d]oxepine-2-carboxamido)propyl acetate to give 254 using a procedure similar to Example 175. MS (ESI) 344.2

Example 165

3-(9-bromo-4,5-dihydrobenzo[b]thieno[2,3-d]oxepin-2-yl)-4-(2,4-dichlorophenyl)-4H-1,2,4-triazole 255

Example 166

4-(2-chlorophenyl)-3-(10-aza-4,5-dihydrobenzo[b]thieno[2,3-d]oxepin-2-yl)-1H-1,2,4-triazol-5(4H)-one 256

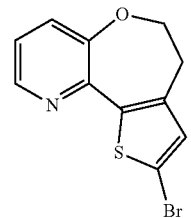 [SMILES: Brc1cc2c(s1)-c1ncccc1OCC2]

To a solution of 2-bromo-10-aza-4,5-dihydrobenzo[b]thieno[2,3-d]oxepine (0.405 g, 1.44 mmol) in tetrahydrofuran (21.8 mL, 269 mmol) was added 2.50 M of n-butyllithium in hexane (0.689 mL) dropwise at −78° C. The reaction mixture was stirred at −78° C. for 1 h. 1-Chloro-2-isocyanatobenzene (2-chlorophenyl isocyanate 0.346 mL, 2.87 mmol) was added to the mixture at −78° C. then let stir overnight. The reaction mixture was quenched with sat. NaHCO₃ then extracted EtOAc (2×). The combined organic layers was dried Na₂SO₄, concentrated. The crude product was purified by flash chromatography (0-100% EtOAc/Hex) (eluted 40%) to give N-(2-chlorophenyl)-10-aza-4,5-dihydrobenzo[b]thieno[2,3-d]oxepine-2-carboxamide (yield 82%). MS: (ESI+) 357.8

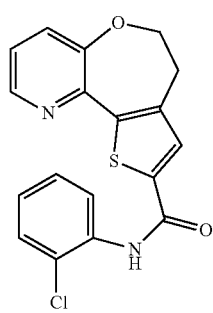 [SMILES: O=C(Nc1ccccc1Cl)c1cc2c(s1)-c1ncccc1OCC2]

To a solution of N-(2-chlorophenyl)-10-aza-4,5-dihydrobenzo[b]thieno[2,3-d]oxepine-2-carboxamide (0.180 g, 0.504 mmol;) in 1,4-dioxane (4.50 mL, 57.7 mmol) was added 2,4-bis(4-methoxyphenyl)-2,4-dithioxo-1,3,2,4-dithiadiphosphetane (Lawesson's reagent, 0.153 g, 0.378 mmol). The reaction mixture was stirred at 85° C. for 3 h. The reaction mixture was concentrated to give the crude thioamide intermediate. To a solution containing crude thioamide intermediate in methanol (10.0 mL, 247 mmol) was added hydrazine (0.80 mL, 25 mmol). The reaction mixture was stirred at room temperature overnight. The reaction mixture was concentrated to give crude hydrazine intermediate which was dissolved in THF. N,N-Carbonyldiimidazole (0.164 g, 1.01 mmol) was added and the reaction mixture was stirred rapidly at room temperature for 4 h. The reaction mixture was concentrated and purified by rHPLC to give 256 (yield 10%). MS: (ESI+) 397.1

Example 167

3-(4,5-dihydrobenzo[b]thieno[2,3-d]oxepin-2-yl)-4-(1-methoxypropan-2-yl)-1H-1,2,4-triazol-5(4H)-one 257

Prepared from N-(1-methoxypropan-2-yl)-4,5-dihydrobenzo[b]thieno[2,3-d]oxepine-2-carboxamide to give 257 using a procedure similar to Example 175. MS (ESI) 358.2. The enantiomers of the racemic mixture were separated by preparative chiral chromatography.

Example 168

N-(2-acetamidoethyl)-N-(2-chlorophenyl)-4,5-dihydrobenzo[b]thieno[2,3-d]oxepine-2-carboxamide 258

To a solution of N-(2-aminoethyl)-N-(2-chlorophenyl)-4,5-dihydrobenzo[b]thieno[2,3-d]oxepine-2-carboxamide 131 (0.300 g, 0.6 mmol) in methylene chloride (1.5 ml) was added DIEA (0.262 ml, 1.5 mmol). The reaction mixture was cooled with an ice water bath and acetyl chloride (0.0944 g, 1.2 mmol) was added drop-wise via syringe. The reaction mixture was stirred at cool temperature for 30 minutes and equilibrated to room temperature. The reaction mixture was washed with water, then saline and concentrated to a solid. The crude solid was taken into DMF and purified by RP-HPLC to give 46 mg of 258 (yield 18% of theoretical). MS: (ESI+) 441.1

Example 169

2-(4-isopropyl-5-oxo-4,5-dihydro-1H-1,2,4-triazol-3-yl)-4,5-dihydrobenzo[b]thieno[2,3-d]oxepine-8-carbonitrile 259

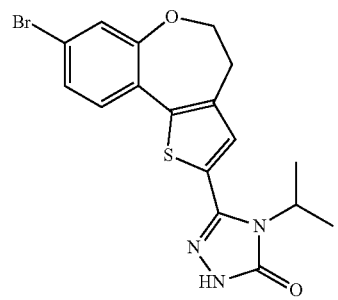 [SMILES: CC(C)n1c(-c2cc3c(s2)-c2ccc(Br)cc2OCC3)n[nH]c1=O]

Following the procedure of Example 53, 3-(8-bromo-4,5-dihydrobenzo[b]thieno[2,3-d]oxepin-2-yl)-4-isopropyl-1H-1,2,4-triazol-5(4H)-one and CuCN were reacted to give 259. MS: (ESI+) 353.1

Example 170

3-(4,5-dihydrobenzo[b]thieno[2,3-d]oxepin-2-yl)-4-isobutyl-1H-1,2,4-triazol-5(4H)-one 260

Prepared from N-isobutyl-4,5-dihydrobenzo[b]thieno[2,3-d]oxepine-2-carboxamide to give 260 using a procedure similar to Example 175. MS (ESI) 342.2

Example 171

N-(2-chlorophenyl)-N-methyl-8-(morpholinomethyl)-4,5-dihydrobenzo[b]thieno[2,3-d]oxepine-2-carboxamide 261

Following the procedure in Example 153 for the synthesis of 243, 8-(bromomethyl)-N-(2-chlorophenyl)-N-methyl-4,5-dihydrobenzo[b]thieno[2,3-d]oxepine-2-carboxamide was reacted with morpholine to give 261. MS: (ESI+) 469.0

Example 172

4-(8-(1H-pyrazol-4-yl)-4,5-dihydrobenzo[b]thieno[2,3-d]oxepin-2-yl)-5-(2-chlorophenyl)thiazol-2-amine 262

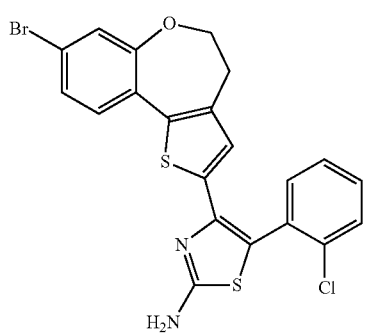 [SMILES: Nc1nc(-c2cc3c(s2)-c2ccc(Br)cc2OCC3)c(-c2ccccc2Cl)s1]

Following the procedure of Example 44, 4-(8-bromo-4,5-dihydrobenzo[b]thieno[2,3-d]oxepin-2-yl)-5-(2-chlorophenyl)thiazol-2-amine and 4-(4,4,5,5-tetramethyl-1,3,2-dioxaborolan-2-yl)-1H-pyrazole were reacted to give 262. MS: (ESI+) 477.1

Example 173

N-(2-chlorophenyl)-N-methyl-(10-aza-4,5-dihydrobenzo[b]thieno[2,3-d]oxepine-2-carboxamide 263

Following the procedures of Examples 156 and 166, N-(2-chlorophenyl)-10-aza-4,5-dihydrobenzo[b]thieno[2,3-d]oxepine-2-carboxamide, was methylated to give 263. MS: (ESI+) 371.1

Example 174

3-(8-(1H-pyrazol-4-yl)-4,5-dihydrobenzo[b]thieno[2,3-d]oxepin-2-yl)-4-isopropyl-1H-1,2,4-triazol-5(4H)-one 264

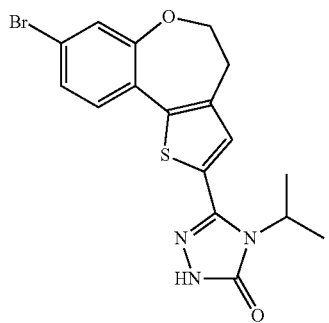 [SMILES: CC(C)n1c(-c2cc3c(s2)-c2ccc(Br)cc2OCC3)n[nH]c1=O]

Following the procedure of Example 44, 3-(8-bromo-4,5-dihydrobenzo[b]thieno[2,3-d]oxepin-2-yl)-4-isopropyl-1H-1,2,4-triazol-5(4H)-one and 4-(4,4,5,5-tetramethyl-1,3,2-dioxaborolan-2-yl)-1H-pyrazole were reacted to give 264. MS: (ESI+) 394.2

Example 175

3-(8-bromo-4,5-dihydrobenzo[b]thieno[2,3-d]oxepin-2-yl)-4-isopropyl-1H-1,2,4-triazol-5(4H)-one 265

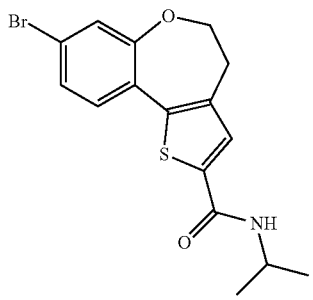 [SMILES: CC(C)NC(=O)c1cc2c(s1)-c1ccc(Br)cc1OCC2]

A solution of 8-bromo-N-isopropyl-4,5-dihydrobenzo[b]thieno[2,3-d]oxepine-2-carboxamide (200 mg, 0.5 mmol) in toluene (5 mL, 0.05 mol) under nitrogen atmosphere was treated with phosphorus pentachloride (0.182 g, 0.87 mmol) in one portion. The flask was sealed and heated at 80° C. for 2 h, cooled to room temperature and the solvent concentrated under reduced pressure with care to avoid atmospheric exposure. The crude residue was taken up in methylene chloride (8 mL, 0.1 mol) and treated with methyl hydrazinecarboxylate (0.123 g, 1.36 mmol). The resulting suspension was stirred at room temperature for 2 h. The reaction mixture was diluted with saturated sodium bicarbonate and extracted with methylene chloride. The combined organics were washed with brine, dried over sodium sulfate and concentrated. The crude residue was dissolved in ethanol (5 mL) and potassium carbonate (0.2264 g, 1.64 mmol) was added. The reaction mixture was stirred at 80° C. for 2 h. 0.5 mL water was added and the heating continued overnight. The mixture was concentrated, diluted with water and extracted with ethyl acetate. The organics were washed with brine, concentrated, and the resultant residue purified by flash column chromatography to give 265 (75 mg). $^1$H NMR (dmso-$d_6$, 500 MHz) δ 11.9 (s, 1H), 7.60 (m, 1H), 7.30-7.23 (m, 3H), 4.44 (pentet, 1H), 4.32 (t, 2H), 3.22 (t, 2H), 1.46 (d, 6H). MS (ESI) 408.1

Example 176

5-(8-bromo-4,5-dihydrobenzo[b]thieno[2,3-d]oxepin-2-yl)-1,3,4-oxadiazol-2(3H)-one 266

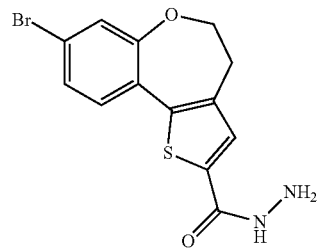 [SMILES: NNC(=O)c1cc2c(s1)-c1ccc(Br)cc1OCC2]

8-Bromo-4,5-dihydrobenzo[b]thieno[2,3-d]oxepine-2-carbohydrazide (150 mg, 0.44 mmol) was suspended in tetrahydrofuran (5.0 mL) and triethylamine (0.12 mL, 0.88 mmol) was added. N,N-Carbonyldiimidazole (108 mg, 0.66 mmol) was added and the whole stirred at room temperature for 1 h. No reaction was observed. The whole was sealed and heat at 80° C. for 2 h. More N,N-carbonyldiimidazole (150 mg, 0.92 mmol) was added and the whole heated at 85° C. for 10 min. LCMS indicated clean conversion to the desired product. The reaction mixture was cooled to room temperature, diluted with saturated sodium bicarbonate and extracted with ethyl acetate. The organics were dried over sodium sulfate. Concentration gave 125 mg colorless solid. A small amount was purified by reverse phase HPLC to give 266 as a colorless solid. $^1$H NMR (400 MHz, DMSO-$d_6$) δ 11.99 (br s, 1H), 7.70-7.00 (overlapping m, 4H), 4.23 (t, 2H), 3.21 (t, 2H). MS: (ESI+) 367.0

Example 177

3-(9-bromo-4,5-dihydrobenzo[b]thieno[2,3-d]oxepin-2-yl)-4-(2-chloro-4-fluorophenyl)-4H-1,2,4-triazole 267

To a stirred solution of 5-bromo-2-hydroxyacetophenone (15.29 g; 71 mmol) in 2-butanone (150 ml) was added $K_2CO_3$ (21 g; 152 mmol) then 1,2-dibromoethane (30 ml; 350 mmol). The reaction mixture was heated at reflux temperature overnight (17 h), cooled, filtered (acetone washing) and the solvent evaporated. The residue was treated with a mixture of $Et_2O/EtOAc$ (4:1; 250 ml) and the resulting solid removed by filtration. The filtrate was washed with 2M NaOH (150 ml), dried (MgSO₄) and concentrated to give 1-[5-bromo-2-(2-bromo-ethoxy)-phenyl]-ethanone as an off-white crystalline solid (15.99 g). This solid was dissolved in anhydrous THF (300 ml), cooled to 0° C. and treated with NaH (2.11 g of a 60 wt % suspension in mineral oil; 53 mmol). The reaction mixture was carefully heated to reflux and heating continued overnight (17 h). The reaction mixture was cooled, quenched with 2M HCl (50 ml) and partitioned between brine (300 ml) and EtOAc (200 ml). The organic layer was dried (MgSO₄), concentrated and purified by ISCO (hexanes/EtOAc) to give 7-bromo-3,4-dihydro-2H-benzo[b]oxepin-5-one as a pale yellow oil (9.84 g; 57%). δ$_H$ (400 MHz, CDCl₃) 2.24 (quintet, J=6.8, 2H), 2.91 (t, J=6.8, 2H), 4.25 (t, J=6.8, 2H), 6.98 (d, J=8.8, 1H), 7.52 (dd, J=8.8 and 2.8, 1H), 7.90 (d, J=2.8, 1H).

To a stirred solution of 7-bromo-3,4-dihydro-2H-benzo[b]oxepin-5-one (9.84 g; 41 mmol) in DMF (50 ml) at 0° C. was added POCl₃ (10 ml; 107 mmol) dropwise over 10 min. The reaction mixture was stirred whilst allowing to warm to room temperature overnight (16 h) upon which time it was quenched by pouring into well-stirred ice/water (500 ml). The resulting solid was extracted into EtOAc (2×400 ml), the combined organics were dried (MgSO₄) and concentrated to give a yellow solid (7-bromo-5-chloro-2,3-dihydro-benzo[b]oxepine-4-carbaldehyde). This solid was dissolved in DMF (50 ml) and treated successively with K₂CO₃ (7 g; 51 mmol) then ethyl mercaptoacetate (5.5 ml; 50 mmol). The reaction mixture was heated at 70° C. for 4 h upon which time it was cooled and poured into well-stirred ice/water (500 ml). The resulting solid was collected by filtration and dried to give 9-Bromo-4,5-dihydro-6-oxa-1-thia-benzo[e]azulene-2-carboxylic acid ethyl ester as an off-white solid (13.69 g; 95%). δ$_H$ (400 MHz, d₆-DMSO) 1.31 (t, J=7.2, 3H), 3.23 (t, J=5.2, 2H), 4.27-4.35 (m, 4H), 7.03 (d, J=8.8, 1H), 7.42 (dd, J=8.8 and 2.4, 1H), 7.70 (s, 1H), 7.80 (d, J=2.4, 1H).

To a stirred suspension of 9-bromo-4,5-dihydro-6-oxa-1-thia-benzo[e]azulene-2-carboxylic acid ethyl ester (4.24 g; 12 mmol) in THF (40 ml) at room temperature was added a solution of NaOH (0.96 g; 24 mmol) in water (20 ml) followed by EtOH (20 ml). The reaction mixture was stirred at room temperature for 4 h (now a clear solution) upon which time it was quenched with 2M HCl (20 ml) and diluted with water (50 ml). The resulting solid was collected by filtration, washed with water and dried to give 9-bromo-4,5-dihydro-6-oxa-1-thia-benzo[e]azulene-2-carboxylic acid as a white solid (3.64 g; 93%). δ$_H$ (400 MHz, d₆-DMSO) 3.22 (t, J=5.2, 2H), 4.31 (t, J=5.2, 2H), 7.02 (d, J=8.4, 1H), 7.43 (dd, J=8.4 and 2.4, 1H), 7.62 (s, 1H), 7.78 (d, J=2.4, 1H).

A stirred solution of 9-bromo-4,5-dihydro-6-oxa-1-thia-benzo[e]azulene-2-carboxylic acid ethyl ester (7.43 g; 21 mmol) and N₂H₄.H₂O (5.1 ml; 105 mmol) in EtOH was heated at reflux temperature overnight (18 h) and the resulting solid was collected by filtration (3.68 g). A further crop (2.88 g) of the intermediate hydrazide was obtained by treating the filtrate with more N₂H₄.H₂O (20 ml) and refluxing overnight to obtain 9-bromo-4,5-dihydro-6-oxa-1-thia-benzo[e]azulene-2-carboxylic acid hydrazide as white needles (6.56 g; 92%). The intermediate hydrazide was heated in a microwave (performed in 4 batches) with p-TsOH (10 mol %) and CH(OMe)₃ (5 ml per 1 g of hydrazide) at 140° C. for 1 h. The batches were combined, the mixture diluted with MeOH and filtered to give the 2-(9-Bromo-4,5-dihydro-6-oxa-1-thia-benzo[e]azulen-2-yl)-[1,3,4]oxadiazole as light yellow needles (4.39 g; 65%). δ$_H$ (400 MHz, CDCl₃) 3.30 (t, J=5.2, 2H), 4.37 (t, J=5.2, 2H), 6.96 (d, J=8.8, 1H), 7.33 (dd, J=8.8 and 2.4, 1H), 7.61 (s, 1H), 7.84 (d, J=2.4, 1H), 8.44 (s, 1H).

A microwave tube was charged with 2-(9-bromo-4,5-dihydro-6-oxa-1-thia-benzo[e]azulen-2-yl)-[1,3,4]oxadiazole (0.64 g; 1.83 mmol), 2-chloro-4-fluoroaniline (0.44 ml; 3.68 mmol), TFA (0.27 ml; 3.63 mmol) and toluene (5 ml). The mixture was heated in a microwave at 160° C. for 30 min., diluted with EtOAc (150 ml) and washed with satd. NaHCO₃. The organic layer was dried (MgSO₄), concentrated and purified by ISCO to give 267 as a cream-coloured solid (0.59 g; 68%). δ$_H$ (400 MHz, CDCl₃) 3.14 (t, J=5.2, 2H), 4.29 (t, J=5.2, 2H), 6.91 (d, J=8.4, 1H), 6.93 (s, 1H), 7.22-7.27 (m, 2H), 7.43-7.51 (m, 2H), 7.65 (d, J=2.4, 1H), 8.22 (s, 1H). [M+H]⁺: 478

Example 178

2-(2-amino-5-(2-chlorophenyl)thiazol-4-yl)-4,5-dihydrobenzo[b]thieno[2,3-d]oxepine-8-carboxamide 268

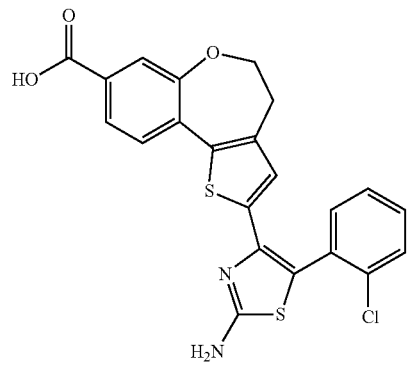 [SMILES: Nc1nc(-c2cc3c(s2)-c2ccc(C(=O)O)cc2OCC3)c(-c2ccccc2Cl)s1]

Following Example 47, 2-(2-amino-5-(2-chlorophenyl)thiazol-4-yl)-4,5-dihydrobenzo[b]thieno[2,3-d]oxepine-8-carboxylic acid and ammonium chloride were coupled with HATU and DIPEA in DMF to give 268.

Example 179

3-(8-(1H-pyrazol-4-yl)-4,5-dihydrobenzo[b]thieno[2,3-d]oxepin-2-yl)-4-ethyl-1H-1,2,4-triazol-5(4H)-one 269

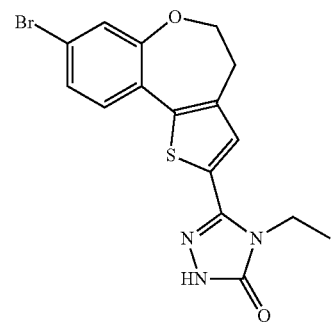 [SMILES: CCn1c(-c2cc3c(s2)-c2ccc(Br)cc2OCC3)n[nH]c1=O]

Following the procedure of Example 44, 3-(8-bromo-4,5-dihydrobenzo[b]thieno[2,3-d]oxepin-2-yl)-4-ethyl-1H-1,2, 4-triazol-5(4H)-one and 4-(4,4,5,5-tetramethyl-1,3,2-dioxaborolan-2-yl)-1H-pyrazole were reacted to give 269. MS: (ESI+) 380.2

Example 180

2-(4-(2-chlorophenyl)-4H-1,2,4-triazol-3-yl)-4,5-dihydrobenzo[b]thieno[2,3-d]oxepine-8-carboxamide 270

2-(4-(2-Chlorophenyl)-4H-1,2,4-triazol-3-yl)-4,5-dihydrobenzo[b]thieno[2,3-d]oxepine-8-carbonyl chloride and ammonium chloride gave 270. (ESI) 423.1.

Example 181

4-(8-bromo-4,5-dihydrobenzo[b]thieno[2,3-d]oxepin-2-yl)-5-(2-chlorophenyl)thiazol-2-amine 271

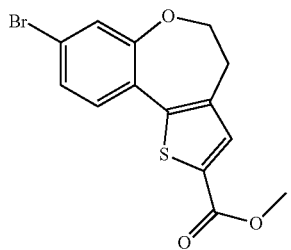 [SMILES: COC(=O)c1cc2c(s1)-c1ccc(Br)cc1OCC2]

1-(8-Bromo-4,5-dihydrobenzo[b]thieno[2,3-d]oxepin-2-yl)-2-(2-chlorophenyl)ethanone (1.0 g, 2.3 mmol) was prepared by reaction of 2-chlorophenylacetic acid with methyl 8-bromo-4,5-dihydrobenzo[b]thieno[2,3-d]oxepine-2-carboxylate. A solution of 1-(8-bromo-4,5-dihydrobenzo[b]thieno[2,3-d]oxepin-2-yl)-2-(2-chlorophenyl)ethanone in ethyl acetate (60 mL) was treated with copper(II) bromide (1.3 g, 5.8 mmol) in one portion in 100 mL rb flask. Acetic acid (2 mL) was added, and the flask sealed and heated at 85° C. After 8 hr, the reaction was removed from heat and allowed to stand overnight. The reaction mixture was concentrated to dryness, diluted with 100 mL diethyl ether and filtered through celite (ether wash). The eluent was re-filtered through the same celite pad, and concentration gave 2-bromo-1-(8-bromo-4,5-dihydrobenzo[b]thieno[2,3-d]oxepin-2-yl)-2-(2-chlorophenyl)ethanone as a crude solid used without purification.

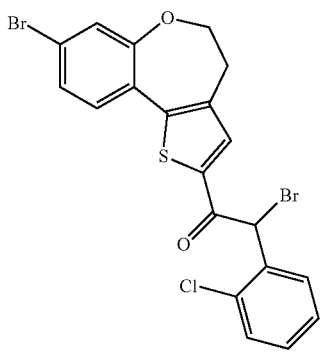 [SMILES: O=C(c1cc2c(s1)-c1ccc(Br)cc1OCC2)C(Br)c1ccccc1Cl]

2-Bromo-1-(8-bromo-4,5-dihydrobenzo[b]thieno[2,3-d]oxepin-2-yl)-2-(2-chlorophenyl)ethanone (ca. 2.3 mmol) was suspended in acetone (15 mL, 0.20 mol) and treated with thiourea (0.26 g, 0.0034 mol;). The mixture was sealed and heated at 80° C. for 3 h. After cooling to room temperature, the reaction mixture was concentrated, suspended in water and the solid was collected by filtration. The solid was rinsed with water to give 953 mg of 271 as a light yellow solid. $^1$H NMR (dmso-d$_6$, 500 MHz) δ 7.64 (m, 1H), 7.53 (m, 2H), 7.45 (m, 1H), 7.35 (m, 1H), 7.23 (m, 1H), 7.17 (m, 1H), 6.47 (s, 1H), 4.19 (t, 2H), 2.95 (t, 2H). MS (ESI) 491.0

Example 182

3-(8-bromo-4,5-dihydrobenzo[b]thieno[2,3-d]oxepin-2-yl)-4-(2-chlorophenyl)-5-methyl-4H-1,2,4-triazole 272

A solution of crude 8-bromo-N-(2-chlorophenyl)-4,5-dihydrobenzo[b]thieno[2,3-d]oxepine-2-carbohydrazonamide (150 mg) was heated in a sealed vessel with triethyl orthoacetate at 90° C. for 3 h. The mixture was cooled to room temperature and concentrated to give a crude residue that was purified by flash column chromatography (10-100% ethyl acetate in hexanes) to give 272. $^1$H NMR (dmso-d$_6$, 400 MHz) δ 7.86 (m, 2H), 7.48 (m, 1H), 7.69 (m, 1H), 7.44 (m, 1H), 7.28-7.23 (m, 2H), 6.57 (s, 1H), 4.22 (t, 2H), 3.00 (t, 2H), 2.18 (s, 3H). MS (ESI) 474.0

Example 183

3-(8-bromo-4,5-dihydrobenzo[b]thieno[2,3-d]oxepin-2-yl)-4-(2-chlorophenyl)-4H-1,2,4-triazole 273

A solution of crude 8-bromo-N-(2-chlorophenyl)-4,5-dihydrobenzo[b]thieno[2,3-d]oxepine-2-carbohydrazonamide (150 mg) was heated in a sealed vessel with methyl orthoformate at 90° C. for 3 h. The mixture was cooled to room temperature and concentrated to give a crude residue that was purified by flash column chromatography (10-100% ethyl acetate in hexanes) to give 273. $^1$H NMR (dmso-d$_6$, 400 MHz) δ 8.89 (s, 1H), 7.84 (m, 2H), 7.75 (m, 1H), 7.66 (m, 1H), 7.46 (m, 2H), 7.28-7.23 (m, 2H), 6.66 (s, 1H), 4.23 (t, 2H), 3.02 (t, 2H). MS (ESI) 460.0

Example 184

2-(4-(2-chlorophenyl)-1H-pyrazol-3-yl)-4,5-dihydrobenzo[b]thieno[2,3-d]oxepine-8-carboxamide 274

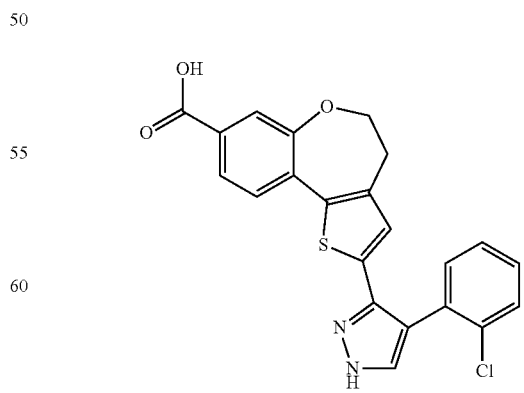

Following Example 47, 2-(4-(2-chlorophenyl)-1H-pyrazol-3-yl)-4,5-dihydrobenzo[b]thieno[2,3-d]oxepine-8-carboxylic acid and ammonium chloride were coupled with HATU and DIPEA in DMF to give 274.

Example 185

2-(4-(2-chlorophenyl)-1H-pyrazol-3-yl)-4,5-dihydrobenzo[b]thieno[2,3-d]oxepine-8-carbonitrile 275

Following the procedure of Example 53, 3-(8-bromo-4,5-dihydrobenzo[b]thieno[2,3-d]oxepin-2-yl)-4-(2-chlorophenyl)-1H-pyrazole and CuCN gave 275. MS: (ESI+) 404.1

Example 186

3-(8-bromo-4,5-dihydrobenzo[b]thieno[2,3-d]oxepin-2-yl)-4-(2-chlorophenyl)-1H-pyrazole 276

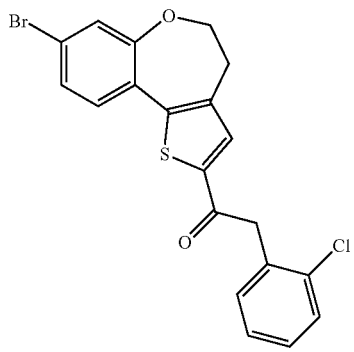 [SMILES: O=C(Cc1ccccc1Cl)c1cc2c(s1)-c1ccc(Br)cc1OCC2]

To a solution of 1-(8-bromo-4,5-dihydrobenzo[b]thieno[2,3-d]oxepin-2-yl)-2-(2-chlorophenyl)ethanone (500 mg, 1.15 mmol) in dry toluene (10 mL) was added 1,1-dimethoxy-N,N-dimethylmethanamine (1.22 mL) The whole vessel was sealed and heated at 90° C. overnight, cooled to room temperature and concentrated. The obtained compound, 1-(8-bromo-4,5-dihydrobenzo[b]thieno[2,3-d]oxepin-2-yl)-2-(2-chlorophenyl)-3-(dimethylamino)prop-2-en-1-one, could be used crude without purification in subsequent reactions.

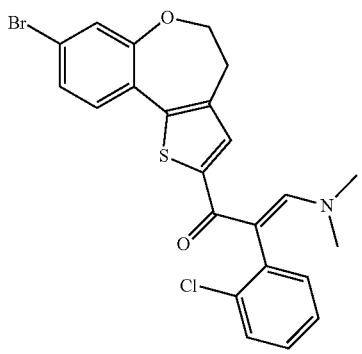 [SMILES: CN(C)/C=C(/C(=O)c1cc2c(s1)-c1ccc(Br)cc1OCC2)c1ccccc1Cl]

Crude 1-(8-bromo-4,5-dihydrobenzo[b]thieno[2,3-d]oxepin-2-yl)-2-(2-chlorophenyl)-3-(dimethylamino)prop-2-en-1-one was suspended in methanol (5 mL) and treated with hydrazine (ca. 1 mL). After 2 h, the mixture was concentrated and the residue purified by flash column chromatography to give 276 as colorless solid (527 mg). MS (ESI): 459.0

Example 187

3-(8-(1H-pyrazol-4-yl)-4,5-dihydrobenzo[b]thieno[2,3-d]oxepin-2-yl)-4-(2-chlorophenyl)-1H-1,2,4-triazol-5(4H)-one 277

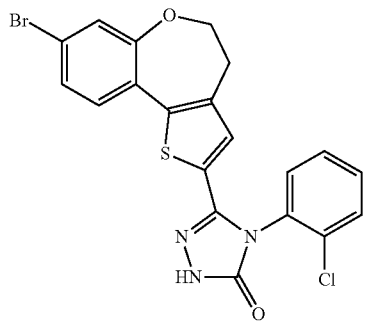 [SMILES: O=c1[nH]nc(-c2cc3c(s2)-c2ccc(Br)cc2OCC3)n1-c1ccccc1Cl]

Following the procedure of Example 44, 3-(8-bromo-4,5-dihydrobenzo[b]thieno[2,3-d]oxepin-2-yl)-4-(2-chlorophenyl)-1H-1,2,4-triazol-5(4H)-one and 4-(4,4,5,5-tetramethyl-1,3,2-dioxaborolan-2-yl)-1H-pyrazole were reacted to give 277. MS: (ESI+) 462.1

Example 188

2-(4-(2-chlorophenyl)-5-oxo-4,5-dihydro-1H-1,2,4-triazol-3-yl)-4,5-dihydrobenzo thieno[2,3-d]oxepine-8-carbonitrile 278

Following the procedure of Example 53, (8-bromo-4,5-dihydrobenzo[b]thieno[2,3-d]oxepin-2-yl)-4-(2-chlorophenyl)-1H-1,2,4-triazol-5(4H)-one and CuCN gave 278. MS: (ESI+) 421.1

Example 189

3-(8-bromo-4,5-dihydrobenzo[b]thieno[2,3-d]oxepin-2-yl)-4-(2-chlorophenyl)-1H-1,2,4-triazol-5(4H)-one 279

To a solution of crude 8-bromo-N-(2-chlorophenyl)-4,5-dihydrobenzo[b]thieno[2,3-d]oxepine-2-carbohydrazonamide (about 1.15 mmol) in dry THF (10 mL) was added carbonyl diimidazole (373 mg, 2.3 mmol). The reaction mixture was stirred at room temperature until completion judged by LCMS. Aqueous sodium bicarbonate was added and the mixture extracted with ethyl acetate. The combined organics were washed with brine, dried over sodium sulfate, concentrated and the residue purified by flash column chromatography (10-100% ethyl acetate in hexanes) to give 279 as a colorless solid (308 mg).

$^1$H NMR (dmso-d$_6$, 400 MHz) δ 12.32 (s, 1H), 7.75-7.59 (m, 4H), 7.42 (m, 1H), 7.27-7.21 (m, 2H), 6.53 (s, 1H), 4.21 (t, 2H), 2.97 (t, 2H). MS (ESI) 476.0.

Example 190

5-(2-chlorophenyl)-4-(4,5-dihydrobenzo[b]thieno[2,3-d]oxepin-2-yl)thiazol-2-amine 280

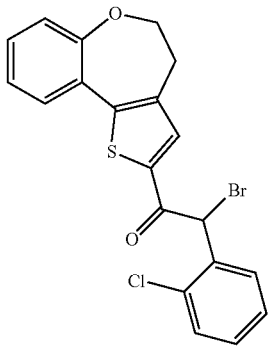 [SMILES: O=C(c1cc2c(s1)-c1ccccc1OCC2)C(Br)c1ccccc1Cl]

A solution of crude 2-bromo-2-(2-chlorophenyl)-1-(4,5-dihydrobenzo[b]thieno[2,3-d]oxepin-2-yl)ethanone (0.21 mmol) in 2 mL acetone was treated with thiourea (48 mg) and the resultant suspension was heated at 80° C. overnight. The reaction mixture was cooled to room temperature and concentrated. The crude residue was purified by reverse phase HPLC to give 280 as a colorless solid. $^1$H NMR (400 MHz, DMSO-$d_6$) δ 7.65 (m, 1H), 7.55-7.53 (m, 2H), 7.47-7.43 (m, 2H), 7.29 (br s, 2H), 7.14 (m, 1H), 7.02 (m, 1H), 6.45 (s, 1H), 4.17 (t, 2H), 2.95 (t, 2H). MS: (ESI+) 411.1

Example 191

2-(4-(2-chloro-4-fluorophenyl)-4H-1,2,4-triazol-3-yl)-4,5-dihydrobenzo[b]thieno[2,3-d]oxepine-9-carboxamide 281

To a stirred solution of 2-[4-(2-chloro-4-fluoro-phenyl)-4H-[1,2,4]-triazol-3-yl]-4,5-dihydro-6-oxa-1-thia-benzo[e]azulene-9-carbonitrile (90 mg; 0.21 mmol) in DMSO (3 ml) and MeOH (5 ml) was added $K_2CO_3$ (36 mg; 0.26 mmol) then $H_2O_2$ (30 µl of a 30% aqueous soln.). The reaction mixture was stirred at room temperature overnight (16 h) upon which time the methanol was removed on a rotary evaporator and the residue was diluted with water (40 ml). The resulting solid was collected by filtration, washed with water and dried to give 281 as a white solid (82 mg; 89%). $δ_H$ (400 MHz, CDCl$_3$) 3.15 (t, J=5.2, 2H), 4.34 (t, J=5.2, 2H), 5.50-6.30 (br s, 2H), 6.88 (s, 1H), 7.07 (d, J=8.4, 1H), 7.22-7.27 (m, 1H), 7.42-7.63 (m, 3H), 8.06 (d, J=2.0, 1H), 8.22 (s, 1H). [M+H]$^+$: 441

Example 192

5-(2-chlorophenyl)-4-(4,5-dihydrobenzo[b]thieno[2,3-d]oxepin-2-yl)pyrimidin-2-amine 282

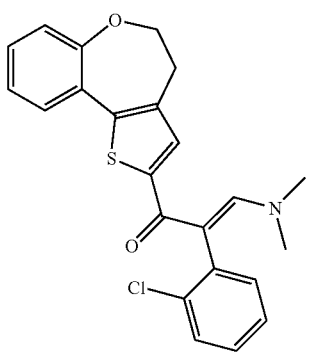 [SMILES: CN(C)/C=C(/C(=O)c1cc2c(s1)-c1ccccc1OCC2)c1ccccc1Cl]

To a solution of crude 2-(2-chlorophenyl)-1-(4,5-dihydrobenzo[b]thieno[2,3-d]oxepin-2-yl)-3-(dimethylamino)prop-2-en-1-one (ca. 0.22 mmol) in ethanol (2 mL) was added potassium carbonate (87 mg, 0.63 mmol) and then guanidine hydrochloride (40 mg, 0.42 mmol). The whole was sealed and heated at 90° C. for 8 h, cooled to room temperature and concentrated. The residue was diluted with water and extracted with ethyl acetate. The combined organics were purified by reverse phase HPLC to give 282. MS (ESI) 406.2

Example 193

4-(2-chlorophenyl)-3-(4,5-dihydrobenzo[b]thieno[2,3-d]oxepin-2-yl)-1H-pyrazole 283

2-(2-Chlorophenyl)-1-(4,5-dihydrobenzo[b]thieno[2,3-d]oxepin-2-yl)-3-(dimethylamino)prop-2-en-1-one was treated with hydrazine in methanol to give 283. MS (ESI) 379.1

Example 194

4-(2-chlorophenyl)-3-(4,5-dihydrobenzo[b]thieno[2,3-d]oxepin-2-yl)-1H-1,2,4-triazol-5(4H)-one 284

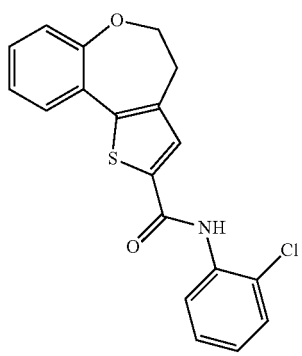 [SMILES: O=C(Nc1ccccc1Cl)c1cc2c(s1)-c1ccccc1OCC2]

Prepared starting from N-(2-chlorophenyl)-4,5-dihydrobenzo[b]thieno[2,3-d]oxepine-2-carboxamide to give 284 using procedures similar to those described in Examples 196 and 189. MS (ESI) 396.1

Example 195

2-(1-(2-chlorophenyl)-1H-tetrazol-5-yl)-4,5-dihydrobenzo[b]thieno[2,3-d]oxepine-8-carboxamide 285

8-Bromo-4,5-dihydrobenzo[b]thieno[2,3-d]oxepin-2-yl)-1-(2-chlorophenyl)-1H-tetrazole 286 was converted to 285 using procedures similar to those in Examples 205 and 53. MS: (ESI+) 424.0

Example 196

5-(8-bromo-4,5-dihydrobenzo[b]thieno[2,3-d]oxepin-2-yl)-1-(2-chlorophenyl)-1H-tetrazole 286

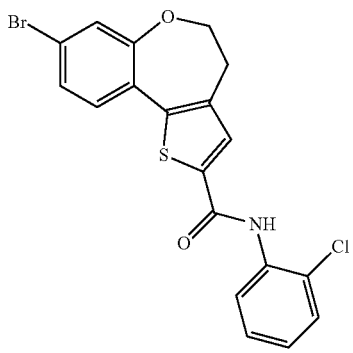 [SMILES: O=C(Nc1ccccc1Cl)c1cc2c(s1)-c1ccc(Br)cc1OCC2]

To a solution of 8-bromo-N-(2-chlorophenyl)-4,5-dihydrobenzo[b]thieno[2,3-d]oxepine-2-carboxamide in dry 1,4-dioxane was added Lawesson's reagent. The 50 mL round-bottom was sealed and heated at 80° C. for 3 h. The reaction mixture was cooled to room temperature and concentrated to give the crude thioamide. The bright yellow crude solid thus obtained was taken up in methanol and methylene chloride and treated with hydrazine. Reaction progress was monitored by LCMS. Upon completion, the mixture was diluted with saturated sodium bicarbonate and extracted with ethyl acetate. The combined organics were washed with brine, dried over sodium sulfate and concentrated to give crude 8-bromo-N-(2-chlorophenyl)-4,5-dihydrobenzo[b]thieno[2,3-d]oxepine-2-carbohydrazonamide as a yellow solid.

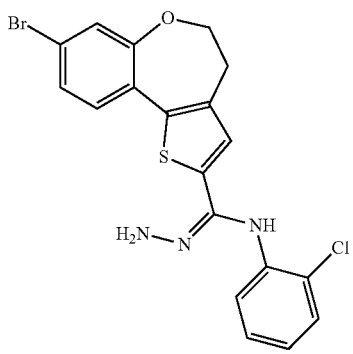 [SMILES: N/N=C(/Nc1ccccc1Cl)c1cc2c(s1)-c1ccc(Br)cc1OCC2]

A solution of crude 8-bromo-N-(2-chlorophenyl)-4,5-dihydrobenzo[b]thieno[2,3-d]oxepine-2-carbohydrazonamide (150 mg, 0.334 mmol) in acetic acid (0.5 mL) was treated with a solution of sodium nitrite (115 mg, 1.6 mmol) in water (0.5 mL) at 0° C. After 30 min, an additional 50 mg of sodium nitrite was added. After 10 min, 3 mL of 10% aqueous sodium hydroxide was added. The mixture was extracted with ethyl acetate and the organics dried over sodium sulfate and concentrated. The crude residue was purified by flash column chromatography to give 286 as a colorless solid (111 mg). $^1$H NMR (dmso-d$_6$, 400 MHz) δ 8.00 (m, 1H), 7.98 (m, 1H), 7.85 (m, 1H), 7.56 (m, 1H), 7.46 (m, 1H), 7.26 (m, 2H), 7.13 (m, 1H), 4.27 (t, 2H), 3.11 (t, 2H). MS (ESI) 461.1

Example 197

5-(8-bromo-4,5-dihydrobenzo[b]thieno[2,3-d]oxepin-2-yl)-4-(2-chlorophenyl)-4H-1,2,4-triazol-3-amine 287

A solution of crude 8-bromo-N-(2-chlorophenyl)-4,5-dihydrobenzo[b]thieno[2,3-d]oxepine-2-carbohydrazonamide (195, 0.434) in methanol (5 mL) was treated with a solution of cyanogen bromide (115 mg, 1.1 mmol) in methanol (1 mL) at room temperature. The reaction vessel was sealed and heated at 45° C. for 2 h, cooled to room temperature, quenched upon addition of saturated sodium bicarbonate and extracted with ethylacetate. The combined organics were dried over sodium sulfate and concentrated and the residue purified by flash column chromatography (1-10% MeOH in methylene chloride to give 287 (43 mg, 21% yield). MS (ESI): 475.0

Example 198

N2-(2,4-dichlorophenyl)-N2,N9,N9-trimethyl-4,5-dihydrobenzo[b]thieno[2,3-d]oxepine-2,9-dicarboxamide 288

2-[(2,4-Dichloro-phenyl)-methyl-carbamoyl]-4,5-dihydro-6-oxa-1-thia-benzo[e]azulene-9-carboxylic acid and dimethylamine hydrochloride salt were reacted in the general amide coupling procedure to give 288. NMR: (CDCl$_3$): 2.73-3.04 (6H, br m), 2.95-3.00 (2H, m), 3.29 (3H, s, Me), 4.17-4.20 (2H, m), 6.79 (1H, s, Ar), 6.93 (1H, d, J 8.3, Ar), 7.19-7.29 (3H, m, Ar) and 7.47-7.48 (2H, m, Ar). MS: (ESI+) MH+=475.04

Example 199

3-(9-bromo-4,5-dihydrobenzo[b]thieno[2,3-d]oxepin-2-yl)-4-(2-chloro-4-(trifluoromethyl)phenyl)-4H-1,2,4-triazole 289

A microwave tube charged with 2-(9-bromo-4,5-dihydro-6-oxa-1-thia-benzo[e]azulen-2-yl)-[1,3,4]oxadiazole (200 mg; 0.57 mmol), 2-chloro-4-trifluoromethylaniline (0.12 ml; 0.86 mmol), TFA (64 µl; 0.86 mmol) and toluene (1.5 ml) was heated in a microwave at 160° C. for 30 min. The reaction mixture was basified with DIPEA (0.2 ml), volatiles removed in vacuo and the residue purified by prep. LCMS to give 289 as a white solid (109 mg; 36%). δ$_H$ (400 MHz, CDCl$_3$) 3.13 (t, J=5.2, 2H), 4.29 (t, J=5.2, 2H), 6.89-6.93 (m, 2H), 7.24-7.28 (m, 1H), 7.62-7.67 (m, 2H), 7.80-7.83 (m, 1H), 7.98 (s, 1H), 8.26 (s, 1H). [M+H]$^+$: 527

Example 200

N-(2-chloro-4-fluorophenyl)-9-cyano-N-methyl-4,5-dihydrobenzo[b]thieno[2,3-d]oxepine-2-carboxamide 290

Compound 290 was prepared using the standard amide coupling conditions to give a white solid (198 mg, 82%). δ$_H$ (400 MHz, CDCl$_3$) 3.11 (t, 2H), 3.39 (s, 3H), 4.31 (t, 2H), 6.93 (s, 1H), 7.06 (d, 1H), 7.13 (m, 1H), 7.32 (dd, 1H), 7.39 (m, 1H), 7.44 (dd, 1H), 7.77 (s, 1H). [M+H]$^+$ (453.97).

Example 201

9-cyano-N-(2,4-difluorophenyl)-N-methyl-4,5-dihydrobenzo[b]thieno[2,3-d]oxepine-2-carboxamide 291

Compound 291 was prepared using the standard amide coupling conditions to give a white solid (151 mg, 65%). $\delta_H$ (400 MHz, CDCl$_3$) 3.11 (t, 2H), 3.42 (s, 3H), 4.32 (t, 2H), 6.94 (s, 1H), 7.00 (t, 2H), 7.07 (d, 1H), 7.33 (m, 1H), 7.43 (dd, 1H), 7.78 (s, 1H). [M+H]$^+$ (438.05).

Example 202

4-(2-chloro-6,7-dihydropyrido[3,2-b]thieno[2,3-d]oxepin-9-yl)-5-(2-chlorophenyl)-2H-1,2,3-triazole 292

Example 203

3-(9-bromo-4,5-dihydrobenzo[b]thieno[2,3-d]oxepin-2-yl)-4-(2,4-difluorophenyl)-4H-1,2,4-triazole 293

To a suspension of 9-bromo-4,5-dihydro-6-oxa-1-thia-benzo[e]azulene-2-carboxylic acid (described previously, 396 mg) in dichloromethane (10 mL) was added oxalyl chloride (0.18 mL) and N,N-dimethylformamide (1 drop). After ~1 hour the reaction mixture was reduced in vacuo and to this was added ammonia in methanol (7N, 10 mL). After stirring overnight water was added, and 9-bromo-4,5-dihydro-6-oxa-1-thia-benzo[e]azulene-2-carboxylic acid amide was collected by filtration (340 mg).

A mixture of 9-bromo-4,5-dihydro-6-oxa-1-thia-benzo[e]azulene-2-carboxylic acid amide (340 mg), dimethylformamide dimethyl acetal (3 ml) and toluene (2.5 mL) was heated to 100° C. for 16 hours. The solvent was then reduced in vacuo and dissolved in acetic acid (3 ml) and water (0.3 mL) and to this was added 2,4-difluorophenylhydrazine hydrochloride (265 mg). The reaction mixture was heated to 100° C. for 3 hours. The reaction mixture was then cooled, and then diluted with dichloromethane, washed with sodium carbonate solution, dried (MgSO$_4$) and the solvent removed in vacuo. Purification using flash chromatography yielded 293. NMR: (CDCl3): 3.15 (2H, t), 4.31 (2H, t), 6.82 (1H, d), 6.86 (1H, s), 7.08-7.13 (2H, m), one proton under chloroform peak, 7.72 (1H, s), 8.10 (1H, s)

Example 204

5-(2-chloro-6,7-dihydropyrido[3,2-b]thieno[2,3-d]oxepin-9-yl)-1-(2,4-difluorophenyl)-1,2,4-triazole 294

Example 205

2-(4-(2-chlorophenyl)-5-oxo-4,5-dihydro-1H-1,2,4-triazol-3-yl)-4,5-dihydrobenzo[b]thieno[2,3-d]oxepine-8-carboxamide 295

A solution of 2-(4-(2-chlorophenyl)-5-oxo-4,5-dihydro-1H-1,2,4-triazol-3-yl)-4,5-dihydrobenzo[b]thieno[2,3-d]oxepine-8-carbonitrile 278 in DMSO was treated with potassium carbonate and the resultant yellow suspension cooled to 0° C. The reaction mixture was treated dropwise with hydrogen peroxide (30% wt. in water). The whole was warmed to room temperature and the reaction quenched with sat. NaHSO$_3$. Extraction with ethylacetate and concentration gave a residue that was purified by reverse phase HPLC to give 295 as a colorless solid.

Example 206

N-(2-aminoethyl)-2-(4-(2-chlorophenyl)-4H-1,2,4-triazol-3-yl)-4,5-dihydrobenzo[b]thieno[2,3-d]oxepine-8-carboxamide 296

2-(4-(2-Chlorophenyl)-4H-1,2,4-triazol-3-yl)-4,5-dihydrobenzo[b]thieno[2,3-d]oxepine-8-carbonyl chloride and 1,2-diaminoethane gave 296. MS (ESI) 465.9

Example 207

8-cyano-4,5-dihydro-6-oxa-1-aza-3-thia-benzo[e]azulene-2-carboxylic acid (2-chloro-(4-methylcarbamoyl)phenyl)-methyl-amide 297

To a solution of 8-bromo-4,5-dihydro-6-oxa-3-thia-1-aza-benzo[e]azulene-2-carboxylic acid (2-chloro-4-methylcarbamoyl-phenyl)-methyl-amide 111 (100 mg) in DMF (6 mL) was added copper cyanide (18 mg) and the reaction mixture was heated at 110° C. overnight. The reaction mixture was then cooled, diluted with ethyl acetate, washed with brine, dried (MgSO$_4$) and the solvent removed in vacuo and the residue purified using prep LCMS to yield 297. (400 MHz, CDCl3), 3.00 (3H, d, J 4.9, NMe), 3.27-3.29 (2H, m), 3.38 (3H, s, Me), 4.20-4.24 (2H, m), 5.92-5.94 (1H, m, NH), 7.01-7.07 (2H, m, Ar), 7.14 (1H, s, Ar), 7.37 (1H, d, J 8.1, Ar), 7.67-7.70 (1H, m, Ar) and 7.84 (1H, d, J 1.8, Ar)

Example 208

N-(2-chloro-4-(methylcarbamoyl)phenyl)-9-cyano-N-methyl-4,5-dihydrobenzo[b]thieno[2,3-d]oxepine-2-carboxamide 298

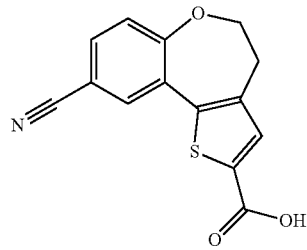

To a solution of 9-cyano-4,5-dihydro-6-oxa-1-thia-benzo[e]azulene-2-carboxylic acid (300 mg) in toluene (10 mL) was added thionyl chloride (2 mL) and the reaction heated at 80° C. for 2 h. After cooling to room temperature, the solvent was reduced in vacuo and the residue redissolved in acetonitrile (10 mL). Potassium carbonate (306 mg) and 3-chloro-N-methyl-4-methylamino-benzamide from Example 21 (263 mg) were added and the reaction stirred at room temperature for 16 h. Water (20 mL) was added and the product extracted into ethyl acetate (2×20 mL). The organics were dried (MgSO$_4$), reduced in vacuo and purified on silica to give 298. NMR: (CDCl3): 2.95-2.98 (5H, m), 3.31 (3H, s, Me), 4.19-4.21 (2H, m), 6.10 (1H, s, NH), 0.76 (1H, s, Ar), 6.96 (1H, d, J 8.4, Ar), 7.31-7.36 (2H, m, Ar), 7.64-7.67 (2H, m, Ar) and 7.87 (1H, d, J 1.8, Ar). MS: (ESI+) MH+ 451.25

Example 209

8-methylcarbamoyl-4,5-dihydro-6-oxa-1-aza-3-thia-benzo[e]azulene-2-carboxylic acid (2-chloro-(4-methylcarbamoyl)phenyl)-methyl-amide 299

A mixture of 8-bromo-4,5-dihydro-6-oxa-3-thia-1-azabenzo[e]azulene-2-carboxylic acid (2-chloro-4-methylcarbamoyl-phenyl)-methyl-amide 111 (60 mg), molybdenum hexacarbonyl (31 mg), Hermann's catalyst (22 mg), methylamine (2.0M solution in THF, 0.20 mL) and diazabicycloundecane (DBU, 8.8 μL) was reacted in a microwave at 150° C. for 20 minutes. The reaction mixture was then cooled, diluted with ethyl acetate, washed with brine, dried (MgSO₄), solvent removed in vacuo, and the residue purified using flash chromatography to yield 299. (400 MHz, CDCl3): 2.92 (3H, d, J 4.8), 2.98 (3H, d, J 4.8), 3.24-3.26 (2H, m), 3.38 (3H, s, Me), 4.18-4.21 (2H, m), 6.12 (2H, s, NH), 7.04-7.10 (2H, m, Ar), 7.19 (1H, s, Ar), 7.36 (1H, d, J 8.1, Ar), 7.62-7.64 (1H, m, Ar) and 7.83 (1H, d, J 1.9, Ar)

Example 210

N2-(2-chlorophenyl)-N-9-ethyl-N2-methyl-4,5-dihydrobenzo[b]thieno[2,3-d]oxepine-2,9-dicarboxamide 300

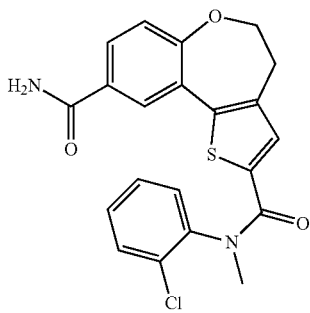 [SMILES: CN(C(=O)c1cc2c(s1)-c1cc(C(N)=O)ccc1OCC2)c1ccccc1Cl]

A mixture of N2-(2-chlorophenyl)-N2-methyl-4,5-dihydrobenzo[b]thieno[2,3-d]oxepine-2,9-dicarboxamide 119 (70 mg), TFA (37.5 μL), triethylsilane (80 μL) and acetaldehyde (28 μL) in dry MeCN (Dube et al (1999) Tet. Letters 40(12):2295-2298) was stirred at room temperature overnight then concentrated in vacuo. Purification on silica yielded 300. NMR: (CDCl₃ δ 7.19 ppm): 1.21 (t, 3H, CH₃, J=7.28 Hz), 2.93 (t, 2H, CH₂, J=5.07 Hz), 3.32 (s, 3H, CH₃), 3.43 (m, 2H, CH₂), 4.17 (t, 2H, CH₂, J=5.10 Hz), 5.94 (m, H, NH), 6.59 (s, H, ArH), 6.91 (d, H, ArH, J=8.41 Hz), 7.29-7.36 (m, 3H, 3×ArH), 7.44-7.47 (m, 2H, 2×ArH), 7.81 (m, H, ArH). MS: (ESI+) MH+ 482.15

Example 211

N-(2-chlorophenyl)-N-methyl-8-(3-(pyridin-2-ylamino)propanamido)-4,5-dihydrobenzo[b]thieno[2,3-d]oxepine-2-carboxamide 301

2-[(2,4-Dichloro-phenyl)-methyl-carbamoyl]-4,5-dihydro-6-oxa-1-thia-benzo[e]azulene-9-carboxylic acid and 1-butyl-1-piperazine carboxylate were reacted in the general amide coupling procedure to give 4-{2-[(2,4-dichloro-phenyl)-methyl-carbamoyl]-4,5-dihydro-6-oxa-1-thia-benzo[e]azulene-9-carbonyl}-piperazine-1-carboxylic acid tert-butyl ester.

To a solution of 4-{2-[(2,4-dichloro-phenyl)-methyl-carbamoyl]-4,5-dihydro-6-oxa-1-thia-benzo[e]azulene-9-carbonyl}-piperazine-1-carboxylic acid tert-butyl ester in THF was added hydrochloric acid (2 eq of a 2 M in diethyl ether solution) and the reaction stirred at room temperature for 16 h. The mixture was then quenched with aqueous sodium hydrogen carbonate solution and extracted into ethyl acetate. The organic layer was dried (MgSO₄), reduced in vacuo and purified on silica to give the title compound. NMR: (CDCl₃): 2.72-2.95 (4H, br m), 2.98-3.01 (2H, m), 3.29 (3H, s, Me), 3.38-3.75 (4H, br m), 4.17-4.20 (2H, m), 6.81 (1H, s, Ar), 6.94 (1H, d, J 8.3, Ar), 7.16 (1H, dd, J 8.9 and 1.3, Ar), 7.23 (1H, d, J 8.5, Ar), 7.28 (1H, dd, J 8.4 and 2.1, Ar), 7.44 (1H, s, Ar) and 7.58 (1H, d, J 2.2, Ar). MS: (ESI+) MH+=557.13

Example 212

N-(2-acetamidoethyl)-2-(4-(2-chlorophenyl)-4H-1,2,4-triazol-3-yl)-4,5-dihydrobenzo[b]thieno[2,3-d]oxepine-8-carboxamide 302

2-(4-(2-Chlorophenyl)-4H-1,2,4-triazol-3-yl)-4,5-dihydrobenzo[b]thieno[2,3-d]oxepine-8-carbonyl chloride and N-(2-aminoethyl)acetamide gave 302. MS (ESI) 508.1

Example 213

2-(4-(2-chlorophenyl)-4H-1,2,4-triazol-3-yl)-N-(2-morpholinoethyl)-4,5-dihydrobenzo[b]thieno[2,3-d]oxepine-8-carboxamide 303

2-(4-(2-Chlorophenyl)-4H-1,2,4-triazol-3-yl)-4,5-dihydrobenzo[b]thieno[2,3-d]oxepine-8-carbonyl chloride and 2-morpholinoethanamine gave 303. MS (ESI) 536.2

Example 214

2-(4-(2-chlorophenyl)-4H-1,2,4-triazol-3-yl)-N-(2-(dimethylamino)ethyl)-4,5-dihydrobenzo[b]thieno[2,3-d]oxepine-8-carboxamide 304

2-(4-(2-Chlorophenyl)-4H-1,2,4-triazol-3-yl)-4,5-dihydrobenzo[b]thieno[2,3-d]oxepine-8-carbonyl chloride and N1,N1-dimethylethane-1,2-diamine gave 304. MS (ESI) 494.2

Example 215

2-(4-(2-chlorophenyl)-4H-1,2,4-triazol-3-yl)-N-(1,3-dihydroxypropan-2-yl)-4,5-dihydrobenzo[b]thieno[2,3-d]oxepine-8-carboxamide 305

2-(4-(2-Chlorophenyl)-4H-1,2,4-triazol-3-yl)-4,5-dihydrobenzo[b]thieno[2,3-d]oxepine-8-carbonyl chloride and 2-aminopropane-1,3-diol gave 305. MS (ESI) 497.3

Example 216

N2-(2-chloro-4-(methylcarbamoyl)phenyl)-N2-methyl-4,5-dihydrobenzo[b]thieno[2,3-d]oxepine-2,9-dicarboxamide 306

To a solution of N-(2-chloro-4-(methylcarbamoyl)phenyl)-9-cyano-N-methyl-4,5-dihydrobenzo[b]thieno[2,3-d]

oxepine-2-carboxamide 298 (100 mg) and potassium carbonate (37 mg) in DMSO (3 mL) at 0° C. was added hydrogen peroxide (30 µL of a 33% solution in water). The reaction was stirred at room temperature for 16 h. Water was then added and the resulting solid collected by filtration and air-dried to give 306. NMR: (DMSO): 2.81 (3H, d, J 4.5, Me), 2.91-2.93 (2H, m), 3.68 (3H, s, Me), 4.19-4.22 (2H, m), 6.41 (1H, s, NH), 7.03 (1H, d, J 8.4, Ar), 7.35 (1H, s), 7.71-7.77 (2H, m, Ar), 7.92 (1H, dd, J 8.3 and 2.0, Ar), 8.03-8.05 (3H, m) and 8.65-8.67 (1H, m). MS: (ESI+) MH+ 469.35

Example 217

5-(8-(1H-pyrazol-4-yl)-4,5-dihydrobenzo[b]thieno[2,3-d]oxepin-2-yl)-4-(2-chlorophenyl)-4H-1,2,4-triazol-3-amine 307

Following the procedure in Example 93, 5-(8-bromo-4,5-dihydrobenzo[b]thieno[2,3-d]oxepin-2-yl)-4-(2-chlorophenyl)-4H-1,2,4-triazol-3-amine was coupled with 4-(4,4,5,5-tetramethyl-1,3,2-dioxaborolan-2-yl)-1H-pyrazole to give 307. MS (ESI) 461.1

Example 218

5-(6,7-dihydropyrido[3,2-b]thieno[2,3-d]oxepin-9-yl)-2-acetaminopyridine 308

5-(6,7-Dihydropyrido[3,2-b]thieno[2,3-d]oxepin-9-yl)pyridin-2-amine 142 (60 mg, 0.2 mmol) was heated in 1 ml of acetic anhydride at 85° C. for 60 min. The reaction mixture was then cooled to room temperature, the precipitate filtered out, washed with cold ethanol and dried in high vacuum to yield 308 (44 mg, 60%). MS: (ESI+) 338.1

Example 219

N-(2-chloro-4-(dimethylcarbamoyl)phenyl)-N-methyl-(3-hydroxymethyl-6,7-dihydropyrido[3,2-b]thieno[2,3-d]oxepine)-9-carboxamide 309

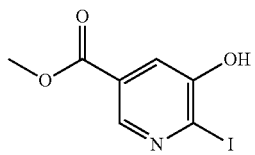

To solution of 5-hydroxy-nicotinic acid methyl ester (2.50 g, 16.3 mmol) in tetrahydrofuran (50.0 mL, 616 mmol)/water (50.0 mL, 2780 mmol) was added sodium carbonate (5.19 g, 49.0 mmol) and iodine (10.4 g, 40.8 mmol). The reaction mixture was stirred at room temperature 4 h. The aqueous layer containing product was separated and wash with hexane. The organic layer was neutralized to pH 7 with HCl, extracted EtOAc 4×. The combined organic layers was dried Na₂SO₄, concentrated. The crude product was purified by flash chromatography (EtOAc/DCM) (eluted at 40 EtOAc) to give methyl 5-hydroxy-6-iodonicotinate (81.2%). MS: (ESI+) 280.0

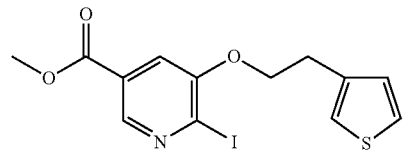 [SMILES: COC(=O)c1cnc(I)c(OCCc2ccsc2)c1]

To a solution containing 5-hydroxy-6-iodonicotinate (3.70 g, 13.3 mmol;), 2-(3-thienyl)ethanol (1.90 mL, 17.2 mmol), and triphenylphosphine (4.52 g, 17.2 mmol;) in tetrahydrofuran (73.3 mL, 903 mmol;) was added Diisopropyl azodicarboxylate (3.39 mL, 17.2 mmol;) dropwise. The reaction mixture was stirred at RT o/n. The reaction mixture was concentrated and purified by flash chromatography EtOAc/Hex (0-100%) (eluted at 30%) to give methyl 6-iodo-5-(2-(thiophen-3-yl)ethoxy)nicotinate (93.2% yield). MS: (ESI+) 390.1

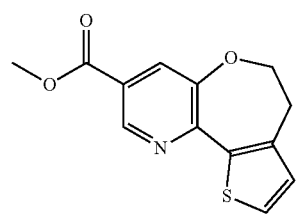 [SMILES: COC(=O)c1cnc2c(c1)OCCc1ccsc1-2]

To a solution of 6-Iodo-5-(2-thiophen-3-yl-ethoxy)-nicotinic acid methyl ester (4.40 g, 11.3 mmol) in N,N-Dimethylformamide (176 mL, 2270 mmol) was added potassium carbonate (9.37 g, 67.8 mmol), triphenylphosphine (1.19 g, 4.52 mmol) and palladium acetate (508 mg, 2.26 mmol). The reaction mixture was stirred at 90° C. 8 h. The reaction mixture was diluted with MeOH then filtered through celite. The filtrate was concentrated. The crude product was purified by flash chromatography EtOAc/Hex (0-100%) (product eluted at 30%) to give 3-methylcarboxy-6,7-dihydropyrido[3,2-b]thieno[2,3-d]oxepine (52.8%). MS: (ESI+) 262.0

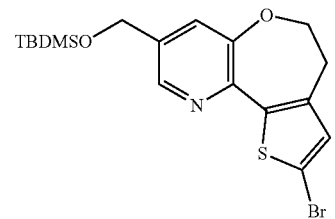 [SMILES: CC(C)(C)[Si](C)(C)OCc1cnc2c(c1)OCCc1cc(Br)sc1-2]

To a solution of 1.00 M of diisobutylaluminum hydride in toluene (4.02 mL) at 0° C. was added 3-methylcarboxy-6,7-dihydropyrido[3,2-b]thieno[2,3-d]oxepine (0.420 g, 1.61 mmol) in toluene (17.8 mL, 167 mmol). The reaction mixture was stirred at 0° C. 2 h. The reaction is diluted with EtOAc then quenched with 1M HCl. The organic layer was dried Na₂SO₄, concentrated to give 3-hydroxymethyl-6,7-dihydropyrido[3,2-b]thieno[2,3-d]oxepine which was dissolved in triethylamine (0.336 mL, 2.41 mmol) and N,N-dimethylformamide (10.5 mL, 136 mmol). Tert-butyldimethylsilyl chloride (0.291 g, 1.93 mmol) was added. The reaction was stirred at room temperature 20 min. The reaction was diluted with EtOAc then wash with water and brine, dried and concentrated to give 3-tert-butyldimethylsilyloxymethyl-6,7-dihydropyrido[3,2-b]thieno[2,3-d]oxepine which was dissolved in DCM/Acetic acid at 0° C. N-Bromosuccinimide (315 mg, 1.77 mmol) was added. The reaction was stirred overnight at room temperature. The reaction was concentrated and purified by flash chromatography (EtOAc/Hex) (eluted 10%) to give 3-tert-butyldimethylsilyloxymethyl-9-bromo-6,7-dihydropyrido[3,2-b]thieno[2,3-d]oxepine (61.3% yield). MS: (ESI+) 426.1

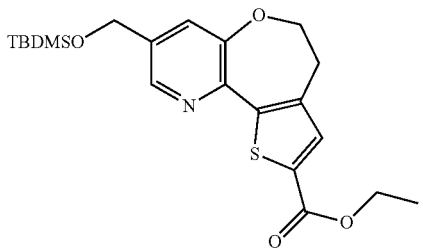 [SMILES: CCOC(=O)c1cc2c(s1)-c1ncc(CO[Si](C)(C)C(C)(C)C)cc1OCC2]

To a solution of 3-tert-butyldimethylsilyloxymethyl-9-bromo-6,7-dihydropyrido[3,2-b]thieno[2,3-d]oxepine (0.0500 g, 0.117 mmol;) in tetrahydrofuran (1.78 mL, 22.0 mmol) was added 1.60 M of n-butyllithium in hexane (0.0806 mL) dropwise at −78° C. The reaction mixture was stirred at −78° C. for 1 h. Ethyl chloroformate (0.0336 mL, 0.352 mmol;) was added to the mixture at −78° C. then let stirred 2 h. The reaction mixture was quenched with sat. NaHCO3 then extracted EtOAc (2×). The combined organic layers was dried Na₂SO₄, concentrated. The crude product was purified by flash chromatography (0-50% EtOAc/Hex) (eluted 15%) to give 3-tert-butyldimethylsilyloxymethyl-9-ethylcarboxy-6,7-dihydropyrido[3,2-b]thieno[2,3-d]oxepine (36% yield). MS: (ESI+) 420.1

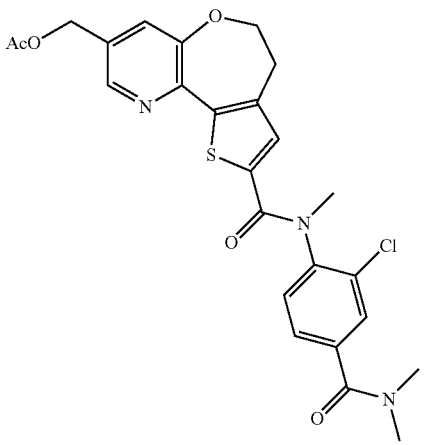 [SMILES: CC(=O)OCc1cnc2c(c1)OCCc1cc(C(=O)N(C)c3ccc(C(=O)N(C)C)cc3Cl)sc1-2]

To a solution of 3-tert-butyldimethylsilyloxymethyl-9-ethylcarboxy-6,7-dihydropyrido[3,2-b]thieno[2,3-d]oxepine (0.100 g, 0.238 mmol) in tetrahydrofuran (0.715 mL, 8.82 mmol) and water (0.715 mL, 39.7 mmol) was added 1.00 M of lithium hydroxide in water (0.715 mL). The reaction mixture was stirred at room temperature overnight. The reaction mixture was concentrated and the residue was acidified with 1M HCl then extracted with EtOAc (3×). The combined organics were dried (Na₂SO₄), filtered and concentrated to give 3-tert-butyldimethylsilyloxymethyl-9-carboxy-6,7-dihydropyrido[3,2-b]thieno[2,3-d]oxepine to which was added 5 ml DCM, triethylamine (0.166 mL, 1.19 mmol) and acetic anhydride (0.112 mL, 1.19 mmol). The reaction was stirred at room temperature 1 h. The reaction was quenched with NaHCO₃, washed with EtOAc. The organic layer was acidified 1M HCl extracted EtOAc (3×). The combined organics were dried (Na₂SO₄), filtered and concentrated to give 3-acetoxymethyl-9-carboxy-6,7-dihydropyrido[3,2-b]thieno[2,3-d]oxepine which was dissolved in 5 ml DCM. A solution of 2.0 M oxalyl chloride in methylene chloride (DCM, 0.357 mL) and 1 drop of DMF was added. The reaction was stirred at room temperature 2 h. The reaction was concentrated to give 3-acetoxymethyl-9-chlorocarbonyl-6,7-dihydropyrido[3,2-b]thieno[2,3-d]oxepine which was dissolved in 5 ml acetonitrile. 3-Chloro-N,N-dimethyl-4-(methylamino)benzamide (0.101 g, 0.477 mmol;) and sodium bicarbonate (0.040 g, 0.47 mmol) were added. The reaction was stirred at room temperature overnight. The reaction was quenched water, extracted three times with ethyl acetate, and concentrated. The crude product was purified by flash chromatography (50-100% EtOAc/Hex) (product eluted at 100% EtOAc, sm at 75% EtOAc) to give N-(2-chloro-4-(dimethylcarbamoyl)phenyl)-N-methyl-(3-acetoxymethyl-6,7-dihydropyrido[3,2-b]thieno[2,3-d]oxepine)-9-carboxamide (41%). MS: (ESI+) 514.3

To a solution of N-(2-chloro-4-(dimethylcarbamoyl)phenyl)-N-methyl-(3-acetoxymethyl-6,7-dihydropyrido[3,2-b]thieno[2,3-d]oxepine)-9-carboxamide (0.050 g, 0.097 mmol;) in tetrahydrofuran (2.28 mL, 28.0 mmol) and water (2.28 mL, 126 mmol) was added lithium hydroxide, monohydrate (0.0163 g, 0.389 mmol). The reaction mixture was stirred at room temperature overnight. The reaction mixture was concentrated and acidified with 1M HCl then extracted with DCM (3×). The combined organics were dried (Na₂SO₄), filtered and concentrated. The crude product was purified by flash chromatography EtOAc/Hex (0-100%) (eluted at 80%) to give 309 (87%). MS: (ESI+) 472.1

Example 220

N-(2-chlorophenyl)-N-methyl-8-(1H-pyrazol-5-yl)-4,5-dihydrobenzo[b]thieno[2,3-d]oxepine-2-carboxamide 310

Following the procedure in Example 93, 8-bromo-N-(2-chlorophenyl)-N-methyl-4,5-dihydrobenzo[b]thieno[2,3-d]oxepine-2-carboxamide was coupled with 5-(4,4,5,5-tetramethyl-1,3,2-dioxaborolan-2-yl)-1H-pyrazole to give 310. MS (ESI) 436.1

Example 221

2-(4-(2-chlorophenyl)-4H-1,2,4-triazol-3-yl)-N—((R)-2-hydroxypropyl)-4,5-dihydrobenzo[b]thieno[2,3-d]oxepine-8-carboxamide 311

2-(4-(2-Chlorophenyl)-4H-1,2,4-triazol-3-yl)-4,5-dihydrobenzo[b]thieno[2,3-d]oxepine-8-carbonyl chloride and (R)-1-aminopropan-2-ol gave 311. MS (ESI) 481.3

Example 222

2-(4-(2-chlorophenyl)-4H-1,2,4-triazol-3-yl)-N-(2-hydroxyethyl)-4,5-dihydrobenzo[b]thieno[2,3-d]oxepine-8-carboxamide 312

2-(4-(2-Chlorophenyl)-4H-1,2,4-triazol-3-yl)-4,5-dihydrobenzo[b]thieno[2,3-d]oxepine-8-carbonyl chloride and 2-aminoethanol gave 312. MS (ESI) 467.3

Example 223

4-(2-chlorophenyl)-3-(4,5-dihydrobenzo[b]thieno[2,3-d]oxepin-2-yl)-4H-1,2,4-triazole 313

Hydrogenation of 3-(8-bromo-4,5-dihydrobenzo[b]thieno[2,3-d]oxepin-2-yl)-4-(2-chlorophenyl)-4H-1,2,4-triazole using 5% Pd on carbon in ethanol under 1 atmosphere of hydrogen gave 313 after filtration, concentration and purification by reverse-phase HPLC. MS (ESI) 380.1

Example 224

8-bromo-2-[4-(2-chloro-phenyl)-4H-[1,2,4]triazol-3-yl]-4,5-dihydro-6-oxa-3-thia-1-aza-benzo[e]azulene 314

To a solution of 8-bromo-4,5-dihydro-6-oxa-3-thia-1-aza-benzo[e]azulene-2-carboxylic acid ethyl ester from Example 21 (518 mg) in tetrahydrofuran (10 ml) was added a solution of sodium hydroxide (117 mg) in water (2 mL) Methanol (5 mL) was also added to aid dissolution. After 2 hours, the reaction mixture was acidified with HCl (2M) and the reaction mixture was then extracted with dichloromethane, dried (MgSO$_4$) and the solvent removed in vacuo to yield 8-bromo-4,5-dihydro-6-oxa-3-thia-1-aza-benzo[e]azulene-2-carboxylic acid.

To a suspension of 8-bromo-4,5-dihydro-6-oxa-3-thia-1-aza-benzo[e]azulene-2-carboxylic acid (396 mg) in dry dichloromethane (20 mL) was added oxalyl chloride (180 μL) and DMF (1 drop). After 3 hours the solvent was removed in vacuo and to the residue was added acetonitrile (20 mL), 2-chloroaniline (140 μL) and sodium bicarbonate (111 mg). After 3 hours, water was added to the reaction mixture and the resulting precipitate was collected by filtration to yield 8-bromo-4,5-dihydro-6-oxa-3-thia-1-aza-benzo[e]azulene-2-carboxylic acid (2-chloro-phenyl)-amide (467 mg).

A mixture of 8-bromo-4,5-dihydro-6-oxa-3-thia-1-aza-benzo[e]azulene-2-carboxylic acid (2-chloro-phenyl)-amide (260 mg), Lawesson's reagent (193 mg) and toluene (10 mL) was heated to reflux. After 5 hours, the reaction mixture was cooled and the precipitate was collected by filtration to yield the corresponding thioamide, 8-bromo-4,5-dihydro-6-oxa-3-thia-1-aza-benzo[e]azulene-2-carbothioic acid (2-chloro-phenyl)-amide (160 mg).

A mixture of 8-bromo-4,5-dihydro-6-oxa-3-thia-1-aza-benzo[e]azulene-2-carbothioic acid (2-chloro-phenyl)-amide (160 mg), methanol (10 mL) and hydrazine hydrate (170 μL) was heated to reflux for 6 hours. The reaction mixture was then cooled and the solid collected by filtration. A mixture of this solid (144 mg) and triethyl orthoformate (5 mL) was heated to 90° C. for 2 hours and then to 130° C. for 2 hours. The reaction mixture was then cooled and the solvent removed in vacuo and the residue purified using flash chromatography to yield 314 (55 mg). NMR: (CDCl3): 3.32 (2H, t), 4.36 (2H, t), 6.96 (1H, dd), 7.11-7.16 (2H, m), 7.49-7.68 (4H, m), 8.30 (1H, s). MS: (ESI+) MH+ 461

Example 225

N-(2-chlorophenyl)-N-methyl-(8-amino-4,5-dihydro-pyrido-[4,3-b]thieno[2,3-d]oxepin-2)-carboxamide 315

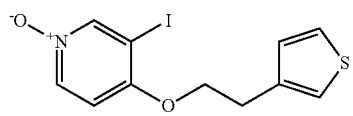

m-Chloroperbenzoic acid (1.55 g, 6.29 mmol) was added portionwise to a solution of 1.0 g (3.02 mmol) of 3-iodo-4-(2-(thiophen-3-yl)ethoxy)pyridine in 150 ml of methylene chloride. The mixture was stirred for 18 hours then mixed with 100 ml of 1 M aqueous sodium carbonate. The organic layer was separated and the aqueous one was extracted 2 times with 10 ml of methylene chloride. Combined organic extracts were washed with brine and dried over sodium sulfate. The solution was concentrated in vacuum to give 3-iodo-4-(2-(thiophen-3-yl)ethoxy)pyridine 1-oxide (1.01 g, 92%). MS: (ESI+) 348.0

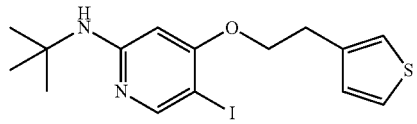 [SMILES: CC(C)(C)Nc1cc(OCCc2ccsc2)c(I)cn1]

A solution of p-toluenesulfonic anhydride (1.47 g, 4.49 mmol) in 15 ml of chloroform was added dropwise to a stirred mixture of 0.78 g (2.25 mmol) of 3-iodo-4-(2-(thiophen-3-yl)ethoxy)pyridine 1-oxide and 1.18 ml (11.2 mmol) of tert-butylamine in 15 ml of chloroform at 0° C. After 30 minutes, the addition of the same quantities of p-toluenesulfonic anhydride and tert-butylamine was repeated to complete the reaction. The reaction mixture was concentrated and partitioned between 100 ml of diethylether and 1 M aqueous sodium carbonate. The aqueous layer was extracted with 50 ml of diethylether again and combined organic extracts were washed with water, brine, dried over sodium sulfate and concentrated in vacuum. The residue was purified by flash chromatography eluting with 10% of ethyl acetate in hexane to give N-tert-butyl-5-iodo-4-(2-(thiophen-3-yl)ethoxy)pyridin-2-amine (0.473 g, 52%). $^1$H NMR (400 MHz, CDCl3) δ 8.15 (s, 1H), 7.28 (dd, J=3.0, 4.8, 1H), 7.18 (s, 1H), 7.12 (d, J=4.9, 1H), 5.85 (s, 1H), 4.44 (s, 1H), 4.15 (t, J=6.5, 2H), 3.18 (t, J=6.5, 2H), 1.39 (s, 9H). MS: (ESI+) 403.2

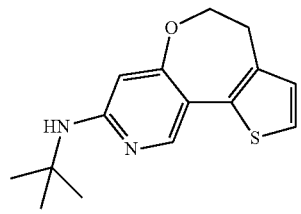 [SMILES: CC(C)(C)Nc1cc2c(cn1)-c1sccc1CCO2]

Following Scheme 4, N-tert-butyl-5-iodo-4-(2-(thiophen-3-yl)ethoxy)pyridin-2-amine was cyclized in the presence of palladium (II) acetate and triphenylphosphine to give N-tert-butyl-4,5-dihydropyrido[4,3-b]thieno[2,3-d]oxepin-8-amine (42%). $^1$H NMR (400 MHz, CDCl$_3$) δ 8.44 (s, 1H), 7.04 (d, J=5.2, 1H), 6.81 (d, J=5.2, 1H), 6.07 (s, 1H), 4.59 (s, 1H), 4.35-4.29 (m, 2H), 3.21-3.07 (m, 2H), 1.42 (s, 9H). MS: (ESI+) 275.1

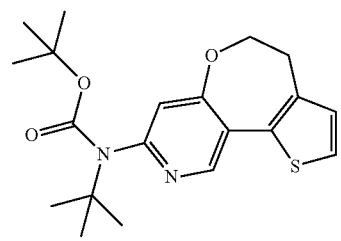 [SMILES: CC(C)(C)OC(=O)N(c1cc2c(cn1)-c1sccc1CCO2)C(C)(C)C]

A mixture of N-tert-butyl-4,5-dihydropyrido[4,3-b]thieno[2,3-d]oxepin-8-amine (115 mg, 0.42 mmol) and di-tertbutyldicarbonate (275 mg, 1.26 mmol) in 3 ml of tert-butyl alcohol was heated at 80° C. for 4 hours. The mixture was concentrated in vacuum, and the residue was purified by flash chromatography eluting with 10% ethyl acetate in hexane to give tert-butyl tert-butyl(4,5-dihydropyrido[4,3-b]thieno[2,3-d]oxepin-8-yl)carbamate (120 mg, 76%). $^1$H NMR (500 MHz, CDCl3) δ 8.80 (s, 1H), 7.26 (s, 1H), 7.23 (d, J=5.1, 1H), 6.90 (d, J=5.2, 1H), 6.69 (s, 1H), 4.39 (t, J=4.8, 2H), 3.25 (t, J=4.8, 2H), 1.40 (s, 9H), 1.37 (s, 9H). MS: (ESI+) 375.4

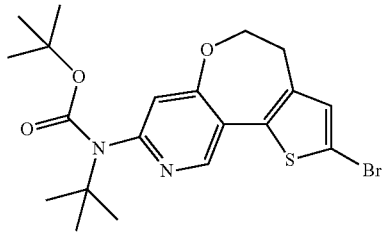 [SMILES: CC(C)(C)OC(=O)N(c1cc2c(cn1)-c1sc(Br)cc1CCO2)C(C)(C)C]

A solution of N-bromosuccinimide (59 mg, 0.33 mmol) in 1 ml of dimethylformamide was added dropwise to a solution of tert-butyl tert-butyl(4,5-dihydropyrido[4,3-b]thieno[2,3-d]oxepin-8-yl)carbamate (120 mg, 0.32 mmol) in 2 ml of dimethylformamide (DMF). The reaction mixture was stirred for 18 hours, concentrated in vacuum and partitioned between water and ethyl acetate. The organic layer was washed with water, brine, dried over sodium sulfate and concentrated in vacuum to give tert-butyl 2-bromo-4,5-dihydropyrido[4,3-b]thieno[2,3-d]oxepin-8-yl(tert-butyl)carbamate which was used in the next step without further purification. MS: (ESI+) 453.2

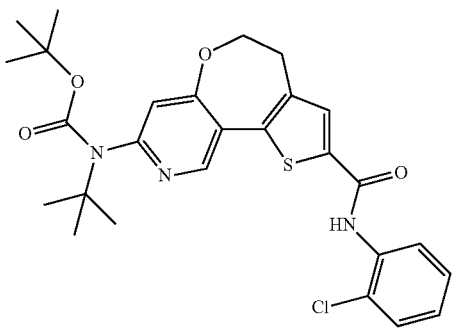 [SMILES: CC(C)(C)OC(=O)N(c1cc2c(cn1)-c1sc(C(=O)Nc3ccccc3Cl)cc1CCO2)C(C)(C)C]

Following Scheme 4, tert-butyl 2-bromo-4,5-dihydropyrido[4,3-b]thieno[2,3-d]oxepin-8-yl(tert-butyl)carbamate and 2-chlorophenylisocyanate were reacted to give tert-Butyl tert-butyl(2-(2-chlorophenylcarbamoyl)-4,5-dihydropyrido[4,3-b]thieno[2,3-d]oxepin-8-yl)carbamate (61%). MS: (ESI+) 528.2

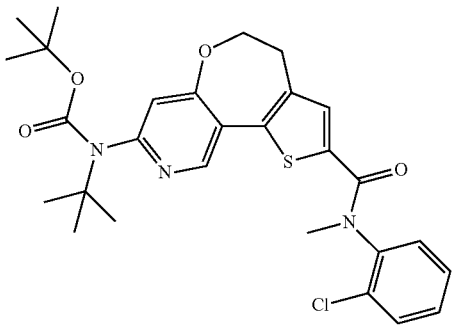 [SMILES: CN(C(=O)c1cc2c(s1)-c1cnc(N(C(=O)OC(C)(C)C)C(C)(C)C)cc1OCC2)c1ccccc1Cl]

Following Scheme 4, tert-butyl tert-butyl(2-(2-chlorophenylcarbamoyl)-4,5-dihydropyrido[4,3-b]thieno[2,3-d]oxepin-8-yl)carbamate, methyl iodide and sodium hydride were reacted to give tert-butyl tert-butyl(2-(2-chlorophenyl)(methyl)carbamoyl)-4,5-dihydropyrido[4,3-b]thieno[2,3-d]oxepin-8-yl)carbamate (78%). MS: (ESI+) 542.3

A solution of 0.10 g (0.185 mmol) of tert-butyl tert-butyl (2-((2-chlorophenyl)(methyl)carbamoyl)-4,5-dihydropyrido[4,3-b]thieno[2,3-d]oxepin-8-yl)carbamate in 3 ml of trifluoroacetic acid was stirred at room temperature for 30 min and then heated at 70° C. for 45 min. The mixture was concentrated in vacuum the residue triturated with ethyl ether, the precipitate filtered out and washed with ethyl ether. The resulting trifluoroacetate salt was converted to a free base by partitioning between saturated aqueous sodium bicarbonate solution and ethyl acetate. Ethyl acetate extract was washed with water, brine, dried over sodium sulfate and concentrated to give 315 (46 mg, 63%). $^1$H NMR (500 MHz, DMSO) δ 8.01 (s, 1H), 7.67 (d, J=9.4, 1H), 7.63 (d, J=8.6, 1H), 7.56-7.48 (m, 2H), 6.47 (s, 1H), 6.21 (s, 2H), 5.94 (s, 1H), 4.14 (s, 2H), 3.26 (s, 3H), 2.87 (s, 2H). MS: (ESI+) 386.1

Example 226

N-(2-chlorophenyl)-N-methyl-(8-acetamino-4,5-dihydropyrido-[4,3-b]thieno[2,3-d]oxepin-2)-carboxamide 316

A mixture of N-(2-chlorophenyl)-N-methyl-(8-amino-4,5-dihydropyrido-[4,3-b]thieno[2,3-d]oxepin-2)-carboxamide 315 (18 mg, 0.047 mmol) in 3 ml of acetic anhydride was heated at 75° C. for 45 min. The mixture was concentrated in vacuum, the residue redissolved in 3 ml of methanol and mixed with 0.3 ml of 28% aqueous ammonia. In 5 min the mixture was poured in 5 ml of water and extracted with ethyl acetate. The organic extract was washed with water, brine, dried over sodium sulfate and concentrated under vacuum. The residue was purified by flash chromatography eluting with 50% ethyl acetate in hexane to give 316 (13 mg, 65%). $^1$H NMR (500 MHz, DMSO) δ 10.59 (s, 1H), 8.35 (s, 1H), 7.71-7.62 (m, 3H), 7.58-7.49 (m, 2H), 6.42 (s, 1H), 4.25 (s, 2H), 3.27 (s, 3H), 2.93 (s, 2H), 2.08 (s, 3H). MS: (ESI+) 428.1

Example 227

N-(2-chloro-4-(piperazine-1-carbonyl)phenyl)-N-(2-hydroxyethyl)-4,5-dihydrobenzo[b]thieno[2,3-d]oxepine-2-carboxamide 317

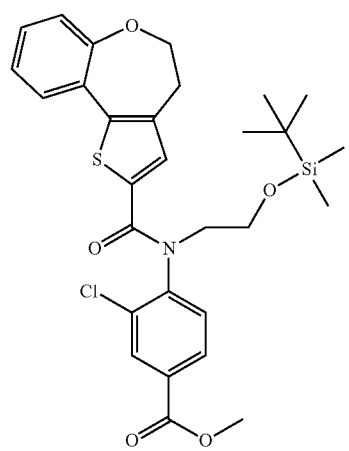 [SMILES: COC(=O)c1ccc(N(CCO[Si](C)(C)C(C)(C)C)C(=O)c2cc3c(s2)-c2ccccc2OCC3)c(Cl)c1]

To a soln. of methyl 3-chloro-4-(2-(tert-butyldimethylsilyloxy)ethylamino)benzoate (1.3 g 3.78 mmol) pretreated with 1M of sodium hexamethyldisilazine in THF (3.46 ml) in tetrahydrofuran (12.2 ml) was added at room temperature 4,5-dihydrobenzo[b]thieno[2,3-d]oxepine-2-carbonyl chloride (1.00 g, 3.79 mmol) portion-wise. The reaction mixture was stirred at room temperature under nitrogen for 1 hour. The reaction mixture was concentrated in vacuo and the residue taken into ethyl acetate and washed with water, then saline and dried (Na$_2$SO$_4$) to give 1.37 grams of crude methyl 4-(N-(2-(tert-butyldimethylsilyloxy)ethyl)-4,5-dihydrobenzo[b]thieno[2,3-d]oxepine-2-carboxamido)-3-chlorobenzoate. MS: (ESI+)=572.1

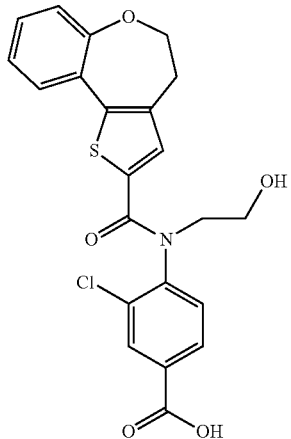 [SMILES: O=C(O)c1ccc(N(CCO)C(=O)c2cc3c(s2)-c2ccccc2OCC3)c(Cl)c1]

A solution of methyl 4-(N-(2-(tert-butyldimethylsilyloxy)ethyl)-4,5-dihydrobenzo[b]thieno[2,3-d]oxepine-2-carboxamido)-3-chlorobenzoate (1.37 grams, 2.39 mmol) and lithium hydroxide (0.229 g, 0.68 mmol) in 5 mL of water and 20 mL of THF was stirred at room temperature to give the expected carboxylic acid as determined by LC/MS (59025-71). The reaction mixture was stripped of THF and diluted with water, and acidified with conc. HCl. This aqueous solution was extracted with ethyl acetate and the organics washed with water, washed with saline and concentrated in vacuo to a solid. This solid material was taken into 20 mL of THF and acetic acid was added (0.135 mL, 2.4 mmol). Next, 1M TBAF in THF was added to the reaction mixture via syringe and the solution was stirred overnight at room temperature. The reaction mixture was then diluted with a large volume of ethyl acetate. This solution was washed with water, then saline and dried (Na$_2$SO$_4$), then concentrated in vacuo to a solid. The crude material was purified by MPLC on a 120 g silica column, eluting with 20-90% ethyl acetate/hexanes to 1 gram of 3-chloro-4-(N-(2-hydroxyethyl)-4,5-dihydrobenzo[b]thieno[2,3-d]oxepine-2-carboxamido)benzoic acid. Yield=90% of theoretical. MS: (ESI+)=443.1

To a solution of 3-chloro-4-(N-(2-hydroxyethyl)-4,5-dihydrobenzo[b]thieno[2,3-d]oxepine-2-carboxamido)benzoic acid (0.100 g, 0.225 mmol) in 1 mL of THF was added as a whole HATU (0.094 g, 0.248 mmol) and DIEA (0.078 mL, 0.450 mmol). This reaction mixture was allowed to stir at room temperature for 30 minutes. Next, tert-butyl piperazine-1-carboxylate (0.12 g, 0.22 mmol) was added to the reaction mixture and stirred at room temperature for 1 hour. The reaction mixture was taken into a large volume of ethyl acetate, washed with water, then saline and dried (Na$_2$SO$_4$). The organic was then conc. in vacuo to a solid residue and purified by RP-HPLC to give tert-butyl 4-(3-chloro-4-(N-(2-hydroxyethyl)-4,5-dihydrobenzo[b]thieno[2,3-d]oxepine-2-carboxamido)benzoyl)piperazine-1-carboxylate.

A solution of tert-butyl 4-(3-chloro-4-(N-(2-hydroxyethyl)-4,5-dihydrobenzo[b]thieno[2,3-d]oxepine-2-carboxamido)benzoyl)piperazine-1-carboxylate (0.04 g, 0.6 mmol) in 0.500 ml of DCM was treated with TFA (0.1 g, 1 mmol) at room temperature with TLC monitor for loss of starting material. The reaction was complete after 1 hour. The reaction mixture was conc. in vacuo to 317 as a solid, purified by RP-HPLC, Yield=22% of theoretical. MS: (ESI+)=512.5

Example 228

N-(2-chlorophenyl)-N-methyl-8-(3-methyl-1H-pyrazol-4-yl)-4,5-dihydrobenzo[b]thieno[2,3-d]oxepine-2-carboxamide 318

Following the procedure in Example 93, 8-bromo-N-(2-chlorophenyl)-N-methyl-4,5-dihydrobenzo[b]thieno[2,3-d]oxepine-2-carboxamide was coupled with 5-methyl-4-(4,4,5,5-tetramethyl-1,3,2-dioxaborolan-2-yl)-1H-pyrazole to give 318. MS (ESI) 450.1

Example 229

5-(6,7-dihydropyrido[3,2-b]thieno[2,3-d]oxepin-9-yl)pyridin-2-methylamine 319

A mixture of 80 mg (0.3 mmol) of 9-bromo-6,7-dihydropyrido[3,2-b]thieno[2,3-d]oxepine, 78.3 (0.34 mmol), 2-cyanopyridine-5-boronic acid pinacole ester, and 10 mg (0.014 mmol) of bis(triphenylphosphine)palladium (II) chloride in 0.35 ml (0.35 mmol) of aqueous 1 M solution of sodium carbonate and 4 ml of acetonitrile was degassed and microwaved on 200 Wt at 140° C. for 30 min. the reaction mixture was filtered through celite and partitioned between ethyl acetate and water. The organic layer was washed with water, brine dried over sodium sulfate and concentrated in vacuum. The residue was purified on a 4 g silica column eluting with 10% of methanol in dichloromethane to give 5-(6,7-dihydropyrido[3,2-b]thieno[2,3-d]oxepin-9-yl)pyridin-2-nitrile. Yield 27 mg (30%). MS: (ESI+) 306.1

A solution of 25 mg (0.082 mmol) of 5-(6,7-dihydropyrido[3,2-b]thieno[2,3-d]oxepin-9-yl)pyridin-2-nitrile in 3 ml of acetic acid and 3 ml of tetrahydrofuran was subjected to hydrogenation over 40 mg of 5% palladium on charcoal for 4 hours. The catalyst was filtered off, the mother liquor was concentrated in vacuum. The residue was triturated with ethyl ether afforded a precipitate which was collected and dried in vacuum to give 319. Yield 24 mg (79%). MS: (ESI+) 310.0. $^1$H NMR (400 MHz, DMSO) δ 8.82 (s, 1H), 8.25 (dd, J=4.4, 1.1, 1H), 8.06 (dd, J=8.1, 1.9, 1H), 7.50 (d, J=9.9, 2H), 7.42 (dd, J=8.1, 1.1, 1H), 7.23 (dd, J=8.1, 4.5, 1H), 4.35 (t, J=4.6, 1H), 3.86 (s, 2H), 3.24 (t, J=4.6, 2H).

Example 230

3-(4,5-dihydropyrido[4,3-b]thieno[2,3-d]oxepin-2-yl)-4-(2-chlorophenyl)-4H-1,2,4-triazole 320

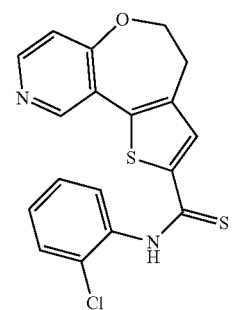 [SMILES: S=C(Nc1ccccc1Cl)c1cc2c(s1)-c1cnccc1OCC2]

Following Scheme 4,2-bromo-4,5-dihydropyrido[4,3-b]thieno[2,3-d]oxepin and 2-chlorophenylisothiocyanate were reacted to give N-(2-chlorophenyl)-4,5-dihydropyrido[4,3-b]thieno[2,3-d]oxepine-2-carbothioamide (66%). MS: (ESI+) 357.0

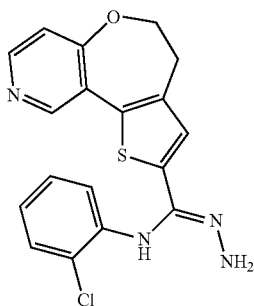 [SMILES: N/N=C(\Nc1ccccc1Cl)c1cc2c(s1)-c1cnccc1OCC2]

Hydrazine (0.32 ml, 10 mmol) was added to a suspension of N-(2-chlorophenyl)-4,5-dihydropyrido[4,3-b]thieno[2,3-d]oxepine-2-carbothioamide (90 mg, 0.2 mmol) in 3 ml of methanol and the reaction mixture was stirred for 24 hour. The precipitate was filtered, washed with methanol and dried in vacuum to give N-(2-chlorophenyl)-4,5-dihydropyrido[4,3-b]thieno[2,3-d]oxepine-2-carbohydrazonamide (94 mg, 90%). MS: (ESI+)=371.1

A mixture of N-(2-chlorophenyl)-4,5-dihydropyrido[4,3-b]thieno[2,3-d]oxepine-2-carbohydrazonamide (44 mg, 0.12 mmol) and 3 ml of triethylorthoformate was heated at 85° C. for 4 hours. The mixture was concentrated in vacuum and triturated with diethylether. The precipitate was collected, washed with diethylether and purified by flash chromatography eluting with 60% of ethyl acetate in hexane to give 320 (17 mg, 38%). MS: (ESI+) 381.1

Example 231

3-(4,5-dihydropyrido[4,3-b]thieno[2,3-d]oxepin-2-yl)-4-(2-chlorophenyl)-1H-1,2,4-triazol-5(4H)-one 321

A mixture of N-(2-chlorophenyl)-4,5-dihydropyrido[4,3-b]thieno[2,3-d]oxepine-2-carbohydrazonamide (42 mg, 0.11 mmol) from Example 230 and 92 mg (0.57 mmol) of N,N-carbonyldiimidazole in 3 ml of dimethylformamide was heated at 65° C. for 18 hours. The mixture was concentrated in vacuum and triturated with diethylether. The precipitate was collected, washed with ethyl ether and purified by flash chromatography eluting with 5% of methanol in methylene chloride to give 321 (14 mg, 31%). MS: (ESI+) 397.0

Example 232

N-(4-carbamoyl-2-chlorophenyl)-N-(2-hydroxyethyl)-4,5-dihydrobenzo[b]thieno[2,3-d]oxepine-2-carboxamide 322

To a solution of 3-chloro-4-(N-(2-hydroxyethyl)-4,5-dihydrobenzo[b]thieno[2,3-d]oxepine-2-carboxamido)benzoic acid, from Example 227, (0.08 g, 0.20 mmol) in 72 mL of THF was added as a whole HATU (0.082 g, 0.22 mmol) and DIEA (0.12 mL, 0.72 mmol). This reaction mixture was allowed to stir at room temperature for 30 minutes. Next, ammonium chloride (0.12 g, 0.22 mmol) was added to the reaction mixture and stirred at room temperature for 1 hour. The reaction mixture was taken into a large volume of ethyl acetate, washed with water, then saline and dried (Na$_2$SO$_4$). The organic was then concentrated in vacuo to give 322 as a solid residue, purified by RP-HPLC. Yield=25% of theoretical. MS: (ESI+)=442.1

Example 233

N2-(2,4-dichlorophenyl)-N2,N8-dimethyl-4,5-dihydrobenzo[b]thieno[2,3-d]oxepine-2,8-dicarboxamide 323

Example 234

4-(4,5-dihydropyrido[4,3-b]thieno[2,3-d]oxepin-2-yl)-5-(2-chlorophenyl)-2H-1,2,3-triazole 324

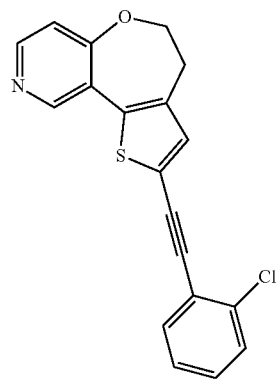 [SMILES: Clc1ccccc1C#Cc1cc2c(s1)-c1cnccc1OCC2]

A mixture of 2-bromo-4,5-dihydropyrido[4,3-b]thieno[2,3-d]oxepine (140 mg, 0.5 mmol) from Example 72, 1-chloro-2-ethynylbenzene, 18 mg (0.025 mmol) of bistriphenylphosphinepalladium(II) chloride and 1 ml (7.17 mmol) of triethylamine in 4 ml of acetonitrile was degassed. Copper (I) iodide (2.4 mg, 0.012 mmol) was then added and the mixture was heated at 85° C. for 3 hours. The mixture was mixed with 20 ml of water and extracted with 10 ml of ethyl acetate twice. The combined extracts were washed with 1% aqueous ammonia, water, brine and dried over sodium sulfate. The solution was concentrated in vacuum, the residue purified by flash chromatography eluting with 30% ethyl acetate in hexane to give 2-((2-chlorophenyl)ethynyl)-4,5-dihydropyrido[4,3-b]thieno[2,3-d]oxepine (137 mg, 81%). MS: (ESI+) 338.1

A mixture of 68 mg (0.2 mmol) of 2-((2-chlorophenyl)ethynyl)-4,5-dihydropyrido[4,3-b]thieno[2,3-d]oxepine and 52 mg (0.8 mmol) of sodium azide in 4 ml of dimethylsulfoxide was heated at 90° C. for 36 hours. Water (20 ml) was added to the mixture and extracted 6 times with 10 ml of ethyl acetate. The combined organic extracts were washed with water, brine and dried over sodium sulfate. The solvent was removed in vacuum and the crude product was recrystallized from ethyl acetate to give 324 (14 mg, 18%). $^1$H NMR (400 MHz, DMSO) δ 8.68 (s, 1H), 8.24 (d, J=5.5, 1H), 7.73-7.46 (m, 4H), 6.98 (d, J=5.5, 1H), 6.77 (s, 1H), 4.31 (t, J=4.7, 2H), 3.08 (t, J=4.7, 2H). MS: (ESI+) 381.1

Example 235

2-(1-(2-chlorophenyl)-1H-1,2,4-triazol-5-yl)-4,5-dihydrobenzo[b]thieno[2,3-d]oxepine-8-carbonitrile 325

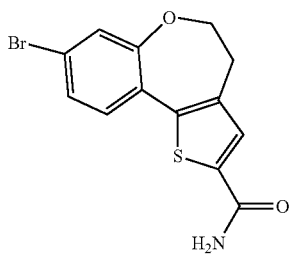 [SMILES: NC(=O)c1cc2c(s1)-c1ccc(Br)cc1OCC2]

8-Bromo-4,5-dihydrobenzo[b]thieno[2,3-d]oxepine-2-carboxamide was suspended in dry toluene and the reaction mixture treated with dimethylformamide dimethylacetal. The whole was heated at 90° C. for about 8 h, cooled to room temperature and concentrated. Crude ¹H NMR indicated clean conversion to the anticipated acylamidine intermediate. (2-Chlorophenyl)hydrazine in acetic acid and water was added to the crude residue in one portion. The whole was sealed and heated at 95° C. to give a bright yellow suspension. LCMS at 8 h indicated significant product formation. The reaction mixture was concentrated, diluted with dichloromethane and saturated sodium bicarbonate and extract with dichloromethane. The combined organics were washed with brine, dried over sodium sulfate, concentrated and the crude residue purified by flash column chromatography to give 5-(8-bromo-4,5-dihydrobenzo[b]thieno[2,3-d]oxepin-2-yl)-1-(2-chlorophenyl)-1H-1,2,4-triazole.

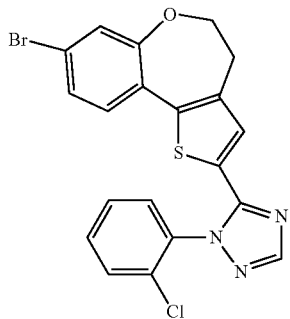 [SMILES: Clc1ccccc1-n1ncnc1-c1cc2c(s1)-c1ccc(Br)cc1OCC2]

Following the procedure in Example 53, 5-(8-bromo-4,5-dihydrobenzo[b]thieno[2,3-d]oxepin-2-yl)-1-(2-chlorophenyl)-1H-1,2,4-triazole was reacted with CuCN in DMF to give 325 as a colorless solid after purification by reverse phase HPLC. MS: (ESI+) 405.1

Example 236

4,5-dihydro-6-oxa-1-thia-3-aza-benzo[e]azulene-2-carboxylic acid (2-chloro-phenyl)-methyl-amide 326

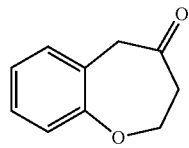

To a solution of 4-chromanone (1 eq, 16.8 mmol, 2.5 g) in anhydrous diethyl ether (70 ml) at 0° C., boron trifluoride diethyl etherate (1.1 eq, 18.6 mmol, 2.4 ml) was added dropwise followed by the dropwise addition of 2M TMS diazomethane in ether (1.1 eq, 18.6 mmol, 9.2 ml), and stirred at 0° C. under N₂ for 1 hr. Saturated NaHCO₃ aq was carefully added (100 ml) and the reaction extracted into diethyl ether, the organic layer was then washed with water before drying over MgSO₄, filtering and absorbing onto silica. The crude material was then purified on the ISCO companion system running a gradient from 0% ethyl acetate/petrol to 20% ethyl acetate/petrol. This gave 2,3-dihydro-5H-benzo[b]oxepin-4-one as a yellow oil (1.15 g, yield 42%).

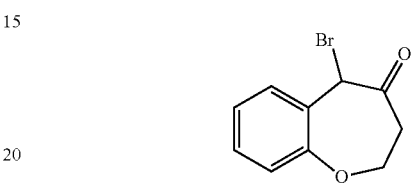

To a solution of 2,3-dihydro-5H-benzo[b]oxepin-4-one (1 eq, 1.6 mmol, 260 mg,), in anhydrous diethyl ether (10 ml), bromine was added dropwise (1.1 eq, 1.76 mmol, 90 ul), and the reaction allowed to stir for an hour. The reaction was absorbed onto silica and purified on the ISCO companion running a gradient from 0% ethyl acetate/petrol to 15% ethyl acetate/petrol, with the product seen at 9% ethyl acetate. This gave 5-bromo-2,3-dihydro-5H-benzo[b]oxepin-4-one as an oil (270 mg, yield 70%).

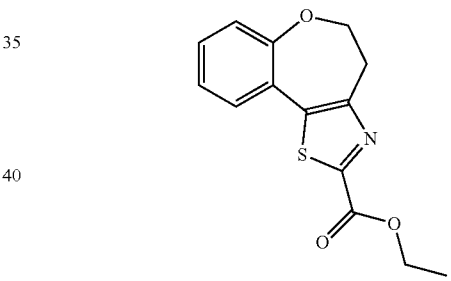

A solution of 5-bromo-2,3-dihydro-5H-benzo[b]oxepin-4-one (1 eq, 4.1 mmol, 1 g), and ethyl thiooxamate (1.5 eq, 6.15 mmol, 818 mg), in ethanol was refluxed for 16 hrs. Reaction cooled and absorbed onto silica and purified on the ISCO companion running a gradient from 0% ethyl acetate/petrol to 40% ethyl acetate/petrol, to give 4,5-dihydro-6-oxa-1-thia-3-aza-benzo[e]azulene-2-carboxylic acid ethyl ester as an oil (530 mg, yield 47%).

A solution of 4,5-dihydro-6-oxa-1-thia-3-aza-benzo[e]azulene-2-carboxylic acid ethyl ester (1 eq, 1.9 mmol, 530 mg), and sodium hydroxide (5 eq, 9.6 mmol, 385 mg), in THF (5 ml) and water (5 ml) was allowed to stir at RT for 3 hrs. Reaction concentrated in vacuo and the solid washed with water to give 4,5-dihydro-6-oxa-1-thia-3-aza-benzo[e]azulene-2-carboxylic acid (290 mg, yield 58%).

To a suspension of 4,5-dihydro-6-oxa-1-thia-3-aza-benzo[e]azulene-2-carboxylic acid (1 eq, 0.38 mmol, 101 mg) in anhydrous DCM (3 ml), 1 drop of DMF was added, followed by 2M oxalyl chloride in DCM (1.7 eq, 0.65 mmol, 330 ul) dropwise. Effervescence was seen and the reaction was stirred at room temperature for 40 mins before evaporating in vacuo. The crude material was dissolved in DCM (3 ml) and 2-chloro-N-methyl aniline (2 eq, 0.76 mmol, 94 ul) was added. The reaction was stirred at room temperature for 16 hr and extracted into DCM, washed with aq K₂CO₃, the organic layer dried over MgSO4, filtered, and purified on silica (ISCO, gradient 0% ethyl acetate/petrol to 25% ethyl acetate/petrol) to give 326 as a white solid (42 mg, yield 30%). $^1$H NMR DMSO, 2.89-2.92 (2H, m), 3.43 (3H, s), 4.23 (2H, br. m), 7.02 (1H, d, J=8.4), 7.08 (1H, t, J=7.6), 7.26 (1H, t, J=8), 7.38-7.41 (2H, m), 7.48-7.51 (2H, m), 7.58 (1H, d, J=8.4). MS: (ESI+): MH+ 371, purity>95%.

Example 237

N-(2-chlorophenyl)-N-methyl-4,5-dihydrobenzo[b]thieno[3,2-d]oxepine-2-carboxamide 327

To a solution of 4-chromanone (9.54 g, 64.3 mmol) in diethyl ether at 0° C. was slowly added boron trifluoride diethyl etherate (16.3 ml, 128.6 mmol), followed by the dropwise addition of 2M TMSCHN₂ in diethyl ether. The mixture was allowed to stir for 1 hour at 0° C. before diluting with sat. sodium bicarbonate solution and diethyl ether. The organic phase was dried, concentrated, and purified on silica to give 2,3-dihydro-5H-benzo[b]oxepin-4-one.

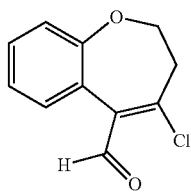 [SMILES: O=CC1=C(Cl)CCOc2ccccc21]

Phosphorus oxychloride (1.4 ml, 15.2 mmol) was added dropwise to anhydrous DMF (5 ml) at 0° C. After 30 minutes a solution of 2,3-dihydro-5H-benzo[b]oxepin-4-one (980 mg, 6.04 mmol) in anhydrous DMF (5 ml) was added dropwise and this was allowed to stir at room temperature for 2 days. The reaction mixture was then added to ice water, and the ice allowed to melt before extracting into ethyl acetate and washing with water and brine to give 4-chloro-2,3-dihydro-benzo[b]oxepine-5-carbaldehyde.

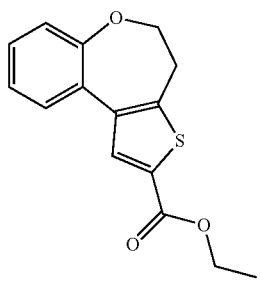 [SMILES: CCOC(=O)c1cc2c(s1)CCOc1ccccc1-2]

To a solution of 4-chloro-2,3-dihydro-benzo[b]oxepine-5-carbaldehyde (605 mg, 5.8 mmol) in dimethyl formamide (8 ml) at 0° C., was added ethyl 2-mercaptoacetate (640 µl, 5.8 mmol) and potassium carbonate (800 mg, 5.8 mmol). The reaction mixture was stirred at room temperature for 30 minutes and then at 70° C. for 2 hours. The reaction mixture was cooled and diluted with water and ethyl acetate, and the organic phase was washed with brine, dried (MgSO₄), and concentrated in-vacuo. Purification on silica gave 4,5-dihydro-6-oxa-3-thia-benzo[e]azulene-2-carboxylic acid ethyl ester.

4,5-Dihydro-6-oxa-3-thia-benzo[e]azulene-2-carboxylic acid ethyl ester was hydrolyzed to its corresponding carboxylic acid to give 4,5-dihydro-6-oxa-3-thia-benzo[e]azulene-2-carboxylic acid, which was coupled with 2-chloro-N-methylaniline. Purification of the crude product on silica gave 327. $^1$H NMR (400 MHz, CDCl3): 3.12 (2H, t), 3.33 (3H, s), 4.22 (2H, t), 9.91-6.96 (2H, m), 7.05-7.09 (1H, m), 7.19-7.24 (1H, m). 7.31-7.36 (3H, m), 7.45-7.49 (1H, m). MS: (ESI+) MH 370

Example 238

2-(1-(2,4-difluorophenyl)-1H-1,2,4-triazol-5-yl)-4,5-dihydrobenzo[b]thieno[2,3-d]oxepine-8-carboxamide 328

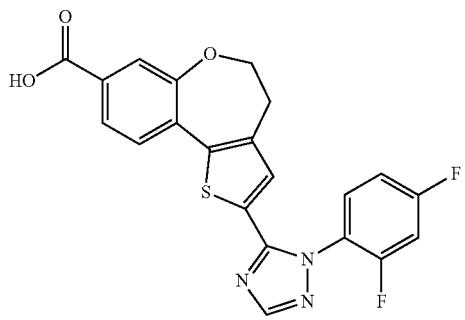 [SMILES: O=C(O)c1ccc2c(c1)OCCc1cc(-c3ncnn3-c3ccc(F)cc3F)sc1-2]

Following the procedures in Examples 47 and 235, 2-(1-(2,4-difluorophenyl)-1H-1,2,4-triazol-5-yl)-4,5-dihydrobenzo[b]thieno[2,3-d]oxepine-8-carboxylic acid was reacted with ammonium chloride, HATU and DIPEA in THF to give 328 as a colorless solid after reverse phase HPLC. MS: (ESI+) 425.0

Example 239

2-(4-(2-chloro-4-(methylcarbamoyl)phenyl)-4H-1,2,4-triazol-3-yl)-N-methyl-4,5-dihydrobenzo[b]thieno[2,3-d]oxepine-8-carboxamide 329

Following the procedures in Examples 47 and 235, 2-(4-(4-carboxy-2-chlorophenyl)-4H-1,2,4-triazol-3-yl)-4,5-dihydrobenzo[b]thieno[2,3-d]oxepine-8-carboxylic acid was reacted with excess methylamine, HATU and DIPEA in THF to give 329 as a colorless solid after reverse phase HPLC. MS: (ESI+) 494.1

Example 240

2-(4-(2-chlorophenyl)-5-oxo-4,5-dihydro-1H-1,2,4-triazol-3-yl)-N-methyl-4,5-dihydrobenzo[b]thieno[2,3-d]oxepine-8-carboxamide 330

Following the procedures in Examples 47 and 235, 2-(4-(2-chlorophenyl)-5-oxo-4,5-dihydro-1H-1,2,4-triazol-3-yl)-4,5-dihydrobenzo[b]thieno[2,3-d]oxepine-8-carboxylic acid was reacted with methylamine, HATU and DIPEA in THF to give 330 as a colorless solid after reverse phase HPLC. MS: (ESI+) 453.0

Example 241

N-(2-acetamidoethyl)-2-(4-(2-chlorophenyl)-5-oxo-4,5-dihydro-1H-1,2,4-triazol-3-yl)-4,5-dihydrobenzo[b]thieno[2,3-d]oxepine-8-carboxamide 331

Following the procedures in Examples 47 and 235, 2-(4-(2-chlorophenyl)-5-oxo-4,5-dihydro-1H-1,2,4-triazol-3-yl)-4,5-dihydrobenzo[b]thieno[2,3-d]oxepine-8-carboxylic acid was reacted with N-(2-aminoethyl)acetamide, HATU and DIPEA in THF to give 331 as a colorless solid after reverse phase HPLC. MS: (ESI+) 524.0

Example 242

N-(2-amino-2-methylpropyl)-2-(4-(2-chlorophenyl)-5-oxo-4,5-dihydro-1H-1,2,4-triazol-3-yl)-4,5-dihydrobenzo[b]thieno[2,3-d]oxepine-8-carboxamide 332

Following the procedures in Examples 47 and 235, 2-(4-(2-chlorophenyl)-5-oxo-4,5-dihydro-1H-1,2,4-triazol-3-yl)-4,5-dihydrobenzo[b]thieno[2,3-d]oxepine-8-carboxylic acid was reacted with 2-methylpropane-1,2-diamine, HATU and DIPEA in THF to give 332 as a colorless solid after reverse phase HPLC. MS: (ESI+) 510.0

Example 243

N8-(2-acetamidoethyl)-N2-(2-chloro-4-(dimethylcarbamoyl)phenyl)-N2-methyl-4,5-dihydrobenzo[b]thieno[2,3-d]oxepine-2,8-dicarboxamide 333

Following the procedures in Examples 47 and 235, 2-((2-chloro-4-(dimethylcarbamoyl)phenyl)(methyl)carbamoyl)-4,5-dihydrobenzo[b]thieno[2,3-d]oxepine-8-carboxylic acid was reacted with N-(2-aminoethyl)acetamide, HATU and DIPEA in THF to give 333 as a colorless solid after reverse phase HPLC. MS: (ESI+) 569.1

Example 244

N2-(2-chloro-4-(dimethylcarbamoyl)phenyl)-N-8-(2-(dimethylamino)ethyl)-N2-methyl-4,5-dihydrobenzo[b]thieno[2,3-d]oxepine-2,8-dicarboxamide 334

Following the procedures in Examples 47 and 235, 2-((2-chloro-4-(dimethylcarbamoyl)phenyl)(methyl)carbamoyl)-4,5-dihydrobenzo[b]thieno[2,3-d]oxepine-8-carboxylic acid was reacted with N1,N1-dimethylethane-1,2-diamine, HATU and DIPEA in THF to give 334 as a colorless solid after reverse phase HPLC. MS: (ESI+) 555.2

Example 245

5-(6,7-dihydropyrido[3,2-b]thieno[2,3-d]oxepin-9-yl)benzen-2-methylamine 335

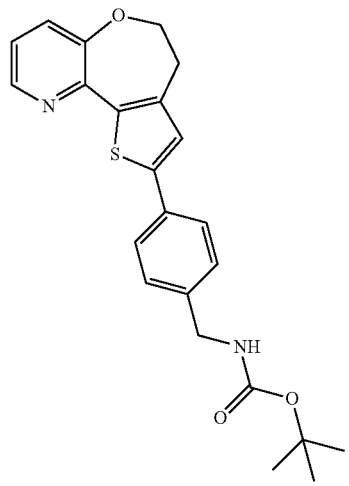 [SMILES: CC(C)(C)OC(=O)NCc1ccc(-c2cc3c(s2)-c2ncccc2OCC3)cc1]

Following Scheme 5,2-bromo-6,7-dihydropyrido[3,2-b]thieno[2,3-d]oxepine and 4-(N-Boc-aminomethyl)-phenylboronic acid were reacted to give tert-butyl 4-(6,7-dihydropyrido[3,2-b]thieno[2,3-d]oxepin-9-yl)benzylcarbamate. MS: (ESI+)=409.1. Hydrogen chloride in dioxane (4 ml, 4 N) was added to a solution of 67 mg (0.16 mmol) of tert-butyl 4-(6,7-dihydropyrido[3,2-b]thieno[2,3-d]oxepin-9-yl)benzylcarbamate in 6 ml of methylene chloride and the mixture was stirred for 2 hours. The precipitate was collected, washed with methylene chloride and ethyl ether and dried in vacuum to give 335 (34 mg, 55%). MS: (ESI+) 309.1.

Example 246

9-cyano-N-(2,4-dichlorophenyl)-N-methyl-4,5-dihydrobenzo[b]thieno[2,3-d]oxepine-2-carboxamide 336

To a solution of 9-cyano-4,5-dihydro-6-oxa-1-thia-benzo[e]azulene-2-carboxylic acid (300 mg) in dichloromethane (10 mL) was added DMF (1 drop) and oxalyl chloride (0.165 mL) and the reaction stirred at room temperature for 30 min. The solvent was then reduced in vacuo and the residue redissolved in acetonitrile (10 mL). To this solution was added 2,4-dichloro-N-methylaniline (0.16 mL) and potassium carbonate (308 mg) and the reaction stirred at room temperature for 16 h. The mixture was partitioned between water (40 mL) and ethyl acetate (30 mL). The organic layer was dried (Na$_2$SO$_4$), reduced in vacuo and purified on silica to give 336. (CDCl3): 3.11 (2H, t), 3.39 (3H, s), 4.32 (2H, t), 6.91 (1H, s), 7.07 (1H, d), 7.32 (1H, d), 7.37-7.44 (2H, m), 7.58 (1H, s), 7.79 (1H, s). MH+ 429:431:433 (3:2:1)

Example 247

3-(8-(pyrazol-4-yl)-4,5-dihydro-6-oxa-1-aza-3-thia-benzo[e]azulen-2-yl)-4-(2-chlorophenyl)-4H-1,2,4-triazole 337

A mixture of 8-bromo-2-[4-(2-chloro-phenyl)-4H-[1,2,4]triazol-3-yl]-4,5-dihydro-6-oxa-3-thia-1-aza-benzo[e]azulene 314 was reacted with 4,4,5,5-tetramethyl-2-(1H-pyrazol-4-yl)-1,3,2-dioxoborolane using Suzuki coupling reaction conditions to yield 337. NMR: (CDCl3): 3.38 (2H, t), 4.39 (2H, t), 6.96 (1H, dd), 7.18 (1H, d), 7.28 (1H, d), 7.51-7.54 (2H, m), 7.61-7.66 (2H, m), 7.85 (2H, s), 8.30 (1H, s). MS: (ESI+) MH+ 447

Example 248

N2-(2-chloro-4-(dimethylcarbamoyl)phenyl)-N-8-(2-hydroxyethyl)-N2-methyl-4,5-dihydrobenzo[b]thieno[2,3-d]oxepine-2,8-dicarboxamide 338

Following the procedures in Examples 47 and 235, 2-((2-chloro-4-(dimethylcarbamoyl)phenyl)(methyl)carbamoyl)-4,5-dihydrobenzo[b]thieno[2,3-d]oxepine-8-carboxylic acid was reacted with 2-aminoethanol, HATU and DIPEA in THF to give 338 as a colorless solid after reverse phase HPLC. MS: (ESI+) 528.0

Example 249

N2-(2-chloro-4-(dimethylcarbamoyl)phenyl)-N-8-isopropyl-N-2-methyl-4,5-dihydrobenzo[b]thieno[2,3-d]oxepine-2,8-dicarboxamide 339

Following the procedures in Examples 47 and 235, 2-((2-chloro-4-(dimethylcarbamoyl)phenyl)(methyl)carbamoyl)-4,5-dihydrobenzo[b]thieno[2,3-d]oxepine-8-carboxylic acid was reacted with isopropylamine, HATU and DIPEA in THF to give 339 as a colorless solid after reverse phase HPLC. MS: (ESI+) 526.1

Example 250

N8-(2-amino-2-methylpropyl)-N2-(2-chloro-4-(dimethylcarbamoyl)phenyl)-N2-methyl-4,5-dihydrobenzo[b]thieno[2,3-d]oxepine-2,8-dicarboxamide 340

Following the procedures in Examples 47 and 235, 2-((2-chloro-4-(dimethylcarbamoyl)phenyl)(methyl)carbamoyl)-4,5-dihydrobenzo[b]thieno[2,3-d]oxepine-8-carboxylic acid was reacted with 2-methylpropane-1,2-diamine, HATU and DIPEA in THF to give 340 as a colorless solid after reverse phase HPLC. MS: (ESI+) 555.3

Example 251

2-(1-(2-chloro-4-(dimethylcarbamoyl)phenyl)-1H-1,2,4-triazol-5-yl)-N-methyl-4,5-dihydrobenzo[b]thieno[2,3-d]oxepine-8-carboxamide 341

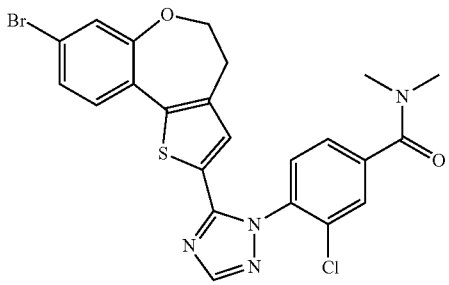 [SMILES: CN(C)C(=O)c1ccc(-n2ncnc2-c2cc3c(s2)-c2ccc(Br)cc2OCC3)c(Cl)c1]

Following the procedure in Example 89 for carbonylative amination, 4-(5-(8-bromo-4,5-dihydrobenzo[b]thieno[2,3-d]oxepin-2-yl)-1H-1,2,4-triazol-1-yl)-3-chloro-N,N-dimethylbenzamide was reacted with methylamine and molybdenum hexacarbonyl to give 341 after reverse phase HPLC. MS: (ESI+) 508.1

Example 252

4-(5-(8-bromo-4,5-dihydrobenzo[b]thieno[2,3-d]oxepin-2-yl)-1H-1,2,4-triazol-1-yl)-3-chloro-N,N-dimethylbenzamide 342

Following the procedure from Example 235, 8-bromo-4,5-dihydrobenzo[b]thieno[2,3-d]oxepine-2-carboxamide was reacted with 3-chloro-4-hydrazinyl-N,N-dimethylbenzamide in acetic acid to give 342 as a colorless solid after purification by flash column chromatography (50-100% ethyl acetate in hexanes). MS: (ESI+) 531.0

Example 253

N-(2-chloro-4-(dimethylcarbamoyl)phenyl)-9-cyano-N-methyl-4,5-dihydrobenzo[b]thieno[2,3-d]oxepine-2-carboxamide 343

3-Chloro-4-methylamino-benzonitrile was prepared by bubbling a stream of methylamine gas was bubbled through a solution of 3-chloro-4-fluorobenzonitrile in acetonitrile. A mixture of 3-chloro-4-methylamino-benzonitrile (1.29 g) was heated to reflux in 2M sodium hydroxide solution (43 mL). After 4 hours the reaction mixture was cooled, and then acidified (HCl, 2N) carefully to pH 5, resulting in a white precipitate which was collected by filtration to yield 3-chloro-4-methylamino-benzoic acid (1.10 g)

To 3-chloro-4-methylamino-benzoic acid (387 mg) in dry N,N-dimethylformamide (10 mL) was added carbonyl diimidazole (440 mg). After one hour, dimethylamine.HCl (221 mg) and triethylamine (0.38 mL) were added. The reaction mixture was stirred overnight, then diluted with ethyl acetate, washed with brine, dried (MgSO$_4$) and the solvent removed in vacuo. Purification using flash chromatography yielded 3-chloro-N,N-dimethyl-4-methylamino-benzamide.

Compound 343 was prepared from the corresponding acid (described previously) and 3-chloro-N,N-dimethyl-4-methylamino-benzamide using General Procedure B. NMR: (CDCl3): 3.10-3.20 (8H, m), 3.39 (3H, s), 4.31 (2H, t), 7.02 (1H, d), 7.19 (1H, s), 7.42 (1H, d), 7.47 (2H, s), 7.63 (2H, s). MS ESI+ 420 (MH+)

Example 254

2-(9-cyano-4,5-dihydro-6-oxa-1-aza-3-thia-benzo[e]azulene)-N-(2-chloro-4-(methylcarbamoyl)phenyl)-N-methyl-carboxamide 344

To a solution of 7-bromo-3,4-dihydro-2H-benzo[b]oxepin-5-one (700 mg) in diethyl ether (20 mL) at 0° C. was added bromine (0.14 mL) dropwise and the reaction was stirred at room temperature for 16 h. The reaction was then quenched with aqueous sodium thiosulfate solution (30 mL) and the product extracted into diethyl ether (2×30 mL) The combined organics were dried (MgSO$_4$), reduced in vacuo and purified on silica to give 4,7-dibromo-3,4-dihydro-2H-benzo[b]oxepin-5-one.

To a solution of 4,7-dibromo-3,4-dihydro-2H-benzo[b]oxepin-5-one (852 mg) in ethanol (20 mL) was added ethyl thiooxamate (1.06 g) and the reaction heated at reflux for 4 days. After cooling to room temperature, the solid was filtered, washed with diethyl ether and air-dried to give 9-bromo-4,5-dihydro-6-oxa-3-thia-1-aza-benzo[e]azulene-2-carboxylic acid ethyl ester.

A mixture of 9-bromo-4,5-dihydro-6-oxa-3-thia-1-aza-benzo[e]azulene-2-carboxylic acid ethyl ester (500 mg), potassium ferrocyanide (dried, 104 mg), copper (I) iodide (27 mg) and 1-butylimidazole (0.37 mL) in toluene (3 mL) was reacted in the microwave at 160° C. for 4 h. The mixture was then partitioned between dichloromethane (30 mL) and water (20 mL). The organic layer was dried (MgSO$_4$), reduced in vacuo and purified on silica to give 9-cyano-4,5-dihydro-6-oxa-3-thia-1-aza-benzo[e]azulene-2-carboxylic acid ethyl ester.

To a suspension of 9-cyano-4,5-dihydro-6-oxa-3-thia-1-aza-benzo[e]azulene-2-carboxylic acid ethyl ester (80 mg) in THF (6 mL) and ethanol (3 mL) was added sodium hydroxide solution (18 mg in 3 mL of water) and the reaction stirred at room temperature for 16 h. The reaction was then acidified with 2M hydrochloric acid and the resulting solid was filtered and air-dried to give 9-cyano-4,5-dihydro-6-oxa-3-thia-1-aza-benzo[e]azulene-2-carboxylic acid.

To a solution of 9-cyano-4,5-dihydro-6-oxa-3-thia-1-aza-benzo[e]azulene-2-carboxylic acid (72 mg) in dichloromethane (10 mL) and DMF (1 drop) was added oxalyl chloride (0.04 mL) and the reaction stirred at room temperature for 3 h. The solvent was then reduced in vacuo and the residue redissolved in acetonitrile (10 mL). Sodium hydrogen carbonate (24 mg) and 3-chloro-N-methyl-4-methylamino-benzamide (58 mg) were added and the reaction stirred at room temperature for 16 h. Water (20 mL) was added and the product extracted into ethyl acetate (2×20 mL). The organics were dried (MgSO$_4$), reduced in vacuo and purified on silica to give 344. NMR: (CDCl$_3$): 2.95 (3H, d, J 4.8, Me), 3.26-3.29 (2H, m), 3.42 (3H, s, Me), 4.21-4.36 (2H, m), 6.85-6.86 (1H, m, NH), 6.94 (1H, d, J 8.4, Ar), 7.29 (1H, dd, J 8.4 and 2.1, Ar), 7.43 (1H, d, J 8.1, Ar), 7.54 (1H, d, J 2.0, Ar), 7.76 (1H, dd, J 8.1 and 1.8, Ar) and 7.93 (1H, d, J 1.7, Ar)

Example 255

2-(1-isopropyl-1H-1,2,4-triazol-5-yl)-4,5-dihydrobenzo[b]thieno[2,3-d]oxepine-8-carboxamide 345

Example 256

N2-(2-chloro-4-(dimethylcarbamoyl)phenyl)-N-8-isobutyl-N-2-methyl-4,5-dihydrobenzo[b]thieno[2,3-d]oxepine-2,8-dicarboxamide 346

Example 257

N2-(2-chloro-4-(dimethylcarbamoyl)phenyl)-N-8-ethyl-N-2-methyl-4,5-dihydrobenzo[b]thieno[2,3-d]oxepine-2,8-dicarboxamide 347

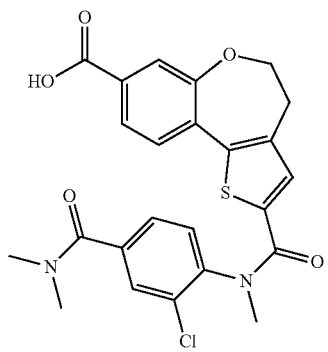

2-((2-Chloro-4-(dimethylcarbamoyl)phenyl)(methyl)carbamoyl)-4,5-dihydrobenzo[b]thieno[2,3-d]oxepine-8-carboxylic acid (0.15 g, 0.31 mmol) was dissolved in SOCl$_2$ (10 mL). The solution was heated at 90-100° C. for 3 hours. Removal of the rest SOCl$_2$ gave the crude product. A solution of the crude acid chloride in THF (12 mL) was treated with a solution of ethanamine (0.14 g, 3.1 mmol) and Pyridine (0.3 mL) in THF (8 mL) at 0° C. The reaction mixture was allowed to reach room temperature and stirred overnight. Concentrated to remove THF to afford the crude product, it was purified by preparative TLC to obtain 347 (48.5 mg, 31%). ESI-MS: 512. $^1$H NMR (CDCl$_3$, 400 MHz): δ7.59 (s, 1H, ArH), 7.44-7.32 (m, 5H, ArH), 6.95 (s, 1H, =CH), 6.12 (s, 1H, NH), 4.23 (t, J=5.0 Hz, 2H, CH$_2$), 3.51-3.44 (m, 2H, CH$_2$), 3.39 (s, 3H, CH$_3$), 3.13 (s, 3H, CH$_3$), 3.05 (t, J=5.0 Hz, 2H, CH$_2$), 3.02 (s, 3H, CH$_3$), 1.24 (t, J=7.2 Hz, 3H, CH$_3$).

Example 258

N2-(2-chloro-4-(dimethylcarbamoyl)phenyl)-N-8-isobutyl-N-2-methyl-4,5-dihydrobenzo[b]thieno[2,3-d]oxepine-2,8-dicarboxamide 348

Following Example 133, compound 348 was prepared with isobutylamine. Yield: 25%. ESI-MS: 540. $^1$H NMR (CDCl$_3$, 400 MHz): δ7.59 (s, 1H, NH), 7.45-7.26 (m, 5H, ArH), 6.94 (s, 1H, ArH), 6.17 (d, J=4.0 Hz, 1H, ArH), 4.24 (t, J=4.8 Hz, 2H, CH$_2$), 3.39 (s, 3H, CH$_3$), 3.28 (t, J=6.0 Hz, 2H, CH$_2$), 3.13 (s, 3H, CH$_3$), 3.06-3.02 (m, 5H, CH$_2$, CH$_3$), 1.91-1.85 (m, 1H, CH), 0.97 (d, J=2.8 Hz, 6H, C(CH$_3$)$_2$)

Example 259

5-(3-methylcarbamoyl-6,7-dihydropyrido[3,2-b]thieno[2,3-d]oxepin-9-yl)pyridin-2-amine 349

Following the procedures for 454, compound 349 was prepared with 9-bromo-6,7-dihydro-pyrido[3,2-b]thieno[2,3-d]oxepine-3-carboxylic acid methylamide and 2-aminopyridine-5-boronic acid pinacole ester. MS: (ESI+) 353.0

Example 260

4-(3-methylcarbamoyl-6,7-dihydropyrido[3,2-b]thieno[2,3-d]oxepin-9-yl)-5-(2-chlorophenyl)-2H-1,2,3-triazole 350

Example 261

N2-(2-chloro-4-(dimethylcarbamoyl)phenyl)-N2-methyl-4,5-dihydrobenzo[b]thieno[2,3-d]oxepine-2,8-dicarboxamide 351

Following Example 257, the acid chloride of 2-((2-Chloro-4-(dimethylcarbamoyl)phenyl)(methyl)carbamoyl)-4,5-dihydrobenzo[b]thieno[2,3-d]oxepine-8-carboxylic acid and ammonia gave 351. Yield: 31%. ESI-MS: 484. $^1$H NMR (CDCl$_3$, 400 MHz): δ7.60 (s, 1H, NH), 7.47-7.37 (m, 5H, ArH), 6.94 (s, 1H, ArH), 6.10 (br, 1H, 0.5 NH$_2$), 5.62 (br, 1H, 0.5NH$_2$), 4.24 (s, 2H, CH$_2$), 3.39 (s, 3H, CH$_3$), 3.13-3.02 (m, 8H, CH$_2$, 2CH$_3$).

Example 262

N8-(2-aminoethyl)-N2-(2-chloro-4-(dimethylcarbamoyl)phenyl)-N2-methyl-4,5-dihydrobenzo[b]thieno[2,3-d]oxepine-2,8-dicarboxamide 352

Following Example 133, compound 352 was prepared with 1,2-diaminoethane. Yield: 28%. ESI-MS: 527. $^1$H NMR (CDCl$_3$, 400 MHz): δ7.66-7.56 (m, 2H, 2NH), 7.40-7.26 (m, 5H, ArH), 6.80 (s, 1H, =CH), 4.10 (s, 2H, CH$_2$), 3.58 (s, 3H, CH$_3$), 3.38-2.93 (m, 13H, 2CH$_2$, 3CH$_3$)

Example 263

N-(2-chloro-4-(2-hydroxypropylcarbamoyl)phenyl)-9-cyano-N-methyl-4,5-dihydrobenzo[b]thieno[2,3-d]oxepine-2-carboxamide 353

Compound 353 was prepared using the standard amide coupling conditions to give a pale yellow solid (80 mg, 10%). δ$_H$ (400 MHz, CDCl$_3$) 1.30 (d, J=6.2, 3H), 2.37 (m, 1H), 3.11 (t, J=4.7, 2H) 3.28 (m, 1H), 3.42 (s, 3H), 3.78 (m, 1H), 4.09 (m, 1H), 4.31 (t, J=4.9H, 2H), 6.69 (m, 1H), 7.06 (m, 2H), 7.41 (dd, 1H), 7.47 (d, J=8.02, 1H), 7.68 (s, 1H), 7.80 (m, 1H), 8.02 (m, 1H). [M+H]$^+$ (406.07).

Example 264

3-(9-bromo-4,5-dihydrobenzo[b]thieno[2,3-d]oxepin-2-yl)-4-(2-chlorophenyl)-4H-1,2,4-triazole 354

Reaction of 2-chloroaniline with 9-bromo-4,5-dihydro-6-oxa-1-thia-benzo[e]azulene-2-carbonyl chloride (prepared from the corresponding carboxylic acid using oxalyl chloride with catalytic N,N-dimethylformamide) yielded 9-bromo-4,5-dihydro-6-oxa-1-thia-benzo[e]azulene-2-carboxylic acid (2-chloro-phenyl)-amide.

A mixture of 9-bromo-4,5-dihydro-6-oxa-1-thia-benzo[e]azulene-2-carboxylic acid (2-chloro-phenyl)-amide (235 mg) and Lawesson's reagent (175 mg) was heated to reflux in o-xylene (10 mL). After heating overnight the reaction mixture was cooled, and ether and hexane were added carefully resulting in the corresponding thioamide precipitating as an orange solid which was collected by filtration (196 mg). A mixture of 9-bromo-4,5-dihydro-6-oxa-1-thia-benzo[e]azulene-2-carbothioic acid (2-chloro-phenyl)-amide (196 mg), methanol (10 mL) and hydrazine hydrate (0.21 mL) was heated to reflux. After 5 hours the reaction mixture was cooled, and the resulting precipitate was collected by filtration. The precipitate (99 mg) was then heated to 90° C. in trimethylorthoformate (5 mL). After 22 hours the reaction mixture was cooled, the volatiles were removed in vacuo and the residue was purified using flash chromatography to yield 354. NMR: (CDCl3): 3.10 (2H, t), 4.30 (2H, t), 6.85-6.90 (2H, d), 7.25 (1H, dd), 7.46-7.72 (5H, m), 8.25 (1H, s). MS. ESI+ 460 (MH+)

Example 265

2-(4-(2-chloro-4-fluorophenyl)-4H-1,2,4-triazol-3-yl)-4,5-dihydrobenzo[b]thieno[2,3-d]oxepine-9-carbonitrile 355

A microwave tube was charged with 3-(9-bromo-4,5-dihydro-6-oxa-1-thia-benzo[e]azulen-2-yl)-4-(2-chloro-4-fluoro-phenyl)-4H-[1,2,4]triazole (0.57 g; 1.2 mmol), K$_4$-[Fe(CN)$_6$] (101 mg; 0.24 mmol), CuI (23 mg; 0.12 mmol), 1-butylimidazole (0.32 ml; 2.4 mmol) and toluene (5 ml). The mixture was flushed with argon and heated in a microwave at 160° C. for 4 h. LCMS shows approx. 40% conversion so the same amount of K$_4$[Fe(CN)$_6$], CuI and 1-butylimidazole was added again and reaction mixture heated in a microwave at 170° C. for a further 4 h. The reaction mixture was partitioned between CH$_2$Cl$_2$ and water, the organic layer was dried (Na$_2$SO$_4$) and purified by ISCO then prep. LCMS to give 355 as a white solid (154 mg; 30%). δ$_H$ (400 MHz, CDCl$_3$) 3.19 (t, J=5.2, 2H), 4.36 (t, J=5.2, 2H), 7.08-7.11 (m, 2H), 7.23-7.32 (m, 1H), 7.43-7.52 (m, 3H), 7.81 (d, J=2.0, 1H), 8.23 (s, 1H). [M+H]$^+$: 423

Example 266

9-bromo-N-(2,4-dichlorophenyl)-N-methyl-4,5-dihydrobenzo[b]thieno[2,3-d]oxepine-2-carboxamide 356

To a solution of 9-bromo-4,5-dihydro-6-oxa-1-thia-benzo[e]azulene-2-carboxylic acid (911 mg) in dichloromethane (20 mL) and DMF (1 drop) was added oxalyl chloride (0.42 mL) and the reaction stirred at room temperature for 3 h. The solvent was then reduced in vacuo and the residue redissolved in acetonitrile. Sodium hydrogen carbonate (259 mg) and 2,4-dichloro-N-methylaniline (546 mg) were added and the reaction stirred at room temperature for 16 h. Water (20 mL) was added and the product extracted into ethyl acetate (2×20 mL). The organics were dried (MgSO$_4$), reduced in vacuo and purified on silica to give 356. NMR: (CDCl$_3$): 2.95-2.98 (2H, m), 3.29 (3H, s, Me), 4.13-4.16 (2H, m), 6.72 (1H, s, Ar), 6.78 (1H, d, J 8.6, Ar), 7.16 (1H, dd, J 8.6 and 2.3, Ar), 7.22 (1H, d, J 8.5, Ar), 7.29 (1H, dd, J 8.4 and 2.2, Ar) and 7.48-7.52 (1H, m, Ar)

Example 267

N-(2-chloro-4-cyanophenyl)-9-cyano-N-methyl-4,5-dihydrobenzo[b]thieno[2,3-d]oxepine-2-carboxamide 357

3-Chloro-4-methylamino-benzonitrile was prepared by bubbling a stream of methylamine gas was bubbled through a solution of 3-chloro-4-fluorobenzonitrile in acetonitrile. Compound 357 was prepared from the corresponding acid (described previously) and 3-chloro-4-methylamino-benzonitrile using General Procedure B. NMR: (CDCl3): 3.05 (2H, t), 3.39 (3H, s), 4.31 (2H, t), 6.80 (1H, s), 7.05 (1H, d), 7.42-7.51 (2H, m), 7.70 (1H, dd), 7.80 (1H, s), 7.88 (1H, s). Analytical trace shows MH+ 420

Example 268

N-(2-chloro-4-(trifluoromethyl)phenyl)-9-cyano-N-methyl-4,5-dihydrobenzo[b]thieno[2,3-d]oxepine-2-carboxamide 358

Compound 358 was prepared using the standard amide coupling conditions to give an off-white solid (94 mg, 37%). δ$_H$ (400 MHz, CDCl$_3$) 3.08 (t, 2H), 3.43 (s, 3H), 4.31 (t, 2H), 8.84 (s, 1H), 7.06 (d, 1H), 7.43 (dd, 1H), 7.52 (d, 1H), 7.67 (d, 1H), 7.77 (s, 1H), 7.84 (s, 1H). [M+H]$^+$ (504.00).

Example 269

N-(2,4-dichlorophenyl)-N-methyl-9-(4-methylpiperazine-1-carbonyl)-4,5-dihydrobenzo[b]thieno[2,3-d]oxepine-2-carboxamide 359

A mixture of 9-bromo-4,5-dihydro-6-oxa-1-thia-benzo[e]azulene-2-carboxylic acid (2,4-dichloro-phenyl)-methyl-amide (1.0 g), molybdenum hexacarbonyl (550 mg), Cataxium C (190 mg), tributylphosphine tetrafluoroborate (120 mg) and 1,8-diazabicycloundec-7-ene (0.90 mL) in methanol (6 mL) and THF (6 mL) was reacted in the microwave at 130° C. for 30 minutes. The mixture was then partitioned between dichloromethane (40 mL) and water (40 mL). The organic layer was dried (MgSO₄), reduced in vacuo and purified on silica to give 2-[(2,4-dichloro-phenyl)-methyl-carbamoyl]-4,5-dihydro-6-oxa-1-thia-benzo[e]azulene-9-carboxylic acid methyl ester.

To a solution of 2-[(2,4-dichloro-phenyl)-methyl-carbamoyl]-4,5-dihydro-6-oxa-1-thia-benzo[e]azulene-9-carboxylic acid methyl ester (700 mg) in THF (8 mL) and ethanol (4 mL) was added sodium hydroxide solution (121 mg in 4 mL of water) and the reaction stirred at room temperature for 16 h. The reaction was then acidified with 2 M hydrochloric acid and the resulting solid was filtered and air-dried to give 2-(2,4-dichloro-phenyl)-methyl-carbamoyl]-4,5-dihydro-6-oxa-1-thia-benzo[e]azulene-9-carboxylic acid.

2-[(2,4-dichloro-phenyl)-methyl-carbamoyl]-4,5-dihydro-6-oxa-1-thia-benzo[e]azulene-9-carboxylic acid and N-methylpiperazine were reacted by General Procedure B to give 359. NMR: (CDCl₃): 2.40 (3H, s, Me), 2.49-2.58 (4H, br m), 3.06-3.09 (2H, m), 3.38 (3H, s, Me), 3.49-3.90 (4H, br m), 4.26-4.29 (2H, m), 6.83 (1H, s, Ar), 7.02 (1H, d, J 8.2, Ar), 7.25 (1H, dd, J 8.3 and 1.9, Ar), 7.31 (1H, d, J 8.4, Ar), 7.37 (1H, dd, J 8.4 and 2.2, Ar) and 7.55-7.57 (2H, m, Ar). MS: (ESI+) MH+=530.13

Example 270

N-(2,4-dichlorophenyl)-9-((3S,5R)-3,5-dimethylpiperazine-1-carbonyl)-N-methyl-4,5-dihydrobenzo[b]thieno[2,3-d]oxepine-2-carboxamide 360

2-[(2,4-Dichloro-phenyl)-methyl-carbamoyl]-4,5-dihydro-6-oxa-1-thia-benzo[e]azulene-9-carboxylic acid and 2,6-dimethylpiperazine were reacted by General Procedure B to give 360. NMR: (CDCl₃): 1.01-1.20 (6H, br m, Me), 2.40-2.62 (2H, br, m), 2.73 (2H, s), 2.82-2.87 (1H, br, m), 2.98-3.00 (2H, m), 3.29 (3H, s, Me), 3.52-3.60 (1H, br m), 4.18-4.21 (2H, m), 4.45-4.55 (1H, br, s, NH), 6.76 (1H, s, Ar), 6.94 (1H, d, J 8.3, Ar), 7.15 (1H, dd, J 8.3 and 1.9, Ar), 7.23 (1H, d, J 8.4, Ar), 7.28 (1H, dd, J 8.5 and 2.2, Ar) and 7.44-7.48 (2H, m, Ar). MS: (ESI+) MH+=544.11

Example 271

N2-(2,4-dichlorophenyl)-N-9-(2-hydroxyethyl)-N2-methyl-4,5-dihydrobenzo[b]thieno[2,3-d]oxepine-2,9-dicarboxamide 361

2-[(2,4-Dichloro-phenyl)-methyl-carbamoyl]-4,5-dihydro-6-oxa-1-thia-benzo[e]azulene-9-carboxylic acid and ethanolamine were reacted by General Procedure B to give 361. NMR: (CDCl₃): 2.70-2.73 (1H, m, OH), 3.04-3.07 (2H, m), 3.38 (3H, s, Me), 3.66-3.70 (2H, m), 3.89-3.91 (2H, m), 4.26-4.29 (2H, m), 6.48-6.51 (1H, m, NH), 6.73 (1H, s, Ar), 7.02 (1H, d, J 8.4, Ar), 7.32 (1H, d, 8.4, Ar), 7.38 (1H, dd, J 8.4 and 2.2, Ar), 7.56-7.61 (2H, m, Ar) and 7.94 (1H, s, Ar). MS: (ESI+) MH+=532.08

Example 272

N-(4-(dimethylcarbamoyl)phenyl)-N-methyl-(2-chloro-6,7-dihydropyrido[3,2-b]thieno[2,3-d]oxepine)-9-carboxamide 362

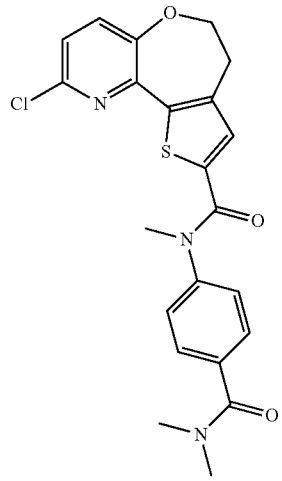 [SMILES: CN(C)C(=O)c1ccc(N(C)C(=O)c2cc3c(s2)-c2nc(Cl)ccc2OCC3)cc1]

To a solution of N-(4-carboxyphenyl)-N-methyl-(2-chloro-6,7-dihydropyrido[3,2-b]thieno[2,3-d]oxepine)-9-carboxamide (0.082 g, 0.20 mmol;) in methylene chloride (2.8 mL, 44 mmol;) was added dimethylamine hydrochloride (0.0322 g, 0.395 mmol;), N,N-diisopropylethylamine (0.344 mL, 1.98 mmol;) then N,N,N',N'-tetramethyl-O-(7-azabenzotriazol-1-yl)uronium hexafluorophosphate (0.150 g, 0.395 mmol). The mixture was stirred at room temperature for 2 h. LCMS indicated the reaction was complete. The reaction was quenched with sat. NH4Cl, extracted with DCM (2×). The combined organics were dried (Na₂SO₄), filtered and concentrated. The crude product was purified by flash chromatography (MeOH/DCM) (eluted at 5% MeOH) to give 362 (61% yield). MS: (ESI+)=442.2

Example 273

2-(4-(2-chlorophenyl)-1-methyl-5-oxo-4,5-dihydro-1H-1,2,4-triazol-3-yl)-4,5-dihydrobenzo[b]thieno[2,3-d]oxepine-8-carboxamide 363

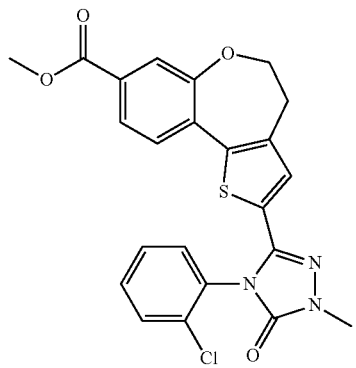

To a mixture of 2-(4-(2-chlorophenyl)-5-oxo-4,5-dihydro-1H-1,2,4-triazol-3-yl)-4,5-dihydrobenzo[b]thieno[2,3-d]oxepine-8-carboxylic acid (1.50 g, 3.41 mmol), $Cs_2CO_3$ (3.33 g, 10.23 mmol) and DMF (30 mL) was added $CH_3I$ (0.5 mL). The whole was stirred at room temperature overnight. Diluted with water, the solids were washed with water and dried in vacuum to give methyl 2-(4-(2-chlorophenyl)-1-methyl-5-oxo-4,5-dihydro-1H-1,2,4-triazol-3-yl)-4,5-dihydrobenzo[b]thieno[2,3-d]oxepine-8-carboxylate (1.45 g, yield 91%). ESI-MS: 468.07.

Methyl 2-(4-(2-chlorophenyl)-1-methyl-5-oxo-4,5-dihydro-1H-1,2,4-triazol-3-yl)-4,5-dihydrobenzo[b]thieno[2,3-d]oxepine-8-carboxylate (1.45 g, 3.10 mmol) was dissolved in 20 mL of THF and 20 mL of water and treated with LiOH (0.325 g, mono-hydrate). The whole was heated at 50° C. for 2 h, cooled to room temperature and acidified. The resulting precipitate was filtered and washed with water. The filter cake was dried to a constant weight under vacuum (1.30 g, yield 92%). ESI-MS: 454.4. $^1H$ NMR (DMSO-$d_6$, 400 MHz): $\delta$13.09 (s, 1H, OH), 7.79-7.46 (m, 7H, ArH), 6.53 (s, 1H, =CH), 4.22 (t, J=5.2 Hz, 2H, $CH_2$), 3.60 (s, 1H, $CH_3$), 3.01 (t, J=5.2 Hz, 2H, $CH_2$).

A solution of 2-(4-(2-chlorophenyl)-1-methyl-5-oxo-4,5-dihydro-1H-1,2,4-triazol-3-yl)-4,5-dihydrobenzo[b]thieno[2,3-d]oxepine-8-carboxylic acid (300 mg, 0.66 mmol) in 10 mL of $SOCl_2$ was heated at 80° C. for 3 h. Concentration gave the crude acid chloride, 2-(4-(2-chlorophenyl)-1-methyl-5-oxo-4,5-dihydro-1H-1,2,4-triazol-3-yl)-4,5-dihydrobenzo[b]thieno[2,3-d]oxepine-8-carbonyl chloride which was slowly added (ca. 312 mg, ca. 0.66 mmol in 10 mL of THF), to a solution of $NH_3$ (saturated solution in THF) and pyridine (0.5 mL) in 5 mL of THF at 0° C. The mixture was stirred at room temperature overnight, Diluted with water, the solids were washed with water and dried in vacuum. The crude product was purified by HPLC separation, gave 160.1 mg of 363, isolated yield: 54%. ESI-MS: 453. $^1H$ NMR (DMSO-$d_6$, 400 MHz): $\delta$ 7.98-7.41 (m, 9H, ArH, $NH_2$), 6.49 (s, 1H, =CH), 4.20 (s, 2H, $CH_2$), 3.49 (s, 3H, $CH_3$), 2.99 (s, 2H, $CH_2$).

Example 274

2-(4-(2-chlorophenyl)-1-methyl-5-oxo-4,5-dihydro-1H-1,2,4-triazol-3-yl)-N-methyl-4,5-dihydrobenzo[b]thieno[2,3-d]oxepine-8-carboxamide 364

Following Example 273, compound 364 was prepared with methylamine. Yield: 52%. ESI-MS: 467. $^1H$ NMR (DMSO-$d_6$, 400 MHz): $\delta$8.46 (t, J=4.4 Hz, 1H, NH), 7.79-7.45 (m, 7H, ArH), 6.49 (s, 1H, =CH), 4.22 (t, J=5.2 Hz, 2H, $CH_2$), 3.50 (s, 3H, $CH_3$), 3.01 (t, J=5.2 Hz, 2H, $CH_2$), 2.76 (d, J=4.4 Hz, 3H, $NCH_3$)

Example 275 p110α (Alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110 alpha PI3K (Upstate Cell Signaling Solutions, Charlottesville, Va.) starting at a final concentration of 20 ug/mL in polarization buffer (10 mM tris pH 7.5, 50 mM NaCl, 4 mM $MgCl_2$, 0.05% Chaps, and 1 mM DTT) to 10 mM $PIP_2$ (Echelon-Inc., Salt Lake City, Utah.) final concentration. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore ($\lambda$ex=530 nm; $\lambda$em=590 nm) in 384-well black low volume Proxiplates (PerkinElmer, Wellesley, Mass.) Fluorescence polarization values were plotted as a function of the protein concentration, and the $EC_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor $IC_{50}$ values were determined by addition of the 0.04 mg/mL p110 alpha PI3K (final concentration) combined with $PIP_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore ($\lambda$ex=530 nm; $\lambda$em=590 nm) in 384-well black low volume proxi plates (PerkinElmer, Wellesley, Mass.) Fluorescence polarization values were plotted as a function of the antagonist concentration, and the $IC_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 hr at room temperature, and the reaction was terminated by the addition of PBS. $IC_{50}$ values were subsequently determined using sigmoidal dose-response curve fit (variable slope).

Example 276

In Vitro Cell Proliferation Assay

Efficacy of Formula I compounds were measured by a cell proliferation assay employing the following protocol (Promega Corp. Technical Bulletin TB288; Mendoza et al (2002) Cancer Res. 62:5485-5488):

1. An aliquot of 100 μl of cell culture containing about $10^4$ cells (PC3, Detroit562, or MDAMB361.1) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 hr before reading at 544 nm excitation, 590 nm emission. $EC_{50}$ values were calculated using a sigmoidal dose response curve fit.

Example 277

Caco-2 Permeability

Caco-2 cells are seeded onto Millipore Multiscreen plates at $1\times10^5$ cells/cm², and cultured for 20 days. Assessment of compound permeability is subsequently conducted. The compounds are applied to the apical surface (A) of cell monolayers and compound permeation into the basolateral (B) compartment was measured. This is performed in the reverse direction (B-A) to investigate active transport. A permeability coefficient value, $P_{app}$, for each compound, a measure of the rate of permeation of the compound across the membrane, is calculated. Compounds are grouped into low ($P_{app}</=1.0\times 10^6$ cm/s) or high ($P_{app}>/=1.0\times 10^6$ cm/s) absorption potential based on comparison with control compounds with established human absorption.

For assessment of a compound's ability to undergo active efflux, the ratio of basolateral (B) to apical (A) transport compared with A to B was determined. Values of B-A/A-B$>/=1.0$ indicate the occurrence of active cellular efflux.

Example 278

Hepatocyte Clearance

Suspensions of cryopreserved human hepatocytes are used. Incubations are performed at compound concentration of 1 mM or 3 μM at a cell density of $0.5\times10^6$ viable cells/mL. The final DMSO concentration in the incubation is about 0.25%. Control incubations are also performed in the absence of cells to reveal any non-enzymatic degradation. Duplicate samples (50 μL) are removed from the incubation mixture at 0, 5, 10, 20, 40 and 60 minutes (control sample at 60 minutes only) and added to methanol containing internal standard (100 μL) —to terminate the reaction. Tolbutamide, 7-hydroxycoumarin, and testosterone may be used as control compounds. Samples are centrifuged and the supernatants at each time point pooled for analysis by LC-MSMS. From a plot of 1 n peak area ratio (parent compound peak area/internal standard peak area) against time, intrinsic clearance ($CL_{int}$) is calculated as follows: $CL_{int}$ (μl/min/million cells)=V×k, where k is the elimination rate constant, obtained from the gradient of 1 n concentration plotted against time; V is a volume term derived from the incubation volume and is expressed as uL $10^6$ cells$^{-1}$.

Example 279

Cytochrome P450 Inhibition

Formula I compounds may be screened against CYP450 targets (1A2, 2C9, 2C19, 2D6, 3A4) at about 10 concentrations in duplicate, with a top concentration of about 100 uM. Standard inhibitors (furafylline, sulfaphenazole, tranylcypromine, quinidine, ketoconazole) may be used as controls. Plates may be read using a BMG LabTechnologies PolarStar in fluorescence mode.

Example 280

Cytochrome P450 Induction

Freshly isolated human hepatocytes from a single donor may be cultured for about 48 hr prior to addition of Formula I compound at three concentrations and incubated for 72 hr. Probe substrates for CYP3A4 and CYP1A2 are added for 30 minutes and 1 hr before the end of the incubation. At 72 hr, cells and media are removed and the extent of metabolism of each probe substrate quantified by LC-MS/MS. The experiment is controlled by using inducers of the individual P450s incubated at one concentration in triplicate.

Example 281

Plasma Protein Binding

Solutions of Formula I compound (5 um, 0.5% final DMSO concentration) are prepared in buffer and 10% plasma (v/v in buffer). A 96 well HT dialysis plate is assembled so that each well is divided in two by a semi-permeable cellulose membrane. The buffer solution is added to one side of the membrane and the plasma solution to the other side; incubations are then conducted at 37° C. over 2 hr in triplicate. The cells are subsequently emptied, and the solutions for each batch of compounds are combined into two groups (plasma-free and plasma-containing) then analyzed by LC-MSMS using two sets of calibration standards for plasma-free (6 points) and plasma-containing solutions (7 points). The fraction unbound value for the compound is calculated.

Example 282 hERG Channel Blockage

Formula I compounds are evaluated for ability to modulate rubidium efflux from HEK-294 cells stably expressing hERG potassium channels using established flux methodology. Cells are prepared in medium containing RbCl, plated into 96-well plates and grown overnight to form monolayers. The efflux experiment is initiated by aspirating the media and washing each well with 3×100 μL of pre-incubation buffer (containing low [K$^+$]) at room temperature. Following the final aspiration, 50 μL of working stock (2×) compound is added to each well and incubated at room temperature for 10 minutes. Stimulation buffer 504 (containing high [K+]) is then added to each well giving the final test compound concentrations. Cell plates are then incubated at room temperature for a further 10 minutes. Supernatant 80 μL from each well is then transferred to equivalent wells of a 96-well plate and analyzed via atomic emission spectroscopy. The compound is screened as 10 pt duplicate $IC_{50}$ curves, n=2, from a top concentration of 100 μM.

Example 283

In Vivo Tumor Xenograft

Animals suitable for transgenic experiments can be obtained from standard commercial sources. Groups of Taconic nude mice (were implanted subcutaneously in the hind flank with MDA-MB-361.1 (PI3K mutant) breast cancer cells. Mouse xenografts were dosed daily for 21 days with drug or vehicle. Tumor sizes were recorded twice weekly over the course of the study. Mouse body weights were also recorded twice weekly, and the mice were observed regularly. Tumor volume was measured in two dimensions (length and width) using Ultra Cal-IV calipers (Model 54-10-111; Fred V. Fowler Co., Inc.; Newton, Mass.) and analyzed using Excel v.11.2 (Microsoft Corporation; Redmond, Wash.). Tumor inhibition graphs were plotted using KaleidaGraph, Version 3.6 (Synergy Software; Reading, Pa.). The tumor volume was calculated with formula: Tumor size (mm³)=(longer measurement×shorter measurement²)×0.5

Animal body weights were measured using an Adventurera Pro AV812 scale (Ohaus Corporation; Pine Brook, N.J.).

Graphs were generated using KaleidaGraph Version 3.6. Percent weight change was calculated using formula: Group percent weight change=(1-(initial weight/new weight))×100.

Mice whose tumor volume exceeded 2000 mm³ or whose body weight loss was >20% of their starting weight were promptly euthanized according to regulatory guidance.

The percent tumor growth inhibition (% INH) at the end of study (EOS) was calculated using formula: % INH=100× (EOS mean volume of tumors in animals given vehicle−EOS mean volume of tumors in animals given the drug)/EOS mean volume of tumors in animals given vehicle.

Tumor incidence (TI) was determined based on the number of measurable tumors remaining in each group at the end of the study. A partial response (PR) was defined as a >50% but <☐100% reduction in tumor volume, compared with the starting tumor volume, observed on any day of the study. A complete response (CR) was defined as a 100% reduction in tumor volume, compared with the initial tumor volume, observed on any day of the study. Data were analyzed and p-values were determined using the Dunnett's test with JMP statistical software, version 5.1.2 (SAS Institute; Cary, N.C.). Individual tumor volumes at end of study and mean tumor volume ±SEM values were calculated using JMP statistical software, version 5.1.2. Body weight data were graphed based on the mean percentage of change from initial body weights ±SEM.

Example 284

Phospho AKT Induction Assay

In a 6-well tissue culture plate cells were seeded at 5×10⁵ cells per well overnight. Cells were treated with an $EC_{80}$ of the Formula I or Formula II compound, including 223, 328, and 345. Following treatment, cells were washed once with cold PBS and lysed in 1× Cell Extraction Buffer from Biosource (Carlsbad, Calif.) supplemented with protease inhibitors (Roche, Mannheim, Germany), 1 mM PMSF, and Phosphatase Inhibitor Cocktails 1 and 2 from Sigma (St. Louis, Mo.). Determination of protein concentration was performed using the Pierce BCA Protein Assay Kit (Rockford, Ill.). Levels of pAkt ($Ser^{473}$) and total Akt were assessed using bead kits from Biosource (Carlsbad, Calif.) and the Luminex Bio-Plex system (Bio-Rad, Hercules, Calif.).

Example 285

(2-(4-(2,4-difluorophenyl)-4H-1,2,4-triazol-3-yl)-4,5-dihydrobenzo[b]thieno[2,3-d]oxepin-9-yl)(4-methylpiperazin-1-yl)methanone 374

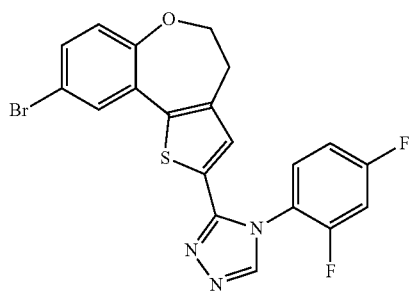 [SMILES: Fc1ccc(-n2cnnc2-c2cc3c(s2)-c2cc(Br)ccc2OCC3)c(F)c1]

A mixture of 3-(9-bromo-4,5-dihydro-6-oxa-1-thia-benzo[e]azulen-2-yl)-4-(2,4-difluoro-phenyl)-4H-[1,2,4]triazole (600 mg), molybdenum hexacarbonyl (344 mg), Cataxium C (122 mg), tributylphosphine tetrafluoroborate (76 mg) and 1,8-diazabicycloundec-7-ene (0.58 mL) in methanol (5 mL) and THF (5 mL) was reacted in the microwave at 130° C. for 30 minutes. The mixture was then partitioned between dichloromethane (30 mL) and water (30 mL). The organic layer was dried ($MgSO_4$), reduced in vacuo and purified on silica to give 2-[4-(2,4-difluoro-phenyl)-4H-[1,2,4]triazol-3-yl]-4,5-dihydro-6-oxa-1-thia-benzo[e]azulene-9-carboxylic acid methyl ester.

To a solution of 2-[4-(2,4-difluoro-phenyl)-4H-[1,2,4]triazol-3-yl]-4,5-dihydro-6-oxa-1-thia-benzo[e]azulene-9-carboxylic acid methyl ester (210 mg) in THF (4 mL) and ethanol (2 mL) was added sodium hydroxide solution (38 mg in 2 mL of water) and the reaction stirred at room temperature for 16 h. The reaction was then acidified with 2 M hydrochloric acid and the resulting solid was filtered and air-dried to give 2-[4-(2,4-difluoro-phenyl)-4H-[1,2,4]triazol-3-yl]-4,5-dihydro-6-oxa-1-thia-benzo[e]azulene-9-carboxylic acid.

2-[4-(2,4-Difluoro-phenyl)-4H-[1,2,4]triazol-3-yl]-4,5-dihydro-6-oxa-1-thia-benzo[e]azulene-9-carboxylic acid and N-methylpiperazine were reacted in the general amide coupling procedure to give 374. NMR: ($CDCl_3$): 2.37 (3H, s, Me), 2.37-2.51 (4H, m), 3.13-3.17 (2H, m), 3.51-3.78 (4H, m), 4.32-4.35 (2H, m), 6.98 (1H, s, Ar), 7.05 (1H, d, J 8.3, Ar), 7.12-7.17 (2H, m, Ar), 7.24-7.27 (1H, m, Ar), 7.42-7.48 (1H, m, Ar), 7.61-7.62 (1H, m, Ar) and 8.24 (1H, s, Ar). MS: (ESI+) MH+=508.22

Example 286

2-(4-(2,4-difluorophenyl)-4H-1,2,4-triazol-3-yl)-N-(2-hydroxyethyl)-4,5-dihydrobenzo[b]thieno[2,3-d]oxepine-9-carboxamide 375

2-[4-(2,4-Difluoro-phenyl)-4H-[1,2,4]triazol-3-yl]-4,5-dihydro-6-oxa-1-thia-benzo[e]azulene-9-carboxylic acid and ethanolamine were reacted in the general amide coupling procedure to give 375. NMR: ($CDCl_3$): 2.72 (1H, s, OH), 3.01-3.04 (2H, m), 3.57-3.61 (2H, m), 3.72-3.81 (2H, m), 4.20-4.23 (2H, m), 6.68-6.72 (1H, m, NH), 6.79 (1H, s, Ar), 6.94 (1H, d, J 8.4, Ar), 7.02-7.06 (2H, m, Ar), 7.33-7.40 (1H, m, Ar), 7.50-7.53 (1H, m, Ar), 7.89-7.90 (1H, m, Ar) and 8.16 (1H, s, Ar). MS: (ESI+) MH+=469.04

Example 287

2-(4-(2,4-difluorophenyl)-4H-1,2,4-triazol-3-yl)-N-(2-hydroxyethyl)-N-methyl-4,5-dihydrobenzo[b]thieno[2,3-d]oxepine-9-carboxamide 376

2-[4-(2,4-Difluoro-phenyl)-4H-[1,2,4]triazol-3-yl]-4,5-dihydro-6-oxa-1-thia-benzo[e]azulene-9-carboxylic acid and 2-(methylamino)ethanol were reacted in the general amide coupling procedure to give 376. NMR: ($CDCl_3$): (400 MHz, CDCl3): 3.13 (3H, s, Me), 3.13-3.16 (2H, m), 3.74-3.78 (2H, m), 3.90-3.95 (2H, m), 4.31-4.34 (2H, m), 6.93 (1H, s, Ar), 7.05 (1H, d, J 8.3, Ar), 7.12-7.16 (2H, m, Ar), 7.31-7.33 (1H, m, Ar), 7.43-7.48 (1H, m, Ar), 7.69-7.70 (1H, m, Ar) and 8.24 (1H, s, Ar). MS: (ESI+) MH+=483.08

Example 288

5-(9-bromo-4,5-dihydrobenzo[b]thieno[2,3-d]oxepin-2-yl)-1-(2,4-difluorophenyl)-1H-1,2,4-triazole 384

A microwave tube charged with 2-(9-bromo-4,5-dihydro-6-oxa-1-thia-benzo[e]azulen-2-yl)-[1,3,4]oxadiazole (200 mg; 0.57 mmol), 2,4-difluoroaniline (0.11 ml; 1.1 mmol), TFA (82 µl; 1.1 mmol) and toluene (1.5 ml) was heated in a microwave at 140° C. for 30 min. The reaction mixture was diluted with $CH_2Cl_2$ (20 ml) and washed with satd. $NaHCO_3$ (20 ml), the organic layer was separated (hydrophobic frit), concentrated and purified by ISCO to give 384 as a pale yellow solid (191 mg; 70%). $\delta_H$ (400 MHz, $CDCl_3$) 3.15 (t, J=5.2, 2H), 4.30 (t, J=5.2, 2H), 6.91 (d, J=8.8, 1H), 6.97 (s, 1H), 7.02-7.18 (m, 2H), 7.25-7.28 (m, 1H), 7.43-7.49 (m, 1H), 7.66 (d, J=2.4, 1H), 8.25 (s, 1H). $[M+H]^+$: 461

Example 289

5-(9-bromo-4,5-dihydrobenzo[b]thieno[2,3-d]oxepin-2-yl)-1-isopropyl-1H-1,2,4-triazole 385

A mixture of 9-bromo-4,5-dihydro-6-oxa-1-thia-benzo[e]azulene-2-carboxylic acid amide (1.01 g), dimethylformamide dimethyl acetal (9 ml) and toluene (7.5 mL) was heated to 100° C. for 16 hours. The solvent was then reduced in vacuo and dissolved in acetic acid (9 ml) and water (1 mL) and to this was added isopropyl hydrazide hydrochloride (482 mg). The reaction mixture was heated to 100° C. for 7 hours. The reaction mixture was then cooled, and then diluted with ethyl acetate, washed with sodium carbonate solution, dried ($MgSO_4$) and the solvent removed in vacuo. Purification using flash chromatography yielded 385. NMR: (CDCl3): 1.61 (6H, d), 3.25 (2H, t), 4.33 (2H, t), 4.99 (1H, septet), 6.90 (1H, d), 7.28-7.31 (2H, m), 7.85 (1H, s), 7.92 (1H, s). MS. ESI+ 432 ($MH^+$+MeCN)

Example 290

1-(2,4-difluorophenyl)-5-(4,5-dihydrobenzo[b]thieno[2,3-d]oxepin-2-yl)-1H-1,2,4-triazole 397

Compound 397 was prepared according to the procedures herein. NMR: (CDCl3): 3.13 (2H, t), 4.31 (2H, t), 6.99-7.21 (6H, m), 7.51-7.58 (2H, m), 8.01 (1H, s). MS. ESI+ 423 ($MH^+$+MeCN)

Example 291

2-(1-(2,4-difluorophenyl)-1H-1,2,4-triazol-5-yl)-N-(2-hydroxyethyl)-4,5-dihydrobenzo[b]thieno[2,3-d]oxepine-9-carboxamide 398

A mixture of 5-(9-bromo-4,5-dihydro-6-oxa-1-thia-benzo[e]azulen-2-yl)-1-(2,4-difluoro-phenyl)-1H-[1,2,4]triazole (847 mg), molybdenum hexacarbonyl (485 mg), Herman's catalyst (173 mg), tributyl phosphine tetrafluoroborate (106 mg), methanol (8 ml), THF (8 ml), and 1,8-diazabicyclo [5.4.0]undec-7-ene (0.82 mL) was heated in the microwave at 130° C. for 30 minutes. The reaction mixture was cooled, and then diluted with dichloromethane, washed with water, dried ($MgSO_4$) and the solvent removed in vacuo. Purification using flash chromatography yielded the corresponding methyl ester, 2-[2-(2,4-difluoro-phenyl)-2H-[1,2,4]triazol-3-yl]-4,5-dihydro-6-oxa-1-thia-benzo[e]azulene-9-carboxylic acid methyl ester. Standard hydrolysis using sodium hydroxide in methanol/THF/water yielded the corresponding carboxylic acid, 2-[2-(2,4-difluoro-phenyl)-2H-[1,2,4]triazol-3-yl]-4,5-dihydro-6-oxa-1-thia-benzo[e]azulene-9-carboxylic acid.
A mixture of 2-[2-(2,4-difluoro-phenyl)-2H-[1,2,4]triazol-3-yl]-4,5-dihydro-6-oxa-1-thia-benzo[e]azulene-9-carboxylic acid (53 mg), HATU (61 mg) and diisopropylethylamine (0.028 mL) and ethanolamine was stirred in N,N-dimethylformamide (3 ml). The reaction mixture was stirred overnight, and then diluted with ethyl acetate, washed with water, dried ($MgSO_4$) and the solvent removed in vacuo. Purification using flash chromatography yielded 398 (24 mg). NMR: (CDCl3): 2.30 (1H, t, br.), 3.05 (2H, t), 3.51-3.55 (2H, m), 3.7-3.75 (2H, m), 4.31 (2H, t), 6.40 (1H, br.), 6.80 (1H, s), 6.99 (1H, d), 7.05-7.12 (2H, m), 7.42-7.52 (2H, m), 7.90 (1H, s), 8.01 (1H, s). MS. ESI+ 510 ($MH^+$+MeCN)

Example 292

9-Bromo-2-[2-(2,4-difluoro-phenyl)-2H-[1,2,4]triazol-3-yl]-4,5-dihydro-6-oxa-3-thia-1-aza-benzo[e]azulene 399

To a stirred suspension of 9-bromo-4,5-dihydro-6-oxa-3-thia-1-aza-benzo[e]azulene-2-carboxylic acid (3.75 g; 11.5 mmol) in $CH_2Cl_2$ (80 ml) at room temperature was added $(COCl)_2$ (2.6 ml; 30 mmol) then DMF (3 drops). The reaction mixture was stirred at room temperature for 3 h upon which time all volatiles were removed in vacuo. The resulting residue was slurried in THF (60 ml) cooled to 0° C. and treated with $NH_3$ (10 ml of a 7M MeOH soln.; 70 mmol). The reaction mixture was stirred whilst allowing to warm to room temperature over 1.5 h. The reaction mixture was diluted with water (200 ml) and the resulting solid collected by filtration to obtain 9-bromo-4,5-dihydro-6-oxa-3-thia-1-aza-benzo[e]azulene-2-carboxylic acid amide as a white solid (3.09 g; 83%). $\delta_H$ (400 MHz, $d_6$-DMSO) 3.30 (t, J=5.2, 2H), 4.29 (t, J=5.2, 2H), 6.98 (d, J=8.8, 1H), 7.39 (dd, J=8.8 and 2.4, 1H), 7.42 (br s, 1H), 7.62 (s, 1H), 7.71 (d, J=2.4, 1H), 7.96 (br s, 1H).
A stirred suspension of 9-bromo-4,5-dihydro-6-oxa-3-thia-1-aza-benzo[e]azulene-2-carboxylic acid amide (0.70 g; 2.2 mmol) and dimethylformamide dimethylacetal (DM-F.DMA, 6 ml) in toluene (5 ml) was heated at 100° C. overnight (16 h) upon which time the reaction mixture was concentrated. To the resulting residue was added AcOH (5 ml), water (0.5 ml) and 2,4-difluorophenylhydrazine hydrochloride (0.56 g; 3.1 mmol) and the resulting solution heated at 100° C. for 3 h. The reaction mixture was concentrated, the residue was dissolved in $CH_2Cl_2$ (50 ml) and washed with satd. $NaHCO_3$ (50 ml). The organic layer was separated (hydrophobic frit), concentrated and purified by ISCO to give 399 as a cream-coloured solid (0.31 g; 31%). $\delta_H$ (400 MHz, $CDCl_3$) 3.41 (t, J=5.2, 2H), 4.36 (t, J=5.2, 2H), 6.89 (d, J=8.8, 1H), 7.14-7.20 (m, 2H), 7.27-7.30 (m, 1H), 7.55-7.61 (m, 1H), 7.69 (d, J=2.8, 1H), 8.16 (s, 1H). $[M+H]^+$: 462

Alternatively, to a suspension of 9-bromo-4,5-dihydro-6-oxa-3-thia-1-aza-benzo[e]azulene-2-carboxylic acid ethyl ester (4.55 g) in ethanol (50 mL) was added hydrazine monohydrate (5 mL) and the reaction heated at reflux for 16 h. After cooling to room temperature, the solid was filtered, washed with diethyl ether and air-dried to give 9-bromo-4,5-dihydro-6-oxa-3-thia-1-aza-benzo[e]azulene-2-carboxylic acid hydrazide.

To a solution of 9-bromo-4,5-dihydro-6-oxa-3-thia-1-aza-benzo[e]azulene-2-carboxylic acid hydrazide (400 mg) in trimethyl orthoformate (10 mL) was added p-toluenesulfonic acid (100 mg) and the reaction heated at 100° C. for 16 h. After cooling to room temperature, the solvent was reduced in vacuo and diethyl ether (10 mL) was added. The resulting solid was filtered and air-dried to give 9-bromo-2-[1,3,4]oxadiazol-2-yl-4,5-dihydro-6-oxa-3-thia-1-aza-benzo[e]azulene.

A mixture of 9-bromo-2-[1,3,4]oxadiazol-2-yl-4,5-dihydro-6-oxa-3-thia-1-aza-benzo[e]azulene (250 mg), 2,4-difluoroaniline (0.15 mL) and trifluoroacetic acid (0.11 mL) in toluene (5 mL) was reacted in the microwave at 110° C. for 20 minutes. The mixture was then partitioned between dichloromethane (20 mL) and aqueous sodium hydrogen carbonate solution (20 mL). The organic layer was dried (MgSO4), reduced in vacuo and purified on silica to give 399. NMR: (CDCl$_3$): 3.38-3.41 (2H, m), 4.33-4.36 (2H, m), 6.89 (1H, d, J 8.6, Ar), 7.15-7.21 (2H, m, Ar), 7.25-7.28 (1H, m, Ar), 7.47-7.53 (1H, m, Ar), 7.61 (1H, d, J 2.4, Ar) and 8.32 (1H, s, Ar). MS: (ESI+) MH+=460.97

Example 293

5-(9-(1H-pyrazol-4-yl)-4,5-dihydrobenzo[b]thieno[2,3-d]oxepin-2-yl)-1-(2,4-difluorophenyl)-1H-1,2,4-triazole 400

5-(9-Bromo-4,5-dihydro-6-oxa-1-thia-benzo[e]azulen-2-yl)-1-(2,4-difluoro-phenyl)-1H-[1,2,4]triazole was treated with 4-pyrazoleboronic acid pinacol ester using standard Suzuki condition to yield 400. NMR: (CDCl3): 3.15 (2H, t), 4.31 (2H, t), 6.82 (1H, s), 7.01 (1H, d), 7.08-7.18 (2H, m), 7.31 (1H, d), 7.51-7.55 (1H, m), 7.72 (1H, s), 7.90 (2H, s, br.), 8.18 (1H, s). MS. ESI+ 489 (MH$^+$+MeCN)

Example 294

2-(1-(2,4-difluorophenyl)-1H-1,2,4-triazol-5-yl)-4,5-dihydrobenzo[b]thieno[2,3-d]oxepine-9-carboxamide 401

The corresponding carboxylic acid was reacted with ammonium chloride to give 401. NMR: (DMSO): 3.15 (2H, t), 4.31 (2H, t), 6.80 (1H, s), 7.01 (1H, d), 7.25 (1H, s, br.), 7.37-7.40 (1H, m), 7.65-7.75 (2H, m), 7.90 (1H, m), 7.99 (1H, s, br.), 8.05 (1H, s), 8.28 (1H, s). MS. ESI+ 466 (MH$^+$+MeCN)

Example 295

(2-(1-(2,4-difluorophenyl)-1H-1,2,4-triazol-5-yl)-4,5-dihydrobenzo[b]thieno[2,3-d]oxepin-9-yl)(piperazin-1-yl)methanone 402

The corresponding carboxylic acid was reacted with 1-BOC-piperazine. The BOC group was cleaved using HCl in ether to yield 402 as the hydrochloride salt. MS. ESI+493 (MH$^+$)

Example 296

2-[4-(2,4-Difluoro-phenyl)-4H-[1,2,4]triazol-3-yl]-4,5-dihydro-6-oxa-3-thia-1-aza-benzo[e]azulene-9-carboxylic acid amide 407

To a solution of 9-bromo-2-[4-(2,4-difluoro-phenyl)-4H-[1,2,4]triazol-3-yl]-4,5-dihydro-6-oxa-3-thia-1-aza-benzo[e]azulene (250 mg) in methanol (0.50 mL) was added palladium acetate (6 mg), XANTPHOS (31 mg) and triethylamine (2 mL) and the reaction heated at 70° C. under a balloon of carbon monoxide for 16 h. After cooling to room temperature, the mixture was filtered through Celite, washing with ethyl acetate. The filtrate was reduced in vacuo and redissolved in THF (8 mL) and ethanol (4 mL). Sodium hydroxide solution (43 mg in 4 mL of water) was added and the reaction stirred at room temperature for 16 h. The reaction was then acidified with 2 M hydrochloric acid and the resulting solid was filtered and air-dried to give 2-[4-(2,4-difluorophenyl)-4H-[1,2,4]triazol-3-yl]-4,5-dihydro-6-oxa-3-thia-1-aza-benzo[e]azulene-9-carboxylic acid.

2-[4-(2,4-Difluoro-phenyl)-4H-[1,2,4]triazol-3-yl]-4,5-dihydro-6-oxa-3-thia-1-aza-benzo[e]azulene-9-carboxylic acid and ammonium chloride were reacted in the general amide coupling procedure to give 407. NMR: (CDCl$_3$): 3.32-3.35 (2H, m), 4.32-4.30 (2H, m), 6.96-6.99 (1H, m, Ar), 7.09-7.14 (1H, m, Ar), 7.48-7.50 (1H, m, Ar), 7.54-7.58 (1H, m, Ar), 8.09-8.11 (1H, m, Ar) and 8.35 (1H, s, Ar). MS: (ESI+) MH+=425.95

Example 297

3-(2-(1-(2,4-difluorophenyl)-1H-1,2,4-triazol-5-yl)-4,5-dihydrobenzo[b]thieno[2,3-d]oxepin-9-yl)pyridine 408

5-(9-Bromo-4,5-dihydro-6-oxa-1-thia-benzo[e]azulen-2-yl)-1-(2,4-difluoro-phenyl)-1H-[1,2,4]triazole was treated with 3-pyridineboronic acid pinacol ester using standard Suzuki condition to yield 408. NMR: (CDCl3): 3.15 (2H, t), 4.31 (2H, t), 6.82 (1H, s), 7.03-7.18 (3H, m), 7.32-7.38 (2H, m), 7.51-7.55 (1H, m), 7.72 (1H, s), 7.82 (1H, d), 8.05 (1H, s), 8.55 (1H, d), 8.80 (1H, s). MS. ESI+ 500 (MH$^+$+MeCN)

Example 298

2-(5-Cyclopropyl-[1,2,3]triazol-1-yl)-4,5-dihydro-6-oxa-3-thia-1-aza-benzo[e]azulene-8-carboxylic acid amide 414

Step 1: 8-Bromo-4,5-dihydro-6-oxa-3-thia-1-aza-benzo[e]azulen-2-ylamine

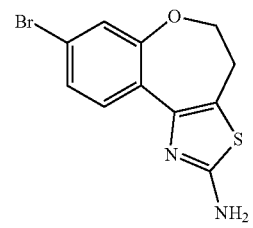 [SMILES: Nc1nc2c(s1)CCOc1cc(Br)ccc1-2]

To a solution of 8-bromo-4,5-dihydro-6-oxa-3-thia-1-aza-benzo[e]azulene-2-carboxylic acid (12.5 g, 38.3 mmol) in tert-butanol (250 mL) were added triethylamine (5.5 mL, 40 mmol) and diphenylphosphoryl-azide (8.6 mL, 40 mmol). The reaction mixture was stirred at 95° C. for 16 h, then allowed to cool down to RT, and concentrated in vacuo. The resultant residue was dissolved in ethyl acetate, washed successively with water, aqueous saturated sodium bicarbonate solution and brine, dried (MgSO$_4$) and concentrated in vacuo. The resultant residue was dissolved in DCM (150 mL) and treated with trifluoroacetic acid (50 mL). The reaction mixture was stirred at RT for 3 h then concentrated in vacuo. The resulting residue was triturated with 20% ethyl acetate/cyclohexane and filtered to afford the title compound as an off-white solid (7.94 g, 70%). LCMS (Method A): R$_T$=3.13 min, [M+H]$^+$=297 and 299. $^1$H NMR (DMSO-d$_6$): 8.01 (1H, d, J=8.6 Hz), 7.30-7.25 (1H, d, J=8.6, 2.1 Hz), 7.19 (1H, d, J=2.1 Hz), 4.27 (2H, t, J=5.1 Hz), 3.08 (2H, t, J=5.1 Hz).

Step 2: 2-Azido-8-bromo-4,5-dihydro-6-oxa-3-thia-1-aza-benzo[e]azulene

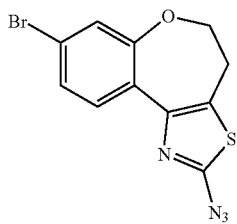 [SMILES: [N-]=[N+]=Nc1nc2c(s1)CCOc1cc(Br)ccc1-2]

To a suspension of 8-bromo-4,5-dihydro-6-oxa-3-thia-1-aza-benzo[e]azulen-2-ylamine (2.38 g, 8 mmol) in acetonitrile at 0° C. was added tert-butyl nitrite (1.43 mL, 12 mmol) followed by trimethylsilyl azide (1.26 mL, 9.6 mmol) dropwise. The reaction mixture was stirred at 0° C. for 90 mins, allowed to warm up to RT and concentrated in vacuo. The resulting residue was purified by flash chromatography (SiO$_2$, 10% ethyl acetate in cyclohexane) to yield the title compound as a red oil which solidified upon standing (956 mg, 37%). $^1$H NMR (CDCl$_3$): 8.21 (1H, d, J=8.6 Hz), 7.24 (1H, dd, J=8.6, 2.1 Hz), 7.20 (1H, d, J=2.1 Hz), 4.34 (2H, t, J=5.1 Hz), 3.21 (2H, t, J=5.1 Hz).

Step 3: 8-Bromo-2-(5-cyclopropyl-[1,2,3]triazol-1-yl)-4,5-dihydro-6-oxa-3-thia-1-aza-benzo[e]azulene

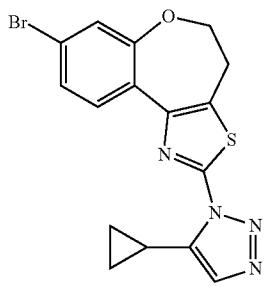 [SMILES: Brc1ccc2c(c1)OCCc1sc(-n3nncc3C3CC3)nc1-2]

To a 1M solution of ethylmagnesium bromide in THF (1.3 mL, 1.3 mmol) under a nitrogen atmosphere, was added dropwise cyclopropylethyne (70% in toluene, 0.154 mL, 1.3 mmol). The reaction mixture was heated at 50° C. for 15 mins then allowed to cool down to RT. A solution of 2-azido-8-bromo-4,5-dihydro-6-oxa-3-thia-1-aza-benzo[e]azulene (425 mg, 1.3 mmol) in THF (1.5 mL) was then added dropwise. The reaction mixture was stirred at RT for 2 h, quenched with aqueous saturated ammonium chloride and diluted with ethyl acetate. The organic layer was washed with brine, dried (Na$_2$SO$_4$) and concentrated in vacuo. The resultant residue was triturated with 20% ethyl acetate/cyclohexane and filtered to afford the title compound as a pale yellow solid (373 mg, 64%). LCMS 110142391 (Method B): R$_T$=4.40 min, [M+H]$^+$=390. $^1$H NMR (DMSO-d$_6$): 8.20 (1H, d, J=8.6 Hz), 7.71 (1H, d, J=0.7 Hz), 7.36 (1H, dd, J=8.6, 2.1 Hz), 7.30 (1H, d, J=2.1 Hz), 4.40 (2H, t, J=5.0 Hz), 3.41 (2H, t, J=5.0 Hz), 2.70-2.63 (1H, m), 1.21-1.15 (2H, m), 0.91-0.86 (2H, m).

Step 4: 2-(5-Cyclopropyl-[1,2,3]triazol-1-yl)-4,5-dihydro-6-oxa-3-thia-1-aza-benzo[e]azulene-8-carboxylic acid amide To a suspension of 8-bromo-2-(5-cyclopropyl-[1,2,3]triazol-1-yl)-4,5-dihydro-6-oxa-3-thia-1-aza-benzo[e]azulene (224 mg, 0.58 mmol), hydroxylamine hydrochloride (81 mg, 1.16 mmol), molybdenum hexacarbonyl (77 mg, 0.29 mmol), tri-tert-butylphosphine tetrafluoroborate (17 mg, 0.058 mmol), trans-di-μ-acetatobis[2-(di-o-tolylphosphino)benzyl]dipalladium(II) (27 mg, 0.029 mmol) in dioxane (7 mL) were added 1,8-diazabicyclo[5.4.0]undec-7-ene (86 μL, 0.58 mmol) and DIPEA (197 μL, 1.16 mmol). The reaction mixture was heated at 150° C. under microwave irradiation for 30 mins, and diluted with ethyl acetate. The organic layer was washed successively with water, aqueous saturated ammonium chloride, aqueous saturated sodium bicarbonate solution and brine, dried (Na$_2$SO$_4$) and concentrated in vacuo. The resultant residue was purified by flash chromatography (SiO$_2$, 3% MeOH in DCM) to give an off-white solid, which was dissolved in DMSO/water. The mixture was left to stand at RT for 7 days, filtered, and the filtrate was diluted with ethyl acetate and water. The organic layer was washed with brine, dried (Na$_2$SO$_4$) and concentrated in vacuo to give 414 as an off-white solid (42 mg, 21%). LCMS (Method C): R$_T$=8.65 min, [M+H]$^+$=354. $^1$H NMR (DMSO-d$_6$): 8.32 (1H, d, J=8.3 Hz), 7.99 (1H, bs), 7.72 (1H, d, J=0.7 Hz), 7.66 (1H, dd, J=8.3, 1.8 Hz), 7.57 (1H, d, J=1.8 Hz), 7.40 (1H, bs), 4.41 (2H, t, J=5.0 Hz), 3.45 (2H, t, J=5.0 Hz), 2.74-2.66 (1H, m), 1.23-1.15 (2H, m), 0.93-0.87 (2H, m).

Example 299

(2-(1-(2,4-difluorophenyl)-1H-1,2,4-triazol-5-yl)-4,5-dihydrobenzo[b]thieno[2,3-d]oxepin-9-yl)((R)-3-(dimethylamino)pyrrolidin-1-yl)methanone 418

To a stirred solution of 2-[2-(2,4-difluoro-phenyl)-2H-[1,2,4]triazol-3-yl]-4,5-dihydro-6-oxa-1-thia-benzo[e]azulene-9-carboxylic acid (82 mg; 0.19 mmol) in DMF (5 ml) was added HATU (103 mg; 0.27 mmol), DIPEA (50 μl; 0.27 mmol) and (R)-(+)-3-(dimethylamino)pyrrolidine (50 μl; 0.38 mmol). The reaction mixture was stirred at room temperature for 4 h upon which time it was diluted with EtOAc (20 ml) and washed successively with satd. NaHCO$_3$ (20 ml) and brine (2×20 ml). The organic layer was dried (Na$_2$SO$_4$), concentrated and purified by prep. LCMS to give 418 as an off-white solid (53 mg; 53%). δ$_H$ (400 MHz, CDCl$_3$) 1.80-1.95 (m, 1H), 2.03-2.15 (br m, 1H), 2.24 (br s, 3H), 2.35 (br s, 3H), 2.62-2.85 (br m, 1H), 3.16 (br s, 2H), 3.30-4.00 (m, 4H), 4.33 (br s, 2H), 6.92-7.20 (m, 4H), 7.40 (br s, 1H), 7.51-7.61 (m, 1H), 7.77 (s, 1H), 8.11 (s, 1H). [M+H]$^+$: 522

Example 300

2-(1-isopropyl-1H-1,2,4-triazol-5-yl)-4,5-dihydrobenzo[b]thieno[2,3-d]oxepine-9-carboxamide 419

A mixture of 5-(9-bromo-4,5-dihydro-6-oxa-1-thia-benzo[e]azulen-2-yl)-1-isopropyl-1H-[1,2,4]-triazole (290 mg), molybdenum hexacarbonyl (196 mg), Herman's catalyst (70 mg), tributyl phosphonic tetrafluoroborate (43 mg), methanol (3 mL), THF (3 mL) and 1,8-diazabicyclo[5.4.0]undec-7-ene (0.33 ml) was heated in the microwave at 130° C. for 30 minutes. The reaction mixture was cooled, and then diluted with dichloromethane, washed with water, dried (MgSO$_4$) and the solvent removed in vacuo to yield 2-(2-isopropyl-2H-[1,2,4]triazol-3-yl)-4,5-dihydro-6-oxa-1-thia-benzo[e]azulene-9-carboxylic acid methyl ester. This was hydrolyzed using sodium hydroxide in water/methanol/THF to yield the corresponding acid. Treatment with HATU, diisopropylethylamine and ammonium chloride in dry DMF yielded 419. NMR: (DMSO): 1.51 (6H, d), 3.25 (2H, t), 4.38 (2H, t), 5.09 (1H, septet), 7.02 (1H, d), 7.33 (1H, br, s), 7.51 (1H, s), 7.75 (1H, dd), 8.00 (1H, s), 8.04 (1H, s, br.), 8.18 (1H, s). MS. ESI+ 3396 (MH$^+$+MeCN)

Example 301

((2-(1-(2,4-difluorophenyl)-1H-1,2,4-triazol-5-yl)-4,5-dihydrobenzo[b]thieno[2,3-d]oxepin-9-yl)((S)-3-(dimethylamino)pyrrolidin-1-yl)methanone 420

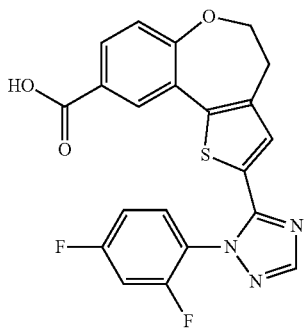 [SMILES: O=C(O)c1ccc2c(c1)-c1sc(-c3ncnn3-c3ccc(F)cc3F)cc1CCO2]

To a stirred solution of 2-[2-(2,4-difluoro-phenyl)-2H-[1,2,4]triazol-3-yl]-4,5-dihydro-6-oxa-1-thia-benzo[e]azulene-9-carboxylic acid (70 mg; 0.16 mmol) in DMF (5 ml) was added HATU (103 mg; 0.27 mmol), DIPEA (50 µl; 0.27 mmol) and (S)-(+3-(dimethylamino)pyrrolidine (50 µl; 0.38 mmol). The reaction mixture was stirred at r.t. for 4 h upon which time it was diluted with EtOAc (20 ml) and washed successively with satd. NaHCO$_3$ (20 ml) and brine (2×20 ml). The organic layer was dried (Na$_2$SO$_4$), concentrated and purified by prep. LCMS to give 420 as an off-white solid (50 mg; 58%). δ$_H$ (400 MHz, CDCl$_3$) 1.77-1.92 (br m, 1H), 2.06-2.17 (m, 1H), 2.24 (br s, 3H), 2.35 (br s, 3H), 2.60-2.83 (m, 1H), 3.16 (br s, 2H), 3.29-3.98 (m, 4H), 4.33 (br s, 2H), 6.94-7.20 (m, 4H), 7.32-7.39 (m, 1H), 7.50-7.60 (m, 1H), 7.77 (s, 1H), 8.11 (s, [M+H]$^+$: 522

Example 302

2-[5-(2,4-Difluoro-phenyl)-[1,2,3]triazol-1-yl]-4,5-dihydro-6-oxa-3-thia-1-aza-benzo[e]azulene-8-carboxylic acid amide 427

Step 1: 8-Bromo-2-[5-(2,4-difluoro-phenyl)-[1,2,3]triazol-1-yl]-4,5-dihydro-6-oxa-3-thia-1-aza-benzo[e]azulene

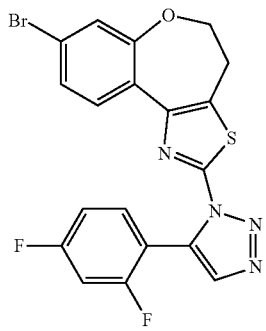 [SMILES: Fc1ccc(-c2cnnn2-c2nc3c(s2)CCOc2cc(Br)ccc2-3)c(F)c1]

Following the procedure for 414, Step 3,2-azido-8-bromo-4,5-dihydro-6-oxa-3-thia-1-aza-benzo[e]azulene was reacted with 1-ethylnyl-2,4-difluorobenzene to afford the title compound as a beige solid. $^1$H NMR (DMSO-d$_6$): 8.26 (1H, s), 7.73 (1H, m), 7.58-7.52 (1H, m), 7.36-7.30 (2H, m), 7.24 (1H, d, J=2.0 Hz), 7.18-7.10 (1H, m), 4.35 (2H, t, J=5.0 Hz), 3.38 (2H, t, J=5.0 Hz).

Step 2: 2-[5-(2,4-Difluoro-phenyl)-[1,2,3]triazol-1-yl]-4,5-dihydro-6-oxa-3-thia-1-aza-benzo[e]azulene-8-carboxylic acid amide Following the procedure for 414, Step 4,8-bromo-2-[5-(2,4-difluoro-phenyl)-[1,2,3]triazol-1-yl]-4,5-dihydro-6-oxa-3-thia-1-aza-benzo[e]azulene was reacted with hydroxylamine hydrochloride to afford 427 as a white solid. LCMS (Method C): R$_T$=9.67 min, [M+H]$^+$=426. $^1$H NMR (DMSO-d$_6$): 8.27 (1H, s), 7.99 (1H, bs), 7.75 (1H, td, J=8.5, 6.4 Hz), 7.59-7.51 (2H, m), 7.46-7.31 (4H, m), 4.36 (2H, t, J=5.0 Hz), 3.41 (2H, t, J=5.0 Hz).

Example 303

2-(5-tert-Butyl-[1,2,3]triazol-1-yl)-4,5-dihydro-6-oxa-3-thia-1-aza-benzo[e]azulene 434

Step 1: 8-Bromo-2-(5-tert-butyl-[1,2,3]triazol-1-yl)-4,5-dihydro-6-oxa-3-thia-1-aza-benzo[e]azulene

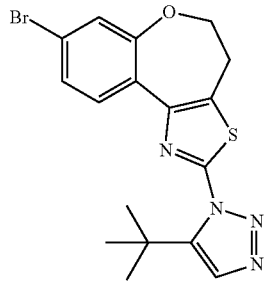 [SMILES: CC(C)(C)c1cnnn1-c1nc2c(s1)CCOc1cc(Br)ccc1-2]

Following the procedure for 414, Step 3,2-azido-8-bromo-4,5-dihydro-6-oxa-3-thia-1-aza-benzo[e]azulene was reacted with 3,3-dimethyl-1-butyne to afford the title compound as a pale yellow solid. LCMS (Method A): R$_T$=4.95 min, [M+H]$^+$=405 and 407. $^1$H NMR (CDCl$_3$): 8.16 (1H, dd, J=8.1, 0.9 Hz), 7.55 (1H, s), 7.28 (2H, m), 4.42 (2H, t, J=5.1 Hz), 3.37 (2H, t, J=5.1 Hz), 1.54 (9H, s).

Step 2: 2-(5-tert-Butyl-[1,2,3]triazol-1-yl)-4,5-dihydro-6-oxa-3-thia-1-aza-benzo[e]azulene A suspension of 8-bromo-2-(5-tert-butyl-[1,2,3]triazol-1-yl)-4,5-dihydro-6-oxa-3-thia-1-aza-benzo[e]azulene (101 mg, 0.25 mmol) and 10% Pd/C (250 mg) in MeOH (5 mL) was stirred at RT under a hydrogen atmosphere for 16 h. The reaction mixture was flushed with nitrogen, filtered through Celite, washed with ethyl acetate and concentrated in vacuo. The resulting residue was purified by flash chromatography (SiO$_2$, 20% ethyl acetate in cyclohexane) to give 434 as a white solid (54 mg, 66%). LCMS (Method C): R$_T$=13.19 min, [M+H]$^+$=327. $^1$H NMR (CDCl$_3$): 8.30 (1H, dd, J=7.9, 1.8

Hz), 7.55 (1H, s), 7.29 (1H, m), 7.17-7.12 (1H, m), 7.08 (1H, dd, J=8.0, 1.4 Hz), 4.43 (2H, t, J=5.1 Hz), 3.39 (2H, t, J=5.1 Hz), 1.55 (9H, s).

Example 304

2-(5-tert-Butyl-[1,2,3]triazol-1-yl)-4,5-dihydro-6-oxa-3-thia-1-aza-benzo[e]azulene-8-carboxylic acid amide 435

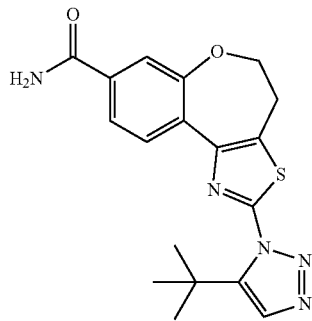 [SMILES: CC(C)(C)c1cnnn1-c1nc2c(s1)CCOc1cc(C(N)=O)ccc1-2]

Following the procedure for 414, Step 4,8-bromo-2-(5-tert-butyl-[1,2,3]triazol-1-yl)-4,5-dihydro-6-oxa-3-thia-1-aza-benzo[e]azulene was reacted with hydroxylamine hydrochloride to afford 435 as a pale yellow solid. LCMS (Method C): $R_T$=9.29 min, [M+H]$^+$=370. $^1$H NMR (DMSO-d$_6$): 8.25 (1H, d, J=8.3 Hz), 8.00 (1H, bs), 7.83 (1H, s), 7.67 (1H, dd, J=8.3, 1.8 Hz), 7.59 (1H, d, J=1.8 Hz), 7.42 (1H, bs), 4.43 (2H, t, J=5.0 Hz), 3.48 (2H, t, J=5.0 Hz), 1.48 (9H, s).

Example 305

2-(5-Isopropyl-[1,2,3]triazol-1-yl)-4,5-dihydro-6-oxa-3-thia-1-aza-benzo[e]azulene-8-carboxylic acid amide 436

Step 1: 8-Bromo-2-(5-isopropyl-[1,2,3]triazol-1-yl)-4,5-dihydro-6-oxa-3-thia-1-aza-benzo[e]azulene

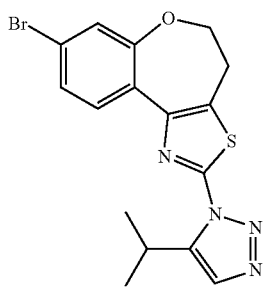 [SMILES: CC(C)c1cnnn1-c1nc2c(s1)CCOc1cc(Br)ccc1-2]

Following the procedure for 414, Step 3,2-azido-8-bromo-4,5-dihydro-6-oxa-3-thia-1-aza-benzo[e]azulene was reacted with 3-methyl-1-butyne to afford the title compound as a beige solid. LCMS (Method A): $R_T$=4.88 min, [M+H]$^+$=391 and 393. $^1$H NMR (CDCl$_3$): 8.12 (1H, d, J=8.5 Hz), 7.59 (1H, s), 7.30-7.25 (2H, m), 4.41 (2H, t, J=5.0 Hz), 3.98-3.90 (1H, m), 3.36 (2H, t, J=5.0 Hz), 1.44 (3H, s), 1.42 (3H, s).

Step 2: 2-(5-Isopropyl-[1,2,3]triazol-1-yl)-4,5-dihydro-6-oxa-3-thia-1-aza-benzo[e]azulene-8-carboxylic acid amide Following the procedure for 414, Step 4,8-bromo-2-(5-isopropyl-[1,2,3]triazol-1-yl)-4,5-dihydro-6-oxa-3-thia-1-aza-benzo[e]azulene was reacted with hydroxylamine hydrochloride to afford 436 as a pale yellow solid. LCMS (Method C): $R_T$=9.07 min, [M+H]$^+$=356. $^1$H NMR (DMSO-d$_6$): 8.26 (1H, d, J=8.3 Hz), 8.00 (1H, bs), 7.91 (1H, d, J=0.7 Hz), 7.68 (1H, dd, J=8.3, 1.8 Hz), 7.58 (1H, d, J=1.8 Hz), 7.41 (1H, bs), 4.41 (2H, t, J=5.0 Hz), 3.91-3.82 (1H, sept, J=6.8 Hz), 3.44 (2H, t, J=5.0 Hz), 1.39 (3H, s), 1.38 (3H, s).

Example 306

2-[5-(2,4-Difluoro-phenyl)-[1,2,4]triazol-1-yl]-4,5-dihydro-6-oxa-3-thia-1-aza-benzo[e]azulene-8-carboxylic acid amide 449

Step 1: 4,8-Dibromo-3,4-dihydro-2H-benzo[b]oxepin-5-one

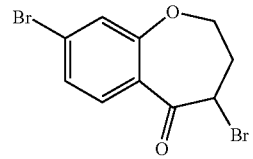 [SMILES: O=C1c2ccc(Br)cc2OCCC1Br]

To a solution of 8-bromo-3,4-dihydro-2H-benzo[b]oxepin-5-one (1.2 g, 5 mmol) in diethyl ether (20 mL) at 0° C. was added bromine (257 µL, 5 mmol) dropwise under nitrogen. The reaction mixture was stirred at 0° C. for 1 h, allowed to warm up to RT and stirred for 3 h. Further bromine (50 µL, 0.97 mmol) was added and stirring was pursued for 16 h. The solvent was removed in vacuo and the resultant residue was purified by flash chromatography (SiO$_2$, 10% ethyl acetate in cyclohexane) to give the title compound as a white solid (1.55 g, 97%). $^1$H NMR (CDCl$_3$): 7.62 (1H, m), 7.26 (2H, m), 4.94 (1H, dd, J=7.7, 6.7 Hz), 4.43 (1H, ddd, J=12.7, 5.6, 4.8 Hz), 4.25-4.15 (1H, m), 2.97-2.86 (1H, m), 2.51 (1H, ddt, J=14.7, 7.7, 4.6 Hz).

Step 2: (8-Bromo-4,5-dihydro-6-oxa-3-thia-1-aza-benzo[e]azulen-2-yl)-hydrazine

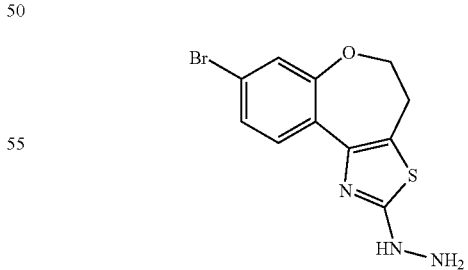

A solution of 4,8-dibromo-3,4-dihydro-2H-benzo[b]oxepin-5-one (1.5 g, 4.7 mmol) and thiosemicarbazide (455 mg, 5 mmol) in IMS (15 mL) was stirred at 85° C. for 2 h, allowed to cool down to RT and filtered to give the title compound as a beige solid (1.03 g, 70%). LCMS (Method B): $R_T$=3.06 min, [M+H]$^+$=312 and 314. $^1$H NMR (DMSO-d$_6$): 10.10 (2H, bs), 9.80 (1H, bs), 8.27 (1H, d, J=8.6 Hz), 7.34 (1H, dd, J=8.6, 2.1 Hz), 7.22 (1H, d, J=2.1 Hz), 4.31 (2H, t, J=5.0 Hz), 3.19 (2H, t, J=5.0 Hz).

Step 3: N-[1-Dimethylamino-meth-(E)-ylidene]-2,4-difluoro-benzamide

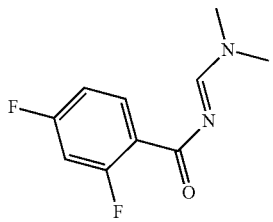

A suspension of 2,4-difluorobenzamide (5 g, 32 mmol) in DMF-DMA (10 mL) was heated at 120° C. for 2.5 h, allowed to cool down to RT and filtered to afford the title compound as a white solid (6.16 g, 91%). $^1$H NMR (CDCl$_3$): 8.60 (1H, s), 8.19-8.12 (1H, m), 6.91-6.79 (2H, m), 3.19 (6H, m).

Step 4: 8-Bromo-2-[5-(2,4-difluoro-phenyl)-[1,2,4]-triazol-1-yl]-4,5-dihydro-6-oxa-3-thia-1-aza-benzo[e]azulene

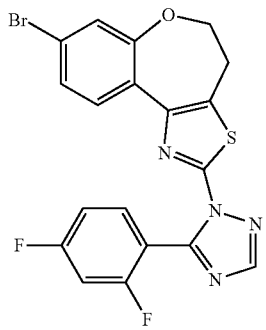 [SMILES: Fc1ccc(-c2ncnn2-c2nc3c(s2)CCOc2cc(Br)ccc2-3)c(F)c1]

A suspension of (8-bromo-4,5-dihydro-6-oxa-3-thia-1-aza-benzo[e]azulen-2-yl)-hydrazine (312 mg, 1 mmol) and N-[1-dimethylamino-meth-(E)-ylidene]-2,4-difluorobenzamide (232 mg, 1.1 mmol) in acetic acid (6 mL) was heated at 90° C. for 3 h, allowed to cool down to RT and filtered. The precipitate was washed with diethyl ether and dried to afford the title compound as a beige solid (300 mg, 65%). LCMS (Method B): R$_T$=4.51 min, [M+H]$^+$=461 and 463. $^1$H NMR (DMSO-d$_6$): 8.50 (1H, s), 7.82 (1H, td, J=8.4, 6.4 Hz), 7.57 (1H, ddd, J=10.4, 9.4, 2.5 Hz), 7.39-7.30 (2H, m), 7.23 (1H, d, J=2.0 Hz), 7.13 (1H, dd, J=8.6, 2.0 Hz), 4.33 (2H, t, J=5.0 Hz), 3.34 (2H, t, J=5.0 Hz).

Step 5: 2-[5-(2,4-Difluoro-phenyl)-[1,2,4]triazol-1-yl]-4,5-dihydro-6-oxa-3-thia-1-aza-benzo[e]azulene-8-carboxylic acid amide Following the procedure for 414, Step 4,8-bromo-2-[5-(2, 4-difluoro-phenyl)-[1,2,4]triazol-1-yl]-4,5-dihydro-6-oxa-3-thia-1-aza-benzo[e]azulene was reacted with hydroxylamine hydrochloride to afford 449 as a white solid. LCMS (Method C): R$_T$=9.22 min, [M+H]$^+$=426. $^1$H NMR (DMSO-d$_6$): 8.51 (1H, m), 7.98 (1H, bs), 7.88-7.80 (1H, m), 7.60-7.53 (1H, m), 7.51 (1H, d, J=1.7 Hz), 7.46-7.34 (4H, m), 4.34 (2H, t, J=5.0 Hz), 3.38 (2H, t, J=5.0 Hz).

Example 307

5-(2-carbamoyl-6,7-dihydropyrido[3,2-b]thieno[2,3-d]oxepin-9-yl)-6-(2,4-difluorophenyl)pyridin-2-amine 454

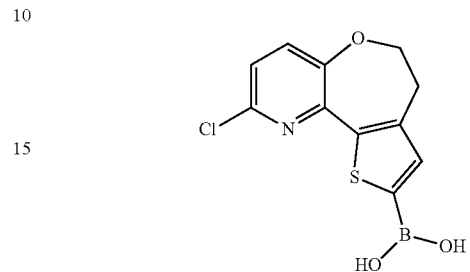

Step 1: 2-Chloro-6,7-dihydro-pyrido[3,2-b]thieno[2,3-d]oxepine-9-boronic acid 4.77 ml (12 mmol) of 2.5 M n-Butyl lithium in hexane was added dropwise to a solution of 3166 mg (10.0 mmol) of 2-chloro-6,7-dihydro-9-bromopyrido[3,2-b]thieno[2,3-d]oxepine in 100 ml of tetrahydrofuran at −76° C. After stirring for 10 min, 3.21 ml (14.0 mmol) of triisopropylborate was added. The mixture was kept at −76° C. for 20 min, then 10 ml of saturated aqueous ammonium chloride were added and the mixture was mixed with 360 ml of water. The product was extracted with 150 ml of ethyl acetate. The organic layer was washed with 100 ml of water, 100 ml of brine and dried over anhydrous sodium sulfate. The solution was filtered and concentrated in vacuum to afford a residue which was then triturated with a mixture of hexane and ethyl ether (1:1). A precipitate was filtered, washed with cold ethyl ether, hexane and dried in vacuum to give 2-Chloro-6,7-dihydro-pyrido[3,2-b] thieno[2,3-d]oxepine-9-boronic acid. Yield 2.20 g (78%). MS: (ESI+)=282.1.

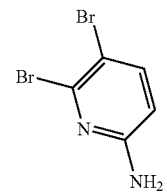

5,6-Dibromopyridin-2-amine was synthesized following a procedure in WO 2005/100353.

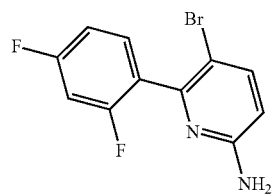 [SMILES: Nc1ccc(Br)c(-c2ccc(F)cc2F)n1]

Step 2:
5-Bromo-6-(2,4-difluorophenyl)pyridin-2-amine

A mixture of 5,6-dibromopyridin-2-amine (315 mg, 1.25 mmol), 2,4-difluorophenylboronic acidboronic acid, pinacol ester (197 mg, 1.25 mmol;) and bis(triphenylphosphine)palladium(II) chloride (44.0 mg, 0.063 mmol;) in 1.0 M of Sodium carbonate in water (1.5 mL, 1.5 mmol)) and 4 ml of Acetonitrile was degassed and microwaved on 200 watts at 130° C. for 30 minutes. The reaction mixture was partitioned between ethyl acetate and water and filtered from inorganic salts. The organic layer was washed with water, brine, dried over MgSO4 and evaporated to dryness. The crude residue was purified on silicagel column, eluting the product with 0.4% of methanol in methylene chloride. Yield 150 mg (42%). MS: (ESI+)=285.0.

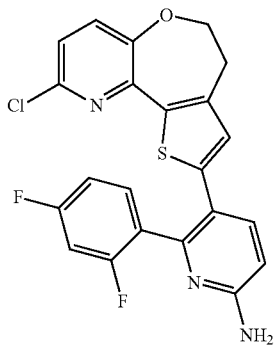 [SMILES: Nc1ccc(-c2cc3c(s2)-c2nc(Cl)ccc2OCC3)c(-c2ccc(F)cc2F)n1]

A mixture of 140 mg (0.49 mmol) of 5-bromo-6-(2,4-difluorophenyl)pyridin-2-amine, 146 mg (0.52 mmol) of 2-chloro-6,7-dihydro-pyrido[3,2-b]thieno[2,3-d]oxepine-9-boronic acid and 20 mg (0.0025 mmol) of [1,1'-bis(diphenylphosphino)ferrocene]dichloropalladium (II), complex with dichloromethane (1:1) in 0.86 ml (0.86 mmol) of 1 M aqueous sodium carbonate and 4 ml of dioxane was degassed microwaved on 200 watts at 130° C. for 30 minutes. The reaction mixture was partitioned between dichloromethane and water and filtered from inorganic salts. The organic layer was washed with water, brine, dried over MgSO4 and evaporated to dryness. The crude residue was purified on silica gel column, eluting the product with 35-40% of ethyl acetate. Yield 110 mg (51%). MS: (ESI+) 442.2

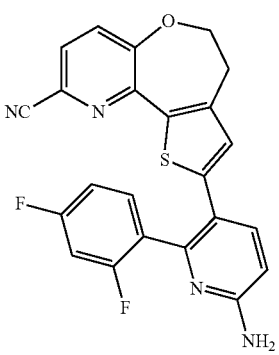 [SMILES: N#Cc1ccc2c(n1)-c1sc(-c3ccc(N)nc3-c3ccc(F)cc3F)cc1CCO2]

A suspension of 75 mg (0.168 mmol) of the above product, 59 mg (0.5 mmol) of zinc cyanide, 33 mg (0.5 mmol) of zinc and 20 mg (0.02 mmol) of [1,1'-bis(diphenylphosphino)ferrocene]dichloropalladium (II), complex with dichloromethane (1:1), in 3 ml of dimethylformamide was degassed and microwaved on 200 watts at 180° C. for 30 minutes. The reaction mixture was mixed with 30 ml of 3% ammonium hydroxide in water and extracted with 20 ml of ethyl acetate three times. The combined organic extract was washed with water, brine, dried over anhydrous sodium sulfate and concentrated in vacuum. The residue was triturated with dichloromethane producing a precipitate, which was collected, washed with cold dichloromethane and dried in vacuum. Yield 47 mg (64%). MS: (ESI+) 432.2

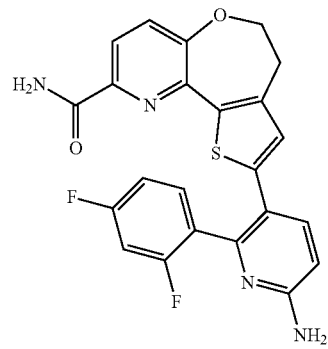 [SMILES: NC(=O)c1ccc2c(n1)-c1sc(-c3ccc(N)nc3-c3ccc(F)cc3F)cc1CCO2]

A mixture of 47 mg (0.11 mmol) of the above nitrile, 61 mg (0.44 mmol) of potassium carbonate and 27 uL (0.44 mmol) of 50% hydrogen peroxide was stirred for 4 hours. Another portion of 27 uM of hydrogen peroxide was added and the mixture was continued to stir for 2 hours. The reaction mixture was mixed with 30 ml of water and extracted with 30 ml of ethyl acetate three times. The combined organic extracts were washed with water, brine, dried over anhydrous sodium sulfate and concentrated in vacuum. The residue was purified by reverse phase HPLC (acetonitrile gradient) to give 454. Yield 19 mg (38%). MS: (ESI+) 451.1 $^1$H NMR (400 MHz, DMSO) δ 8.19 (s, 1H), 7.74 (d, J=8.2, 6H), 7.51-7.41 (m, 4H), 7.29-7.19 (m, 4H), 7.14 (td, J=8.5, 2.4, 2H), 6.66 (s, 2H), 6.57 (d, J=8.6, 2H), 6.42 (s, 4H), 4.31 (t, J=4.6, 4H), 3.06 (t, J=4.6, 5H).

Example 308

8-(1H-pyrazol-4-yl)-(4H-4-isobutyl-1,2,4-triazol-5-yl)-4,5-dihydro-6-oxa-3-thia-1-aza-benzo[e]azulene 455

Step 1: Preparation of (1B)

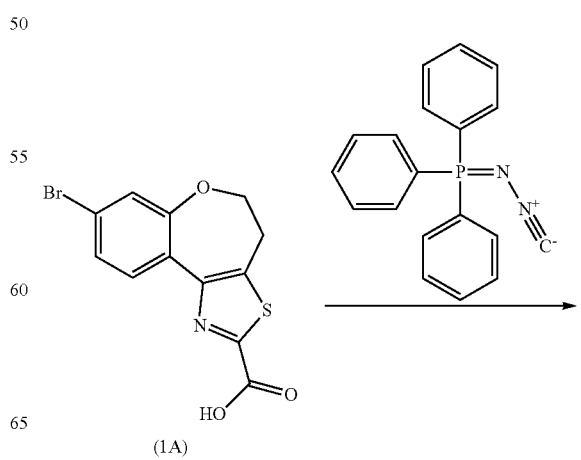

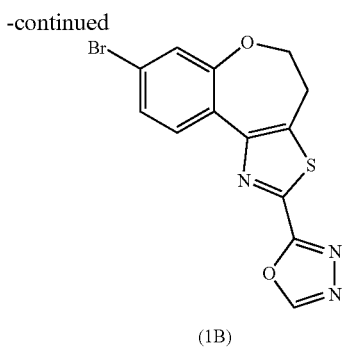

(1B)

To (1A) (2.5 g, 7.7 mmol) was added DCM (20 mL). To this mixture was added (isocyanoimino)triphenylphosphorane (2.3 g, 7.7 mmol) dissolved in DCM (20 mL) dropwise over 20 minutes. The reaction was allowed to stir 5 hours at room temperature. The reaction mixture was diluted with water and extracted with ethyl acetate. The combined organic extracts were washed sequentially with water and brine. The organic layer was dried over MgSO$_4$, filtered and concentrated under reduced pressure. The crude material was purified by column chromatography on silica gel eluting with 60% EtOAc in hexanes to provide 0.66 g (25%) of the desired product (1B): LC/MS (APCI): m/z 352.0 (M+H).

Step 2: Preparation of (1C)

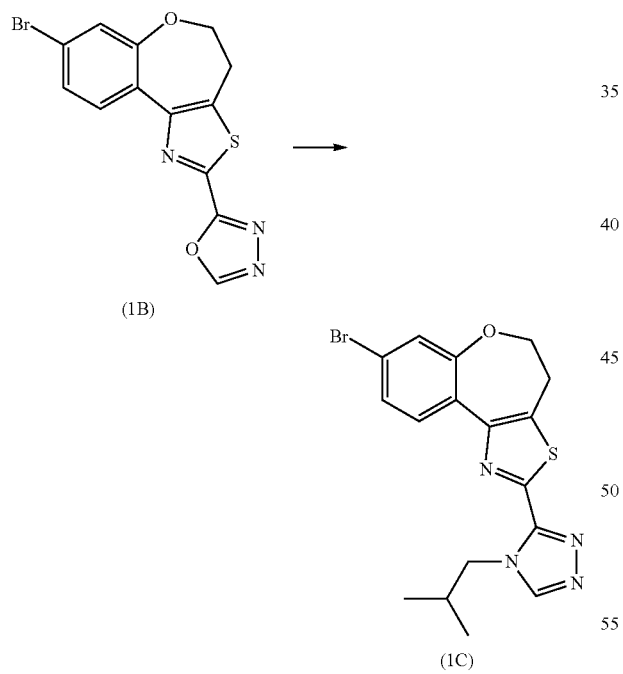

To (1B) (0.236 g, 0.674 mmol) and isobutylamine (0.2 mL, 2 mmol) was added toluene (2 mL) and TFA (0.3 mL) and allowed to stir and heat at 65° C. in a sealed vial for 24 hours. The reaction was monitored by LCMS. To the reaction mixture was added isobutylamine (0.2 mL, 2 mmol) and TFA (0.3 mL) and allowed to stir and heat at 65° C. in a sealed vial for 24 hours. Allowed to cool to room temperature, added EtOAc, filtered, and concentrated the filtrate under reduced pressure to provide 0.273 g (quantitative yield) of the desired product 8-bromo-(4H-4-isobutyl-1,2,4-triazol-5-yl)-4,5-dihydro-6-oxa-3-thia-1-aza-benzo[e]azulene (1C): LC/MS (APCI): m/z 405.0 (M+H).

Step 3: Preparation of 455

To 8-bromo-(4H-4-isobutyl-1,2,4-triazol-5-yl)-4,5-dihydro-6-oxa-3-thia-1-aza-benzo[e]azulene (1C) (0.273 g, 0.674 mmol), 4-pyrazole boronic acid (0.060 g, 0.808 mmol), potassium acetate (0.264 g, 2.69 mmol) and tetrakis(triphenylphosphine)palladium(0) (39 mg, 0.03 mmol) was added DMF (10 mL) and water (1 mL). Nitrogen was bubbled through the reaction mixture for 5 minutes. The reaction mixture was allowed to stir and heat at 105° C. for 24 hours. The reaction mixture was concentrated under reduced pressure and purified by reverse phase HPLC provide 0.023 g (9%) of 455: LC/MS (APCI): m/z 393.1 (M+H).

Example 309

2-(5-Isopropyl-[1,2,4]triazol-1-yl)-4,5-dihydro-6-oxa-3-thia-1-aza-benzo[e]azulene-8-carboxylic acid amide 478

Step 1:
[1-Dimethylamino-meth-(E)-ylidene]-isobutyramide

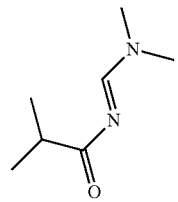

Following the procedure for 449, Step 3, isobutyramide was reacted with DMF-DMA to afford the title compound as a yellow oil. $^1$H NMR (CDCl$_3$): 8.39 (1H, s), 3.10 (3H, m), 3.07 (3H, d, J=0.67 Hz), 2.68-2.56 (1H, m), 1.17 (3H, s), 1.18-1.11 (3H, s).

Step 2: 8-Bromo-2-(5-isopropyl-[1,2,4]triazol-1-yl)-4,5-dihydro-6-oxa-3-thia-1-aza-benzo[e]azulene

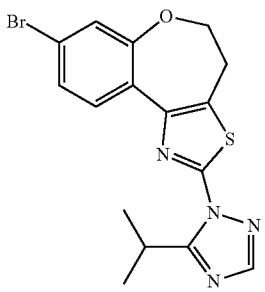 [SMILES: CC(C)c1ncnn1-c1nc2c(s1)CCOc1cc(Br)ccc1-2]

Following the procedure for 449, Step 4, (8-bromo-4,5-dihydro-6-oxa-3-thia-1-aza-benzo[e]azulen-2-yl)-hydrazine was reacted with [1-dimethylamino-meth-(E)-ylidene]-isobutyramide to afford the title compound as a beige solid. LCMS (Method D): R$_T$=5.09 min, [M+H]$^+$=391 and 393. $^1$H NMR (CDCl$_3$): 8.14 (1H, d, J=8.5 Hz), 7.89 (1H, s), 7.31-7.24 (2H, m), 4.40 (2H, t, J=5.0 Hz), 4.15-4.07 (1H, m), 3.33 (2H, t, J=5.0 Hz), 1.50 (3H, s), 1.48 (3H, s).

Step 3: 2-(5-Isopropyl-[1,2,4]-triazol-1-yl)-4,5-dihydro-6-oxa-3-thia-1-aza-benzo[e]azulene-8-carboxylic acid amide Following the procedure for 414, Step 4, 8-bromo-2-(5-isopropyl-[1,2,4]triazol-1-yl)-4,5-dihydro-6-oxa-3-thia-1-aza-benzo[e]azulene was reacted with hydroxylamine hydrochloride to afford 478 as a white solid. LCMS (Method C): $R_T$=8.56 min, [M+H]$^+$=356.
$^1$H NMR (DMSO-d$_6$): 8.26 (1H, d, J=8.3 Hz), 8.17 (1H, s), 7.99 (1H, bs), 7.69 (1H, dd, J=8.3, 1.8 Hz), 7.57 (1H, d, J=1.8 Hz), 7.41 (1H, bs), 4.39 (2H, t, J=5.0 Hz), 4.10-4.00 (1H, m), 3.41 (2H, t, J=5.0 Hz), 1.42 (3H, s), 1.41 (3H, s).

Example 310

2-(2-carbamoyl-6,7-dihydropyrido[3,2-b]thieno[2,3-d]oxepin-9-yl)-3-(2,4-difluorophenyl)-5-aminopyrazine 480

Following the procedures for 454, compound 480 was prepared. MS: (ESI+) 452.0. $^1$H NMR (400 MHz, DMSO) δ 8.49 (d, 1H), 7.99 (s, 2H), 7.77 (d, J=8.3, 5H), 7.57 (dd, J=15.0, 8.5, 4H), 7.49 (d, J=8.3, 2H), 7.38 (d, J=12.1, 4H), 7.27 (t, J=9.9, 3H), 6.96 (s, 4H), 6.34 (s, 2H), 4.30 (t, J=4.6, 3H), 3.00 (t, J=4.4, 3H)

Example 311

2-(5-Isopropyl-[1,2,4]triazol-1-yl)-8-(1H-pyrazol-4-yl)-4,5-dihydro-6-oxa-3-thia-1-aza-benzo[e]azulene 484

A suspension of 8-bromo-2-(5-isopropyl-[1,2,4]triazol-1-yl)-4,5-dihydro-6-oxa-3-thia-1-aza-benzo[e]azulene (84 mg, 0.21 mmol), 4,4,5,5-tetramethyl-2-(1H-pyrazol-4-yl)-1,3,2-dioxaborolane (62 mg, 0.32 mmol), tetrakis(triphenylphosphine) palladium (0) (24 mg, 0.021 mmol) and sodium carbonate (45 mg, 0.42 mmol) in acetonitrile (6 mL) and water (3 mL) under nitrogen was heated at 140° C. for 25 mins under microwave irradiation. More tetrakis(triphenylphosphine) palladium (0) (24 mg, 0.021 mmol) was added, and heating was pursued for 30 mins at 150° C. The reaction mixture was diluted with ethyl acetate and water. The organic layer was washed with brine, dried (Na$_2$SO$_4$), concentrated in vacuo and purified twice by flash chromatography (SiO$_2$, gradient 50 to 75% ethyl acetate in cyclohexane, then 60% ethyl acetate in cyclohexane) to afford 484 as an off-white solid (16 mg, 20%). LCMS (Method C): $R_T$=10.30 min, [M+H]$^+$=379. $^1$H NMR (DMSO-d$_6$): 12.98 (1H, bs), 8.28 (1H, bs), 8.18 (1H, d, J=8.3 Hz), 8.16 (1H, s), 7.99 (1H, bs), 7.46 (1H, dd, J=8.3, 1.8 Hz), 7.34 (1H, d, J=1.8 Hz), 4.38 (2H, t, J=5.0 Hz), 4.13-4.01 (1H, m), 3.37 (2H, t, J=5.0 Hz), 1.43 (3H, s), 1.41 (3H, s).

Example 312

2-(5-Isopropyl-[1,2,4]triazol-1-yl)-9-(1H-pyrazol-4-yl)-4,5-dihydro-6-oxa-3-thia-1-aza-benzo[e]azulene 489

Step 1:
4,7-Dibromo-3,4-dihydro-2H-benzo[b]oxepin-5-one

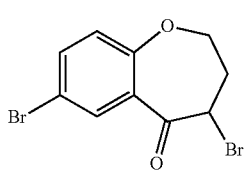 [SMILES: O=C1c2cc(Br)ccc2OCCC1Br]

Following the procedure for 449, Step 1, 7-bromo-3,4-dihydro-2H-benzo[b]oxepin-5-one was reacted with bromine to afford the title compound as a white solid.
$^1$H NMR (CDCl$_3$): 7.86 (1H, d, J=2.6 Hz), 7.53 (1H, dd, J=8.7, 2.6 Hz), 6.96 (1H, d, J=8.7 Hz), 4.94 (1H, dd, J=7.6, 6.7 Hz), 4.43 (1H, ddd, J=12.7, 5.6, 4.7 Hz), 4.18 (1H, ddd, J=12.7, 9.7, 4.4 Hz), 2.97-2.87 (1H, m), 2.51 (1H, ddt, J=14.7, 7.6, 4.6 Hz).

Step 2: (9-Bromo-4,5-dihydro-6-oxa-3-thia-1-aza-benzo[e]azulen-2-yl)-hydrazine

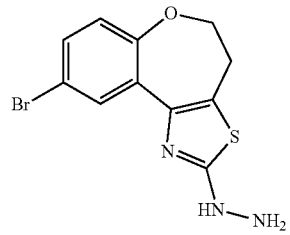 [SMILES: NNc1nc2c(s1)CCOc1ccc(Br)cc1-2]

Following the procedure for 449, Step 2, 4,7-dibromo-3,4-dihydro-2H-benzo[b]oxepin-5-one was reacted with thiosemicarbazide to afford the title compound as a beige solid. LCMS (Method E): $R_T$=3.85 min, [M+H]$^+$=312 and 314. $^1$H NMR (DMSO-d$_6$): 10.13 (2H, bs), 9.80 (1H, bs), 8.49 (1H, d, J=2.6 Hz), 7.37 (1H, dd, J=8.6, 2.6 Hz), 6.97 (1H, d, J=8.6 Hz), 4.29 (2H, t, J=5.0 Hz), 3.21 (2H, t, J=5.0 Hz).

Step 3: 9-Bromo-2-(5-isopropyl-[1,2,4]triazol-1-yl)-4,5-dihydro-6-oxa-3-thia-1-aza-benzo[e]azulene

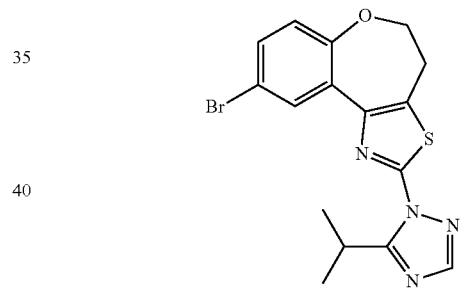

Following the procedure for 449, Step 4, (9-Bromo-4,5-dihydro-6-oxa-3-thia-1-aza-benzo[e]azulen-2-yl)-hydrazine was reacted with [1-dimethylamino-meth-(E)-ylidene]-isobutyramide to afford the title compound as a beige solid. LCMS (Method E): $R_T$=5.22 min, [M+H]$^+$=391 and 393. $^1$H NMR (DMSO-d$_6$): 8.32 (1H, d, J=2.6 Hz), 8.17 (1H, s), 7.44 (1H, dd, J=8.6, 2.6 Hz), 7.04 (1H, d, J=8.6 Hz), 4.37 (2H, t, J=5.0 Hz), 4.01-3.93 (1H, m), 3.38 (2H, t, J=5.0 Hz), 1.43 (3H, s), 1.41 (3H, s).

Step 4: 2-(5-Isopropyl-[1,2,4]triazol-1-yl)-9-(1H-pyrazol-4-yl)-4,5-dihydro-6-oxa-3-thia-1-aza-benzo[e]azulene Following the procedure for 484, Step 4, 9-bromo-2-(5-isopropyl-[1,2,4]triazol-1-yl)-4,5-dihydro-6-oxa-3-thia-1-aza-benzo[e]azulene was reacted with 4-(4,4,5,5-tetramethyl-[1,3,2]dioxaborolan-2-yl)-1H-pyrazole to afford 489 as a white solid. LCMS (Method C): $R_T$=10.17 min, [M+H]$^+$=379. $^1$H NMR (DMSO-d$_6$): 12.95 (1H, bs), 8.42 (1H, d, J=2.3 Hz), 8.18 (1H, s), 8.07 (1H, bs), 7.81 (1H, bs), 7.51 (1H, dd, J=8.3, 2.3 Hz), 7.06 (1H, d, J=8.3 Hz), 4.36 (2H, t, J=5.0 Hz), 4.12-4.04 (1H, m), 3.38 (2H, t, J=5.0 Hz), 1.47 (3H, s), 1.46 (3H, s).

Example 313

2-(5-Isopropyl-[1,2,4]triazol-1-yl)-4,5-dihydro-6-oxa-3-thia-1-aza-benzo[e]azulene-9-carboxylic acid amide 490

Following the procedure for 414, Step 4,9-bromo-2-(5-isopropyl-[1,2,4]triazol-1-yl)-4,5-dihydro-6-oxa-3-thia-1-aza-benzo[e]azulene was reacted with hydroxylamine hydrochloride to afford 490 as a white solid. LCMS (Method C): $R_T$=8.44 min, [M+H]$^+$=356.
$^1$H NMR (DMSO-$d_6$): 8.82 (1H, d, J=2.3 Hz), 8.17 (1H, s), 7.91 (1H, bs), 7.75 (1H, dd, J=8.4, 2.3 Hz), 7.24 (1H, bs), 7.09 (1H, d, J=8.4 Hz), 4.40 (2H, t, J=5.0 Hz), 4.10-4.02 (1H, m), 3.39 (2H, t, J=5.0 Hz), 1.43 (3H, s), 1.41 (3H, s).

Example 314

2-(5-Isopropyl-[1,2,4]triazol-1-yl)-4,5-dihydro-6-oxa-3-thia-1-aza-benzo[e]azulene-8-carboxylic acid (2-hydroxy-ethyl)-amide 498

Following the procedure for 414, Step 4,8-bromo-2-(5-isopropyl-[1,2,4]triazol-1-yl)-4,5-dihydro-6-oxa-3-thia-1-aza-benzo[e]azulene was reacted with 2-aminoethanol to afford 498 as an off-white solid. LCMS (Method C): $R_T$=8.12 min, [M+H]$^+$=400. $^1$H NMR (DMSO-$d_6$): 8.45 (1H, t, J=5.6 Hz), 8.27 (1H, d, J=8.3 Hz), 8.17 (1H, s), 7.67 (1H, dd, J=8.3, 1.8 Hz), 7.56 (1H, d, J=1.8 Hz), 4.71 (1H, t, J=5.6 Hz), 4.39 (2H, t, J=5.0 Hz), 4.10-4.02 (1H, m), 3.51 (2H, q, J=6.0 Hz), 3.41 (2H, t, J=5.0 Hz), 3.34 (2H, q, J=6.0 Hz), 1.42 (3H, s), 1.40 (3H, s).

Example 315

2-(5-Isopropyl-[1,2,4]triazol-1-yl)-4,5-dihydro-6-oxa-3-thia-1-aza-benzo[e]azulene-9-carboxylic acid (2-hydroxy-ethyl)-amide 499

Following the procedure for 414, Step 4,9-bromo-2-(5-isopropyl-[1,2,4]triazol-1-yl)-4,5-dihydro-6-oxa-3-thia-1-aza-benzo[e]azulene was reacted with 2-aminoethanol to afford 499 as an off-white solid. LCMS (Method C): $R_T$=8.02 min, [M+H]$^+$=400. $^1$H NMR (DMSO-$d_6$): 8.81 (1H, d, J=2.3 Hz), 8.35 (1H, t, J=5.6 Hz), 8.17 (1H, s), 7.75 (1H, dd, J=8.4, 2.3 Hz), 7.11 (1H, d, J=8.4 Hz), 4.71 (1H, t, J=5.6 Hz), 4.40 (2H, t, J=4.9 Hz), 4.11-4.01 (1H, m), 3.52 (2H, q, J=6.0 Hz), 3.40 (2H, t, J=4.9 Hz), 3.34 (2H, q, J=6.1 Hz), 1.44 (3H, s), 1.42 (3H, s).

Example 316

8-(morpholinomethanimine)-2-isopropyl-2H-1,2,4-triazol-3-yl-4,5-dihydro-6-oxa-3-thia-1-aza-benzo[e]azulene 501

Prepared as for 512, 8-methylthioamide-(2-isopropyl-2H-1,2,4-triazol-3-yl)-4,5-dihydro-6-oxa-3-thia-1-aza-benzo[e]azulene (162 mg, 0.42 mmoles) was reacted in a round-bottom flask equipped with a magnetic stir-bar, with morpholine (73.3 µL, 0.84 mmoles, 2 equiv.), acetic acid (48.1 µL, 0.84 mmoles, 2 equiv.) and methanol (2.1 mL) and stirred at room temperature for 2 hours. The mixture was concentrated to dryness and purified by reverse-phase HPLC to obtain 119.8 mg 67% yield of 501 as a colorless solid.

Example 317

2-(2-carbamoyl-6,7-dihydropyrido[3,2-b]thieno[2,3-d]oxepin-9-yl)-5-aminopyrazine 503

Following the procedures for 454, compound 503 was prepared. MS: (ESI+) 340.0. $^1$H NMR (400 MHz, DMSO) δ 8.50 (d, J=1.2, 1H), 7.89 (d, J=1.3, 1H), 7.79 (d, J=8.3, 1H), 7.68 (s, 1H), 7.56 (s, 1H), 7.51 (d, J=8.3, 1H), 7.48 (s, 1H), 6.70 (s, 2H), 4.40 (t, J=4.5, 2H), 3.24 (t, J=4.6, 2H).

Example 318

8-(morpholinomethanimine)-2-isopropyl-2H-1,2,4-triazol-3-yl-4,5-dihydro-6-oxa-3-thia-1-aza-benzo[e]azulene 511

Prepared as for 512, 8-methylthioamide-(2-isopropyl-2H-1,2,4-triazol-3-yl)-4,5-dihydro-6-oxa-3-thia-1-aza-benzo[e]azulene (150 mg, 0.39 mmoles) was reacted in a round-bottom flask equipped with a magnetic stir-bar with ammonium acetate (749.8 mg, 9.73 mmoles, 25 equiv.) and methanol (1.95 mL). The reaction mixture was stirred at room temperature for 4 hours. Saturated Na$_2$CO$_3$ was added and the reaction mixture was extracted with methylene chloride (3×). The organic phases were combined, dried with MgSO$_4$, and concentrated. The product was purified by reverse phase HPLC to obtain 11.5 mg (8.3% yield) of 511 as a colorless solid.

Example 319

8-(methylformamidinyl)-2-isopropyl-2H-1,2,4-triazol-3-yl-4,5-dihydro-6-oxa-3-thia-1-aza-benzo[e]azulene 512

8-Bromo-2-isopropyl-2H-1,2,4-triazol-3-yl-4,5-dihydro-6-oxa-3-thia-1-aza-benzo[e]azulene (330 mg, 0.84 mmol) and degassed dimethylformamide (4.2 mL) were added to a CEM microwave vial. The mixture was thoroughly purged with nitrogen. Zinc cyanide (99.0 mg, 0.84 mmol, 1.0 equiv.) and Pd(PPh$_3$)$_4$ (48.7 mg, 0.04 mmol, 0.05 equiv.) were added to the reaction mixture in one portion and the vial was sealed immediately. The reaction was submitted to MW irradiation at 60 W for 15 minutes (T=175° C.). The mixture was diluted with methylene chloride, filtered through celite, and washed with saturated NH$_4$Cl. The organic layers were combined, dried with MgSO$_4$ and concentrated. The crude mixture was loaded onto silica gel and purified by flash chromatography (0-100% EtOAc in hexanes) to give 202 mg (71.3% yield) of 8-cyano-2-isopropyl-2H-1,2,4-triazol-3-yl-4,5-dihydro-6-oxa-3-thia-1-aza-benzo[e]azulene a yellow solid.

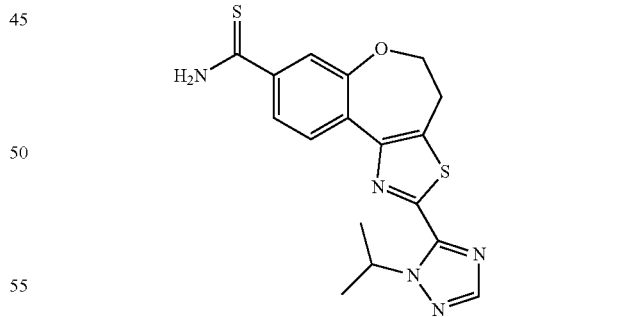

In a round-bottom flask equipped with a magnetic stir-bar, hydrogen sulfide was bubbled through a solution of 8-cyano-2-isopropyl-2H-1,2,4-triazol-3-yl-4,5-dihydro-6-oxa-3-thia-1-aza-benzo[e]azulene (750 mg, 2.22 mmoles) in pyridine (10.0 mL) and triethylamine (1.11 mL) for 20 minutes. The reaction mixture was stirred at room temperature overnight, concentrated, and partitioned between 5% methanol in methylene chloride and H$_2$O. The combined organics were washed with brine, dried over MgSO$_4$, and concentrated to give 8-thioamide-(2-isopropyl-2H-1,2,4-triazol-3-yl)-4,5-dihydro-6-oxa-3-thia-1-aza-benzo[e]azulene. LCMS showed clean conversion to product-product was carried forward crude without further purification (obtained as a yellow solid).

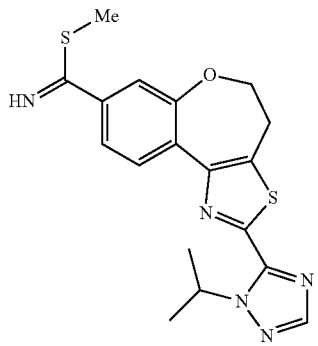 [SMILES: CSC(=N)c1ccc2c(c1)OCCc1sc(-c3ncnn3C(C)C)nc1-2]

To a solution of 8-thioamide-(2-isopropyl-2H-1,2,4-triazol-3-yl)-4,5-dihydro-6-oxa-3-thia-1-aza-benzo[e]azulene (820 mg, 2.21 mmoles) in acetone (5.52 mL) in a round bottom flask equipped with a magnetic stir-bar was added methyl iodide (0.69 mL, 11.04 mmoles, 5 equiv.) via syringe. The mixture was stirred at room temperature overnight. LCMS showed clean conversion to 8-methylthioamide-(2-isopropyl-2H-1,2,4-triazol-3-yl)-4,5-dihydro-6-oxa-3-thia-1-aza-benzo[e]azulene. The solution was concentrated to dryness and used crude in a round-bottom flask equipped with a magnetic stir-bar, monomethylamine (2M in methanol, 0.39 mL, 0.78 mmoles, 2 equiv.) and acetic acid (45 µL, 0.78 mmoles, 2 equiv.) in methanol (1.95 mL). The mixture was added to the thiomethyl imidate (150 mg, 0.39 mmoles) and stirred at room temperature for 4 hours. The mixture was concentrated to dryness and purified by reverse-phase HPLC to obtain 512, 32.8 mg (22.9% yield) of a colorless solid.

Example 320

5-(2-carbamoyl-6,7-dihydropyrido[3,2-b]thieno[2,3-d]oxepin-9-yl)-2-amino-6-ethylpyridine 521

Following the procedures for 454, compound 521 was prepared. MS: (ESI+) 367.0. $^1$H NMR (400 MHz, DMSO) δ 7.79 (d, J=8.3, 1H), 7.65 (s, 1H), 7.52 (d, J=8.4, 2H), 7.40 (d, J=8.4, 1H), 6.94 (s, 1H), 6.34 (d, J=8.4, 1H), 6.09 (s, 2H), 4.40 (t, J=4.5, 2H), 3.25 (t, J=4.5, 2H), 2.73 (q, J=7.5, 2H), 1.17 (t, J=7.5, 3H).

Example 321

3-(9-Bromo-4,5-dihydro-6-oxa-1-thia-benzo[e]azulen-2-yl)-4-(2,4-dichloro-phenyl)-4H-[1,2,4]triazole 532

A microwave tube charged with 2-(9-bromo-4,5-dihydro-6-oxa-1-thia-benzo[e]azulen-2-yl)-[1,3,4]oxadiazole (200 mg; 0.57 mmol), 2,4-dichloroaniline (139 mg; 0.86 mmol), TFA (64 µl; 0.86 mmol) and toluene (1.5 ml) was heated in a microwave at 160° C. for 30 min. The reaction mixture was basified with DIPEA (0.2 ml), volatiles removed in vacuo and the residue purified by prep. LCMS to give 532 as a pale yellow solid (129 mg; 46%). δ$_H$ (400 MHz, CDCl$_3$) 3.14 (t, J=5.2, 2H), 4.29 (t, J=5.2, 2H), 6.89-6.92 (m, 2H), 7.25-7.28 (m, 1H), 7.42 (d, J=8.4, 1H), 7.52 (dd, J=8.4 and 2.4, 1H), 7.66 (d, J=2.4, 1H), 7.71 (d, J=2.0, 1H), 8.22 (s, 1H). [M+H]$^+$: 493

Example 322

N-(2-aminoethyl)-2-(4-(2-chlorophenyl)-5-oxo-4,5-dihydro-1H-1,2,4-triazol-3-yl)-4,5-dihydrobenzo[b]thieno[2,3-d]oxepine-8-carboxamide 533

Step 1: Preparation of 8-bromo-N-(2-chlorophenyl)-4,5-dihydrobenzo[b]thieno[2,3-d]oxepine-2-carbothioamide

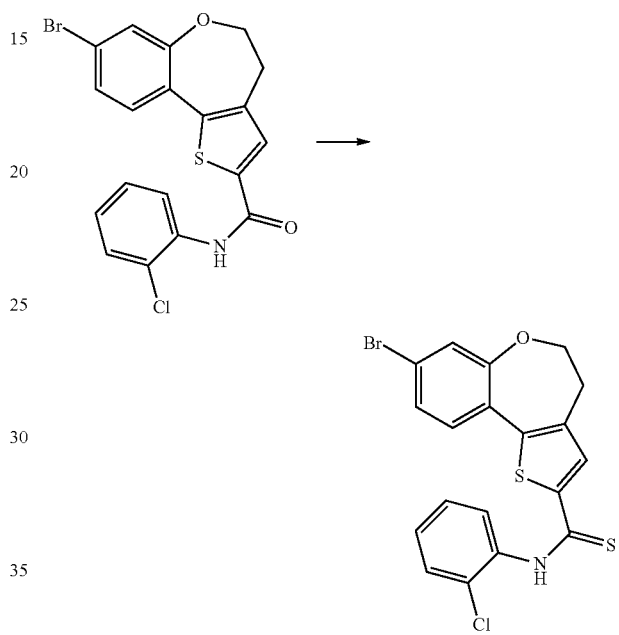

A solution of 8-bromo-N-(2-chlorophenyl)-4,5-dihydrobenzo[b]thieno[2,3-d]oxepine-2-carboxamide (10 g, 0.023 mol) in anhydrous 1,4-dioxane (400 mL) was treated with Lawesson's reagent (7.44 g, 0.018 mol) and heated at 85° C. for 4 h. The orange solution was cooled to room temperature and concentrated in vacuo. The crude product was washed with CH$_2$Cl$_2$ and then dried to give 8-bromo-N-(2-chlorophenyl)-4,5-dihydrobenzo[b]thieno[2,3-d]oxepine-2-carbothioamide as a yellow solid (9.41 g, yield 91%). ESI-MS: 449.9.

Step 2: Preparation of 8-bromo-N-(2-chlorophenyl)-4,5-dihydrobenzo[b]thieno[2,3-d]oxepine-2-carbohydrazonamide

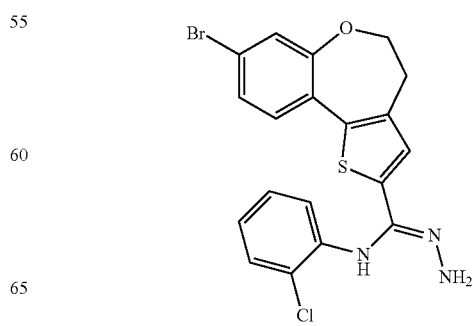

8-Bromo-4,5-dihydro-6-oxa-1-thia-benzo[e]azuene-2-carbothiolic acid (2-chloro-phenyl)-methyl-amide (9 g, 19.96 mmol) was suspended in ethanol (150 mL), mixed with 85% hydrazine aqueous solution (30 mL) and heated under reflux for 3 h. At this time, it was observed that the suspension was decolored. After cooling to room temperature, the solid was filtered and washed with ethanol, concentrated under vacuum to give 8-bromo-N-(2-chlorophenyl)-4,5-dihydrobenzo[b]thieno[2,3-d]oxepine-2-carbohydrazonamide as a yellow solid (7.41 g, yield 83%). ESI-MS: 447.98

Step 3: Preparation of 3-(8-bromo-4,5-dihydrobenzo[b]thieno[2,3-d]oxepin-2-yl)-4-(2-chlorophenyl)-1H-1,2,4-triazol-5(4H)-one

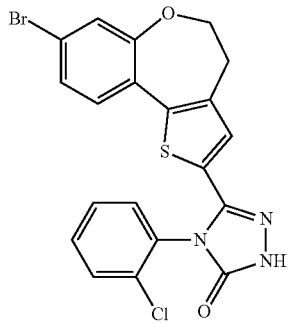 [SMILES: O=c1[nH]nc(-c2cc3c(s2)-c2ccc(Br)cc2OCC3)n1-c1ccccc1Cl]

A solution of 8-bromo-N-(2-chlorophenyl)-4,5-dihydrobenzo[b]thieno[2,3-d]oxepine-2-carbohydrazonamide (200 mg, 0.45 mmol) in anhydrous THF (8 mL) was treated with CDI (145 mg, 0.89 mmol) and stirred at room temperature overnight, diluted with water. The solid was washed with water and dried in vacuum to give 3-(8-bromo-4,5-dihydrobenzo[b]thieno[2,3-d]oxepin-2-yl)-4-(2-chlorophenyl)-1H-1,2,4-triazol-5(4H)-one (195 mg, yield: 92%). ESI-MS: 473.96

Step 4: Preparation of methyl 2-(4-(2-chlorophenyl)-5-oxo-4,5-dihydro-1H-1,2,4-triazol-3-yl)-4,5-dihydrobenzo[b]thieno[2,3-d]oxepine-8-carboxylate

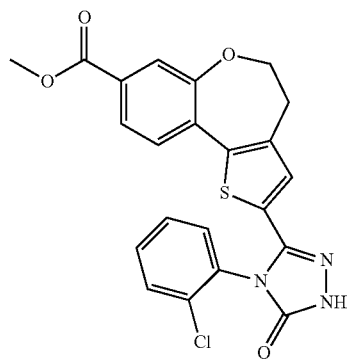 [SMILES: COC(=O)c1ccc2c(c1)OCCc1cc(-c3n[nH]c(=O)n3-c3ccccc3Cl)sc1-2]

The mixture of 3-(8-bromo-4,5-dihydrobenzo[b]thieno[2,3-d]oxepin-2-yl)-4-(2-chlorophenyl)-1H-1,2,4-triazol-5(4H)-one (6.5 g, 13.7 mmol), Pd(OAc)$_2$ (1.54 g, 6.85 mmol), dppf (6.1 g, 11.0 mmol), TEA (3.8 mL) in DMF (30 mL) and MeOH (60 mL) was stirred under CO (50 psi) atmosphere at 70° C. for 2 days. Filtered and concentrated, the crude product was purified by column chromatography (Hexanes:EtOAc=2: 1-1:1) to give methyl 2-(4-(2-chlorophenyl)-5-oxo-4,5-dihydro-1H-1,2,4-triazol-3-yl)-4,5-dihydrobenzo[b]thieno[2,3-d]oxepine-8-carboxylate (5.83 g, yield 94%). ESI-MS: 454.2.

Step 5: Preparation of 2-(4-(2-chlorophenyl)-5-oxo-4,5-dihydro-1H-1,2,4-triazol-3-yl)-4,5-dihydrobenzo[b]thieno[2,3-d]oxepine-8-carboxylic acid

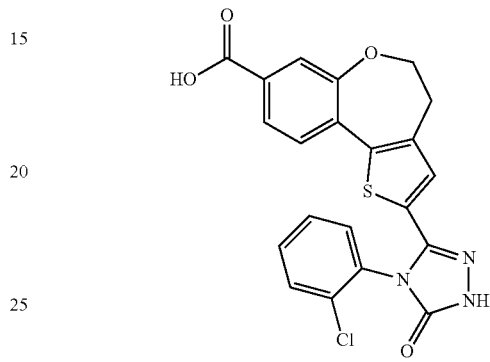

Methyl 2-(4-(2-chlorophenyl)-5-oxo-4,5-dihydro-1H-1,2,4-triazol-3-yl)-4,5-dihydrobenzo[b]thieno[2,3-d]oxepine-8-carboxylate (5.83 g, 12.8 mmol) was dissolved in 25 mL of THF and 25 mL of water and treated with LiOH (1.35 g, mono-hydrate). The whole was heated at 50° C. for 3 h, cooled to room temperature and acidified. The resulting precipitate was filtered and washed with water. The filter cake was dried to a constant weight under vacuum to give 2-(4-(2-chlorophenyl)-5-oxo-4,5-dihydro-1H-1,2,4-triazol-3-yl)-4,5-dihydrobenzo[b]thieno[2,3-d]oxepine-8-carboxylic acid (5.47 g, yield 97%). ESI-MS: 440.2. $^1$H NMR (DMSO-d$_6$, 400 MHz): δ12.34 (s, 1H, NH), 7.74-7.42 (m, 7H, ArH), 6.50 (s, 1H, =CH), 4.18 (t, J=5.2 Hz, 2H, CH$_2$), 2.98 (t, J=5.2 Hz, 2H, CH$_2$).

Step 6: Preparation of 2-(4-(2-chlorophenyl)-5-oxo-4,5-dihydro-1H-1,2,4-triazol-3-yl)-4,5-dihydrobenzo[b]thieno[2,3-d]oxepine-8-carbonyl chloride

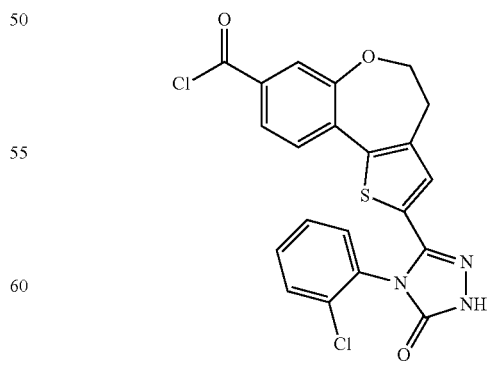

A solution of 2-(4-(2-chlorophenyl)-5-oxo-4,5-dihydro-1H-1,2,4-triazol-3-yl)-4,5-dihydrobenzo[b]thieno[2,3-d]oxepine-8-carboxylate acid (400 mg, 0.91 mmol) in 20 mL of SOCl$_2$ was heated at 80° C. for 3 h. Concentration gave 2-(4-(2-chlorophenyl)-5-oxo-4,5-dihydro-1H-1,2,4-triazol-3-yl)-4,5-dihydrobenzo[b]thieno[2,3-d]oxepine-8-carbonyl chloride.

To a solution of ethane-1,2-diamine (82 mg, 1.36 mmol) and pyridine (0.5 mL) in 5 mL of THF was slowly added 2-(4-(2-chlorophenyl)-5-oxo-4,5-dihydro-1H-1,2,4-triazol-3-yl)-4,5-dihydrobenzo[b]thieno[2,3-d]oxepine-8-carbonyl chloride (ca. 417 mg, ca. 0.91 mmol) in 20 mL of THF at 0° C. The mixture was stirred at room temperature overnight, diluted with water and purified by preparative HPLC to afford 66 mg of 533, isolated yield: 20%. ESI-MS: 482. $^1$H NMR (DMSO-d$_6$, 400 MHz): δ 8.74 (s, 1H, NH), 8.37 (s, 1H, NH), 7.74-7.47 (m, 7H, ArH), 6.47 (s, 1H, =CH), 4.19 (t, J=4.8 Hz, 2H, CH$_2$), 3.40-3.36 (m, 4H, 2CH$_2$), 2.98 (t, J=5.2 Hz, 2H, CH$_2$), 2.86 (t, J=6.0 Hz, 2H, CH$_2$).

Example 323

3-(2-cyano-6,7-dihydropyrido[3,2-b]thieno[2,3-d]oxepin-9-yl)-2-(2,4-difluorophenyl)-2H-1,2,4-triazole 366

To solution containing 3-(2-chloro-6,7-dihydropyrido[3,2-b]thieno[2,3-d]oxepin-9-yl)-2-(2,4-difluorophenyl)-2H-1,2,4-triazole (0.030 g, 0.072 mmol), zinc cyanide (16.9 mg, 0.144 mmol), and tetrakis(triphenylphosphine)palladium(0) (4.16 mg, 0.00360 mmol) in N,N-dimethylformamide (1.00 mL, 12.9 mmol) was evacuated then back-filled with nitrogen. The reaction mixture was heated in microwave to 200° C. for 10 min. The reaction mixture was quenched with sat. NH4Cl then extracted EtOAc (3×). The crude product was purified by column chromatography (EtOAc/Hex) (eluted 50% EtOAc) to give 366 (60% yield). MS: (ESI+)=408.0

Example 324

4-(2-cyano-6,7-dihydropyrido[3,2-b]thieno[2,3-d]oxepin-9-yl)-5-(2,4-difluorophenyl)-2H-1,2,3-triazole 367

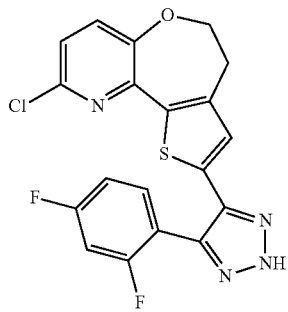 [SMILES: Fc1ccc(-c2n[nH]nc2-c2cc3c(s2)-c2nc(Cl)ccc2OCC3)c(F)c1]

To solution containing 4-(2-chloro-6,7-dihydropyrido[3,2-b]thieno[2,3-d]oxepin-9-yl)-5-(2,4-difluorophenyl)-2H-1,2,3-triazole (0.085 g, 0.20 mmol), zinc cyanide (47.9 mg, 0.408 mmol;), and tetrakis(triphenylphosphine)palladium(0) (11.8 mg, 0.0102 mmol;) in N,N-dimethylformamide (2.83 mL, 36.6 mmol;) was evacuated then back-filled with nitrogen. The reaction mixture was heated in microwave to 200° C. for 10 min. The reaction mixture was quenched with sat. NH4Cl then extracted EtOAc (3×). The crude product was purified by column chromatography (EtOAc/Hex) to give 367 (84% yield). MS: (ESI+)=408.2

Example 325

N-(4-(dimethylcarbamoyl)phenyl)-N-methyl-(2-cyano-6,7-dihydropyrido[3,2-b]thieno[2,3-d]oxepine)-9-carboxamide 378

Following the procedure for 366, compound 362, zinc cyanide, and tetrakis(triphenylphosphine)palladium(0) in N,N-dimethylformamide were reacted to give 378. Yield 38% MS: (ESI+)=433.2

Example 326

4-(2-carbamoyl-6,7-dihydropyrido[3,2-b]thieno[2,3-d]oxepin-9-yl)-5-(2,4-difluorophenyl)-2H-1,2,3-triazole 379

To a solution of 367 (70.0 mg, 0.172 mmol) in dimethyl sulfoxide (0.439 mL, 6.18 mmol) and treated with a solution of potassium carbonate (65.5 mg, 0.474 mmol;) in water (0.433 mL, 24.0 mmol;). After cooling at 0° C., hydrogen peroxide (0.540 mL, 7.04 mmol) was added slowly. The reaction was complete by LCMS at 15 min. Saturated sodium bisulfite (0.894 g, 8.59 mmol) was added and the reaction mixture extracted into ethyl acetate. The organics were washed with brine, dried over sodium sulfate and concentrated to give crude C which was submitted to reverse-phase HPLC to give 379 (27% yield). MS: (ESI+)=426.1

Example 327

3-(2-carbamoyl-6,7-dihydropyrido[3,2-b]thieno[2,3-d]oxepin-9-yl)-4-(2,4-difluorophenyl)-4H-1,2,4-triazole 392

Following the procedure to prepare 379, compound 393, hydrogen peroxide, potassium carbonate in water and DMSO were reacted to give 392. Yield 38% MS: (ESI+)=426.2

Example 328

3-(2-cyano-6,7-dihydropyrido[3,2-b]thieno[2,3-d]oxepin-9-yl)-4-(2,4-difluorophenyl)-4H-1,2,4-triazole 393

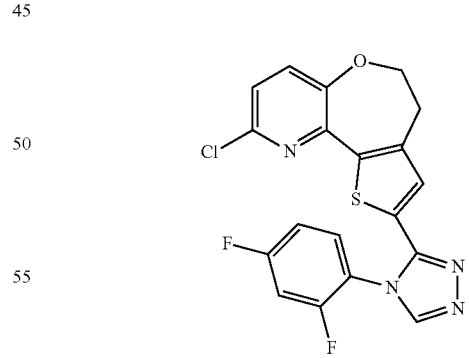

Following the procedure to give 366, 4-(2-chloro-6,7-dihydropyrido[3,2-b]thieno[2,3-d]oxepin-9-yl)-5-(2,4-difluorophenyl)-2H-1,2,3-triazole, 3-(2-chloro-6,7-dihydropyrido[3,2-b]thieno[2,3-d]oxepin-9-yl)-4-(2,4-difluorophenyl)-4H-1,2,4-triazole, zinc cyanide, and tetrakis(triphenylphosphine)palladium(0) in N,N-dimethylformamide were reacted to give 393. Yield 80% MS: (ESI+)=408.0

Example 329

5-(2-carbamoyl-6,7-dihydropyrido[3,2-b]thieno[2,3-d]oxepin-9-yl)-1-(2,4-difluorophenyl)-1H-1,2,4-triazole 432

Following the procedure to prepare 379, compound 366, hydrogen peroxide, potassium carbonate in water and DMSO were reacted to give 432. Yield 38% MS: (ESI+)=426.1

Example 330

(9-(1-(2,4-difluorophenyl)-1H-1,2,4-triazol-5-yl)-6,7-dihydropyrido[3,2-b]thieno[2,3-d]oxepin-2-yl)(4-methylpiperazin-1-yl)methanone 433

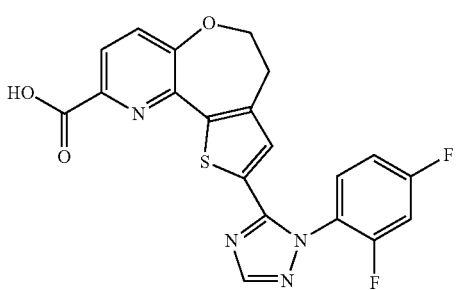 [SMILES: O=C(O)c1ccc2c(n1)-c1sc(-c3ncnn3-c3ccc(F)cc3F)cc1CCO2]

5-(2-Carboxy-6,7-dihydropyrido[3,2-b]thieno[2,3-d]oxepin-9-yl)-1-(2,4-difluorophenyl)-1H-1,2,4-triazole (0.052 g, 0.12 mmol) was dissolved in N,N-dimethylformamide (0.904 mL, 0.0117 mol) and treated sequentially with N,N-diisopropylethylamine (0.127 mL, 0.732 mmol) 1-methylpiperazine, (0.0541 mL, 0.488 mmol), then N,N,N',N'-tetramethyl-O-(7-azabenzotriazol-1-yl)uronium hexafluorophosphate (HATU, 0.0556 g, 0.146 mmol). The reaction was stirred at room temperature overnight. Saturated sodium bicarbonate was added and extracted with ethyl acetate. Organics were dried over sodium sulfate and concentrated. The crude product was submitted HPLC purification to give 433 (32% yield). MS: (ESI+)=509.3

Example 331

5-(2-(2-methylpyrid-3-yl)-6,7-dihydropyrido[3,2-b]thieno[2,3-d]oxepin-9-yl)-1-(2,4-difluorophenyl)-1H-1,2,4-triazole 474

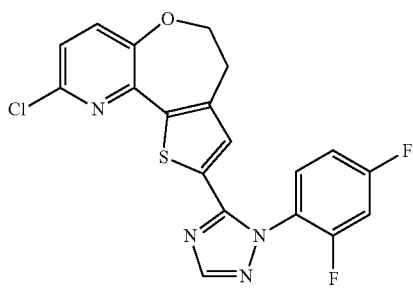 [SMILES: Fc1ccc(-n2ncnc2-c2cc3c(s2)-c2nc(Cl)ccc2OCC3)c(F)c1]

5-(2-(Chloro)-6,7-dihydropyrido[3,2-b]thieno[2,3-d]oxepin-9-yl)-1-(2,4-difluorophenyl)-1H-1,2,4-triazole (50 mg, 0.1 mmol) was dissolved in 1 ml acetonitrile and 1 ml water, with potassium acetate (39.9 mg, 0.406 mmol). The solution was degassed by bubbling with nitrogen for 5 min. 2-Methylpyridin-3-ylboronic acid (21.4 mg, 0.156 mmol) was added, then tetrakis(triphenylphosphine)palladium(0) (19 mg, 0.016 mmol). The reaction was microwaved at 300 watts, 140° C. for 20 minutes, cooled to room temperature, and extracted with ethyl acetate. The combined organics were concentrated and purified by reverse phase HPLC to give 474 (70% yield). MS: (ESI+)=474.0

Example 2bp

Methyl 8-bromo-4H-thieno[3,2-c]chromene-2-carboxylate 2bp

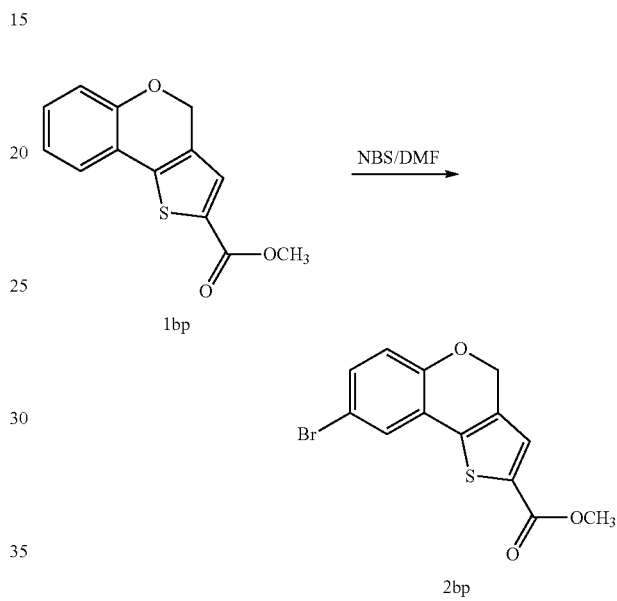

To a solution of methyl 4H-thieno[3,2-c]chromene-2-carboxylate 1bp (Sigma Aldrich, CAS Reg. 126522-01-8; Sekhar et al (1989) Sulfur Letters 9(6):271-7; 2.00 g, 8.12 mmol, 1 equiv) in N,N-dimethylformamide (31 mL) was added N-bromosuccinimide (1.91 g, 10.7 mmol, 1.32 equiv) at 24° C. over 5 min, as in General Procedure A. After 20 hr, the reaction mixture was diluted with water (100 mL). The resulting suspension was filtered through a Buchner funnel. The resulting tan solid was air dried to yield 2bp (2.77 g). $^1$H NMR (500 MHz, CDCl$_3$), δ: 7.52 (s, 1H), 7.45 (d, J=2.3 Hz, 1H), 7.29 (dd, J=8.6, 2.3 Hz, 1H), 6.83 (d, J=8.6 Hz, 1H), 5.26 (s, 2H), 3.91 (s, 3H).

Example 3bp

8-Bromo-4H-thieno[3,2-c]chromene-2-carboxylic acid 3bp

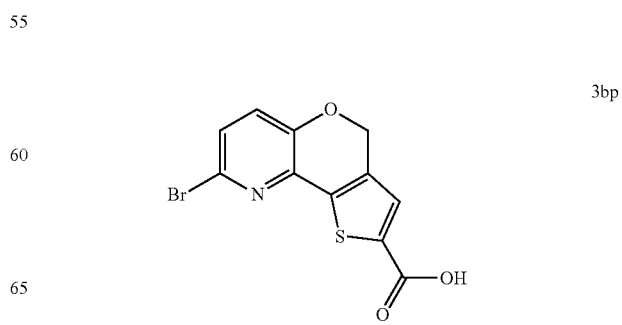

To a suspension of methyl 8-bromo-4H-thieno[3,2-c]chromene-2-carboxylate 2 (2.64 g, 8.12 mmol, 1 equiv) in 4:1 tetrahydrofuran/water (80 mL) was added aqueous potassium hydroxide (24 mL, 24 mmol, 3.0 equiv, 1.0 M solution in water) at 24° C. After 15 hr, the tetrahydrofuran was removed in vacuo (<20 mm Hg). The resulting aqueous suspension was diluted with water until all the solids were dissolved. To the resulting solution was added concentrated hydrochloric acid until the solution reached pH=1. The resulting solids were collected by filtration and dried in vacuo (<1 mm Hg) to afford 3bp as a yellow solid (2.36 g, 93%). $^1$H NMR (500 MHz, CDCl$_3$), δ: 13.28 (br s, 1H), 7.64 (d, J=2.4 Hz, 1H), 7.60 (s, 1H), 7.40 (dd, J=8.7, 2.4 Hz, 1H), 6.94 (d, J=8.7 Hz, 1H), 5.30 (s, 3H).

Example 4bp 8-bromo-4H-thieno[3,2-c]chromene-2-carbonyl chloride 4bp

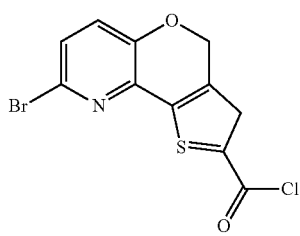

To a suspension of 8-bromo-4H-thieno[3,2-c]chromene-2-carboxylic acid 3bp (1.50 g, 4.82 mmol, 1 equiv) in dichloromethane (45 mL) at 24° C. was sequentially added oxalyl chloride (3.1 mL, 6.3 mmol, 1.3 equiv, 2.0 M in dichloromethane) and N,N-dimethylformamide (56 µL, 0.72 mmol, 0.15 equiv), as in General Procedure B. After 2 hr, the clear yellow solution was concentrated in vacuo (~20 mm Hg) to afford crude 4bp.

Example 5bp

8-Bromo-N-(2,4-difluorophenyl)-4H-thieno[3,2-c]chromene-2-carboxamide 5bp

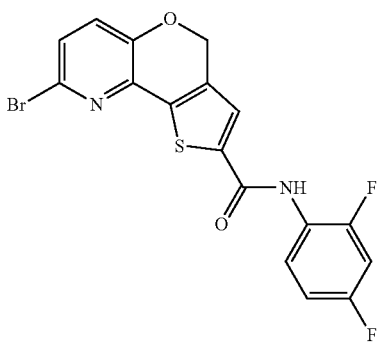

8-Bromo-4H-thieno[3,2-c]chromene-2-carbonyl chloride 4bp is reacted with 2,4-difluoroaniline to give 5bp, as in General Procedure B-bp.

Example 6bp (R)—N-(2,4-difluorophenyl)-8-(3-hydroxypiperidine-1-carbonyl)-N-methyl-4H-thieno[3,2-c]chromene-2-carboxamide 105bp

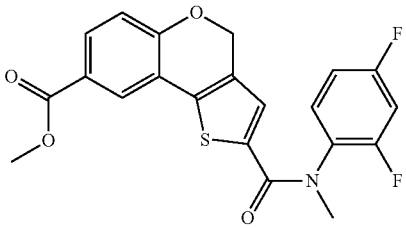 [SMILES: COC(=O)c1ccc2c(c1)-c1sc(C(=O)N(C)c3ccc(F)cc3F)cc1CO2]

A solution of 8-bromo-N-(2,4-difluorophenyl)-N-methyl-4H-thieno[3,2-c]chromene-2-carboxamide 160bp (3.0 g, 6.9 mmol), palladium (II) acetate (1.5 g, 6.9 mmol), dppf (7.6 g, 13.8 mmol), and triethylamine (1.38 g, 13.8 mmol) in N,N-dimethylformamide (50 mL) and methanol (50 mL) was stirred at 70° C. for 48 hr under a carbon monoxide atmosphere. The reaction mixture was filtered, and the filtrate was concentrated in vacuo. The resulting black residue was purified by flash column chromatography to afford 1.2 g of methyl 2-((2,4-difluorophenyl)(methyl)carbamoyl)-4H-thieno[3,2-c]chromene-8-carboxylate. LCMS (ESI) m/z: 416.

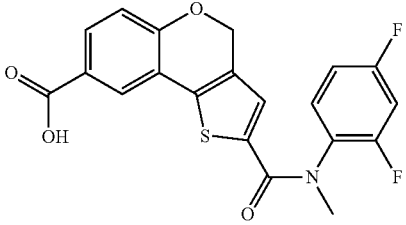 [SMILES: CN(C(=O)c1cc2c(s1)-c1cc(C(=O)O)ccc1OC2)c1ccc(F)cc1F]

A solution of methyl 2-((2,4-difluorophenyl)(methyl)carbamoyl)-4H-thieno[3,2-c]chromene-8-carboxylate, sodium hydroxide (115 mg, 2.9 mmol) in ethanol (20 mL), tetrahydrofuran (20 mL) and water (20 mL) was stirred at room temperature for 16 hr. The reaction mixture was acidified to pH=2 with concentrated hydrochloric acid, and the organic solvents were removed in vacuo. The resulting aqueous solution was extracted with ethylacetate. The collected organic was dried over anhydrous sodium sulfate, filtered, and concentrated to afford 2-((2,4-difluorophenyl)(methyl)carbamoyl)-4H-thieno[3,2-c]chromene-8-carboxylic acid (1.0 g). LCMS (ESI) m/z: 402.

A solution of 2-((2,4-difluorophenyl)(methyl)carbamoyl)-4H-thieno[3,2-c]chromene-8-carboxylic acid (0.100 g, 0.250 mmol), (R)-3-hydroxypiperidine (50.5 mg, 0.500 mmol), O-(7-azabenzotriazol-1-yl)-N,N,N',N'-tetramethyluronium hexafluorophosphate (114 mg, 0.3 mmol), N,N-diisopropylethylamine (39 mg, 0.3 mmol) in N,N-dimethylformamide (2 mL) was stirred at room temperature overnight. The reaction mixture was diluted with ethylacetate, and the resulting solution was washed with water. The collected organic was concentrated. Purification by preparative thin layer chromatog-

Example 7bp

N2-(2,4-difluorophenyl)-N-8-(2-(dimethylamino) ethyl)-N-2-methyl-4H-thieno[3,2-c]chromene-2,8-dicarboxamide 109bp Following the procedure of Example 15 and General Procedure C, 2-((2,4-difluorophenyl)(methyl)carbamoyl)-4H-thieno[3,2-c]chromene-8-carboxylic acid and N1,N1-dimethyl-1,2-ethanediamine were coupled to give 109bp. $^1$H NMR (400 MHz, CDCl$_3$) δ 8.28 (br s, 1H), 7.67 (s, 1H), 7.56 (m, 1H), 7.25 (m, 1H), 6.88 (m, 2H), 6.78 (m, 1H), 6.69 (s, 1H), 5.07 (s, 2H), 3.78 (m, 2H), 3.31 (s, 3H), 3.27 (m, 2H), 2.84 (s, 6H). LCMS (ESI) m/z: 472.2

Example 8bp (S)—N-(2,4-difluorophenyl)-8-(3-hydroxypiperidine-1-carbonyl)-N-methyl-4H-thieno[3,2-c]chromene-2-carboxamide 110bp Following the procedure of Example 15 and General Procedure C, 2-((2,4-difluorophenyl)(methyl)carbamoyl)-4H-thieno[3,2-c]chromene-8-carboxylic acid and (S)-3-hydroxypiperidine were coupled to give 110bp. LCMS (ESI) m/z: 485.0

Example 9bp

N2-(2,4-difluorophenyl)-N2,N8,N8-trimethyl-4H-thieno[3,2-c]chromene-2,8-dicarboxamide 111bp Following the procedure of Example 15 and General Procedure C, 2-((2,4-difluorophenyl)(methyl)carbamoyl)-4H-thieno[3,2-c]chromene-8-carboxylic acid and dimethylamine were coupled to give 111bp. $^1$H NMR (400 MHz, CDCl$_3$) δ 7.15-7.31 (m, 3H), 6.82-7.00 (m, 4H), 5.13 (s, 2H), 3.33 (m, 3H), 2.94-3.13 (m, 6H). LCMS (ESI) m/z: 429.1.

Example 10bp

N-(2,4-difluorophenyl)-N-methyl-8-(4-(4-methylpiperazin-1-yl)piperidin-1-yl)-4H-thieno[3,2-c]chromene-2-carboxamide 112bp A solution of 8-bromo-N-(2,4-difluorophenyl)-N-methyl-4H-thieno[3,2-c]chromene-2-carboxamide 160bp (250 mg, 0.57 mmol), 1-methyl-4-(4-piperidinyl)piperazine (157 mg, 0.86 mmol), sodium tert-butoxide (82 mg, 0.86 mmol), tris(dibenzylidineacetone)dipalladium (0) (25 mg, 0.3 mmol) and 2,2'-bis(diphenylphosphino)-1,1'-binaphthalene (1.14 mmol, 2.00 equiv) in toluene (10 mL) was refluxed under nitrogen for 1 hr. The reaction mixture was cooled to room temperature and filtered through silica gel, and the filtrate was concentrated. Purification by flash column chromatography followed by HPLC afforded 112bp (100 mg). $^1$H NMR (400 MHz, CDCl$_3$) δ 7.22 (m, 1H), 6.90-6.93 (m, 2H), 6.78-6.88 (m, 3H), 6.63 (m, 1H), 4.97 (s, 2H), 3.51-3.57 (m, 2H), 3.40-3.56 (m, 8H), 3.32 (s, 3H), 2.71-2.85 (m, 6H), 2.12-2.16 (m, 2H), 1.96-2.01 (m, 2H). LCMS (ESI) m/z: 539.3.

Example 11bp

N-(2,4-difluorophenyl)-8-(2-(dimethylamino)ethylamino)-N-methyl-4H-thieno[3,2-c]chromene-2-carboxamide 113bp Following Example 70 and General Procedure C, 8-bromo-N-(2,4-difluorophenyl)-N-methyl-4H-thieno[3,2-c]chromene-2-carboxamide 160bp and N1,N1-dimethyl-1,2-ethanediamine were reacted to give 113bp. $^1$H NMR (400 MHz, CDCl$_3$), δ: 7.23 (m, 1H), 6.87-6.92 (m, 2H), 6.67-6.74 (m, 2H), 6.47-6.54 (m, 2H), 4.93 (s, 2H), 3.84 (m, 2H), 3.31-3.39 (m, 5H), 2.86 (s, 6H). LCMS (ESI) m/z: 444.0

Example 12bp (R)—N-(2,4-difluorophenyl)-8-((3-hydroxypyrrolidin-1-yl)methyl)-N-methyl-4H-thieno[3,2-c]chromene-2-carboxamide 115bp

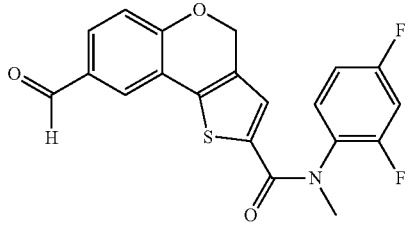 [SMILES: CN(C(=O)c1cc2c(s1)-c1cc(C=O)ccc1OC2)c1ccc(F)cc1F]

To the solution of 8-bromo-N-(2,4-difluorophenyl)-N-methyl-4H-thieno[3,2-c]chromene-2-carboxamide (1.0 g, 2.3 mmol) in tetrahydrofuran (20 mL) at −78° C. was added n-BuLi (2.2 mL, 5.5 mmol, 2.5 M in hexane) under a nitrogen atmosphere. After 3 hr, N,N-dimethylformamide (2 mL) was added. The solution was then warmed to −60° C. After 3 hr, aqueous ammonium chloride solution (1 mL, 10%) was added to the reaction mixture, and the resulting solution was extracted with dichloromethane. The collected organic was dried over anhydrous sodium sulfate, filtered, and concentrated to yield crude aldehyde, N-(2,4-difluorophenyl)-8-formyl-N-methyl-4H-thieno[3,2-c]chromene-2-carboxamide (800 mg), LCMS (ESI) m/z: 386.

A solution of crude aldehyde, N-(2,4-difluorophenyl)-8-formyl-N-methyl-4H-thieno[3,2-c]chromene-2-carboxamide (0.20 g, 0.52 mmol), (3R)-hydroxypyrrolidine (1.04 mmol), and acetic acid (37.4 mg, 0.62 mmol) in 1,2-dichloroethane (15 mL) was stirred for 3 hours. Sodium triacetoxyborohydride (0.50 g, 2.3 mmol) was added, the resulting suspension was stirred at room temperature overnight. The reaction mixture was concentrated in vacuo. Sequential purification by preparative thin layer chromatography and HPLC afforded 115bp (25 mg). $^1$H NMR (* denotes minor rotamer peaks, 400 MHz, CDCl$_3$), δ: 7.71*(m, 1H), 7.51 (m, 1H), 7.31-7.38*(m, 3H), 7.11-7.19 (m, 3H), 6.84-6.93 (m, 3H), 5.09 (s, 2H), 4.52 (m, 1H), 4.45 (m, 2H), 4.33 (m, 2H), 3.44* (s, 3H), 3.40 (s, 3H), 2.20 (m, 1H), 2.00 (m, 1H). LCMS (ESI) m/z: 457.2.

Example 13bp

N-(2,4-difluorophenyl)-N-methyl-8-(morpholinomethyl)-4H-thieno[3,2-c]chromene-2-carboxamide 116bp Following Examples 25 and 70 and General Procedure E, reductive amination of N-(2,4-difluorophenyl)-8-formyl-N- methyl-4H-thieno[3,2-c]chromene-2-carboxamide and morpholine gave 116bp. $^1$H NMR (* denotes minor rotamer peaks, 400 MHz, CDCl$_3$), δ: 7.69* (m, 1H), 7.53 (m, 1H), 7.31-7.39* (m, 3H), 7.12-7.23 (m, 3H), 6.99-7.05* (m, 2H), 6.88-6.93 (m, 2H), 6.83 (s, 1H), 5.10 (s, 2H), 4.23* (m, 4H), 3.82 (m, 4H), 3.67* (m, 4H), 3.48* (s, 3H), 3.42 (s, 3H), 3.00 (m, 4H). LCMS (ESI) m/z: 458.2.

Example 14bp

N-(2,4-difluorophenyl)-N-methyl-8-(pyrrolidin-1-ylmethyl)-4H-thieno[3,2-c]chromene-2-carboxamide 117bp Following Example 25 and 70 and General Procedure E, reductive amination of N-(2,4-difluorophenyl)-8-formyl-N-methyl-4H-thieno[3,2-c]chromene-2-carboxamide and pyrrolidine gave 117bp. $^1$H NMR (* denotes minor rotamer peaks, 400 MHz, CDCl$_3$), δ: 7.65* (m, 1H), 7.45 (m, 1H), 7.28-7.30* (m, 3H), 7.04-7.24 (m, 3H), 6.89-6.96* (m, 3H), 6.80-6.87 (m, 3H), 5.04 (s, 2H), 4.27 (m, 2H), 3.65 (m, 2H), 3.40* (s, 3H), 3.38 (s, 3H), 2.62* (m, 4H), 1.96 (m, 4H). LCMS (ESI) m/z: 441.2

Example 15bp

N-(2,4-difluorophenyl)-8-(4-hydroxypiperidine-1-carbonyl)-N-methyl-4H-thieno[3,2-c]chromene-2-carboxamide 118bp Following the procedure of Example 15 and General Procedure C, 2-((2,4-difluorophenyl)(methyl)carbamoyl)-4H-thieno[3,2-c]chromene-8-carboxylic acid and 4-hydroxypiperidine were coupled to give 118bp. $^1$H NMR (400 MHz, DMSO-d$_6$), δ: 7.68 (m, 1H), 7.46 (m, 1H), 7.21-7.25 (m, 3H), 6.93 (m, 1H), 6.69 (m, 1H), 5.16 (s, 2H), 3.65 (m, 3H), 3.29 (s, 3H), 3.17 (m, 2H), 1.73 (m, 2H), 1.36 (m, 2H). LCMS (ESI) m/z: 485.1

Example 16bp

N2-(2,4-difluorophenyl)-N2-methyl-4H-thieno[3,2-c]chromene-2,8-dicarboxamide 119bp Following the procedure of Example 15 and General Procedure C, 2-((2,4-difluorophenyl)(methyl)carbamoyl)-4H-thieno[3,2-c]chromene-8-carboxylic acid and ammonium chloride were coupled to give 119bp. LCMS (ESI) m/z: 401.1

Example 17bp 8-(4-acetylpiperazin-1-yl)-N-(2,4-difluorophenyl)-N-methyl-4H-thieno[3,2-c]chromene-2-carboxamide 120bp Following Example 70 and General Procedure D, 8-bromo-N-(2,4-difluorophenyl)-N-methyl-4H-thieno[3,2-c]chromene-2-carboxamide 160bp and 1-acetylpiperazine were reacted to give 120bp. $^1$H NMR (400 MHz, CDCl$_3$) δ 7.23 (m, 1H), 6.82-6.93 (m, 5H), 5.99 (s, 1H), 5.01 (s, 2H), 3.86 (m, 2H), 3.73 (m, 2H), 3.32 (s, 3H), 3.21 (m, 2H), 3.16 (m, 2H), 2.13 (s, 3H). LCMS (ESI) m/z: 484.1

Example 18bp 8-acetamido-N-(2,4-difluorophenyl)-N-methyl-4H-thieno[3,2-c]chromene-2-carboxamide 121bp Following Example 70 and General Procedure D, 8-bromo-N-(2,4-difluorophenyl)-N-methyl-4H-thieno[3,2-c]chromene-2-carboxamide 160bp and acetamide were reacted to give 121bp. $^1$H NMR (400 MHz, CDCl$_3$) δ 6.84-7.31 (m, 6H), 6.76 (s, 1H), 5.05 (s, 2H), 3.40 (s, 3H), 2.16 (s, 3H). LCMS (ESI) m/z: 414.9

Example 19bp

N-(2,4-difluorophenyl)-N-methyl-8-(4-morpholinopiperidin-1-yl)-4H-thieno[3,2-c]chromene-2-carboxamide 127bp Following Example 70 and General Procedure D, 8-bromo-N-(2,4-difluorophenyl)-N-methyl-4H-thieno[3,2-c]chromene-2-carboxamide 160bp and 4-(4-piperidinyl)morpholine were reacted to give 127bp. $^1$H NMR (400 MHz, CDCl$_3$) δ 7.20 (m, 1H), 7.05-7.10 (m, 2H), 6.84-6.93 (m, 3H), 6.74 (m, 1H), 5.05 (s, 2H), 4.00 (m, 4H), 3.63-3.68 (m, 3H), 3.29-3.50 (m, 5H), 3.18 (m, 2H), 3.05 (m, 2H), 2.47 (m, 2H), 2.21 (m, 2H). LCMS (ESI) m/z: 526.1

Example 20bp

N-(2,4-difluorophenyl)-N-methyl-8-(4-methylpiperazin-1-yl)-4H-thieno[3,2-c]chromene-2-carboxamide 128bp Following Example 70 and General Procedure D, 8-bromo-N-(2,4-difluorophenyl)-N-methyl-4H-thieno[3,2-c]chromene-2-carboxamide 160bp and N-methylpiperazine were reacted to give 128bp. $^1$H NMR (400 MHz, CDCl$_3$) δ 7.30 (m, 1H), 6.94-7.00 (m, 2H), 6.85 (m, 1H), 6.75-6.82 (m, 2H), 6.68 (s, 1H), 5.03 (s, 2H), 3.69 (m, 2H), 3.46 (m, 2H), 3.39 (s, 3H), 3.30 (m, 2H), 3.07 (m, 2H), 2.90 (s, 3H). LCMS (ESI) m/z: 456.2.

Example 21bp

N-(2,4-difluorophenyl)-N-methyl-8-morpholino-4H-thieno[3,2-c]chromene-2-carboxamide 129bp Following Example 70 and General Procedure D, 8-bromo-N-(2,4-difluorophenyl)-N-methyl-4H-thieno[3,2-c]chromene-2-carboxamide 160bp and morpholine were reacted to give 129bp. $^1$H NMR (400 MHz, CDCl$_3$) δ: 7.27 (m, 1H), 7.11-7.14 (m, 2H), 6.90-6.98 (m, 3H), 6.75 (s, 1H), 5.09 (s, 2H), 4.04 (m, 2H), 3.38 (s, 3H), 3.32 (m, 2H). LCMS (ESI) m/z: 442.9

Example 22bp

N-(2,4-difluorophenyl)-N-methyl-8-((4-methylpiperazin-1-yl)methyl)-4H-thieno[3,2-c]chromene-2-carboxamide 136bp Following the procedure of Examples 25 and 70 and General Procedure E, 2-((2,4-difluorophenyl)(methyl)carbamoyl)-4H-thieno[3,2-c]chromene-8-carboxylic acid and 1-methylpiperazine were coupled to give 136bp.

Example 23bp

N-(2-chlorophenyl)-N,4,4-trimethyl-4H-thieno[3,2-c]chromene-2-carboxamide 140bp

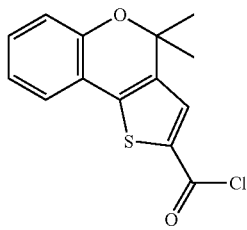 [SMILES: CC1(C)Oc2ccccc2-c2sc(C(=O)Cl)cc21]

To a solution of 2,4-difluoroaniline (0.03936 g, 0.2750 mmol) in 1.2 M of Pyridine in methylene chloride (0.8333 mL) was added a catalytic amount of DMAP, followed by the addition of 4,4-dimethyl-4H-thieno[3,2-c]chromene-2-carbonyl chloride (70.2 mg, 0.250 mmol). The reaction was stirred at room temperature under $N_2$ with LC/MS monitor. The crude product was purified on silica to give 38 mg 140bp. Yield=40% of theoretical. MS: (ESI+)=386

Example 24bp

N-(2-chlorophenyl)-N,4,4-trimethyl-4H-thieno[3,2-c]chromene-2-carboxamide 141bp

To a solution of 2-chloro-N-methylaniline (32.10 uL, 0.2750 mmol) in 1.2 M of Pyridine in methylene chloride (0.8333 mL) was added a pinch of DMAP, followed by the addition of 4,4-dimethyl-4H-thieno[3,2-c]chromene-2-carbonyl chloride (70.2 mg, 0.250 mmol). The reaction was stirred at room temperature under $N_2$ with LC/MS monitor. The crude product was purified on silica to give 30 mg 141bp. Yield=31% of theoretical. MS: (ESI+)=385

Example 25bp

N-(2-chlorophenyl)-6,8-difluoro-N-methyl-4H-thieno[3,2-c]chromene-2-carboxamide 142bp Following the procedure of Example 70 and General Procedure B, 142bp was prepared from 6,8-difluoro-4H-thieno[3,2-c]chromene-2-carboxylic acid and 2-chloro-N-methylaniline. MS: (ESI+)=392.1

Example 26bp

N2-(2,4-difluorophenyl)-N2,N8-dimethyl-4H-thieno[3,2-c]chromene-2,8-dicarboxamide 152bp To a microwave reaction vessel charged with 8-bromo-N-(2,4-difluorophenyl)-N-methyl-4H-thieno[3,2-c]chromene-2-carboxamide 160bp (0.100 g, 0.229 mmol, 1 equiv), methylamine (0.34 mL, 0.68 mmol, 3.0 equiv, 2.0 M in tetrahydrofuran), molybdenumhexacarbonyl (60.5 mg, 0.229 mmol, 1.00 equiv), and trans-di(mu-acetato)bis[o-(di-o-tolylphosphino)benzyl]dipalladium (II) (0.15 equiv) in tetrahydrofuran (1 mL) at 24° C. was added 1,8-diazabicyclo[5.4.0]undec-7-ene (15.4 μL, 0.103 mmol, 0.450 equiv), following the procedures of Wannberg et al (2003) J. Org. Chem. 68:5750-5753. The reaction mixture was heated in the microwave at 150° C. for 15 min, and filtered through Celite. The resulting filtrate was concentrated in vacuo. Purification by flash column chromatography (95:5 dichloromethane/methanol) afforded 152bp (58 mg, 61%). $^1$H NMR (500 MHz, CDCl$_3$), δ: 7.62 (d, J=2.1 Hz, 1H), 7.50 (dd, J=8.4, 2.2 Hz, 1H), 7.30 (m, 1H), 6.95-6.99 (m, 2H), 6.88 (d, J=8.4 Hz, 1H), 6.84 (br s, 1H), 6.08 (br s, 1H), 5.16 (s, 2H), 3.38 (s, 3H), 3.00 (d, J=4.8 Hz, 3H). LCMS (ESI) m/z: 415.2

Example 27bp

N-(2,4-difluorophenyl)-N-methyl-8-(4-methylpiperazine-1-carbonyl)-4H-thieno[3,2-c]chromene-2-carboxamide 153bp Following Example 62, 8-bromo-N-(2,4-difluorophenyl)-N-methyl-4H-thieno[3,2-c]chromene-2-carboxamide 160bp and 1-methylpiperidine gave 153bp. $^1$H NMR (500 MHz, CDCl$_3$) δ 7.29 (m, 1H), 7.26 (m, 1H), 7.18 (dd, J=8.3, 2.0 Hz, 1H), 6.95-6.98 (m, 2H), 6.87 (d, J=8.3 Hz, 1H), 6.86 (s, 1H), 5.14 (s, 2H), 3.65 (br s, 4H), 3.38 (s, 3H), 2.42 (br s, 4H), 2.33 (s, 3H). LCMS (ESI) m/z: 484.2.

Example 28bp (S)—N-(2,4-difluorophenyl)-8-(3-hydroxypyrrolidine-1-carbonyl)-N-methyl-4H-thieno[3,2-c]chromene-2-carboxamide 154bp Following Example 62, 8-bromo-N-(2,4-difluorophenyl)-N-methyl-4H-thieno[3,2-c]chromene-2-carboxamide 160bp and S-3-hydroxypyrrolidine gave 154bp. $^1$H NMR (500 MHz, DMSO-d$_6$) δ 7.68 (m, 1H), 7.47 (m, 1H), 7.38-7.40 (m, 2H), 7.25 (m, 1H), 6.94 (d, J=8.6 Hz, 1H), 6.71 (br s, 1H), 5.18 (s, 2H), 4.95 (m, 1H), 4.27 (m, 1H), 3.20-3.61 (m, 3H), 3.30 (s, 3H), 1.90 (m, 1H), 1.79 (m, 1H).

Example 29bp (R)—N-(2,4-difluorophenyl)-8-(3-hydroxypyrrolidine-1-carbonyl)-N-methyl-4H-thieno[3,2-c]chromene-2-carboxamide 155bp Following Example 62, 8-bromo-N-(2,4-difluorophenyl)-N-methyl-4H-thieno[3,2-c]chromene-2-carboxamide 160bp and R-3-hydroxypyrrolidine gave 155bp. $^1$H NMR (500 MHz, DMSO-d$_6$) δ 7.68 (m, 1H), 7.47 (m, 1H), 7.38-7.40 (m, 2H), 7.25 (m, 1H), 6.94 (d, J=8.6 Hz, 1H), 6.71 (br s, 1H), 5.18 (s, 2H), 4.95 (m, 1H), 4.27 (m, 1H), 3.20-3.61 (m, 3H), 3.30 (s, 3H), 1.90 (m, 1H), 1.79 (m, 1H). LCMS (ESI) m/z: 471.2.

Example 30bp

N-(2,4-difluorophenyl)-N-methyl-8-(morpholine-4-carbonyl)-4H-thieno[3,2-c]chromene-2-carboxamide 158bp Following Example 62, 8-bromo-N-(2,4-difluorophenyl)-N-methyl-4H-thieno[3,2-c]chromene-2-carboxamide 160bp and morpholine gave 158bp. $^1$H NMR (500 MHz, DMSO-d$_6$) δ 7.68 (m, 1H), 7.47 (m, 1H), 7.23-7.30 (m, 2H), 6.96 (d, J=8.3 Hz, 1H), 6.71 (br s, 1H), 5.17 (s, 2H), 3.59 (m, 4H), 3.48 (m, 4H), 3.30 (s, 3H). LCMS (ESI) m/z: 471.0.

Example 31bp

N-(2,4-difluorophenyl)-8-(hydroxymethyl)-N-methyl-4H-thieno[3,2-c]chromene-2-carboxamide 159bp To a solution of 8-bromo-N-(2,4-difluorophenyl)-N-methyl-4H-thieno[3,2-c]chromene-2-carboxamide 160bp (19.6 mg, 0.0449 mmol, 1 equiv) in tetrahydrofuran (1 mL) at −78° C. was added n-butyllithium (54 µL, 0.14 mmol, 3.0 equiv, 2.5 M in hexanes) dropwise. After 15 min, N,N-dimethylformamide (35 µL, 0.45 mmol, 10 equiv) was added. After 40 min, the reaction mixture was warmed to 24° C. for 50 min. Saturated aqueous ammonium chloride solution (5 mL) was added to the reaction mixture, and the resulting solution was extracted with ethylacetate (3×3 mL). The collected organic was dried over anhydrous sodium sulfate, filtered, and concentrated to afford the corresponding aldehyde, N-(2,4-difluorophenyl)-8-formyl-N-methyl-4H-thieno[3,2-c]chromene-2-carboxamide. LCMS (ESI) m/z: 386.

To an ice-cooled solution of N-(2,4-difluorophenyl)-8-formyl-N-methyl-4H-thieno[3,2-c]chromene-2-carboxamide in ethanol (1 mL) was added sodium borohydride (10 mg, 0.3 mmol, 6 equiv). After 3 hr, excess sodium borohydride was quenched with saturated aqueous ammonium chloride solution (3 mL). The ethanol was removed in vacuo, and the resulting aqueous solution was extracted with ethylacetate (3×3 mL). The collected organic was dried over anhydrous sodium sulfate, filtered, and concentrated. Purification by flash column chromatography (3:2 hexanes/ethylacetate) provided 159bp (5.2 mg, 30%). $^1$H NMR (500 MHz, CDCl$_3$) δ 7.26 (m, 1H), 7.15 (m, 1H), 7.05 (m, 1H), 6.86-6.93 (m, 4H), 5.25 (s, 2H), 4.55 (d, J=6.7 Hz, 2H), 4.06 (m, 1H), 3.40 (s, 3H). LCMS (ESI) m/z: 388.1.

Example 32bp 8-bromo-N-(2,4-difluorophenyl)-N-methyl-4H-thieno[3,2-c]chromene-2-carboxamide 160bp To a solution of crude 8-bromo-4H-thieno[3,2-c]chromene-2-carbonyl chloride 4 (~4.82 mmol), N-methyl-2,4-difluoroaniline (1.03 g, 7.23 mmol, 1.50 equiv), and triethylamine (3.36 mL, 24.1 mmol, 5.00 equiv) in dichloromethane (46 mL) was added N,N-dimethyl-4-aminopyridine (118 mg, 0.964 mmol, 0.200 equiv) at 24° C. The reaction mixture became a yellow/orange suspension within 5 min of N,N-dimethyl-4-aminopyridine addition. After 22 hr, the reaction mixture was diluted with dichloromethane (50 mL), and the resulting solution was washed with saturated aqueous sodium bicarbonate (30 mL). The collected organic was dried over anhydrous sodium sulfate, filtered, and concentrated. Purification by flash column chromatography (5:2 hexanes/ethylacetate) provided 160bp as a yellow solid (1.59 g, 76%).

$^1$H NMR (500 MHz, CDCl$_3$) δ 7.30 (m, 1H), 7.26 (m, 1H), 7.23 (dd, J=8.6, 2.4, 1H), 6.95-7.00 (m, 2H), 6.81 (s, 1H), 6.76 (d, J=8.6 Hz, 1H), 5.10 (s, 2H), 3.39 (s, 3H). LCMS (ESI) m/z: 436.

Alternatively, 160bp may be prepared by methylation of 8-bromo-N-(2,4-difluorophenyl)-4H-thieno[3,2-c]chromene-2-carboxamide 5 with methyl iodide and sodium hydride.

Example 33bp

8-Cyano-N-(2,4-difluorophenyl)-N-methyl-4H-thieno[3,2-c]chromene-2-carboxamide 161bp A solution of 8-bromo-N-(2,4-difluorophenyl)-N-methyl-4H-thieno[3,2-c]chromene-2-carboxamide 160bp (33.7 mg, 0.0772 mmol, 1 equiv) and copper cyanide (22 mg, 0.24 mmol, 3.2 equiv) in N,N-dimethylformamide (1 mL) was heated at 250° C. in the microwave for 30 min. The reaction mixture was diluted with 9:1 saturated aqueous ammonium chloride solution/ammonium hydroxide (10 mL). The resulting mixture was extracted with dichloromethane (3×5 mL). The collected organic was dried over anhydrous sodium sulfate, filtered, and concentrated. Purification by flash column chromatography (11:4/hexanes:ethylacetate) provided 161bp as a white solid (23.4 mg, 79%). $^1$H NMR (500 MHz, CDCl$_3$) δ 7.40-7.42 (m, 2H), 7.32 (m, 1H), 6.99 (t, J=8.1 Hz, 1H), 6.92 (m, 1H), 6.88 (s, 1H), 5.23 (s, 2H), 3.40 (s, 3H). LCMS (ESI) m/z: 383.1

Example 34bp

N-(2-bromophenyl)-8-fluoro-N-methyl-4H-thieno[3,2-c]chromene-2-carboxamide 162bp To a reaction vial charged with 8-fluoro-4H-thieno[3,2-c]chromene-2-carbonyl chloride (0.05 g, 0.2 mmol) and 2-bromo-N-methylaniline (0.044 g, 0.24 mmol) was added a catalytic amount of DMAP. Pyridine in methylene chloride (1.2 M, 0.66 mL) was added and the reaction was stirred at room temperature with LC/MS monitor. The reaction was complete in a couple hours. After aqueous work up, the reaction mixture was concentrated in vacuo, taken into DMF at 100 mg/ml and purified by preparative RP-HPLC to give 162bp. Yield=24% of theoretical. MS: (ESI+)=419.5

Example 35bp

N-(2,4-difluorophenyl)-8-fluoro-N-methyl-4H-thieno[3,2-c]chromene-2-carboxamide 163bp To a reaction vial charged with 8-fluoro-4H-thieno[3,2-c]chromene-2-carbonyl chloride (0.120 g, 0.447 mmol) and 2,4-difluoroaniline (0.0959 g, 0.670 mmol) was added a catalytic amount of DMAP. Pyridine in methylene chloride (1.2 M, 1.49 mL) was added. The reaction was stirred at room temperature with LC/MS monitor. The reaction was complete in a couple hours. After aqueous work up, the reaction was concentrated in vacuo, taken into DMF at a concentrated of 100 mg/ml and purified by preparative RP-HPLC to give 163bp. Yield=31% of theoretical. MS: (ESI+)=376.4

Example 36bp

N-(2,4-dichlorophenyl)-8-fluoro-N-methyl-4H-thieno[3,2-c]chromene-2-carboxamide 164bp Following Example 75, 8-fluoro-4H-thieno[3,2-c]chromene-2-carbonyl chloride and 2,4-dichloro-N-methylaniline gave 164bp. MS: (ESI+)=408.0

Example 37bp

N-(2-chlorophenyl)-8-fluoro-N-methyl-4H-thieno[3,2-c]chromene-2-carboxamide 165bp To a reaction vial charged with 8-fluoro-4H-thieno[3,2-c]chromene-2-carbonyl chloride (0.05 g, 0.2 mmol) and 2-chloro-N-methylaniline (0.034 g, 0.24 mmol) was added a catalytic amount of DMAP. Pyridine in methylene chloride (1.2 M, 0.66 mL) was added and the reaction was stirred at room temperature with LC/MS monitor. The reaction was complete in a couple hours. After aqueous work up, the reac-

Example 38bp

N-(2-chloro-5-cyanophenyl)-8-fluoro-N-methyl-4H-thieno[3,2-c]chromene-2-carboxamide 166bp

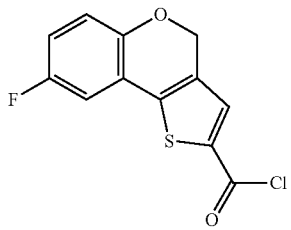 [SMILES: O=C(Cl)c1cc2c(s1)-c1cc(F)ccc1OC2]

To a reaction vial charged with 8-fluoro-4H-thieno[3,2-c]chromene-2-carbonyl chloride (0.08 g, 0.3 mmol) and 3-chloro-2-aminobenzonitrile (0.054 g, 0.36 mmol) was added a catalytic amount of DMAP. Pyridine in methylene chloride (1.2 M, 1 mL) was added and the reaction was stirred at room temperature with LC/MS monitor. The reaction was complete in a couple hours. After aqueous work up, the reaction mixture was concentrated in vacuo, taken into DMF and treated with Sodium hydride (0.03 g, 1 mmol) for several minutes at room temperature. This was followed by the addition of methyl iodide (0.06 g, 0.4 mmol) 100 mg/ml. The reaction mixture was stirred at room temperature for several hours, then concentrated in vacuo and after 2nd aqueous work up, purified by preparative RP-HPLC to give 166bp. Yield=32% of theoretical. MS: (ESI+)=385.8

Example 39bp

N-(2,4-difluorophenyl)-N,8-dimethyl-4H-thieno[3,2-c]chromene-2-carboxamide 167bp

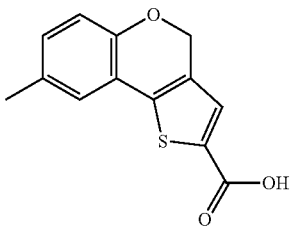 [SMILES: Cc1ccc2c(c1)-c1sc(C(=O)O)cc1CO2]

8-Methyl-4H-thieno[3,2-c]chromene-2-carboxylic acid was converted to the acid chloride as in Example 3, then treated with N-methyl-2,4-difluoroaniline (1.5 equiv), and triethylamine (5 equiv) in dichloromethane and N,N-dimethyl-4-aminopyridine (0.2 equiv) at 24° C. After about 24 hr, the reaction mixture was diluted with dichloromethane, and the resulting solution was washed with saturated aqueous sodium bicarbonate. The collected organic was dried over anhydrous sodium sulfate, filtered, and concentrated. Purification by flash column chromatography (5:2 hexanes/ethylacetate) provided 167bp. $^1$H NMR (500 MHz, CDCl$_3$) δ 7.29 (m, 1H), 6.95-6.98 (m, 4H), 6.78 (d, J=8.2 Hz, 1H), 5.04 (s, 2H), 3.39 (s, 3H), 2.27 (s, 3H). LCMS (ESI) m/z: 372.1.

Example 40bp

N-(2-chlorophenyl)-N,8-dimethyl-4H-thieno[3,2-c]chromene-2-carboxamide 168bp

8-Methyl-4H-thieno[3,2-c]chromene-2-carboxylic acid was converted to the acid chloride as in Example 3, then treated with N-methyl-2-chloroaniline (1.5 equiv), and triethylamine (5 equiv) in dichloromethane and N,N-dimethyl-4-aminopyridine (0.2 equiv) at 24° C. After about 24 hr, the reaction mixture was diluted with dichloromethane, and the resulting solution was washed with saturated aqueous sodium bicarbonate. The collected organic was dried over anhydrous sodium sulfate, filtered, and concentrated. Purification by flash column chromatography (5:2 hexanes/ethylacetate) provided 168bp. $^1$H (500 MHz, CDCl$_3$) δ 7.53 (d, J=7.7 Hz, 1H), 7.35-7.41 (m, 3H), 6.97 (s, 1H), 6.94 (d, J=8.2 Hz, 1H), 6.76 (d, J=8.2 Hz, 1H), 6.56 (s, 1H), 5.00 (s, 2H), 3.39 (s, 3H), 2.26 (s, 3H). LCMS (ESI) m/z: 370.1

Example 41bp

N-(2-fluorophenyl)-N,8-dimethyl-4H-thieno[3,2-c]chromene-2-carboxamide 169bp

8-Methyl-4H-thieno[3,2-c]chromene-2-carboxylic acid was converted to the acid chloride as in Example 3, then treated with N-methyl-2-fluoroaniline (1.5 equiv), and triethylamine (5 equiv) in dichloromethane and N,N-dimethyl-4-aminopyridine (0.2 equiv) at 24° C. After about 24 hr, the reaction mixture was diluted with dichloromethane, and the resulting solution was washed with saturated aqueous sodium bicarbonate. The collected organic was dried over anhydrous sodium sulfate, filtered, and concentrated. Purification by flash column chromatography (5:2/hexanes:ethylacetate) provided 169bp. $^1$H NMR (500 MHz, CDCl$_3$) δ 7.40 (m, 1H), 7.31 (m, 1H), 7.18-7.22 (m, 2H), 6.80 (s, 1H), 6.94 (d, J=8.3 Hz, 1H), 6.77 (d, J=8.2 Hz, 1H), 6.60 (s, 1H), 5.00 (s, 2H), 3.42 (s, 3H), 2.26 (s, 3H). LCMS (ESI) m/z: 354.1

Example 42bp (8-fluoro-4H-thieno[3,2-c]chromen-2-yl)(morpholino)methanone 170bp To a cooled solution (ice/H$_2$O) of morpholine in DCE was added slowly dropwise 2 equiv. of dimethylaluminum chloride. This reaction was stirred for greater than 30 minutes until reaching ambient temperature. Next the reaction was again cooled (ice/H$_2$O) and 8-fluoro-4H-thieno[3,2-c]chromene-2-carboxylate was added as a solid portion wise. The reaction was allowed to equilibrate to ambient temp and monitored by LC/MS. The completed reaction was quenched with an aqueous solution of Na, K-tartrate (20% wt/wt). This mixture was extracted with EtOAc and the organic was washed with saline and dried (MgSO4). The dried org. was concentrated in vacuo to a residue. This residue was not soluble in DMF and 170bp as a white solid was collected by vacuum filtration, Yield=40% of theoretical. MS: (ESI+)=320.5

Example 43bp 8-fluoro-N-methyl-N-(pyridin-2-yl)-4H-thieno[3,2-c]chromene-2-carboxamide 171bp

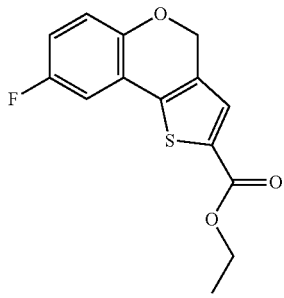 [SMILES: CCOC(=O)c1cc2c(s1)-c1cc(F)ccc1OC2]

To a cooled solution (ice/H₂O) of 2-fluoroaniline in DCE was added slowly dropwise 2 equiv. of dimethylaluminum chloride. The reaction was then stirred for greater than 30 minutes until reaching ambient temperature. Next the reaction was again cooled (ice/H₂O) and ethyl 8-fluoro-4H-thieno[3,2-c]chromene-2-carboxylate was added as a solid portion wise. The reaction was allowed to equilibrate to ambient temp and monitored by LC/MS. Reaction was quenched with an aqueous solution of Na, K-tartrate (20% wt./wt.). This mixture was extracted with EtOAc and the organic was washed with saline and dried (MgSO4). The dried org. was concentrated in vacuo to a residue. This residue was taken into a min. of DMF and filtered, and purified by preparative RP-HPLC to give 98 mg of 171bp as the TFA salt. Yield=40% of theoretical. MS: (ESI+)=341.4

Example 44bp 8-fluoro-N-(2-fluorophenyl)-N-methyl-4H-thieno[3,2-c]chromene-2-carboxamide 172bp

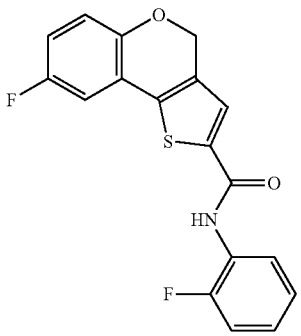 [SMILES: O=C(Nc1ccccc1F)c1cc2c(s1)-c1cc(F)ccc1OC2]

N-(2-fluororophenyl)-7-fluoro-4H-thieno[3,2-c]chromene-2-carboxamide (0.200 g, 0.582 mmol) was taken into dichloromethane (DCM) and placed under nitrogen (N2). Cesium carbonate was added as a solid and stirred into solution for several minutes. This solution was cooled (ice/H₂O) and methyl iodide (MeI) was added slowly dropwise. The cooling bath was immediately removed and reaction was monitored by LC/MS for loss of starting material. The completed reaction was diluted with EtOAc and the organic phase was washed with water×2, followed by saline×1, then dried (MgSO₄). The dried organic phase was concentrated in vacuo and the resulting residue was taken into DMF at a concentration of 100 mg/mL, and purified by preparative RP-HPLC to give 172bp. MS: Yield=25% of theoretical. (ESI+)=358.4

Example 45bzOH

N-(2-chlorophenyl)-4-hydroxy-N-methyl-4,5-dihydrobenzo[b]thieno[2,3-d]oxepine-2-carboxamide 191bzOH Sodium borohydride (8 mg, 0.2 mmol) was added to a solution of N-(2-chlorophenyl)-N-methyl-4-oxo-4,5-dihydrobenzo[b]thieno[2,3-d]oxepine-2-carboxamide 193bzO (38 mg, 0.1 mmol) in 2 ml of methanol. The mixture was stirred for 30 min, poured into 4 ml of water and extracted with 3 ml of ethylacetate. The ethylacetate layer was washed with water, brine and dried over magnesium sulfate. The crude product was purified by normal phase column chromatography using dichloromethane/ethylacetate mobile phase (ethylacetate gradient 0-20%) to yield 191bzOH (0.022 g, 57%). MS: (ESI+) MH+=386.1

Example 46bp

N-(2-chlorophenyl)-3-fluoro-N-methyl-4H-thieno[3,2-c]chromene-2-carboxamide 192bp

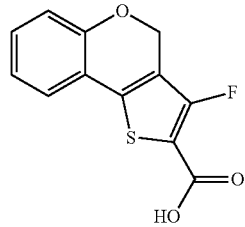 [SMILES: O=C(O)c1sc2c(c1F)COc1ccccc1-2]

To 4H-thieno[3,2-c]chromene-2-carboxylic acid (1.65 g, 7.10 mmol) in THF (70 mL) at −78° C. was added a 1.5 M solution of tert-butyllithium in pentane (15 mL). The resulting solution stirred 1 hr at −78° C. N-fluoro-N-(phenylsulfonyl)benzenesulfonamide (7.2 g, 23 mmol) was added and the reaction warmed to room temperature over 2 hr. The reaction was quenched by the addition of 1 M HCl to effect pH 3. The aqueous layer was extracted with CH₂Cl₂. The combined organics were dried over Na₂SO₄, filtered, and concentrated in vacuo to yield 3-fluoro-4H-thieno[3,2-c]chromene-2-carboxylic acid, which contained less than 40% 4H-thieno[3,2-c]chromene-2-carboxylic acid, which was utilized in the next step without purification (1.0 g). MS (Q1) 249 (M)+

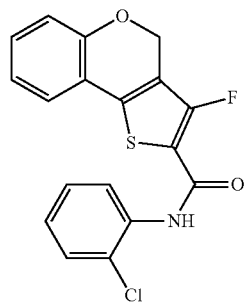 [SMILES: O=C(Nc1ccccc1Cl)c1sc2c(c1F)COc1ccccc1-2]

To 3-fluoro-4H-thieno[3,2-c]chromene-2-carboxylic acid (1.0 g, >60% purity) in CH₂Cl₂ (17 mL) was added thionyl chloride (0.6 mL) followed by a few drops of DMF. The reaction was heated to reflux for several hours. The crude reaction mixture was concentrated in vacuo. To the residue was added CH$_2$Cl$_2$ (50 mL), 2-chloroaniline (1.1 mL), and a catalytic amount of 4-dimethylaminopyridine. Next, pyridine (5 mL) and the reaction stirred at room temperature. After 4 hr the reaction was concentrated in vacuo and partially purified by silica gel chromatography (hexane/ethylacetate as eluent) to provide N-(2-chlorophenyl)-3-fluoro-4H-thieno[3,2-c]chromene-2-carboxamide along with an unidentified by-product. MS (Q1) 360 (M)+

To N-(2-chlorophenyl)-3-fluoro-4H-thieno[3,2-c]chromene-2-carboxamide in DMF was added sodium hydride (0.16 g) then methyl iodide (0.37 mL). The resulting solution stirred 45 min at room temperature. The reaction was quenched by pouring into ice water. The aqueous layer was extracted with EtOAc. The combined organics were washed with brine, dried over Na$_2$SO$_4$, filtered, and concentrated in vacuo. After partial purification by silica gel chromatography (CH$_2$Cl$_2$/EtOAc) the product was purified by reverse phase HPLC to afford 192bp (18 mg). MS (Q1) 374 (M)+

Example 47bzO

N-(2-chlorophenyl)-N-methyl-4-oxo-4,5-dihydrobenzo[b]thieno[2,3-d]oxepine-2-carboxamide 193bzO

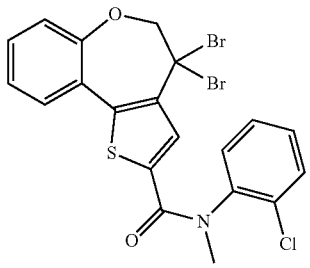 [SMILES: CN(C(=O)c1cc2c(s1)-c1ccccc1OCC2(Br)Br)c1ccccc1Cl]

N-(2-chlorophenyl)-N-methyl-4,5-dihydrobenzo[b]thieno[2,3-d]oxepine-2-carboxamide, N-bromosuccinimide (157 mg, 0.88 mmol) and benzoyl peroxide (2 mg, 0.008 mmol) was heated at 90° C. for 6 hours. The mixture was filtered, the solvent evaporated to dryness, and the residue partitioned between 10 ml of ethylacetate and 20 ml of water. The organic layer was washed with water, brine and dried over magnesium sulfate. The crude product was purified by normal phase column chromatography using dichloromethane-ethylacetate mixture (ethylacetate gradient 0-20%) to yield 0.16 g 4,4-dibromo-N-(2-chlorophenyl)-N-methyl-4,5-dihydrobenzo[b]thieno[2,3-d]oxepine-2-carboxamide (76%). MS: (ESI+) MH+=525.9

A mixture of 4,4-dibromo-N-(2-chlorophenyl)-N-methyl-4,5-dihydrobenzo[b]thieno[2,3-d]oxepine-2-carboxamide (0.16 g, 0.3 mmol) and silver acetate (0.15 g, 0.9 mmol) in toluene was heated at 60° C. for 14 hours. The mixture was filtered and evaporated to dryness. The residue was dissolved in 10 ml of methanol and 1 ml 0.5% aqueous sodium hydroxide was added. The mixture was stirred for 10 min and neutralized by addition of 1 N aqueous hydrogen chloride. The solvents were evaporated in vacuo, the residue was purified by normal phase column chromatography using dichloromethane/ethylacetate mobile phase (ethylacetate gradient 0-20%) to yield 193bzO (0.064 g, 42%). MS: (ESI+) MH+=384.1

The foregoing description is considered as illustrative only of the principles of the invention. Further, since numerous modifications and changes will be readily apparent to those skilled in the art, the invention is not limited to the exact examples shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of treating breast cancer, prostate cancer or pharynx cancer in a mammal comprised of administering to said mammal a pharmaceutical formulation comprised of:
(i) a pharmaceutically acceptable carrier, glidant, diluent, or excipient; and
(ii) a compound of Formula I:

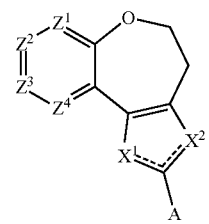

or a stereoisomer, geometric isomer, tautomer, or pharmaceutically acceptable salt thereof, wherein:
$Z^1$ is $CR^1$;
$Z^2$ is $CR^2$;
$Z^3$ is $CR^3$;
$Z^4$ is $CR^4$;
where $X^1$ is S and $X^2$ is $CR^7$;
$R^1$, $R^2$, $R^3$, $R^4$, and $R^7$ are independently selected from H, F, Cl, Br, I, —CN, —CF$_3$, —CH$_2$OR$^{10}$, —CH$_2$R$^{10}$, —(C$_1$-C$_{12}$ alkylene)NR$^{10}$R$^{11}$, —(C$_1$-C$_{12}$ alkylene)NR$^{12}$C(=O)R$^{10}$, —(C$_1$-C$_{12}$ alkylene)C(=O)OR$^{10}$, —(C$_1$-C$_{12}$ alkylene)OR$^{10}$, —CO$_2$R$^{10}$, —C(=O)N(R$^{10}$)OR$^{11}$, —NO$_2$, —NR$^{10}$R$^{11}$, —OR$^{10}$, —S(O)$_2$R$^{10}$, —C(=O)NR$^{10}$R$^{11}$, —C(=O)NR$^{10}$(C$_1$-C$_{12}$ alkylene)NR$^{10}$R$^{11}$, —C(=O)NR$^{10}$(C$_1$-C$_{12}$ alkylene)NR$^{10}$C(=O)OR$^{11}$, —C(=O)NR$^{10}$(C$_1$-C$_{12}$ alkylene)NR$^{10}$C(=O)R$^{11}$, —C(=O)NR$^{10}$(C$_1$-C$_{12}$ alkylene)R$^{10}$, —C(=NR$^{10}$)NR$^{10}$R$^{11}$, —NR$^{12}$C(=O)R$^{10}$, —NR$^{12}$C(=O)OR$^{11}$, —NR$^{12}$C(=O)NR$^{10}$R$^{11}$, —NR$^{12}$C(=O)(C$_1$-C$_{12}$ alkylene)NR$^{10}$R$^{11}$, —NR$^{12}$(C$_1$-C$_{12}$ alkylene)NR$^{10}$R$^{11}$, —NR$^{12}$(C$_1$-C$_{12}$ alkylene)OR$^{10}$, —NR$^{12}$(C$_1$-C$_{12}$ alkylene)C(=O)NR$^{10}$R$^{11}$, —C≡CR$^{10}$, —CH=CHR$^{10}$, C$_2$-C$_{20}$ heterocyclyl, C$_1$-C$_{20}$ heteroaryl, and phenyl, where heterocyclyl, heteroaryl, phenyl and alkylene are optionally substituted with one or more groups selected from F, Cl, Br, I, —CH$_2$OH, —(CH$_2$)$_2$OH, —CH$_2$CO$_2$H, —CN, —CH$_2$NH$_2$, —(CH$_2$)$_2$N(CH$_3$)$_2$, —CH$_3$, —C(=O)CH$_3$, —C(=O)NHCH$_3$, —CO$_2$H, —CH$_2$CO$_2$CH$_3$, —NH$_2$, —OCH$_3$, —S(O)$_2$CH$_3$, 4-methylpiperazin-1-yl, and 4-morpholinyl;

A is selected from —C(=O)NR$^5$R$^6$, C$_2$-C$_{20}$ heterocyclyl and C$_1$-C$_{20}$ heteroaryl wherein C$_2$-C$_{20}$ heterocyclyl and C$_1$-C$_{20}$ heteroaryl are optionally substituted with one or more groups independently selected from F, Cl, Br, I, —CH$_2$OH, —CH$_2$CO$_2$H, —CH(CH$_3$)CH$_2$OCH$_3$, —CN, C$_1$-C$_{12}$ alkyl, —(C$_1$-C$_{12}$ alkylene)NR$^{10}$R$^{11}$, —(C$_1$-C$_{12}$ alkylene)OR$^{10}$, —CH$_3$, —C(=O)CH$_3$, —C(=O)NHCH$_3$, —C(=O)N(CH$_3$)$_2$, —CO$_2$H, —CO$_2$CH$_3$, —CH$_2$CO$_2$CH$_3$, —NH$_2$, —NHC(=O)CH$_3$, —OCH$_3$, —S(O)$_2$CH$_3$, 1-methylpiperid-4-yl, 4-methylpiperazin-1-yl, 4-morpholinyl, isopropyl, isobutyl, cyclopropyl, cyclopropylmethyl, cyclobutyl, triazolylmethyl, benzyl, and phenyl, where alkyl, alkylene, benzyl and phenyl are optionally substituted with one or more groups independently selected from F, Cl, Br, I, —CF$_3$, —CH$_2$OH, —CH$_2$CO$_2$H, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, —OH, —OCH$_3$, —S(O)$_2$CH$_3$, 1-methylpiperid-4-yl, (4-methylpiperazin-1-yl)carboxamide, —CH$_2$(1H-1,2,4-triazol-5-yl), 4-methylpiperazin-1-yl, and 4-morpholinyl;

R$^5$ is selected from H, C$_1$-C$_{12}$ alkyl, optionally substituted with one or more groups independently selected from F, Cl, Br, I, —CN, —CO$_2$H, —CONH$_2$, —CONHCH$_3$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

R$^6$ is selected from C$_1$-C$_{12}$ alkyl, C$_3$-C$_{12}$ carbocyclyl, C$_2$-C$_{20}$ heterocyclyl, C$_1$-C$_{20}$ heteroaryl, and C$_6$-C$_{20}$ aryl, each optionally substituted with one or more groups independently selected from F, Cl, Br, I, —CH$_2$OH, —CH$_2$C$_6$H$_5$, —CN, —CF$_3$, —CO$_2$H, —C(=O)NR$^{10}$R$^{11}$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, —S(O)$_2$CH$_3$, —C(=O)NR$^{10}$(C$_1$-C$_{12}$ alkylene)NR$^{10}$R$^{11}$, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR$^{13}$, —CH=CHR$^{13}$, and —C(=O)NR$^{10}$R$^{11}$;

or R$^5$ and R$^6$ together with the nitrogen atom to which they are attached form morpholin-4-yl, piperidin-1-yl, piperazinyl, piperazin-4-yl-2-one, piperazin-4-yl-3-one, pyrrolidin-1-yl, thiomorpholin-4-yl or S-dioxothiomorpholin-4-yl, each optionally substituted with one or more groups selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

R$^{10}$, R$^{11}$ and R$^{12}$ are independently selected from H, C$_1$-C$_{12}$ alkyl, C$_1$-C$_{12}$ alkylene-C$_2$-C$_{20}$ heterocyclyl, C$_1$-C$_{12}$ alkylene-C$_6$-C$_{20}$ aryl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl, where C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl are optionally substituted with one or more groups independently selected from F, Cl, Br, I, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, —OCH$_3$, —OCH$_2$CH$_3$, 2-oxopyrrolidin-1-yl, —S(O)$_2$NH$_2$, and —S(O)$_2$CH$_3$;

or R$^{10}$ and R$^{11}$ together with the nitrogen atom to which they are attached form a C$_2$-C$_{20}$ heterocyclyl ring or C$_1$-C$_{20}$ heteroaryl each optionally substituted with one or more groups independently selected from F, Cl, Br, I, —CH$_3$, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, oxo, —OCH$_3$, —OCH$_2$CH$_3$, —S(O)$_2$NH$_2$, and —S(O)$_2$CH$_3$; and R$^{13}$ is selected from H, F, Cl, Br, I, —CH$_3$, —CH$_2$CH$_3$, —CN, —CF$_3$, —CH$_2$N(CH$_3$)$_2$, —CH$_2$OH, —CO$_2$H, —CONH$_2$, —CON(CH$_3$)$_2$, —NO$_2$, and —S(O)$_2$CH$_3$.

2. The method of claim 1 wherein the pharmaceutical formulation is a pill, capsule, or tablet.

3. The method of claim 1 wherein the pharmaceutical formulation is a sterile injectable solution.

4. The method of claim 1 wherein the pharmaceutical formulation is administered by injection into the patient.

5. The method of claim 1 wherein the pharmaceutical formulation is a sustained-release preparation.

6. The method of claim 1 wherein the pharmaceutical formulation is administered to a patient by application as a topical ointment or cream.

7. The method of claim 1 wherein A is a C$_1$-C$_{20}$ heteroaryl selected from pyridyl, isoxazolyl, imidazolyl, pyrazolyl, pyrrolyl, thiazolyl, pyridazinyl, pyrimidinyl, pyrazinyl, oxazolyl, oxadiazolyl, 1,3,4-oxadiazol-2(3H)-one, furanyl, thienyl, 1,2,3-triazolyl, 1,2,4-triazolyl, 1,2,4-triazol-5(4H)-one, 4,5-dihydro-1,2,4-triazin-6(1H)-one, tetrazolyl; pyrrolo[2,3-b]pyridinyl, indazolyl, 3,4-dihydroquinolinyl, and benzo[d]thiazole.

8. The method of claim 1 wherein A is selected from the structures:

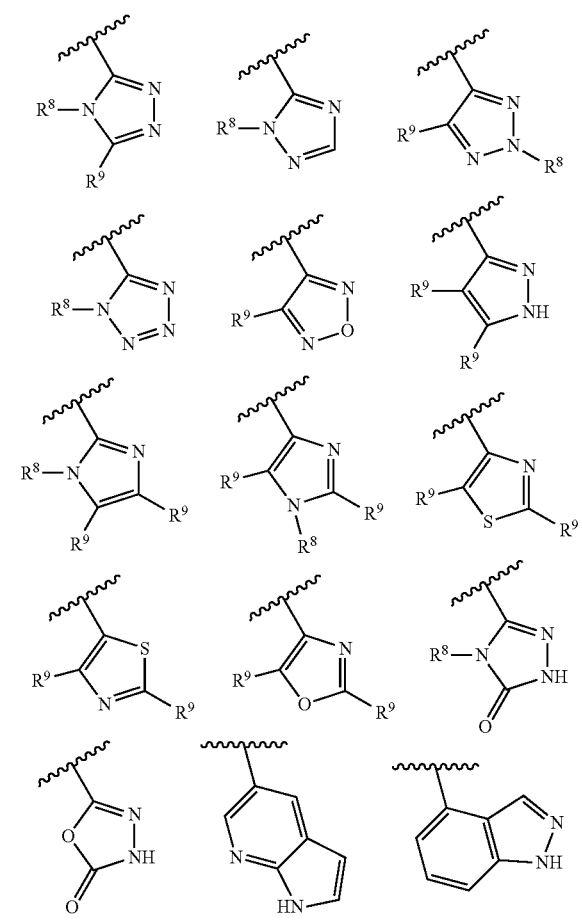

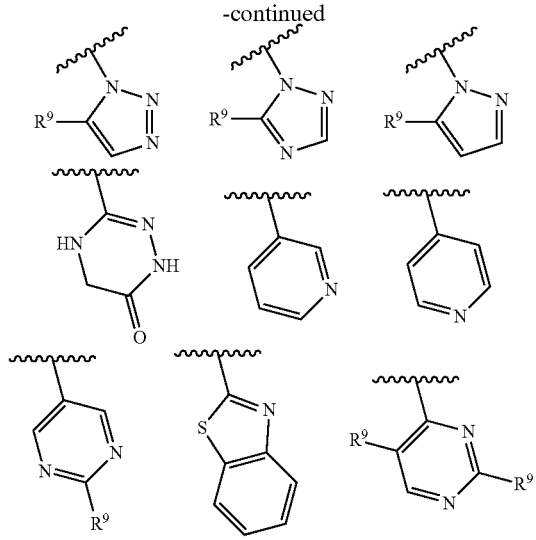

where R[8] and R[9] are independently selected from H, F, Cl, Br, I, —CH$_2$OH, —CH$_2$CO$_2$H, —CH(CH$_3$)CH$_2$OCH$_3$, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, —OCH$_3$, —S(O)$_2$CH$_3$, 1-methylpiperid-4-yl, 4-methylpiperazin-1-yl, 4-morpholinyl, isopropyl, isobutyl, benzyl, and phenyl, where benzyl and phenyl are optionally substituted with one or more groups selected from F, Cl, Br, I, —CH$_2$OH, —CH$_2$CO$_2$H, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, —OCH$_3$, —S(O)$_2$CH$_3$, 1-methylpiperid-4-yl, 4-methylpiperazin-1-yl, and 4-morpholinyl.

9. The method of claim 1 wherein A is selected from the structures:

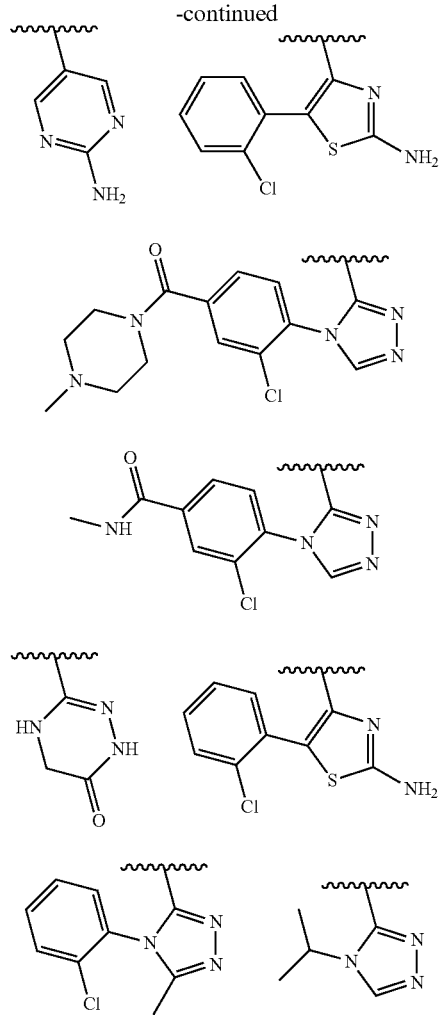

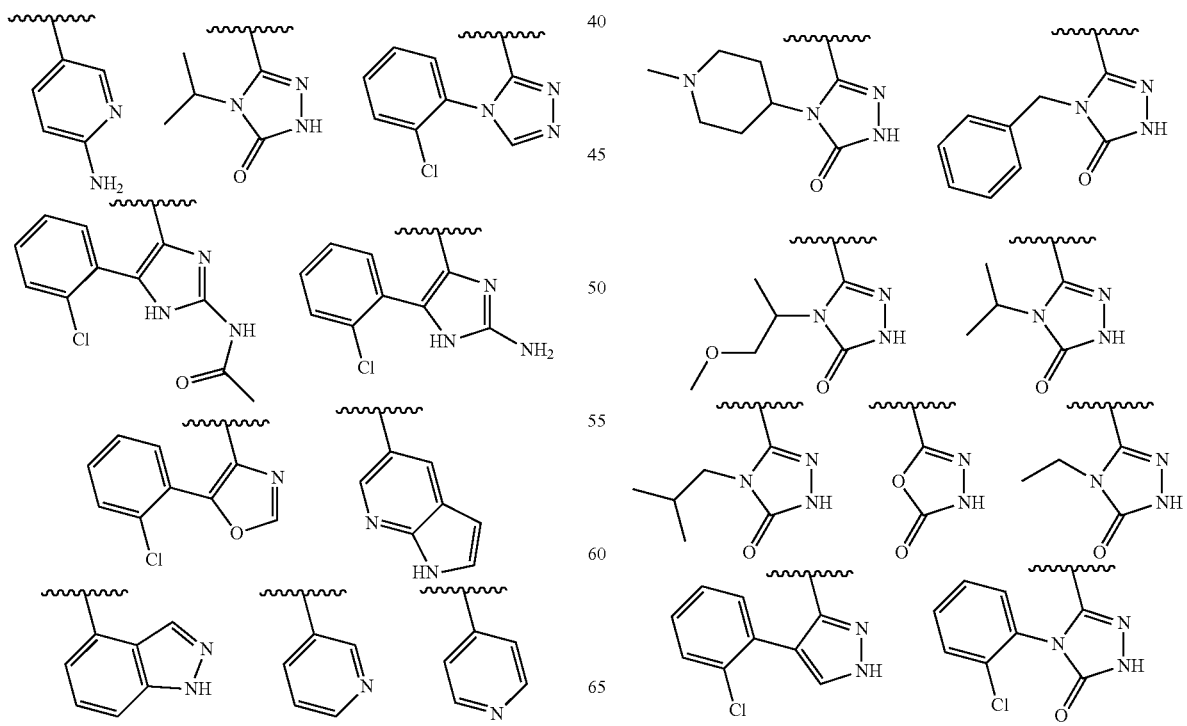

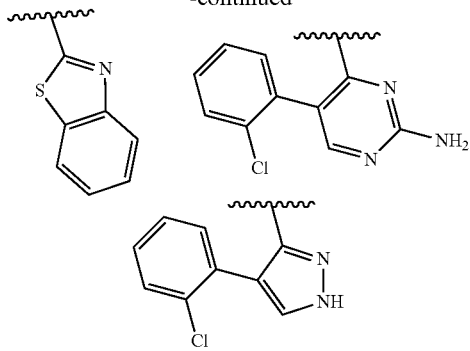

where the wavy line indicates the site of attachment.

10. The method of claim 1 wherein the pharmaceutically acceptable excipient is selected from sodium carboxymethylcellulose, croscarmellose, povidone, methylcellulose, hydroxypropyl methylcellulose, sodium alginate, polyvinylpyrrolidone, gum tragacanth and gum acacia.

11. The method of claim 1 wherein the compound of formula I is selected from:

N2-(2-chlorophenyl)-N2,N8,N8-trimethyl-4,5-dihydrobenzo[b]thieno[2,3-d]oxepine-2,8-dicarboxamide;
7-acetamido-N-(2-chlorophenyl)-N-methyl-4,5-dihydrobenzo[b]thieno[2,3-d]oxepine-2-carboxamide;
N2-(2-chlorophenyl)-N8-(3-(diethylamino)propyl)-N2-methyl-4,5-dihydrobenzo[b]thieno[2,3-d]oxepine-2,8-dicarboxamide;
N-(2-chlorophenyl)-7-cyano-N-methyl-4,5-dihydrobenzo[b]thieno[2,3-d]oxepine-2-carboxamide;
N-(2-chlorophenyl)-N-(2-hydroxyethyl)-4,5-dihydrobenzo[b]thieno[2,3-d]oxepine-2-carboxamide;
N-(2-chloro-4-fluorophenyl)-N-methyl-4,5-dihydrobenzo[b]thieno[2,3-d]oxepine-2-carboxamide;
N-(2,4-dichlorophenyl)-N-methyl-4,5-dihydrobenzo[b]thieno[2,3-d]oxepine-2-carboxamide;
2-(4-isopropyl-5-oxo-4,5-dihydro-1H-1,2,4-triazol-3-yl)-4,5-dihydrobenzo[b]thieno[2,3-d]oxepine-8-carboxamide;
1-(2-(4-(2-chlorophenyl)-4H-1,2,4-triazol-3-yl)-4,5-dihydrobenzo[b]thieno[2,3-d]oxepin-8-yl)-3-methylurea;
methyl 2-(4-(2-chlorophenyl)-4H-1,2,4-triazol-3-yl)-4,5-dihydrobenzo[b]thieno[2,3-d]oxepin-8-ylcarbamate;
7-bromo-N-(2-chlorophenyl)-N-methyl-4,5-dihydrobenzo[b]thieno[2,3-d]oxepine-2-carboxamide;
N-(2-(4-(2-chlorophenyl)-4H-1,2,4-triazol-3-yl)-4,5-dihydrobenzo[b]thieno[2,3-d]oxepin-8-yl)acetamide;
N-(4-(3-amino-5-methyl-1H-pyrazole-1-carbonyl)-2-chlorophenyl)-N-(2-hydroxyethyl)-4,5-dihydrobenzo[b]thieno[2,3-d]oxepine-2-carboxamide;
N-(4-(2-acetamidoethylcarbamoyl)-2-chlorophenyl)-N-(2-hydroxyethyl)-4,5-dihydrobenzo[b]thieno[2,3-d]oxepine-2-carboxamide;
N-(2-chloro-4-((2-(dimethylamino)ethyl)(methyl)carbamoyl)phenyl)-N-(2-hydroxyethyl)-4,5-dihydrobenzo[b]thieno[2,3-d]oxepine-2-carboxamide;
N2-(2-chlorophenyl)-N2-methyl-4,5-dihydrobenzo[b]thieno[2,3-d]oxepine-2,9-dicarboxamide;
N-(2-chlorophenyl)-9-cyano-N-methyl-4,5-dihydrobenzo[b]thieno[2,3-d]oxepine-2-carboxamide;
N-(2-chlorophenyl)-N-methyl-8-(pyridin-3-yl)-4,5-dihydrobenzo[b]thieno[2,3-d]oxepine-2-carboxamide;
N-(2-chlorophenyl)-N-methyl-4,5-dihydrobenzo[b]thieno[2,3-d]oxepine-2-carbothioamide;
8-(3-aminophenyl)-N-(2-chlorophenyl)-N-methyl-4,5-dihydrobenzo[b]thieno[2,3-d]oxepine-2-carboxamide;
N-(2-chlorophenyl)-8-(3-(dimethylamino)prop-1-ynyl)-N-methyl-4,5-dihydrobenzo[b]thieno[2,3-d]oxepine-2-carboxamide;
N-(2-chlorophenyl)-8-(3-hydroxyprop-1-ynyl)-N-methyl-4,5-dihydrobenzo[b]thieno[2,3-d]oxepine-2-carboxamide;
N-methyl-N-(2-(trifluoromethyl)phenyl)-4,5-dihydrobenzo[b]thieno[2,3-d]oxepine-2-carboxamide;
N-(2-aminoethyl)-N-(2-chlorophenyl)-4,5-dihydrobenzo[b]thieno[2,3-d]oxepine-2-carboxamide;
N-(2-chlorophenyl)-N-methyl-8-(1H-pyrazol-4-yl)-4,5-dihydrobenzo[b]thieno[2,3-d]oxepine-2-carboxamide;
N-(2-chlorophenyl)-8-ethynyl-N-methyl-4,5-dihydrobenzo[b]thieno[2,3-d]oxepine-2-carboxamide;
N-(2-chlorophenyl)-N-methyl-8-(pyridin-4-yl)-4,5-dihydrobenzo[b]thieno[2,3-d]oxepine-2-carboxamide;
N-(2-chlorophenyl)-N-methyl-8-phenyl-4,5-dihydrobenzo[b]thieno[2,3-d]oxepine-2-carboxamide;
5-(4,5-dihydrobenzo[b]thieno[2,3-d]oxepin-2-yl)-1H-pyrrolo[2,3-b]pyridine;
N2-(2-chlorophenyl)-N2-methyl-4,5-dihydrobenzo[b]thieno[2,3-d]oxepine-2,8-dicarboxamide;
methyl 2-((2-chlorophenyl)(methyl)carbamoyl)-4,5-dihydrobenzo[b]thieno[2,3-d]oxepine-8-carboxylate;
tert-butyl 2-(2-((2-chlorophenyl)(methyl)carbamoyl)-4,5-dihydrobenzo[b]thieno[2,3-d]oxepine-8-carboxamido)ethyl(methyl)carbamate;
4-(4,5-dihydrobenzo[b]thieno[2,3-d]oxepin-2-yl)-1H-indazole;
N-(2-chlorophenyl)-8-cyano-N-methyl-4,5-dihydrobenzo[b]thieno[2,3-d]oxepine-2-carboxamide;
3-(2-((2-chlorophenyl)(methyl)carbamoyl)-4,5-dihydrobenzo[b]thieno[2,3-d]oxepin-8-yl)benzoic acid;
N-(2-chlorophenyl)-N-methyl-8-(morpholine-4-carbonyl)-4,5-dihydrobenzo[b]thieno[2,3-d]oxepine-2-carboxamide;
N-(2-chlorophenyl)-N-methyl-8-(3-(methylsulfonyl)phenyl)-4,5-dihydrobenzo[b]thieno[2,3-d]oxepine-2-carboxamide;
8-acetamido-N-(2-chloro-4-(4-methylpiperazine-1-carbonyl)phenyl)-N-methyl-4,5-dihydrobenzo[b]thieno[2,3-d]oxepine-2-carboxamide;
N2-(2-chlorophenyl)-N2,N8-dimethyl-4,5-dihydrobenzo[b]thieno[2,3-d]oxepine-2,8-dicarboxamide;
methyl 2-((2-chlorophenyl)(methyl)carbamoyl)-4,5-dihydrobenzo[b]thieno[2,3-d]oxepin-8-ylcarbamate;
8-bromo-N-(2-chlorophenyl)-N-methyl-4,5-dihydrobenzo[b]thieno[2,3-d]oxepine-2-carboxamide;
8-acetamido-N-(2-chlorophenyl)-N-methyl-4,5-dihydrobenzo[b]thieno[2,3-d]oxepine-2-carboxamide;
3-(4,5-dihydrobenzo[b]thieno[2,3-d]oxepin-2-yl)pyridine;
4-(4,5-dihydrobenzo[b]thieno[2,3-d]oxepin-2-yl)pyridine;
N2-(2-chlorophenyl)-N2-(2-hydroxyethyl)-N8-methyl-4,5-dihydrobenzo[b]thieno[2,3-d]oxepine-2,8-dicarboxamide;
N2-(4-chloropyridin-3-yl)-N2,N8-dimethyl-4,5-dihydrobenzo[b]thieno[2,3-d]oxepine-2,8-dicarboxamide;
N-(2,4-difluorophenyl)-N-methyl-4,5-dihydrobenzo[b]thieno[2,3-d]oxepine-2-carboxamide;
N-(2-chlorophenyl)-N-methyl-4,5-dihydrobenzo[b]thieno[2,3-d]oxepine-2-carboxamide;

N-(2-chlorophenyl)-8-(2-hydroxyacetamido)-N-methyl-4,5-dihydrobenzo[b]thieno[2,3-d]oxepine-2-carboxamide;
N-(2-chlorophenyl)-8-(3-(dimethylamino)propanamido)-N-methyl-4,5-dihydrobenzo[b]thieno[2,3-d]oxepine-2-carboxamide;
5-(4,5-dihydrobenzo[b]thieno[2,3-d]oxepin-2-yl)pyrimidin-2-amine;
N-(2-chlorophenyl)-8-(3-ethylureido)-N-methyl-4,5-dihydrobenzo[b]thieno[2,3-d]oxepine-2-carboxamide;
N-(2-chlorophenyl)-N-methyl-8-(3-methylureido)-4,5-dihydrobenzo[b]thieno[2,3-d]oxepine-2-carboxamide;
N-(2-chlorophenyl)-N-methyl-8-ureido-4,5-dihydrobenzo[b]thieno[2,3-d]oxepine-2-carboxamide;
N-(2-chlorophenyl)-8-(2-(diethylamino)acetamido)-N-methyl-4,5-dihydrobenzo[b]thieno[2,3-d]oxepine-2-carboxamide;
N-(2-chlorophenyl)-N-methyl-8-(2-morpholinoacetamido)-4,5-dihydrobenzo[b]thieno[2,3-d]oxepine-2-carboxamide;
N-(2-chlorophenyl)-N-methyl-8-(2-(4-methylpiperazin-1-yl)acetamido)-4,5-dihydrobenzo[b]thieno[2,3-d]oxepine-2-carboxamide;
(3-chloro-4-(3-(4,5-dihydrobenzo[b]thieno[2,3-d]oxepin-2-yl)-4H-1,2,4-triazol-4-yl)phenyl)(4-methylpiperazin-1-yl)methanone;
N2-(2-chlorophenyl)-N2-methyl-N8-(pyridin-3-ylmethyl)-4,5-dihydrobenzo[b]thieno[2,3-d]oxepine-2,8-dicarboxamide;
N2-(2-chlorophenyl)-N8-(1-(hydroxymethyl)cyclopentyl)-N2-methyl-4,5-dihydrobenzo[b]thieno[2,3-d]oxepine-2,8-dicarboxamide;
N2-(2-chlorophenyl)-N8-((S)-1-hydroxy-3,3-dimethylbutan-2-yl)-N2-methyl-4,5-dihydrobenzo[b]thieno[2,3-d]oxepine-2,8-dicarboxamide;
N-(2-chlorophenyl)-8-(4-hydroxypiperidine-1-carbonyl)-N-methyl-4,5-dihydrobenzo[b]thieno[2,3-d]oxepine-2-carboxamide;
N2-(2-chlorophenyl)-N8-(S)-2-hydroxypropyl)-N2-methyl-4,5-dihydrobenzo[b]thieno[2,3-d]oxepine-2,8-dicarboxamide;
N2-(2-chlorophenyl)-N8-((S)-1-hydroxypropan-2-yl)-N2-methyl-4,5-dihydrobenzo[b]thieno[2,3-d]oxepine-2,8-dicarboxamide;
N2-(2-chloro-4-(methylcarbamoyl)phenyl)-N2,N8-dimethyl-4,5-dihydrobenzo[b]thieno[2,3-d]oxepine-2,8-dicarboxamide;
N-(2-chloro-4-(methylcarbamoyl)phenyl)-8-cyano-N-methyl-4,5-dihydrobenzo[b]thieno[2,3-d]oxepine-2-carboxamide;
N2-(2-chloro-4-(4-methylpiperazine-1-carbonyl)phenyl)-N2,N8-dimethyl-4,5-dihydrobenzo[b]thieno[2,3-d]oxepine-2,8-dicarboxamide;
N-(2-chloro-4-(4-methylpiperazine-1-carbonyl)phenyl)-8-cyano-N-methyl-4,5-dihydrobenzo[b]thieno[2,3-d]oxepine-2-carboxamide;
N-(3-chloropyridin-4-yl)-N-methyl-8-(1H-pyrazol-4-yl)-4,5-dihydrobenzo[b]thieno[2,3-d]oxepine-2-carboxamide;
N-(3-chloropyridin-4-yl)-N-methyl-4,5-dihydrobenzo[b]thieno[2,3-d]oxepine-2-carboxamide;
N8-(2-aminoethyl)-N2-(2-chlorophenyl)-N2-methyl-4,5-dihydrobenzo[b]thieno[2,3-d]oxepine-2,8-dicarboxamide;
N8-(2-acetamidoethyl)-N2-(2-chlorophenyl)-N2-methyl-4,5-dihydrobenzo[b]thieno[2,3-d]oxepine-2,8-dicarboxamide;
N2-(2-chlorophenyl)-N2-methyl-N8-(2-(methylamino)ethyl)-4,5-dihydrobenzo[b]thieno[2,3-d]oxepine-2,8-dicarboxamide;
N2-(2-chlorophenyl)-N8-methoxy-N2,N8-dimethyl-4,5-dihydrobenzo[b]thieno[2,3-d]oxepine-2,8-dicarboxamide;
N2-(2-chlorophenyl)-N8-methoxy-N2-methyl-4,5-dihydrobenzo[b]thieno[2,3-d]oxepine-2,8-dicarboxamide;
N-(2-chlorophenyl)-8-(hydroxymethyl)-N-methyl-4,5-dihydrobenzo[b]thieno[2,3-d]oxepine-2-carboxamide;
N8-(3-(1H-imidazol-1-yl)propyl)-N2-(2-chlorophenyl)-N2-methyl-4,5-dihydrobenzo[b]thieno[2,3-d]oxepine-2,8-dicarboxamide;
N8-(2-amino-2-methylpropyl)-N2-(2-chlorophenyl)-N2-methyl-4,5-dihydrobenzo[b]thieno[2,3-d]oxepine-2,8-dicarboxamide;
8-(3-(aminomethyl)phenyl)-N-(2-chlorophenyl)-N-methyl-4,5-dihydrobenzo[b]thieno[2,3-d]oxepine-2-carboxamide;
N-(2-chlorophenyl)-8-(2-(dimethylamino)ethylamino)methyl)-N-methyl-4,5-dihydrobenzo[b]thieno[2,3-d]oxepine-2-carboxamide;
2-(3-(2-((2-chlorophenyl)(methyl)carbamoyl)-4,5-dihydrobenzo[b]thieno[2,3-d]oxepin-8-yl)phenyl)acetic acid;
N-(2-chlorophenyl)-8-(3-cyanophenyl)-N-methyl-4,5-dihydrobenzo[b]thieno[2,3-d]oxepine-2-carboxamide;
methyl 2-(3-(2-((2-chlorophenyl)(methyl)carbamoyl)-4,5-dihydrobenzo[b]thieno[2,3-d]oxepin-8-yl)phenyl)acetate;
N-(2-chlorophenyl)-8-(3-(hydroxymethyl)phenyl)-N-methyl-4,5-dihydrobenzo[b]thieno[2,3-d]oxepine-2-carboxamide;
N-(2-chlorophenyl)-N-methyl-8-(4-methylpiperazine-1-carbonyl)-4,5-dihydrobenzo[b]thieno[2,3-d]oxepine-2-carboxamide;
N2-(2-chlorophenyl)-N2-methyl-N8-(2-(4-methylpiperazin-1-yl)ethyl)-4,5-dihydrobenzo[b]thieno[2,3-d]oxepine-2,8-dicarboxamide;
N2-(2-chlorophenyl)-N8-(2-(dimethylamino)ethyl)-N2-methyl-4,5-dihydrobenzo[b]thieno[2,3-d]oxepine-2,8-dicarboxamide;
N2-(2-chlorophenyl)-N8-isopropyl-N2-methyl-4,5-dihydrobenzo[b]thieno[2,3-d]oxepine-2,8-dicarboxamide;
N2-(2-chlorophenyl)-N8-ethyl-N2-methyl-4,5-dihydrobenzo[b]thieno[2,3-d]oxepine-2,8-dicarboxamide;
N-(3-chloropyridin-2-yl)-N-methyl-4,5-dihydrobenzo[b]thieno[2,3-d]oxepine-2-carboxamide;
N-methyl-N-(4-(trifluoromethyl)pyridin-3-yl)-4,5-dihydrobenzo[b]thieno[2,3-d]oxepine-2-carboxamide;
3-chloro-4-(3-(4,5-dihydrobenzo[b]thieno[2,3-d]oxepin-2-yl)-4H-1,2,4-triazol-4-yl)-N-methylbenzamide;
N-(2-chlorophenyl)-8-(2-(dimethylamino)acetamido)-N-methyl-4,5-dihydrobenzo[b]thieno[2,3-d]oxepine-2-carboxamide;
8-(2-acetamidoacetamido)-N-(2-chlorophenyl)-N-methyl-4,5-dihydrobenzo[b]thieno[2,3-d]oxepine-2-carboxamide;
3-(8-(1H-pyrazol-4-yl)-4,5-dihydrobenzo[b]thieno[2,3-d]oxepin-2-yl)-4,5-dihydro-1,2,4-triazin-6(1H)-one;
2-(2-amino-5-(2-chlorophenyl)thiazol-4-yl)-N-methyl-4,5-dihydrobenzo[b]thieno[2,3-d]oxepine-8-carboxamide;
2-(4-(2-chlorophenyl)-5-methyl-4H-1,2,4-triazol-3-yl)-N-methyl-4,5-dihydrobenzo[b]thieno[2,3-d]oxepine-8-carboxamide;

(4,5-dihydrobenzo[b]thieno[2,3-d]oxepin-2-yl)(3,4-dihydroquinolin-1(2H)-yl)methanone N-(4-chloropyridin-3-yl)-N-methyl-4,5-dihydrobenzo[b]thieno[2,3-d]oxepine-2-carboxamide;

N-(2-chloro-4-(dimethylcarbamoyl)phenyl)-N-(2-hydroxyethyl)-4,5-dihydrobenzo[b]thieno[2,3-d]oxepine-2-carboxamide;

N-(2-chloro-4-(4-methylpiperazine-1-carbonyl)phenyl)-N-(2-hydroxyethyl)-4,5-dihydrobenzo[b]thieno[2,3-d]oxepine-2-carboxamide;

N2-(2-chloro-4-(piperazine-1-carbonyl)phenyl)-N2,N8-dimethyl-4,5-dihydrobenzo[b]thieno[2,3-d]oxepine-2,8-dicarboxamide;

N2-(2-chloro-4-(dimethylcarbamoyl)phenyl)-N2,N8-dimethyl-4,5-dihydrobenzo[b]thieno[2,3-d]oxepine-2,8-dicarboxamide;

3-(8-bromo-4,5-dihydrobenzo[b]thieno[2,3-d]oxepin-2-yl)-4-isopropyl-4H-1,2,4-triazole;

3-(4,5-dihydrobenzo[b]thieno[2,3-d]oxepin-2-yl)-4-(1-methylpiperidin-4-yl)-1H-1,2,4-triazol-5(4H)-one;

N-(2-chloro-4-(2-hydroxypropylcarbamoyl)phenyl)-N-methyl-4,5-dihydrobenzo[b]thieno[2,3-d]oxepine-2-carboxamide;

N-(2-chloro-4-(1-hydroxypropan-2-ylcarbamoyl)phenyl)-N-methyl-4,5-dihydrobenzo[b]thieno[2,3-d]oxepine-2-carboxamide;

N-(4-(3-(1H-imidazol-1-yl)propylcarbamoyl)-2-chlorophenyl)-N-methyl-4,5-dihydrobenzo[b]thieno[2,3-d]oxepine-2-carboxamide;

N-(4-(2-acetamidoethylcarbamoyl)-2-chlorophenyl)-N-methyl-4,5-dihydrobenzo[b]thieno[2,3-d]oxepine-2-carboxamide;

N-(2-chloro-4-(isopropylcarbamoyl)phenyl)-N-methyl-4,5-dihydrobenzo[b]thieno[2,3-d]oxepine-2-carboxamide;

N-(2-chloro-4-(dipropylcarbamoyl)phenyl)-N-methyl-4,5-dihydrobenzo[b]thieno[2,3-d]oxepine-2-carboxamide;

8-bromo-N-(2-chlorophenyl)-N-(2-hydroxyethyl)-4,5-dihydrobenzo[b]thieno[2,3-d]oxepine-2-carboxamide;

2-(4-(2-chlorophenyl)-4H-1,2,4-triazol-3-yl)-4,5-dihydrobenzo[b]thieno[2,3-d]oxepine-8-carboxylic acid;

2-(4-(2-chlorophenyl)-4H-1,2,4-triazol-3-yl)-4,5-dihydrobenzo[b]thieno[2,3-d]oxepin-8-amine;

N-(2-(4-(2-chlorophenyl)-4H-1,2,4-triazol-3-yl)-4,5-dihydrobenzo[b]thieno[2,3-d]oxepin-8-yl)-2-morpholinoacetamide;

N-(2-(4-(2-chlorophenyl)-4H-1,2,4-triazol-3-yl)-4,5-dihydrobenzo[b]thieno[2,3-d]oxepin-8-yl)-2-(dimethylamino)acetamide;

N-(2-amino-2-methylpropyl)-2-(4-(2-chlorophenyl)-4H-1,2,4-triazol-3-yl)-4,5-dihydrobenzo[b]thieno[2,3-d]oxepine-8-carboxamide;

2-(4-(2-chlorophenyl)-4H-1,2,4-triazol-3-yl)-N-ethyl-4,5-dihydrobenzo[b]thieno[2,3-d]oxepine-8-carboxamide;

2-(4-(2-chlorophenyl)-4H-1,2,4-triazol-3-yl)-N-methyl-4,5-dihydrobenzo[b]thieno[2,3-d]oxepine-8-carboxamide;

N-(2-chlorophenyl)-N-methyl-8-((4-methylpiperazin-1-yl)methyl)-4,5-dihydrobenzo[b]thieno[2,3-d]oxepine-2-carboxamide;

N-(2-chlorophenyl)-8-((dimethylamino)methyl)-N-methyl-4,5-dihydrobenzo[b]thieno[2,3-d]oxepine-2-carboxamide;

N-(2-chlorophenyl)-N-methyl-8-((methylamino)methyl)-4,5-dihydrobenzo[b]thieno[2,3-d]oxepine-2-carboxamide;

8-(aminomethyl)-N-(2-chlorophenyl)-N-methyl-4,5-dihydrobenzo[b]thieno[2,3-d]oxepine-2-carboxamide;

4-benzyl-3-(4,5-dihydrobenzo[b]thieno[2,3-d]oxepin-2-yl)-1H-1,2,4-triazol-5(4H)-one;

N-(2,4-dichlorophenyl)-9-(4-(dimethylamino)piperidine-1-carbonyl)-N-methyl-4,5-dihydrobenzo[b]thieno[2,3-d]oxepine-2-carboxamide;

N-(2-chloro-4-(2-(dimethylamino)ethylcarbamoyl)phenyl)-N-methyl-4,5-dihydrobenzo[b]thieno[2,3-d]oxepine-2-carboxamide;

N-(2-chloro-4-(dimethylcarbamoyl)phenyl)-N-methyl-4,5-dihydrobenzo[b]thieno[2,3-d]oxepine-2-carboxamide;

N-(2-chloro-4-(methylcarbamoyl)phenyl)-N-methyl-4,5-dihydrobenzo[b]thieno[2,3-d]oxepine-2-carboxamide;

N-(2-chloro-4-(morpholine-4-carbonyl)phenyl)-N-methyl-4,5-dihydrobenzo[b]thieno[2,3-d]oxepine-2-carboxamide;

N-(2-chloro-4-(4-methylpiperazine-1-carbonyl)phenyl)-N-methyl-4,5-dihydrobenzo[b]thieno[2,3-d]oxepine-2-carboxamide;

N-(2-chloro-4-(piperazine-1-carbonyl)phenyl)-N-methyl-4,5-dihydrobenzo[b]thieno[2,3-d]oxepine-2-carboxamide;

3-(4,5-dihydrobenzo[b]thieno[2,3-d]oxepin-2-yl)-4-(1-hydroxypropan-2-yl)-1H-1,2,4-triazol-5(4H)-one;

3-(9-bromo-4,5-dihydrobenzo[b]thieno[2,3-d]oxepin-2-yl)-4-(2,4-dichlorophenyl)-4H-1,2,4-triazole;

3-(4,5-dihydrobenzo[b]thieno[2,3-d]oxepin-2-yl)-4-(1-methoxypropan-2-yl)-1H-1,2,4-triazol-5(4H)-one;

N-(2-acetamidoethyl)-N-(2-chlorophenyl)-4,5-dihydrobenzo[b]thieno[2,3-d]oxepine-2-carboxamide;

2-(4-isopropyl-5-oxo-4,5-dihydro-1H-1,2,4-triazol-3-yl)-4,5-dihydrobenzo[b]thieno[2,3-d]oxepine-8-carbonitrile;

3-(4,5-dihydrobenzo[b]thieno[2,3-d]oxepin-2-yl)-4-isobutyl-1H-1,2,4-triazol-5(4H)-one;

N-(2-chlorophenyl)-N-methyl-8-(morpholinomethyl)-4,5-dihydrobenzo[b]thieno[2,3-d]oxepine-2-carboxamide;

4-(8-(1H-pyrazol-4-yl)-4,5-dihydrobenzo[b]thieno[2,3-d]oxepin-2-yl)-5-(2-chlorophenyl)thiazol-2-amine;

3-(8-(1H-pyrazol-4-yl)-4,5-dihydrobenzo[b]thieno[2,3-d]oxepin-2-yl)-4-isopropyl-1H-1,2,4-triazol-5(4H)-one;

3-(8-bromo-4,5-dihydrobenzo[b]thieno[2,3-d]oxepin-2-yl)-4-isopropyl-1H-1,2,4-triazol-5(4H)-one;

5-(8-bromo-4,5-dihydrobenzo[b]thieno[2,3-d]oxepin-2-yl)-1,3,4-oxadiazol-2(3H)-one;

3-(9-bromo-4,5-dihydrobenzo[b]thieno[2,3-d]oxepin-2-yl)-4-(2-chloro-4-fluorophenyl)-4H-1,2,4-triazole;

2-(2-amino-5-(2-chlorophenyl)thiazol-4-yl)-4,5-dihydrobenzo[b]thieno[2,3-d]oxepine-8-carboxamide;

3-(8-(1H-pyrazol-4-yl)-4,5-dihydrobenzo[b]thieno[2,3-d]oxepin-2-yl)-4-ethyl-1H-1,2,4-triazol-5(4H)-one;

2-(4-(2-chlorophenyl)-4H-1,2,4-triazol-3-yl)-4,5-dihydrobenzo[b]thieno[2,3-d]oxepine-8-carboxamide;

4-(8-bromo-4,5-dihydrobenzo[b]thieno[2,3-d]oxepin-2-yl)-5-(2-chlorophenyl)thiazol-2-amine;

3-(8-bromo-4,5-dihydrobenzo[b]thieno[2,3-d]oxepin-2-yl)-4-(2-chlorophenyl)-5-methyl-4H-1,2,4-triazole;

3-(8-bromo-4,5-dihydrobenzo[b]thieno[2,3-d]oxepin-2-yl)-4-(2-chlorophenyl)-4H-1,2,4-triazole;

2-(4-(2-chlorophenyl)-1H-pyrazol-3-yl)-4,5-dihydrobenzo[b]thieno[2,3-d]oxepine-8-carboxamide;

2-(4-(2-chlorophenyl)-1H-pyrazol-3-yl)-4,5-dihydrobenzo[b]thieno[2,3-d]oxepine-8-carbonitrile;
3-(8-bromo-4,5-dihydrobenzo[b]thieno[2,3-d]oxepin-2-yl)-4-(2-chlorophenyl)-1H-pyrazole;
3-(8-(1H-pyrazol-4-yl)-4,5-dihydrobenzo[b]thieno[2,3-d]oxepin-2-yl)-4-(2-chlorophenyl)-1H-1,2,4-triazol-5(4H)-one;
2-(4-(2-chlorophenyl)-5-oxo-4,5-dihydro-1H-1,2,4-triazol-3-yl)-4,5-dihydrobenzo[b]thieno[2,3-d]oxepine-8-carbonitrile;
3-(8-bromo-4,5-dihydrobenzo[b]thieno[2,3-d]oxepin-2-yl)-4-(2-chlorophenyl)-1H-1,2,4-triazol-5(4H)-one;
5-(2-chlorophenyl)-4-(4,5-dihydrobenzo[b]thieno[2,3-d]oxepin-2-yl)thiazol-2-amine;
2-(4-(2-chloro-4-fluorophenyl)-4H-1,2,4-triazol-3-yl)-4,5-dihydrobenzo[b]thieno[2,3-d]oxepine-9-carboxamide;
5-(2-chlorophenyl)-4-(4,5-dihydrobenzo[b]thieno[2,3-d]oxepin-2-yl)pyrimidin-2-amine;
4-(2-chlorophenyl)-3-(4,5-dihydrobenzo[b]thieno[2,3-d]oxepin-2-yl)-1H-pyrazole;
4-(2-chlorophenyl)-3-(4,5-dihydrobenzo[b]thieno[2,3-d]oxepin-2-yl)-1H-1,2,4-triazol-5(4H)-one;
2-(1-(2-chlorophenyl)-1H-tetrazol-5-yl)-4,5-dihydrobenzo[b]thieno[2,3-d]oxepine-8-carboxamide;
5-(8-bromo-4,5-dihydrobenzo[b]thieno[2,3-d]oxepin-2-yl)-1-(2-chlorophenyl)-1H-tetrazole;
5-(8-bromo-4,5-dihydrobenzo[b]thieno[2,3-d]oxepin-2-yl)-4-(2-chlorophenyl)-4H-1,2,4-triazol-3-amine;
N2-(2,4-dichlorophenyl)-N2,N9,N9-trimethyl-4,5-dihydrobenzo[b]thieno[2,3-d]oxepine-2,9-dicarboxamide;
3-(9-bromo-4,5-dihydrobenzo[b]thieno[2,3-d]oxepin-2-yl)-4-(2-chloro-4-(trifluoromethyl)phenyl)-4H-1,2,4-triazole;
N-(2-chloro-4-fluorophenyl)-9-cyano-N-methyl-4,5-dihydrobenzo[b]thieno[2,3-d]oxepine-2-carboxamide;
9-cyano-N-(2,4-difluorophenyl)-N-methyl-4,5-dihydrobenzo[b]thieno[2,3-d]oxepine-2-carboxamide;
3-(9-bromo-4,5-dihydrobenzo[b]thieno[2,3-d]oxepin-2-yl)-4-(2,4-difluorophenyl)-4H-1,2,4-triazole;
2-(4-(2-chlorophenyl)-5-oxo-4,5-dihydro-1H-1,2,4-triazol-3-yl)-4,5-dihydrobenzo[b]thieno[2,3-d]oxepine-8-carboxamide;
N-(2-aminoethyl)-2-(4-(2-chlorophenyl)-4H-1,2,4-triazol-3-yl)-4,5-dihydrobenzo[b]thieno[2,3-d]oxepine-8-carboxamide;
N-(2-chloro-4-(methylcarbamoyl)phenyl)-9-cyano-N-methyl-4,5-dihydrobenzo[b]thieno[2,3-d]oxepine-2-carboxamide;
N2-(2-chlorophenyl)-N9-ethyl-N2-methyl-4,5-dihydrobenzo[b]thieno[2,3-d]oxepine-2,9-dicarboxamide;
N-(2,4-dichlorophenyl)-N-methyl-9-(piperazine-1-carbonyl)-4,5-dihydrobenzo[b]thieno[2,3-d]oxepine-2-carboxamide;
N-(2-acetamidoethyl)-2-(4-(2-chlorophenyl)-4H-1,2,4-triazol-3-yl)-4,5-dihydrobenzo[b]thieno[2,3-d]oxepine-8-carboxamide;
2-(4-(2-chlorophenyl)-4H-1,2,4-triazol-3-yl)-N-(2-morpholinoethyl)-4,5-dihydrobenzo[b]thieno[2,3-d]oxepine-8-carboxamide;
2-(4-(2-chlorophenyl)-4H-1,2,4-triazol-3-yl)-N-(2-(dimethylamino)ethyl)-4,5-dihydrobenzo[b]thieno[2,3-d]oxepine-8-carboxamide;
2-(4-(2-chlorophenyl)-4H-1,2,4-triazol-3-yl)-N-(1,3-dihydroxypropan-2-yl)-4,5-dihydrobenzo[b]thieno[2,3-d]oxepine-8-carboxamide;
N2-(2-chloro-4-(methylcarbamoyl)phenyl)-N2-methyl-4,5-dihydrobenzo[b]thieno[2,3-d]oxepine-2,9-dicarboxamide;
5-(8-(1H-pyrazol-4-yl)-4,5-dihydrobenzo[b]thieno[2,3-d]oxepin-2-yl)-4-(2-chlorophenyl)-4H-1,2,4-triazol-3-amine;
N-(2-chlorophenyl)-N-methyl-8-1H-pyrazol-5-yl)-4,5-dihydrobenzo[b]thieno[2,3-d]oxepine-2-carboxamide;
2-(4-(2-chlorophenyl)-4H-1,2,4-triazol-3-yl)-N-((R)-2-hydroxypropyl)-4,5-dihydrobenzo[b]thieno[2,3-d]oxepine-8-carboxamide;
2-(4-(2-chlorophenyl)-4H-1,2,4-triazol-3-yl)-N-(2-hydroxyethyl)-4,5-dihydrobenzo[b]thieno[2,3-d]oxepine-8-carboxamide;
4-(2-chlorophenyl)-3-(4,5-dihydrobenzo[b]thieno[2,3-d]oxepin-2-yl)-4H-1,2,4-triazole;
N-(2-chloro-4-(piperazine-1-carbonyl)phenyl)-N-(2-hydroxyethyl)-4,5-dihydrobenzo[b]thieno[2,3-d]oxepine-2-carboxamide;
N-(2-chlorophenyl)-N-methyl-8-(3-methyl-1H-pyrazol-4-yl)-4,5-dihydrobenzo[b]thieno[2,3-d]oxepine-2-carboxamide;
N-(4-carbamoyl-2-chlorophenyl)-N-(2-hydroxyethyl)-4,5-dihydrobenzo[b]thieno[2,3-d]oxepine-2-carboxamide;
N2-(2,4-dichlorophenyl)-N2,N8-dimethyl-4,5-dihydrobenzo[b]thieno[2,3-d]oxepine-2,8-dicarboxamide;
2-(1-(2-chlorophenyl)-1H-1,2,4-triazol-5-yl)-4,5-dihydrobenzo[b]thieno[2,3-d]oxepine-8-carbonitrile;
2-(1-(2,4-difluorophenyl)-1H-1,2,4-triazol-5-yl)-4,5-dihydrobenzo[b]thieno[2,3-d]oxepine-8-carboxamide;
2-(4-(2-chloro-4-(methylcarbamoyl)phenyl)-4H-1,2,4-triazol-3-yl)-N-methyl-4,5-dihydrobenzo[b]thieno[2,3-d]oxepine-8-carboxamide;
2-(4-(2-chlorophenyl)-5-oxo-4,5-dihydro-11-1-1,2,4-triazol-3-yl)-N-methyl-4,5-dihydrobenzo[b]thieno[2,3-d]oxepine-8-carboxamide;
N-(2-acetamidoethyl)-2-(4-(2-chlorophenyl)-5-oxo-4,5-dihydro-1H-1,2,4-triazol-3-yl)-4,5-dihydrobenzo[b]thieno[2,3-d]oxepine-8-carboxamide;
N-(2-amino-2-methylpropyl)-2-(4-(2-chlorophenyl)-5-oxo-4,5-dihydro-1H-1,2,4-triazol-3-yl)-4,5-dihydrobenzo[b]thieno[2,3-d]oxepine-8-carboxamide;
N8-(2-acetamidoethyl)-N2-(2-chloro-4-(dimethylcarbamoyl)phenyl)-N2-methyl-4,5-dihydrobenzo[b]thieno[2,3-d]oxepine-2,8-dicarboxamide;
N2-(2-chloro-4-(dimethylcarbamoyl)phenyl)-N8-(2-(dimethylamino)ethyl)-N2-methyl-4,5-dihydrobenzo[b]thieno[2,3-d]oxepine-2,8-dicarboxamide;
9-cyano-N-(2,4-dichlorophenyl)-N-methyl-4,5-dihydrobenzo[b]thieno[2,3-d]oxepine-2-carboxamide;
N2-(2-chloro-4-(dimethylcarbamoyl)phenyl)-N8-(2-hydroxyethyl)-N2-methyl-4,5-dihydrobenzo[b]thieno[2,3-d]oxepine-2,8-dicarboxamide;
N2-(2-chloro-4-(dimethylcarbamoyl)phenyl)-N8-isopropyl-N2-methyl-4,5-dihydrobenzo[b]thieno[2,3-d]oxepine-2,8-dicarboxamide;
N8-(2-amino-2-methylpropyl)-N2-(2-chloro-4-(dimethylcarbamoyl)phenyl)-N2-methyl-4,5-dihydrobenzo[b]thieno[2,3-d]oxepine-2,8-dicarboxamide;
2-(1-(2-chloro-4-(dimethylcarbamoyl)phenyl)-1H-1,2,4-triazol-5-yl)-N-methyl-4,5-dihydrobenzo[b]thieno[2,3-d]oxepine-8-carboxamide;
4-(5-(8-bromo-4,5-dihydrobenzo[b]thieno[2,3-d]oxepin-2-yl)-1H-1,2,4-triazol-1-yl)-3-chloro-N,N-dimethylbenzamide;

N-(2-chloro-4-(dimethylcarbamoyl)phenyl)-9-cyano-N-methyl-4,5-dihydrobenzo[b]thieno[2,3-d]oxepine-2-carboxamide;

2-(1-isopropyl-1H-1,2,4-triazol-5-yl)-4,5-dihydrobenzo[b]thieno[2,3-d]oxepine-8-carboxamide;

N2-(2-chloro-4-(dimethylcarbamoyl)phenyl)-N8-isobutyl-N2-methyl-4,5-dihydrobenzo[b]thieno[2,3-d]oxepine-2,8-dicarboxamide;

N2-(2-chloro-4-(dimethylcarbamoyl)phenyl)-N8-ethyl-N2-methyl-4,5-dihydrobenzo[b]thieno[2,3-d]oxepine-2,8-dicarboxamide;

N2-(2-chloro-4-(dimethylcarbamoyl)phenyl)-N8-isobutyl-N2-methyl-4,5-dihydrobenzo[b]thieno[2,3-d]oxepine-2,8-dicarboxamide;

N2-(2-chloro-4-(dimethylcarbamoyl)phenyl)-N2-methyl-4,5-dihydrobenzo[b]thieno[2,3-d]oxepine-2,8-dicarboxamide;

N8-(2-aminoethyl)-N2-(2-chloro-4-(dimethylcarbamoyl)phenyl)-N2-methyl-4,5-dihydrobenzo[b]thieno[2,3-d]oxepine-2, 8-dicarboxamide;

N-(2-chloro-4-(2-hydroxypropylcarbamoyl)phenyl)-9-cyano-N-methyl-4,5-dihydrobenzo[b]thieno[2,3-d]oxepine-2-carboxamide;

3-(9-bromo-4,5-dihydrobenzo[b]thieno[2,3-d]oxepin-2-yl)-4-(2-chlorophenyl)-4H-1,2,4-triazole;

2-(4-(2-chloro-4-fluorophenyl)-4H-1,2,4-triazol-3-yl)-4,5-dihydrobenzo[b]thieno[2,3-d]oxepine-9-carbonitrile;

9-bromo-N-(2,4-dichlorophenyl)-N-methyl-4,5-dihydrobenzo[b]thieno[2,3-d]oxepine-2-carboxamide;

N-(2-chloro-4-cyanophenyl)-9-cyano-N-methyl-4,5-dihydrobenzo[b]thieno[2,3-d]oxepine-2-carboxamide;

N-(2-chloro-4-(trifluoromethyl)phenyl)-9-cyano-N-methyl-4,5-dihydrobenzo[b]thieno[2,3-d]oxepine-2-carboxamide;

N-(2,4-dichlorophenyl)-N-methyl-9-(4-methylpiperazine-1-carbonyl)-4,5-dihydrobenzo[b]thieno[2,3-d]oxepine-2-carboxamide;

N-(2,4-dichlorophenyl)-9-((3S,5R)-3,5-dimethylpiperazine-1-carbonyl)-N-methyl-4,5-dihydrobenzo[b]thieno[2,3-d]oxepine-2-carboxamide;

N2-(2,4-dichlorophenyl)-N9-(2-hydroxyethyl)-N2-methyl-4,5-dihydrobenzo[b]thieno[2,3-d]oxepine-2,9-dicarboxamide;

2-(4-(2-chlorophenyl)-1-methyl-5-oxo-4,5-dihydro-1H-1,2,4-triazol-3-yl)-4,5-dihydrobenzo[b]thieno[2,3-d]oxepine-8-carboxamide; and 2-(4-(2-chlorophenyl)-1-methyl-5-oxo-4,5-dihydro-1H-1,2,4-triazol-3-yl)-N-methyl-4, 5-dihydrobenzo[b]thieno[2,3-d]oxepine-8-carboxamide.

12. The method of claim 1 wherein the compound of formula I is selected from:

N2-(2-chloro-4-fluorophenyl)-N2,N8-dimethyl-4,5-dihydrobenzo[b]thieno[2,3-d]oxepine-2,8-dicarboxamide;

2-(1-(2-chloro-4-(dimethylcarbamoyl)phenyl)-1H-1,2,4-triazol-5-yl)-4,5-dihydrobenzo[b]thieno[2,3-d]oxepine-8-carboxamide;

2-(1-(2,4-difluorophenyl)-1H-1,2,4-triazol-5-yl)-N-methyl-4,5-dihydrobenzo[b]thieno[2,3-d]oxepine-8-carboxamide;

N2-(2-chloro-4-(methylcarbamoyl)phenyl)-N2-(2-hydroxyethyl)-N8-methyl-4,5-dihydrobenzo[b]thieno[2,3-d]oxepine-2,8-dicarboxamide;

(2-(4-(2,4-difluorophenyl)-4H-1,2,4-triazol-3-yl)-4,5-dihydrobenzo[b]thieno[2,3-d]oxepin-9-yl)(4-methylpiperazin-1-yl)methanone;

2-(4-(2,4-difluorophenyl)-4H-1,2,4-triazol-3-yl)-N-(2-hydroxyethyl)-4, 5-dihydrobenzo[b]thieno[2,3-d]oxepine-9-carboxamide;

2-(4-(2,4-difluorophenyl)-4H-1,2,4-triazol-3-yl)-N42-hydroxyethyl)-N-methyl-4,5-dihydrobenzo[b]thieno[2,3-d]oxepine-9-carboxamide;

2-(1-(2,4-difluorophenyl)-1H-1,2,4-triazol-5-yl)-4,5-dihydrobenzo[b]thieno[2,3-d]oxepine-8-carbonitrile;

2-(1-(2-hydroxyethyl)-1H-1,2,4-triazol-5-yl)-4,5-dihydrobenzo[b]thieno[2,3-d]oxepine-8-carboxamide;

5-(9-bromo-4,5-dihydrobenzo[b]thieno[2,3-d]oxepin-2-yl)-1-(2,4-difluorophenyl)-1H-1,2,4-triazole;

5-(9-bromo-4,5-dihydrobenzo[b]thieno[2,3-d]oxepin-2-yl)-1-isopropyl-1H-1,2,4-triazole;

N2-(2-chloro-4-fluorophenyl)-N2-methyl-4, -dihydrobenzo[b]thieno[2,3-d]oxepine-2, 8-dicarboxamide;

N2-(2-chloro-5-(dimethylcarbamoyl)phenyl)-N2-methyl-4,5-dihydrobenzo[b]thieno[2,3-d]oxepine-2,8-dicarboxamide;

N2-(2-chloro-5-(dimethylcarbamoyl)phenyl)-N2,N8-dimethyl-4,5-dihydrobenzo[b]thieno[2,3-d]oxepine-2, 8-dicarboxamide;

2-(4-isopropyl-1-methyl-5-oxo-4,5-dihydro-1H-1,2,4-triazol-3-yl)-4,5-dihydrobenzo[b]thieno[2,3-d]oxepine-8-carboxamide;

5-(8-(1H-pyrazol-4-yl)-4,5-dihydrobenzo[b]thieno[2,3-d]oxepin-2-yl)-1-isopropyl-1H-1,2,4-triazole;

1-(2,4-difluorophenyl)-5-(4,5-dihydrobenzo[b]thieno[2,3-d]oxepin-2-yl)-1H-1,2,4-triazole;

2-(1-(2,4-difluorophenyl)-1H-1,2,4-triazol-5-yl)-N-(2-hydroxyethyl)-4,5-dihydrobenzo[b]thieno[2,3-d]oxepine-9-carboxamide;

5-(9-(1H-pyrazol-4-yl)-4,5-dihydrobenzo[b]thieno[2,3-d]oxepin-2-yl)-1-(2,4-difluorophenyl)-1H-1,2,4-triazole;

2-(1-(2,4-difluorophenyl)-1H-1,2,4-triazol-5-yl)-4,5-dihydrobenzo[b]thieno[2,3-d]oxepine-9-carboxamide;

(2-(1-(2,4-difluorophenyl)-1H-1,2,4-triazol-5-yl)-4,5-dihydrobenzo[b]thieno[2,3-d]oxepin-9-yl)(piperazin-1-yl)methanone;

N2-(4-carbamoyl-2-chlorophenyl)-N2,N8-dimethyl-4,5-dihydrobenzo[b]thieno[2,3-d]oxepine-2,8-dicarboxamide;

2-(1-(2-chloro-5-(dimethylcarbamoyl)phenyl)-1H-1,2,4-triazol-5-yl)-4,5-dihydrobenzo[b]thieno[2,3-d]oxepine-8-carboxamide;

3-(2-(1-(2,4-difluorophenyl)-1H-1,2,4-triazol-5-yl)-4,5-dihydrobenzo[b]thieno[2,3-d]oxepin-9-yl)pyridine;

2-(1-(1,1,1-trifluoropropan-2-yl)-1H-1,2,4-triazol-5-yl)-4,5-dihydrobenzo[b]thieno[2,3-d]oxepine-8-carboxamide;

N2-(2-chloro-4-(4-methylpiperazine-1-carbonyl)phenyl)-N2-methyl-4,5-dihydrobenzo[b]thieno[2,3-d]oxepine-2,8-dicarboxamide;

2-(1-(2,4-difluorophenyl)-1H-1,2,4-triazol-5-yl)-N-(2-hydroxyethyl)-4,5-dihydrobenzo[b]thieno[2,3-d]oxepine-8-carboxamide;

N-(2-acetamidoethyl)-2-(1-(2,4-difluorophenyl)-1H-1,2,4-triazol-5-yl)-4,5-dihydrobenzo[b]thieno[2,3-d]oxepine-8-carboxamide;

2-(1-(2,4-difluorophenyl)-1H-1,2,4-triazol-5-yl)-N-(2-(pyrrolidin-1-yl)ethyl)-4,5-dihydrobenzo[b]thieno[2,3-d]oxepine-8-carboxamide;

(2-(1-(2,4-difluorophenyl)-1H-1,2,4-triazol-5-yl)-4,5-dihydrobenzo[b]thieno[2,3-d]oxepin-9-yl)((R)-3-(dimethylamino)pyrrolidin-1-yl)methanone;

2-(1-isopropyl-1H-1,2,4-triazol-5-yl)-4,5-dihydrobenzo[b]thieno[2,3-d]oxepine-9-carboxamide;

(2-(1-(2,4-difluorophenyl)-1H-1,2,4-triazol-5-yl)-4,5-dihydrobenzo[b]thieno[2,3-d]oxepin-9-yl)((S)-3-(dimethylamino)pyrrolidin-1-yl)methanone;

2-(1-(2,2,2-trifluoroethyl)-1H-1,2,4-triazol-5-yl)-4,5-dihydrobenzo[b]thieno[2,3-d]oxepine-8-carboxamide;

N2-(2-chloro-4-(piperazine-1-carbonyl)phenyl)-N2-methyl-4,5-dihydrobenzo[b]thieno[2,3-d]oxepine-2,8-dicarboxamide;

N2-(4-(4-acetylpiperazine-1-carbonyl)-2-chlorophenyl)-N2,N8-dimethyl-4,5-dihydrobenzo[b]thieno[2,3-d]oxepine-2,8-dicarboxamide;

2-(1-isobutyl-1H-1,2,4-triazol-5-yl)-4,5-dihydrobenzo[b]thieno[2,3-d]oxepine-8-carboxamide;

2-(1-(1,1,1-trifluoropropan-2-yl)-1H-1,2,4-triazol-5-yl)-4,5-dihydrobenzo[b]thieno[2,3-d]oxepine-8-carboxamide;

2-(1-(1,1,1-trifluoropropan-2-yl)-1H-1,2,4-triazol-5-yl)-4,5-dihydrobenzo[b]thieno[2,3-d]oxepine-8-carboxamide;

2-(1-(2-hydroxy-2-methylpropyl)-1H-1,2,4-triazol-5-yl)-4,5-dihydrobenzo[b]thieno[2,3-d]oxepine-8-carboxamide;

N2-(4-carbamoyl-2-chlorophenyl)-N2-methyl-4,5-dihydrobenzo[b]thieno[2,3-d]oxepine-2,8-dicarboxamide;

N2-(2-chloro-4-(2-hydroxypropylcarbamoyl)phenyl)-N2,N8-dimethyl-4,5-dihydrobenzo[b]thieno[2,3-d]oxepine-2,8-dicarboxamide;

N2-(2-chloro-4-(2-hydroxypropylcarbamoyl)phenyl)-N2-methyl-4,5-dihydrobenzo[b]thieno[2,3-d]oxepine-2,8-dicarboxamide;

2-(1-cyclobutyl-1H-1,2,4-triazol-5-yl)-4,5-dihydrobenzo[b]thieno[2,3-d]oxepine-9-carboxamide;

2-(1-cyclobutyl-1H-1,2,4-triazol-5-yl)-4,5-dihydrobenzo[b]thieno[2,3-d]oxepine-8-carboxamide;

(3-chloro-4-(5-(4,5-dihydrobenzo[b]thieno[2,3-d]oxepin-2-yl)-1H-1,2,4-triazol-1-yl)phenyl)(4-methylpiperazin-1-yl)methanone;

2-(1-(2-(dimethylamino)ethyl)-1H-1,2,4-triazol-5-yl)-4,5-dihydrobenzo[b]thieno[2,3-d]oxepine-8-carboxamide;

(2-(1-(2-hydroxy-2-methylpropyl)-1H-1,2,4-triazol-5-yl)-4,5-dihydrobenzo[b]thieno[2,3-d]oxepin-9-yl)(4-methylpiperazin-1-yl)methanone;

N2-(2-chloro-4-(2-(dimethylamino)ethylcarbamoyl)phenyl)-N2,N8-dimethyl-4,5-dihydrobenzo[b]thieno[2,3-d]oxepine-2,8-dicarboxamide;

N2-(2-chloro-4-(2-(dimethylamino)ethylcarbamoyl)phenyl)-N2-methyl-4,5-dihydrobenzo[b]thieno[2,3-d]oxepine-2,8-dicarboxamide;

5-(8-(4H-1,2,4-triazol-3-yl)-4,5-dihydrobenzo[b]thieno[2,3-d]oxepin-2-yl)-1-isopropyl-1H-1,2,4-triazole;

2-(2-aminopyridin-4-yl)-4,5-dihydrobenzo[b]thieno[2,3-d]oxepine-8-carbonitrile;

(2-(1-(2,4-difluorophenyl)-1H-1,2,4-triazol-5-yl)-4,5-dihydrobenzo[b]thieno[2,3-d]oxepin-9-yl)(4-methylpiperazin-1-yl)methanone;

(2-(1-(2-chlorophenyl)-1H-1,2,4-triazol-5-yl)-4,5-dihydrobenzo[b]thieno[2,3-d]oxepin-9-yl)(4-methylpiperazin-1-yl)methanone;

2-(1-(3-methylbutan-2-yl)-1H-1,2,4-triazol-5-yl)-4,5-dihydrobenzo[b]thieno[2,3-d]oxepine-8-carboxamide;

2-(5-(2-(4-(2-chlorophenyl)-4H-1,2,4-triazol-3-yl)-4,5-dihydrobenzo[b]thieno[2,3-d]oxepin-8-yl)-1H-1,2,4-triazol-1-yl)-N,N-dimethylethanamine;

2-(5-(2-(4-(2-chlorophenyl)-4H-1,2,4-triazol-3-yl)-4,5-dihydrobenzo[b]thieno[2,3-d]oxepin-8-yl)-1H-1,2,4-triazol-1-yl)ethanol;

2-(1-(2-(trifluoromethyl)-1H-benzo [d] imidazol-5-yl)-1H-1,2,4-triazol-5-yl)-4,5-dihydrobenzo[b]thieno[2,3-d]oxepine-8-carboxamide;

2-(1-(4-((1H-1,2,4-triazol-1-yl)methyl)phenyl)-1H-1,2,4-triazol-5-yl)-4,5-dihydrobenzo[b]thieno[2,3-d]oxepine-8-carboxamide;

(4-methylpiperazin-1-yl)(2-(1-(2,2,2-trifluoroethyl)-1H-1,2,4-triazol-5-yl)-4,5-dihydrobenzo[b]thieno[2,3-d]oxepin-9-yl)methanone;

2-(1-(1,1,1-trifluoro-3-methylbutan-2-yl)-1H-1,2,4-triazol-5-yl)-4,5-dihydrobenzo[b]thieno[2,3-d]oxepine-8-carboxamide;

5-(8-bromo-4,5-dihydrobenzo[b]thieno[2,3-d]oxepin-2-yl)-1-isopropyl-1H-1,2,4-triazole;

2-(1-isopropyl-1H-1,2,4-triazol-5-yl)-4,5-dihydrobenzo[b]thieno[2,3-d]oxepine-8-carbonitrile;

3-(9-bromo-4,5-dihydro-6-oxa-1-thia-benzo [e] azulen-2-yl)-4-(2,4-dichloro-phenyl)-4H-[1,2,4]triazole; and N-(2-aminoethyl)-2-(4-(2-chlorophenyl)-5-oxo-4,5-dihydro-1H-1,2,4-triazol-3-yl)-4,5-dihydrobenzo[b]thieno[2,3-d]oxepine-8-carboxamide.

* * * * *